US012742011B2

(12) United States Patent
Novobrantseva et al.

(10) Patent No.: US 12,742,011 B2
(45) Date of Patent: Sep. 22, 2026

(54) ANTI-VSIG4 COMPOSITIONS AND METHODS FOR MODULATING MYELOID CELL INFLAMMATORY PHENOTYPES AND USES THEREOF

(71) Applicant: Verseau Therapeutics, Inc., Bedford, MA (US)

(72) Inventors: Tatiana I. Novobrantseva, Wellesley, MA (US); Igor Feldman, Waltham, MA (US); Stephen L. Sazinsky, Winchester, MA (US); Elizabeth Culyba, Arlington, MA (US); Phuong Anh Nguyen, Melrose, MA (US); Maja Razlog, Somerville, MA (US)

(73) Assignee: Verseau Therapeutics, Inc., Bedford, MA (US)

( * ) Notice: Subject to any disclaimer, the term of this patent is extended or adjusted under 35 U.S.C. 154(b) by 862 days.

(21) Appl. No.: 17/999,503

(22) PCT Filed: May 28, 2021

(86) PCT No.: PCT/US2021/034784
§ 371 (c)(1),
(2) Date: Nov. 21, 2022

(87) PCT Pub. No.: WO2021/243169
PCT Pub. Date: Dec. 2, 2021

(65) Prior Publication Data

US 2023/0348603 A1 Nov. 2, 2023

Related U.S. Application Data

(60) Provisional application No. 63/032,337, filed on May 29, 2020.

(51) Int. Cl.
*C07K 16/28* (2006.01)

(52) U.S. Cl.
CPC ...... *C07K 16/2827* (2013.01); *C07K 2317/33* (2013.01); *C07K 2317/34* (2013.01); *C07K 2317/55* (2013.01); *C07K 2317/565* (2013.01); *C07K 2317/76* (2013.01)

(58) Field of Classification Search
CPC ............ C07K 16/2827; C07K 2317/33; C07K 2317/34; C07K 2317/55; C07K 2317/565; C07K 2317/76; C07K 2317/24; C07K 2317/73; C07K 2317/92; A61K 2039/505; A61P 35/00; G01N 33/574
See application file for complete search history.

(56) References Cited

FOREIGN PATENT DOCUMENTS

| | | | |
|---|---|---|---|
| CN | 105924515 | A | 9/2016 |
| KR | 101730868 | B1 | 4/2017 |
| WO | WO-2008/130204 | A1 | 10/2008 |
| WO | WO-2010/062904 | A2 | 6/2010 |
| WO | WO-2010/119704 | A1 | 10/2010 |
| WO | WO-2019/005817 | A2 | 1/2019 |
| WO | WO-2020/069507 | A1 | 4/2020 |
| WO | WO-2021/243169 | A1 | 12/2021 |

OTHER PUBLICATIONS

Zhou et al. "Engineered Fc-glycosylation switch to eliminate antibody effector function" MABS. 2020, 12(1), e1814583, 1-13 (Year: 2020).*

Sazinsky et al. "Antibodies Targeting Human or Mouse VSIG4 Repolarize Tumor-Associated Macrophages Providing the Potential of Potent and Specific Clinical Anti-Tumor Response Induced across Multiple Cancer Types" Int. J. Mol. Sci. 2024, 25(11), 6160, 1-22 (Year: 2024).*

DeLuca et al. "Production and purification of recombinant monoclonal antibodies from human cells based on a primary sequence." STAR Protocols. 2022, 3, 101915, 1-17 (Year: 2022).*

International Search Report and Written Opinion for International Application No. PCT/US21/34784 mailed Nov. 3, 2021.

Invitation to Pay Additional Fees for International Application No. PCT/US21/34784 mailed Aug. 30, 2021.

Munawara et al., "Human Dendritic Cells Express the Complement Receptor Immunoglobulin Which Regulates T Cell Responses," Front Immunol, 10(2802) (14 pages) (2019).

Extended European Search Report for EP Application No. 21814040.8 dated Sep. 13, 2024.

Supplementary Partial European Search Report for EP Application No. 21814040.8 dated Jun. 21, 2024.

* cited by examiner

*Primary Examiner* — Misook Yu
*Assistant Examiner* — Grace H Lunde
(74) *Attorney, Agent, or Firm* — Foley Hoag LLP; Philip S. Choi; Erin M. Foley

(57) ABSTRACT

The present invention is based, in part, on the discovery of anti-VSIG4 composition (e.g., monoclonal antibodies and antigen-binding fragments thereof), that regulate myeloid cell inflammatory phenotypes, such as suppressive myeloid cells, monocytes, macrophages, neutrophils, and/or dendritic cells, including polarization, activation, and/or function, and methods of using such anti-VSIG4 compositions for therapeutic, diagnostic, prognostic, and screening purposes.

31 Claims, 49 Drawing Sheets

Specification includes a Sequence Listing.

Figure 1B
VSIG4 is Enriched on M2-like and M0-like Tumor Associated Myeloid Populations
Neutrophil
Monocyte/
Macrophage/
DC
NK
T cells
B cells
Mast
Plasma
cells
pDC
t-SNE
Clustering plot
Zilionis,et al. Immunity, 2019
7 human primary NSCLC samples + matching blood
scRNA seq, reanalyzed at Verseau
Sub-cluster
UMAP
Dendritic
cells
M2-like
macrophages
M0-like
macrophages
Monocytes
VSIG4

M1 activated
M0
Isotype
VSIG4 siRNA
WT
M2a
M2c
M2d
100
80
60
40
20
0

| Residue | Mutation | 14C05 | 14D12 | 12A12 | 16E10 | 15C03 | 12A08 | 16E03 | 13H11 | 15A06 | 15C04 | 16G02 | 1C6.D6 | 1H7.C7 | 5D2.C8 | 9A10.C4 | 10E8.B6 | 13E11.A4 | 14F8.H6 | 16F6.E1 |
|---|---|---|---|---|---|---|---|---|---|---|---|---|---|---|---|---|---|---|---|---|
| 1 | R1A | 1.06 | 0.75 | 1.08 | 0.01 | 0.61 | 0.38 | 1.36 | 0.73 | 0.73 | 0.58 | 1.03 | 0.99 | 1.02 | 1.03 | 1.03 | 1.01 | 0.98 | 1.05 | 1.06 |
| 3 | I3A | 1.01 | 0.65 | 0.97 | 2.14 | 1.00 | 0.29 | 0.04 | 0.70 | 0.89 | 0.90 | 0.98 | 0.91 | 0.92 | 0.96 | 0.96 | 0.94 | 0.90 | 0.98 | 0.98 |
| 5 | E5A | 1.06 | 0.60 | 1.03 | 1.15 | 0.92 | 0.01 | 0.03 | 0.78 | 0.83 | 0.74 | 1.00 | 0.91 | 0.98 | 1.04 | 1.11 | 0.99 | 1.03 | 1.03 | 1.03 |
| 7 | P7A | 0.87 | 0.84 | 0.90 | 0.86 | 0.75 | 0.49 | 0.79 | 0.93 | 0.87 | 0.77 | 1.00 | 1.04 | 1.01 | 0.99 | 1.08 | 1.03 | 1.04 | 1.02 | 1.04 |
| 8 | E8A | 1.14 | 0.92 | 1.08 | 0.98 | 0.53 | 0.45 | 0.94 | 1.05 | 1.12 | 0.82 | 1.09 | 1.03 | 1.02 | 1.00 | 1.10 | 1.06 | 1.07 | 1.05 | 1.04 |
| 9 | S9A | 1.09 | 1.08 | 1.01 | 1.08 | 0.83 | 1.13 | 0.97 | 0.96 | 1.09 | 0.75 | 0.99 | 1.11 | 1.07 | 1.05 | 1.16 | 1.09 | 1.05 | 1.08 | 1.07 |
| 11 | T11A | 0.85 | 1.00 | 0.81 | 0.81 | 0.79 | 0.81 | 0.54 | 0.93 | 0.86 | 0.71 | 0.80 | 0.71 | 0.65 | 0.75 | 0.75 | 0.75 | 0.75 | 0.66 | 0.74 |
| 13 | P13A | 1.10 | 0.82 | 0.96 | 0.78 | 0.87 | 0.90 | 1.04 | 0.84 | 0.82 | 0.77 | 0.98 | 0.94 | 0.97 | 1.05 | 1.02 | 1.08 | 0.99 | 0.99 | 0.99 |
| 15 | K15A | 1.00 | 0.68 | 0.94 | 0.78 | 0.75 | 0.76 | 0.96 | 0.76 | 0.60 | 0.85 | 0.93 | 0.67 | 0.86 | 0.94 | 0.91 | 0.97 | 0.89 | 0.91 | 0.91 |
| 17 | D17A | 0.96 | 0.66 | 0.91 | 0.79 | 0.94 | 0.93 | 0.92 | 0.84 | 0.64 | 0.77 | 1.01 | 0.86 | 0.96 | 1.00 | 1.01 | 0.92 | 0.97 | 0.98 | 0.95 |
| 19 | N19A | 1.07 | 0.88 | 0.97 | 0.89 | 1.04 | 1.04 | 1.02 | 1.02 | 0.94 | 0.89 | 1.01 | 0.93 | 0.96 | 1.04 | 1.08 | 0.98 | 0.99 | 1.01 | 1.01 |
| 21 | P21A | 0.85 | 0.97 | 0.76 | 0.80 | 0.72 | 0.83 | 0.81 | 1.08 | 0.88 | 0.95 | 0.85 | 0.72 | 0.71 | 0.77 | 0.81 | 0.76 | 0.75 | 0.57 | 0.58 |
| 23 | T23A | 0.82 | 0.96 | 0.75 | 0.82 | 0.96 | 0.75 | 1.00 | 1.06 | 0.88 | 0.83 | 0.78 | 0.72 | 0.68 | 0.75 | 0.73 | 0.75 | 0.74 | 0.74 | 0.74 |
| 25 | D25A | 1.20 | 1.16 | 1.15 | 1.45 | 0.89 | 1.28 | 0.45 | 1.20 | 1.10 | 1.05 | 1.08 | 1.08 | 0.99 | 1.05 | 1.00 | 1.07 | 1.04 | 1.04 | 1.08 |
| 26 | P26A | 0.76 | 0.81 | 0.80 | 0.66 | 0.41 | 0.70 | 0.75 | 0.81 | 0.77 | 0.86 | 0.87 | 0.79 | 0.84 | 0.84 | 0.87 | 0.81 | 0.85 | 0.84 | 0.84 |
| 28 | Q28A | 1.01 | 0.71 | 1.03 | 0.47 | 0.87 | 0.71 | 0.99 | 0.65 | 0.68 | 0.87 | 1.02 | 0.94 | 0.98 | 1.02 | 1.04 | 0.96 | 0.99 | 1.00 | 1.01 |
| 29 | G29A | 0.67 | 0.49 | 0.67 | 0.39 | 0.84 | 0.58 | 0.44 | 0.60 | 0.71 | 0.69 | 0.67 | 0.58 | 0.59 | 0.64 | 0.62 | 0.61 | 0.63 | 0.61 | 0.63 |
| 31 | T31A | 0.84 | 0.61 | 0.85 | 0.75 | 0.86 | 0.74 | 0.79 | 0.71 | 0.86 | 0.84 | 0.84 | 0.75 | 0.80 | 0.85 | 0.86 | 0.80 | 0.83 | 0.80 | 0.84 |
| 32 | Q32A | 0.65 | 0.75 | 0.70 | 0.61 | 0.72 | 0.64 | 0.64 | 0.74 | 0.74 | 0.70 | 0.69 | 0.68 | 0.69 | 0.66 | 0.74 | 0.67 | 0.69 | 0.65 | 0.69 |
| 34 | L34A | 1.01 | 0.86 | 1.00 | 0.99 | 1.10 | 0.92 | 1.05 | 0.97 | 1.07 | 0.95 | 0.98 | 0.94 | 1.01 | 0.91 | 1.06 | 1.00 | 1.01 | 0.99 | 1.03 |
| 40 | Q40A | 0.99 | 0.96 | 0.67 | 1.01 | 0.94 | 0.92 | 0.92 | 0.90 | 1.00 | 0.83 | 0.92 | 0.69 | 0.94 | 0.93 | 1.03 | 0.97 | 0.93 | 0.93 | 0.94 |
| 41 | R41A | 1.08 | 1.22 | 0.27 | 1.04 | 1.01 | 1.04 | 1.03 | 1.10 | 1.18 | 0.96 | 1.07 | 0.24 | 0.11 | 0.17 | 0.62 | 0.98 | 0.17 | 0.31 | 0.53 |
| 42 | G42A | 1.00 | 0.75 | 0.21 | 0.67 | 0.68 | 0.77 | 0.92 | 0.75 | 0.78 | 0.72 | 0.87 | 0.50 | 0.43 | 0.86 | 0.87 | 0.93 | 0.63 | 0.81 | 0.65 |
| 43 | S43A | 1.07 | 0.71 | 0.23 | 0.72 | 0.92 | 0.77 | 0.97 | 0.77 | 0.59 | 0.86 | 0.90 | 0.37 | 0.34 | 0.84 | 0.92 | 0.94 | 0.89 | 0.89 | 0.86 |
| 44 | D44A | 1.02 | 0.63 | 0.17 | 0.87 | 0.52 | 0.96 | 1.00 | 0.79 | 0.70 | 0.89 | 0.95 | 0.12 | 0.13 | 0.17 | 0.52 | 0.89 | 0.60 | 0.86 | 0.14 |
| 45 | P45A | 1.08 | 0.81 | 1.15 | 0.83 | 0.98 | 0.99 | 0.99 | 0.92 | 0.90 | 0.87 | 0.96 | 0.80 | 0.84 | 0.91 | 1.03 | 0.91 | 0.86 | 0.92 | 0.95 |
| 46 | V46A | 0.79 | 0.90 | 0.64 | 0.67 | 0.67 | 0.72 | 0.72 | 0.84 | 0.73 | 0.78 | 0.70 | 0.12 | 0.39 | 0.59 | 0.67 | 0.65 | 0.57 | 0.60 | 0.52 |
| 50 | L50A | 0.82 | 0.94 | 0.84 | 0.86 | 0.93 | 0.79 | 0.89 | 0.90 | 0.77 | 0.85 | 0.76 | 0.77 | 0.74 | 0.79 | 0.82 | 0.62 | 0.79 | 0.80 | 0.81 |
| 54 | S54A | 0.81 | 0.77 | 1.06 | 0.81 | 0.98 | 1.08 | 0.90 | 1.06 | 1.08 | 0.98 | 1.01 | 1.07 | 0.99 | 1.02 | 0.99 | 1.02 | 1.01 | 0.99 | 1.05 |
| 59 | Q59A | 0.51 | 0.82 | 0.62 | 0.74 | 0.82 | 0.83 | 0.95 | 0.79 | 0.83 | 0.86 | 0.75 | 0.50 | 0.25 | 0.79 | 0.57 | 0.81 | 0.49 | 0.73 | 0.85 |
| 61 | A61G | 1.00 | 0.72 | 0.90 | 0.70 | 0.00 | 0.70 | 1.00 | 0.61 | 0.67 | 0.79 | 0.91 | 0.79 | 0.89 | 0.95 | 0.99 | 0.92 | 0.95 | 0.97 | 0.97 |

| | | | | | | | | | | | | | | | | | | | | |
|---|---|---|---|---|---|---|---|---|---|---|---|---|---|---|---|---|---|---|---|---|
| 62 | K62A | 0.82 | 0.58 | 0.88 | 0.89 | 0.87 | 0.82 | 0.77 | 0.57 | 0.84 | 0.86 | 0.64 | 0.13 | 0.81 | 0.85 | 0.83 | 0.62 | 0.82 | 0.82 | 0.26 |
| 64 | Q64A | 0.13 | 0.62 | 0.93 | 0.93 | 0.73 | 0.87 | 0.91 | 0.71 | 0.94 | 0.70 | 0.62 | 0.81 | 0.96 | 0.95 | 0.99 | 0.81 | 0.94 | 0.92 | 0.95 |
| 68 | H68A | 0.76 | 0.62 | 0.97 | 0.69 | 0.87 | 0.96 | 0.95 | 0.76 | 1.02 | 0.87 | 0.98 | 1.03 | 1.08 | 0.92 | 1.08 | 0.98 | 0.98 | 0.96 | 1.00 |
| 71 | H71A | 1.02 | 0.84 | 0.98 | 0.96 | 0.84 | 0.88 | 0.99 | 0.89 | 1.01 | 0.85 | 1.04 | 0.90 | 0.90 | 0.88 | 0.96 | 0.94 | 0.95 | 0.91 | 0.94 |
| 72 | K72A | 1.00 | 0.92 | 0.89 | 0.98 | 0.66 | 0.92 | 0.91 | 0.82 | 1.01 | 0.81 | 0.92 | 0.91 | 0.88 | 0.89 | 1.01 | 0.96 | 0.92 | 0.91 | 0.92 |
| 73 | V73A | 1.10 | 1.19 | 1.00 | 1.08 | 0.17 | 1.01 | 0.96 | 1.06 | 1.19 | 1.02 | 1.01 | 0.87 | 0.84 | 0.88 | 0.96 | 0.94 | 0.91 | 0.77 | 0.91 |
| 74 | P74A | 1.12 | 0.87 | 0.90 | 0.81 | 0.18 | 0.87 | 1.06 | 0.76 | 0.89 | 0.86 | 0.89 | 0.94 | 1.03 | 1.05 | 1.07 | 1.15 | 0.99 | 1.01 | 0.98 |
| 80 | Q80A | 0.89 | 0.67 | 0.74 | 0.70 | 0.77 | 0.66 | 0.89 | 0.76 | 0.53 | 0.75 | 0.81 | 0.67 | 0.73 | 0.79 | 0.80 | 0.84 | 0.78 | 0.76 | 0.77 |
| 83 | T83A | 1.15 | 0.71 | 0.97 | 0.90 | 0.98 | 0.98 | 1.05 | 0.76 | 0.71 | 0.92 | 1.02 | 0.78 | 0.97 | 0.97 | 1.01 | 0.96 | 0.98 | 0.98 | 0.91 |
| 85 | E85A | 0.92 | 0.79 | 0.84 | 0.78 | 0.99 | 0.82 | 0.88 | 0.92 | 0.82 | 0.78 | 0.78 | 0.75 | 0.75 | 0.84 | 0.84 | 0.75 | 0.79 | 0.78 | 0.78 |
| 86 | M86A | 0.88 | 0.87 | 0.77 | 0.73 | 0.77 | 0.84 | 0.77 | 0.87 | 0.84 | 0.89 | 0.78 | 0.63 | 0.69 | 0.75 | 0.79 | 0.72 | 0.72 | 0.73 | 0.72 |
| 87 | D87A | 0.97 | 1.05 | 0.89 | 0.99 | 0.85 | 0.92 | 1.02 | 1.00 | 0.94 | 0.86 | 0.88 | 0.95 | 0.89 | 0.94 | 0.95 | 0.91 | 0.92 | 0.81 | 0.80 |
| 89 | R89A | 1.09 | 0.82 | 1.05 | 0.87 | 0.98 | 0.96 | 1.00 | 1.07 | 0.91 | 1.00 | 1.02 | 0.75 | 1.02 | 1.04 | 0.96 | 1.01 | 1.04 | 1.00 | 1.03 |
| 91 | H91A | 0.92 | 0.88 | 0.91 | 0.80 | 0.75 | 0.93 | 0.97 | 0.76 | 0.90 | 0.92 | 0.96 | 0.95 | 0.89 | 0.89 | 0.95 | 0.90 | 0.88 | 0.93 | 0.91 |
| 95 | E95A | 0.85 | 0.68 | 0.37 | 0.46 | 0.86 | 0.76 | 0.92 | 0.60 | 0.69 | 0.86 | 0.88 | 0.67 | 0.85 | 0.87 | 0.88 | 0.85 | 0.82 | 0.83 | 0.84 |
| 99 | Q99A | 0.88 | 0.60 | 0.84 | 0.85 | 0.70 | 0.87 | 0.81 | 0.58 | 0.88 | 0.87 | 0.95 | 0.84 | 0.95 | 0.94 | 0.98 | 0.90 | 0.91 | 0.92 | 0.87 |
| 101 | P101A | 0.82 | 0.63 | 0.87 | 1.06 | 0.91 | 0.91 | 0.88 | 0.70 | 0.93 | 0.85 | 0.89 | 0.80 | 0.86 | 0.89 | 0.92 | 0.84 | 0.87 | 0.83 | 0.88 |
| 102 | D102A | 0.94 | 0.90 | 0.95 | 0.15 | 0.94 | 1.01 | 0.91 | 0.77 | 1.07 | 0.95 | 0.99 | 0.99 | 0.00 | 0.87 | 1.04 | 0.96 | 0.92 | 0.90 | 0.94 |
| 104 | N104A | 1.00 | 0.86 | 0.95 | 0.30 | 0.98 | 0.88 | 0.96 | 0.87 | 0.93 | 0.90 | 1.03 | 0.92 | 0.93 | 0.86 | 0.96 | 0.95 | 0.92 | 0.90 | 0.92 |
| 105 | Q105A | 1.01 | 0.96 | 0.87 | 1.05 | 0.88 | 0.95 | 0.91 | 0.85 | 1.06 | 0.83 | 0.90 | 0.98 | 0.96 | 0.88 | 1.00 | 0.96 | 0.88 | 0.90 | 0.91 |
| 107 | V107A | 0.91 | 1.08 | 0.78 | 0.76 | 0.79 | 1.06 | 1.02 | 0.99 | 1.05 | 0.84 | 0.86 | 0.74 | 0.72 | 0.77 | 0.80 | 0.80 | 0.77 | 0.64 | 0.78 |
| 108 | R108A | 1.12 | 0.85 | 0.90 | 0.12 | 0.78 | 0.23 | 1.28 | 0.76 | 0.92 | 0.81 | 0.98 | 0.92 | 1.01 | 0.99 | 0.96 | 1.09 | 0.93 | 0.95 | 0.94 |
| 109 | D109A | 1.07 | 0.70 | 0.44 | 0.25 | 0.97 | 0.73 | 0.90 | 0.76 | 0.63 | 0.90 | 0.96 | 0.79 | 0.92 | 0.93 | 0.93 | 1.01 | 0.88 | 0.92 | 0.95 |
| 110 | K110A | 1.16 | 0.70 | 1.01 | 1.14 | 0.91 | 0.22 | 1.20 | 0.76 | 0.78 | 0.89 | 1.06 | 0.91 | 1.05 | 0.98 | 1.01 | 0.97 | 0.94 | 0.99 | 0.98 |
| 111 | I111A | 0.96 | 0.90 | 0.77 | 0.69 | 0.92 | 0.32 | 1.02 | 0.94 | 0.99 | 0.93 | 0.98 | 0.97 | 0.95 | 1.00 | 1.03 | 0.92 | 0.94 | 0.95 | 0.97 |
| 115 | R115A | 0.81 | 0.90 | 0.71 | 0.76 | 0.68 | 0.76 | 0.70 | 0.89 | 0.78 | 0.80 | 0.68 | 0.00 | 0.00 | 0.62 | 0.65 | 0.61 | 0.61 | 0.62 | 0.63 |
| 117 | Q117A | 1.02 | 1.08 | 0.94 | 1.04 | 0.97 | 1.00 | 0.98 | 0.96 | 1.01 | 0.94 | 0.94 | 0.89 | 0.90 | 0.89 | 0.92 | 0.89 | 0.89 | 0.91 | 0.90 |
| 119 | L119A | 0.90 | 0.89 | 0.90 | 0.92 | 0.81 | 0.84 | 0.82 | 0.85 | 0.80 | 0.74 | 1.02 | 0.98 | 0.94 | 0.97 | 0.93 | 1.00 | 0.98 | 0.87 | 0.91 |
| 120 | S120A | 0.81 | 0.90 | 0.83 | 0.80 | 0.82 | 0.84 | 0.91 | 0.80 | 0.87 | 0.96 | 0.96 | 0.81 | 0.86 | 0.89 | 0.93 | 0.87 | 0.89 | 0.92 | 0.91 |

| | | | | | | | | | | B | | | | | | | | | | |
|---|---|---|---|---|---|---|---|---|---|---|---|---|---|---|---|---|---|---|---|---|
| 121 | V121A | 0.89 | 0.68 | 0.85 | 0.75 | 0.93 | 0.74 | 0.92 | 0.57 | 0.72 | 0.97 | 0.96 | 0.87 | 0.94 | 0.96 | 1.01 | 0.91 | 0.94 | 0.96 | 0.94 |
| 122 | S122A | 0.77 | 0.41 | 0.76 | 0.79 | 0.68 | 0.78 | 0.69 | 0.44 | 0.65 | 0.62 | 0.79 | 0.63 | 0.70 | 0.76 | 0.74 | 0.74 | 0.75 | 0.75 | 0.72 |
| 125 | T125A | 0.85 | 0.58 | 0.87 | 0.98 | 0.89 | 0.93 | 0.75 | 0.66 | 0.93 | 0.75 | 0.91 | 0.80 | 0.89 | 0.91 | 0.95 | 0.87 | 0.88 | 0.87 | 0.91 |
| 149 | R149A | 0.83 | 0.82 | 0.85 | 0.97 | 0.92 | 0.93 | 0.89 | 0.77 | 0.96 | 0.88 | 0.94 | 0.89 | 0.93 | 0.84 | 0.94 | 0.88 | 0.88 | 0.84 | 0.88 |
| 151 | S151A | 0.86 | 0.67 | 0.85 | 0.83 | 0.87 | 0.82 | 0.84 | 0.69 | 0.83 | 0.69 | 0.92 | 0.76 | 0.76 | 0.76 | 0.82 | 0.83 | 0.82 | 0.81 | 0.83 |
| 152 | P152A | 0.87 | 0.64 | 0.81 | 0.95 | 0.85 | 0.88 | 0.83 | 0.63 | 0.80 | 0.59 | 0.84 | 0.78 | 0.75 | 0.75 | 0.89 | 0.88 | 0.77 | 0.85 | 0.86 |
| 155 | S155A | 0.87 | 1.40 | 0.80 | 0.98 | 0.84 | 0.90 | 0.85 | 1.03 | 0.94 | 0.80 | 0.89 | 0.75 | 0.75 | 0.81 | 0.82 | 0.82 | 0.82 | 0.69 | 0.80 |
| 195 | K195A | 0.92 | 0.37 | 0.77 | 0.68 | 0.97 | 0.73 | 0.90 | 0.27 | 0.65 | 0.59 | 0.86 | 0.77 | 0.86 | 0.83 | 0.86 | 0.95 | 0.81 | 0.85 | 0.82 |
| 196 | G196A | 0.89 | 0.70 | 0.73 | 0.70 | 0.90 | 0.69 | 0.81 | 0.78 | 0.46 | 0.63 | 0.84 | 0.67 | 0.75 | 0.81 | 0.80 | 0.84 | 0.79 | 0.79 | 0.79 |
| 197 | Q197A | 1.14 | 0.56 | 1.00 | 0.98 | 0.99 | 0.99 | 1.02 | 0.90 | 0.79 | 0.97 | 1.04 | 0.84 | 1.01 | 0.98 | 1.05 | 0.97 | 0.97 | 0.97 | 0.95 |
| 198 | V198A | 0.87 | 0.84 | 0.80 | 0.84 | 0.89 | 0.83 | 0.87 | 0.86 | 0.79 | 0.75 | 0.85 | 0.74 | 0.77 | 0.00 | 0.86 | 0.80 | 0.00 | 0.80 | 0.82 |
| 200 | S200A | 0.86 | 0.99 | 0.76 | 0.93 | 0.82 | 0.90 | 0.82 | 0.94 | 0.83 | 0.88 | 0.84 | 0.74 | 0.79 | 0.78 | 0.81 | 0.75 | 0.76 | 0.76 | 0.75 |
| 201 | E201A | 1.02 | 1.10 | 0.94 | 1.06 | 0.85 | 1.01 | 1.03 | 1.61 | 0.31 | 0.28 | 0.98 | 0.92 | 0.95 | 0.98 | 0.99 | 0.95 | 0.97 | 0.96 | 0.95 |

Figure 25 (Continued)

| Residue | Mutation | 14C05 | 14D12 | 12A12 | 16E10 | 15C03 | 12A08 | 16E03 | 13H11 | 15A06 | 15C04 | 16G02 | 1C6.D6 | 1H7.C7 | 5D2.C8 | 9A10.C4 | 10E8.B6 | 13E11.A4 | 14F8.H6 | 16F6.E1 |
|---|---|---|---|---|---|---|---|---|---|---|---|---|---|---|---|---|---|---|---|---|
| 1 | R1A | 0.92 | 0.99 | 0.94 | n.d. | 1.43 | 3.53 | 0.12 | 0.86 | 1.18 | 1.09 | 0.95 | 0.95 | 1.06 | 1.14 | 0.64 | 0.84 | 0.82 | 1.40 | 1.01 |
| 3 | I3A | 0.92 | 1.05 | 0.97 | 0.11 | 0.99 | 7.99 | 1.9E+04 | 1.32 | 1.21 | 1.06 | 0.81 | 1.04 | 1.04 | 0.95 | 0.49 | 0.88 | 1.03 | 0.75 | 0.94 |
| 5 | E5A | 0.80 | 1.11 | 1.01 | 0.81 | 2.33 | 1.8E+43 | | 1.15 | 1.27 | 1.08 | 0.58 | 1.19 | 0.99 | 1.32 | 0.97 | 0.79 | 1.29 | 0.40 | 0.87 |
| 7 | P7A | 0.58 | 1.19 | 1.02 | 1.35 | 1.83 | 4.92 | 0.32 | 1.42 | 1.13 | 0.99 | 0.44 | 1.03 | 1.01 | 1.30 | 0.95 | 0.65 | 1.26 | 2.10 | 0.72 |
| 8 | E8A | 0.88 | 1.01 | 1.00 | 1.12 | 1.05 | 5.01 | 0.20 | 0.79 | 1.18 | 1.07 | 0.46 | 1.15 | 1.01 | 1.20 | 1.32 | 0.71 | 1.40 | 0.80 | 0.89 |
| 9 | S9A | 0.82 | 0.97 | 0.99 | 0.96 | 1.05 | 0.77 | 0.83 | 0.88 | 1.00 | 1.06 | 0.47 | 0.99 | 0.99 | 1.16 | 1.11 | 0.82 | 1.08 | 1.12 | 1.00 |
| 11 | T11A | 0.89 | 1.02 | 1.02 | 1.07 | 0.95 | 1.09 | 0.24 | 2.18 | 1.04 | 1.06 | 0.26 | 1.11 | 1.02 | 1.49 | 1.21 | 1.14 | 1.37 | 2.19 | 1.53 |
| 13 | P13A | 0.85 | 0.96 | 0.96 | 1.03 | 0.94 | 0.85 | 0.84 | 0.84 | 1.06 | 0.92 | 0.42 | 0.84 | 0.98 | 0.02 | 0.00 | 0.23 | 0.51 | n.d. | 0.67 |
| 15 | K15A | 0.69 | 1.09 | 0.87 | 1.10 | 1.04 | 1.00 | 0.14 | 1.19 | 0.96 | 0.95 | 0.98 | 1.84 | 1.22 | 1.54 | 0.91 | 0.55 | 1.12 | 1.89 | 0.81 |
| 17 | D17A | 1.17 | 1.01 | 1.01 | 1.22 | 0.95 | 1.06 | 0.15 | 1.19 | 1.01 | 1.00 | 0.85 | 1.01 | 1.12 | 1.17 | 0.84 | 0.75 | 1.04 | 1.31 | 1.00 |
| 19 | N19A | 1.24 | 1.04 | 1.03 | 1.17 | 0.77 | 0.94 | 0.15 | 0.93 | 1.10 | 1.10 | 1.09 | 1.10 | 1.07 | 1.00 | 1.19 | 0.67 | 1.46 | 2.64 | 1.11 |
| 21 | P21A | 0.78 | 1.12 | 1.01 | 1.26 | 1.81 | 1.37 | 0.94 | 1.04 | 1.05 | 1.04 | 1.04 | 1.26 | 1.11 | 1.29 | 0.97 | 0.88 | 1.41 | n.d. | 1.75 |
| 23 | T23A | 0.74 | 1.17 | 0.94 | 1.36 | 0.31 | 1.72 | 1.12 | 1.25 | 1.07 | 1.48 | 0.71 | 1.22 | 1.08 | 0.54 | 2.26 | 0.50 | 2.01 | n.d. | 1.37 |
| 25 | D25A | 0.90 | 1.02 | 1.00 | 0.83 | 3.07 | 0.81 | 2.04 | 0.78 | 1.03 | 1.06 | 1.03 | 1.00 | 1.08 | 0.89 | 1.02 | 0.60 | 1.05 | 1.01 | 1.22 |
| 26 | P26A | 0.94 | 1.12 | 0.96 | 1.07 | 2.68 | 1.22 | 0.31 | 1.66 | 1.05 | 1.06 | 0.29 | 1.06 | 0.95 | 0.03 | 0.00 | 0.80 | 0.73 | 0.00 | 0.06 |
| 28 | Q28A | 0.95 | 1.07 | 0.99 | 1.91 | 1.11 | 1.12 | 0.16 | 0.92 | 1.10 | 1.01 | 1.00 | 1.04 | 1.15 | 0.92 | 0.48 | 0.80 | 0.96 | 0.59 | 1.08 |
| 29 | G29A | 0.80 | 1.40 | 0.91 | 0.12 | 0.95 | 1.43 | 0.97 | 3.37 | 1.06 | 1.09 | 0.57 | 1.31 | 1.21 | 0.61 | 0.00 | 0.03 | 0.82 | 0.49 | 0.88 |
| 31 | T31A | 0.87 | 1.17 | 0.97 | 1.29 | 1.09 | 1.18 | 0.97 | 1.58 | 1.09 | 1.04 | 0.62 | 1.19 | 1.20 | 0.77 | 0.21 | 0.25 | 0.71 | 0.01 | 0.69 |
| 32 | Q32A | 1.14 | 1.32 | 0.98 | 1.89 | 0.98 | 1.52 | 2.85 | 2.21 | 0.98 | 1.07 | 0.59 | 1.30 | 1.05 | 0.62 | 0.00 | 0.47 | 1.23 | n.d. | 0.57 |
| 34 | L34A | 2.10 | 1.04 | 1.29 | 1.08 | 0.81 | 1.20 | 0.86 | 1.03 | 1.15 | 1.10 | 1.72 | 1.53 | 1.21 | 2.01 | 0.75 | 0.75 | 0.75 | 0.03 | 0.77 |
| 40 | Q40A | 0.99 | 1.04 | 2.21 | 0.95 | 1.00 | 1.08 | 0.82 | 1.40 | 1.04 | 1.05 | 0.48 | 1.62 | 0.91 | 1.27 | 0.24 | 0.91 | 0.85 | 1.70 | 1.10 |
| 41 | R41A | 1.34 | 0.99 | 0.84 | 1.00 | 0.94 | 0.98 | 0.13 | 1.02 | 1.04 | 1.00 | 0.75 | 3.15 | 2.54 | 19.10 | 15.22 | 0.84 | 4.95 | 8.01 | 34.55 |
| 42 | G42A | 1.05 | 1.03 | 0.58 | 1.07 | 0.96 | 0.99 | 0.15 | 1.37 | 1.06 | 0.94 | 0.35 | 1.53 | 12.80 | 2.87 | 0.00 | 0.84 | 3.77 | 0.02 | 6.30 |
| 43 | S43A | 1.10 | 0.99 | 0.70 | 1.06 | 0.96 | 1.04 | 0.84 | 1.23 | 1.08 | 1.02 | 0.99 | 1.09 | 19.07 | 7.00 | 0.67 | 1.15 | 0.79 | 1.13 | 2.53 |
| 44 | D44A | 1.06 | 1.00 | 0.60 | 0.90 | 0.96 | 1.09 | 0.15 | 1.26 | 1.11 | 1.00 | 0.86 | 1.67 | 1.34 | 5.37 | 19.81 | 0.68 | 10.77 | 4.37 | n.d. |
| 45 | P45A | 1.07 | 0.97 | 0.18 | 1.14 | 0.93 | 0.98 | 0.80 | 0.93 | 1.17 | 1.02 | 1.25 | 1.50 | 2.33 | 4.71 | 0.74 | 0.85 | 1.25 | 1.02 | 0.68 |
| 46 | V46A | 1.02 | 1.16 | 1.93 | 1.18 | 1.08 | 1.33 | 0.16 | 1.12 | 1.16 | 1.06 | 0.79 | 3.42 | 9.85 | 16.83 | 1.73 | 0.93 | 2.79 | 3.00 | 25.68 |
| 50 | L50A | 2.45 | 1.06 | 1.22 | 1.07 | 0.93 | 1.32 | 0.14 | 1.06 | 1.09 | 1.11 | 2.22 | 1.27 | 1.62 | 3.14 | 0.84 | 6.11 | 0.73 | 0.50 | 0.91 |
| 54 | S54A | 5.00 | 1.24 | 1.01 | 1.33 | 1.03 | 1.03 | 0.96 | 1.00 | 1.07 | 1.02 | 1.25 | 1.07 | 1.21 | 0.66 | 0.64 | 1.20 | 0.94 | 1.14 | 1.03 |
| 59 | Q59A | 2.87 | 0.95 | 0.89 | 0.95 | 0.93 | 1.02 | 0.92 | 1.31 | 1.01 | 0.97 | 4.75 | 1.32 | 13.19 | 4.00 | 8.04 | 1.93 | 10.34 | 9.92 | 1.39 |
| 61 | A61G | 0.36 | 0.90 | 1.26 | 1.09 | 0.87 | 1.19 | 0.80 | 0.86 | 1.04 | 0.97 | 1.36 | 1.51 | 1.27 | 1.88 | 0.80 | 1.02 | 0.85 | 0.70 | 0.84 |

| | | | | | | | | | | | | | | | | | | | | |
|---|---|---|---|---|---|---|---|---|---|---|---|---|---|---|---|---|---|---|---|---|
| 62 | K62A | 2.28 | 0.96 | 0.88 | 0.79 | 0.32 | 1.03 | 0.93 | 1.55 | 1.08 | 0.98 | 6.38 | 1.75 | 1.56 | 1.51 | 0.29 | 3.72 | 0.86 | 1.04 | 70.63 |
| 64 | Q64A | 0.00 | 0.97 | 1.02 | 1.02 | 1.16 | 1.15 | 0.15 | 1.11 | 1.09 | 0.99 | 8.82 | 1.25 | 0.88 | 1.17 | 0.80 | 1.91 | 0.76 | 0.01 | 0.76 |
| 68 | H68A | 5.49 | 1.33 | 1.06 | 1.46 | 1.52 | 1.07 | 0.90 | 1.07 | 1.08 | 0.91 | 0.95 | 1.04 | 1.02 | 1.04 | 0.45 | 0.84 | 1.13 | 0.21 | 0.89 |
| 71 | H71A | 1.48 | 0.99 | 1.05 | 1.08 | 1.25 | 1.20 | 0.85 | 0.92 | 1.11 | 0.94 | 0.77 | 1.21 | 1.04 | 1.10 | 0.33 | 0.58 | 0.85 | 0.01 | 0.72 |
| 72 | K72A | 1.47 | 1.00 | 1.05 | 1.03 | 3.45 | 1.10 | 0.14 | 1.18 | 1.00 | 1.01 | 0.56 | 1.12 | 1.06 | 1.54 | 0.73 | 1.04 | 0.96 | 0.02 | 0.85 |
| 73 | V73A | 1.43 | 0.95 | 1.00 | 0.96 | 1.25 | 1.03 | 0.15 | 0.86 | 1.04 | 1.01 | 0.70 | 0.98 | 1.07 | 1.88 | 4.21 | 1.13 | 1.55 | 3.11 | 2.30 |
| 74 | P74A | 0.88 | 0.90 | 0.95 | 0.93 | 1.29 | 0.94 | 0.14 | 1.12 | 1.03 | 1.01 | 0.34 | 0.92 | 1.18 | 0.26 | 0.00 | 0.46 | 1.64 | 0.00 | 2.18 |
| 80 | Q80A | 1.31 | 1.02 | 1.03 | 1.10 | 1.25 | 1.18 | 0.76 | 1.58 | 1.04 | 1.02 | 0.93 | 1.22 | 1.46 | 2.95 | 0.76 | 1.06 | 1.20 | 1.73 | 1.72 |
| 83 | T83A | 1.09 | 0.90 | 1.04 | 0.93 | 1.10 | 1.04 | 0.80 | 1.03 | 1.08 | 0.98 | 0.89 | 1.27 | 1.22 | 1.47 | 2.21 | 0.93 | 2.87 | 3.16 | 0.68 |
| 85 | E85A | 1.29 | 1.01 | 0.91 | 1.16 | 1.01 | 1.16 | 0.74 | 1.24 | 1.06 | 1.12 | 1.05 | 1.14 | 1.33 | 2.40 | 0.97 | 0.94 | 1.36 | 1.48 | 0.93 |
| 86 | M86A | 0.81 | 1.17 | 0.98 | 1.28 | 1.09 | 1.22 | 0.18 | 1.49 | 0.99 | 1.10 | 1.15 | 1.37 | 1.63 | 3.14 | 1.18 | 1.00 | 1.63 | 1.72 | 2.79 |
| 87 | D87A | 0.90 | 1.06 | 1.00 | 1.10 | 1.01 | 1.20 | 0.14 | 1.11 | 1.05 | 1.14 | 0.93 | 1.20 | 1.24 | 1.74 | 1.25 | 2.59 | 1.06 | 0.02 | 1.16 |
| 89 | R89A | 1.05 | 1.25 | 0.97 | 1.21 | 1.16 | 1.05 | 0.77 | 0.99 | 1.01 | 1.06 | 0.91 | 2.28 | 1.11 | 1.17 | 1.02 | 0.89 | 0.90 | 1.04 | 0.61 |
| 91 | H91A | 1.01 | 0.97 | 1.06 | 1.00 | 0.95 | 0.95 | 0.79 | 1.16 | 0.93 | 1.01 | 1.06 | 0.67 | 1.15 | 1.52 | 2.64 | 1.02 | 2.42 | 5.11 | 0.70 |
| 95 | E95A | 1.00 | 1.02 | 0.99 | 2.49 | 1.04 | 1.09 | 0.76 | 1.11 | 0.94 | 1.02 | 1.23 | 1.72 | 1.23 | 1.92 | 0.96 | 1.09 | 0.86 | 0.32 | 0.88 |
| 99 | Q99A | 0.98 | 1.08 | 0.97 | 0.98 | 0.98 | 1.07 | 0.15 | 1.54 | 0.98 | 1.04 | 2.11 | 1.11 | 1.12 | 1.15 | 0.65 | | 0.89 | 0.66 | 1.15 |
| 101 | P101A | 0.91 | 1.03 | 0.99 | 0.61 | 1.09 | 1.16 | 0.75 | 1.29 | 1.01 | 1.03 | 2.36 | 1.19 | 1.16 | 0.78 | 1.18 | 1.20 | 1.00 | 0.01 | 1.06 |
| 102 | D102A | 1.13 | 1.05 | 1.06 | 2.46 | 1.08 | 1.07 | 0.16 | 1.16 | 0.99 | 0.98 | 0.92 | 1.05 | n.d. | 0.66 | 0.43 | 0.92 | 0.91 | 0.62 | 0.58 |
| 104 | N104A | 1.05 | 1.03 | 1.03 | 1.83 | 1.05 | 1.26 | 0.76 | 0.98 | 1.00 | 1.06 | 0.76 | 1.15 | 1.19 | 1.04 | 1.20 | 0.84 | 0.62 | 0.31 | 0.77 |
| 105 | Q105A | 0.98 | 1.03 | 1.22 | 0.92 | 1.05 | 1.14 | 0.77 | 1.03 | 0.96 | 1.03 | 0.94 | 1.12 | 1.12 | 1.18 | 0.71 | 0.74 | 0.36 | 0.66 | 0.98 |
| 107 | V107A | 1.01 | 1.05 | 1.32 | 2.17 | 1.12 | 0.88 | 0.91 | 1.16 | 0.89 | 1.03 | 0.88 | 1.15 | 1.16 | 1.31 | 3.11 | 1.35 | 1.07 | 2.91 | 2.58 |
| 108 | R108A | 0.95 | 0.94 | 1.01 | 1.68 | 1.08 | 1.93 | 0.77 | 1.09 | 1.08 | 0.85 | 0.38 | 0.93 | 1.18 | 0.04 | 0.00 | 0.29 | 0.99 | 0.01 | 1.18 |
| 109 | D109A | 1.18 | 1.04 | 1.87 | 1.77 | 0.96 | 1.41 | 0.17 | 1.27 | 0.98 | 1.01 | 1.03 | 1.10 | 1.26 | 2.30 | 1.00 | 1.06 | 0.95 | 1.13 | 1.40 |
| 110 | K110A | 0.89 | 0.95 | 0.98 | 0.65 | 1.13 | 2.01 | 0.95 | 0.93 | 1.12 | 0.93 | 1.16 | 0.85 | 1.05 | 1.30 | 1.76 | 0.88 | 1.53 | 2.21 | 0.81 |
| 111 | I111A | 1.19 | 1.01 | 1.48 | 1.75 | 1.01 | 2.56 | 0.80 | 1.00 | 1.15 | 1.00 | 1.22 | 0.80 | 1.18 | 1.92 | 0.88 | 0.77 | 1.23 | 1.18 | 1.18 |
| 115 | R115A | 0.96 | 1.20 | 0.99 | 1.35 | 1.21 | 1.36 | 0.87 | 1.82 | 0.93 | 1.13 | 1.17 | n.d. | n.d. | 2.67 | 1.19 | 1.13 | 1.37 | 1.64 | 2.44 |
| 117 | Q117A | 1.03 | 1.08 | 1.00 | 1.06 | 1.04 | 1.22 | 0.14 | 1.14 | 0.99 | 1.08 | 0.91 | 1.20 | 1.20 | 1.14 | 1.31 | 1.87 | 1.08 | 0.02 | 0.92 |
| 119 | L119A | 1.13 | 1.02 | 1.03 | 1.09 | 1.03 | 1.18 | 0.82 | n.d. | 0.92 | 1.01 | 0.95 | 1.07 | 1.21 | 0.96 | 0.91 | 1.10 | 0.98 | 0.55 | 0.67 |
| 120 | S120A | 1.05 | 0.96 | 1.07 | 1.00 | 1.07 | 1.06 | 0.14 | 1.48 | 0.90 | 0.93 | 1.02 | 1.08 | 0.98 | 0.99 | 1.89 | 0.96 | 1.87 | 3.84 | 0.74 |
| 121 | V121A | 0.95 | 0.98 | 1.07 | 1.11 | 1.03 | 1.18 | 0.56 | 1.53 | 0.59 | 0.66 | 1.30 | 1.14 | 1.15 | 1.38 | 0.80 | 0.84 | 1.04 | 1.32 | 1.08 |

(B)

| | | | | | | | | | | | | | | | | | | | | |
|---|---|---|---|---|---|---|---|---|---|---|---|---|---|---|---|---|---|---|---|---|
| 122 | S122A | 1.02 | 1.29 | 1.00 | 1.02 | 1.03 | 1.17 | 0.15 | 3.72 | 0.82 | 1.06 | 1.65 | 1.29 | 1.19 | 1.46 | 0.41 | 1.34 | 0.87 | 0.88 | 1.55 |
| 125 | T125A | 0.97 | 1.02 | 1.01 | 1.05 | 1.04 | 1.15 | 0.16 | 2.26 | 0.85 | 0.99 | 1.67 | 1.16 | 1.08 | 0.87 | 0.55 | 0.95 | 1.02 | 0.19 | 1.06 |
| 149 | R149A | 1.13 | 1.12 | 1.10 | 1.19 | 1.10 | 1.17 | 0.14 | 1.46 | 0.96 | 1.00 | 0.78 | 1.15 | 1.21 | 1.04 | 0.01 | 0.80 | 1.22 | 0.05 | 0.85 |
| 151 | S151A | 1.05 | 1.11 | 1.03 | 1.29 | 0.98 | 1.27 | 0.16 | 1.74 | 0.82 | 1.02 | 0.72 | 1.22 | 1.19 | 1.05 | 0.23 | 0.96 | 0.97 | 0.36 | 1.33 |
| 152 | P152A | 0.95 | 1.23 | 1.05 | 1.16 | 0.99 | 1.17 | 0.15 | 2.29 | 0.77 | 1.12 | 0.68 | 1.10 | 1.12 | 1.07 | 0.37 | 1.22 | 1.50 | 1.41 | 1.27 |
| 155 | S155A | 0.99 | 0.41 | 1.04 | 1.25 | 1.08 | 1.16 | 0.14 | 1.17 | 0.81 | 0.94 | 0.91 | 1.11 | 1.14 | 1.44 | 2.29 | 1.20 | 1.70 | 3.06 | 2.23 |
| 195 | K195A | 0.97 | 1.79 | 0.99 | 1.27 | 0.97 | 1.06 | 0.96 | n.d. | 0.93 | 0.86 | 0.05 | 0.97 | 1.11 | 0.04 | 0.00 | 0.38 | 1.76 | 0.00 | 1.18 |
| 196 | G196A | 1.05 | 0.83 | 1.06 | 1.23 | 1.03 | 1.22 | 0.18 | 1.49 | 1.30 | 1.77 | 1.12 | 1.25 | 1.33 | 2.14 | 1.05 | 1.43 | 1.55 | 1.31 | 1.56 |
| 197 | Q197A | 1.16 | 1.33 | 1.08 | 0.95 | 1.07 | 1.04 | 0.14 | 0.84 | 1.17 | 1.11 | 0.97 | 1.15 | 1.15 | 1.65 | 1.42 | 0.78 | 1.63 | 2.29 | 0.88 |
| 198 | V198A | 1.06 | 0.84 | 1.00 | 1.26 | 1.00 | 1.17 | 0.17 | 1.43 | 1.09 | 1.20 | 1.10 | 1.12 | 1.38 | n.d. | 0.63 | 0.94 | n.d. | 2.36 | 1.22 |
| 200 | S200A | 1.07 | 1.03 | 1.12 | 1.17 | 1.16 | 1.23 | 0.16 | 1.41 | 1.19 | 1.34 | 0.98 | 1.21 | 1.34 | 2.49 | 0.73 | 1.14 | 1.66 | 1.66 | 1.79 |
| 201 | E201A | 1.09 | 1.02 | 1.04 | 1.13 | 1.05 | 1.18 | 0.85 | 0.37 | 1.05 | 13.84 | 0.73 | 1.12 | 1.25 | 1.46 | 0.81 | 1.63 | 1.24 | 1.52 | 1.04 |

| mAb name | Parent name | Overall Properties: Binds Human VSIG4-L | Binds Human VSIG4-S | Binds Cyno VSIG4 | Binds Mouse VSIG4 | Ligand Competition (C3b) | Ligand Competition (iC3b) | Functional Macrophage assay |
|---|---|---|---|---|---|---|---|---|
| Rc4.m.FIP2_12A08.hG4 | 12A08 | YES | YES | YES | NO | YES | YES | YES |
| Rc4.m.FIP2_12A12.hG4 | 12A12 | YES | YES | YES | NO | YES | YES | YES |
| Rc4.m.FIP2_13H11.hG4 | 13H11 | YES | WEAK | YES | NO | WEAK | WEAK | YES |
| Rc4.m.FIP2_14C05.hG4 | 14C05 | YES | YES | YES | NO | YES | not determined | YES |
| Rc4.m.FIP2_14D12.hG4 | 14D12 | YES | YES | YES | NO | YES | YES | YES |
| Rc4.m.FIP2_15A06.hG4 | 15A06 | YES | WEAK | YES | NO | NO | NO | YES |
| Rc4.m.FIP2_15C03.hG4 | 15C03 | YES | YES | YES | NO | YES | YES | YES |
| Rc4.m.FIP2_15C04.hG4 | 15C04 | YES | YES | YES | NO | YES | YES | YES |
| Rc4.m.FIP2_16E08.hG4 | 16E08 | YES | YES | YES | NO | NO | NO | YES |
| Rc4.m.FIP2_16E10.hG4 | 16E10 | YES | YES | YES | NO | WEAK | WEAK | YES |
| Rc4.m.FIP2_16G02.hG4 | 16G02 | YES | YES | YES | NO | YES | YES | YES |

| mAb name | Parent name | Target Binding: ELISA FJB Binding (50 nM) Human huVSIG4-L-Fc (OD 450 nm) | Target Binding: ELISA FJB Binding (50 nM) Human huVSIG4-S-Fc (OD 450 nm) | Target Binding: ELISA FJB Binding (50 nM) Cyno cyVSIG4-L-His (OD 450 nm) | Target Binding: ELISA FJB Binding (50 nM) Mouse moVSIG4-His (OD 450 nm) | Affinity: SPR FJB KD Human huVSIG4-L-His (nM) | Affinity: SPR FJB KD Cyno cyVSIG4-L-His (nM) | Affinity: Octet Verseau KD Human huVSIG4-L-His (nM) |
|---|---|---|---|---|---|---|---|---|
| Rc4.m.FIP2_12A08.hG4 | 12A08 | 4.338 | 3.974 | 4.427 | 0.056 | 9.7 | 5.9 | 20.8 |
| Rc4.m.FIP2_12A12.hG4 | 12A12 | 4.460 | 4.376 | 4.397 | 0.054 | 8.6 | 5.9 | 19.1 |
| Rc4.m.FIP2_13H11.hG4 | 13H11 | 4.172 | 0.449 | 4.374 | 0.048 | 8.0 | 20.3 | 50.6 |
| Rc4.m.FIP2_14C05.hG4 | 14C05 | 4.506 | 4.357 | 4.519 | 0.059 | 1.7 | 5.4 | 3.5 |
| Rc4.m.FIP2_14D12.hG4 | 14D12 | 4.530 | 3.430 | 4.515 | 0.050 | 10.3 | 4.4 | 21.5 |
| Rc4.m.FIP2_15A06.hG4 | 15A06 | 4.377 | 0.359 | 4.349 | 0.067 | 15.0 | 19.5 | 19.5 |
| Rc4.m.FIP2_15C03.hG4 | 15C03 | 4.595 | 5.655 | 4.495 | 0.057 | 17.9 | N.D. | 52.1 |
| Rc4.m.FIP2_15C04.hG4 | 15C04 | 4.326 | 3.277 | 4.527 | 0.052 | 5.4 | 15.6 | 25.3 |
| Rc4.m.FIP2_16E08.hG4 | 16E08 | 4.502 | 4.520 | 4.563 | 0.054 | 26.7 | N.D. | 49.3 |
| Rc4.m.FIP2_16E10.hG4 | 16E10 | 4.441 | 1.049 | 4.497 | 0.048 | 98.1 | 1.2 | 69.5 |
| Rc4.m.FIP2_16G02.hG4 | 16G02 | 4.420 | 4.219 | 4.535 | 0.051 | 1.5 | 1.3 | not determined |

| mAb name | On Cell Binding: FACS FJB EC50 Human huVSIG4-L CHO-K1 (nM) | On Cell Binding: FACS FJB Binding (500 nM) Human huVSIG4-L CHO-K1 (MFI) | On Cell Binding: FACS FJB Binding (200 nM) Parental CHO-K1 (MFI) | On Cell Binding: FACS FJB Binding (200 nM) Fold Over Parental | Ligand Competition: ELISA FJB % Block C3b (200 nM mAb) | Ligand Competition: ELISA FJB % Block iC3b (200 nM mAb) | Ligand Competition: ELISA FJB IC50 C3b (nM) | Ligand Competition: ELISA FJB IC50 iC3b (nM) | mAb Competition: Octet Verseau 12A12 | mAb Competition: Octet Verseau 14C05 |
|---|---|---|---|---|---|---|---|---|---|---|
| Rc4.m.FIP2_12A08.hG4 | 6.8 | 130573 | 328 | 957 | 95 | 98 | 1.0 | 0.4 | NO | NO |
| Rc4.m.FIP2_12A12.hG4 | 4.4 | 105517 | 362 | 291 | 99 | 98 | 0.9 | 0.5 | YES | NO |
| Rc4.m.FIP2_13H11.hG4 | 1.2 | 54921 | 358 | 140 | 73 | 78 | 1.7 | 429.5 | NO | NO |
| Rc4.m.FIP2_14C05.hG4 | 4.4 | 339920 | 360 | 304 | 95 | N.D. | 1.4 | N.D. | NO | YES |
| Rc4.m.FIP2_14D12.hG4 | 1.8 | 36368 | 326 | 112 | 97 | 98 | 0.8 | 0.6 | NO | YES |
| Rc4.m.FIP2_15A06.hG4 | 2.4 | 35697 | 379 | 63 | -24 | 2 | enhanced | no competition | NO | NO |
| Rc4.m.FIP2_15C03.hG4 | 2.5 | 45914 | 591 | 83 | 90 | 92 | 2.4 | 17.8 | NO | NO |
| Rc4.m.FIP2_15C04.hG4 | 8.8 | 53161 | 733 | 73 | 56 | 34 | 15.7 | 17.0 | NO | NO |
| Rc4.m.FIP2_16E08.hG4 | 1.0 | 30366 | 1513 | 25 | -100 | -3 | enhanced | no competition | NO | NO |
| Rc4.m.FIP2_16E10.hG4 | 2.0 | 14673 | 194 | 50 | 93 | 72 | 0.7 | 3.5 | NO | NO |
| Rc4.m.FIP2_16G02.hG4 | 5.2 | 35119 | 294 | 130 | 96 | 98 | 1.1 | 1.3 | YES | YES |

ANTI-VSIG4 COMPOSITIONS AND METHODS FOR MODULATING MYELOID CELL INFLAMMATORY PHENOTYPES AND USES THEREOF

CROSS-REFERENCE TO RELATED APPLICATIONS

This application is the U.S. national phase of International Patent Application No. PCT/US2021/034784, filed on 28 May 2021, which claims the benefit of priority to U.S. Provisional Application Ser. No. 63/032,337, filed on 29 May 2020; the entire contents of each of said applications are incorporated herein in their entirety by this reference.

SEQUENCE LISTING

The instant application contains a Sequence Listing which has been submitted electronically in ASCII format and is hereby incorporated by reference in its entirety. Said ASCII copy, created on Jul. 14, 2021, is named VTC-00725_SL.txt and is 162,324 bytes in size.

BACKGROUND OF THE INVENTION

Monocytes and macrophages are types of phagocytes, which are cells that protect the body by ingesting harmful foreign particles, bacteria, and dead or dying cells. In addition to monocytes and macrophages, phagocytes include neutrophils, dendritic cells, and mast cells.

Macrophages are classically known as large white blood cells that patrol the body and engulf and digest cellular debris, and foreign substances, such as pathogens, microbes, and cancer cells, through a process known as phagocytosis. In addition, macrophages, including tissue macrophages and circulating monocyte-derived macrophages, are important mediators of both the innate and adaptive immune system.

Macrophage phenotype is dependent on activation via a classical or an alternative pathway (see, e.g., Classen et al. (2009) *Methods Mol. Biol.* 531:29-43). Classically activated macrophages are activated by interferon gamma (IFNγ) or lipopolysaccharide (LPS) and display an M1 phenotype. This pro-inflammatory phenotype is associated with increased inflammation and stimulation of the immune system. Alternatively activated macrophages are activated by cytokines like IL-4, IL-10, and IL-13, and display an M2 phenotype. This anti-inflammatory phenotype is associated with decreased immune response, increased wound healing, increased tissue repair, and embryonic development.

Under non-pathological conditions, a balanced population of immune-stimulatory and immune-regulatory macrophages exists in the immune system. Perturbation of the balance can result in a variety of disease conditions. In some cancers, for example, tumors secrete immune factors (e.g., cytokines and interleukins) that polarize macrophage populations in favor of the anti-inflammatory, pro-tumorigenic M2 phenotype, which activates wound-healing pathways, promotes the growth of new blood vessels (i.e., angiogenesis), and provides nutrients and growth signals to the tumor. These M2 macrophages are referred to as tumor associated macrophages (TAMs), or tumor infiltrating macrophages. TAMs in the tumor microenvironment are important regulators of cancer progression and metastasis (Pollard (2004) *Nat. Rev. Cancer* 4:71-78). Small molecules and monoclonal antibodies designed to inhibit macrophage gene targets (e.g., CSF1R and CCR2) have been investigated as modulators of macrophage phenotypes, such as by modulating the balance of pro-tumorigenic macrophages (e.g., TAMs) and pro-inflammatory macrophages that can inhibit tumorigenesis.

Therapies that modulate the recruitment, polarization, activation, and/or function of monocytes and macrophages in order to modulate the balance of macrophage populations are referred to as macrophage immunotherapies. Despite advances in the field of macrophage biology, however, there remains a need for new targets (e.g., genes and/or gene products) for modulating the inflammatory phenotype of macrophages and agents for use in macrophage immunotherapy.

SUMMARY OF THE INVENTION

The present invention is based, at least in part, on the discovery of anti-VSIG4 compositions and methods for modulating myeloid cell inflammatory phenotypes, such as in suppressive myeloid cells, monocytes, macrophages, neutrophils, and/or dendritic cells, and uses thereof, such as for treating, diagnosing, prognosing, and screening purposes. For example, it has been determined herein that VSIG4 expression is increased upon activation in myeloid cell types and that anti-VSIG4 antibodies, including antigen-binding fragments thereof, can be used to increase myeloid cell inflammatory phenotypes, such as in suppressive myeloid cells (e.g., M2-like TAMs and M0-like TAMs), dendritic cells (DCs), and the like.

For example, in one aspect, a monoclonal antibody, or antigen-binding fragment thereof, that binds myeloid cells expressing VSIG4 polypeptide and increases an inflammatory phenotype of the myeloid cells, optionally wherein the myeloid cells comprise suppressive myeloid cells, monocytes, macrophages, neutrophils, and/or dendritic cells, is provided.

Numerous embodiments are further provided that may be applied to any aspect of the present invention and/or combined with any other embodiment described herein. For example, in one embodiment, the monoclonal antibody, or antigen-binding fragment thereof, has one or more of the following properties: a) increases the inflammatory phenotype of the myeloid cells by resulting in one or more of the following after contact with the monoclonal antibody, or antigen-binding fragment thereof: i) increased expression and/or secretion of cluster of differentiation 80 (CD80), CD86, MHCII, MHCI, interleukin 1-beta (IL-1β), IL-6, CCL3, CCL4, CXCL10, CXCL9, GM-CSF and/or tumor necrosis factor alpha (TNF-α); ii) decreased expression and/or secretion of CD206, CD163, CD16, CD53, VSIG4, VSIG4, TGFb and/or IL-10; iii) increased secretion of at least one cytokine or chemokine selected from the group consisting of IL-1β, TNF-α, IL-12, IL-18, GM-CSF, CCL3, CCL4, and IL-23; iv) increased ratio of expression of IL-1β, IL-6, and/or TNF-α to expression of IL-10; v) increased CD8+ cytotoxic T cell activation; vi) increased recruitment of CD8+ cytotoxic T cell activation; vii) increased CD4+ helper T cell activity; viii) increased recruitment of CD4+ helper T cell activity; ix) increased NK cell activity; x) increased recruitment of NK cell; xi) increased neutrophil activity; xii) increased macrophage and/or dendritic cell activity; and/or xiii) increased spindle-shaped morphology, flatness of appearance, and/or number of dendrites, as assessed by microscopy; b) selectively binds human VSIG4 polypeptide at least 1.1-fold greater than a polypeptide selected from the group consisting of C3b, iC3b, wherein the polypeptides are expressed on cells or in vitro; c) binds to the human VSIG4 polypeptide with a KD of between about 0.00001 nanomolar (nM) and 1000 nM, optionally as measured in an ELISA or biolayer interferometry assay; d) binds to the IgV domain of human VSIG4 polypeptide and/or binds to a linear or conformational epitope of VSIG4 polypeptide, optionally wherein the linear or conformational epitope comprises one or more residues listed in Table 21 (e.g., Q59) either within or in addition to a portion of VSIG4 selected from the group consisting of the IgV domain, the Q40-V46 loop, the V107-V116 loop, and the Q40-V46-D109 surface; e) binds one or more VSIG4 isoforms, optionally wherein the VSIG4 isoforms are VSIG4-L and/or VSIG4-S; f) cross-reacts with cynomolgus VSIG4 polypeptide and/or murine VSIG4 polypeptide; g) competes or cross-competes with an antibody that binds VSIG4 polypeptide, or antigen-binding fragment thereof, listed in Table 2 or 3, such as mAb 12A12 and/or 14C05; h) competes with, inhibits, or blocks binding of VSIG4 with a VSIG4 ligand, optionally wherein the VSIG4 ligand is C3b and/or iC3b; i) is obtainable as a monoclonal antibody deposited with ATCC described herein; j) does not activate unstimulated monocytes; k) does not have an ADCC activity against VSIG4-expressing cells; l) does not have a CDC activity against VSIG4-expressing cells; m) does not kill VSIG4-expressing cells upon binding the VSIG4-expressing cells and/or internalization by the VSIG4-expressing cells; n) is not conjugated to another therapeutic moiety, optionally wherein the another therapeutic moiety is a cytotoxic agent; o) competes with, inhibits, or blocks binding of VSIG4 with a T cell VSIG4 ligand, optionally wherein the VSIG4-T cell interaction is a direct interaction between VSIG4 and a VSIG4 ligand expressed on the T cell; p) directly re-represses and/or activates T cells by inhibiting VSIG4-T cell interactions, optionally wherein the VSIG4-T cell interaction is a direct interaction or an indirect interaction; q) indirectly re-represses and/or activates T cells by increasing the inflammatory phenotype of myeloid cells; and/or r) has an antitumor activity in vivo. In another embodiment, the monoclonal antibody, or antigen-binding fragment thereof, comprises: a) a heavy chain CDR sequence with at least about 90% identity to a heavy chain CDR sequence selected from the group consisting of the sequences listed in Table 2; and/or b) a light chain CDR sequence with at least about 90% identity to a light chain CDR sequence selected from the group consisting of the sequences listed in Table 2. In still another embodiment, the monoclonal antibody, or antigen-binding fragment thereof, comprises: a) a heavy chain sequence with at least about 90% identity to a heavy chain sequence selected from the group consisting of the heavy chain sequences listed in Table 2; and/or b) a light chain sequence with at least about 90% identity to a light chain sequence selected from the group consisting of the light chain sequences listed in Table 2. In yet another embodiment, the monoclonal antibody, or antigen-binding fragment thereof, comprises: a) a heavy chain CDR sequence selected from the group consisting of the heavy chain sequences listed in Table 2; and/or b) a light chain CDR sequence selected from the group consisting of the light chain sequences listed in Table 2. In another embodiment, the monoclonal antibody, or antigen-binding fragment thereof, comprises: a) a heavy chain sequence selected from the group consisting of the heavy chain sequences listed in Table 2; and/or b) a light chain sequence selected from the group consisting of the light chain sequences listed in Table 2. In still another embodiment, the monoclonal antibody, or antigen-binding fragment thereof, is chimeric, humanized, murine, or human. In yet another embodiment, the monoclonal antibody, or antigen-binding fragment thereof, is detectably labeled, comprises an effector domain, and/or comprises an Fc domain. In another embodiment, the monoclonal antibody, or antigen-binding fragment thereof, is selected from the group consisting of Fv, Fav, F(ab')2, Fab', dsFv, scFv, sc(Fv)2, Fde, sdFv, single domain antibody (dAb), and diabodies fragments. In still another embodiment, the monoclonal antibody, or antigen-binding fragment thereof, comprises an immunoglobulin constant domain selected from the group consisting of IgG1, IgG2, IgG3, IgG4, IgA1, IgA2, IgD, IgE, and IgM. In yet another embodiment, the monoclonal antibody, or antigen-binding fragment thereof, comprises a constant domain derived from a human immunoglobulin. In another embodiment, the monoclonal antibody, or antigen-binding fragment thereof, is conjugated to an agent, optionally wherein the agent is selected from the group consisting of a binding protein, an enzyme, a drug, a chemotherapeutic agent, a biologic agent, a toxin, a radionuclide, an immunomodulatory agent, a detectable moiety, and a tag.

In another aspect, a pharmaceutical composition comprising a therapeutically effective amount of at least one monoclonal antibody, or antigen-binding fragment thereof, encompassed by the present invention, and a pharmaceutically acceptable carrier or excipient, is provided.

As described above, numerous embodiments are further provided that can be applied to any aspect of the present invention and/or combined with any other embodiment described herein. For example, in one embodiment, the pharmaceutically acceptable carrier or excipient is selected from the group consisting of a diluent, solubilizing agent, emulsifying agent, preservative, and adjuvant. In another embodiment, the pharmaceutical composition has less than about 20 EU endotoxin/mg protein. In still another embodiment, the pharmaceutical composition has less than about 1 EU endotoxin/mg protein.

In still another aspect, an isolated nucleic acid molecule that i) hybridizes, under stringent conditions, with the complement of a nucleic acid encoding an immunoglobulin heavy and/or light chain polypeptide of a monoclonal antibody, or antigen-binding fragment thereof, encompassed by the present invention; ii) has a sequence with at least about 90% identity across its full length to a nucleic acid encoding an immunoglobulin heavy and/or light chain polypeptide of a monoclonal antibody, or antigen-binding fragment thereof encompassed by the present invention; or iii) encodes an immunoglobulin heavy and/or light chain polypeptide selected from the group consisting of polypeptide sequences listed in Table 2, is provided.

In yet another aspect, an isolated immunoglobulin heavy and/or light chain polypeptide encoded by a nucleic acid encompassed by the present invention, is provided.

In another aspect, a vector comprising an isolated nucleic acid encompassed by the present invention, optionally wherein the vector is an expression vector, is provided.

In still another aspect, a host cell which comprises an isolated nucleic acid encompassed by the present invention, is provided. In some embodiments, the host cell a) expresses a monoclonal antibody, or antigen-binding fragment thereof, encompassed by the present invention; b) comprises an immunoglobulin heavy and/or light chain polypeptide encompassed by the present invention; c) comprises a vector encompassed by the present invention; and/or d) is accessible as a monoclonal antibody deposited under an ATCC deposit accession number described herein, is provided.

In yet another aspect, a device or kit comprising at least one monoclonal antibody, or antigen-binding fragment thereof, encompassed by the present invention, said device or kit optionally comprising a label to detect the at least one monoclonal antibody, or antigen-binding fragment thereof, or a complex comprising the monoclonal antibody, or antigen-binding fragment thereof, is provided.

In another aspect, a device or kit comprising a pharmaceutical composition, isolated nucleic acid molecule, isolated unoglobulin heavy and/or light chain polypeptide, vector, and/or host cell encompassed by the present invention, is provided.

In still another aspect, a method of producing at least one monoclonal antibody, or antigen-binding fragment thereof, encompassed by the present invention, which method comprises the steps of: (i) culturing a transformed host cell which has been transformed by a nucleic acid comprising a sequence encoding the at least one monoclonal antibody, or antigen-binding fragment thereof, under conditions suitable to allow expression of said monoclonal antibody, or antigen-binding fragment thereof; and (ii) recovering the expressed monoclonal antibody, or antigen-binding fragment thereof, is provided.

In yet another aspect, a method of detecting the presence or level of a VSIG4 polypeptide comprising obtaining a sample and detecting said polypeptide in the sample by use of at least one monoclonal antibody, or antigen-binding fragment thereof, encompassed by the present invention, is provided. In one embodiment, the at least one monoclonal antibody, or antigen-binding fragment thereof, forms a complex with the VSIG4 polypeptide and the complex is detected in the form of an enzyme linked immunosorbent assay (ELISA), radioimmune assay (RIA), immunochemical assay, Western blot, mass spectrometry assay, nuclear magnetic resonance assay, or using an intracellular flow assay, is provided.

In another aspect, a method of generating myeloid cells having an increased inflammatory phenotype after contact with an agent encompassed by the present invention comprising contacting myeloid cells with an effective amount of the agent, optionally wherein the myeloid cells comprise suppressive myeloid cells, monocytes, macrophages, neutrophils, and/or dendritic cells, is provided.

As described above, numerous embodiments are further provided that can be applied to any aspect of the present invention and/or combined with any other embodiment described herein. For example, in one embodiment, the myeloid cells having an increased inflammatory phenotype exhibit one or more of the following after contact with the monoclonal antibody, or antigen-binding fragment thereof: a) increased expression and/or secretion of cluster of differentiation 80 (CD80), CD86, MHCII, MHCI, interleukin 1-beta (IL-1β), IL-6, CCL3, CCL4, CXCL10, CXCL9, GM-CSF and/or tumor necrosis factor alpha (TNF-α); b) decreased expression and/or secretion of CD206, CD163, CD16, CD53, VSIG4, VSIG4, TGFb and/or IL-10; c) increased secretion of at least one cytokine or chemokine selected from the group consisting of IL-1β, TNF-α, IL-12, IL-18, GM-CSF, CCL3, CCL4, and IL-23; d) increased ratio of expression of IL-1β, IL-6, and/or TNF-α to expression of IL-10; e) increased CD8+ cytotoxic T cell activation; f) increased recruitment of CD8+ cytotoxic T cell activation; g) increased CD4+ helper T cell activity; h) increased recruitment of CD4+ helper T cell activity; i) increased NK cell activity; j) increased recruitment of NK cell; k) increased neutrophil activity; l) increased macrophage and/or dendritic cell activity; and/or m) increased spindle-shaped morphology, flatness of appearance, and/or number of dendrites, as assessed by microscopy. In another embodiment, the myeloid cells contacted with the monoclonal antibody, or antigen-binding fragment thereof, are comprised within a population of cells and the monoclonal antibody, or antigen-binding fragment thereof, increases the number of Type 1 and/or M1 macrophages, and/or decrease the number of Type 2 and/or M2 macrophages, in the population of cells. In still another embodiment, the myeloid cells contacted with the monoclonal antibody, or antigen-binding fragment thereof, are comprised within a population of cells and the monoclonal antibody, or antigen-binding fragment thereof, increases the ratio of i) to ii), wherein i) is Type 1 and/or M1 macrophages and ii) is Type 2 and/or M2 macrophages in the population of cells. In yet another embodiment, the myeloid cells comprise Type 1 macrophages, M1 macrophages, Type 2 macrophages, M2 macrophages, M2c macrophages, M2d macrophages, tumor-associated macrophages (TAM), CD11b+ cells, CD14+ cells, and/or CD11b+/CD14+ cells. In another embodiment, the myeloid cells are contacted in vitro or ex vivo. In still another embodiment, the myeloid cells are primary myeloid cells. In yet another embodiment, the myeloid cells are purified and/or cultured prior to contact with the agent. In another embodiment, the myeloid cells are contacted in vivo (e.g., by systemic, peritumoral, or intratumoral administration of the agent). In still another embodiment, the myeloid cells are contacted in a tissue microenvironment. In yet another embodiment, the method further comprises contacting the myeloid cells with at least one immunotherapeutic agent that modulates the inflammatory phenotype, optionally wherein the immunotherapeutic agent comprises an immune checkpoint inhibitor, immune-stimulatory agonist, inflammatory agent, cells, a cancer vaccine, and/or a virus.

In still another aspect, a composition comprising a myeloid cell generated according to a method encompassed by the present invention, optionally wherein the myeloid cell is a suppressive myeloid cell, monocyte, macrophage, and/or dendritic cell, is provided.

In yet another aspect, a method of increasing an inflammatory phenotype of myeloid cells in a subject after contact with an agent encompassed by the present invention, comprising administering to the subject an effective amount of the agent, optionally wherein the myeloid cells comprise suppressive myeloid cells, monocytes, macrophages, neutrophils, and/or dendritic cells, is provided.

As described above, numerous embodiments are further provided that can be applied to any aspect of the present invention and/or combined with any other embodiment described herein. For example, in one embodiment, the myeloid cells having the increased inflammatory phenotype exhibit one or more of the following after contact with the agent: a) increased expression and/or secretion of cluster of differentiation 80 (CD80), CD86, MHCII, MHCI, interleukin 1-beta (IL-1β), IL-6, CCL3, CCL4, CXCL10, CXCL9, GM-CSF and/or tumor necrosis factor alpha (TNF-α); b) decreased expression and/or secretion of CD206, CD163, CD16, CD53, VSIG4, PSGL-1 and/or IL-10; c) increased secretion of at least one cytokine selected from the group consisting of IL-1β, TNF-α, IL-12, IL-18, and IL-23; d) increased ratio of expression of IL-1β, IL-6, and/or TNF-α to expression of IL-10; e) increased CD8+ cytotoxic T cell activation; f) increased CD4+ helper T cell activity; g) increased NK cell activity; h) increased neutrophil activity; i) increased macrophage and/or dendritic cell activity; and/or j) increased spindle-shaped morphology, flatness of appearance, and/or number of dendrites, as assessed by microscopy. In another embodiment, the agent increases the number of Type 1 and/or M1 macrophages, decrease the number of Type 2 and/or M2 macrophages, and/or increase the ratio of i) to ii), wherein i) is Type 1 and/or M1 macrophages and ii) is Type 2 and/or M2 macrophages, in the subject. In still another embodiment, a) the number and/or activity of cytotoxic CD8+ T cells in the subject is increased, b) the agent directly re-represses and/or activates T cells by inhibiting VSIG4-T cell interactions, optionally wherein the VSIG4-T cell interaction is a direct interaction or an indirect interaction, and/or c) the agent indirectly re-represses and/or activates T cells by increasing the inflammatory phenotype of myeloid cells, after administration of the agent. In yet another embodiment, the myeloid cells comprise Type 1 macrophages, M1 macrophages, Type 2 macrophages, M2 macrophages, M2c macrophages, M2d macrophages, tumor-associated macrophages (TAM), CD11b+ cells, CD14+ cells, and/or CD11b+/CD14+ cells. In another embodiment, the agent is administered in vivo by systemic, peritumoral, or intratumoral administration of the agent. In still another embodiment, the agent contacts the myeloid cells in a tissue microenvironment. In yet another embodiment, the method further comprises contacting the myeloid cells with at least one immunotherapeutic agent that modulates the inflammatory phenotype, optionally wherein the immunotherapeutic agent comprises an immune checkpoint inhibitor, immune-stimulatory agonist, inflammatory agent, cells, a cancer vaccine, and/or a virus.

In another aspect, a method of increasing inflammation in a subject comprising administering to the subject an effective amount of myeloid cells contacted with an agent encompassed by the present invention, optionally wherein the myeloid cells comprise suppressive myeloid cells, monocytes, macrophages, neutrophils, and/or dendritic cells, is provided.

As described above, numerous embodiments are further provided that can be applied to any aspect of the present invention and/or combined with any other embodiment described herein. For example, in one embodiment, the myeloid cells comprise Type 1 macrophages, M1 macrophages, Type 2 macrophages, M2 macrophages, M2c macrophages, M2d macrophages, tumor-associated macrophages (TAM), CD11b+ cells, CD14+ cells, and/or CD11b+/CD14+ cells. In another embodiment, the myeloid cells are genetically engineered, autologous, syngeneic, or allogeneic relative to the subject's myeloid cells. In still another embodiment, the agent is administered systemically, peritumorally, or intratumorally.

In still another aspect, a method of sensitizing cancer cells in a subject to cytotoxic CD8+ T cell-mediated killing and/or immune checkpoint therapy comprising administering to the subject a therapeutically effective amount of an agent encompassed by the present invention, is provided.

In yet another aspect, a method of sensitizing cancer cells in a subject afflicted with a cancer to cytotoxic CD8+ T cell-mediated killing and/or immune checkpoint therapy comprising administering to the subject a therapeutically effective amount of myeloid cells contacted with an agent encompassed by the present invention, optionally wherein the myeloid cells comprise suppressive myeloid cells, monocytes, macrophages, neutrophils, and/or dendritic cells, is provided.

As described above, numerous embodiments are further provided that can be applied to any aspect of the present invention and/or combined with any other embodiment described herein. For example, in one embodiment, the myeloid cells comprise Type 1 macrophages, M1 macrophages, Type 2 macrophages, M2 macrophages, M2c macrophages, M2d macrophages, tumor-associated macrophages (TAM), CD11b+ cells, CD14+ cells, and/or CD11b+/CD14+ cells. In another embodiment, the myeloid cells are genetically engineered, autologous, syngeneic, or allogeneic relative to the subject's myeloid cells. In still another embodiment, the agent is administered systemically, peritumorally, or intratumorally. In yet another embodiment, the method further comprises treating the cancer in the subject by administering to the subject at least one immunotherapy, optionally wherein the immunotherapy comprises an immune checkpoint inhibitor, immune-stimulatory agonist, inflammatory agent, cells, a cancer vaccine, and/or a virus. In another embodiment, the immune checkpoint is selected from the group consisting of PD-1, PD-L1, PD-L2, and CTLA-4. In still another embodiment, the immune checkpoint is PD-1. In yet another embodiment, the method further comprises treating the cancer in the subject by administering to the subject an additional therapeutic agent or regimen for treating cancer, optionally, wherein the additional therapeutic agent or regimen is selected from the group consisting chimeric antigen receptors, chemotherapy, radiation, targeted therapy, and surgery. In another embodiment, the agent reduces the number of proliferating cells in the cancer and/or reduce the volume or size of a tumor comprising the cancer cells. In still another embodiment, the agent a) increases the amount and/or activity of CD8+ T cells infiltrating a tumor comprising the cancer cells, b) directly re-represses and/or activates T cells by inhibiting VSIG4-T cell interactions, optionally wherein the VSIG4-T cell interaction is a direct interaction or an indirect interaction, and/or c) indirectly re-represses and/or activates T cells by increasing the inflammatory phenotype of myeloid cells. In yet another embodiment, the agent a) increases the amount and/or activity of M1 macrophages infiltrating a tumor comprising the cancer cells and/or b) decreases the amount and/or activity of M2 macrophages infiltrating a tumor comprising the cancer cells. In another embodiment, the method further comprises administering to the subject at least one additional therapy or regimen for treating the cancer. In still another embodiment, the therapy is administered before, concurrently with, or after the agent.

In another aspect, a method of identifying myeloid cells that can increase an inflammatory phenotype thereof by modulating at least one target comprising: a) determining the amount and/or activity of at least one target listed in Table 1 from the myeloid cells using an agent, wherein the agent is at least one monoclonal antibody, or antigen-binding fragment thereof, encompassed by the present invention; b) determining the amount and/or activity of the at least one target in a control using the agent; and c) comparing the amount and/or activity of the at least one target detected in steps a) and b); wherein the presence of, or an increase in, the amount and/or activity of, the at least one target listed in Table 1, in the myeloid cells relative to the control amount and/or activity of the at least one target indicates that the myeloid cells can increase the inflammatory phenotype thereof by modulating the at least one target, optionally wherein the myeloid cells comprise suppressive myeloid cells, monocytes, macrophages, neutrophils, and/or dendritic cells, is provided.

As described above, numerous embodiments are further provided that can be applied to any aspect of the present invention and/or combined with any other embodiment described herein. For example, in one embodiment, the method further comprises contacting the cells with, recommending, prescribing, or administering an agent that modulates the at least one target listed in Table 1. In another embodiment, the method further comprises contacting the cells with, recommending, prescribing, or administering cancer therapy other than an agent that modulates the at least one target listed in Table 1 if the subject is determined not to benefit from increasing an inflammatory phenotype by modulating the at least one target (e.g., immunotherapy). In still another embodiment, the method further comprises contacting the cells with and/or administering at least one additional agent that increases an immune response. In yet another embodiment, the additional agent is selected from the group consisting of targeted therapy, chemotherapy, radiation therapy, and/or hormonal therapy. In another embodiment, the control is from a member of the same species to which the subject belongs. In still another embodiment, the control is a sample comprising cells. In yet another embodiment, the subject is afflicted with a cancer. In another embodiment, the control is a cancer sample from the subject. In still another embodiment, the control is a non-cancer sample from the subject.

In still another aspect, a method for predicting the clinical outcome of a subject afflicted with a cancer, the method comprising: a) determining the amount and/or activity of at least one target listed in Table 1 from myeloid cells from the subject using an agent, wherein the agent is at least one monoclonal antibody, or antigen-binding fragment thereof, encompassed by the present invention; b) determining the amount and/or activity of the at least one target from a control having a poor clinical outcome using the agent; and c) comparing the amount and/or activity of the at least one target in the subject sample and in the sample from the control subject; wherein the presence of, or an increase in, the amount and/or activity of the at least one target listed in Table 1 from the myeloid cells from the subject as compared to the amount and/or activity in the control, indicates that the subject does not have a poor clinical outcome, optionally wherein the myeloid cells comprise suppressive myeloid cells, monocytes, macrophages, neutrophils, and/or dendritic cells, is provided.

In yet another aspect, a method for monitoring the inflammatory phenotype of myeloid cells in a subject, the method comprising: a) detecting in a first subject sample at a first point in time the amount and/or activity of at least one target listed in Table 1 from myeloid cells from the subject using an agent, wherein the agent is at least one monoclonal antibody, or antigen-binding fragment thereof, encompassed by the present invention; b) repeating step a) using a subsequent sample comprising myeloid cells obtained at a subsequent point in time; and c) comparing the amount or activity of the at least one target listed in Table 1 detected in steps a) and b), wherein the absence of, or a decrease in, the amount and/or activity of, the at least one target listed in Table 1 from the myeloid cells from the subsequent sample as compared to the amount and/or activity from the myeloid cells from the first sample indicates that the subject's myeloid cells have an upregulated inflammatory phenotype; or wherein the presence of, or an increase in, the amount and/or activity of, the at least one target listed in Table 1 from the myeloid cells from the subsequent sample as compared to the amount and/or activity from the myeloid cells from the first sample indicates that the subject's myeloid cells have a downregulated inflammatory phenotype, optionally wherein the myeloid cells comprise suppressive myeloid cells, monocytes, macrophages, neutrophils, and/or dendritic cells, is provided.

As described above, numerous embodiments are further provided that can be applied to any aspect of the present invention and/or combined with any other embodiment described herein. For example, in one embodiment, the first and/or at least one subsequent sample comprises myeloid cells that are cultured in vitro. In another embodiment, the first and/or at least one subsequent sample comprises myeloid cells that are not cultured in vitro. In still another embodiment, the first and/or at least one subsequent sample is a portion of a single sample or pooled samples obtained from the subject. In another embodiment, the sample comprises blood, serum, peritumoral tissue, and/or intratumoral tissue obtained from the subject.

In another aspect, a method of assessing the efficacy of a test agent for increasing an inflammatory phenotype of myeloid cells in a subject, comprising: a) detecting in a subject sample comprising myeloid cells at a first point in time i) the amount or activity of at least one target listed in Table 1 in or on the myeloid cells using an agent, wherein the agent is at least one monoclonal antibody, or antigen-binding fragment thereof, encompassed by the present invention and/or ii) an inflammatory phenotype of the myeloid cells; b) repeating step a) during at least one subsequent point in time after the myeloid cells are contacted with the test agent; and c) comparing the value of i) and/or ii) detected in steps a) and b), wherein the absence of, or a decrease in, the amount and/or activity of the at least one target listed in Table 1, and/or an increase in ii) in the subsequent sample as compared to the amount and/or activity in the sample at the first point in time, indicates that the test agent increases the inflammatory phenotype of myeloid cells in the subject, optionally wherein the myeloid cells comprise suppressive myeloid cells, monocytes, macrophages, neutrophils, and/or dendritic cells, is provided.

As described above, numerous embodiments are further provided that can be applied to any aspect of the present invention and/or combined with any other embodiment described herein. For example, in one embodiment, the myeloid cells contacted with the agent are comprised within a population of cells and the agent increases the number of Type 1 and/or M1 macrophages in the population of cells. In another embodiment, the myeloid cells contacted with the agent are comprised within a population of cells and the agent decreases the number of Type 2 and/or M2 macrophages in the population of cells. In still another embodiment, the myeloid cells are contacted in vitro or ex vivo. In yet another embodiment, the myeloid cells are primary myeloid cells. In another embodiment, the myeloid cells are purified and/or cultured prior to contact with the agent. In still another embodiment, the myeloid cells are contacted in vivo. In yet another embodiment, the myeloid cells are contacted in vivo by systemic, peritumoral, or intratumoral administration of the agent. In another embodiment, the myeloid cells are contacted in a tissue microenvironment. In still another embodiment, the method further comprises contacting the myeloid cells with at least one immunotherapeutic agent that modulates the inflammatory phenotype, optionally wherein the immunotherapeutic agent comprises an immune checkpoint inhibitor, immune-stimulatory agonist, inflammatory agent, cells, a cancer vaccine, and/or a virus. In yet another embodiment, the subject is a mammal (e.g., a non-human animal model or a human).

In still another aspect, a method of assessing the efficacy of a test agent for treating a cancer in a subject, comprising: a) detecting in a subject sample comprising myeloid cells at a first point in time i) the amount and/or or activity of at least one target listed in Table 1 in or on myeloid cells using an agent, wherein the agent is at least one monoclonal antibody, or antigen-binding fragment thereof, encompassed by the present invention and/or ii) an inflammatory phenotype of the myeloid cells; b) repeating step a) during at least one subsequent point in time after administration of the agent; and c) comparing the value of i) and/or ii) detected in steps a) and b), wherein the absence of, or a decrease in, the amount and/or activity of the at least one target listed in Table 1, and/or an increase in ii) in or on the myeloid cells of the subject sample at the subsequent point in time as compared to the amount and/or activity in or on the myeloid cells of the subject sample at the first point in time, indicates that the test agent treats the cancer in the subject, optionally wherein the myeloid cells comprise suppressive myeloid cells, monocytes, macrophages, neutrophils, and/or dendritic cells, is provided.

As described above, numerous embodiments are further provided that can be applied to any aspect of the present invention and/or combined with any other embodiment described herein. For example, in one embodiment, the subject has undergone treatment, completed treatment, and/or is in remission for the cancer between the first point in time and the subsequent point in time. In another embodiment, the first and/or at least one subsequent sample is selected from the group consisting of ex vivo and in vivo samples. In still another embodiment, the first and/or at least one subsequent sample is obtained from a non-human animal model of the cancer. In yet another embodiment, the first and/or at least one subsequent sample is a portion of a single sample or pooled samples obtained from the subject. In another embodiment, the sample comprises cells, serum, peritumoral tissue, and/or intratumoral tissue obtained from the subject.

In another aspect, a method for screening for test agents that sensitize cancer cells to cytotoxic T cell-mediated killing and/or immune checkpoint therapy comprising: a) contacting cancer cells with cytotoxic T cells and/or immune checkpoint therapy in the presence of myeloid cells contacted with the test agent, wherein the test agent modulates the amount and/or activity of at least one target listed in Table 1 in or on myeloid cells as determined using an agent, wherein the agent is at least one monoclonal antibody, or antigen-binding fragment thereof, encompassed by the present invention; b) contacting cancer cells with cytotoxic T cells and/or immune checkpoint therapy in the presence of control myeloid cells that are not contacted with the test agent; and c) identifying test agents that sensitize cancer cells to cytotoxic T cell-mediated killing and/or immune checkpoint therapy by identifying agents that increase cytotoxic T cell-mediated killing and/or immune checkpoint therapy efficacy in a) compared to b), optionally wherein the myeloid cells comprise suppressive myeloid cells, monocytes, macrophages, neutrophils, and/or dendritic cells, is provided.

As described above, numerous embodiments are further provided that can be applied to any aspect of the present invention and/or combined with any other embodiment described herein. For example, in one embodiment, the step of contacting occurs in vivo, ex vivo, or in vitro. In another embodiment, the method further comprises determining a reduction in i) the number of proliferating cells in the cancer and/or ii) a reduction in the volume or size of a tumor comprising the cancer cells. In still another embodiment, the method further comprises determining i) an increased number of CD8+ T cells and/or ii) an increased number of Type 1 and/or M1 macrophages infiltrating a tumor comprising the cancer cells. In yet another embodiment, the method further comprises determining responsiveness to the test agent that modulates the at least one target listed in Table 1 measured by at least one criterion selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In another embodiment, the method further comprises contacting the cancer cells with at least one additional cancer therapeutic agent or regimen.

Again, as described above, numerous embodiments are further provided that can be applied to any aspect of the present invention and/or combined with any other embodiment described herein. For example, in one embodiment, the myeloid cells having a modulated inflammatory phenotype exhibit one or more of the following: a) modulated expression of cluster of differentiation 80 (CD80), CD86, MHCII, MHCI, interleukin 1-beta (IL-1β), IL-6, CCL3, CCL4, CXCL10, CXCL9, GM-CSF and/or tumor necrosis factor alpha (TNF-α); b) modulated expression of CD206, CD163, CD16, CD53, VSIG4, PSGL-1 and/or IL-10; c) modulated secretion of at least one cytokine selected from the group consisting of IL-1β, TNF-α, IL-12, IL-18, and IL-23; d) modulated ratio of expression of IL-1β, IL-6, and/or TNF-α to expression of IL-10; e) modulated CD8+ cytotoxic T cell activation; f) modulated CD4+ helper T cell activity; g) modulated NK cell activity; h) modulated neutrophil activity; i) modulated macrophage and/or dendritic cell activity; and/or j) modulated spindle-shaped morphology, flatness of appearance, and/or dendrite numbers, as assessed by microscopy. In another embodiment, the cells and/or myeloid cells comprise Type 1 macrophages, M1 macrophages, Type 2 macrophages, M2 macrophages, M2c macrophages, M2d macrophages, tumor-associated macrophages (TAM), CD11b+ cells, CD14+ cells, and/or CD11b+/CD14+ cells, optionally wherein the cells and/or myeloid cells express or are determined to express VSIG4. In still another embodiment, the human VSIG4 polypeptide, the human VSIG4 IgV domain, the cynomolgus VSIG4 polypeptide, and/or the murine VSIG4 polypeptide has an amino acid sequences shown in Table 1 or the working examples. In yet another embodiment, the cancer is a solid tumor that is infiltrated with macrophages, wherein the infiltrating macrophages represent at least about 5% of the mass, volume, and/or number of cells in the tumor or the tumor microenvironment, and/or wherein the cancer is selected from the group consisting of mesothelioma, kidney renal clear cell carcinoma, glioblastoma, lung adenocarcinoma, lung squamous cell carcinoma, pancreatic adenocarcinoma, breast invasive carcinoma, acute myeloid leukemia, adrenocortical carcinoma, bladder urothelial carcinoma, brain lower grade glioma, breast invasive carcinoma, cervical squamous cell carcinoma and endocervical adenocarcinoma, cholangiocarcinoma, colon adenocarcinoma, esophageal carcinoma, glioblastoma multiforme, head and neck squamous cell carcinoma, kidney chromophobe, kidney renal clear cell carcinoma, kidney renal papillary cell carcinoma, liver hepatocellular carcinoma, lung adenocarcinoma, lung squamous cell carcinoma, lymphoid neoplasm diffuse large B-cell lymphoma, mesothelioma, ovarian serous, cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thymoma, thyroid carcinoma, uterine carcinosarcoma, uterine corpus endometrial carcinoma, and uveal melanoma. In another embodiment, the myeloid cells comprise Type 1 macrophages, M1 macrophages, Type 2 macrophages, M2 macrophages, M2c macrophages, M2d macrophages, tumor-associated macrophages (TAM), CD11b+ cells, CD14+ cells, and/or CD11b+/CD14+ cells, optionally wherein the myeloid cells are TAMs and/or M2 macrophages. In still another embodiment, the myeloid cells express or are determined to express VSIG4. In yet embodiment, the myeloid cells are primary myeloid cells. In another embodiment, the myeloid cells are comprised within a tissue microenvironment. In still another embodiment, the myeloid cells are comprised within a human tumor model or an animal model of cancer. In yet another embodiment, the subject is a mammal. In another embodiment, the mammal is a human (e.g., a human afflicted with a cancer).

BRIEF DESCRIPTION OF THE DRAWINGS

FIG. 1A shows that VSIG4 is restricted to myeloid populations within tumor associated immune cells, including dendritic cells (DCs), myeloid derived suppressor cells like inhibitory-type macrophages (e.g., M2-like TAMs and M0-like TAMs), and the like. FIG. 1B shows that VSIG4 expression is strongly enriched in M2-like and M0-like suppressive myeloid populations within tumor-associated myeloid populations. Comparison data for FIG. 1A and FIG. 1B obtained from Zillionis et al. (2019) *Immunity* 50:1317-1334 providing single cell RNA sequencing data such as from seven non-small cell lung cancer patients. FIG. 1C shows that VSIG4 expression is dominant on suppressive macrophage subsets and not particularly expressed on circulating monocytes or T cells.

FIG. 21 discloses SEQ ID NO: 112.

FIG. 28 provides a summary of biophysical and functional properties of representative anti-VSIG4 antibodies.

Figure 1A:
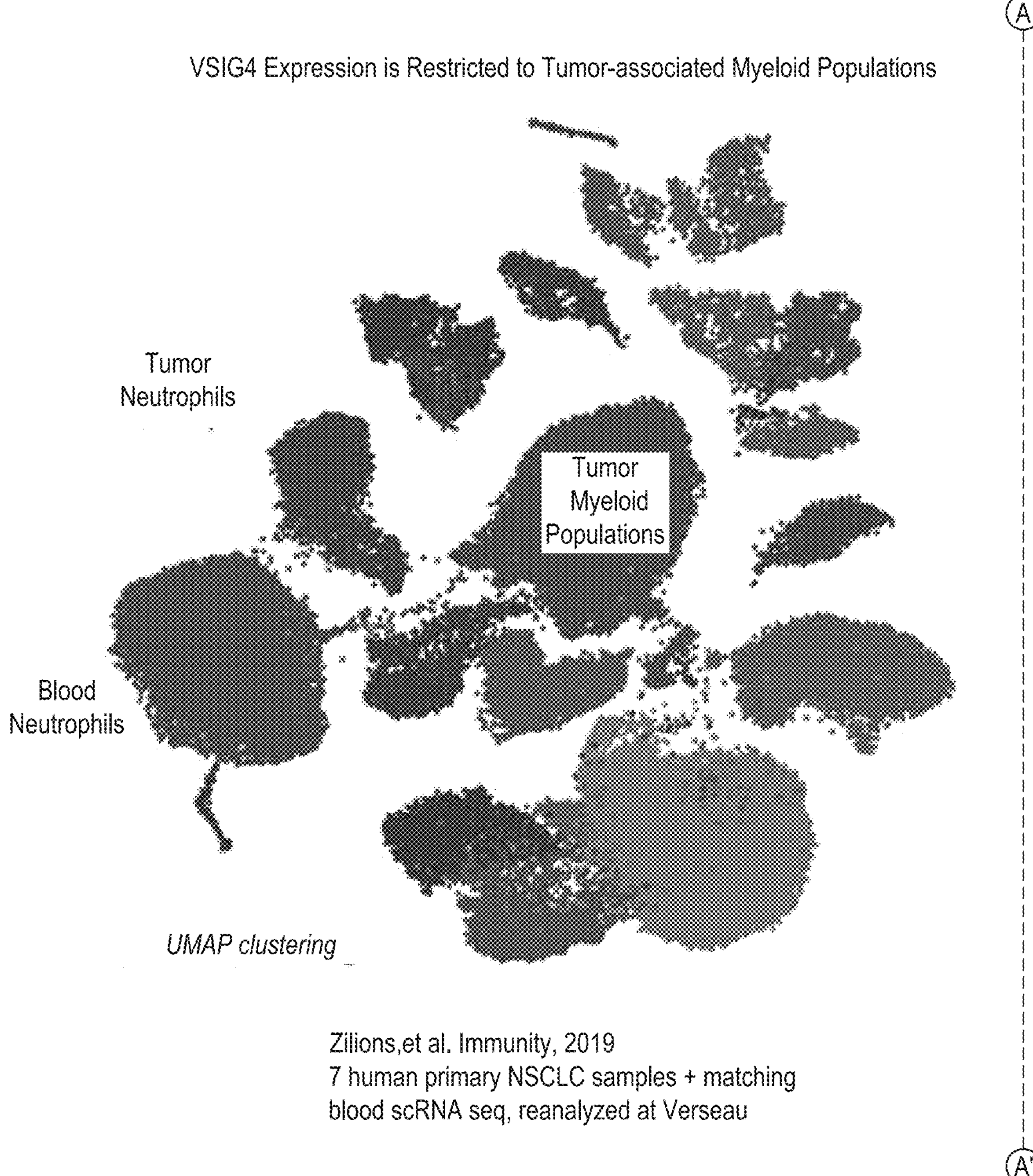
FIG. 1A-FIG. 1C show VSIG4 expression matters.
Figure 1A:
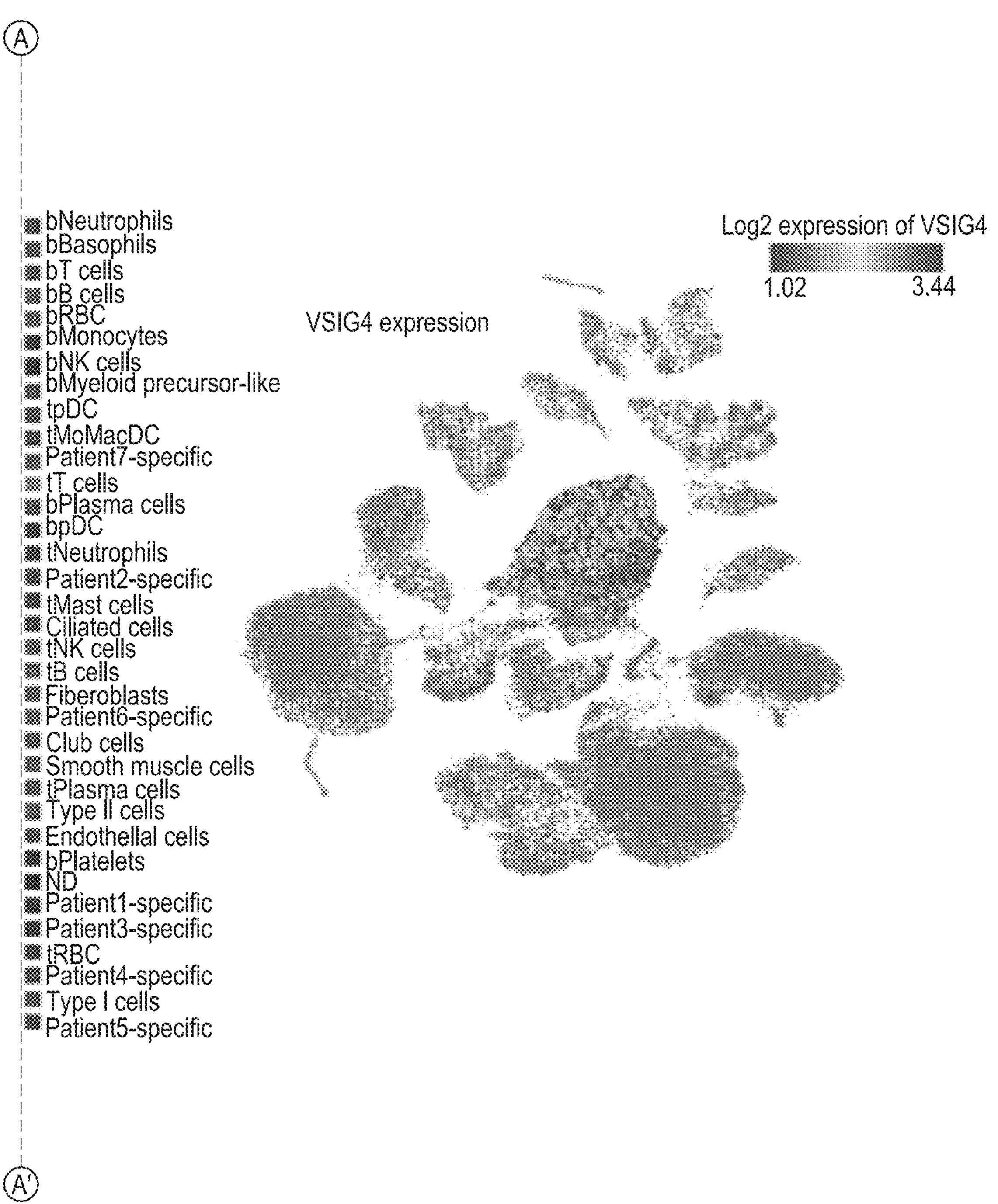

For any figure showing a bar histogram, curve, or other data associated with a legend, the bars, curve, or other data presented from left to right for each indication correspond directly and in order to the boxes from top to bottom of the legend.

DETAILED DESCRIPTION OF THE INVENTION

The present invention is based, at least in part, on the discovery of anti-VSIG4 compositions (e.g., monoclonal antibodies) that regulate myeloid cell inflammatory phenotypes, including polarization, activation, and/or function. Accordingly, the present invention provides anti-VSIG4 compositions, as well as methods and uses thereof, including, without limitation, modulation of myeloid cell inflammatory phenotypes for treatment, diagnosis, prognosis, and screening.

I. Definitions

The term "about," in some embodiments, encompasses values that are within 1%, 2%, 3%, 4%, 5%, 6%, 7%, 8%, 9%, or 10%, inclusive, or any range in between (e.g., plus or minus 2%-6%), of a value that is measured. In some embodiments, the term "about" refers to the inherent variation of error in a method, assay, or measured value, such as the variation that exists among experiments.

The term "activating receptor" includes immune cell receptors that bind antigen, complexed antigen (e.g., in the context of major histocompatibility complex (MHC) polypeptides), or bind to antibodies. Such activating receptors include T cell receptors (TCR), B cell receptors (BCR), cytokine receptors, LPS receptors, complement receptors, Fc receptors, and other ITAM containing receptors. For example, T cell receptors are present on T cells and are associated with CD3 polypeptides. T cell receptors are stimulated by antigen in the context of MHC polypeptides (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes. Similar to T cells, activation of macrophages via activation receptors such as, cytokine receptors or pattern associated molecular pattern (PAMP) receptors, results in changes, such as protein phosphorylation, alteration to surface receptor phenotype, protein synthesis and release, as well as morphologic changes.

The term "activity," when used with respect to a polypeptide, includes activities that are inherent in the structure of the protein. For example, with regard to a myeloid cell protein, the term "activity" includes the ability to modulate an inflammatory phenotype of the myeloid cell protein by modulating natural binding protein binding or cellular signaling of the cell (e.g., by engaging a natural receptor or ligand on an immune cell).

The term "administering" relates to the actual physical introduction of an agent into or onto (as appropriate) a biological target of interest, such as a host and/or subject. A composition may be administered to the cell (e.g., "contacting") in vitro or in vivo. A composition may be administered to the subject in vivo via an appropriate route of administration. Any and all methods of introducing the composition into the host are contemplated according to the present invention. The method is not dependent on any particular means of introduction and is not to be so construed. Means of introduction are well-known to those skilled in the art, and are also exemplified herein. The term include routes of administration which allow an agent to perform its intended function. Examples of routes of administration for treatment of a body which may be used include injection (subcutaneous, intravenous, parenterally, intraperitoneally, intrathecal, etc.), oral, inhalation, and transdermal routes. The injection may be bolus injections or may be continuous infusion. Depending on the route of administration, the agent may be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

The term "agent" refers to a compound, supramolecular complex, material, and/or combination or mixture thereof. A compound (e.g., a molecule) may be represented by a chemical formula, chemical structure, or sequence. Representative, non-limiting examples of agents, include, e.g., antibodies, small molecules, polypeptides, polynucleotides (e.g., RNAi agents, siRNA, miRNA, piRNA, mRNA, antisense polynucleotides, aptamers, and the like), lipids, and polysaccharides. In general, agents may be obtained using any suitable method known in the art. In some embodiments, an agent may be a "therapeutic agent" for use in treating a disease or disorder (e.g., cancer) in a subject (e.g., a human).

The term "agonist" refers to an agent that binds to a target(s) (e.g., a receptor) and activates or increases the biological activity of the target(s). For example, an "agonist" antibody is an antibody that activates or increases the biological activity of the antigen(s) it binds.

The term "altered amount" or "altered level" encompasses increased or decreased copy number (e.g., germline and/or somatic) of a biomarker nucleic acid, or increased or decreased expression level in a sample of interest, as compared to the copy number or expression level in a control sample. The term "altered amount" of a biomarker also includes an increased or decreased protein level of a biomarker protein in a sample, e.g., a cancer sample, as compared to the corresponding protein level in a normal and/or control sample. Furthermore, an altered amount of a biomarker protein may be determined by detecting post-translational modification such as methylation status of the marker, which may affect the expression or activity of the biomarker protein. In some embodiments, the "altered amount" refers to the presence or absence of a biomarker because the reference baseline may be the absence or presence of the biomarker, respectively. The absence or presence of the biomarker may be determined according to the threshold of sensitivity of a given assay used to measure the biomarker.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least about 10%, 15%, 20%, 25%, 30%, 35%, 40%, 45% 50%, 55%, 60%, 65%, 70%, 75%, 80%, 85%, 90%, 95%, 100%, 150%, 200%, 300%, 350%, 400%, 500%, 600%, 700%, 800%, 900%, 1000%, or more than that amount. Alternatively, the amount of the biomarker in the subject may be considered "significantly" higher or lower than the normal amount if the amount is at least about two, and preferably at least about three, four, or five times, higher or lower, respectively, than the normal amount of the biomarker. Such "significance" may also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. In some embodiments, the level of the biomarker refers to the level of the biomarker itself, the level of a modified biomarker (e.g., phosphorylated biomarker), or to the level of a biomarker relative to another measured variable, such as a control (e.g., phosphorylated biomarker relative to an unphosphorylated biomarker). The term "expression" encompasses the processes by which nucleic acids (e.g., DNA) are transcribed to produce RNA, and may also refer to the processes by which RNA transcripts are processed and translated into polypeptides. The sum of expression of nucleic acids and their polypeptide counterparts, if any, contributes to the amount of a biomarker, such as one or more targets listed in Table 1.

The term "altered activity" of a biomarker refers to an activity of the biomarker which is increased or decreased in a disease state, e.g., in a cancer sample, or a treated state, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

The term "altered subcellular localization" of a biomarker refers to the mislocalization of the biomarker within a cell relative to the normal localization within the cell e.g., within a healthy and/or wild-type cell. An indication of normal localization of the marker may be determined through an analysis of subcellular localization motifs known in the field that are harbored by biomarker polypeptides.

The term "antagonist" or "blocking" refers to an agent that binds to a target(s) (e.g., a receptor) and inhibits or reduces the biological activity of the target(s). For example, an "antagonist" antibody is an antibody that significantly inhibits or reduces biological activity of the antigen(s) it binds.

Unless otherwise specified here within, the terms "antibody" and "antibodies" broadly encompass naturally-occurring forms of antibodies (e.g., IgG, IgA, IgM, IgE) and recombinant antibodies, such as single-chain antibodies, chimeric and humanized antibodies and multi-specific antibodies, as well as fragments, fusion proteins, and derivatives of all of the foregoing, which fragments and derivatives have at least an antigenic binding site. Antibody derivatives may comprise a protein or chemical moiety conjugated to an antibody.

The term "biomarker" refers to a gene or gene product that is a target for modulating one or more phenotypes of interest, such as a phenotype of interest in myeloid cells, such as suppressive myeloid cells, monocytes, macrophages, and/or dendritic cells. In this context, the term "biomarker" is synonymous with "target." In some embodiments, however, the term further encompasses a measurable entity of the target that has been determined to be indicative of an output of interest, such as one or more diagnostic, prognostic, and/or therapeutic outputs (e.g., for modulating an inflammatory phenotype, cancer state, and the like). In still other embodiments, the team further encompasses compositions that modulate the gene or gene product, including anti-gene product antibodies and antigen-binding fragments thereof. Thus, biomarkers may include, without limitation, nucleic acids (e.g., genomic nucleic acids and/or transcribed nucleic acids), proteins, and antibodies (as well as antigen-binding fragments thereof), particularly those listed in Table 1.

The terms "cancer" or "tumor" or "hyperproliferative" refer to the presence of cells possessing characteristics typical of cancer-causing cells, such as uncontrolled proliferation, immortality, invasive or metastatic potential, rapid growth, and certain characteristic morphological features. In some embodiments, such cells exhibit such characteristics in part or in full due to the expression and activity of immune checkpoint proteins, such as PD-1, PD-L1, PD-L2, and/or CTLA-4.

Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, a variety of cancers, carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, bone cancer, bone tumors, adult malignant fibrous histiocytoma of bone; childhood, malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma, chronic myeloid leukemia, acute lymphoblastic leukemia, Philadelphia chromosome positive acute lymphoblastic leukemia (Ph+ ALL), multiple myeloma, acute myelogenous leukemia, chronic lymphocytic leukemia, mastocytosis and any symptom associated with mastocytosis, and any metastasis thereof. In addition, disorders include urticaria pigmentosa, mastocytosis such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, mast cell leukemia, in addition to other cancers. Other cancers are also included within the scope of disorders including, but are not limited to, the following: carcinoma, including that of the bladder, urothelial carcinoma, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma, and any metastasis thereof. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, bone cancer, brain tumor, lung carcinoma (including lung adenocarcinoma), small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In some embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated. In some embodiments, the cancer is selected from the group consisting of (advanced) non-small cell lung cancer, melanoma, head and neck squamous cell cancer, (advanced) urothelial bladder cancer, (advanced) kidney cancer (RCC), microsatellite instability-high cancer, classical Hodgkin lymphoma, (advanced) gastric cancer, (advanced) cervical cancer, primary mediastinal B-cell lymphoma, (advanced) hepatocellular carcinoma, and (advanced) merkel cell carcinoma.

The term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "compete" with regard to an antibody, or antigen-binding fragment thereof, refers to the situation wherein a first antibody, or an antigen binding fragment thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not, be the case. That is, a first antibody may inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies, and antigen-binding fragments thereof, are encompassed by the present invention (e.g., antibodies and antigen-binding fragments described herein that compete or cross-compete with other antibodies and antigen-binding fragments described herein and/or known in the art). Regardless of the mechanism by which such competition or cross-competition occurs (e.g., steric hindrance, conformational change, or binding to a common epitope, or portion thereof), the skilled artisan appreciates, based on the disclosures provided herein and the state of the art, that such competing and/or cross-competing antibodies are encompassed and may be useful for the methods disclosed herein.

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 60%, 65%, 70%, 75%, 80%, 85%, 90%, 95%, 98%, 99%, 99.5%, 99.9%, or greater of the nucleotide residues of the first portion are capable of base pairing with nucleotide residues in the second portion. More preferably, all nucleotide residues of the first portion are capable of base pairing with nucleotide residues in the second portion. In some embodiments, complementary polynucleotides may be "sufficiently complementary" or may have "sufficient complementarity," that is, complementarity sufficient to maintain a duplex and/or have a desired activity. For example, in the case of RNAi agents, such complementarity is complementarity between the agent and a target mRNA that is sufficient to partly or completely prevent translation of the mRNA. For example, an siRNA having a "sequence sufficiently complementary to a target mRNA sequence to direct target-specific RNA interference (RNAi)" means that the siRNA has a sequence sufficient to trigger the destruction of the target mRNA by the RNAi machinery or process.

The term "substantially complementary" refers to complementarity in a base-paired, double-stranded region between two nucleic acids and not any single-stranded region such as a terminal overhang or a gap region between two double-stranded regions. The complementarity does not need to be perfect; there may be any number of base pair mismatches. In some embodiments, when two sequences are referred to as "substantially complementary" herein, it is meant that the sequences are sufficiently complementary to each other to hybridize under the selected reaction conditions. Accordingly, substantially complementary sequences may refer to sequences with base-pair complementarity of at least 100, 99, 98, 97, 96, 95, 94, 93, 92, 91, 90, 85, 80, 75, 70, 65, 60 percent or more, or any number in between, in a double-stranded region.

The terms "conjoint therapy" and "combination therapy," as used herein, refer to the administration of two or more therapeutic agents, e.g., combination of modulators of more than one target listed in Table 1, combination of at least one modulator of at least one target listed in Table 1 and an additional therapeutic agent, such as an immune checkpoint therapy, combination of more than one modulators of one or more targets listed in Table 1 and the like), and combinations thereof. The different agents comprising the combination therapy may be administered concomitant with, prior to, or following, the administration of the other or others. The combination therapy is intended to provide a beneficial (additive or synergistic) effect from the co-action of these therapeutic agents. Administration of these therapeutic agents in combination may be carried out over a defined time period (usually minutes, hours, days, or weeks depending upon the combination selected). In combination therapy, combined therapeutic agent may be applied in a sequential manner, or by substantially simultaneous application.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from subject, such as a subject having myeloid cells, such as suppressive myeloid cells, monocytes, macrophages, and/or dendritic cells, and/or a control cancer patient (may be a stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels may be used in combination as controls in the methods encompassed by the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient may be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. The methods encompassed by the present invention are not limited to use of a specific cut-off point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number may be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The term "costimulate," as used with reference to activated immune cells, includes the ability of a costimulatory polypeptide to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "costimulatory receptor" includes receptors which transmit a costimulatory signal to a immune cell, e.g., CD28. As used herein, the term "inhibitory receptors" includes receptors which transmit a negative signal to an immune cell (e.g., PD-1, CTLA-4, etc.). An inhibitory signal as transduced by an inhibitory receptor can occur even if a costimulatory receptor (such as CD28) is not present on the immune cell and, thus, is not simply a function of competition between inhibitory receptors and costimulatory receptors for binding of costimulatory polypeptides (Fallarino et al. (1998) *J. Exp. Med.* 188:205). Transmission of an inhibitory signal to an immune cell can result in unresponsiveness or anergy or programmed cell death in the immune cell. Preferably transmission of an inhibitory signal operates through a mechanism that does not involve apoptosis. As used herein the term "apoptosis" includes programmed cell death which may be characterized using techniques which are known in the art. Apoptotic cell death may be characterized, e.g., by cell shrinkage, membrane blebbing and chromatin condensation culminating in cell fragmentation. Cells undergoing apoptosis also display a characteristic pattern of internucleosomal DNA cleavage. Depending upon the form of the polypeptide that binds to a receptor, a signal can either be transmitted (e.g., by a multivalent form of an inhibitory receptor ligand) or a signal may be inhibited (e.g., by a soluble, monovalent form of an inhibitory receptor ligand), for instance by competing with activating forms of the ligand for binding to one or more natural binding partners. However, there are instances in which a soluble polypeptide may be stimulatory. The effects of a modulatory agent may be easily demonstrated using routine screening assays as described herein.

The term "cytokine" refers to a substance secreted by certain cells of the immune system and has a biological effect on other cells. Cytokines may be a number of different substances such as interferons, interleukins and growth factors.

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of a biomarker-mediated analysis encompassed by the present invention. One example is determining whether to provide targeted therapy against a cancer to provide therapy using an agent encompassed by the present invention that modulates one or more biomarkers. Another example is starting an adjuvant therapy after surgery whose purpose is to decrease the risk of recurrence. Still another example is to modify the dosage of a particular chemotherapy. The determination may, in addition to the results of the analysis according to the present invention, be based on personal characteristics of the subject to be treated. In most cases, the actual determination of the suitable treatment regimen for the subject will be performed by the attending physician or doctor.

The term "endotoxin-free" or "substantially endotoxin-free" refers to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art. Endotoxins may be detected using routine techniques known in the art. For example, the limulus amebocyte lysate assay, which utilizes blood from the horseshoe crab, is a very sensitive assay for detecting presence of endotoxin. In this test, very low levels of LPS may cause detectable coagulation of the limulus lysate due a powerful enzymatic cascade that amplifies this reaction. Endotoxins may also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/ml, or any range in between, inclusive, such as 0.05 to 10 EU/ml. Typically, 1 ng lipopolysaccharide (LPS) corresponds to about 1-10 EU.

The term "epitope" refers to a determinant or site on an antigen against which an antigen-binding protein (e.g., an immunoglobulin, antibody, or antigen-binding fragment) binds. The epitopes of protein antigens may be either linear epitopes or conformational epitopes. A linear epitope refers to an epitope formed from a contiguous, linear sequence of linked amino acids. Linear epitopes of protein antigens are typically retained upon exposure to chemical denaturants (e.g., acids, bases, solvents, cross-linking reagents, chaotropic agents, disulfide bond reducing agents) or physical denaturants (e.g., thermal heat, radioactivity, or mechanical shear or stress). By contrast, a conformational epitope refers to an epitope formed from non-contiguous amino acids juxtaposed by tertiary folding of a polypeptide. Conformational epitopes are typically lost upon treatment with denaturants. An epitope typically includes at least 3, 4, 5, 6, 7, 8, 9, 10, 11, 12, 13, 14, 15, or more amino acids in a unique spatial conformation. In some embodiments, an epitope includes fewer than 25, 24, 23, 22, 21, 20, 19, 18, 17, 16, 15, 14, 13, 12, 11, 10, 9, 8, 7, 6 or 5 amino acids in a unique spatial conformation. Generally, an antibody, or antigen-binding fragment thereof, specific for a particular target molecule will preferentially recognize and bind to a specific epitope on the target molecule within a complex mixture of proteins and/or macromolecules. In some embodiments, an epitope does not include all amino acids of the extracellular domain of a biomarker protein.

The term "expression signature" or "signature" refers to a group of one or more expressed biomarkers indicative of a state of interest. For example, the genes, proteins, and the like making up this signature may be expressed in a specific cell lineage, stage of differentiation, or during a particular biological response. The biomarkers may reflect biological aspects of the tumors in which they are expressed, such as the inflammatory state of a cell, the cell of origin of a cancer, the nature of a non-malignant cells in the biopsy, and the oncogenic mechanisms responsible for the cancer. Expression data and gene expression levels may be stored on computer readable media, e.g., the computer readable medium used in conjunction with a microarray or chip reading device. Such expression data may be manipulated to generate expression signatures.

The term "fixed" or "affixed" refers to a substance that is covalently or non-covalently associated with a substrate such the substrate may be rinsed with a fluid (e.g. standard saline citrate, pH 7.4) without a substantial fraction of the molecule dissociating from the substrate.

The term "gene" encompasses a nucleotide (e.g., DNA) sequence that encodes a molecule (e.g., RNA, protein, etc.) that has a function. A gene generally comprises two complementary nucleotide strands (i.e., dsDNA), a coding strand and a non-coding strand. When referring to DNA transcription, the coding strand is the DNA strand whose base sequence corresponds to the base sequence of the RNA transcript produced (although with thymine replaced by uracil). The coding strand contains codons, while the non-coding strand contains anticodons. During transcription, RNA Pol II binds the non-coding strand, reads the anti-codons, and transcribes their sequence to synthesize an RNA transcript with complementary bases. In some embodiments, the gene sequence (i.e., DNA sequence) listed is the sequence of the coding strand.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. In some embodiments, a "function-conservative variant" also includes a polypeptide which has at least 80%, 81%, 82%, 83%, 83%, 84%, 85%, 86%, 87%, 88%, 89%, 90%, 91%, 92%, 93%, 94%, 95%, 96%, 97%, 98%, 99%, or more amino acid identity as determined by BLAST or FASTA algorithms, and which has the same or substantially similar properties or functions as the native or parent protein to which it is compared.

The term "gene product" (also referred to herein as "gene expression product" or "expression product") encompasses products resulting from expression of a gene, such as nucleic acids (e.g., mRNA) transcribed from the gene, and polypeptides or proteins arising from translation of such mRNA. It will be appreciated that certain gene products may undergo processing or modification, e.g., in a cell. For example, mRNA transcripts may be spliced, polyadenylated, etc., prior to translation, and/or polypeptides may undergo co-translational or post-translational processing, such as removal of secretion signal sequences, removal of organelle targeting sequences, or modifications such as phosphorylation, glycosylation, methylation, fatty acylation, etc. The term "gene product" encompasses such processed or modified forms. Genomic mRNA and polypeptide sequences from a variety of species, including human, are known in the art and are available in publicly accessible databases such as those available at the National Center for Biotechnology Information (ncbi.nih.gov) or Universal Protein Resource (uniprot.org). Other databases include, e.g., GenBank, RefSeq, Gene, UniProtKB/SwissProt, UniProtKB/Trembl, and the like. In general, sequences in the NCBI Reference Sequence database may be used as gene product sequences for a gene of interest. It will be appreciated that multiple alleles of a gene may exist among individuals of the same species. Multiple isoforms of certain proteins may exist, e.g., as a result of alternative RNA splicing or editing. In general, where aspects of this disclosure pertain to a gene or gene product, embodiments pertaining to allelic variants or isoforms are encompassed, if applicable, unless indicated otherwise. Certain embodiments may be directed to particular sequence(s), e.g., particular allele(s) or isoform(s).

The term "generating" encompasses any manner in which a desired result is achieved, such as by direct or indirect action. For example, cells having modulated phenotypes described herein may be generated by direct action, such as by contact with at least one agent that modulates one or more biomarkers described herein, and/or by indirect action, such as by propagating cells having a desired physical, genetic, and/or phenotypic attributes.

The term "glycosylation pattern" is the pattern of carbohydrate units that are covalently attached to a protein, more specifically to an immunoglobulin protein. A glycosylation pattern of a heterologous antibody may be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The terms "high," "low," "intermediate," and "negative" in connection with cellular biomarker expression refers to the amount of the biomarker expressed relative to the cellular expression of the biomarker by one or more reference cells. Biomarker expression may be determined according to any method described herein including, without limitation, an analysis of the cellular level, activity, structure, and the like, of one or more biomarker genomic nucleic acids, ribonucleic acids, and/or polypeptides. In one embodiment, the terms refer to a defined percentage of a population of cells expressing the biomarker at the highest, intermediate, or lowest levels, respectively. Such percentages may be defined as the top 0.1%, 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15% or more, or any range in between, inclusive, of a population of cells that either highly express or weakly express the biomarker. The term "low" excludes cells that do not detectably express the biomarker, since such cells are "negative" for biomarker expression. The term "intermediate" includes cells that express the biomarker, but at levels lower than the population expressing it at the "high" level. In another embodiment, the terms may also refer to, or in the alternative refer to, cell populations of biomarker expression identified by qualitative or statistical plot regions. For example, cell populations sorted using flow cytometry may be discriminated on the basis of biomarker expression level by identifying distinct plots based on detectable moiety analysis, such as based on mean fluorescence intensities and the like, according to well-known methods in the art. Such plot regions may be refined according to number, shape, overlap, and the like based on well-known methods in the art for the biomarker of interest. In still another embodiment, the terms may also be determined according to the presence or absence of expression for additional biomarkers.b The term "substantially identical" refers to a nucleic acid or amino acid sequence that, when optimally aligned, for example using the methods described below, share at least 60%, 65%, 70%, 75%, 80%, 85%, 90%, 95%, 96%, 97%, 98%, 99%, or 100% sequence identity with a second nucleic acid or amino acid sequence. "Substantial identity" may be used to refer to various types and lengths of sequence, such as full-length sequence, functional domains, coding and/or regulatory sequences, exons, introns, promoters, and genomic sequences. Percent sequence identity between two polypeptides or nucleic acid sequences is determined in various ways that are within the skill in the art, for instance, using publicly available computer software such as BLAST program (Basic Local Alignment Search Tool; (Altschul et al. (1995) *J. Mol. Biol.* 215:403-410), BLAST-2, BLAST-P, BLAST-N, BLAST-X, WU-BLAST-2, ALIGN, ALIGN-2, CLUSTAL, or Megalign (DNASTAR) software. In addition, those skilled in the art may determine appropriate parameters for measuring alignment, including any algorithms needed to achieve maximal alignment over the length of the sequences being compared. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "immune cell" refers to a cell that is capable of participating, directly or indirectly, in an immune response. Immune cells include, but are not limited to T cells, B cells, antigen presenting cells, dendritic cells, natural killer (NK) cells, natural killer T (NK) cells, lymphokine-activated killer (LAK) cells, monocytes, macrophages, eosinophils, basophils, neutrophils, granulocytes, mast cells, platelets, Langerhan's cells, stem cells, peripheral blood mononuclear cells, cytotoxic T cells, tumor infiltrating lymphocytes (TIL), and the like. An "antigen presenting cell" (APC) is a cell that are capable of activating T cells, and includes, but is not limited to, monocytes/macrophages, B cells and dendritic cells (DCs). The term "dendritic cell" or "DC" refers to any member of a diverse population of morphologically similar cell types found in lymphoid or non-lymphoid tissues. These cells are characterized by their distinctive morphology and high levels of surface MHC-class II expression. DCs may be isolated from a number of tissue sources. DCs have a high capacity for sensitizing MHC-restricted T cells and are very effective at presenting antigens to T cells in situ. The antigens may be self-antigens that are expressed during T cell development and tolerance, and foreign antigens that are present during normal immune processes. The term "neutrophil" generally refers to a white blood cell that makes up part of the innate immune system. Neutrophils typically have segmented nucleic containing about 2-5 lobes. Neutrophils frequently migrate to the site of an injury within minutes following trauma. Neutrophils function by releasing cytotoxic compounds, including oxidants, proteases, and cytokines, at a site of injury or infection. The term "activated DC" is a DC that has been pulsed with an antigen and capable of activating an immune cell. The term "NK cell" has its general meaning in the art and refers to a natural killer (NK) cell. One skilled in the art may easily identify NK cells by determining for instance the expression of specific phenotypic marker (e.g., CD56) and identify its function based on, for example, the ability to express different kind of cytokines or the ability to induce cytotoxicity. The term "B cell" refers to an immune cell derived from the bone marrow and/or spleen. B cells may develop into plasma cells which produce antibodies. The term "T cell" refers to a thymus-derived immune cell that participates in a variety of cell-mediated immune reactions, including CD8+ T cell and CD4+ T cell. Conventional T cells, also known as Tconv or Teffs, have effector functions (e.g., cytokine secretion, cytotoxic activity, anti-self-recognition, and the like) to increase immune responses by virtue of their expression of one or more T cell receptors. Tconv or Teffs are generally defined as any T cell population that is not a Treg and include, for example, naïve T cells, activated T cells, memory T cells, resting Tconv, or Tconv that have differentiated toward, for example, the Th1 or Th2 lineages. In some embodiments, Teffs are a subset of non-regulatory T cells (Tregs). In some embodiments, Teffs are CD4+ Teffs or CD8+ Teffs, such as CD4+ helper T lymphocytes (e.g., Th0, Th1, Tfh, or Th17) and CD8+ cytotoxic T cells (lymphocytes). As described further herein, cytotoxic T cells are CD8+ T lymphocytes. "Naïve Tconv" are $CD4^+$ T cells that have differentiated in bone marrow, and successfully underwent a positive and negative processes of central selection in a thymus, but have not yet been activated by exposure to an antigen. Naïve Tconv are commonly characterized by surface expression of L-selectin (CD62L), absence of activation markers such as CD25, CD44 or CD69, and absence of memory markers such as CD45RO. Naïve Tconv are therefore believed to be quiescent and non-dividing, requiring interleukin-7 (IL-7) and interleukin- 15 (IL-15) for homeostatic survival (see, at least WO 2010/101870). The presence and activity of such cells are undesired in the context of suppressing immune responses. Unlike Tregs, Tconv are not anergic and may proliferate in response to antigen-based T cell receptor activation (Lechler et al. (2001) *Philos. Trans. R. Soc. Lond. Biol. Sci.* 356:625-637). In tumors, exhausted cells may present hallmarks of anergy.

The term "immune disorder" includes immune diseases, conditions, and predispositions to, including, but not limited to, cancer, chronic inflammatory disease and disorders (including, e.g., Crohn's disease, inflammatory bowel disease, reactive arthritis, and Lyme disease), insulin-dependent diabetes, organ specific autoimmunity (including, e.g., multiple sclerosis, Hashimoto's thyroiditis, autoimmune uveitis, and Grave's disease), contact dermatitis, psoriasis, graft rejection, graft versus host disease, sarcoidosis, atopic conditions (including, e.g., asthma and allergy including, but not limited to, allergic rhinitis and gastrointestinal allergies such as food allergies), eosinophilia, conjunctivitis, glomerular nephritis, systemic lupus erythematosus, scleroderma, certain pathogen susceptibilities such as helminthic (including, e.g., leishmaniasis) and certain viral infections (including, e.g., HIV and bacterial infections such as tuberculosis and lepromatous leprosy) and malaria.

The term "immune response" means a defensive response a body develops against a "foreigner," such as bacteria, viruses, and pathogens, as well as against targets that may not necessarily originate outside the body, including, without limitation, a defensive response against substances naturally present in the body (e.g., autoimmunity against self-antigens) or against transformed (e.g., cancer) cells. An immune response in particular is the activation and/or action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including antibodies (humoral response), cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues. An anti-cancer immune response refers to an immune surveillance mechanism by which a body recognizes abnormal tumor cells and initiates both the innate and adaptive of the immune system to eliminate dangerous cancer cells.

The term "immunoregulator" refers to a substance, an agent, a signaling pathway or a component thereof that regulates an immune response. The terms "regulating," "modifying," or "modulating" with respect to an immune response refer to any alteration in a cell of the immune system or in the activity of such cell. Such regulation includes stimulation or suppression of the immune system (or a distinct part thereof), which may be manifested by an increase or decrease in the number of various cell types, an increase or decrease in the activity of these cells, or any other changes which may occur within the immune system. Both inhibitory and stimulatory immunoregulators have been identified, some of which may have enhanced function in the cancer microenvironment.

The term "immunotherapeutic agent" may include any molecule, peptide, antibody or other agent which may stimulate a host immune system to generate an immune response to a tumor or cancer in the subject. Various immunotherapeutic agents are useful in the compositions and methods described herein.

The term "inhibit" or "downregulate" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. Similarly, a biological function, such as the function of a protein, is inhibited if it is decreased as compared to a reference state, such as a control like a wild-type state. Such inhibition or deficiency may be induced, such as by application of an agent at a particular time and/or place, or may be constitutive, such as by a heritable mutation. Such inhibition or deficiency may also be partial or complete (e.g., essentially no measurable activity in comparison to a reference state, such as a control like a wild-type state). In some embodiments, essentially complete inhibition or deficiency is referred to as "blocked." In one embodiment, the term refers to reducing the level of a given output or parameter to a quantity (e.g., background staining, biomarker signaling, biomarker immunoinhibitory function, and the like) which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. A reduced level of a given output or parameter need not, although it may, mean an absolute absence of the output or parameter. The invention does not require, and is not limited to, methods that wholly eliminate the output or parameter. The given output or parameter may be determined using methods well-known in the art, including, without limitation, immunohistochemical, molecular biological, cell biological, clinical, and biochemical assays, as discussed herein and in the examples. The term "promote" or "upregulate" has the opposite meaning.

The term "inhibitory signal" refers to a signal transmitted via an inhibitory receptor (e.g., CTLA4, PD-1, and the like) for a polypeptide on an immune cell. Such a signal antagonizes a signal via an activating receptor (e.g., via a TCR, CD3, BCR, TMIGD2, or Fc polypeptide) and may result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

The "innate immune system" is a non-specific immune system that comprises the cells (e.g., natural killer cells, mast cells, eosinophils, basophils; and the phagocytic cells including macrophages, neutrophils, and dendritic cells) and mechanisms that defend the host from infection by other organisms. An innate immune response may initiate the productions of cytokines, and active complement cascade and adaptive immune response. The adaptive immune system is specific immune system that is required and involved in highly specialized systemic cell activation and processes, such as antigen presentation by an antigen presenting cell; antigen specific T cell activation and cytotoxic effect.

The term "interaction," when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting costimulation). To inhibit such an interaction results in the disruption of the activity of one or more molecules involved in the interaction. To enhance such an interaction is to prolong or increase the likelihood of said physical contact, and prolong or increase the likelihood of said activity.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

The term "isotype" refers to the antibody class (e.g., IgM, IgG1, IgG2C, and the like) that is encoded by heavy chain constant region genes.

The term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA. In some embodiments, the $K_D$ of an antibody, or antigen binding fragment thereof, described herein to a biomarker of interest, such as one or more biomarkers listed in Table 1, may be about 0.002 to about 200 nM. In some embodiments, the binding affinity is any of about 250 nM, 200 nM, about 100 nM, about 50 nM, about 45 nM, about 40 nM, about 35 nM, about 30 nM, about 25 nM, about 20 nM, about 15 nM, about 10 nM, about 8 nM, about 7.5 nM, about 7 nM, about 6.5 nM, about 6 nM, about 5.5 nM, about 5 nM, about 4 nM, about 3 nM, about 2 nM, about 1 nM, about 500 pM, about 100 pM, about 60 pM, about 50 pM, about 20 pM, about 15 pM, about 10 pM, about 5 pM, about 2 pM, or less. In some embodiments, the binding affinity is less than any of about 250 nM, about 200 nM, about 100 nM, about 50 nM, about 30 nM, about 20 nM, about 10 nM, about 7.5 nM, about 7 nM, about 6.5 nM, about 6 nM, about 5 nM, about 4.5 nM, about 4 nM, about 3.5 nM, about 3 nM, about 2.5 nM, about 2 nM, about 1.5 nM, about 1 nM, about 500 pM, about 100 pM, about 50 pM, about 20 pM, about 10 pM, about 5 pM, or about 2 pM, or less, or any range in between, such as about 5 nM to about 35 nM.

The term "kd" or "$k_{off}$" refers to the off-rate constant for the dissociation of an antibody from an antibody/antigen complex. The value of kd is a numeric representation of the fraction of complexes that decay or dissociate per second, and is expressed in units $sec^{-1}$.

The term "ka" or "$k_{on}$" refers to the on-rate constant for the association of an antibody with an antigen. The value of ka is a numeric representation of the number of antibody/antigen complexes formed per second in a 1 molar (1M) solution of antibody and antigen, and is expressed in units $M^{-1}sec^{-1}$.

The term "microenvironment" generally refers to the localized area in a tissue area of interest and may, for example, refer to a "tumor microenvironment." The term "tumor microenvironment" or "TME" refers to the surrounding microenvironment that constantly interacts with tumor cells which is conducive to allow cross-talk between tumor cells and its environment. The tumor microenvironment may include the cellular environment of the tumor, surrounding blood vessels, immune cells, fibroblasts, bone marrow derived inflammatory cells, lymphocytes, signaling molecules and the extracellular matrix. The tumor environment may include tumor cells or malignant cells that are aided and influenced by the tumor microenvironment to ensure growth and survival. The tumor microenvironment may also include tumor-infiltrating immune cells, such as lymphoid and myeloid cells, which may stimulate or inhibit the antitumor immune response, and stromal cells such as tumor-associated fibroblasts and endothelial cells that contribute to the tumor's structural integrity. Stromal cells may include cells that make up tumor-associated blood vessels, such as endothelial cells and pericytes, which are cells that contribute to structural integrity (fibroblasts), as well as tumor-associated macrophages (TAMs) and infiltrating immune cells, including monocytes, neutrophils (PMN), dendritic cells (DCs), T and B cells, mast cells, and natural killer (NK) cells. The stromal cells make up the bulk of tumor cellularity, while the dominating cell type in solid tumors is the macrophage.

The term "modulating" and its grammatical equivalents refer to either increasing or decreasing (e.g., silencing), in other words, either up-regulating or down-regulating.

The "normal" level of expression of a biomarker is the level of expression of the biomarker in cells of a subject, e.g., a human patient, not afflicted with a cancer.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

Such "significance" levels may also be applied to any other measured parameter described herein, such as for expression, inhibition, cytotoxicity, cell growth, and the like.

The term "peripheral blood cell subtypes" refers to cell types normally found in the peripheral blood including, but is not limited to, eosinophils, neutrophils, T cells, monocytes, macrophages, NK cells, granulocytes, and B cells.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus, internally, or at the carboxyl-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. They may be, for example, at least and/or including 10, 15, 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340 or more long so long as they are less than the length of the full-length polypeptide. Alternatively, they may be no longer than and/or excluding such a range so long as they are less than the length of the full-length polypeptide.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as one or more modulators of one or more biomarkers described herein and/or evaluate the disease state. A pre-determined biomarker amount and/or activity measurement(s) may be determined in populations of patients, such as those with or without cancer. The pre-determined biomarker amount and/or activity measurement(s) may be a single number, equally applicable to every patient, or the pre-determined biomarker amount and/or activity measurement(s) may vary according to specific subpopulations of patients. Age, weight, height, and other factors of a subject may affect the pre-determined biomarker amount and/or activity measurement(s) of the individual. Furthermore, the pre-determined biomarker amount and/or activity may be determined for each subject individually. In one embodiment, the amounts determined and/or compared in a method described herein are based on absolute measurements. In another embodiment, the amounts determined and/or compared in a method described herein are based on relative measurements, such as ratios (e.g., cell ratios or serum biomarker normalized to the expression of housekeeping or otherwise generally constant biomarker). The pre-determined biomarker amount and/or activity measurement(s) may be any suitable standard. For example, the pre-determined biomarker amount and/or activity measurement(s) may be obtained from the same or a different human for whom a patient selection is being assessed. In one embodiment, the pre-determined biomarker amount and/or activity measurement(s) may be obtained from a previous assessment of the same patient. In such a manner, the progress of the selection of the patient may be monitored over time. In addition, the control may be obtained from an assessment of another human or multiple humans, e.g., selected groups of humans, if the subject is a human. In such a manner, the extent of the selection of the human for whom selection is being assessed may be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of a desired. Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g., a human, afflicted with cancer; (3) its absolute or relatively modulated presence or absence in clinical subset of patients with cancer (e.g., those responding to a particular modulator of T-cell mediated cytotoxicity alone or in combination with immunotherapy or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes may be either synthesized by one skilled in the art, or derived from appropriate biological preparations. For purposes of detection of the target molecule, probes may be specifically designed to be labeled, as described herein. Examples of molecules that may be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis may be surgery, development of a clinical subtype of cancer (e.g., solid tumors, such as lung cancer, melanoma, and renal cell carcinoma), development of one or more clinical factors, development of intestinal cancer, or recovery from the disease.

The term "ratio" refers to a relationship between two numbers (e.g., scores, summations, and the like). Although, ratios may be expressed in a particular order (e.g., a to b or a:b), one of ordinary skill in the art will recognize that the underlying relationship between the numbers may be expressed in any order without losing the significance of the underlying relationship, although observation and correlation of trends based on the ratio may be reversed.

The term "rearranged" refers to a configuration of a heavy chain or light chain immunoglobulin locus wherein a V segment is positioned immediately adjacent to a D-J or J segment in a conformation encoding essentially a complete $V_H$ and $V_L$ domain, respectively. A rearranged immunoglobulin gene locus may be identified by comparison to germline DNA; a rearranged locus will have at least one recombined heptamer/nonamer homology element. By contrast, the term "unrearranged" or "germline configuration" in reference to a V segment refers to the configuration wherein the V segment is not recombined so as to be immediately adjacent to a D or J segment.

The term "receptor" refers to a naturally occurring molecule or complex of molecules that is generally present on the surface of cells of a target organ, tissue or cell type.

The term "cancer response," "response to immunotherapy," or "response to modulators of T-cell mediated cytotoxicity/immunotherapy combination therapy" relates to any response of the hyperproliferative disorder (e.g., cancer) to an cancer agent, such as a modulator of T-cell mediated cytotoxicity, and an immunotherapy, preferably to a change in tumor mass and/or volume after initiation of neoadjuvant or adjuvant therapy. The term "neoadjuvant therapy" refers to a treatment given before the primary treatment. Examples of neoadjuvant therapy may include chemotherapy, radiation therapy, and hormone therapy. Hyperproliferative disorder response may be assessed, for example for efficacy or in a neoadjuvant or adjuvant situation, where the size of a tumor after systemic intervention may be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment may be expanded to include response to chemotherapy, probability of survival, probability of metastasis within a given time period, and probability of tumor recurrence. For example, in order to determine appropriate threshold values, a particular cancer therapeutic regimen may be administered to a population of subjects and the outcome may be correlated to biomarker measurements that were determined prior to administration of any cancer therapy. The outcome measurement may be pathologic response to therapy given in the neoadjuvant setting. Alternatively, outcome measures, such as overall survival and disease-free survival may be monitored over a period of time for subjects following cancer therapy for which biomarker measurement values are known. In certain embodiments, the doses administered are standard doses known in the art for cancer therapeutic agents. The period of time for which subjects are monitored may vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy may be determined using well-known methods in the art, such as those described in the Examples section.

As indicated, the terms may also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 5%, 10%, 15%, 20%, 25%, 30%, 35%, 40%, 45%, 50%, 55%, 60%, 65%, 70%, 75%, 80%, 85%, 90%, 95%, 100%, or more, such 2-fold, 3-fold, 4-fold, 5-fold, 10-fold, 15-fold, 20-fold or more, or any range in between, inclusive. The reduction in response may be measured by comparing with the same cancer sample or mammal before the resistance is acquired, or by comparing with a different cancer sample or a mammal that is known to have no resistance to the therapeutic treatment. A typical acquired resistance to chemotherapy is called "multidrug resistance." The multidrug resistance may be mediated by P-glycoprotein or may be mediated by other mechanisms, or it may occur when a mammal is infected with a multi-drug-resistant microorganism or a combination of microorganisms. The determination of resistance to a therapeutic treatment is routine in the art and within the skill of an ordinarily skilled clinician, for example, may be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The term "sample" used for detecting or determining the presence or level of at least one biomarker is typically brain tissue, cerebrospinal fluid, whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the methods encompassed by the present invention further comprise obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the therapies. An increased sensitivity or a reduced sensitivity to a therapeutic treatment is measured according to a known method in the art for the particular treatment and methods described herein below, including, but not limited to, cell proliferative assays (Tanigawa et al. (1982) *Cancer Res.* 42:2159-2164) and cell death assays (Weisenthal et al. (1984) *Cancer Res.* 94:161-173; Weisenthal et al. (1985) *Cancer Treat Rep.* 69:615-632; Weisenthal et al., In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993:415-432; Weisenthal (1994) *Contrib. Gynecol. Obstet.* 19:82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 5%, 10%, 15%, 20%, 25%, 30%, 35%, 40%, 45%, 50%, 55%, 60%, 65%, 70%, 75%, 80%, 85%, 90%, 95%, 100%, or more, such 2-fold, 3-fold, 4-fold, 5-fold, 10-fold, 15-fold, 20-fold or more, or any range in between, inclusive, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy may be equally applied to methods for sensitizing hyperproliferative or otherwise cancerous cells (e.g., resistant cells) to the cancer therapy.

The term "selective modulator" or "selectively modulate" as applied to a biologically active agent refers to the agent's ability to modulate the target, such as a cell population, signaling activity, etc. as compared to off-target cell population, signaling activity, etc. via direct or interact interaction with the target. For example, an agent that selectively inhibits the interaction between a protein and one natural binding partner over another interaction between the protein and another binding partner, and/or such interaction(s) on a cell population of interest, inhibits the interaction at least about 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 2× (times), 3×, 4×, 5×, 6×, 7×, 8×, 9×, 10×, 15×, 20×, 25×, 30×, 35×, 40×, 45×, 50×, 55×, 60×, 65×, 70×, 75×, 80×, 85×, 90×, 95×, 100×, 105×, 110×, 120×, 125×, 150×, 200×, 250×, 300×, 350×, 400×, 450×, 500×, 600×, 700×, 800×, 900×, 1000×, 1500×, 2000×, 2500×, 3000×, 3500×, 4000×, 4500×, 5000×, 5500×, 6000×, 6500×, 7000×, 7500×, 8000×, 8500×, 9000×, 9500×, 10000×, or greater, or any range in between, inclusive, against at least one other binding partner. Such metrics are typically expressed in terms of relative amounts of agent required to reduce the interaction/activity by half. Such metrics apply to any other selectivity arrangement, such as binding of a nucleic acid molecule to one or more target sequences.

More generally, the term "selective" refers to a preferential action or function. The term "selective" may be quantified in terms of the preferential effect in a particular target of interest relative to other targets. For example, a measured variable (e.g., modulation of biomarker expression in desired cells versus other cells, the enrichment and/or deletion of desired cells versus other cells, etc.) may be 10%, 20%, 25%, 30%, 35%, 40%, 45%, 50%, 55%, 60%, 65%, 70%, 75%, 80%, 85%, 90%, 95%, 1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 45-fold, 50-fold, 55-fold, 60-fold, 70-fold, 80-fold, 90-fold, 100-fold, or greater or any range in between inclusive (e.g., 50% to 16-fold), different in a target of interest versus unintended or undesired targets. The same fold analysis may be used to confirm the magnitude of an effect in a given tissue, cell population, measured variable, and/or measured effect, and the like, such as cell ratios, hyperproliferative cell growth rate or volume, cell proliferation rate, etc. cell numbers, and the like.

By contrast, the term "specific" refers to an exclusionary action or function. For example, specific modulation of an interaction between a protein and one binding partner refers to the exclusive modulation of that interaction and not to any significant modulation of the interaction between the protein and another binding partner. In another example, specific binding of an antibody to a predetermined antigen refers to the ability of the antibody to bind to the antigen of interest without binding to other antigens. Typically, the antibody binds with an affinity ($K_D$) of approximately less than $1\times10^{-7}$ M, such as approximately less than $10^{-8}$ M, $10^{-9}$ M, $10^{-10}$ M, $10^{-11}$ M, or even lower when determined using an appropriate assays, such as using surface plasmon resonance (SPR) technology in a BIACORE® assay instrument, using an antigen of interest as the analyte and the antibody as the ligand. The phrases "an antibody recognizing an antigen" and "an antibody specific for an antigen" are used interchangeably herein with the term "an antibody which binds specifically to an antigen."

Methods for determining cross-reactivity include standard binding assays as described herein, such as using surface plasmon resonance (SPR) analyses, flow cytometric analyses, etc.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which may be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. The term is intended to encompass all stereoisomers, geometric isomers, tautomers, and isotopes of a chemical structure of interest, unless otherwise indicated.

The term "subject" refers to an animal, vertebrate, mammal, or human, especially one to whom an agent is administered, e.g., for experimental, diagnostic, and/or therapeutic purposes, or from whom a sample is obtained or on whom a procedure is performed. In some embodiments, a subject is a mammal, e.g., a human, non-human primate, rodent (e.g., mouse or rat), domesticated animals (e.g., cows, sheep, cats, dogs, and horses), or other animals, such as llamas and camels. In some embodiments, the subject is human. In some embodiments, the subject is a human subject with a cancer. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment may be expanded to include response to chemotherapy, probability of survival, probability of metastasis within a given time period, and probability of tumor recurrence.

The term "synergistic effect" refers to the combined effect of two or more agents (e.g., a modulator of biomarkers listed in Table 1 and immunotherapy combination therapy) that is greater than the sum of the separate effects of the cancer agents/therapies alone.

The term "target" refers to a gene or gene product that is modulated, inhibited, or silenced by an agent, composition, and/or formulation described herein. A target gene or gene product includes wild-type and mutant forms. Non-limiting, representative lists of targets encompassed by the present invention are provided in Table 1. Similarly, the term "target", "targets", or "targeting" used as a verb refers to modulating the activity of a target gene or gene product. Targeting may refer to upregulating or downregulating the activity of a target gene or gene product.

The term "therapeutic effect" encompasses a local or systemic effect in animals, particularly mammals, and more particularly humans, caused by a pharmacologically active substance. The term thus means any substance intended for use in the diagnosis, cure, mitigation, treatment, or prevention of disease or in the enhancement of desirable physical or mental development and conditions in an animal or human. A prophylactic effect encompassed by the term encompasses delaying or eliminating the appearance of a disease or condition, delaying or eliminating the onset of symptoms of a disease or condition, slowing, halting, or reversing the progression of a disease or condition, or any combination thereof.

The term "effective amount" or "effective dose" of an agent (including a composition and/or formulation comprising such an agent) refers to the amount sufficient to achieve a desired biological and/or pharmacological effect, e.g., when delivered to a cell or organism according to a selected administration form, route, and/or schedule. As will be appreciated by those of ordinary skill in this art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered to a subject in a single dose, or through use of multiple doses, in various embodiments. The term "effective amount" may be a "therapeutically effective amount."

The terms "therapeutically effective amount" refers to that amount of an agent that is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) may be measured and may be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) may be measured and may be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, similarly, the $IC_{50}$ (i.e., the concentration which achieves half-maximal cytotoxic or cytostatic effect on cancer cells) may be measured and may be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay may be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy may be achieved.

More generally, the term "$EC_{50}$" refers to the concentration of an agent, like an antibody or antigen-binding fragment thereof, which induces a response that is 50% of the maximal response, such as hallway between the maximum and baseline response in an in vitro and/or in vivo assay.

The term "tolerance" or "unresponsiveness" includes refractivity of cells, such as immune cells, to stimulation, e.g., stimulation via an activating receptor or a cytokine. Unresponsiveness may occur, e.g., because of exposure to immunosuppressants or exposure to high doses of antigen. Several independent methods may induce tolerance. One mechanism is referred to as "anergy," which is defined as a state where cells persist in vivo as unresponsive cells rather than differentiating into cells having effector functions. Such refractivity is generally antigen-specific and persists after exposure to the tolerizing antigen has ceased. For example, anergy in T cells is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells may, however, proliferate if cultured with cytokines (e.g., IL-2). For example, T cell anergy may also be observed by the lack of IL-2 production by T lymphocytes as measured by ELISA or by a proliferation assay using an indicator cell line. Alternatively, a reporter gene construct may be used. For example, anergic T cells fail to initiate IL-2 gene transcription induced by a heterologous promoter under the control of the 5' IL-2 gene enhancer or by a multimer of the AP1 sequence that may be found within the enhancer (Kang et al. (1992) *Science* 257:1134). Another mechanism is referred to as "exhaustion." T cell exhaustion is a state of T cell dysfunction that arises during many chronic infections and cancer. It is defined by poor effector function, sustained expression of inhibitory receptors and a transcriptional state distinct from that of functional effector or memory T cells.

A "transcribed polynucleotide" or "nucleotide transcript" is a polynucleotide (e.g., an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g., splicing), if any, of the RNA transcript, and reverse transcription of the RNA transcript.

The term "treat" refers to the therapeutic management or improvement of a condition (e.g., a disease or disorder) of interest. Treatment may include, but is not limited to, administering an agent or composition (e.g., a pharmaceutical composition) to a subject. Treatment is typically undertaken in an effort to alter the course of a disease (which term is used to indicate any disease, disorder, syndrome or undesirable condition warranting or potentially warranting therapy) in a manner beneficial to the subject. The effect of treatment may include reversing, alleviating, reducing severity of, delaying the onset of, curing, inhibiting the progression of, and/or reducing the likelihood of occurrence or recurrence of the disease or one or more symptoms or manifestations of the disease. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. A therapeutic agent may be administered to a subject who has a disease or is at increased risk of developing a disease relative to a member of the general population. In some embodiments, a therapeutic agent may be administered to a subject who has had a disease but no longer shows evidence of the disease. The agent may be administered e.g., to reduce the likelihood of recurrence of evident disease. A therapeutic agent may be administered prophylactically, i.e., before development of any symptom or manifestation of a disease. "Prophylactic treatment" refers to providing medical and/or surgical management to a subject who has not developed a disease or does not show evidence of a disease in order, e.g., to reduce the likelihood that the disease will occur or to reduce the severity of the disease should it occur. The subject may have been identified as being at risk of developing the disease (e.g., at increased risk relative to the general population or as having a risk factor that increases the likelihood of developing the disease.

The term "unresponsiveness" includes refractivity of cancer cells to therapy or refractivity of therapeutic cells, such as immune cells, to stimulation, e.g., stimulation via an activating receptor or a cytokine. Unresponsiveness may occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells may, however, proliferate if cultured with cytokines (e.g., IL-2). For example, T cell anergy may also be observed by the lack of IL-2 production by T lymphocytes as measured by ELISA or by a proliferation assay using an indicator cell line. Alternatively, a reporter gene construct may be used. For example, anergic T cells fail to initiate IL-2 gene transcription induced by a heterologous promoter under the control of the 5' IL-2 gene enhancer or by a multimer of the AP1 sequence that may be found within the enhancer (Kang et al. (1992) *Science* 257:1134).

The term "vaccine" refers to a composition for generating immunity for the prophylaxis and/or treatment of diseases.

In addition, there is a known and definite correspondence between the amino acid sequence of a particular protein and the nucleotide sequences that may code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) may be used to derive the polypeptide amino acid sequence, using the genetic code to translate the DNA or RNA into an amino acid sequence. Likewise, for polypeptide amino acid sequence, corresponding nucleotide sequences that may encode the polypeptide may be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that may encode the amino acid sequence.

II. Monocytes and Macrophages

Monocytes are myeloid-derived immune effector cells that circulate in the blood, bone marrow, and spleen and have limited proliferation in a steady state condition. The term "myeloid cells" may refer to a granulocyte or monocyte precursor cell in bone marrow or spinal cord, or a resemblance to those found in the bone marrow or spinal cord. The myeloid cell lineage includes circulating monocytic cells in the peripheral blood and the cell populations that they become following maturation, differentiation, and/or activation. These populations include non-terminally differentiated myeloid cells, myeloid derived suppressor cells, and differentiated macrophages. Differentiated macrophages include non-polarized and polarized macrophages, resting and activated macrophages. Without being limiting, the myeloid lineage may also include granulocytic precursors, polymorphonuclear derived suppressor cells, differentiated polymorphonuclear white blood cells, neutrophils, granulocytes, basophils, eosinophils, monocytes, macrophages, microglia, myeloid derived suppressor cells, dendritic cells and erythrocytes. Monocytes are found among peripheral blood mononuclear cells (PBMCs), which also comprise other hematopoietic and immune cells, such as B cells, T cells, NK cells, and the like. Monocytes are produced by the bone marrow from hematopoietic stem cell precursors called monoblasts. Monocytes have two main functions in the immune system: (1) they may exit the bloodstream to replenish resident macrophages and dendritic cells (DCs) under normal states, and (2) they may quickly migrate to sites of infection in the tissues and divide/differentiate into macrophages and inflammatory dendritic cells to elicit an immune response in response to inflammation signals. Monocytes are usually identified in stained smears by their large bilobate nucleus. Monocytes also express chemokine receptors and pathogen recognition receptors that mediate migration from blood to tissues during infection. They produce inflammatory cytokines and phagocytose cells. In some embodiments, myeloid cells, such as suppressive myeloid cells, monocytes, macrophages, and/or dendritic cells, of interest are identified according to CD11b+ expression and/or CD14+ expression.

As described in detail below, monocytes may differentiate into macrophages. Monocytes may also differentiate into dendritic cells, such as through the action of the cytokines granulocyte macrophage colony-stimulating factor (GM-CSF) and interleukin 4 (IL-4). In general, the term "monocytes" encompasses undifferentiated monocytes, as well as cell types that are differentiated therefrom, including macrophages and dendritic cells. In some embodiments, the term "monocytes" may refer to undifferentiated monocytes.

Macrophages are critical immune effectors and regulators of inflammation and the innate immune response. Macrophages are heterogeneous, tissue-resident, terminally-differentiated, innate myeloid cells, which have remarkable plasticity and may change their physiology in response to local cues from the microenvironment and may assume a spectrum of functional requirements from host defense to tissue homeostasis (Ginhoux et al. (2016) *Nat. Immunol.* 17:34-40). Macrophages are present in virtually all tissues in the body. They are either tissue resident macrophages, for example Kupffer cells that reside in liver, or derived from circulating monocytic precursors (i.e., monocytes) which mainly originate from bone marrow and spleen reservoirs and migrate into tissue in the steady state or in response to inflammation or other stimulating cues. For example, monocytes may be recruited from the blood to tissue to replenish tissue specific macrophages of the bone, alveoli (lung), central nervous system, connective tissues, gastrointestinal tract, live, spleen and peritoneum.

The term "tissue-resident macrophages" refers to a heterogeneous populations of immune cells that fulfill tissue-specific and/or micro-anatomical niche-specific functions such as tissue immune-surveillance, response to infection and the resolution of inflammation, and dedicated homeostatic functions. Tissue resident macrophages Local proliferation of tissue resident macrophages, which maintain colony-forming capacity, may directly give rise to populations of mature macrophages in the tissue. Tissue resident macrophages may also be identified and named according to the tissues they occupy. For example, adipose tissue macrophages occupy adipose tissue, Kupffer cells occupy liver tissue, sinus histiocytes occupy lymph nodes, alveolar macrophages (dust cells) occupy pulmonary alveoli, Langerhans cells occupy skin and mucosal tissue, histiocytes leading to giant cells occupy connective tissue, microglia occupy central nervous system (CNS) tissue, Hofbauer cells occupy placental tissue, intraglomerular mesangial cells occupy kidney tissue, osteoclasts occupy bone tissue, epithelioid cells occupy granulomas, red pulp macrophages (sinusoidal lining cells) occupy the red pulp of spleen tissue, peritoneal cavity macrophages occupy peritoneal cavity tissue, lysomac cells occupy Peyer's patch tissue, and pancreatic macrophages occupy pancreatic tissue.

Macrophages, in addition to host defense against infectious agents and other inflammation reaction, may perform different homeostatic functions, including but not limited to, development, wound healing and tissue repairing, and regulation of immune response. Macrophages, first recognized as phagocytosis cells in the body which defend infections through phagocytosis, are essential components of innate immunity. In response to pathogens and other inflammation stimuli, activated macrophages may engulf infected bacteria and other microbes; stimulate inflammation and release a cocktail of pro-inflammatory molecules to these intracellular microorganisms. After engulfing the pathogens, macrophages present pathogenic antigens to T cells to further activate adaptive immune response for defense. Exemplary pro-inflammatory molecules include cytokines IL-1β, IL-6 and TNF-α, chemokine MCP-1, CXC-5 and CXC-6, and CD40L.

In addition to their contribution to host defense against infections, macrophages play vital homeostatic roles, independent of their involvement in immune responses. Macrophages are prodigious phagocytic cells that clear erythrocytes and the released substances such as iron and hemoglobin may be recycled for the host to reuse. This clearance process is a vital metabolic contribution without which the host would not survive.

Macrophages are also involved in the removal of cellular debris that is generated during tissue remodeling, and rapidly and efficiently clear cells that have undergone apoptosis. Macrophages are believed to be involved in steady-state tissue homeostasis via the clearance of apoptotic cells. These homeostatic clearance processes are generally mediated by surface receptors on macrophages including scavenger receptors, phosphatidyl serine receptors, the thrombospondin receptor, integrins and complement receptors. These receptors that mediate phagocytosis either fail to transduce signals that induce cytokine-gene transcription or actively produce inhibitory signals and/or cytokines. The homeostatic function of macrophages is independent of other immune cells.

Macrophages may also clear cellular debris/necrotic cells that results from trauma or other damages to cells. Macrophages detect the endogenous danger signals that are present in the debris of necrotic cells through toll-like receptors (TLRs), intracellular pattern-recognition receptors and the interleukin-1 receptor (IL-1R), most of which signal through the adaptor molecule myeloid differentiation primary-response gene 88 (MyD88). The clearance of cellular debris may markedly alter the physiology of macrophages. Macrophages that clear necrosis may undergo dramatic changes in their physiology, including alterations in the expression of surface proteins and the production of cytokines and pro-inflammatory mediators. The alterations in macrophage surface-protein expression in response to these stimuli could potentially be used to identify biochemical markers that are unique to these altered cells.

Macrophages have important functions in maintaining homeostasis in many tissues such as white adipose tissue, brown adipose tissue, liver and pancreas. Tissue macrophages may quickly respond to changing conditions in a tissue, by releasing cell signaling molecules that trigger a cascade of changes allowing tissue cells to adapt. For instance, macrophages in adipose tissue regulate the production of new fat cells in response to changes in diet (e.g., macrophages in white adipose tissue) or exposure to cold temperatures (e.g., macrophages in brown adipose tissue). Macrophages in the liver, known as Kupffer cells, regulate the breakdown of glucose and lipids in response to dietary changes. Macrophages in pancreas may regulate insulin production in response to high fat diet.

Macrophages may also contribute to wound healing and tissue repair. For example, macrophages, in response to signals derived from injured tissues and cells, may be activated and induce a tissue-repair response to repair damaged tissue (Minutti et al. (2017) *Science* 356:1076-1080).

During embryonic development, macrophages also play a key role in tissue remodeling and organ development. For example, resident macrophages actively shape the development of blood vessels in neonatal mouse hearts (Leid et al. (2016) *Circ. Res.* 118:1498-1511). Microglia in the brain may produce growth factors that guide neurons and blood vessels in developing brain during embryonic development. Similarly, CD95L, a macrophage-produced protein, binds to CD95 receptors on the surface of neurons and developing blood vessels in the brains of mouse embryos and increases neuron and blood vessel development (Chen et al. (2017) *Cell Rep.* 19:1378-1393). Without the ligand, neurons branch less frequently, and the resulting adult brain exhibits less electrical activity. Monocyte-derived cells known as osteoclasts are involved in bone development, and mice that lack these cells develop dense, hardened bones—a rare condition known as osteopetrosis. Macrophages also orchestrate development of the mammary gland and assist in retinal development in the early postnatal period (Wynn et al. (2013) *Nature* 496:445-455).

As described above, macrophages regulate immune systems. In addition to the presentation of antigens to T cells, macrophages may provide immunosuppressive/inhibitory signals to immune cells in some conditions. For example, in the testis, macrophages help create a protective environment for sperm from being attacked by the immune system. Tissue resident macrophages in the testis produce immunosuppressant molecules that prevent immune cell reaction against sperm (Mossadegh-Keller et al. (2017) *J. Exp. Med.* 214: 10.1084/jem.20170829).

In addition to monocytes and macrophages, the mononuclear phagocyte system (MPS) encompasses dendritic cells (DCs). As described herein, these cell types can be classified by their ontogeny, as well as by their location, function and phenotype, according to well-known criteria in the field (see, for example, Guilliams et al. (2015) *Nat. Rev. Immunol.* 14:571-578. It is believed that this system permits a more robust classification during both steady-state and disease-associated conditions, with the benefit of spanning different tissues and across species. For example, human DCs found in lymphoid and non-lymphoid tissues are generally classified into two main groups (pDCs and 'classical' or 'myeloid' DCs). Classical or myeloid DCs have been further subdivided into two subsets on the basis of their expression of CD141 (also known as BDCA3 and thrombomodulin) and CD1c (also known as BDCA1). The gene-expression profiles and functions of human CD141+ DCs and CD1c+ DCs resemble those of mouse cDC1s and cDC2s, respectively, such that human CD141+ DCs can be referred to as cDC1s and human CD1c+ DCs can be referred to as cDC2s under a unifying nomenclature scheme. Further support for the equivalence of the mouse and human DC systems is that the injection of FLT3L into human volunteers dramatically increased the number of blood pDCs, CD141+ cDCs (cDC1s) and CD1c+(cDC2s).

The plasticity of macrophages in response to different environment signals and in agreement with their functional requirements has resulted in a spectrum of macrophage activation states, including two extremes of the continuum, namely "classically activated" M1 and "alternatively activated" M2 macrophages.

The term "activation" refers to the state of a myeloid cell that has been sufficiently stimulated to induce detectable cellular proliferation and/or has been stimulated to exert its effector function, such as induced cytokine expression and secretion, phagocytosis, cell signaling, antigen processing and presentation, target cell killing, and pro-inflammatory function.

The term "M1 macrophages" or "classically activated macrophages" refers to macrophages having a pro-inflammatory phenotype. The term "macrophage activation" (also referred to as "classical activation") was introduced by Mackaness in the 1960s in an infection context to describe the antigen-dependent, but non-specific enhanced, microbicidal activity of macrophages toward BCG (bacillus Calmette-Guerin) and *Listeria* upon secondary exposure to the pathogens (Mackaness (1962) *J. Exp. Med.* 116:381-406). The enhancement was later linked with Th1 responses and IFN-γ production by antigen-activated immune cells (Nathan et al. (1983) *J Exp. Med.* 158:670-689) and extended to cytotoxic and antitumoral properties (Pace et al. (1983) *Proc. Natl. Acad. Sci. U.S.A.* 80:3782-3786; Celada et al. (1984) *J. Exp. Med.* 160:55-74). Therefore, any macrophage functionality that enhances inflammation by cytokine secretion, antigen presentation, phagocytosis, cell-cell interactions, migration, etc. is considered pro-inflammatory. In vitro and in vivo assays may measure different endpoints: general in vitro measurements include pro-inflammatory cell stimulation as measured by proliferation, migration, pro-inflammatory Th1 cytokine/chemokine secretion and/or migration, while general in vivo measurements further include analyzing pathogen fighting, tissue injury immediate responders, other cell activators, migration inducers, etc. For both in vitro and in vivo, pro-inflammatory antigen presentation may be assessed. Bacterial moieties, such as lipopolysaccharide (LPS), certain Toll-like receptor (TLR) agonists, the Th1 cytokine interferon-gamma (IFNγ) (e.g., IFNγ produced by NK cells in response to stress and infections, and T helper cells with sustained production) and TNF polarize macrophages along the M1 pathway. Activated M1 macrophages phagocytose and destroy microbes, eliminate damaged cells (e.g., tumor cells and apoptotic cells), present antigen to T cells for increasing adaptive immune responses, and produce high levels of pro-inflammatory cytokines (e.g., IL-1, IL-6, and IL-23), reactive oxygen species (ROS), and nitric oxide (NO), as well as activate other immune and non-immune cells. Characterized by their expression of inducible nitric oxide synthase (iNOS), reactive oxygen species (ROS), and production of the Th1-associated cytokine, IL-12, M1 macrophages are well-adapted to promote a strong immune response. The metabolism of M1 macrophages is characterized by enhanced aerobic glycolysis, converting glucose into lactate, increased flux through the pentose phosphate pathway (PPP), fatty acid synthesis, and a truncated tricarboxylic acid (TCA) cycle, leading to accumulation of succinate and citrate.

A "Type 1" or "M1-like" myeloid cell is a myeloid cell capable of contributing to a pro-inflammatory response that is characterized by at least one of the following: producing inflammatory stimuli by secreting at least one pro-inflammatory cytokine, expressing at least one cell surface activating molecule/a ligand for an activating molecule on its surface, recruiting/instructing/interacting with at least one other cell (including other macrophages and/or T cells) to stimulate pro-inflammatory responses, presenting antigen in a pro-inflammatory context, migrating to the site allowing for pro-inflammatory response initiation or starting to express at least one gene that is expected to lead to pro-inflammatory functionality. In some embodiments, the term includes activating cytotoxic CD8+ T cells, mediating increased sensitivity of cancer cells to immunotherapy, such as immune checkpoint therapy, and/or mediating reversal of cancer cells to resistance. In certain embodiments, such modulation toward a pro-inflammatory state may be measured in a number of well-known manners, including, without limitation, one or more of a) increased cluster of differentiation 80 (CD80), CD86, MHCII, MHCI, interleukin 1-beta (IL-1β, IL-6, CCL3, CCL4, CXCL10, CXCL9, GM-CSF and/or tumor necrosis factor alpha (TNF-α); b) decreased expression and/or secretion of CD206, CD163, CD16, CD53, VSIG4, VSIG4, TGFb and/or IL-10; c) increased secretion of at least one cytokine or chemokine selected from the group consisting of IL-1β, TNF-α, IL-12, IL-18, GM-CSF, CCL3, CCL4, and IL-23; d) increased ratio of expression of IL-1β, IL-6, and/or TNF-α to expression of IL-10; e) increased CD8+ cytotoxic T cell activation; f) increased recruitment of CD8+ cytotoxic T cell activation; g) increased CD4+ helper T cell activity; h) increased recruitment of CD4+ helper T cell activity; i) increased NK cell activity; j) increased recruitment of NK cell; k) increased neutrophil activity; l) increased macrophage activity; and/or m) increased spindle-shaped morphology, flatness of appearance, and/or number of dendrites, as assessed by microscopy.

In cells that are already pro-inflammatory, an increased inflammatory phenotype refers to an even more pro-inflammatory state.

By contrast, the term "M2 macrophages" refers to macrophages having an anti-inflammatory phenotype. Th2- and tumor-derived cytokines, such as IL-4, IL-10, IL-13, transforming growth factor beta (TGF-β), or prostaglandin E2 (PGE2) may promulgate M2 polarization. The metabolic profile of M2 macrophages is defined by OXPHOS, FAO, a decreased glycolysis, and PPP. The discovery that the mannose receptor was selectively enhanced by the Th2 IL-4 and IL-13 in murine macrophages, and induced high endocytic clearance of mannosylated ligands, increased major histocompatibility complex (MHC) class II antigen expression, and reduced pro-inflammatory cytokine secretion, led Stein, Doyle, and colleagues to propose that IL-4 and IL-13 induced an alternative activation phenotype, a state altogether different from IFN-γ activation but far from deactivation (Martinez and Gordon (2014) *F1000 Prime Reports* 6:13). In vitro and in vivo definition/assays may measure different endpoints: general in vitro endpoints include anti-inflammatory cell stimulation measured by proliferation, migration, anti-inflammatory Th2 cytokine/chemokine secretion and/or migration, while general in vivo M2 endpoints further include analyzing pathogen fighting, tissue injury delayed/pro-fibrotic response, other cell Th2 polarization, migration inducers, etc. For both in vitro and in vivo, pro-tolerogenic antigen presentation may be assessed.

A "Type 2" or "M2-like" myeloid cell is a myeloid cell capable of contributing to an anti-inflammatory response that is characterized by at least one of the following: producing anti-inflammatory stimuli by secreting at least one anti-inflammatory cytokine, expressing at least one cell surface inhibiting molecule/ligand for an inhibitory molecule on its surface, recruiting/instructing/interacting at least one other cell to stimulate anti-inflammatory responses, presenting antigen in a pro-tolerogenic context, migrating to the site allowing for pro-tolerogenic response initiation or starting to express at least one gene that is expected to lead to pro-tolerogenic/anti-inflammatory functionality. In certain embodiments, such modulation toward a pro-inflammatory state may be measured in a number of well-known manners, including, without limitation, the opposite of the Type 1 pro-inflammatory state measurements described above.

A cell that has an "increased inflammatory phenotype" is one that has a more pro-inflammatory response capacity related to a) an increase in one or more of the Type 1 listed-criteria and/or b) a decrease in one or more of the Type 2-listed criteria, after modulation of at least one biomarker (e.g., at least one target listed in Table 1) encompassed by the present invention, such as contact by an agent that modulates the at least one biomarker (e.g., at least one target listed in Table 1) encompassed by the present invention.

A cell that has a "decreased inflammatory phenotype" is one that has a more anti-inflammatory response capacity related to a) an decrease in one or more of the Type 1 listed-criteria and/or b) an increase of one or more of the Type 2-listed criteria, after modulation of at least one biomarker (e.g., at least one target listed in Table 1) encompassed by the present invention, such as contact by an agent that modulates the at least one biomarker (e.g., at least one target listed in Table 1) encompassed by the present invention.

Thus, macrophages may adopt a continuum of alternatively activated states with intermediate phenotypes between the Type 1 and Type 2 states (see, e.g., Biswas et al. (2010) *Nat. Immunol.* 11: 889-=896; Mosser and Edwards (2008) *Nat. Rev. Immunol.* 8:958-969; Mantovani et al. (2009) *Hum. Immunol.* 70:325-330) and such increased or decreased inflammatory phenotypes may be determined as described above.

As used herein, the term "alternatively activated macrophages" or "alternatively activated states" refers to essentially all types of macrophage populations other than the classically activated M1 pro-inflammatory macrophages. Originally, the alternatively activated state was designated only to M2 type anti-inflammatory macrophages. The term has expanded to include all other alternative activation states of macrophages with dramatic difference in their biochemistry, physiology and functionality.

For example, one type of alternatively activated macrophages is those involved in wound healing. In response to innate and adaptive signals released during tissue injury (e.g., surgical wound), such as IL-4 produced by basophils and mast cells, tissue-resident macrophages may be activated to promote wound healing. The wound healing macrophages, instead of producing high levels of pro-inflammatory cytokines, secret large amounts of extracellular matrix components, e.g., chitinase and chitinase-like proteins YM1/CHI3L3, YM2, AMCase and Stabilin, all of which exhibit carbohydrate and matrix-binding activities and involve in tissue repair.

Another example of alternatively activated macrophages involves regulatory macrophages that may be induced by innate and adaptive immune response. Regulatory macrophages may contribute to immuno-regulatory function. For example, macrophages may respond to hormones from the hypothalamic-pituitary-adrenal (HPA) axis (e.g., glucocorticoids) to adopt a state with inhibited host defense and inflammatory function such as inhibition of the transcriptions of pro-inflammatory cytokines. Regulatory macrophages may produce regulatory cytokine TGF-β to dampen immune responses in certain conditions, for instance, at late stage of adaptive immune response. Many regulatory macrophages may express high levels of co-stimulatory molecules (e.g., CD80 and CD86) and therefore enhance antigen presentation to T cells.

Many stimuli/cues may induce polarization of regulatory macrophages. The cues may include, but are not limited to, the combination of TLR agonist and immune complexes, apoptotic cells, IL-10, prostaglandins, GPcR ligands, adenosine, dopamine, histamine, sphingosine1-phosphate, melanocortin, vasoactive intestinal peptides and Siglec-9. Some pathogens, such as parasites, viruses, and bacteria, may specifically induce the differentiation of regulatory macrophages, resulting in defective pathogen killing and enhanced survival and spread of the infected microorganisms.

Regulatory macrophages share some common features. For example, regulatory macrophages need two stimuli to induce their anti-inflammatory activity. Differences among the regulatory macrophage subpopulations that are induced by different cues/stimuli are also observed, reflecting their heterogeneity.

Regulatory macrophages also are a heterogeneous population of macrophages, including a variety of subpopulations found in metabolism, during development, in the maintenance of homeostasis. In one example, a subpopulation of alternatively activated macrophages are immunoregulatory macrophages with unique immunoregulatory properties which may be induced in the presence of M-CSF/GM-CSF, a CD16 ligand (such as an immunoglobulin), and IFN-γ (PCT application publication NO. WO2017/153607).

Macrophages in a tissue may change their activation states in vivo over time. This dynamic reflects constant influx of migrating macrophages to the tissue, dynamic changes of activated macrophages, and macrophages that switch back the rest state. In some conditions, different signals in an environment may induce macrophages to a mix of different activation states. For example, in a condition with chronic wound, macrophages over time, may include pro-inflammatory activation subpopulation, macrophages that are pro-wound healing, and macrophages that exhibit some pro-resolving activities. Under non-pathological conditions, a balanced population of immune-stimulatory and immune-regulatory macrophages exist in the immune system. In some disease conditions, the balance is interrupted and the imbalance causes many clinical conditions.

The apparent plasticity of macrophages also make them vulnerably responsive to environmental cues they receive in a disease condition. Macrophages may be repolarized in response to a variety of disease conditions, demonstrating distinct characteristics. One example is macrophages that are attracted and filtrate into tumor tissues from peripheral blood monocytes, which are often called "tumor associated macrophages" ("TAMs") or "tumor infiltrating macrophages" ("TIMs"). Tumor-associated macrophages are amongst the most abundant inflammatory cells in tumors and a significant correlation was found between high TAM density and a worse prognosis for most cancers (Zhang et al. (2012) *PloS One* 7:e50946.10.1371/journal.pone.0050946).

TAMs are a mixed population of both M1-like pro-inflammatory and M2-like anti-inflammatory subpopulations. In the earliest stage of neoplasia, classically activated macrophages that have a pro-inflammatory phenotype are present in the normoxic tumor regions, are believed to contribute to early eradication of transformed tumor cells. However, as a tumor grows and progresses, the majority of TAMs in late stage tumors is M2-like regulatory macrophages that reside in the hypoxic regions of the tumor. This phenotypic change of macrophages is markedly influenced by the tumor microenvironmental stimuli, such as tumor extracellular matrix, anoxic environment and cytokines secreted by tumor cells. The M2-like TAMs demonstrate a hybrid activation state of wound healing macrophages and regulatory macrophages, demonstrating various unique characteristics, including the production of high levels of IL-10 but little or no IL-12, defective TNF production, suppression of antigen presenting cells, and contribution to tumor angiogenesis.

Generally, TAMs are characterized by a M2 phenotype and suppress M1 macrophage-mediated inflammation through IL-10 and IL-1β production. Thus, TAMs promote tumor growth and metastasis through activation of wound-healing (i.e., anti-inflammatory) pathways that provide nutrients and growth signals for proliferation and invasion and promote the creation of new blood vessels (i.e., angiogenesis). In addition, TAMs contribute to the immune-suppressive tumor microenvironment by secreting anti-inflammatory signals that prevent other components of the immune system from recognizing and attacking the tumor. It has been reported that TAMs are key players in promoting cancer growth, proliferation, and metastasis in many types of cancers (e.g., breast cancer, astrocytoma, head and neck squamous cell cancer, papillary renal cell carcinoma Type II, lung cancer, pancreatic cancer, gall bladder cancer, rectal cancer, glioma, classical Hodgkin's lymphoma, ovarian cancer, and colorectal cancer). In general, a cancer characterized by a large population of TAMs is associated with poor disease prognosis.

The diversified functions and activation states may have dangerous consequences if not appropriately regulated. For example, classically activated macrophages may cause damage to host tissue, predispose surrounding tissue and influence glucose metabolism if over activated.

In many disease conditions, the balanced dynamics of macrophage activation states is interrupted and the imbalance causes diseases. For example, tumors are abundantly populated with macrophages. Macrophages may be found in 75 percent of cancers. The aggressive types of cancer are often associated with higher infiltration of macrophages and other immune cells. In most malignant tumors, TAM exert several tumor-promoting functions, including promotion of cancer cell survival, proliferation, invasion, extravasation and metastasis, stimulation of angiogenesis, remodeling of the extracellular matrix, and suppression of antitumor immunity (Qian and Pollard, 2010*, Cell,* 141(1): 39-51). They also could produce growth-promoting molecules such as ornithine, VEGF, EGF and TGF-β.

TAMs stimulate tumor growth and survival in response to CSF1 and IL4/IL13 encountered in the tumor microenvironment. TAMs also may remodel the tumor microenvironment through the expression of proteases, such as MMPs, cathepsins and uPA and matrix remodeling enzymes (e.g., lysyl oxidase and SPARC).

TAMs play an important role in tumor angiogenesis regulating the dramatic increase of blood vessel in tumor tissues which is required for the transition of the malignant state of tumor. These angiogenic TAMs express angiopoietin receptor, TIE2 and secrete many angiogenic molecules including VEGF family members, TNFα, IL1β, IL8, PDGF and FGF.

A diversity of subpopulations of macrophages perform these individual pro-tumoral functions. These TAMs are different in the extent of macrophage infiltrate as well as phenotype in different tumor types. For example, detailed profiling in human hepatocellular carcinoma shows various macrophage sub-types defined in terms of their anatomic location, and pro-tumoral and anti-tumoral properties. It has been shown that M2-like macrophages are a major resource of pro-tumoral functions of TAMs. M2-like TAMs have been shown to affect the efficacy of anti-cancer treatments, contribute to therapy resistance, and mediate tumor relapse following conventional cancer therapy.

III. Targets and Biomarkers Useful for Modulating Myeloid Cell Inflammatory Phenotype The present invention encompasses biomarkers like VSIG4 useful for modulating the inflammatory phenotype of myeloid cells, such as suppressive myeloid cells, monocytes, macrophages, and/or dendritic cells, as well as corresponding immune responses (e.g., to increase anti-cancer macrophage immunotherapy).

Downregulation of VSIG4 is associated with and results in an increased inflammatory phenotype (e.g., a Type 1 phenotype) and upregulation is associated with and results in a decreased inflammatory phenotype (e.g., a Type 2 phenotype).

Nucleic acid and amino acid sequence information for the loci and biomarkers encompassed by the present invention (e.g., biomarkers listed in Table 1) are well-known in the art and readily available on publicly available databases, such as the National Center for Biotechnology Information (NCBI). For example, exemplary nucleic acid and amino acid sequences derived from publicly available sequence databases are provided below.

As discussed further below, agents that modulate the expression, translation, degradation, amount, subcellular localization, and other activities of biomarkers encompassed by the present invention in myeloid cells, such as suppressive myeloid cells, monocytes, macrophages, and/or dendritic cells, are useful in modulating the inflammatory phenotype of these cells, as well as modulating immune responses mediated by these cells.

Although numerous representative orthologs to human sequences are provided below, in some embodiments, human biomarkers (including modulation and modulatory agents thereof) are preferred. For some biomarkers, it is believed that immune responses mediated by such biomarkers in humans is particularly useful in view of differences between the human immune system and the immune system of other vertebrates.

The term "VSIG4" refers to V-Set And Immunoglobulin Domain Containing 4, a v-set and immunoglobulin-domain containing protein that is structurally related to the B7 family of immune regulatory proteins. The VSIG4 protein is a negative regulator of T-cell responses. It is also a receptor for the complement component 3 fragments C3b and iC3b. VSIG4 protein is a phagocytic receptor, and a strong negative regulator of T-cell proliferation and IL2 production. It is also a potent inhibitor of the alternative complement pathway convertases. Diseases associated with VSIG4 include T-Cell/Histiocyte Rich Large B Cell Lymphoma and Langerhans Cell Sarcoma. Among its related pathways are complement and coagulation cascades. In some embodiments, the VSIG4 gene, located on chromosome Xq in humans, consists of 8 exons. Orthologs are known from chimpanzee, rhesus monkey, dog, mouse, and rat. Knockout mouse lines, including Vsig4$^{tm1Gne}$ (Helmy et al. (2006) *Cell* 124:915-927) and Vsig4$^{tm1b(EUCOMM)Hmgu}$ (Skarnes et al. (2011) *Nature* 474:337-342), exist. In some embodiments, human VSIG4 protein has 399 amino acids and/or a molecular mass of 43987 Da.

The term "VSIG4" is intended to include fragments, variants (e.g., allelic variants), and derivatives thereof. Representative human VSIG4 cDNA and human VSIG4 protein sequences are well-known in the art and are publicly available from the National Center for Biotechnology Information (NCBI) (see, for example, ncbi.nlm.nih.gov/gene/11326). For example, at least five different human VSIG4 isoforms are known. Human VSIG4 isoform 1 (NP_009199.1) is encodable by the transcript variant 1 (NM_007268.2), which is the longest transcript. Human VSIG4 isoform 2 (NP_001093901.1) is encodable by the transcript variant 2 (NM_001100431.1), which lacks an alternate in-frame segment compared to variant 1. Human VSIG4 isoform 3 (NP_001171760.1) is encodable by the transcript variant 3 (NM_001184831.1), which has multiple differences, compared to variant 1. Human VSIG4 isoform 4 (NP_001171759.1) is encodable by the transcript variant 4

(NM_001184830.1), which differs in the 3' UTR and 3' coding region, compared to variant 1. Human VSIG4 isoform 5 (NP_001244332.1) is encodable by the transcript variant 5 (NM_001257403.1), which lacks two alternate in-frame exons in the 3' coding region, compared to variant 1. Nucleic acid and polypeptide sequences of VSIG4 orthologs in organisms other than humans are well-known and include, for example, chimpanzee VSIG4 (NM_001279873.1 and NP_001266802.1), rhesus monkey VSIG4 (XM_015127596.1 and XP_014983082.1, XM_015127593.1 and XP_014983079.1, XM_015127595.1 and XP_014983081.1, XM_001099264.2 and XP_001099264.2, and XM_015127594.1 and XP_014983080.1), dog VSIG4 (XM_005641424.3 and XP_005641481.1; XM_005641423.3 and XP_005641480.1; XM_022416007.1 and XP_022271715.1; XM_005641421.3 and XP_005641478.1; and XM_005641422.3 and XP_005641479.1), mouse VSIG4 (NM_177789.4 and NP_808457.1), and rat VSIG4 (NM_001025004.1 and NP_001020175.1). Representative sequences of VSIG4 orthologs are presented below in Table 1.

Anti-VSIG4 antibodies suitable for detecting VSIG4 protein are well-known in the art and include, for example, antibodies AF4646 and AF4674 (R&D systems, Minneapolis, MN), antibodies NBP1-86843, AF4646, AF4674, and NBP1-69631 (Novus Biologicals, Littleton, CO), antibodies ab56037, ab197161, and ab138594 (AbCam, Cambridge, MA), antibodies Cat #: TA346124 (Origene, Rockville, MD), etc. In addition, reagents are well-known for detecting VSIG4 expression. Multiple clinical tests of VSIG4 are available in NIH Genetic Testing Registry (GTR®) (e.g., GTR Test ID: GTR000544515.2, offered by Fulgent Clinical Diagnostics Lab (Temple City, CA)). Moreover, multiple siRNA, shRNA, CRISPR constructs for reducing VSIG4 expression may be found in the commercial product lists of the above-referenced companies, such as siRNA product #SR323415, shRNA products #TG308440, TL308440, TF308440, and CRISPR products #KN203751 from Origene Technologies (Rockville, MD), CRISPR gRNA products from Applied Biological Materials (K7367508) and from Santa Cruz (sc-404067), and RNAi products from Santa Cruz (Cat #sc-72190 and sc-72196). It is to be noted that the term may further be used to refer to any combination of features described herein regarding VSIG4 molecules. For example, any combination of sequence composition, percentage identify, sequence length, domain structure, functional activity, etc. may be used to describe a VSIG4 molecule encompassed by the present invention.

TABLE 1

```
VSIG4
Human and/or cynomolgous VSIG4
SEQ ID NO: 7 Human VSIG4 Transcript Variant 1 cDNA Sequence
(NM 007268.2; CDS: 128-1327)
     1  ggagtttgag tgagagatat agggaaggaa gggaagtaag cagtcacaga cgctggcggc

    61  caccagaagt ttgagcctct ttggtagcag gaggctggaa gaaaggacag aagtagctct

   121  ggctgtgatg gggatcttac tgggcctgct actcctgggg cacctaacag tggacactta

   181  tggccgtccc atcctggaag tcccagagag tgtaacagga ccttggaaag gggatgtgaa

   241  tcttccctgc acctatgacc ccctgcaagg ctacacccaa gtcttggtga agtggctggt

   301  acaacgtggc tcagaccctg tcaccatctt tctacgtgac tcttctggag accatatcca

   361  gcaggcaaag taccagggcc gcctgcatgt gagccacaag gttccaggag atgtatccct

   421  ccaattgagc accctggaga tcgatgaccg gagccactac acgtgtgaag tcacctggca

   481  gactcctgat ggcaaccaag tcgtgagaga taagattact gagctccgtg tccagaaact

   541  ctctgtctcc aagcccacag tgacaactgg cagcggttat ggcttcacgg tgccccaggg

   601  aatgaggatt agccttcaat gccaggctcg gggttctcct cccatcagtt atatttggta

   661  taagcaacag actaataacc aggaacccat caaagtagca accctaagta ccttactctt

   721  caagcctgcg gtgatagccg actcaggctc ctatttctgc actgccaagg gccaggttgg

   781  ctctgagcag cacagcgaca ttgtgaagtt tgtggtcaaa gactcctcaa agctactcaa

   841  gaccaagact gaggcaccta caaccatgac ataccccttg aaagcaacat ctacagtgaa

   901  gcagtcctgg gactggacca ctgacatgga tggctacctt ggagagacca gtgctgggcc

   961  aggaaagagc ctgcctgtct ttgccatcat cctcatcatc tccttgtgct gtatggtggt

  1021  ttttaccatg gcctatatca tgctctgtcg gaagacatcc caacaagagc atgtctacga

  1081  agcagccagg gcacatgcca gagaggccaa cgactctgga gaaaccatga gggtggccat

  1141  cttcgcaagt ggctgctcca gtgatgagcc aacttcccag aatctgggca acaactactc

  1201  tgatgagccc tgcataggac aggagtacca gatcatcgcc cagatcaatg gcaactacgc

  1261  ccgcctgctg gacacagttc ctctggatta tgagtttctg gccactgagg gcaaaagtgt
```

TABLE 1-continued

```
1321  ctgttaaaaa tgccccatta ggccaggatc tgctgacata attgcctagt cagtccttgc

1381  cttctgcatg gccttcttcc ctgctacctc tcttcctgga tagcccaaag tgtccgccta

1441  ccaacactgg agccgctggg agtcactggc tttgccctgg aatttgccag atgcatctca

1501  agtaagccag ctgctggatt tggctctggg cccttctagt atctctgccg gggcttctg

1561  gtactcctct ctaaatacca gagggaagat gcccatagca ctaggacttg gtcatcatgc

1621  ctacagacac tattcaactt tggcatcttg ccaccagaag acccgaggga ggctcagctc

1681  tgccagctca gaggaccagc tatatccagg atcatttctc tttcttcagg gccagacagc

1741  ttttaattga aattgttatt tcacaggcca gggttcagtt ctgctcctcc actataagtc

1801  taatgttctg actctctcct ggtgctcaat aaatatctaa tcataacagc aaaaaaaaaa

1861  aaaaaaaaa
```

SEQ ID NO: 8 Human VSIG4 Isoform 1 Amino Acid Sequence (NP_009199.1)

```
  1  mgillgllll ghltvdtygr pilevpesvt gpwkgdvnlp ctydplqgyt qvlvkwlvqr

 61  gsdpvtiflr dssgdhiqqa kyqgrlhvsh kvpgdvslql stlemddrsh ytcevtwqtp

121  dgnqvvrdki telrvqklsv skptvttgsg ygftvpqgmr islqcqargs ppisyiwykq

181  qtnnqepikv atlstllfkp aviadsgsyf ctakgqvgse qhsdivkfvv kdssklltkt

241  teapttmtyp lkatstvkqs wdwttdmdgy lgetsagpgk slpvfaiili islccmvvft

301  mayimlerkt sqqehvyeaa rahareands getmrvaifa sgcssdepts qnlgnnysde

361  pcigqeyqii aqingnyarl ldtvpldyef lategksvc
```

SEQ ID NO: 9 Human VSIG4 Transcript Variant 2 cDNA Sequence (NM_001100431.1; CDS: 128-1045)

```
   1  ggagtttgag tgagagatat agggaaggaa gggaagtaag cagtcacaga cgctggcggc

  61  caccagaagt ttgagcctct ttggtagcag gaggctggaa gaaaggacag aagtagctct

 121  ggctgtgatg gggatcttac tgggcctgct actcctgggg cacctaacag tggacactta

 181  tggccgtccc atcctggaag tcccagagag tgtaacagga ccttggaaag gggatgtgaa

 241  tcttccctgc acctatgacc ccctgcaagg ctacacccaa gtcttggtga agtggctggt

 301  acaacgtggc tcagaccctg tcaccatctt tctacgtgac tcttctggag accatatcca

 361  gcaggcaaag taccagggcc gcctgcatgt gagccacaag gttccaggag atgtatccct

 421  ccaattgagc accctggaga tcgatgaccg gagccactac acgtgtgaag tcacctggca

 481  gactcctgat ggcaaccaag tcgtgagaga taagattact gagctccgtg tccagaaaca

 541  ctcctcaaag ctactcaaga ccaagactga ggcacctaca accatgacat accccttgaa

 601  agcaacatct acagtgaagc agtcctggga ctggaccact gacatggatg gctaccttgg

 661  agagaccagt gctgggccag gaaagagcct gcctgtcttt gccatcatcc tcatcatctc

 721  cttgtgctgt atggtggttt ttaccatggc ctatatcatg ctctgtcgga agacatccca

 781  acaagagcat gtctacgaag cagccagggc acatgccaga gaggccaacg actctggaga

 841  aaccatgagg gtggccatct tcgcaagtgg ctgctccagt gatgagccaa cttcccagaa

 901  tctgggcaac aactactctg atgagccctg cataggacag gagtaccaga tcatcgccca

 961  gatcaatggc aactacgccc gcctgctgga cacagttcct ctggattatg agtttctggc

1021  cactgagggc aaaagtgtct gttaaaaatg ccccattagg ccaggatctg ctgacataat

1081  tgcctagtca gtccttgcct tctgcatggc cttcttccct gctacctctc ttcctggata

1141  gcccaaagtg tccgcctacc aacactggag ccgctgggag tcactggctt tgccctggaa

1201  tttgccagat gcatctcaag taagccagct gctggatttg gctctgggcc cttctagtat

1261  ctctgccggg ggcttctggt actcctctct aaataccaga gggaagatgc ccatagcact
```

TABLE 1-continued

```
1321  aggacttggt catcatgcct acagacacta ttcaactttg gcatcttgcc accagaagac
1381  ccgagggagg ctcagctctg ccagctcaga ggaccagcta tatccaggat catttctctt
1441  tcttcagggc cagacagctt ttaattgaaa ttgttatttc acaggccagg gttcagttct
1501  gctcctccac tataagtcta atgttctgac tctctcctgg tgctcaataa atatctaatc
1561  ataacagcaa aaaaaaaaaa aaaaaa
```

SEQ ID NO: 10 Human VSIG4 Isoform 2 Amino Acid Sequence (NP_001093901.1)

```
  1  mgillgllll ghltvdtygr pilevpesvt gpwkgdvnlp ctydplqgyt qvlvkwlvqr
 61  gsdpvtiflr dssgdhiqqa kyqgrlhvsh kvpgdvslql stlemddrsh ytcevtwqtp
121  dgnqvvrdki telrvqkhss kllktkteap ttmtyplkat stvkqswdwt tdmdgylget
181  sagpgkslpv faiiliislc cmvvftmayi mlerktsqqe hvyeaaraha reandsgetm
241  rvaifasgcs sdeptsqnlg nnysdepcig qeyqiiaqin gnyarlldtv pldyeflate
301  gksvc
```

SEQ ID NO: 11 Human VSIG4 Transcript Variant 3 cDNA Sequence (NM_001184831.1; CDS: 128-811)

```
   1  ggagtttgag tgagagatat agggaaggaa gggaagtaag cagtcacaga cgctggcggc
  61  caccagaagt ttgagcctct ttggtagcag gaggctggaa gaaaggacag aagtagctct
 121  ggctgtgatg ggatcttac tgggcctgct actcctgggg cacctaacag tggacactta
 181  tggccgtccc atcctggaag tcccagagag tgtaacagga ccttggaaag gggatgtgaa
 241  tcttccctgc acctatgacc ccctgcaagg ctacacccaa gtcttggtga agtggctggt
 301  acaacgtggc tcagaccctg tcaccatctt tctacgtgac tcttctggag accatatcca
 361  gcaggcaaag taccagggcc gcctgcatgt gagccacaag gttccaggag atgtatccct
 421  ccaattgagc accctggaga tggatgaccg gagccactac acgtgtgaag tcacctggca
 481  gactcctgat ggcaaccaag tcgtgagaga taagattact gagctccgtg tccagaaaca
 541  ctcctcaaag ctactcaaga ccaagactga ggcacctaca accatgacat accccttgaa
 601  agcaacatct acagtgaagc agtcctggga ctggaccact gacatggatg gctaccttgg
 661  agagaccagt gctgggccag gaaagagcct gcctgtcttt gccatcatcc tcatcatctc
 721  cttgtgctgt atggtggttt ttaccatggc ctatatcatg ctctgtcgga agacatccca
 781  acaagagcat gtctacgaag cagccaggta agaaagtctc tcctcttcca tttttgaccc
 841  cgtccctgcc ctcaattttg attactggca ggaaatgtgg aggaaggggg gtgtggcaca
 901  gacccaatcc taaggccgga ggccttcagg gtcaggacat agctgccttc cctctctcag
 961  gcaccttctg aggttgtttt ggccctctga acacaaagga taatttagat ccatctgcct
1021  tctgcttcca gaatccctgg gtggtaggat cctgataatt aattggcaag aattgaggca
1081  gaagggtggg aaaccaggac cacagcccca agtcccttct tatgggtggt gggctcttgg
1141  gccatagggc acatgccaga gaggccaacg actctggaga aaccatgagg gtggccatct
1201  tcgcaagtgg ctgctccagt gatgagccaa cttcccagaa tctgggcaac aactactctg
1261  atgagccctg cataggacag gagtaccaga tcatcgccca gatcaatggc aactacgccc
1321  gcctgctgga cacagttcct ctggattatg agtttctggc cactgagggc aaaagtgtct
1381  gttaaaaatg ccccattagg ccaggatctg ctgacataat tgcctagtca gtccttgcct
1441  tctgcatggc cttcttccct gctacctctc ttcctggata gcccaaagtg tccgcctacc
1501  aacactggag ccgctgggag tcactggctt tgccctggaa tttgccagat gcatctcaag
1561  taagccagct gctggatttg gctctgggcc cttctagtat ctctgccggg ggcttctggt
```

TABLE 1-continued

```
1621  actcctctct aaataccaga gggaagatgc ccatagcact aggacttggt catcatgcct

1681  acagacacta ttcaactttg gcatcttgcc accagaagac ccgagggagg ctcagctctg

1741  ccagctcaga ggaccagcta tatccaggat catttctctt tcttcagggc cagacagctt

1801  ttaattgaaa ttgttatttc acaggccagg gttcagttct gctcctccac tataagtcta

1861  atgttctgac tctctcctgg tgctcaataa atatctaatc ataacagcaa aaaaaaaaaa

1921  aaaaaaa
```

SEQ ID NO: 12 Human VSIG4 Isoform 3 Amino Acid Sequence (NP_001171760.1)

```
   1  mgillglll ghltvdtygr pilevpesvt gpwkgdvnlp ctydplqgyt qvlvkwlvqr

  61  gsdpvtiflr dssgdhiqqa kyqgrlhvsh kvpgdvslql stlemddrsh ytcevtwqtp

 121  dgnqvvrdki telrvqkhss kllktkteap ttmtyplkat stvkqswdwt tdmdgylget

 181  sagpgkslpv faiiliislc cmvvftmayi mlerktsqqe hvyeaar
```

SEQ ID NO: 13 Human VSIG4 Transcript Variant 4 cDNA Sequence (NM_001184830.1; CDS: 128-1093)

```
   1  ggagtttgag tgagagatat agggaaggaa gggaagtaag cagtcacaga cgctggcggc

  61  caccagaagt ttgagcctct ttggtagcag gaggctggaa gaaaggacag aagtagctct

 121  ggctgtgatg gggatcttac tgggcctgct actcctgggg cacctaacag tggacactta

 181  tggccgtccc atcctggaag tcccagagag tgtaacagga ccttggaaag gggatgtgaa

 241  tcttccctgc acctatgacc ccctgcaagg ctacacccaa gtcttggtga agtggctggt

 301  acaacgtggc tcagaccctg tcaccatctt tctacgtgac tcttctggag accatatcca

 361  gcaggcaaag taccagggcc gcctgcatgt gagccacaag gttccaggag atgtatccct

 421  ccaattgagc accctggaga tggatgaccg gagccactac acgtgtgaag tcacctggca

 481  gactcctgat ggcaaccaag tcgtgagaga taagattact gagctccgtg tccagaaact

 541  ctctgtctcc aagcccacag tgacaactgg cagcggttat ggcttcacgg tgccccaggg

 601  aatgaggatt agccttcaat gccaggctcg gggttctcct cccatcagtt atatttggta

 661  taagcaacag actaataacc aggaacccat caaagtagca accctaagta ccttactctt

 721  caagcctgcg gtgatagccg actcaggctc ctatttctgc actgccaagg gccaggttgg

 781  ctctgagcag cacagcgaca ttgtgaagtt tgtggtcaaa gactcctcaa agctactcaa

 841  gaccaagact gaggcaccta caaccatgac atacccottg aaagcaacat ctacagtgaa

 901  gcagtcctgg gactggacca ctgacatgga tggctacctt ggagagacca gtgctgggcc

 961  aggaaagagc ctgcctgtct ttgccatcat cctcatcatc tccttgtgct gtatggtggt

1021  ttttaccatg gcctatatca tgctctgtcg gaagacatcc caacaagagc atgtctacga

1081  agcagccagg taagaaagtc tctcctcttc catttttgac cccgtccctg ccctcaattt

1141  tgattactgg caggaaatgt ggaggaaggg gggtgtggca cagacccaat cctaaggccg

1201  gaggccttca gggtcaggac atagctgcct tccctctctc aggcaccttc tgaggttgtt

1261  ttggccctct gaacacaaag gataatttag atccatctgc cttctgcttc cagaatccct

1321  gggtggtagg atcctgataa ttaattggca agaattgagg cagaagggtg ggaaaccagg

1381  accacagccc caagtccctt cttatgggtg gtgggctctt gggccatagg gcacatgcca

1441  gagaggccaa cgactctgga gaaaccatga gggtggccat cttcgcaagt ggctgctcca

1501  gtgatgagcc aacttcccag aatctgggca acaactactc tgatgagccc tgcataggac

1561  aggagtacca gatcatcgcc cagatcaatg gcaactacgc ccgcctgctg gacacagttc

1621  ctctggatta tgagtttctg gccactgagg gcaaaagtgt ctgttaaaaa tgccccatta

1681  ggccaggatc tgctgacata attgcctagt cagtccttgc cttctgcatg gccttcttcc
```

TABLE 1-continued

```
1741 ctgctacctc tcttcctgga tagcccaaag tgtccgccta ccaacactgg agccgctggg
1801 agtcactggc tttgccctgg aatttgccag atgcatctca agtaagccag ctgctggatt
1861 tggctctggg cccttctagt atctctgccg ggggcttctg gtactcctct ctaaatacca
1921 gagggaagat gcccatagca ctaggacttg gtcatcatgc ctacagacac tattcaactt
1981 tggcatcttg ccaccagaag acccgaggga ggctcagctc tgccagctca gaggaccagc
2041 tatatccagg atcatttctc tttcttcagg gccagacagc ttttaattga aattgttatt
2101 tcacaggcca gggttcagtt ctgctcctcc actataagtc taatgttctg actctctcct
2161 ggtgctcaat aaatatctaa tcataacagc aaaaaaaaaa aaaaaaaaa
```

SEQ ID NO: 14 Human VSIG4 Isoform 4 Amino Acid Sequence (NP_001171759.1)

```
  1 mgillgllll ghltvdtygr pilevpesvt gpwkgdvnlp ctydplqgyt qvlvkwlvqr
 61 gsdpvtiflr dssgdhiqqa kyqgrlhvsh kvpgdvslql stlemddrsh ytcevtwqtp
121 dgnqvvrdki telrvqklsv skptvttgsg ygftvpqgmr islqcqargs ppisyiwykq
181 qtnnqepikv atlstllfkp aviadsgsyf ctakgqvgse qhsdivkfvv kdssklltk
241 teapttmtyp lkatstvkqs wdwttdmdgy lgetsagpgk slpvfaiili islccmvvft
301 mayimlerkt sqqehvyeaa r
```

SEQ ID NO: 15 Human VSIG4 Transcript Variant 5 cDNA Sequence (NM_001257403.1; CDS: 128-1171)

```
   1 ggagtttgag tgagagatat agggaaggaa gggaagtaag cagtcacaga cgctggcggc
  61 caccagaagt ttgagcctct ttggtagcag gaggctggaa gaaaggacag aagtagctct
 121 ggctgtgatg gggatcttac tgggcctgct actcctgggg cacctaacag tggacactta
 181 tggccgtccc atcctggaag tgccagagag tgtaacagga ccttggaaag gggatgtgaa
 241 tcttccctgc acctatgacc ccctgcaagg ctacacccaa gtcttggtga agtggctggt
 301 acaacgtggc tcagaccctg tcaccatctt tctacgtgac tcttctggag accatatcca
 361 gcaggcaaag taccagggcc gcctgcatgt gagccacaag gttccaggag atgtatccct
 421 ccaattgagc accctggaga tcgatgaccg gagccactac acgtgtgaag tcacctggca
 481 gactcctgat ggcaaccaag tcgtgagaga taagattact gagctccgtg tccagaaact
 541 ctctgtctcc aagcccacag tgacaactgg cagcggttat ggcttcacgg tgccccaggg
 601 aatgaggatt agccttcaat gccaggctcg gggttctcct cccatcagtt atatttggta
 661 taagcaacag actaataacc aggaacccat caaagtagca accctaagta ccttactctt
 721 caagcctgcg gtgatagccg actcaggctc ctatttctgc actgccaagg gccaggttgg
 781 ctctgagcag cacagcgaca ttgtgaagtt tgtggtcaaa gactcctcaa agctactcaa
 841 gaccaagact gaggcaccta caaccatgac ataccccttg aaagcaacat ctacagtgaa
 901 gcagtcctgg gactggacca tggctacctt ggagagacca gtgctgggcc ctgcctgtct
 961 aggaaagagc ctgacatgga ttgccatcat cctcatcatc tccttgtgct gtatggtggt
1021 ttttaccatg gcctatatca tgctctgtcg gaagacatcc caacaagagc atgtctacga
1081 agcagccagc ccaaagtgtc cgcctaccaa cactggagcc gctgggagtc actggctttg
1141 ccctggaatt tgccagatgc atctcaagta agccagctgc tggatttggc tctgggccct
1201 tctagtatct ctgccggggg cttctggtac tcctctctaa ataccagagg gaagatgccc
1261 atagcactag gacttggtca tcatgcctac agacactatt caactttggc atcttgccac
1321 cagaagaccc gagggaggct cagctctgcc agctcagagg accagctata tccaggatca
1381 tttctctttc ttcagggcca gacagctttt aattgaaatt gttatttcac aggccagggt
```

TABLE 1-continued

```
1441  tcagttctgc tcctccacta taagtctaat gttctgactc tctcctggtg ctcaataaat

1501  atctaatcat aacagcaaaa aaaaaaaaaa aaaaa
```

SEQ ID NO: 16 Human VSIG4 Isoform 5 Amino Acid Sequence (NP_001244332.1)

```
   1  mgillglll1 ghltvdtygr pilevpesvt gpwkgdvnlp ctydplqgyt qvlvkwlvqr

  61  gsdpvtiflr dssgdhiqqa kyqgrlhvsh kvpgdvslql stlemddrsh ytcevtwqtp

 121  dgnqvvrdki telrvqklsv skptvttgsg ygftvpqgmr islqcqargs ppisyiwykq

 181  qtnnqepikv atlstllfkp aviadsgsyf ctakgqvgse qhsdivkfvv kdssklltk

 241  teapttmtyp lkatstvkqs wdwttdmdgy lgetsagpgk slpvfaiili islccmvvft

 301  mayimlerkt sqqehvyeaa spkcpptntg aagshwlcpg icqmhlk
```

SEQ ID NO: 17 Mouse VSIG4 cDNA Sequence (NM_177789.4; CDS: 71-913)

```
   1  agctaccagc acttccaggt tcttcagcag caagaggatg gaaggatgaa tagaagtagc

  61  ttcaaatagg atggagatct catcaggctt gctgttcctg ggccacctaa tagtgctcac

 121  ctatggccac cccaccctaa aaacacctga gagtgtgaca gggacctgga aaggagatgt

 181  gaagattcag tgcatctatg atcccctgag aggctacagg caagttttgg tgaaatggct

 241  ggtaagacac ggctctgact ccgtcaccat cttcctacgt gactccactg gagaccatat

 301  ccagcaggca aagtacagag gccgcctgaa agtgagccac aaagttccag gagatgtgtc

 361  cctccaaata aataccctgc agatggatga caggaatcac tatacatgtg aggtcacctg

 421  gcagactcct gatggaaacc aagtaataag agataagatc attgagctcc gtgttcggaa

 481  atataatcca cctagaatca atactgaagc acctacaacc ctgcactcct ctttggaagc

 541  aacaactata atgagttcaa cctctgactt gaccactaat gggactggaa aacttgagga

 601  gaccattgct ggttcaggga ggaacctgcc aatctttgcc ataatcttca tcatctccct

 661  ttgctgcata gtagctgtca ccataccttta tatcttgttc cgctgcagga cattccaaca

 721  agagtatgtc tatggagtga gcagggtgtt tgccaggaag acaagcaact ctgaagaaac

 781  cacaagggtg actaccatcg caactgatga accagattcc caggctctga ttagtgacta

 841  ctctgatgat ccttgcctca gccaggagta ccaaataacc atcagatcaa caatgtctat

 901  tcctgcctgc tgaacacagt ttccagaaac taagaagttc ttgctactga agaaaataac

 961  atctgctaaa atgcccctac taagtcaagg tctactggcg taattacctg ttacttattt

1021  actacttgcc ttcaacatag ctttctccct ggcttccttt cttcttagac aacctaaagt

1081  atctatctag tctgccaatt ctggggccat tgagaaatcc tgggtttggc taagaatata

1141  ctacatgcac ctcaagaaat ctagcttctg ggcttcaccc agaacaattt tcttcctagg

1201  gccttcacaa ctcttctcca aacagcagag aaattccata gcagtagagg ttctttatca

1261  tgcctccaga cagcgtgagt ctcagtccta caaactcaga caagcacatg ggtctaggat

1321  tactcctctt tctctagggc cagatgactt ttaattgata ttactattgc tacattatga

1381  atctaatgca catgtattct tttgttgtta ataaatgttt aatcatgaca tc
```

SEQ ID NO: 18 Mouse VSIG4 Amino Acid Sequence (NP_808457.1)

```
   1  meissgllfl ghlivltygh ptlktpesvt gtwkgdvkiq ciydplrgyr qvlvkwlvrh

  61  gsdsvtiflr dstgdhiqqa kyrgrlkvsh kvpgdvslqi ntlqmddrnh ytcevtwqtp

 121  dgnqvirdki ielrvrkynp printeaptt lhssleatti msstsdlttn gtgkleetia

 181  gsgrnlpifa iifiislcci vavtipyilf rcrtfqqeyv ygvsrvfark tsnseettrv

 241  ttiatdepds qalisdysdd pclsqeyqit irstmsipac
```

TABLE 1-continued

SEQ ID NO: 19
Human VSIG4-L-Fc Amino Acid Sequence
RPILEVPESVTGPWKGDVNLPCTYDPLQGYTQVLVKWLVQRGSDPVTIFLRDSSGDHIQQAKYQGRLHVSHKV
PGDVSLQLSTLEMDDRSHYTCEVTWQTPDGNQVVRDKITELRVQKLSVSKPTVTTGSGYGFTVPQGMRISLQC
QARGSPPISYIWYKQQTNNQEPIKVATLSTLLFKPAVIADSGSYFCTAKGQVGSEQHSDIVKFVVKDSSKLLK
TKTEAPTTMTYPLKATSTVKQSWDWTTDMDGYLGETSAGPGKSLPGSGGDKTHTCPPCPAPELLGGPSVFLFP
PKPKDTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK SEQ ID NO: 20
Human VSIG4-S-Fc Amino Acid Sequence
RPILEVPESVTGPWKGDVNLPCTYDPLQGYTQVLVKWLVQRGSDPVTIFLRDSSGDHIQQAKYQGRLHVSHKV
PGDVSLQLSTLEMDDRSHYTCEVTWQTPDGNQVVRDKITELRVQKHSSKLLKTKTEAPTTMTYPLKATSTVKQ
SWDWTTDMDGYLGETSAGPGKSLPGSGGDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDSDGSFFLYSKLT
VDKSRWQQGNVFSCSVMHEALHNHYTQKSLSLSPGK SEQ ID NO: 21
Mouse VSIG4-Fc Amino Acid Sequence
HPTLKTPESVTGTWKGDVKIQCIYDPLRGYRQVLVKWLVRHGSDSVTIFLRDSTGDHIQQAKYRGRLKVSHKV
PGDVSLQINTLQMDDRNHYTCEVTWQTPDGNQVIRDKIIELRVRKYNPPRINTEAPTTLHSSLEATTIMSSTS
DLTTNGTGKLEETIAGSGRNLPGSGGDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK SEQ ID NO: 22
Human VSIG4-L-CHO Amino Acid Sequence
MGILLGLLLLGHLTVDTYGRPILEVPESVTGPWKGDVNLPCTYDPLQGYTQVLVKWLVQRGSDPVTIFLRDSS
GDHIQQAKYQGRLHVSHKVPGDVSLQLSTLEMDDRSHYTCEVTWQTPDGNQVVRDKITELRVQKLSVSKPTVT
TGSGYGFTVPQGMRISLQCQARGSPPISYIWYKQQTNNQEPIKVATLSTLLFKPAVIADSGSYFCTAKGQVGS
EQHSDIVKFVVKDSSKLLKTKTEAPTTMTYPLKATSTVKQSWDWTTDMDGYLGETSAGPGKSLPVFAIILIIS
LCCMVVFTMAYIMLCRKTSQQEHVYEAARAHAREANDSGETMRVAIFASGCSSDEPTSQNLGNNYSDEPCIGQ
EYQIIAQINGNYARLLDTVPLDYEFLATEGKSVC SEQ ID NO: 23
Human VSIG4-S-CHO Amino Acid Sequence
MGILLGLLLLGHLTVDTYGRPILEVPESVTGPWKGDVNLPCTYDPLQGYTQVLVKWLVQRGSDPVTIFLRDSS
GDHIQQAKYQGRLHVSHKVPGDVSLQLSTLEMDDRSHYTCEVTWQTPDGNQVVRDKITELRVQKHSSKLLKTK
TEAPTTMTYPLKATSTVKQSWDWTTDMDGYLGETSAGPGKSLPVFAIILIISLCCMVVFTMAYIMLCRKTSQQ
EHVYEAARAHAREANDSGETMRVAIFASGCSSDEPTSQNLGNNYSDEPCIGQEYQIIAQINGNYARLLDTVPL
DYEFLATEGKSVC SEQ ID NO: 24
Mouse VSIG4-S-CHO Amino Acid Sequence
MEISSGLLFLGHLIVLTYGHPTLKTPESVTGTWKGDVKIQCIYDPLRGYRQVLVKWLVRHGSDSVTIFLRDST
GDHIQQAKYRGRLKVSHKVPGDVSLQINTLQMDDRNHYTCEVTWQTPDGNQVIRDKIIELRVRKYNPPRINTE
APTTLHSSLEATTIMSSTSDLTTNGTGKLEETIAGSGRNLPIFAIIFIISLCCIVAVTIPYILFRCRTFQQEY
VYGVSRVFARKTSNSEETTRVTTIATDEPDSQALISDYSDDPCLSQEYQITIRSTMSIPAC SEQ ID NO: 25
Human VSIG4-L-His Amino Acid Sequence
RPILEVPESVTGPWKGDVNLPCTYDPLQGYTQVLVKWLVQRGSDPVTIFLRDSSGDHIQQAKYQGRLHVSHKV
PGDVSLQLSTLEMDDRSHYTCEVTWQTPDGNQVVRDKITELRVQKLSVSKPTVTTGSGYGFTVPQGMRISLQC
QARGSPPISYIWYKQQTNNOEPIKVATLSTLLFKPAVIADSGSYFCTAKGQVGSEQHSDIVKFVVKDSSKLLK
TKTEAPTTMTYPLKATSTVKQSWDWTTDMDGYLGETSAGPGKSLPGSGHHHHHHHHHH SEQ ID NO: 26
Cynomolgus Monkey VSIG4-L-His Amino Acid Sequence
RPILEVPESITGPWKGDVNIPCTYGPLQGYTQVLVKWLVQRGSDPVTIFLRDSSGDHIQQAKYQGRLHVNQKV
PGDVSLQLSTLEMDDQSHYTCEVTWQTPDGNQVVRDKITELRVQKLSVSKPTVTTGSGYGFTVPQGMRISLQC
QARGSPPISYIWYKEQTNNQEPIKVATLSTLLFKPAMVADSGSYFCAAKGRVGSEQRSDIVKFVVKDSSKLLK SEQ ID NO: 27
Human VSIG4-S-His Amino Acid Sequence
RPILEVPESVTGPWKGDVNLPCTYDPLQGYTQVLVKWLVQRGSDPVTIFLRDSSGDHIQQAKYQGRLHVSHKV
PGDVSLQLSTLEMDDRSHYTCEVTWQT PDGNQVVRDKITELRVQKHSSKLLKTKTEAPTTMTYPLKATSTVKQ
SWDWTTDMDGYLGETSAGPGKSLPGSGHHHHHHHHHH SEQ ID NO: 28
Mouse VSIG4-His Amino Acid Sequence
HPTLKTPESVTGTWKGDVKIQCIYDPLRGYRQVLVKWLVRHGSDSVTIFLRDSTGDHIQQAKYRGRLKVSHKV
PGDVSLQINTLQMDDRNHYTCEVTWQTPDGNQVIRDKIIELRVRKYNPPRINTEAPTTLHSSLEATTIMSSTS
DLTTNGTGKLEETIAGSGRNLPGSGHHHHHHHHHH TABLE 1-continued

*The nucleic acid and polypeptide sequences of the biomarkers encompassed by the present invention listed in Table 1 have been submitted at GenBank under the unique identifier provided herein and each such uniquely identified sequence submitted at GenBank is hereby incorporated in its entirety by reference.
*Included in Table 1 are RNA nucleic acid molecules (e.g., thymidines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any publicly available sequence listed in Table 1 (see below for example), or a portion thereof. Such nucleic acid molecules may have a function of the full-length nucleic acid as described further herein.
*Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any publicly available sequence listed in and Table 1 (see below for example), or a portion thereof. Such polypeptides may have a function of the full-length polypeptide as described further herein.
*Included in Table 1 are additional known nucleic acid and amino acid sequences for the listed biomarkers.

IV. Antibodies and Antigen-Binding Fragments Thereof

Inflammatory phenotype of myeloid cells, such as suppressive myeloid cells, monocytes, macrophages, and/or dendritic cells, may be regulated by modulating the amount and/or activity of certain biomarkers (e.g., at least one target listed in Table 1), and such inflammatory phenotype modulation also modulates immune responses.

The present invention provides antibodies, and antigen-binding fragments thereof, that modulate targets listed in Table 1. Such compositions are useful to upregulate or downregulate monocyte and/or macrophage inflammatory phenotypes and, thereby, upregulate or downregulate, respectively, immune responses. Such compositions are also useful to detect the amount and/or activity of the targets listed in Table 1, such that the agents are useful for diagnosing, prognosing, and screening effects mediated by such targets.

Representative, exemplary, non-limiting antibodies are presented in Table 2 below.

TABLE 2

| Representative exemplary antibodies encompassed by the present invention |
|---|
| 12A08 |
| Light Chain |
| QILLTQSPAIMSASPGEKVTITC**SASSSVSYMH**WFQQKPGTSPKLWIY**STSNLAS**GVPARFSGSGSGTSYSLTISRMEAEDAATYYC**QQRSSYPLT**FGAGTKLELK (SEQ ID NO: 1) |
| Heavy Chain |
| EVMLVESGGGLVKPGGSLKLSCAAS**GFTFDDF**YMYWVRQTPEKRLEWVASIS**DGGTY**TYYPDSVKGRFTISRDNAKNTLYLQLSSLKSEDTAMYYCAR**GVDKYYYAMDY**WGQGTSVTVSS (SEQ ID NO: 2) |
| 12A12 |
| Light Chain |
| DIQMTQTTSSLSASLGDRVTISC**RASQDISNYLN**WYQQKPDGTLKLLIY**YTSRLHS**GVPSRFSGSGSGTDYSLTISNLEQEDIATYFC**RQGNTLPWT**FGGGTKLEIK (SEQ ID NO: 3) |
| Heavy Chain |
| QVQMKQSGAELAKPGASVKMSCKAS**GYTFTNY**WMHWVKQRPGQGLEWIGYI**NPSTGY**TDYNQNFKDRATLTADKSSSTAYMQLSSLTSEDSAVYYCIR**GSDYYGRDY**WGQGTTLTVSS (SEQ ID NO: 4) |
| 13H11 |
| Light Chain |
| ETTVTQSPASLSVATGEKVTIRC**ITSTDIDDDMN**WYQQKPGEPPKLLIS**EGNTLRP**GVPSRFSSSGYGTDFVFTIENMLSEDVADYYC**LQSDNLPLT**FGAGTKLELK (SEQ ID NO: 5) |
| Heavy Chain |
| QIQLVQSGPELKKPGETVKISCKAS**GYTFENF**GMNWVKQAPGKGLKWMGWI**NTYTGE**ATYADDFKGRFAFSLETSASTAYLQINNLKNEDTATYFCAR**DGGFRHFDV**WGAGTTVTVSS (SEQ ID NO: 6) |

TABLE 2-continued

| Representative exemplary antibodies encompassed by the present invention |
|---|
| 14C05 |
| Light Chain |
| ETTVTQSHKFMSTSVGDRVSITC**KASQDVSTAVA**WYQQKPGQSPKLLIY**SASYRYP**GVPDRFTGSGSGTDFTFTISSVQAEDLAVYYC**QQDYSSPWT**FGGGTKLEIK (SEQ ID NO: 29) |
| Heavy Chain |
| EVMLVESGPELKKPGETVKISCKAS**GYTFTNY**GMNWVKQAPGKGLKWMGSI**NTYTGE**ATYADDFKGRFAFSLETSANTAYLQIDNLKNEDTATYFCAR**GDYYGRGTWFAY**WGQGTLVTVSA (SEQ ID NO: 30) |
| 14D12 |
| Light Chain |
| DVVMTQTPASLAVSLGQRATISC**KASQSVDYDGDSYMN**WYQQKPGQPPKLLIY**AASNLES**GIPARFSGSGSGTDFTLNIHPVEEEDAATYYC**QQSNEDPRT**FGGGTKLEIK (SEQ ID NO: 31) |
| Heavy Chain |
| QIQLVQSGPELKKPGETVKISCKAS**GYTFTNY**GMNWVKQTPGKGLKWMGLI**NTYTGE**PTYADDFKGRFAFSLETSASTAYLQINNLKNEDMATYFCAR**ERIYGYLHYFDY**WGQGTTLTVSS (SEQ ID NO: 32) |
| 15A06 |
| Light Chain |
| DVVMTQTPLSLPVSLGDQASISC**RSSQSLVHSNGNTYLH**WYLQKPGQSPKLLIY**KVSNRFS**GVPDRFSGSGSGTDFTLKISRVEAEDLGVYFC**SQSTHVPFT**FGSGTKLEIK (SEQ ID NO: 33) |
| Heavy Chain |
| QVQMKQSGPSLVRPSQTLSLTCSVT**GDSITSG**YWNWIRKFPGDKFEYLGYI**SYSGF**TYYNPSLKSRVSITRDTSKNQYYLQLHSVTTEDTATYYCAS**SKYGSSLGFPY**WGQGTLVTVSA (SEQ ID NO: 34) |
| 15C03 |
| Light Chain |
| ENVLTQSPAIMSASPGEKVTMTC**RASSSVSSSYLH**WYQQKSGASPKLWIY**STSNLAS**GVPARFSGSGSGTSYSLTISSVEAEDAATYYC**QQYSGYPLT**FGSGTKLEIK (SEQ ID NO: 35) |
| Heavy Chain |
| EVKLLESGPGLVKPSQSLSLTCTVT**GYSITSDY**AWNWIRQFPGNKLEWMGYI**SYSGS**TRYNPSLKSRISITRDTSNNQFFLQLNSVTTEDTATYYCAR**SGYAAMDY**WGQGTSVTVSS (SEQ ID NO: 36) |
| 15C04 |
| Light Chain |
| DVVMTQTPLSLPVSLGDQASISC**RSSQSLVHSNGNTYLH**WYLQKPGQSPKLLIY**KVSNRFS**GVPDRFSGSGSGTDFTLKISRVEAEDLGVYFC**SQSTHVPWT**FGGGTKLEIK (SEQ ID NO: 37) |
| Heavy Chain |
| QIQLQESGPSLVRPSQTLSLTCSVT**GDSITSG**YWNWIRKFPGDKLEYLGYI**SYSGF**TYYNPSLKSRISITRDTSKNQYYLQLNSVTTEDTATYYCAS**SYYGSSLGFPY**WGQGTLVTVSA (SEQ ID NO: 38) |
| 16E03 |
| Light Chain |
| EIQMTQSHKFMSTSVGDRVSITC**KASQDVGTAVA**WYQQKPGQSPKLLIY**WASTRHT**GVPDRFTGSGSGTDFTLTISNVQSEDLADYFC**QQYSSYPLT**FGAGTKLELK (SEQ ID NO: 39) |

TABLE 2-continued

Representative exemplary antibodies encompassed by the present invention

Heavy Chain
QVQLQQSGAELARPGASVKMSCKASGYTFTSYTMHWIKQRPGQGLEWIGYINPSSGHTYYNQKFKDKATLTPDKSSSTAYMQLTSLTSEDSAVYYCARRIPTAYAMDYWGQGTSVTVSS (SEQ ID NO: 40)

16E10
Light Chain
DIVLTQSPSSLSVSAGEKVTLSCKSSQSLLNSGNQENYLAWYQQKPGQPPKLLIYGASTRESGVPDRFTGSGSGTDFTLTISSVQAEDLAVYYCQNDHSYPLTFGAGTKLELK (SEQ ID NO: 41)

Heavy Chain
QVQLQQSGAELVRPGTSVKISCKASGYTFTNYWLGWVKQRPGHGLEWIGDIYPGGGYTNYNEKFKGKATLTADTSSSTAYMQLSSLTSEDSAVYFCAKFYYYGSSYYFDSWGQGTTLTVSS (SEQ ID NO: 42)

16F6.E1
Light Chain
NIVLTQSPPSLAVSLGQRATISCRASESVDSYGNSFMHWYQQKPGQPPKLLIYLASNLESGVPARFSGSGSRTDFTLTIDPVEADDAATYFCHQNNEDPWTFGGGTKLEIK (SEQ ID NO: 43)

Heavy Chain
QVQLQQPGAEMVRPGASLKLSCKASGYTFTSYWMHWVKQRPGQGLEWIGKIDPSKNTTHYNQNFRDKATLTVDRSSSTAYMQLNSLTSEDSAVYFCVTWDGDFTYWGQGTLVTISA (SEQ ID NO: 44)

1C6.D6b
Light Chain
NIVLTQSPASLTVSLGQRATISCRASESVDSYGNSFMHWYQQKPGQPPKLLIYITSNLQSGVPARFSGGGSRTDFTLTIDPVEADDAATYYCQQNNEDPWTFGGGTKLEIK (SEQ ID NO: 45)

Heavy Chain
QVQLQQPGAEMVRPGTSVKLSCKASGYTFTSYWMHWVKQRPGQGLEWIGKIDPSHNKTHYIQKFEDKATLTVDKSSSTAYMHLNSLTSEDSAVYYCVTWDGDFLYWGQGTLVTVSA (SEQ ID NO: 46)

10E8.B6
Light Chain
DIVMSQSPSSLAVSAGEKVTMSCKSSQSLLNSRTRKNYLAWYQQKPGQSPKLLIYWASTRESGVPDRFTGSGSGTDFTLTISSVQAEDLAVYYCKQSYDLFTFGSGTKLEIK (SEQ ID NO: 47)

Heavy Chain
EVQLQQSGPELMKPGDSVKMSCKASGYTFTDYYMDWVKQSHGKSLEWIGYIYPNIDFTTYNQKFKGKATLTVDKSSNTAYMELHSLTSEDSAVYYCTRRDLPLHGSAYYFDYWGQGTTLTVSS (SEQ ID NO: 48)

13E11.A4
Light Chain
DIVMTQSHKFMSTSVGDNVSITCKASQYVSNTVAWYQQKPGQSPKLLIYSASYRNTGVPDRFTGSGSGTNFTFTISNMQAEDLAFYYCQQHYTSPLTFGAGTKLELK (SEQ ID NO: 49)

Heavy Chain
EVQLVESGGALVKPGGSLKLSCVASRFNLNNCVMSWIRQTPEKRLEWVATIDSGSIYTYYPDSVKGRFTISRDNAKNTLYLQMSSLRSEDTAVYYCVRHIYGYDVVDNWGQGTTLTVAS (SEQ ID NO: 50)

14F8.H6
Light Chain
DIVMTQSHRFMSTSVGDRVSITCKASHDVSNVVAWYQQKPGQSPELLIYSASYRYTGVPARFTGSGSGTDFTFTISSVQAEDLAVYFCQQHFTTPLTFGAGTSLEVR (SEQ ID NO: 51)

Heavy Chain
EVHLVESGGALVKPGGSLKLSCTASGFTFSNSVMSWIRQTPEKRLEWVATIGSGGTYIYYPDSVKGRFTISRDNSKNTLFLQMTSLRSEDTALYYCARHIYGYDVVDYWGQGTTLTVST (SEQ ID NO: 52)

9A10.C4
Light Chain
DIVMTQSHKFMSTSVGDRVTITCKASQDVSNVVAWFQQKPGQSPKLLIYSASYRFGGVPDRFTGSGSGTDFTFTISSVQAEDLAVYYCQQHYDTPLTFGTGTTLELK (SEQ ID NO: 53)

Heavy Chain
EVQLVESGGALVQPGGSLKLSCVASGFSFSNCVMSWVRQSPEKRLEWVATIGSDGSYSYYQDNVKGRFTVSRDNAKNTLYLQMSSLGSEDTALYYCGRHIYGYDVVDYWGQGTSLTVSS (SEQ ID NO: 54)

5D2.C8
Light Chain
DILLTQSPAILSVSPGERVSFSCRASQNIGTSIHWYQQRTNGSPRLLIKYASQSISGIPSRFSGSGSGTDFTLSINSVESEDIADYYCQQSYSWPLTFGTGTQLELK (SEQ ID NO: 55)

Heavy Chain
EVKLVESGGGLVKPGGSLKLSCAVSGFTFSNSAMSWVRQTPAKRLEWVAYISISGDNTYYPDSVKGRFTISRDNAKNTLYLQMSSLRSEDTAMYYCARRGYDYDGFTHWGQGTLVTVSA (SEQ ID NO: 56)

1H7.C7
Light Chain
DIVMTQSHKFMSTSVGDRVSITCKASQDVSNVVAWYQQKPGQSPKLLIYSASYRYTGVPDRFAGSGSGTDFTFTISSVQAEDLAVYYCQQHYSTPWTFGGGTKLEIK (SEQ ID NO: 57)

Heavy Chain
EVQLVESGGGLVMPGGSRRLSCAASGFTFSDSGMYWVRQAPEKGLEWIAYISSGSDTLYYAATVKGRFTISRDNAKNTLFLQMTSLRSEDTAIYYCAKRNFYGYDVMDYWGQGTSVTVSS (SEQ ID NO: 58)

16G02
Light Chain
DIVLTQSPASLAMSVGQKVTMSCKSSQSLLNSSNQKNYLAWYQQKPGQSPKLLLYFASTRESGVPDRFIGSGSGTDFTLTISSVQAEDLADYFCQQHYSNPLTFGAGTKLELK (SEQ ID NO: 59)

Heavy Chain
QVQLQQSGAELMKPGASVKISCKATGYTFSSYWIEWVKQRPGHGLEWIGEILPGSSTTNYNEKFKGKATFTADTSSNTAYMQLSSLTSEDSAVYYCAREDHFITTARYAMDYWGQGTSVTVSS (SEQ ID NO: 60)

h12A12.A
Light Chain
DIQMTQSPSSLSASVGDRVTITCQASQDISNYLNWYQQKPGKALKLLIYYTSRLHSGVPSRFSGSGSGTDYTFTISSLQPEDIATYFCRQGNTLPWTFGGGTKLEIK (SEQ ID NO: 61)

Heavy Chain
QVQMVQSGAEVKKPGASVKVSCKASGYTFTNYWMHWVRQAPGQGLEWMGYINPSTGYTDYNQKFQGRVTMTADKSTSTAYMELSSLRSEDTAVYYCIRGSDYYGRDYWGQGTTVTVSS (SEQ ID NO: 62)

h12A12.B
Light Chain
DIQMTQSPSSLSASVGDRVTITCQASQDISNYLNWYQQKPGKALKLLIYYTSRLHTGVPSRFSGSGSGTDYTFTISSLQPEDIATYYCRQGNTLPWTFGGGTKLEIK (SEQ ID NO: 63)

Heavy Chain
QVQMVQSGAEVKKPGASVKVSCKASGYTFTNYWMHWVRQAPGQGLEWMGYINPSTGYTDYNQKFQGRVTMTADKSTSTAYMELSSLRSEDTAVYYCIRGSDYYGRDYWGQGTTVTVSS (SEQ ID NO: 62)

h12A12.C
Light Chain
DIQMTQSPSSLSASVGDRVTITCQASQDISNYLNWYQQKPGKALKLLIYYTSRLHTGVPSRFSGSGSGTDYTFTISSLQPEDIATYYCRQGNTLPWTFGGGTKLEIK (SEQ ID NO: 63)

Heavy Chain
QVQMVQSGSELKKPGASVKVSCKASGYTFTNYWMHWVRQAPGQGLEWIGYINPSTGYTDYNQGFTGRFVLSADKSSSTAYLQISSLKAEDTAVYYCIRGSDYYGRDYWGQGTTVTVSS (SEQ ID NO: 64)

h12A12.D
Light Chain
EIVMTQSPATLSLSPGERATLSCRASQDISNYLNWYQQKPGQALRLLIYYTSRRHTGIPARFSGSGSGTDYTLTISSLEPEDFAVYYCRQGNTLPWTFGGGTKLEIK (SEQ ID NO: 65)

TABLE 2-continued

| Representative exemplary antibodies encompassed by the present invention |
| --- |
| Heavy Chain<br>QVQMVQSGSELKKPGASVKVSCKAS**GYTFTNY**WMHWVRQAPGQGLEWMGY<br>**INPSTGY**TDYNQGFTGRFVFSADKSVSTAYLQISSLKAEDTAVYYCIR**GS**<br>**DYYGRDY**WGQGTTVTVSS (SEQ ID NO: 66) |
| h12A12.E<br>Light Chain<br>DIQMTQSPSSLSASVGDRVTITC**QASQDISNYLN**WYQQKPGKAPKLLIY**Y**<br>**TSRLHS**GVPSRFSGSGSGTDYTFTISSLQPEDIATYYC**RQGNTLPWT**FGG<br>GTKLEIK (SEQ ID NO: 67) |
| Heavy Chain<br>QVQMVQSGAEVKKPGASVKVSCKAS**GYTFTNY**WMHWVRQAPGQGLEWMGY<br>**INPSTGY**TDYNQKFQGRVTMTADKSTSTAYMELSSLRSEDTAVYYCIR**GS**<br>**DYYGRDY**WGQGTTVTVSS (SEQ ID NO: 62) |
| h12A12.F<br>Light Chain<br>DIQMTQSPSSLSASVGDRVTITC**QASQDISNYLN**WYQQKPGKAPKLLIY**Y**<br>**TSRLHS**GVPSRFSGSGSGTDYTFTISSLQPEDIATYYC**RQGNTLPWT**FGG<br>GTKLEIK (SEQ ID NO: 67) |
| Heavy Chain<br>QVQMVQSGSELKKPGASVKVSCKAS**GYTFTNY**WMHWVRQAPGQGLEWIGY<br>**INPSTGY**TDYNQGFTGRFVLSADKSSSTAYLQISSLKAEDTAVYYCIR**GS**<br>**DYYGRDY**WGQGTTVTVSS (SEQ ID NO: 64) |
| h12A12.G<br>Light Chain<br>DIQMTQSPSSLSASVGDRVTITC**QASQDISNYLN**WYQQKPGKAPKLLIY**Y**<br>**TSRLHS**GVPSRFSGSGSGTDYTFTISSLQPEDIATYYC**RQGNTLPWT**FGG<br>GTKLEIK (SEQ ID NO: 67) |
| Heavy Chain<br>QVQLVQSGAEVKKPGASVKVSCKAS**GYTFTNY**WMHWVRQAPGQGLEWMGY<br>**INPSTGY**TDYNQKFQGRVTMTADTSTSTVYMELSSLRSEDTAVYYCIR**GS**<br>**DYYGRDY**WGQGTTVTVSS (SEQ ID NO: 68) |
| h12A12.H<br>Light Chain<br>DIQMTQSPSSLSASVGDRVTITC**QASQDISNYLN**WYQQKPGKAPKLLIY**Y**<br>**TSRLHS**GVPSRFSGSGSGTDYTFTISSLQPEDIATYY**CRQGNTLPWT**FGG<br>GTKLEIK (SEQ ID NO: 67) |
| Heavy Chain<br>QVQLVQSGSELKKPGASVKVSCKAS**GYTFTNY**WMHWVRQAPGQGLEWMGY<br>**INPSTGY**TDYNQGFTGRFVFSADTSVSTAYLQISSLKAEDTAVYYCIR**GS**<br>**DYYGRDY**WGQGTTVTVSS (SEQ ID NO: 69) |
| h13H11.A<br>Light Chain<br>ETQVTQSPSSLSASVGDRVTITC**QTSTDIDDDMN**WYQQKPGKAPKLLIS**E**<br>**GNTLRP**GVPSRFSSSGYGTDFTFTISSLQPEDIATYYC**LQSDNLPLT**FGG<br>GTKLEIK (SEQ ID NO: 70) |
| Heavy Chain<br>QIQLVQSGSELKKPGASVKVSCKAS**GYTFENF**GMNWVRQAPGQGLEWMGW<br>**INTYTGE**ATYADGFTGRFVFSLDTSVSTAYLQISSLKAEDTAVYYCAR**DG**<br>**GFRHFDV**WGQGTTVTVSS (SEQ ID NO: 71) |
| h13H11.B<br>Light Chain<br>ETQVTQSPSSLSASVGDRVTITC**QTSTDIDDDMN**WYQQKPGKAPKLLIS**E**<br>**GNTLRP**GVPSRFSSSGYGTDFTFTISSLQPEDIATYYC**LQSDNLPLT**FGG<br>GTKLEIK (SEQ ID NO: 70) |
| Heavy Chain<br>QIQLVQSGAEVKKPGASVKVSCKAS**GYTFENF**GMNWVRQAPGQRLEWMGW<br>**INTYTGE**ATYADKFQGRVTFTLDTSASTAYMELSSLRSEDTAVYFCAR**DG**<br>**GFRHFDV**WGQGTTVTVSS (SEQ ID NO: 72) |
| h13H11.C<br>Light Chain<br>DTQVTQSPSSLSASVGDRVTITC**QTSTDIDDDMN**WYQQKPGKAPKLLIS**E**<br>**GNTLRT**GVPSRFSSSGSGTDFTFTISSLQPEDIATYYC**LQSDNLPLT**FGG<br>GTKLEIK (SEQ ID NO: 73) |

TABLE 2-continued

| Representative exemplary antibodies encompassed by the present invention |
| --- |
| Heavy Chain<br>QIQLVQSGSELKKPGASVKVSCKAS**GYTFENF**GMNWVRQAPGQGLEWMGW<br>**INTYTGE**ATYADGFTGRFVFSLDTSVSTAYLQISSLKAEDTAVYYCAR**DG**<br>**GFRHFDV**WGQGTTVTVSS (SEQ ID NO: 71) |
| h13H11.D<br>Light Chain<br>DTQVTQSPSSLSASVGDRVTITC**QTSTDISNYMN**WYQQKPGKAPKLLIS**E**<br>**GNTLRP**GVPSRFSSSGSGTDFTFTISSLQPEDIATYYC**LQSDNLPLT**FGG<br>GTKLEIK (SEQ ID NO: 74) |
| Heavy Chain<br>QIQLVQSGSELKKPGASVKVSCKAS**GYTFENF**GMNWVRQAPGQGLEWMGW<br>**INTYTGE**ATYADGFTGRFVFSLDTSVSTAYLQISSLKAEDTAVYYCAR**DG**<br>**GFRHFDV**WGQGTTVTVSS (SEQ ID NO: 71) |
| h13H11.E<br>Light Chain<br>DTQVTQSPSSLSASVGDRVTITC**QTSTDISNYMN**WYQQKPGKAPKLLIS**E**<br>**GNTLRP**GVPSRFSSSGSGTDFTFTISSLQPEDIATYYC**LQSDNLPLT**FGG<br>GTKLEIK (SEQ ID NO: 74) |
| Heavy Chain<br>QIQLVQSGAEVKKPGASVKVSCKAS**GYTFENF**GMNWVRQAPGQRLEWMGW<br>**INTYTGE**ATYADKFQGRVTITLDTSASTAYMELSSLRSEDTAVYYCAR**DG**<br>**GFRHFDV**WGQGTTVTVSS (SEQ ID NO: 75) |
| h13H11.F<br>Light Chain<br>ETQVTQSPSSLSASVGDRVTITC**QTSTDIDDDMN**WYQQKPGKAPKLLIS**E**<br>**GNTLRP**GVPSRFSSSGYGTDFTFTISSLQPEDIATYYC**LQSDNLPLT**FGG<br>GTKLEIK (SEQ ID NO: 70) |
| Heavy Chain<br>QIQLVQSGSELKKPGASVKVSCKAS**GYTFENF**GMNWVRQAPGQGLEWMGW<br>**INTYTGE**ATYADDFKGRFVFSLDTSVSTAYLQISSLKAEDTAVYYCAR**DG**<br>**GFRHFDV**WGQGTTVTVSS (SEQ ID NO: 76) |
| h13H11.G<br>Light Chain<br>DTQVTQSPSSLSASVGDRVTITC**QTSTDIDDDMN**WYQQKPGKAPKLLIS**E**<br>**GNTLRT**GVPSRFSSSGSGTDFTFTISSLQPEDIATYYC**LQSDNLPLT**FGG<br>GTKLEIK (SEQ ID NO: 73) |
| Heavy Chain<br>QIQLVQSGSELKKPGASVKVSCKAS**GYTFENF**GMNWVRQAPGQGLEWMGW<br>**INTYTGE**ATYADDFKGRFVFSLDTSVSTAYLQISSLKAEDTAVYYCAR**DG**<br>**GFRHFDV**WGQGTTVTVSS (SEQ ID NO: 76) |
| h13H11.H<br>Light Chain<br>DTQVTQSPSSLSASVGDRVTITC**QTSTDISNYMN**WYQQKPGKAPKLLIS**E**<br>**GNTLRP**GVPSRFSSSGSGTDFTFTISSLQPEDIATYYC**LQSDNLPLT**FGG<br>GTKLEIK (SEQ ID NO: 74) |
| Heavy Chain<br>QIQLVQSGSELKKPGASVKVSCKAS**GYTFENF**GMNWVRQAPGQGLEWMGW<br>**INTYTGE**ATYADDFKGRFVFSLDTSVSTAYLQISSLKAEDTAVYYCAR**DG**<br>**GFRHFDV**WGQGTTVTVSS (SEQ ID NO: 76) |
| h14C05.A<br>Light Chain<br>ETQVTQSPSSLSASVGDRVTITC**RASQDVSTAVA**WYQQKPGKAPKLLIY**S**<br>**ASYRYP**GVPSRFSGSGSGTDFTLTISSLQPEDFATYYC**QQDYSSPWT**FGG<br>GTKLEIK (SEQ ID NO: 77) |
| Heavy Chain<br>EVMLVQSGSELKKPGASVKVSCKAS**GYTFTNY**GMNWVRQAPGQGLEWMGS<br>**INTYTGE**ATYADGFTGRFVFSLDTSANTAYLQISSLKAEDTAVYFCAR**GD**<br>**YYGRGTWFAY**WGQGTLVTVSS (SEQ ID NO: 78) |
| h14C05.B<br>Light Chain<br>ETQVTQSPSSLSASVGDRVTITC**RASQDVSTAVA**WYQQKPGKAPKLLIY**S**<br>**ASYRYP**GVPSRFSGSGSGTDFTLTISSLQPEDFATYYC**QQDYSSPWT**FGG<br>GTKLEIK (SEQ ID NO: 77) |

TABLE 2-continued

Representative exemplary antibodies encompassed by the present invention

Heavy Chain
QVQLVQSGSELKKPGASVKVSCKASGYTFTNYGMNWVRQAPGQGLEWMGSINTYTGEATYADGFTGRFVFSLDTSVNTAYLQISSLKAEDTAVYYCARGDYYGRGTWFAYWGQGTLVTVSS (SEQ ID NO: 79)

h14C05.C
Light Chain
ETQVTQSPSSLSASVGDRVTITCRASQDVSTAVAWYQQKPGKAPKLLIYSASYRYPGVPSRFSGSGSGTDFTLTISSLQPEDFATYYCQQDYSSPWTFGGGTKLEIK (SEQ ID NO: 77)

Heavy Chain
QVQLVQSGAEVKKPGASVKVSCKASGYTFTNYGMNWVRQAPGQGLEWMGSINTYTGEATYADKFQGRVTMTLDTSTNTAYMELSSLRSEDTAVYYCARGDYYGRGTWFAYWGQGTLVTVSS (SEQ ID NO: 80)

h14C05.D
Light Chain
ETVVTQSPATLSLSPGERATLSCRASQDVSTAVAWYQQKPGQAPRLLIYSASYRYPGIPARFSGSGSGTDFTLTISSLEPEDFAVYYCQQDYSSPWTFGGGTKLEIK (SEQ ID NO: 81)

Heavy Chain
QVQLVQSGSELKKPGASVKVSCKASGYTFTNYGMNWVRQAPGQGLEWMGSINTYTGEATYADGFTGRFVFSLDTSVNTAYLQISSLKAEDTAVYYCARGDYYGRGTWFAYWGQGTLVTVSS (SEQ ID NO: 79)

h14C05.E
Light Chain
ETVVTQSPATLSLSPGERATLSCRASQDVSTAVAWYQQKPGQAPRLLIYSASYRYPGIPARFSGSGSGTDFTLTISSLEPEDFAVYYCQQDYSSPWTFGGGTKLEIK (SEQ ID NO: 81)

Heavy Chain
QVQLVQSGAEVKKPGASVKVSCKASGYTFTNYGMNWVRQAPGQGLEWMGSINTYTGEATYADKFQGRVTMTLDTSTNTAYMELSSLRSEDTAVYYCARGDYYGRGTWFAYWGQGTLVTVSS (SEQ ID NO: 80)

h14C05.F
Light Chain
ETQVTQSPSSLSASVGDRVTITCRASQDVSTAVAWYQQKPGKAPKLLIYSASYRYPGVPSRFSGSGSGTDFTLTISSLQPEDFATYYCQQDYSSPWTFGGGTKLEIK (SEQ ID NO: 77)

Heavy Chain
QVQLVQSGSELKKPGASVKVSCKASGYTFTNYGMNWVRQAPGQGLEWMGSINTYTGEATYADDFKGRFVFSLDTSVNTAYLQISSLKAEDTAVYYCARGDYYGRGTWFAYWGQGTLVTVSS (SEQ ID NO: 82)

h14C05.G
Light Chain
ETQVTQSPSSLSASVGDRVTITCRASQDVSTAVAWYQQKPGKAPKLLIYSASYRYPGVPSRFSGSGSGTDFTLTISSLQPEDFATYYCQQDYSSPWTFGGGTKLEIK (SEQ ID NO: 77)

Heavy Chain
QVQLVQSGSELKKPGASVKVSCKASGYTFTNYGMNWVRQAPGQGLEWMGSINTYTGEATYAQGFTGRFVFSLDTSVSTAYLQISSLKAEDTAVYYCARGDYYGRGTWFAYWGQGTLVTVSS (SEQ ID NO: 83)

h14C05.H
Light Chain
ETQVTQSPSSLSASVGDRVTITCRASQDVSTAVAWYQQKPGKAPKLLIYSASYRYPGVPSRFSGSGSGTDFTLTISSLQPEDFATYYCQQDYSSPWTFGGGTKLEIK (SEQ ID NO: 77)

Heavy Chain
QVQLVQSGAEVKKPGASVKVSCKASGYTFTNYGMNWVRQAPGQGLEWMGSINTYTGEATYAQKFQGRVTMTLDTSTSTVYMELSSLRSEDTAVYYCARGDYYGRGTWFAYWGQGTLVTVSS (SEQ ID NO: 84)

h14D12.A
Light Chain
DVVMTQSPDSLAVSLGERATINCKASQSVDYDGDSYMNWYQQKPGQPPKLLIYAASNLESGVPDRFSGSGSGTDFTLTISSLQAEDVAVYYCQQSNEDPRTFGGGTKLEIK (SEQ ID NO: 85)

TABLE 2-continued

Representative exemplary antibodies encompassed by the present invention

Heavy Chain
QIQLVQSGSELKKPGASVKVSCKASGYTFTNYGMNWVRQAPGQGLEWMGLINTYTGEPTYADGFTGRFVFSLDTSASTAYLQISSLKAEDTAVYFCARERIYGYLHYFDYWGQGTTVTVSS (SEQ ID NO: 86)

h14D12.B
Light Chain
DVVMTQSPDSLAVSLGERATINCKASQSVDYDGDSYMNWYQQKPGQPPKLLIYAASNLESGVPDRFSGSGSGTDFTLTISSLQAEDVAVYYCQQSNEDPRTFGGGTKLEIK (SEQ ID NO: 85)

Heavy Chain
QIQLVQSGAEVKKPGASVKVSCKASGYTFTNYGMNWVRQAPGQGLEWMGLINTYTGEPTYADKFQGRVTMTLDTSTSTAYMELSSLRSEDTAVYFCARERIYGYLHYFDYWGQGTTVTVSS (SEQ ID NO: 87)

h14D12.C
Light Chain
DVVMTQSPDSLAVSLGERATINCKASQSVDYDGDSYMNWYQQKPGQPPKLLIYAASNRESGVPDRFSGSGSGTDFTLTISSLQAEDVAVYYCQQSNEDPRTFGGGTKLEIK (SEQ ID NO: 88)

Heavy Chain
QIQLVQSGAEVKKPGASVKVSCKASGYTFTNYGMNWVRQAPGQGLEWMGLINTYTGEPTYADKFQGRVTFTLDTSASTAYMELSSLRSEDTAVYFCARERIYGYLHYFDYWGQGTTVTVSS (SEQ ID NO: 89)

h14D12.D
Light Chain
DVQMTQSPSSLSASVGDRVTITCRASQSVDYDGDSYMNWYQQKPGKAPKLLIYAASNLESGVPSRFSGSGSGTDFTLTISSLQPEDFATYYCQQSNEDPRTFGGGTKLEIK (SEQ ID NO: 90)

Heavy Chain
QIQLVQSGSELKKPGASVKVSCKASGYTFTNYGMNWVRQAPGQGLEWMGLINTYTGEPTYADGFTGRFVFSLDTSASTAYLQISSLKAEDTAVYFCARERIYGYLHYFDYWGQGTTVTVSS (SEQ ID NO: 86)

h14D12.E
Light Chain
DVQMTQSPSSLSASVGDRVTITCRASQSVDYDGDSYMNWYQQKPGKAPKLLIYAASNLESGVPSRFSGSGSGTDFTLTISSLQPEDFATYYCQQSNEDPRTFGGGTKLEIK (SEQ ID NO: 90)

Heavy Chain
QIQLVQSGSELKKPGASVKVSCKASGYTFTNYGMNWVRQAPGQGLEWMGLINTYTGEPTYADGFTGRFVFSLDTSVSTAYLQISSLKAEDTAVYFCARERIYGYLHYFDYWGQGTTVTVSS (SEQ ID NO: 91)

h14D12.F
Light Chain
DVQMTQSPSSLSASVGDRVTITCRASQSVDYDGDSYMNWYQQKPGKAPKLLIYAASNLESGVPSRFSGSGSGTDFTLTISSLOPEDFATYYCQQSNEDPRTFGGGTKLEIK (SEQ ID NO: 90)

Heavy Chain
QIQLVQSGAEVKKPGASVKVSCKASGYTFTNYGMNWVRQAPGQGLEWMGLINTYTGEPTYADKFQGRVTMTLDTSTSTAYMELSSLRSEDTAVYFCARERIYGYLHYFDYWGQGTTVTVSS (SEQ ID NO: 87)

h14D12.G
Light Chain
DIQMTQSPSSLSASVGDRVTITCRASQSVDYDGDSYMNWYQQKPGKAPKLLIYAASNLESGVPSRFSGSGSGTDFTLTISSLOPEDFATYYCQQSNEDPRTFGGGTKLEIK (SEQ ID NO: 92)

Heavy Chain
QIQLVQSGSELKKPGASVKVSCKASGYTFTNYGMNWVRQAPGQGLEWMGLINTYTGEPTYADGFTGRFVFSLDTSASTAYLQISSLKAEDTAVYFCARERIYGYLHYFDYWGQGTTVTVSS (SEQ ID NO: 86)

h14D12.H
Light Chain
DIQMTQSPSSLSASVGDRVTITCRASQSVDYDGDSYMNWYQQKPGKAPKLLIYAASNLESGVPSRFSGSGSGTDFTLTISSLQPEDFATYYCQQSNEDPRTFGGGTKLEIK (SEQ ID NO: 92)

TABLE 2-continued

Representative exemplary antibodies encompassed by the present invention

Heavy Chain
QIQLVQSGAEVKKPGASVKVSCKASGYTFTNYGMNWVRQAPGQGLEWMGLINTYTGEPTYADKFQGRVTFTLDTSASTAYMELSSLRSEDTAVYFCARERIYGYLHYFDYWGQGTTVTVSS (SEQ ID NO: 89)

h16E10.A
Light Chain
DIVLTQSPDSLAVSLGERATINCKSSQSLLNSGNQENYLAWYQQKPGQPPKLLIYGASTRESGVPDRFSGSGSGTDFTLTISSLQAEDVAVYYCQNDHSYPLTFGGGTKLEIK (SEQ ID NO: 93)

Heavy Chain
QVQLVQSGAEVKKPGASVKVSCKASGYTFTNYWLGWVRQAPGQGLEWIGDIYPGGGYTNYNEKFQGRVTLTADTSSSTAYMELSSLRSEDTAVYFCAKFYYYGSSYYFDSWGQGTTVTVSS (SEQ ID NO: 94)

h16E10.B
Light Chain
DIVMTQSPDSLAVSLGERATINCKSSQSLLNSGNQENYLAWYQQKPGQPPKLLIYGASTRESGVPDRFSGSGSGTDFTLTISSLQAEDVAVYYCQNDHSYPLTFGGGTKLEIK (SEQ ID NO: 95)

Heavy Chain
QVQLVQSGAEVKKPGASVKVSCKASGYTFTNYWLGWVRQAPGQGLEWIGDIYPGGGYTNYNEKFQGRVTLTADTSSSTAYMELSSLRSEDTAVYFCAKFYYYGSSYYFDSWGQGTTVTVSS (SEQ ID NO: 94)

h16E10.C
Light Chain
DIVMTQSPDSLAVSLGERATINCKSSQSLLNSGNQENYLAWYQQKPGQPPKLLIYGASTRESGVPDRFSGSGSGTDFTLTISSLQAEDVAVYYCQNDHSYPLTFGGGTKLEIK (SEQ ID NO: 95)

Heavy Chain
QVQLVQSGAEVKKPGASVKVSCKASGYTFTNYWLGWVRQAPGQGLEWMGDIYPGGGYTNYNEKFQGRVTMTADTSTSTAYMELSSLRSEDTAVYYCAKFYYYGSSYYFDSWGQGTTVTVSS (SEQ ID NO: 96)

h16E10.D
Light Chain
DIVLTQSPLSLPVTPGEPASISCRSSQSLLNSGNQENYLAWYLQKPGQSPQLLIYGASTRESGVPDRFSGSGSGTDFTLKISRVEAEDVGVYYCQNDHSYPLTFGGGTKLEIK (SEQ ID NO: 97)

Heavy Chain
QVQLVQSGAEVKKPGASVKVSCKASGYTFTNYWLGWVRQAPGQGLEWIGDIYPGGGYTNYNEKFQGRVTLTADTSSSTAYMELSSLRSEDTAVYFCAKFYYYGSSYYFDSWGQGTTVTVSS (SEQ ID NO: 94)

h16E10.E
Light Chain
DIVLTQSPLSLPVTPGEPASISCRSSQSLLNSGNQENYLAWYLQKPGQSPQLLIYGASTRESGVPDRFSGSGSGTDFTLKISRVEAEDVGVYYCQNDHSYPLTFGGGTKLEIK (SEQ ID NO: 97)

Heavy Chain
QVQLVQSGAEVKKPGASVKVSCKASGYTFTNYWLGWVRQAPGQGLEWMGDIYPGGGYTNYNEKFQGRVTMTADTSTSTAYMELSSLRSEDTAVYYCAKFYYYGSSYYFDSWGQGTTVTVSS (SEQ ID NO: 96)

h16E10.F
Light Chain
DIVMTQSPLSLPVTPGEPASISCRSSQSLLNSGNQENYLAWYLQKPGQSPQLLIYGASTRESGVPDRFSGSGSGTDFTLKISRVEAEDVGVYYCQNDHSYPLTFGGGTKLEIK (SEQ ID NO: 98)

Heavy Chain
QVQLVQSGAEVKKPGASVKVSCKASGYTFTNYWLGWVRQAPGQGLEWIGDIYPGGGYTNYNEKFQGRVTLTADTSSSTAYMELSSLRSEDTAVYFCAKFYYYGSSYYFDSWGQGTTVTVSS (SEQ ID NO: 94)

h16E10.G
Light Chain
DIVMTQSPLSLPVTPGEPASISCRSSQSLLNSGNQENYLAWYLQKPGQSPQLLIYGASTRESGVPDRFSGSGSGTDFTLKISRVEAEDVGVYYCQNDHSYPLTFGGGTKLEIK (SEQ ID NO: 98)

TABLE 2-continued

Representative exemplary antibodies encompassed by the present invention

Heavy Chain
QVQLVQSGAEVKKPGASVKVSCKASGYTFTNYWLGWVRQAPGQGLEWMGDIYPGGGYTNYNEKFQGRVTMTADTSTSTAYMELSSLRSEDTAVYYCAKFYYYGSSYYFDSWGQGTTVTVSS (SEQ ID NO: 96)

Table 2 lists underlined sequences as CDR sequences according to Kabat nomenclature and bold sequences as CDR sequences according to Chothia nomenclature. CDR1, CDR2, and CDR3 are shown in standard order of appearance from left (N-terminus) to right (C-terminus).

Table 2 provides representative CDR sequences of antibodies, and antigen-binding fragments, including, but not limited to, Chothia CDRs, Kabat CDRs, AbM, CDR contact regions, and/or conformational definitions. In some embodiments, the CDRs are the Kabat CDRs. In other embodiments, the CDRs are the Chothia CDRs. In some embodiments, the CDRs are extended CDRs, which refers to all of the amino acid residues identified according to the Kabat and Chothia nomenclature. Thus, in some embodiments with more than one CDR, one or more of the CDRs may be any of Kabat, Chothia, extended CDRs, or combinations thereof.

Table 2 provides representative sequences of light chain and heavy chain sequences. In some embodiments, antibodies, and antigen-binding fragments, comprise CDRL1, CDRL2, and CDRL3 of a light chain shown in Table 2. In some embodiments, antibodies, and antigen-binding fragments, comprise CDRH1, CDRH2, and CDRH3 of a heavy chain shown in Table 2. In some embodiments, antibodies, and antigen-binding fragments, comprise CDRL1, CDRL2, CDRL3, CDRH1, CDRH2, and CDRH3 of a pair of light and heavy chains shown in Table 2. In some embodiments, antibodies, and antigen-binding fragments, comprise CDRL1, CDRL2, CDRL3, CDRH1, CDRH2, and CDRH3 of a pair of light and heavy chains from the same representative antibody shown in Table 2.

a. Compositions of Antibodies, and Antigen-Binding Fragments Thereof.

In general, antibodies, and antigen-binding fragments thereof, encompassed by the present invention are characterized in that they exhibit the ability to bind myeloid cells, such as suppressive myeloid cells, monocytes, macrophages, and/or dendritic cells, expressing VSIG4 polypeptide and increases an inflammatory phenotype of the myeloid cells, such as suppressive myeloid cells, monocytes, macrophages, and/or dendritic cells.

Antibodies (e.g., isolated monoclonal antibodies), as well as antigen-binding fragments thereof, that are directed against VSIG4 are provided. In some embodiments, mAbs have been deposited at the American Type Culture Collection (ATCC), in accordance with the terms of Budapest Treaty as described further below.

Since it is well-known in the art that antibody heavy and light chain CDR3 domains play a particularly important role in the binding specificity/affinity of an antibody for an antigen, antibodies encompassed by the present invention, such as those set forth in Table 2, preferably comprise the heavy and light chain CDR3s of variable regions encompassed by the present invention (e.g., including the sequences of Table 2, or portions thereof). The antibodies further may comprise the CDR2s of variable regions encompassed by the present invention (e.g., including the sequences of Table 2, or portions thereof). The antibodies further may comprise the CDR's of variable regions encompassed by the present invention (e.g., including the sequences of Table 2, or portions thereof). In other embodiments, the antibodies may comprise any combinations of the CDRs. In some embodiments, the CDR1s, CDR2s, and/or CDR3s may be selected from within the same heavy chain or light chain sequences encompassed by the present invention (e.g., including the sequences of Table 2, or portions thereof). In other embodiments, the CDR1s, CDR2s, and/or CDR3s may be selected from within the same heavy chain and light chain sequence pairs encompassed by the present invention (e.g., including the sequences of Table 2, or portions thereof).

The CDR1, CDR2, and/or CDR3 regions of the antibodies and antigen-binding fragments thereof described above may comprise the exact amino acid sequence(s) as those of variable regions encompassed by the present invention (e.g., including the sequences of Table 2, or portions thereof) disclosed herein. However, the ordinarily skilled artisan will appreciate that some deviation from the exact CDR sequences may be possible while still retaining the ability of the antibody to bind VSIG4 effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs encompassed by the present invention (e.g., including the sequences of Table 2, or portions thereof).

The structural features of known, non-human or human antibodies (e.g., a mouse or a non-rodent anti-human VSIG4 antibody) may be used to create structurally related human anti-human VSIG4 antibodies that retain at least one functional property of the antibodies encompassed by the present invention, such as binding of VSIG4. Another functional property includes inhibiting binding of the original known, non-human or human antibodies in a competition ELISA assay.

In some embodiments, antibodies, and antigen-binding fragments thereof, capable of binding human VSIG4 are provided, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 2.

Similarly, antibodies, and antigen-binding fragments thereof, capable of binding human VSIG4, comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 2, are also provided.

Antibodies, and antigen-binding fragments thereof, capable of binding human VSIG4, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 2; and comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 2, are also provided.

A skilled artisan will note that such percentage homology is equivalent to, or instead variation encompassed by the present invention, may be achieved by introducing 1, 2, 3, 4, 5, 6, 7, 8, 9, 10, or more amino acid substitutions, such as a conservative substitution, within a given CDR of interest.

Antibodies, and antigen-binding fragments thereof, encompassed by the present invention may comprise a heavy chain, wherein the variable domain comprises at least a CDR having a sequence selected from the group consisting of the heavy chain variable domain CDRs presented in Table 2 and a light chain, wherein the variable domain comprises at least a CDR having a sequence selected from the group consisting of the light chain variable domain CDRs presented in Table 2.

Such antibodies, and antigen-binding fragments thereof, may comprise a light chain, wherein the variable domain comprises at least a CDR having a sequence selected from the group consisting of CDR-L1, CDR-L2, and CDR-L3, as described herein; and/or a heavy chain, wherein the variable domain comprises at least a CDR having a sequence selected from the group consisting of CDR-H1, CDR-H2, and CDR-H3, as described herein. In some embodiments, the antibodies, and antigen-binding fragments thereof, capable of binding human VSIG4 comprises or consists of CDR-L1, CDR-L2, CDR-L3, CDR-H1, CDR-H2, and CDR-H3, as described herein.

The heavy chain variable domain of the antibodies, and antigen-binding fragments thereof, encompassed by the present invention may comprise or consist of the vH amino acid sequence set forth in Table 2 and/or the light chain variable domain of the antibodies, and antigen-binding fragments thereof, encompassed by the present invention may comprise or consist of the vκ amino acid sequence set forth in Table 2.

The antibodies, and antigen-binding fragments thereof, encompassed by the present invention may be produced and modified by any technique well-known in the art. For example, such antibodies, and antigen-binding fragments thereof, may be murine or non-rodent antibodies. Similarly, such antibodies, and antigen-binding fragments thereof, may be chimeric, preferably chimeric mouse/human antibodies. In some embodiments, the antibodies, and antigen-binding fragments thereof, are humanized antibodies such that the variable domain comprises human acceptor frameworks regions, and optionally human constant domain where present, and non-human donor CDRs, such as mouse or non-rodent CDRs as defined above.

In other embodiments, an immunoglobulin heavy and/or light chain according to the present invention comprises or consists of a vH or vκ variable domain sequence, respectively, provided in Table 2.

The present invention further provides polypeptides which have a sequence selected from the group consisting of vH variable domain, vκ variable domain, CDR-L1, CDR-L2, CDR-L3, CDR-H1, CDR-H2, and CDR-H3 sequences described herein. Antibodies, immunoglobulins, and polypeptides of the invention may be use in an isolated (e.g., purified) form or contained in a vector, such as a membrane or lipid vesicle (e.g. a liposome).

A number of modifications, fragments, and the like are further contemplated.

Generally, the term "antibody" or "Ab" is used in the broadest sense and specifically includes, without limitation, whole antibodies, monoclonal antibodies, polyclonal antibodies, multispecific antibodies (e.g., bispecific antibodies formed from at least two intact antibodies, trispecific, or antibodies of greater multispecificity), naturally-occurring forms of antibodies (e.g. IgG, IgA, IgM, IgE) and recombinant antibodies, antibody fragments, diabodies, antibody variants, and antibody-derived binding domains that are part of or associated with other peptides. Antibodies are primarily amino-acid based molecules but may also comprise one or more modifications (including, but not limited to the addition of sugar moieties, fluorescent moieties, chemical tags, etc.). In some cases, antibodies may include non-amino acid-based molecules. Antibodies encompassed by the present invention may be naturally occurring or produced by bioengineering.

Antibodies, and antigen-binding fragments thereof, may be isolated. As used herein, the term an "isolated antibody" is intended to refer to an antibody composition (such as having a desired antigenic specificity) which is substantially free of other antibodies (such as those having different antigenic specificities) (e.g., an isolated antibody that binds to VSIG4 and is substantially free of antibodies that do not bind to VSIG4). In some embodiments, however, an isolated antibody that specifically binds to VSIG4 may, however, have cross-reactivity to other proteins of interest, such as those from different family members, species, etc. For example, in some embodiments, the antibody maintains specific binding affinity for at least two species, such as human and other animals, such as non-rodent animals, or other mammal or non-mammal species. However, in some embodiments, the antibody maintains higher or indeed specific affinity and/or selectivity for human VSIG4. As described above, such differential or cross binding can be measured as a fold difference relative to a control, such as about 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 100-, 200-, 300-, 400-, 500-, 600-, 700-, 800-, 900-, 1000-fold, or greater, or any range in between, inclusive, such as about 1.5-fold to about 100-fold different relative to a control. In addition, an isolated antibody is typically substantially free of other cellular material and/or chemicals. In one embodiment, a combination of "isolated" monoclonal antibodies having different specificities to human VSIG4 are combined in a well-defined composition.

In some embodiments, an antibody or antigen-binding fragment thereof may comprise a heavy and light variable domain as well as an Fc region. Generally, the term "Fc region" is used to define a C-terminal region of an immunoglobulin heavy chain, including native-sequence Fc regions and variant Fc regions. Although the boundaries of the Fc region of an immunoglobulin heavy chain might vary, the human VSIG4IgG heavy-chain Fc region is usually defined to stretch from an amino acid residue at position Cys226, or from Pro230, to the carboxyl-terminus thereof. Suitable native-sequence Fc regions for use in the antibodies encompassed by the present invention include human IgG1, IgG2 (IgG2A, IgG2B, etc.), IgG3 and IgG4.

The term "native antibody" refers to a usually heterotetrameric glycoprotein of about 150,000 daltons that is composed of two identical light (L) chains and two identical heavy (H) chains. Each light chain is linked to a heavy chain by one covalent disulfide bond, while the number of disulfide linkages varies among the heavy chains of different immunoglobulin isotypes (e.g., IgG, IgA, IgE and IgM). Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. The rest of the constant domains of a heavy chain of an antibody's two heavy chains compose of the fragment crystallizable (Fc) region of the antibody.

The Fc region in the tail region of an antibody interacts with cell surface receptors called Fc receptors and some proteins of the complement system. Generally, the term "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγR1, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "light chain" refers to a component of an antibody from any vertebrate species assigned to one of two clearly distinct types, called kappa and lambda, based on amino acid sequences of constant domains. Depending on the amino acid sequence of the constant domain of their heavy chains, antibodies may be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The CL of an antibody, such as a human or human chimeric antibody, may be any region which belongs to Ig, such as the kappa class or lambda class.

The term "variable domain" refers to specific antibody domains on both the antibody heavy and light chains that differ extensively in sequence among antibodies and are used in the binding and specificity of each particular antibody for its particular antigen. For example, the term "VH" refers to "heavy chain variable domain" and the term "VL" refers to "light chain variable chain." Variable domains comprise hypervariable regions. The term "hypervariable region" refers to a region within a variable domain comprising amino acid residues responsible for antigen binding. These regions are hypervariable in sequence and/or form structurally defined loops The amino acids present within the hypervariable regions determine the structure of the complementarity determining regions (CDRs) that become part of the antigen-binding site of the antibody. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies (see, e.g., Xu et al. (2000) *Immunity* 13, 37-45; Johnson and Wu (2003) *Meth. Mol. Biol.* 248:1-25). The term "CDR" refers to a region of an antibody comprising a structure that is complimentary to its target antigen or epitope.

Other portions of the variable domain that do not interact with the antigen are referred to as framework (FW) regions. The antigen-binding site (also known as the antigen combining site or paratope) comprises the amino acid residues necessary to interact with a particular antigen. The exact residues making up the antigen-binding site are typically elucidated by co-crystallography with bound antigen, however computational assessments based on comparisons with other antibodies may also be used (Strohl, W. R. Therapeutic Antibody Engineering. Woodhead Publishing, Philadelphia PA. 2012. Ch. 3, p 47-54). Determining residues that make up CDRs may include the use of numbering schemes including, but not limited to, those taught by Kabat (Wu et al. (1970) *JEM* 132:211-250; Kabat et al. (1992) in "Sequences of Proteins of Immunological Interest," 5$^{th}$ Edition, U.S. Department of Health and Human Services; Johnson et al. (2000) *Nucl. Acids Res.* 28:214-218), Chothia (Chothia and Lesk (1987) *J. Mol. Biol.* 196:901; Chothia et al. (1989) *Nature* 342:877; Al-Lazikani et al. (1997) *J. Mol. Biol.* 273:927-948), Lefranc (Lefranc et al. (1995) *Immunome Res.* 1:3), Honegger (Honegger and Pluckthun (2001) *J. Mol. Biol.* 309: 657-670), and MacCallum (MacCallum et al. (1996) *J. Mol. Biol.* 262:732). CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," $5^{th}$ Edition, U.S. Department of Health and Human Services, 1992; Chothia et al. (1987) J. Mol. Biol. 196, 901; and MacCallum et al., J. Mol. Biol. (1996) 262, 732, each of which is incorporated by reference in its entirety).

VH and VL domains each have three CDRs. VL CDRs are referred to herein as CDR-L1, CDR-L2 and CDR-L3, in order of occurrence when moving from N- to C-terminus along the variable domain polypeptide. VH CDRs are referred to herein as CDR-H1, CDR-H2 and CDR-H3, in order of occurrence when moving from N- to C-terminus along the variable domain polypeptide. Each of CDRs has favored canonical structures, with the exception of the CDR-H3, which comprises amino acid sequences that may be highly variable in sequence and length between antibodies resulting in a variety of three-dimensional structures in antigen-binding domains (Nikoloudis et al. (2014) *Peer J.* 2:e456). In some cases, CDR-H3s may be analyzed among a panel of related antibodies to assess antibody diversity. Various methods of determining CDR sequences are known in the art and may be applied to known antibody sequences (Strohl, W. R. Therapeutic Antibody Engineering. Woodhead Publishing, Philadelphia PA. 2012. Ch. 3, p 47-54).

Antibodies, and antigen-binding fragments thereof, described herein include, but are not limited to, those comprising CDRs defined according to Chothia CDRs, Kabat CDRs, AbM, CDR contact regions, and/or conformational definitions. Determination of CDR regions is well within the skill of the art. It is understood that in some embodiments, CDRs may be a combination of the Kabat and Chothia CDR (also termed "combined CRs" or "extended CDRs"). In some embodiments, the CDRs are the Kabat CDRs. In other embodiments, the CDRs are the Chothia CDRs. In some embodiments, the CDRs are extended CDRs, which refers to all of the amino acid residues identified according to the Kabat and Chothia nomenclature. Thus, in some embodiments with more than one CDR, one or more of the CDRs may be any of Kabat, Chothia, extended CDRs, or combinations thereof.

In some embodiments, antibody fragments and variants may comprise any portion of an intact antibody. The terms "antibody fragments" and "antibody variants" also include any synthetic or genetically engineered proteins/polypeptides that act like an antibody by binding to a specific antigen to form a complex. In some embodiments, antibody fragments and variants comprise antigen binding regions from intact antibodies. Examples of antibody fragments may include, but are not limited to Fab, Fab', $F(ab')_2$, and Fv fragments; Fd, diabodies; intrabodies, linear antibodies; single-chain antibody molecules such as single chain variable fragment (scFv); multi-specific antibodies formed from antibody fragments, and the like. Regardless of structure, an antibody fragment or variant binds with the same antigen that is recognized by the parent full-length antibody.

Antibody fragments produced by limited proteolysis of wild-type antibodies are called proteolytic antibody fragments. These include, but are not limited to, Fab fragments, Fab' fragments and $F(ab')_2$ fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin or ficin treatment yields a $F(ab')_2$ fragment that has two antigen-binding sites and is still capable of cross-linking antigen. In general, an F(ab')2 fragment comprises two "arms," each of which comprises a variable region that is directed to and specifically binds a common antigen. The two Fab' molecules are joined by interchain disulfide bonds in the hinge regions of the heavy chains; the Fab' molecules may be directed toward the same (bivalent) or different (bispecific) epitopes. As used herein, the "Fab' fragments" contain a single anti-binding domain including an Fab and an additional portion of the heavy chain through the hinge region. Compounds and/or compositions encompassed by the present invention may comprise one or more of these fragments.

The term "Fv" refers to antibody fragments comprising complete antigen-recognition and antigen-binding sites. These regions consist of a dimer of one heavy chain and one light chain variable domain in tight, non-covalent association. Fv fragments may be generated by proteolytic cleavage, but are largely unstable. Recombinant methods are known in the art for generating stable Fv fragments, typically through insertion of a flexible linker between the light chain variable domain and the heavy chain variable domain (to form a single chain Fv (scFv) or through the introduction of a disulfide bridge between heavy and light chain variable domains (Strohl, W. R. Therapeutic Antibody Engineering. Woodhead Publishing, Philadelphia PA. 2012. Ch. 3, p 46-47).

The term "single-chain Fv" or "scFv" refers to a fusion protein of VH and VL antibody domains, wherein these domains are linked together into a single polypeptide chain by a flexible peptide linker. In some embodiments, the Fv polypeptide linker enables the scFv to form the desired structure for antigen binding. In some embodiments, the VH and VL domains may be linked by a peptide of 10 to 30 amino acid residues. In some embodiments, scFvs are utilized in conjunction with phage display, yeast display or other display methods where they may be expressed in association with a surface member (e.g., phage coat protein) and used in the identification of high affinity peptides for a given antigen. In some embodiments, the term "single-chain antibody" may further include, but is not limited to, a disulfide-linked Fv (dsFv) in which two single-chain antibodies (each of which may be directed to a different epitope) linked together by a disulfide bond. Using molecular genetics, two scFvs may be engineered in tandem into a single polypeptide, separated by a linker domain, called a "tandem scFv" (tascFv). Construction of a tascFv with genes for two different scFvs yields a "bispecific single-chain variable fragments" (bis-scFvs) (Nelson (2010) *Mabs* 2:77-83). Maxibodies (bivalent scFv fused to the amino terminus of the Fc (CH2-CH3 domains) of IgG may also be included.

In some embodiments, the antibody may comprise a modified Fc region. As a non-limiting example, the modified Fc region may be made by the methods or may be any of the regions described in U.S. Pat. Publ. No. US 2015-0065690.

Antibodies and antigen-binding fragments encompassed by the present invention may be "recombinant," which term includes antibodies and antigen-binding fragments thereof that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies may be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies may be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline VII and VL sequences, may not naturally exist within the human antibody germline repertoire in vivo.

The term "polyclonal antibodies" includes antibodies generated in an immunogenic response to a protein having many epitopes. A composition (e.g., serum) of polyclonal antibodies thus includes a variety of different antibodies directed to the same and to different epitopes within the protein. Methods for producing polyclonal antibodies are known in the art (see, e.g., Cooper et al., Section III of Chapter 11 in: *Short Protocols in Molecular Biology,* 2nd Ed., Ausubel et al., eds., John Wiley and Sons, New York, 1992, pages 11-37 to 11-41).

By contrast, the term "monoclonal antibody" refers to an antibody obtained from a population of substantially homogeneous cells (or clones), i.e., the individual antibodies comprising the population are identical and/or bind the same specific epitope of an antigen, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

The term "antibody variant" refers to a modified antibody (in relation to a native or starting antibody) or a biomolecule resembling a native or starting antibody in structure and/or function which includes some differences in their amino acid sequence, composition or structure as compared to the native or starting antibody (e.g., an antibody mimetic). Antibody variants may be altered in their amino acid sequence, composition or structure as compared to a native antibody. Antibody variants may include, but are not limited to, antibodies with altered isotypes (e.g., IgA, IgD, IgE, IgG1, IgG2, IgG3, IgG4, or IgM), humanized variants, optimized variants, multispecific antibody variants (e.g., bispecific variants), and antibody fragments. For example, mutant constant chain regions, such as mutant IgG4 having a substitution at Ser 228 like S228P, are contemplated.

In some embodiments, antibodies encompassed by the present invention may comprise antibody fusion proteins. As used herein, the term "antibody fusion protein" is a recombinantly produced antigen-binding molecule in which two or more of the same or different natural antibody, single-chain antibody or antibody fragment segments with the same or different specificities are linked. Valency of the fusion protein indicates the total number of binding arms or sites the fusion protein has to an antigen or epitope; i.e., monovalent, bivalent, trivalent or multivalent. The multivalency of the antibody fusion protein means that it may take advantage of multiple interactions in binding to an antigen, thus increasing the avidity of binding to the antigen. Specificity indicates how many different antigens or epitopes an antibody fusion protein is able to bind, i.e., monospecific, bispecific, trispecific, multispecific, etc. Using these definitions, a natural antibody, e.g., an IgG, is bivalent because it has two binding arms but is monospecific because it binds to one antigen. Monospecific, multivalent fusion proteins have more than one binding site for an epitope but only bind with the same epitope on the same antigen, for example a diabody with two binding sites reactive with the same antigen. The fusion protein may include a multivalent or multispecific combination of different antibody components or multiple copies of the same antibody component. The fusion protein may additionally include a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

In some embodiments, antibodies encompassed by the present invention may include multispecific antibodies. As used herein, the term "multispecific antibody" refers to an antibody that binds more than one epitope. As used herein, the terms "multibody" or "multispecific antibody" refer to an antibody wherein two or more variable regions bind to different epitopes. The epitopes may be on the same or different targets. In one embodiment, the multispecific antibody may be generated and optimized by the methods described in PCT Publ. No. WO 2011/109726 and U.S. Pat. Publ. No. 2015-0252119. These antibodies are able to bind to multiple antigens with high specificity and high affinity. In some embodiments, a multispecific antibody is a "bispecific antibody." As used herein, the term "bispecific antibody" refers to an antibody capable of binding two different epitopes on the same or different antigens. In one aspect, bispecific antibodies are capable of binding two different antigens. Such antibodies typically comprise antigen-binding regions from at least two different antibodies. For example, a bispecific monoclonal antibody (BsMAb, BsAb) is an artificial protein composed of fragments of two different monoclonal antibodies, thus allowing the BsAb to bind to two different types of antigen. Bispecific antibodies may include any of those described in Riethmuller (2012) *Cancer Immun.* 12:12-18, Marvin et al. (2005) *Acta Pharmacol. Sinica* 26:649-658, and Schaefer et al. (2011) *Proc. Natl. Acad. Sci. U.S.A.* 108:11187-11192. New generations of BsMAb, called "trifunctional bispecific" antibodies, have been developed. These consist of two heavy and two light chains, one each from two different antibodies, where the two Fab regions (the arms) are directed against two antigens, and the Fc region (the foot) comprises the two heavy chains and forms the third binding site.

In some embodiments, compositions encompassed by the present invention may include anti-peptide antibodies. As used herein, the term "anti-peptide antibodies" refers to "monospecific antibodies" that are generated in a humoral response to a short (typically, 5 to 20 amino acids) immunogenic polypeptide that corresponds to a few (preferably one) isolated epitopes of the protein from which it is derived (e.g., a target protein encompassed by the present invention). A plurality of antipeptide antibodies includes a variety of different antibodies directed to a specific portion of the protein, i.e., to an amino acid sequence that contains at least one, preferably only one, epitope. Methods for producing antipeptide antibodies are known in the art (see, e.g., Cooper et al., Section III of Chapter 11 in: *Short Protocols in Molecular Biology,* 2nd Ed., Ausubel et al., eds., John Wiley and Sons, New York, 1992, pages 11-42 to 11-46).

In some embodiments, antibodies encompassed by the present invention may include diabodies. As used herein, the term "diabody" refers to a small antibody fragment with two antigen-binding sites. Diabodies comprise a heavy chain variable domain VH connected to a light chain variable domain VL in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. U.S.A.* 90:6444-6448.

In some embodiments, antibodies encompassed by the present invention may include intrabodies. The term "intrabody" refers to a form of antibody that is not secreted from a cell in which it is produced, but instead targets one or more intracellular proteins. Intrabodies are a type of well-known antigen-binding molecules having the characteristic of antibodies, but that are capable of being expressed within cells in order to bind and/or inhibit intracellular targets of interest (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies may also be introduced and expressed in one or more cells, tissues or organs of a multicellular organism, for example for prophylactic and/or therapeutic purposes (e.g., as a gene therapy) (see, at least PCT Publ. Numbers WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett* 508:407-412; Shaki-Loewenstein et al. (2005) *J. Immunol. Meth.* 303:19-39).

Intrabodies may be used to affect a multitude of cellular processes including, but not limited to intracellular trafficking, transcription, translation, metabolic processes, proliferative signaling and cell division. In some embodiments, methods encompassed by the present invention may include intrabody-based therapies. In some such embodiments, variable domain sequences and/or CDR sequences disclosed herein may be incorporated into one or more constructs for intrabody-based therapy. For example, intrabodies may target one or more glycated intracellular proteins or may modulate the interaction between one or more glycated intracellular proteins and an alternative protein. The intracellular expression of intrabodies in different compartments of mammalian cells allows blocking or modulation of the function of endogenous molecules (Biocca et al. (1990) *EMBO J.* 9:101-108; Colby et al. (2004) *Proc. Natl. Acad. Sci. U.S.A.* 101: 17616-17621). Intrabodies may alter protein folding, protein-protein, protein-DNA, protein-RNA interactions and protein modification. They may induce a phenotypic knockout and work as neutralizing agents by direct binding to the target antigen, by diverting its intracellular trafficking or by inhibiting its association with binding partners. With high specificity and affinity to target antigens, intrabodies have advantages to block certain binding interactions of a particular target molecule, while sparing others. Sequences from donor antibodies may be used to develop intrabodies. Intrabodies are often recombinantly expressed as single domain fragments such as isolated VH and VL domains or as a single chain variable fragment (scFv) antibody within the cell. For example, intrabodies are often expressed as a single polypeptide to form a single chain antibody comprising the variable domains of the heavy and light chains joined by a flexible linker polypeptide. Intrabodies typically lack disulfide bonds and are capable of modulating the expression or activity of target genes through their specific binding activity. Single chain intrabodies are often expressed from a recombinant nucleic acid molecule and engineered to be retained intracellularly (e.g., retained in the cytoplasm, endoplasmic reticulum, or periplasm). Intrabodies may be produced using methods known in the art, such as those disclosed and reviewed in, for example, Marasco et al. (1993) *Proc. Natl. Acad. Sci. U.S.A.* 90:7889-7893; Chen et al. (1994) *Hum. Gene Ther.* 5:595-601; Chen et al. (1994) *Proc. Natl. Acad. Sci. U.S.A.* 91:5932-5936; Maciejewski et al. (1995) *Nat. Med.* 1:667-673; Marasco (1995) *Immunotech.* 1: 1-19; Mhashilkar et al. (1995) *EMBO J.* 14: 542-1451; Chen et al. (1996) *Hum. Gene Therap.* 7:1515-1525; Marasco (1997) *Gene Ther.* 4:11-15; Rondon and Marasco (1997) *Annu. Rev. Microbiol.* 51:257-283; Cohen et al. (1998) *Oncogene* 17:2445-2456; Proba et al. (1998) *J Mol. Biol.* 275:245-253; Cohen et al. (1998) *Oncogene* 17:2445-2456; Hassanzadeh et al. (1998) *FEBS Lett* 437:81-86; Richardson et al. (1998) *Gene Ther.* 5:635-644; Ohage and Steipe (1999) *J. Mol. Biol.* 291:1119-1128; Ohage et al. (1999) *J. Mol. Biol.* 291:1129-1134; Wirtz and Steipe (1999) *Protein Sci.* 8:2245-2250; Zhu et al. (1999) *J. Immunol. Methods* 231:207-222; Arafat et al. (2000) *Cancer*

*Gene Ther.* 7:1250-1256; der Maur et al. (2002) *J. Biol. Chem.* 277:45075-45085; Mhashilkar et al. (2002) *Gene Ther.* 9:307-319; and Wheeler et al. (2003) *FASEB J.* 17:1733-1735).

In some embodiments, antibodies encompassed by the present invention may include chimeric antibodies. As used herein, the term "chimeric antibody" refers to a recombinant antibody in which a portion of the heavy and light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, for example, U.S. Pat. No. 4,816,567; Morrison et al. (1984) *Proc. Natl. Acad. Sci. U.S.A.* 81:6851-6855). For example, a chimeric antibodies of interest herein may include "primatized" antibodies comprising variable domain antigen-binding sequences derived from a non-human primate (e.g., Old World Monkey, such as baboon, rhesus or cynomolgus monkey) and human constant region sequences.

In some embodiments, antibodies encompassed by the present invention may be composite antibodies. As used herein, the term "composite antibody" refers to an antibody which has variable regions comprising germline or non-germline immunoglobulin sequences from two or more unrelated variable regions. Additionally, the term "composite, human antibody" refers to an antibody which has constant regions derived from human germline or non-germline immunoglobulin sequences and variable regions comprising human germline or non-germline sequences from two or more unrelated human variable regions. A composite, human antibody is useful as an effective component in a therapeutic agent according to the present invention since the antigenicity of the composite, human antibody in the human body is lowered.

In some embodiments, antibodies encompassed by the present invention may include heterologous antibodies. The term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

In some embodiments, antibodies encompassed by the present invention may be humanized antibodies. As used herein, the term "humanized antibody" refers to a chimeric antibody comprising a minimal portion from one or more non-human (e.g., murine) antibody source with the remainder derived from one or more human immunoglobulin sources. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and/or capacity. In one embodiment, the antibody may be a humanized full-length antibody. Humanized antibodies may be generated using protein engineering techniques (e.g., Gussow and Seemann (1991) *Meth. Enzymol.* 203:99-121). As a non-limiting example, the antibody may have been humanized using the methods taught in U.S. Pat. Publ. No. 2013/0303399. The term "humanized antibody", as used herein, also includes antibodies in which CDR sequences derived from the germline of another mammalian species, such as a mouse, have been grafted onto human framework sequences.

A humanized mouse, as used herein, is a mouse carrying functioning human genes, cells, tissues, and/or organs. Humanized mice are commonly used as small animal models in biological and medical research for human therapeutics. The nude mouse and severe combined immunodeficiency (SCID) mouse may be used for this purpose. The NCG mouse, NOG mouse and the NSG mouse may be used to engraft human cells and tissues more efficiently than other models. Such humanized mouse models may be used to model the human immune system in scenarios of health and pathology, and may enable evaluation of therapeutic candidates in an in vivo setting relevant to human physiology.

In some embodiments, antibodies encompassed by the present invention may include cysteine-modified antibodies. In "cysteine-modified antibodies," a cysteine amino acid is inserted or substituted on the surface of antibody by genetic manipulation and used to conjugate the antibody to another molecule via, e.g., a disulfide bridge. Cysteine substitutions or insertions for antibodies have been described (see, e.g., U.S. Pat. No. 5,219,996). Methods for introducing cysteine residues into the constant region of the IgG antibodies for use in site-specific conjugation of antibodies are described by Stimmel et al. (2000) *J. Biol. Chem.* 275:330445-30450).

In some embodiments, antibody variants encompassed by the present invention may be antibody mimetics. As used herein, the term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (see U.S. Pat. Nos. 6,673,901 and 6,348,584). In some embodiments, antibody mimetics may include any of those known in the art including, but are not limited to affibody molecules, affilins, affitins, anticalins, avimers, Centyrins, DARPINS™, Fynomers and Kunitz and domain peptides. In other embodiments, antibody mimetics may include one or more non-peptide region.

In some embodiments, antibodies encompassed by the present invention may comprise a single antigen-binding domain. These molecules are extremely small, with molecular weights approximately one-tenth of those observed for full-sized mAbs. Further antibodies may include "nanobodies" derived from the antigen-binding variable heavy chain regions (VHHs) of heavy chain antibodies found in camels and llamas, which lack light chains (see, e.g., Nelson (2010) *Mabs* 2:77-83).

In some embodiments, antibodies encompassed by the present invention may be "miniaturized." On example of mAb miniaturization is small modular immunopharmaceuticals (SMIPs). These molecules, which may be monovalent or bivalent, are recombinant single-chain molecules containing one VL, one VH antigen-binding domain, and one or two constant "effector" domains, all connected by linker domains. (see, e.g., Nelson (2010) *Mabs* 2:77-83). Such a molecule is believed to offer the advantages of increased tissue or tumor penetration claimed by fragments while retaining the immune effector functions conferred by constant domains. Another example of miniaturized antibodies is called a "unibody" in which the hinge region has been removed from IgG4 molecules. While IgG4 molecules are unstable and may exchange light-heavy chain heterodimers with one another, deletion of the hinge region prevents heavy chain-heavy chain pairing entirely, leaving highly specific monovalent light/heavy heterodimers, while retaining the Fc region to ensure stability and half-life in vivo. This configuration may minimize the risk of immune activation or oncogenic growth, as IgG4 interacts poorly with FcRs and monovalent unibodies fail to promote intracellular signaling complex formation (see, e.g., Nelson (2010) *Mabs* 2:77-83).

In some embodiments, antibody variants encompassed by the present invention may be single-domain antibodies (sdAbs, or nanobodies). As used herein the term "sdAb" or "nanobody" refers to an antibody fragment consisting of a single monomeric variable antibody domain. Like a whole antibody, it is able to bind selectively to a specific antigen. In one aspect, a sdAb may be a "Camel Ig or "camelid VHH." As used herein, the term "camel Ig" refers to the smallest known antigen-binding unit of a heavy chain antibody (Koch-No lte et al (2007) *FASEB J.* 21:3490-3498). A "heavy chain antibody" or a "camelid antibody" refers to an antibody that contains two VH domains and no light chains (Hamers-Casterman et al. (1993) *Nature* 363:446-448 (1993); Sheriff et al. (1996) *Nat. Struct. Biol.* 3:733-736; Riechmann et al (1999) *J. Immunol. Meth.* 231:25-38; PCT Publ. Numbers WO1 994/04678 and WO 1994/025591; and U.S. Pat. No. 6,005,079). In another aspect, a sdAb may be a "immunoglobulin new antigen receptor" (IgNAR). The term "immunoglobulin new antigen receptor" refers to class of antibodies from the shark immune repertoire that consist of homodimers of one variable new antigen receptor (VNAR) domain and five constant new antigen receptor (CNAR) domains. IgNARs represent some of the smallest known immunoglobulin-based protein scaffolds and are highly stable and possess efficient binding characteristics. The inherent stability may be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulphide bridges, and patterns of intra-loop hydrogen bonds. Other miniaturized antibody fragments may include "complementary determining region peptides" or "CDR peptides." A CDR peptide (also known as "minimal recognition unit") is a peptide corresponding to a single complementarity-determining region (CDR), and may be prepared by constructing genes encoding the CDR of an antibody of interest. Such genes are prepared, for example, by using the polymerase chain reaction to synthesize the variable region from RNA of antibody-producing cells (see, e.g., Larrick et al (1991) *Methods Enzymol.* 2:106).

Other variants comprising antigen-binding fragments of antibodies may include but are not limited to, disulfide-linked Fvs (sdFv), $V_L$, $V_H$, Camel Ig, V-NAR, VHH, trispecific ($Fab_3$), bispecific ($Fab_2$), triabody (trivalent), tetrabody (tetravalent), minibody ($(scFv\text{-}CH3)_2$), bispecific single-chain Fv (Bis-scFv), IgGdeltaCH2, scFv-Fc, $(scFv)_2$-Fc, affibody, peptide aptamer, avimer or nanobody, or other antigen binding subsequences of an intact immunoglobulin.

In some embodiments, antibodies encompassed by the present invention may be antibodies as described in U.S. Pat. No. 5,091,513. Such an antibody may include one or more sequences of amino acids constituting a region which behaves as a biosynthetic antibody binding site (BABS). The sites comprise 1) non-covalently associated or disulfide bonded synthetic VH and VL dimers, 2) VH-VL or VL-VH single chains wherein the VH and VL are attached by a polypeptide linker, or 3) individuals VH or VL domains. The binding domains comprise linked CDR and FR regions, which may be derived from separate immunoglobulins. The biosynthetic antibodies may also include other polypeptide sequences which function, e.g., as an enzyme, toxin, binding site, or site of attachment to an immobilization media or radioactive atom. Methods are disclosed for producing the biosynthetic antibodies, for designing BABS having any specificity that may be elicited by in vivo generation of antibody, and for producing analogs thereof.

In some embodiments, antibodies encompassed by the present invention may be antibodies with antibody acceptor frameworks taught in U.S. Pat. No. 8,399,625. Such antibody acceptor frameworks may be particularly well suited accepting CDRs from an antibody of interest.

In one embodiment, the antibody may be a conditionally active biologic protein. An antibody may be used to generate a conditionally active biologic protein which are reversibly or irreversibly inactivated at the wild-type normal physiological conditions, as well as to such conditionally active biologic proteins and uses of such conditional active biologic proteins are provided. Such methods and conditionally active proteins are taught in, for example, PCT. Publ. Numbers WO 2015/175375 and WO 2016/036916 and U.S. Pat. Publ. No. 2014/0378660.

In some embodiments, antibodies encompassed by the present invention are therapeutic antibodies. As used herein, the term "therapeutic antibody" means an antibody that is effective in treating a disease or disorder in a mammal with or predisposed to the disease or disorder. An antibody may be a cell penetrating antibody, a neutralizing antibody, an agonist antibody, partial agonist, inverse agonist, partial antagonist or an antagonist antibody.

In some embodiments, antibodies encompassed by the present invention may be naked antibodies. As used herein, the term "naked antibody" is an intact antibody molecule that contains no further modifications such as conjugation with a toxin, or with a chelate for binding to a radionuclide. The Fc portion of the naked antibody may provide effector functions, such as complement fixation and ADCC (antibody dependent cell cytotoxicity), which set mechanisms into action that may result in cell lysis (see, e.g., Markrides (1998) *Pharmacol. Rev.* 50:59-87).

It is well-known that antibodies can lead to the depletion of cells extracellularly bearing the antigen specifically recognized by the antibody. This depletion may be mediated through at least three mechanisms: antibody-mediated cellular cytotoxicity (ADCC), complement-dependent lysis, and direct anti-tumour inhibition of tumour growth through signals given via the antigen targeted by the antibody.

"Complement dependent cytotoxicity" or "CDC" refers to the lysis of a target cell in the presence of complement. Activation of the classical complement pathway is initiated by the binding of the first component of the complement system to antibodies which are bound to their cognate antigen. To assess complement activation, a CDC assay, e.g. as described in Gazzano-Santoro et al. (1997) may be performed.

"Antibody-dependent cell-mediated cytotoxicity" or "ADCC" refers to a form of cytotoxicity in which secreted antibodies bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell. To assess ADCC activity of a molecule of interest, an in vitro ADCC assay, such as that described in U.S. Pat. No. 5,500,362 or 5,821,337 may be performed. As is well-known in the art, the Fc portions may be engineered to effect a desired interaction or lack thereof with Fc receptors.

Fc receptors are found on many cells which participate in immune responses. Fc receptors (FcRs) are cell surface receptors for the Fc portion of immunoglobulin polypeptides (Igs). Among the human FcRs that have been identified so far are those which recognize IgG (designated Fcγ R), IgE (Fcε R1), IgA (Fcα), and polymerized IgM/A (Fcμα R). FcRs are found in the following cell types: FCε R I (mast cells), FCε R.II (many leukocytes), Fcα R (neutrophils), and Fcμα R (glandular epithelium, hepatocytes) (Hogg, N. (1988) *Immunol. Today* 9:185-86). The widely studied FcγRs are central in cellular immune defenses, and are responsible for stimulating the release of mediators of inflammation and hydrolytic enzymes involved in the pathogenesis of autoimmune disease (Unkeless, J. C. et al. (1988) *Annu. Rev. Immunol.* 6:251-81). The FcγRs provide a crucial link between effector cells and the lymphocytes that secrete Ig, since the macrophage/monocyte, polymorphonuclear leukocyte, and natural killer (NK) cell FcγRs confer an element of specific recognition mediated by IgG. Human leukocytes have at least three different receptors for IgG: h Fcγ RI (found on monocytes/macrophages), hFcγ RII (on monocytes, neutrophils, eosinophils, platelets, possibly B cells, and the K562 cell line), and Fcγ III (on NK cells, neutrophils, eosinophils, and macrophages).

In some embodiments, antibodies encompassed by the present invention may be conjugated with one or more detectable label for purposes of detection according to methods well-known in the art. The label may be a radioisotope, fluorescent compound, chemiluminescent compound, enzyme, or enzyme co-factor, or any other labels known in the art. In some embodiments, the antibody that binds to a desired target (also referred to herein as a "primary antibody") is not labeled, but may be detected by binding of a second antibody that specifically binds to the primary antibody (referred to herein as a "secondary antibody"). According to such methods, the secondary antibody may include a detectable labeled.

In some embodiments, enzymes that may be attached to antibodies may include, but are not limited to horseradish peroxidase (HRP), alkaline phosphatase, and glucose oxidase (GOx). Fluorescent compounds may include, but are not limited to, ethidium bromide; fluorescein and derivatives thereof (e.g., FITC); cyanine and derivatives thereof (e.g., indocarbocyanine, oxacarbocyanine, thiacarbocyanine, and merocyanine); rhodamine; oregon green; eosin; texas red; nile red; nile blue; cresyl violet; oxazine 170; proflavin; acridine orange; acridine yellow; auramine; crystal violet; malachite green; porphin; phthalocyanine; bilirubin; allophycocyanin (APC); green fluorescent protein (GFP) and variants thereof (e.g., yellow fluorescent protein YFP, blue fluorescent protein BFP, and cyan fluorescent protein CFP); ALEXIFLOUR® compounds (Thermo Fisher Scientific, Waltham, MA); and quantum dots. Other conjugates that may be used to label antibodies may include biotin, avidin, and streptavidin.

For example, conjugation of antibodies or other proteins encompassed by the present invention with heterologous agents may be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6 diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies that specifically bind a biomarker of interest, conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody encompassed by the present invention may be conjugated to a radioisotope, e.g., radioactive iodine, to generate cytotoxic radiopharmaceuticals for treating a related disorder, such as a cancer.

Conjugated anti-biomarker antibodies may be used diagnostically or prognostically to monitor polypeptide levels in tissue as part of a clinical testing procedure, e.g., to determine the efficacy of a given treatment regimen or to select patients most likely to response to an immunotherapy. For example, cells may be permeabilized in a flow cytometry assay to allow antibodies that bind a biomarker of interest to target its recognized intracellular epitope and allow detection of the binding by analyzing signals emanating from the conjugated molecules. Detection may be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}I$, $^{131}S$, $^{35}S$, or $^{3}H$. As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or indocyanine (Cy5)) to the antibody, as well as indirect labeling of the antibody by reactivity with a detectable substance.

The antibody conjugates encompassed by the present invention may be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well-known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

In some embodiments, conjugations may be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

In some embodiments, the present invention encompasses antibody-drug conjugate (ADCs) agents. ADCs are conjugates of an antibody with another moiety such that the agent has targeting ability conferred by the antibody and an additional effect conferred by the moiety. For example, a cytotoxic drug may be tethered to an antibody, or antigen-binding fragment thereof, that targets the drug to a cell of interest that contribute to disease progression (e.g., tumor progression) and, upon internalization, releases its toxic payload to the cell. Different effects are achieved based on the conjugated moiety as described above.

In some embodiments, additional modifications and changes may be made in the structure of the antibodies (and antigen-binding fragments thereof), and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions may be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

In one embodiment, amino acid changes may be achieved by changing codons in the DNA sequence to encode conservative substitutions based on conservation of the genetic code. Specifically, there is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code (see genetic code chart above).

As described above, an important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well-known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies may be achieved by the use of a variety of endo- and exo-glycosidases as described by Thotakura, N R. et al. (1987).

Other modifications may involve the formation of immunoconjugates. For example, in one type of covalent modification, antibodies or proteins are covalently linked to one of a variety of non-proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

b. Antibody Engineering

As described above, techniques that may be used to produce antibodies and antibody fragments, such as Fabs and scFvs, are well-known in the art and include those described in U.S. Pat. Nos. 4,946,778 and 5,258,498; Miersch et al. (2012) *Methods* 57:486-498; Chao et al. (2006) *Nat. Protoc.* 1:755-768), Huston et al. (1991) *Methods Enzymol.* 203:46-88; Shu et al. (1993) *Proc. Natl. Acad. Sci. U.S.A.* 90:7995-7999; and Skerra et al. (1988) *Science* 240:1038-1041). Representative examples of engineered antibodies are described herein, such as those having alterations in residues capable of chemical modification were altered, as well as those having useful sequence modifications (e.g., CDR sequences to be more similar to the human germline, and the like). Such antibody variants are encompassed by the present invention.

After isolation or selection of target antigen-specific antibodies, antibody sequences may be used for recombinant production and/or optimization of such antibodies. In the case of antibody fragment isolation from a display library, coding regions from the isolated fragment may be used to generate whole antibodies, including human antibodies, or any other desired target binding fragment, and expressed in any desired host, including mammalian cells, insect cells, plant cells, yeast, and bacteria, e.g., as described in detail below. If desired, IgG antibodies (e.g., IgG1, IgG2, IgG3 or IgG4) may be synthesized for further testing and/or product development from variable domain fragments produced or selected according to the methods described herein. Such antibodies may be produced by insertion of one or more segments of cDNA encoding desired amino acid sequences into expression vectors suited for IgG production. Expression vectors may comprise mammalian expression vectors suitable for IgG expression in mammalian cells. Mammalian expression of IgGs may be carried out to ensure that antibodies produced comprise modifications (e.g., glycosylation) characteristic of mammalian proteins and/or to ensure that antibody preparations lack endotoxin and/or other contaminants that may be present in protein preparations from bacterial expression systems.

In some embodiments, affinity maturation is performed. The term "affinity maturation" refers to a method whereby antibodies are produced with increasing affinity for a given target through successive rounds of mutation and selection of antibody- or antibody fragment-encoding cDNA sequences. In some cases, this process is carried out in vitro. To accomplish this, amplification of variable domain sequences (in some cases limited to CDR coding sequences) may be carried out using error-prone PCR to produce millions of copies containing mutations including, but not limited to point mutations, regional mutations, insertional mutations and deletional mutations. As used herein, the term "point mutation" refers to a nucleic acid mutation in which one nucleotide within a nucleotide sequence is changed to a different nucleotide. As used herein, the term "regional mutation" refers to a nucleic acid mutation in which two or more consecutive nucleotides are changed to different nucleotides. As used herein, the term "insertional mutation" refers to a nucleic acid mutation in which one or more nucleotides are inserted into a nucleotide sequence. As used herein, the term "deletional mutation" refers to a nucleic acid mutation in which one or more nucleotides are removed from a nucleotide sequence. Insertional or deletional mutations may include the complete replacement of an entire codon or the change of one codon to another by altering one or two nucleotides of the starting codon.

Mutagenesis may be carried out on CDR-encoding cDNA sequences to create millions of mutants with singular mutations in heavy and light chain CDR regions. In another approach, random mutations are introduced only at CDR residues most likely to improve affinity. These newly generated mutagenic libraries may be used to repeat the process to screen for clones that encode antibody fragments with even higher affinity for the target peptide. Continued rounds of mutation and selection promote the synthesis of clones with greater and greater affinity (see, e.g., Chao et al. (2006) *Nat. Protoc.* 1:755-768).

Affinity matured clones may be selected based on affinity as determined by binding assay (e.g., FACS, ELISA, surface plasmon resonance, etc.). Select clones may then be converted to IgG and tested further for affinity and functional activity. In some cases, the goal of affinity optimization is to increase the affinity by at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100 fold, at least 500-fold or at least 1,000-fold or more as compared to the affinity of the original antibody. In cases where optimized affinity is less than desired, the process may be repeated.

In some embodiments, generating chimeric and/or humanized antibodies is useful. For example, for some uses, including the in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal immunoglobulin and a human immunoglobulin constant region. Methods for producing chimeric antibodies are well-known in the art (see, e.g., Morrison (1985) *Science* 229: 1202-1207; Gillies et al. (1989) *J. Immunol. Meth.* 125:191-202; and U.S. Pat. Nos. 5,807,715; 4,816,567; and 4,816, 397).

Humanized antibodies are antibody molecules from non-human species that bind to the desired target and have one or more complementarity determining regions (CDRs) from the nonhuman species and framework regions from a human immunoglobulin molecule. Often, framework residues in the human framework regions are substituted with corresponding residues from the CDR and framework regions of the donor antibody to alter, preferably improve, target binding. These framework substitutions are identified by methods well-known in the art, e.g., by modeling of the interactions of the CDR and framework residues to identify framework residues important for target binding, and by sequence comparison to identify unusual framework residues at particular positions (see, e.g., U.S. Pat. Nos. 5,693,762 and 5,585,089; Riechmann et al. (1988) *Nature* 332:323-327).

Antibodies may be humanized using a variety of techniques known in the art, including, for example, CDR-grafting (see, e.g., EP Pat. Publ. No. 239,400; PCT Publ. No. WO 91/09967; U.S. Pat. Nos. 5,225,539; 5,530,101; and 5,585,089); veneering or resurfacing (see, e.g., EP Pat. Publ. No. 592,106; EP Pat. Publ. No. 519,596; Padlan (1991) *Mol. Immunol.* 28:489-498; Studnicka et al. (1994) Protein Eng. 7:805-814; Roguska et al. (1994) *Proc. Natl. Acad. Sci.* U.S.A. 91:969-973); and chain shuffling (see, e.g., U.S. Pat. No. 5,565,332).

Completely human antibodies are particularly desirable for therapeutic treatment of human patients, so as to avoid or alleviate immune reaction to foreign protein. Human antibodies may be made by a variety of methods known in the art, including the antibody display methods described above, using antibody libraries derived from human immunoglobulin sequences (see, e.g., U.S. Pat. Nos. 4,444,887 and 4,716,111; and PCT Publ. Numbers WO 98/46645, WO 98/50433, WO 98/24893, WO 98/16654, WO 96/34096, WO 96/33735, and WO 91/10741). Human antibodies may also be produced using transgenic mice which are incapable of expressing functional endogenous immunoglobulins, but which may express human immunoglobulin polynucleotides. For example, the human heavy and light chain immunoglobulin polynucleotide complexes may be introduced randomly, or by homologous recombination, into mouse embryonic stem cells. Alternatively, the human variable region, constant region, and diversity region may be introduced into mouse embryonic stem cells, in addition to the human heavy and light chain polynucleotides. The mouse heavy and light chain immunoglobulin polynucleotides may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected immunogen (e.g., target antigen). Using such a technique, it is possible to produce useful human IgG, IgA, IgM, IgD and IgE antibodies. As illustrated above, methods for producing human antibodies and human monoclonal antibodies and protocols for producing such antibodies are well-known in the art (see also, e.g., PCT Publ. Numbers WO 98/24893, WO 92/01047, WO 96/34096, and WO 96/33735; and U.S. Pat. Nos. 5,413,923; 5,625,126; 5,633, 425; 5,569,825; 5,661,016; 5,545,806; 5,814,318; 5,885, 793; 5,916,771; 5,939,598; 6,075,181; and 6,114,598).

Once an antibody molecule encompassed by the present invention has been produced by an animal, a cell line, chemically synthesized, or recombinantly expressed, it may be purified (i.e., isolated) by any method known in the art for the purification of an immunoglobulin or polypeptide molecule, for example, by chromatography (e.g., ion 5 exchange, affinity, particularly by affinity for the specific target, Protein A, and sizing column chromatography), centrifugation, differential solubility, or by any other standard technique for the purification of proteins. In addition, the antibodies encompassed by the present invention or fragments thereof may be fused to heterologous polypeptide sequences described herein or otherwise known in the art, to facilitate purification.

In accordance with the present invention, antibodies specifically binding to an antigen may be present in a solution or bound to a substrate. In some embodiments, the antibodies are bound to cellulose nanobeads and confined in one or more detection area of a substrate of a detection device.

c. Antibody Generation

Antibodies, and antigen-binding fragments thereof, encompassed by the present invention may be naturally occurring or man-made through any methods known in the art, such as monoclonal antibodies (mAbs) produced by conventional hybridoma technology, recombinant technology, mutation or optimization of a known antibody, selection from a an antibody library or antibody fragment library, and immunization. The generation of antibodies, whether monoclonal or polyclonal, is well-known in the art. Techniques for the production of antibodies are well-known in the art and described, e.g., in Harlow and Lane "Antibodies, A Laboratory Manual", Cold Spring Harbor Laboratory Press, 1988; Harlow and Lane "Using Antibodies: A Laboratory Manual" Cold Spring Harbor Laboratory Press, 1999 and "Therapeutic Antibody Engineering: Current and Future Advances Driving the Strongest Growth Area in the Pharmaceutical Industry" Woodhead Publishing, 2012.

The antibodies, as well as variants and/or fragments thereof, as described herein may be produced using recombinant polynucleotides. In one embodiment, the polynucleotides have a modular design to encode at least one of the antibodies, fragments or variants thereof. As a non-limiting example, the polynucleotide construct may encode any of the following designs: (1) the heavy chain of an antibody, (2) the light chain of an antibody, (3) the heavy and light chain of the antibody, (4) the heavy chain and light chain separated by a linker, (5) the VH1, CH1, CH2, CH3 domains, a linker and the light chain or (6) the VH1, CH1, CH2, CH3 domains, VL region, and the light chain. Any of these designs may also comprise optional linkers between any domain and/or region. The polynucleotides encompassed by the present invention may be engineered to produce any standard class of immunoglobulins using an antibody described herein or any of its component parts as a starting molecule.

Methods of antibody development typically rely on the use of a target molecule for selection, immunization, and/or confirmation of antibody affinity and/or specificity. In some embodiments, antibodies may be prepared through immunization of a host with one or more target antigens, which act as immunogens to elicit an immunological response, using well-established methods known by those skilled in the art.

d. Antibody Characterization and Effects

Antibodies, and antigen-binding fragments thereof, encompassed by the present invention may be characterized by one or more of characteristics selected from the group consisting of structure, isotype, binding (e.g., affinity and specificity), conjugation, glycosylation, and other distinguishing features.

Such agents encompassed by the present invention may be from any animal origin including birds and mammals. Preferably, such antibodies are of human, murine (e.g., mouse and rat), donkey, sheep, rabbit, goat, guinea pig, camel, horse, or chicken origin. Antibodies encompassed by the present invention may be monospecific or multispecific. Multispecific antibodies may be specific for different epitopes of a peptide encompassed by the present invention, or may be specific for both a peptide encompassed by the present invention, and a heterologous epitope, such as a heterologous peptide or solid support material (see, e.g., PCT Publ. Numbers WO 93/17715, WO 92/08802, WO 91/00360, and WO 92/05793; Tuft et al. (1991) *J. Immunol.* 147:60-69; U.S. Pat. Nos. 4,474,893; 4,714,681; 4,925,648; 5,573,920; and 5,601,819; and Kostelny et al. (1992) *J. Immunol.* 148:1547-1553). For example, the antibodies may be produced against a peptide containing repeated units of a peptide sequence encompassed by the present invention, or they may be produced against a peptide containing two or more peptide sequences encompassed by the present invention, or the combination thereof. As a non-limiting example, a heterobivalent ligand (HBL) system that competitively inhibits antigen binding to mast cell bound IgE antibody, thereby inhibiting mast cell degranulation, has been designed (Handlogten et al. (2011) *Chem. Biol.* 18:1179-1188).

Antibody characteristics may be determined relative to a standard under normal physiologic conditions, either in vitro or in vivo. Measurements may also be made relative to the presence or absence of the antibodies. Such methods of measuring include standard measurement in tissue or fluids such as serum or blood such as Western blot, enzyme-linked immunosorbent assay (ELISA), activity assays, reporter assays, luciferase assays, polymerase chain reaction (PCR) arrays, gene arrays, real time reverse transcriptase (RT) PCR and the like.

Antibodies may bind or interact with any number of locations on or along a target protein. Antibody target sites contemplated include any and all possible sites on the target protein. Antibodies may be selected for their ability to bind (reversibly or irreversibly) to one or more epitopes on a specific target. Epitopes on targets may include, but are not limited to, one or more feature, region, domain, chemical group, functional group, or moiety. Such epitopes may be made up of one or more atom, group of atoms, atomic structure, molecular structure, cyclic structure, hydrophobic structure, hydrophilic structure, sugar, lipid, amino acid, peptide, glycopeptide, nucleic acid molecule, or any other antigen structure.

Methods for epitope mapping are well-known in the art and include, without limitation, structural, functional, and computational methods. X-ray crystallography is a well-known structural approach, wherein a crystal structure of a bonded antibody-antigen pair enables very accurate determination of key interactions between individual amino acids from both side chains and main chain atoms in both the epitope of the antigen and the paratope of the antibody. Amino acids that are within 4 angstroms of each other are generally considered to be contacting residues. The methodology typically involves purification of antibody and antigen, formation and purification of the complex, and then successive rounds of crystallization screens and optimization to obtain diffraction-quality crystals. Structural solution is obtained following x-ray crystallography frequently at a synchrotron source. Other structural methods for epitope mapping include, but are not limited to, hydrogen-deuterium exchange coupled to mass spectrometry, crosslinking-coupled mass spectrometry, and nuclear magnetic resonance (NMR) (Epitope Mapping Protocols in Methods in Molecular Biology, Vol. 66, G. E. Morris, Ed. (1996); Abbott et al. (2014) *Immunol.* 142:526-535).

Functional methods for epitope mapping are also well-known in the art and typically involve an assessment or quantification of antibody binding to whole proteins, protein fragments, or peptides. Functional methods for epitope mapping may be used, for example, to identify linear or conformational epitopes and/or may be used to infer when two or more distinct antibodies bind to the same or similar epitopes. Functional methods for epitope mapping include, for example, immunoblotting and immunoprecipitation assays, wherein overlapping or contiguous peptides from a biomarker of interest are tested for reactivity with an anti-biomarker antibody such as those described herein. Other functional methods for epitope mapping include array-based oligopeptide scanning (alternatively known as "overlapping peptide scanning" or "pepscan analysis"), site-directed mutagenesis (e.g., alanine-scanning mutagenesis), and high-throughput mutagenesis mapping (e.g., shotgun mutagenesis mapping).

Numerous types of competitive binding assays are known, which include the following, non-limiting examples: solid phase direct or indirect radioimmunoassay (RIA), solid phase direct or indirect enzyme immunoassay (EIA), sandwich competition assay (Stahli et al. (1983) *Meth. Enzymol.* 9:242); solid phase direct biotin-avidin EIA (Kirkland et al. (1986) *J. Immunol.* 137:3614); solid phase direct labeled assay or solid phase direct labeled sandwich assay (Harlow and Lane, Antibodies: A Laboratory Manual, Cold Spring Harbor Press (1988)); solid phase direct label RIA using $I^{125}$ label (Morel et al. (1988) *Mol. Immunol.* 25:7); solid phase direct biotin-avidin EIA (Cheung et al. (1990) *Virol.* 176:546); and direct labeled RIA (Moldenhauer et al. (1990) *Scand. J. Immunol.* 32:77). Typically, such assays involve the use of purified antigen bound to a solid surface or cells and either 1) an unlabeled test antigen-binding protein and a labeled reference antigen-binding protein, or 2) a labeled test antigen-binding protein and an unlabeled reference antigen-binding protein. Competitive inhibition is measured by determining the amount of label bound to the solid surface or cells in the presence of the test antigen-binding protein. Usually the test antigen-binding protein is present in excess. Antigen-binding proteins identified by competition assay (competing antigen-binding proteins) include antigen-binding proteins binding to the same epitope as the reference antigen-binding proteins and antigen-binding proteins binding to an adjacent epitope sufficiently proximal to the epitope bound by the reference antigen-binding protein for steric hindrance to occur. Additional details regarding methods for determining competitive binding are provided in the examples herein. Usually, when a competing antigen-binding protein is present in excess (e.g., about 1-, about 5-, about 10-, about 20- about 50-, or about 100-fold excess), it will inhibit or block specific binding of a reference antigen-binding protein to a common antigen by at least about 40-45%, about 45-50%, about 50-55%, about 55-60%, about 60-65%, about 65-70%, about 70-75% or about 75% or more. In some instances, binding is inhibited by at least about 80-85%, about 85-90%, about 90-95%, about 95-97%, or about 97% or more.

Effects of agents described herein, such as antibodies, antigen-binding fragments thereof, cells, and the like, may be assessed using reagents, methods, and assays well-known to the ordinarily skilled artisan, especially in view of the Examples. In some embodiments, controls are used for comparison, such as those described in the definitions above. For example, an assay may involve contacting a biomarker target, such as on a cell or substrate, with an agent of interest, determining a desired measurement (e.g., amount, activity, cytokine production, cellular proliferation, cell death, etc.), and comparing the measurement to that from a reference or control, such as the measurement resulting from contact with a control agent like a control antibody or antigen-binding fragment thereof that does not specifically bind an antigen of interest. Any known measurement or assay may be used, especially those presented in the Examples, such as conventional cytokine production determination assays, cell activation assays, cell proliferation assays, cell death assays, cell migration assays, cell signaling assays, and the like.

Also as described in the definitions above, "significant" modulation of a desired measurement may be quantified numerically, such as being above a certain numerical value (e.g., percentage), below a certain numerical value (e.g., percentage), or within a certain numerical range (e.g., percentage range). Representative, non-limiting examples of quantitative measurements include affinity ($K_D$), $k_d$, $k_a$, percentage increase or decrease of biomarker expression, percentage increase or decrease of cells (e.g., desired cells, undesired cells, ratio of desired cells to undesired cells, ratio of desired cells to total cells, ratio of undesired cells to total cells, and the like, at one time point or compared over different time points, and the like).

V. Nucleic Acids, Vectors, and Cells, Including Host Cells

A further object of the invention relates to nucleic acid sequences encoding antibodies and antigen-binding fragments thereof described herein (and fragments thereof), as well as polypeptides, vectors, and cells, including host cells.

a. Nucleic Acid Agents

One aspect encompassed by the present invention involves the use of nucleic acid molecules. Nucleic acid molecules may be deoxyribonucleic acid (DNA) molecules (e.g., cDNA, genomic DNA, and the like), ribonucleic acid (RNA) molecules (e.g., mRNA, long non-coding RNA, small RNA species, and the like), DNA/RNA hybrids, and analogs of the DNA or RNA generated using nucleotide analogs. RNA agents may include RNAi (RNA interfering) agents (e.g., small interfering RNA (siRNA)), single-strand RNA (ssRNA) molecules (e.g., antisense oligonucleotides) or double-stranded RNA (dsRNA) molecules. A dsRNA molecule comprises a first strand and a second strand, wherein the second strand is substantially complementary to the first strand, and the first strand and the second strand form at least one double-stranded duplex region. The dsRNA molecule may be blunt-ended or have at least one terminal overhang. When used as agents that bind target nucleic acid sequences, nucleic acid agents encompassed by the present invention may n hybridize to any region of a target sequence, such as genomic sequence and/or mRNA sequence, including, but not limited to, the enhancer region, the promoter region, the transcriptional start and/or stop region, splice sites, the coding region, the 3'-untranslated region (3'-UTR), the 5'-untranslated region (5'-UTR), the 5' cap, the 3' poly adenylyl tail, or any combination thereof.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule may contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, may be substantially free of other cellular material or culture medium when produced by recombinant techniques, or substantially free of chemical precursors or other chemicals when chemically synthesized.

A nucleic acid molecule encompassed by the present invention may be isolated using standard molecular biology techniques and the sequence information in the database records described herein. Using all or a portion of such nucleic acid sequences, nucleic acid molecules encompassed by the present invention may be isolated using standard hybridization and cloning techniques (e.g., as described in Sambrook et al., ed., *Molecular Cloning: A Laboratory Manual,* 4th ed., Cold Spring Harbor Laboratory Press, Cold Spring Harbor, N Y, 2012).

A nucleic acid molecule encompassed by the present invention may be amplified using cDNA, mRNA, or genomic DNA as a template and appropriate oligonucleotide primers according to standard PCR amplification techniques. The nucleic acid molecules so amplified may be cloned into an appropriate vector and characterized by DNA sequence analysis. Furthermore, nucleic acid molecules corresponding to all or a portion of a nucleic acid molecule encompassed by the present invention may be prepared by standard synthetic techniques, e.g., using an automated nucleic acid synthesizer. Alternatively, the nucleic acid molecules may be produced biologically using an expression vector into which a nucleic acid has been sub-cloned. For example, antisense nucleic acid molecules may be cloned in an antisense orientation (i.e., RNA transcribed from the inserted nucleic acid will be of an antisense orientation to a target nucleic acid of interest as described further below).

Moreover, a nucleic acid molecule encompassed by the present invention may comprise only a portion of a nucleic acid sequence, wherein the full length nucleic acid sequence comprises a marker encompassed by the present invention or which encodes a polypeptide corresponding to a marker encompassed by the present invention. Such nucleic acid molecules may be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule may be used to detect transcripts or genomic sequences corresponding to one or more markers encompassed by the present invention. The probe comprises a label group attached thereto, e.g., a radioisotope, a fluorescent compound, an enzyme, or an enzyme co-factor.

Biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence may exist within a population (e.g., the human population). Such genetic polymorphisms may exist among individuals within a population due to natural allelic variation. An allele is one of a group of genes which occur alternatively at a given genetic locus. In addition, it will be appreciated that DNA polymorphisms that affect RNA expression levels may also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles may differ from each other in a single nucleotide, or several nucleotides, and may include substitutions, deletions, and insertions of nucleotides. An allele of a gene may also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs may also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele may contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker encompassed by the present invention. Such natural allelic variations may typically result in 1-5% variance in the nucleotide sequence of a given gene. Alternative alleles may be identified by sequencing the gene of interest in a number of different individuals. This may be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope encompassed by the present invention.

In another embodiment, a biomarker nucleic acid molecule may be at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker encompassed by the present invention or to a nucleic acid molecule encoding a protein corresponding to a marker encompassed by the present invention. The term "hybridizes under stringent conditions" is intended to describe conditions for hybridization and washing under which nucleotide sequences at least 60% (65%, 70%, 75%, 80%, 85%, 90%, 95%, or higher) identical to each other typically remain hybridized to each other. Such stringent conditions are known to those skilled in the art and may be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule encompassed by the present invention that may exist in the population, the skilled artisan will further appreciate that sequence changes may be introduced by mutation thereby leading to changes in the amino acid sequence of the encoded protein, without altering the biological activity of the protein encoded thereby. For example, one may make nucleotide substitutions leading to amino acid substitutions at "non-essential" amino acid residues. A "non-essential" amino acid residue is a residue that may be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect encompassed by the present invention encompasses nucleic acid molecules encoding a polypeptide encompassed by the present invention that contain changes in amino acid residues that are not essential for activity. Such polypeptides differ in amino acid sequence from the naturally-occurring proteins which correspond to the markers encompassed by the present invention, yet retain biological activity. In one embodiment, a biomarker protein has an amino acid sequence that is at least about 60%, 65%, 70%, 75%, 80%, 85%, 86%, 87%, 88%, 89%, 90%, 91%, 92%, 93%, 94%, 95%, 96%, 97%, 98%, 99% identical, or more, or any range in between, such as 90%-95% identical, to the amino acid sequence of a biomarker protein described herein. Similarly, nucleic acid molecules having a sequence encoding such biomarker proteins are contemplated.

An isolated nucleic acid molecule encoding a variant protein may be created by introducing one or more nucleotide substitutions, additions or deletions into the nucleotide sequence of nucleic acids encompassed by the present invention, such that one or more amino acid residue substitutions, additions, or deletions are introduced into the encoded protein. Mutations may be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations may be introduced randomly along all or part of the coding sequence, such as by saturation mutagenesis, and the resultant mutants may be screened for biological activity to identify mutants that retain activity. Following mutagenesis, the encoded protein may be expressed recombinantly and the activity of the protein may be determined.

In some embodiments, nucleic acids in genomes are useful and may be used as targets and/or agents. For example, target DNA in the genome may be manipulated using well-known methods in the art. Target DNA in the genome may be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

b. Vectors and Other Nucleic Acid Vehicles

In accordance with the present invention, nucleic acid molecules and variants thereof may be produced by any methods known in the art, such as direct synthesis and genetic recombination techniques. Nucleic acid molecules may be present in any forms such as pure nucleic acid molecules, plasmids, DNA vectors, RNA vectors, viral vectors and particles. The term "vector" refers to a nucleic acid molecule capable of transporting another nucleic acid to which it has been linked. Vectors encompassed by the present invention may also be used to deliver the packaged polynucleotides to a cell, a local tissue site or a subject.

One type of vector is a "plasmid," which refers to a circular double-stranded DNA loop into which additional nucleic acid segments may be ligated. Another type of vector is a "viral vector," wherein additional DNA segments may be ligated into a viral genome. Viral nucleic acid delivery vectors may be of any kind, including Retroviruses, Adenoviruses, Adeno-associated viruses, Herpes simplex viruses and variants thereof. Viral vector technology is well-known and described in Sambrook et al. (2012, Molecular Cloning: A Laboratory Manual, Cold Spring Harbor Laboratory (4th Ed.), New York).

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

Recombinant expression vectors encompassed by the present invention comprise a nucleic acid encompassed by the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, CA (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, and the like. The expression vectors encompassed by the present invention may be introduced into host cells to thereby produce proteins or peptides, including fusion proteins or peptides, encoded by nucleic acids as described herein. For example, in general, vectors contain an origin of replication functional in at least one organism, a promoter sequence and convenient restriction endonuclease site, and one or more selectable markers e.g., a drug resistance gene. Vectors may comprise native or non-native promoters operably linked to the polynucleotides encompassed by the present invention. The promoters selected may be strong, weak, constitutive, inducible, tissue specific, development stage-specific, and/or organism specific. In some embodiments, the vector may comprise regulatory sequences, such as, enhancers, transcription and translation initiation and termination codons, which are specific to the type of host cell into which the vector is to be introduced.

Recombinant expression vectors for use according to the present invention may be designed for expression of a polypeptide corresponding to a biomarker encompassed by the present invention in prokaryotic (e.g., *E. coli*) or eukaryotic cells (e.g., insect cells, such as using baculovirus expression vectors, yeast cells or mammalian cells). Suitable host cells are discussed further in Goeddel, supra. Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, MA) and pRIT5 (Pharmacia, Piscataway, NJ), which fuse glutathione S-transferase (GST), maltose E binding protein, or protein A, respectively, to the target recombinant protein.

Representative, non-limiting examples of suitable inducible non-fusion *E. coli* expression vectors include pTrc (Amann et al. (1988) *Gene* 69:301-315) and pET 11d (Studier et al. (1991) *Meth. Enzymol.* 185:60-89). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman (1990) *Meth. Enzymol.* 185:119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences encompassed by the present invention may be carried out by standard DNA synthesis techniques.

In some embodiments, the expression vector is a yeast expression vector. Examples of vectors for expression in yeast *S. cerevisiae* include pYepSec1 (Baldari et al. (1987) *EMBO J.* 6:229-234), pMFa (Kurjan and Herskowitz (1982) *Cell* 30:933-943), pJRY88 (Schultz et al. (1987) *Gene* 54:113-123), pYES2 (Invitrogen Corporation, San Diego, CA), and pPicZ (Invitrogen Corp, San Diego, CA).

Alternatively, the expression vector is a baculovirus expression vector. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In some embodiments, a nucleic acid encompassed by the present invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. U.S.A.* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the $\alpha$-fetoprotein promoter (Camper and Tilghman (1989) *Genes Dev.* 3:537-546).

The present invention also provides recombinant expression vectors for expressing antisense nucleic acids, as described further below. For example, DNA molecule may be operably linked to a regulatory sequence in a manner which allows for expression (by transcription of the DNA molecule) of an RNA molecule which is antisense to the mRNA encoding a polypeptide encompassed by the present invention. Regulatory sequences operably linked to a nucleic acid cloned in the antisense orientation may be chosen which direct the continuous expression of the antisense RNA molecule in a variety of cell types, for instance viral promoters and/or enhancers, or regulatory sequences may be chosen which direct constitutive, tissue-specific or cell type specific expression of antisense RNA. The antisense expression vector may be in the form of a recombinant plasmid, phagemid, or attenuated virus in which antisense nucleic acids are produced under the control of a high efficiency regulatory region, the activity of which may be determined by the cell type into which the vector is introduced. For a discussion of the regulation of gene expression using antisense genes (see Weintraub et al. (1986) *Trends Genet.* 1(1)).

In some embodiments, a retroviral vector is useful according to the present invention. Retroviruses are named because reverse transcription of viral RNA genomes to DNA is required before integration into the host cell genome. As such, the most important features of retroviral vectors are the permanent integration of their genetic material into the genome of a target/host cell. The most commonly used retroviral vectors for nucleic acid delivery are lentiviral vehicles/particles. Some examples of lentiviruses include the Human Immunodeficiency Viruses: HIV-1 and HIV-2, the Simian Immunodeficiency Virus (SIV), feline immunodeficiency virus (FIV), bovine immunodeficiency virus (BIV), Jembrana Disease Virus (JDV), equine infectious anemia virus (EIAV), equine infectious anemia virus, visna-maedi and caprine arthritis encephalitis virus (CAEV).

Typically, lentiviral particles making up the gene delivery vehicle are replication defective on their own, such that they are unable to replicate in the host cell and may infect only one cell (also referred to as "self-inactivating"). Lentiviruses are able to infect both dividing and non-dividing cells by virtue of the entry mechanism through the intact host nuclear envelope (Naldini et al. (1998) *Curr. Opin. Biotechnol.* 9:457-463). Recombinant lentiviral vehicles/particles have been generated by multiply attenuating the HIV virulence genes, for example, the genes Env, Vif, Vpr, Vpu, Nef and Tat are deleted making the vector biologically safe. Correspondingly, lentiviral vehicles, for example, derived from HIV-1/HIV-2 may mediate the efficient delivery, integration and long-term expression of transgenes into non-dividing cells. The term "recombinant" refers to a vector or other nucleic acid containing both lentiviral sequences and non-lentiviral retroviral sequences. Lentiviral particles may be generated by co-expressing the virus packaging elements and the vector genome itself in a producer cell such as HEK293T cells, 293G cells, STAR cells, and other viral expression cell lines. These elements are usually provided in three (in second generation lentiviral systems) or four separate plasmids (in third generation lentiviral systems). The producer cells are co-transfected with plasmids that encode lentiviral components including the core (i.e., structural proteins) and enzymatic components of the virus, and the envelope protein(s) (referred to as the packaging systems), and a plasmid that encodes the genome including a foreign transgene, to be transferred to the target cell, the vehicle itself (also referred to as the transfer vector).

The envelope proteins of recombinant lentiviral vectors may be heterologous envelope proteins from other viruses, such as the G protein of vesicular stomatitis virus (VSV G) or baculoviral gp64 envelop proteins. The VSV-G glycoprotein may especially be chosen among species classified in the vesiculovirus genus: Carajas virus (CJSV), Chandipura virus (CHPV), Cocal virus (COCV), Isfahan virus (ISFV), Maraba virus (MARAV), Piry virus (PIRYV), Vesicular stomatitis Alagoas virus (VSAV), Vesicular stomatitis Indiana virus (VSIV) and Vesicular stomatitis New Jersey virus (VSNJV) and/or stains provisionally classified in the vesiculovirus genus as Grass carp rhabdovirus, BeAn 157575 virus (BeAn 157575), Boteke virus (BTKV), Calchaqui virus (CQIV), Eel virus Amerimay (EVA), Gray Lodge virus (GLOV), Jurona virus (JURY), Klamath virus (KLAV), Kwatta virus (KWAV), La Joya virus (LJV), Malpais Spring virus (MSPV), Mount Elgon bat virus (MEBV), Perinet virus (PERV), Pike fry rhabdovirus (PFRV), Porton virus (PORV), Radi virus (RADIV), Spring viremia of carp virus (SVCV), Tupaia virus (TUPV), Ulcerative disease rhabdovirus (UDRV) and Yug Bogdanovac virus (YBV). The gp64 or other baculoviral env protein may be derived from *Autographa californica* nucleopolyhedrovirus (AcMNPV), *Anagrapha falcifera* nuclear polyhedrosis virus, *Bombyx mori* nuclear polyhedrosis virus, *Choristoneura fumiferana* nucleopolyhedrovirus, *Orgyia pseudotsugata* single capsid nuclear polyhedrosis virus, *Epiphyas postvittana* nucleopolyhedrovirus, *Hyphantria cunea* nucleopolyhedrovirus, *Galleria mellonella* nuclear polyhedrosis virus, Dhori virus, Thogoto virus, Antheraea pemyi nucleopolyhedrovirus or Batken virus.

Methods for generating recombinant lentiviral particles are discussed in the art, for example, U.S. Pat. Nos. 8,846,385; 7,745,179; 7,629,153; 7,575,924; 7,179,903; and 6,808,905.

Lentivirus vectors used may be selected from, but are not limited to pLVX, pLenti, pLenti6, pLJM1, FUGW, pWPXL, pWPI, pLenti CMV puro DEST, pLJM1-EGFP, pULTRA, pInducer20, pHIV-EGFP, pCW57.1, pTRPE, pELPS, pRRL, and pLionII. Lentiviral vehicles known in the art may also be used (See, U.S. Pat. Nos. 9,260,725; 9,068,199; 9,023,646; 8,900,858; 8,748,169; 8,709,799; 8,420,104; 8,329,462; 8,076,106; 6,013,516; and 5,994,136; PCT Publ. No. WO 2012079000).

Additional elements may be included in recombinant lentiviral particles including, retroviral LTR (long-terminal repeat) at either 5' or 3' terminus, a retroviral export element, optionally a lentiviral reverse response element (RRE), a promoter or active portion thereof, and a locus control region (LCR) or active portion thereof. Other elements include central polypurine tract (cPPT) sequence to improve transduction efficiency in non-dividing cells, Woodchuck Hepatitis Virus (WHP) Posttranscriptional Regulatory Element (WPRE) which enhances the expression of the transgene, and increases titer. The effector module is linked to the vector. In addition to lentiviral vectors based on complex HIV-1/2, retroviral vectors based on simple gamma-retroviruses have been widely used to deliver therapeutic nucleic acids and demonstrated clinically as one of the most efficient and powerful nucleic acid delivery systems capable of transducing a broad range of cell types. Example species of gamma retroviruses include the murine leukemia viruses (MLVs) and the feline leukemia viruses (FeLV). Gamma-retroviral vectors derived from a mammalian gamma-retrovirus such as murine leukemia viruses (MLVs) may be recombinant. The MLV families of gamma retroviruses include the ecotropic, amphotropic, xenotropic and polytropic subfamilies. Ecotropic viruses are able to infect only murine cells using mCAT-1 receptor. Examples of ecotropic viruses are Moloney MLV and AKV. Amphotropic viruses infect murine, human and other species through the Pit-2 receptor. One example of an amphotropic virus is the 4070A virus. Xenotropic and polytropic viruses utilize the same (Xpr1) receptor, but differ in their species tropism. Xenotropic viruses such as NZB-9-1 infect human and other species but not murine species, whereas polytropic viruses such as focus-forming viruses (MCF) infect murine, human and other species.

Gamma-retroviral vectors may be produced in packaging cells by co-transfecting the cells with several plasmids including one encoding the retroviral structural and enzymatic (gag-pol) polyprotein, one encoding the envelope (env) protein, and one encoding the vector mRNA comprising polynucleotide encoding the compositions encompassed by the present invention that is to be packaged in newly formed viral particles. The recombinant gamma-retroviral vectors may be pseudotyped with envelope proteins from other viruses. Envelope glycoproteins are incorporated in the outer lipid layer of the viral particles which may increase/alter the cell tropism. Exemplary envelop proteins include the gibbon ape leukemia virus envelope protein (GALV) or vesicular stomatitis virus G protein (VSV-G), or Simian endogenous retrovirus envelop protein, or Measles Virus H and F proteins, or Human immunodeficiency virus gp120 envelope protein, or cocal vesiculovirus envelop protein (see, e.g., U.S. Publ. No. 2012/164118). In other embodiments, envelope glycoproteins may be genetically modified to incorporate targeting/binding ligands into gamma-retroviral vectors, binding ligands including, but not limited to, peptide ligands, single chain antibodies and growth factors (Waehler et al. (2007) *Nat. Rev. Genet.* 8:573-587). These engineered glycoproteins may retarget vectors to cells expressing their corresponding target moieties. In other aspects, a "molecular bridge" may be introduced to direct vectors to specific cells. The molecular bridge has dual specificities: one end may recognize viral glycoproteins, and the other end may bind to the molecular determinant on the target cell. Such molecular bridges, such as ligand-receptor, avidin-biotin, chemical conjugations, monoclonal antibodies, and engineered fusogenic proteins, may direct the attachment of viral vectors to target cells for transduction (Yang et al. (2008) *Biotechnol. Bioeng.* 101: 357-368; Maetzig et al. (2011) *Viruses* 3:677-713). The recombinant gamma-retroviral vectors may be self-inactivating (SIN) gammaretroviral vectors. The vectors are replication incompetent. SIN vectors may harbor a deletion within the 3' U3 region initially comprising enhancer/promoter activity. Furthermore, the 5' U3 region may be replaced with strong promoters (needed in the packaging cell line) derived from cytomegalovirus or RSV, or an internal promoter of choice, and/or an enhancer element. The choice of the internal promoters may be made according to specific requirements of gene expression needed for a particular purpose encompassed by the present invention.

Similarly, recombinant adeno-associated viral (rAAV) vectors may be used to package and deliver nucleic acid molecules encompassed by the present invention. Such vectors or viral particles may be designed to utilize any of the known serotype capsids or combinations of serotype capsids. The serotype capsids may include capsids from any identified AAV serotypes and variants thereof, for example, AAV1, AAV2, AAV2G9, AAV3, AAV4, AAV4-4, AAV5, AAV6, AAV7, AAV8, AAV9, AAV10, AAV11, AAV12 and AAVrh10 (see, for example. U.S. Pat. Publ. 20030138772) or variants thereof. AAV vectors include not only single stranded vectors but self-complementary AAV vectors (scAAVs). scAAV vectors contain DNA which anneals together to form double stranded vector genome. By skipping second strand synthesis, scAAVs allow for rapid expression in the cell. The rAAV vectors may be manufactured by standard methods in the art such as by triple transfection, in sf9 insect cells or in suspension cell cultures of human cells such as HEK293 cells. Nucleic acid molecules encompassed by the present invention may be encoded in one or more viral genomes to be packaged in the AAV capsids. Such vectors or viral genomes may also include, in addition to at least one or two ITRs (inverted terminal repeats), certain regulatory elements necessary for expression from the vector or viral genome. Such regulatory elements are well-known in the art and include for example promoters, introns, spacers, stuffer sequences, and the like.

In addition, non-viral delivery systems of nucleic acid molecules are well-known in the art. The term "non-viral vectors" collectively refers to any vehicles that transfer nucleic acid molecules encompassed by the present invention into cells of interest without using viral particles. Representative examples of such non-viral delivery vectors are vectors that coat nucleic acids based on the electrical interaction between cationic sites on the vectors and anionic sites on the negatively charged nucleic acids constituting genes. Some exemplary non-viral vectors for delivery may include naked nucleic acid delivery systems, polymeric delivery systems and liposomal delivery systems. Cationic polymers and cationic lipids are used for nucleic acids delivery because they may easily complex with the anionic nucleotides. Commonly used polymers may include, but are not limited to, polyethylenimine, poly-L-lysin, chitosans, and dendrimers. Cationic lipids may include but are not limited to, monovalent cationic lipids, polyvalent cationic lipids, guanidine containing lipids, cholesterol derivative compounds, cationic polymers: Poly(ethylenimine) (PEI), poly-1-lysine) (PLL), protamine, other cationic polymers and lipid-polymer hybrid.

Vector DNA may be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells may be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics like neo, DHFR, Gln synthetase, ADA, and the like) is generally introduced into the host cells along with the gene of interest. Preferred selectable markers include those which confer resistance to drugs, such as G418, hygromycin and methotrexate. Cells stably transfected with the introduced nucleic acid may be identified by drug selection (e.g., cells that have incorporated the selectable marker gene will survive, while the other cells die).

Accordingly, the present invention encompasses host cells, which are described further below, into which a nucleic acid and/or recombinant expression vector encompassed by the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell may be any prokaryotic (e.g., *E. coli*) or eukaryotic cell (e.g., insect cells, yeast or mammalian cells).

c. Protein Agents

Another aspect encompassed by the present invention involves the use of amino acid-based agents. The agents may include, but are not limited to, fusion proteins, synthetic polypeptides, and peptides, as well as fragments thereof (e.g., biologically active fragments). Polynucleotides that encode such amino acid-based compounds are also provided.

Amino acid-based agents (e.g., antibodies and recombinant proteins) encompassed by the present invention may exist as a whole polypeptide, a plurality of polypeptides or fragments of polypeptides, which independently may be encoded by one or more nucleic acids, a plurality of nucleic acids, fragments of nucleic acids or variants of any of the aforementioned.

The term "polypeptide" refers to a polymer of amino acid residues (natural or unnatural) linked together most often by peptide bonds. The term, as used herein, refers to proteins, polypeptides, and peptides of any size, structure, or function. Thus, the term polypeptide is mutually inclusive of the terms "peptide" and "protein." The term "fusion protein" refers to a fusion polypeptide molecule comprising at least two amino acid sequences from different resources, wherein the component amino acid sequences are linked to each other by peptide-bonds, either directly or through one or more peptide linkers. In some instances the polypeptide encoded is smaller than about 50 amino acids and the polypeptide is then termed a "peptide." If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

In some embodiments, the native polypeptide corresponding to a marker may be isolated from cells or tissue sources by an appropriate purification scheme using standard protein purification techniques. In another embodiment, polypeptides corresponding to a marker encompassed by the present invention are produced by recombinant DNA techniques. Alternative to recombinant expression, a polypeptide corresponding to a marker encompassed by the present invention may be synthesized chemically using standard peptide synthesis techniques.

Polypeptide fragments include polypeptides comprising amino acid sequences sufficiently identical to or derived from an amino acid sequence of interest, but which includes fewer amino acids than the full length protein. They may also exhibit at least one activity of the corresponding full-length protein. Typically, biologically active portions comprise a domain or motif with at least one activity of the corresponding protein. A biologically active portion of a protein encompassed by the present invention may be a polypeptide which is, for example, 10, 25, 50, 100 or more amino acids in length. Moreover, other biologically active portions, in which other regions of the protein are deleted, may be prepared by recombinant techniques and evaluated for one or more of the functional activities of the native form of a polypeptide encompassed by the present invention.

Preferred polypeptides have an amino acid sequence of a polypeptide of interest, such as a polypeptide encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

The term "identity" as is applies to amino acid sequences is defined as the percentage of residues in the candidate amino acid sequence that are identical with the residues in the amino acid sequence of a second sequence after aligning the sequences and introducing gaps, if necessary, to achieve the maximum percent identity. Methods and computer programs for alignment are well-known in the art. It is understood that homology depends on a calculation of percent identity but may differ in value due to gaps and penalties introduced in the calculation.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences may be accomplished using a mathematical algorithm. A preferred, non-limiting example of a mathematical algorithm utilized for the comparison of two sequences is the algorithm of Karlin and Altschul (1990) *Proc. Natl. Acad. Sci. U.S.A.* 87:2264-2268, modified as in Karlin and Altschul (1993) *Proc. Natl. Acad. Sci. U.S.A.* 90:5873-5877. Such an algorithm is incorporated into the NBLAST and XBLAST programs of Altschul, et al. (1990) *J. Mol. Biol.* 215:403-410. BLAST nucleotide searches may be performed with the NBLAST program, score=100, wordlength=12 to obtain nucleotide sequences homologous to a nucleic acid molecules encompassed by the present invention. BLAST protein searches may be performed with the XBLAST program, score=50, wordlength=3 to obtain amino acid sequences homologous to a protein molecules encompassed by the present invention. To obtain gapped alignments for comparison purposes, Gapped BLAST may be utilized as described in Altschul et al. (1997) *Nucl. Acids Res.* 25:3389-3402. Alternatively, PSI-Blast may be used to perform an iterated search which detects distant relationships between molecules. When utilizing BLAST, Gapped BLAST, and PSI-Blast programs, the default parameters of the respective programs (e.g., XBLAST and NBLAST) may be used (see, for example, ncbi.nlm.nih.gov). Another preferred, non-limiting example of a mathematical algorithm utilized for the comparison of sequences is the algorithm of Myers and Miller (1988) *Comput. Appl. Biosci.* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 may be used. Yet another useful algorithm for identifying regions of local sequence similarity and alignment is the FASTA algorithm as described in Pearson and Lipman (1988) *Proc. Natl. Acad. Sci. U.S.A.* 85:2444-2448. When using the FASTA algorithm for comparing nucleotide or amino acid sequences, a PAM120 weight residue table may, for example, be used with a k-tuple value of 2. The percent identity between two sequences may be determined using techniques similar to those described above, with or without allowing gaps. In calculating percent identity, only exact matches are counted.

The term "polypeptide variant" or "amino acid sequence variant" refers to molecules which differ in their amino acid sequence from a native or reference sequence. The amino acid sequence variants may possess substitutions, deletions, and/or insertions at certain positions within the amino acid sequence, as compared to a native or reference sequence. The terms "native" or "reference" when referring to sequences are relative terms referring to an original molecule against which a comparison may be made. Native or reference sequences should not be confused with wild type sequences. Native sequences or molecules may represent the wild-type (that sequence found in nature) but do not have to be identical to the wild-type sequence. Variants may possess at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.5% or at least about 99.9% amino acid sequence identity (homology) to a native or reference sequence.

Polypeptide variants have an altered amino acid sequence and, in some embodiments, may function as either agonists or as antagonists. Variants may be generated by mutagenesis, e.g., discrete point mutation or truncation. An agonist may retain substantially the same, or a subset, of the biological activities of the naturally occurring form of the protein. An antagonist of a protein may inhibit one or more of the activities of the naturally occurring form of the protein by, for example, competitively binding to a downstream or upstream member of a cellular signaling cascade which includes the protein of interest. Thus, specific biological effects may be elicited by treatment with a variant of limited function. Treatment of a subject with a variant having a subset of the biological activities of the naturally occurring form of the protein may have fewer side effects in a subject relative to treatment with the naturally occurring form of the protein.

In some embodiments, "variant mimics" are provided. As used herein, the term "variant mimic" refers to a variant which contains one or more amino acids which would mimic an activated sequence. For example, glutamate may serve as a mimic for phospho-threonine and/or phospho-serine. Alternatively, variant mimics may result in deactivation or in an inactivated product containing the mimic, e.g., phenylalanine may act as an inactivating substitution for tyrosine; or alanine may act as an inactivating substitution for serine. The amino acid sequences may comprise naturally occurring amino acids and as such may be considered to be proteins, peptides, polypeptides, or fragments thereof Alternatively, the agents encompassed by the present invention may comprise both naturally and non-naturally occurring amino acids. Non-naturally occurring amino acids may include, but are not limited to, amino acids comprising a carbonyl group, or an aminooxy group or a hydrazide group, or a semicarbazide group, or an azide group.

The term "homolog" as it applies to amino acid sequences is meant the corresponding sequence of other species having substantial identity to a second sequence of a second species.

The term "analog" is meant to include polypeptide variants which differ by one or more amino acid alterations, e.g., substitutions, additions or deletions of amino acid residues that still maintain the properties of the parent polypeptide.

The term "derivative" is used synonymously with the term "variant" and refers to a molecule that has been modified or changed in any way relative to a reference molecule or starting molecule. The present invention contemplates several types of compounds and/or compositions which are amino acid based including variants and derivatives. These include substitutional, insertional, deletional and covalent variants and derivatives. As such, included within the scope encompassed by the present invention is agents comprising substitutions, insertions, additions, deletions and/or covalent modifications. Amino acid residues located at the carboxy- and amino-terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to proteins are those that have at least one amino acid residue in a native or reference sequence removed and a different amino acid inserted in its place at the same position. The substitutions may be single, where only one amino acid in the molecule has been substituted, or they may be multiple, where two or more amino acids have been substituted in the same molecule. In one example, an amino acid in a polypeptide encompassed by the present invention is substituted with another amino acid having similar structural and/or chemical properties, e.g., conservative amino acid substitution. As used herein, the term "conservative amino acid substitution" refers to the substitution of an amino acid that is normally present in the sequence with a different amino acid of similar size, charge, polarity, solubility, hydrophobicity, hydrophilicity, and/or the amphipathic nature of the residues involved. Examples of conservative substitutions include the substitution of a non-polar (hydrophobic) residue such as alanine, proline, phenylalanine, tryptophan, isoleucine, valine, leucine and methionine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue, such as lysine, arginine or histidine for another, or the substitution of one acidic residue such as aspartic acid or glutamic acid for another acidic residue are additional examples of conservative substitutions. "Non-conservative substitutions" entail exchanging a member of one of these classes for another class. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue. Amino acid substitutions may be generated using genetic or chemical methods well-known in the art. Genetic methods may include site-directed mutagenesis, PCR, gene synthesis and the like. It is contemplated that methods of altering the side chain group of an amino acid by methods other than genetic engineering, such as chemical modification, may also be useful.

The term "insertional variants" when referring to proteins are those with one or more amino acids inserted immediately adjacent to an amino acid at a particular position in a native or starting sequence. As used herein, the term "immediately adjacent" refers to an adjacent amino acid that is connected to either the alpha-carboxy or alpha-amino functional group of a starting or reference amino acid. By contrast, the term "deletional variants" when referring to proteins, are those with one or more amino acids in the native or starting amino acid sequence removed. Ordinarily, deletional variants will have one or more amino acids deleted in a particular region of the molecule.

The term "derivatives" includes variants of a native or reference protein comprising one or more modifications with organic proteinaceous or non-proteinaceous derivatizing agents, and post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the proteins used in accordance with the present invention. Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)).

In some embodiments, covalently modified polypeptides (e.g., fusion proteins) are provided, such as polypeptides modified with a heterologous polypeptide and/or a non-polypeptide modification. For example, covalent derivatives specifically include fusion molecules in which proteins encompassed by the present invention are covalently bonded to a non-proteinaceous polymer. The non-proteinaceous polymer ordinarily is a hydrophilic synthetic polymer (i.e., a polymer not otherwise found in nature). However, polymers which exist in nature and are produced by recombinant or in vitro methods are useful, as are polymers which are isolated from nature. Hydrophilic polyvinyl polymers fall within the scope of this invention, e.g., polyvinylalcohol and polyvinylpyrrolidone. Particularly useful are polyvinylalkylene ethers such a polyethylene glycol, polypropylene glycol (PEG). The proteins may be linked to various non-proteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. Fusion molecules may further comprise proteins encompassed by the present invention which are covalently bonded to other biologically active molecules, or linkers.

The terms "chimeric protein" or "fusion protein" refer to polypeptides comprising all or part (preferably a biologically active part) of a polypeptide corresponding to a polypeptide encompassed by the present invention operably linked to a heterologous polypeptide (e.g., a polypeptide other than the biomarker polypeptide). Within the fusion protein, the term "operably linked" is intended to indicate that the polypeptide encompassed by the present invention and the heterologous polypeptide are fused in-frame to each other. The heterologous polypeptide may be fused to the amino-terminus or the carboxyl-terminus of the polypeptide encompassed by the present invention.

One useful fusion protein is a GST fusion protein in which a polypeptide corresponding to a marker encompassed by the present invention is fused to the carboxyl terminus of GST sequences. Such fusion proteins may facilitate the purification of a recombinant polypeptide encompassed by the present invention. In another embodiment, the fusion protein contains a heterologous signal sequence, immunoglobulin fusion protein, toxin, or other useful protein sequence. Chimeric and fusion proteins encompassed by the present invention may be produced by standard recombinant DNA techniques. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide encompassed by the present invention may be cloned into such an expression vector such that the fusion moiety is linked in-frame to the polypeptide encompassed by the present invention.

A signal sequence may be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention encompasses the described polypeptides having a signal sequence, as well as to polypeptides from which the signal sequence has been proteolytically cleaved (i.e., the cleavage products). In one embodiment, a nucleic acid sequence encoding a signal sequence may be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein may then be readily purified from the extracellular medium by art recognized methods. Alternatively, the signal sequence may be linked to the protein of interest using a sequence which facilitates purification, such as with a GST domain.

The term "features" when referring to proteins are defined as distinct amino acid sequence-based components of a molecule. Features of the proteins encompassed by the present invention include surface manifestations, local conformational shape, folds, loops, half-loops, domains, half-domains, sites, termini or any combination thereof. For example, the term "surface manifestation" when referring to proteins refers to a polypeptide based component of a protein appearing on an outermost surface. The term "local conformational shape" when referring to proteins refers to a polypeptide based structural manifestation of a protein which is located within a definable space of the protein. The term "fold" when referring to proteins refers to the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like. The term "turn" as it relates to protein conformation refers to a bend which alters the direction of the backbone of a peptide or polypeptide and may involve one, two, three or more amino acid residues. The term "loop" as it relates to proteins refers to a structural feature of a peptide or polypeptide which reverses the direction of the backbone of a peptide or polypeptide and comprises four or more amino acid residues (Oliva et al. (1997) *J. Mol. Biol.* 266:814-830). The term "half-loop" when referring to proteins refers to a portion of an identified loop having at least half the number of amino acid resides as the loop from which it is derived. It is understood that loops do not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4). The term "domain" when referring to proteins refers to a motif of a polypeptide having one or more identifiable structural or functional characteristics or properties (e.g., binding capacity and/or serving as a site for protein-protein interactions). The term "half-domain" when referring to proteins refers to a portion of an identified domain having at least half the number of amino acid resides as the domain from which it is derived. It is understood that domains do not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain). The term "site" as it pertains to amino acid-based embodiments is used synonymously with "amino acid residue" and "amino acid side chain." A site represents a position within a peptide or polypeptide that may be modified, manipulated, altered, derivatized or varied within the amino acid based molecules encompassed by the present invention. The terms "termini" or "terminus" when referring to proteins refer to an extremity of a peptide or polypeptide. Such extremities are not limited only to the first or final site of the peptide or polypeptide but may include additional amino acids in the terminal regions. The polypeptide based molecules encompassed by the present invention may be characterized as having both an N-terminus (i.e., terminated by an amino acid with a free amino group (NH2)) and a C-terminus (i.e., terminated by an amino acid with a free carboxyl group (COOH)). Proteins encompassed by the present invention are in some cases made up of multiple polypeptide chains brought together by disulfide bonds or by non-covalent forces, such as multimers or oligomers. These proteins have multiple N- and C-termini. Alternatively, the termini of the polypeptides may be modified such that they begin or end, as the case may be, with a non-polypeptide based moiety such as an organic conjugate.

Once any of the features have been identified or defined as a component of a molecule encompassed by the present invention, any of several manipulations and/or modifications of these features may be performed by moving, swapping, inverting, deleting, randomizing or duplicating. Furthermore, it is understood that manipulation of features may result in the same outcome as a modification to the molecules encompassed by the present invention. For example, a manipulation which involved deleting a domain would result in the alteration of the length of a molecule just as modification of a nucleic acid to encode less than a full length molecule would. Modifications and manipulations may be accomplished by methods known in the art such as site directed mutagenesis.

In some embodiments, agents described herein may comprise one or more atoms that are isotopes. As used herein, the term "isotope" refers to a chemical element that has one or more additional neutrons, such as deuterium isotopes.

d. Cell-Based Agents, Including Host Cells

In another aspect, cell-based agents are contemplated.

In some embodiments, the present invention encompasses a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed."

The nucleic acids encompassed by the present invention may be used to produce a recombinant polypeptide of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL 1662, hereinafter referred to as "YB2/0 cell"), and the like. The YB2/0 cell is preferred, since ADCC activity of chimeric or humanized antibodies is enhanced when expressed in this cell.

In another aspect, cells are provided that are contacted with agents encompassed by the present invention. For example, in some embodiments, myeloid cells, such as suppressive myeloid cells, monocytes, macrophages, and/or dendritic cells, are manipulated, such as being contacted with one or more agents to modulate one or more biomarkers encompassed by the present invention (e.g., one or more targets listed in Table 1). For example, cultured cells and/or primary cells may be contacted with agents, processed, and introduced into assays, subjects, and the like. Progeny of such cells are encompassed by the cell-based agents described herein.

In some embodiments, myeloid cells, such as suppressive myeloid cells, monocytes, macrophages, and/or dendritic cells, are recombinantly engineered to modulate one or more biomarkers encompassed by the present invention (e.g., one or more targets listed in Table 1). For example, as describe above, genome editing may be used to modulate the copy number or genetic sequence of a biomarker of interest, such as constitutive or induced knockout or mutation of a biomarker of interest. For example, the CRISPR-Cas system may be used for precise editing of genomic nucleic acids (e.g., for creating non-functional or null mutations). In such embodiments, the CRISPR guide RNA and/or the Cas enzyme may be expressed. For example, a vector containing only the guide RNA may be administered to an animal or cells transgenic for the Cas9 enzyme. Similar strategies may be used (e.g., zinc finger nucleases (ZFNs), transcription activator-like effector nucleases (TALENs), or homing meganucleases (HEs), such as MegaTAL, MegaTev, Tev-mTALEN, CPF1, and the like). Such systems are well-known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. Numbers 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47). Such genetic strategies may use constitutive expression systems or inducible expression systems according to well-known methods in the art.

Cell-based agents have an immunocompatibility relationship to a subject host and any such relationship is contemplated for use according to the present invention. For example, the cells, such as adoptive myeloid cells, such as suppressive myeloid cells, monocytes, macrophages, and/or dendritic cells, T cells, and the like, may be syngeneic. The term "syngeneic" may refer to the state of deriving from, originating in, or being members of the same species that are genetically identical, particularly with respect to antigens or immunological reactions. These include identical twins having matching MHC types. Thus, a "syngeneic transplant" refers to transfer of cells from a donor to a recipient who is genetically identical to the donor or is sufficiently immunologically compatible as to allow for transplantation without an undesired adverse immunogenic response (e.g., such as one that would work against interpretation of immunological screen results described herein).

A syngeneic transplant may be "autologous" if the transferred cells are obtained from and transplanted to the same subject. An "autologous transplant" refers to the harvesting and reinfusion or transplant of a subject's own cells or organs. Exclusive or supplemental use of autologous cells may eliminate or reduce many adverse effects of administration of the cells back to the host, particular graft versus host reaction.

A syngeneic transplant may be "matched allogeneic" if the transferred cells are obtained from and transplanted to different members of the same species yet have sufficiently matched major histocompatibility complex (MHC) antigens to avoid an adverse immunogenic response. Determining the degree of MHC mismatch may be accomplished according to standard tests known and used in the art. For instance, there are at least six major categories of MHC genes in humans, identified as being important in transplant biology. HLA-A, HLA-B, HLA-C encode the HLA class I proteins while HLA-DR, HLA-DQ, and HLA-DP encode the HLA class II proteins. Genes within each of these groups are highly polymorphic, as reflected in the numerous HLA alleles or variants found in the human population, and differences in these groups between individuals is associated with the strength of the immune response against transplanted cells. Standard methods for determining the degree of MHC match examine alleles within HLA-B and HLA-DR, or HLA-A, HLA-B and HLA-DR groups. Thus, tests may be made of at least 4, and even 5 or 6 MHC antigens within the two or three HLA groups, respectively. In serological MHC tests, antibodies directed against each HLA antigen type are reacted with cells from one subject (e.g., donor) to determine the presence or absence of certain MHC antigens that react with the antibodies. This is compared to the reactivity profile of the other subject (e.g., recipient). Reaction of the antibody with an MHC antigen is typically determined by incubating the antibody with cells, and then adding complement to induce cell lysis (i.e., lymphocytotoxicity testing). The reaction is examined and graded according to the amount of cells lysed in the reaction (see, for example, Mickelson and Petersdorf (1999) *Hematopoietic Cell Transplantation*, Thomas, E. D. et al. eds., pg 28-37, Blackwell Scientific, Malden, Mass.). Other cell-based assays include flow cytometry using labeled antibodies or enzyme linked immunoassays (ELISA). Molecular methods for determining MHC type are well-known and generally employ synthetic probes and/or primers to detect specific gene sequences that encode the HLA protein. Synthetic oligonucleotides may be used as hybridization probes to detect restriction fragment length polymorphisms associated with particular HLA types (Vaughn (2002) *Method. Mol. Biol. MHC Protocol.* 210:45-60). Alternatively, primers may be used for amplifying the HLA sequences (e.g., by polymerase chain reaction or ligation chain reaction), the products of which may be further examined by direct DNA sequencing, restriction fragment polymorphism analysis (RFLP), or hybridization with a series of sequence specific oligonucleotide primers (SSOP) (Petersdorf et al. (1998) *Blood* 92:3515-3520; Morishima et al. (2002) *Blood* 99:4200-4206; and Middleton and Williams (2002) *Method. Mol. Biol. MHC Protocol.* 210:67-112).

A syngeneic transplant may be "congenic" if the transferred cells and cells of the subject differ in defined loci, such as a single locus, typically by inbreeding. The term "congenic" refers to deriving from, originating in, or being members of the same species, where the members are genetically identical except for a small genetic region, typically a single genetic locus (i.e., a single gene). A "congenic transplant" refers to transfer of cells or organs from a donor to a recipient, where the recipient is genetically identical to the donor except for a single genetic locus. For example, CD45 exists in several allelic forms and congenic mouse lines exist in which the mouse lines differ with respect to whether the CD45.1 or CD45.2 allelic versions are expressed.

By contrast, "mismatched allogeneic" refers to deriving from, originating in, or being members of the same species having non-identical major histocompatibility complex (MHC) antigens (i.e., proteins) as typically determined by standard assays used in the art, such as serological or molecular analysis of a defined number of MHC antigens, sufficient to elicit adverse immunogenic responses. A "partial mismatch" refers to partial match of the MHC antigens tested between members, typically between a donor and recipient. For instance, a "half mismatch" refers to 50% of the MHC antigens tested as showing different MHC antigen type between two members. A "full" or "complete" mismatch refers to all MHC antigens tested as being different between two members.

Similarly, in contrast, "xenogeneic" refers to deriving from, originating in, or being members of different species, e.g., human and rodent, human and swine, human and chimpanzee, etc. A "xenogeneic transplant" refers to transfer of cells or organs from a donor to a recipient where the recipient is a species different from that of the donor.

In addition, cells may be obtained from a single source or a plurality of sources (e.g., a single subject or a plurality of subjects). A plurality refers to at least two (e.g., more than one). In still another embodiment, the non-human mammal is a mouse. The animals from which cell types of interest are obtained may be adult, newborn (e.g., less than 48 hours old), immature, or in utero. Cell types of interest may be primary cancer cells, cancer stem cells, established cancer cell lines, immortalized primary cancer cells, and the like. In certain embodiments, the immune systems of host subjects may be engineered or otherwise elected to be immunological compatible with transplanted cancer cells. For example, in one embodiment, the subject may be "humanized" in order to be compatible with human cancer cells. The term "immune-system humanized" refers to an animal, such as a mouse, comprising human HSC lineage cells and human acquired and innate immune cells, survive without being rejected from the host animal, thereby allowing human hematopoiesis and both acquired and innate immunity to be reconstituted in the host animal. Acquired immune cells include T cells and B cells. Innate immune cells include macrophages, granulocytes (basophils, eosinophils, neutrophils), DCs, NK cells and mast cells. Representative, non-limiting examples include SCID-hu, Hu-PBL-SCID, Hu-SRC-SCID, NSG (NOD-SCID IL2r-gamma(null) lack an innate immune system, B cells, T cells, and cytokine signaling), NOG (NOD-SCID IL2r-gamma(truncated)), BRG (BALB/c-Rag2(null)IL2r-gamma(null)), and H2dRG (Stock-H2d-Rag2(null)IL2r-gamma(null)) mice (see, for example, Shultz et al. (2007) *Nat. Rev. Immunol.* 7:118; Pearson et al. (2008) *Curr. Protocol. Immunol.* 15:21; Brehm et al. (2010) *Clin. Immunol.* 135:84-98; McCune et al. (1988) *Science* 241:1632-1639, U.S. Pat. No. 7,960,175, and U.S. Pat. Publ. No. 2006/0161996), as well as related null mutants of immune-related genes like Rag1 (lack B and T cells), Rag2 (lack B and T cells), TCR alpha (lack T cells), perforin (cD8+ T cells lack cytotoxic function), FoxP3 (lack functional CD4+ T regulatory cells), IL2rg, or Prfl, as well as mutants or knockouts of PD-1, PD-L1, Tim3, and/or 2B4, allow for efficient engraftment of human immune cells in and/or provide compartment-specific models of immunocompromised animals like mice (see, for example, PCT Publ. No. WO 2013/062134). In addition, NSG-CD34+ (NOD-SCID IL2r-gamma(null) CD34+) humanized mice are useful for studying human gene and tumor activity in animal models like mice.

As used herein, "obtained" from a biological material source means any conventional method of harvesting or partitioning a source of biological material from a donor. For example, biological material may obtained from a solid tumor, a blood sample, such as a peripheral or cord blood sample, or harvested from another body fluid, such as bone marrow or amniotic fluid. Methods for obtaining such samples are well-known to the artisan. In the present invention, the samples may be fresh (i.e., obtained from a donor without freezing). Moreover, the samples may be further manipulated to remove extraneous or unwanted components prior to expansion. The samples may also be obtained from a preserved stock. For example, in the case of cell lines or fluids, such as peripheral or cord blood, the samples may be withdrawn from a cryogenically or otherwise preserved bank of such cell lines or fluid. Such samples may be obtained from any suitable donor.

The obtained populations of cells may be used directly or frozen for use at a later date. A variety of mediums and protocols for cryopreservation are known in the art. Generally, the freezing medium will comprise DMSO from about 5-10%, 10-90% serum albumin, and 50-90% culture medium. Other additives useful for preserving cells include, by way of example and not limitation, disaccharides such as trehalose (Scheinkonig et al. (2004) *Bone Marrow Transplant.* 34:531-536), or a plasma volume expander, such as hetastarch (i.e., hydroxyethyl starch). In some embodiments, isotonic buffer solutions, such as phosphate-buffered saline, may be used. An exemplary cryopreservative composition has cell-culture medium with 4% HSA, 7.5% dimethyl sulfoxide (DMSO), and 2% hetastarch. Other compositions and methods for cryopreservation are well-known and described in the art (see, e.g., Broxmeyer et al. (2003) *Proc. Natl. Acad. Sci. U.S.A.* 100:645-650). Cells are preserved at a final temperature of less than about −135° C.

In some embodiments, the immunotherapy may be CAR (chimeric antigen receptor)-T therapy, where T cells engineered to express CARs comprising an antigen-binding domain specific to an antigen on tumor cells of interest. The term "chimeric antigen receptor" or "CAR" refers to receptors having a desired antigen specificity and signaling domains to propagate intracellular signals upon antigen binding. For example, T lymphocytes recognize specific antigens through interaction of the T cell receptor (TCR) with short peptides presented by major histocompatibility complex (MHC) class I or II molecules. For initial activation and clonal expansion, naive T cells are dependent on professional antigen-presenting cells (APCs) that provide additional co-stimulatory signals. TCR activation in the absence of co-stimulation may result in unresponsiveness and clonal anergy. To bypass immunization, different approaches for the derivation of cytotoxic effector cells with grafted recognition specificity have been developed. CARs have been constructed that consist of binding domains derived from natural ligands or antibodies specific for cell-surface components of the TCR-associated CD3 complex. Upon antigen binding, such chimeric antigen receptors link to endogenous signaling pathways in the effector cell and generate activating signals similar to those initiated by the TCR complex. Since the first reports on chimeric antigen receptors, this concept has steadily been refined and the molecular design of chimeric receptors has been optimized and routinely use any number of well-known binding domains, such as scFV, Fav, and another protein binding fragments described herein.

In some embodiments, monocytes and macrophages may be engineered to, for example, express a chimeric antigen receptor (CAR). The modified cell may be recruited to the tumor microenvironment where it acts as a potent immune effector by infiltrating the tumor and killing target cancer cells. The CAR includes an antigen binding domain, a transmembrane domain and an intracellular domain. The antigen binding domain binds to an antigen on a target cell. Examples of cell surface markers that may act as an antigen that binds to the antigen binding domain of the CAR include those associated with viral, bacterial, parasitic infections, autoimmune disease and cancer cells (e.g., tumor antigens).

In one embodiment, the antigen binding domain binds to a tumor antigen, such as an antigen that is specific for a tumor or cancer of interest. Non-limiting examples of tumor associated antigens include BCMA, CD19, CD24, CD33, CD38; CD44v6, CD123, CD22, CD30, CD117, CD171, CEA, CS-1, CLL-1, EGFR, ERBB2, EGFRvIII, FLT3, GD2, NY-BR-1, NY-ESO-1, p53, PRSS21, PSMA, ROR1, TAG72, Tn Ag, VEGFR2.

In one embodiment, the transmembrane domain is naturally associated with one or more of the domains in the CAR. The transmembrane domain may be derived either from a natural or from a synthetic source. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD134, CD137, CD154, Toll-like receptor 1 (TLR1), TLR2, TLR3, TLR4, TLRS, TLR6, TLR7, TLR8, and TLR9. In some instances, a variety of human hinges may be employed as well including the human Ig (immunoglobulin) hinge.

In one embodiment, the intracellular domain of the CAR includes a domain responsible for signal activation and/or transduction. Examples of the intracellular domain include a fragment or domain from one or more molecules or receptors including, but are not limited to, TCR, CD3 zeta, CD3 gamma, CD3 delta, CD3 epsilon, CD86, common FcR gamma, FcR beta (Fc Epsilon Rib), CD79a, CD79b, Fcgamma RIIa, DAP10, DAP 12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD 1 id, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), VSIG4 (CD 162), LTBR, LAT, GADS, SLP-76, PAG/Cbp, NKp44, NKp30, NKp46, NKG2D, Toll-like receptor 1 (TLR1), TLR2, TLR3, TLR4, TLRS, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

In some embodiments, agents, compositions and methods encompassed by the present invention may be used to re-engineer monocytes and macrophages to increase their ability to present antigens to other immune effector cells, for example, T cells. Engineered monocytes and macrophages as antigen presenting cells (APCs) will process tumor antigens and present antigenic epitopes to T cells to stimulate adaptive immune responses to attack tumor cells.

VI. Uses and Methods

The compositions and agents described herein may be used in a variety of modulatory, therapeutic, screening, diagnostic, prognostic, and therapeutic applications regarding biomarkers described herein (e.g., one or more targets listed in Table 1). In any method described herein, such as a modulatory method, therapeutic method, screening method, diagnostic method, prognostic method, or combination thereof, all steps of the method may be performed by a single actor or, alternatively, by more than one actor. For example, diagnosis may be performed directly by the actor providing therapeutic treatment. Alternatively, a person providing a therapeutic agent may request that a diagnostic assay be performed. The diagnostician and/or the therapeutic interventionist may interpret the diagnostic assay results to determine a therapeutic strategy. Similarly, such alternative processes may apply to other assays, such as prognostic assays.

In addition, any aspect encompassed by the present invention described herein may be performed either alone or in combination with any other aspect encompassed by the present invention, including one, more than one, or all embodiments thereof. For example, diagnostic and/or screening methods may be performed alone or in combination with a treatment step, such as providing an appropriate therapy upon determining an appropriate diagnosis and/or screening result.

Although certain preferred compositions are described herein, including antibodies and antigen-binding fragments thereof, it is contemplated that such agents may be used alone or in combination with other useful agents, such as those that modulate the amount and/or activity of at least one biomarker (e.g., at least one target listed in Table 1) so as to upregulate or downregulate the inflammatory phenotype and, thereby, upregulate or downregulate, respectively, an immune response. These agents are also useful to detect the amount and/or activity of the at least one biomarker (e.g., at least one target listed in Table 1), such that the agents are useful for diagnosing, prognosing, and screening effects mediated by the at least one biomarker (e.g., at least one target listed in Table 1).

An agent that downregulates the amount and/or activity of at least one target listed in Table 1 increases the inflammatory phenotype of myeloid cells, such as suppressive myeloid cells, monocytes, macrophages, and/or dendritic cells.

Similarly, an agent that upregulates the amount and/or activity of at least one target listed in Table 1 decreases the inflammatory phenotype of myeloid cells, such as suppressive myeloid cells, monocytes, macrophages, and/or dendritic cells.

An agent that modulates the at least one biomarker (e.g., at least one target listed in Table 1), including antibodies and antigen-binding fragments thereof, cells contacted by casme, etc., may be used either alone or in combination with other agents. Such agents may modulate genetic sequence, copy number, gene expression, translation, post-translational modification, subcellular localization, degradation, conformation, stability, secretion, enzymatic activity, transcription factors, receptor activation, signal transduction, and other biochemical functions mediated by the at least one biomarker. Such agents may bind any cell moiety, such as a receptor, a cell membrane, an antigenic determinant, or other binding site present on a target molecule or a target cell. In some embodiments, the agent may diffuse or be transported into the cell, where it may act intracellularly. In some embodiments, the agent is cell-based. Representative agents include, without limitation, nucleic acids (DNA and RNA like cDNA and mRNA), oligonucleotides, polypeptides, peptides, antibodies, fusion proteins, antibiotics, small molecules, lipids/fats, sugars, vectors, conjugates, vaccines, gene therapy agents, cell therapy agents, and the like, such as a small molecule, mRNA encoding a polypeptide, CRISPR guide RNA (gRNA), RNA interfering agent, small interfering RNA (siRNA), CRISPR RNA (crRNA and tracrRNA), a small hairpin RNA (shRNA), a microRNA (miRNA), a piwi-interacting RNA (piRNA), antisense oligonucleotide, peptide or peptidomimetic inhibitor, aptamer, natural ligands and derivative thereof that bind and either activate or inhibit protein biomarkers, antibody, intrabody, or cells, either alone or in combination with other agents.

Such agents encompassed by the present invention may comprise any number, type, and modality. For example, agents may comprise 1, 2, 3, 4, 5, or more, or any range in between, inclusive, number of agents that modulates a biomarker or more than one biomarker (e.g., 2 agents that modulate the same target listed in Table 1, an agent that modulates a target listed in Table 1 and another range that also modulates the same target listed in Table 1, an agent that modulates a target listed in Table 1 and another agent that modulates another target listed in Table 1, etc.).

In some embodiments, modulatory agents encompassed by the present invention further comprise one or more additional agents that target phagocytes, e.g., myeloid cells, such as suppressive myeloid cells, monocytes, macrophages, and/or dendritic cells. Such myeloid cell targeting agents include, but are not limited to, rovelizumab which targets CD11b, small molecules, including MNRP1685A (which targets Neurophilin-1), nesvacumab targeting ANG2, pascolizumab specific to IL-4, dupilumab specific to IL4Ra, tocilizumab and sarilumab specific to IL-6R, adalimumab, certolizumab, tanercept, golimumab, and infliximab specific to TNF-α, and CP-870 and CP-893 targeting CD40.

Exemplary agents for use with the antibodies, and antigen-binding fragments thereof, encompassed by the present invention are described further herein and in the art (see, e.g., U.S. Ser. No. 62/692,463 filed on Jun. 29, 2018, U.S. Ser. No. 62/810,683 filed on Feb. 26, 2019, U.S. Ser. No. 62/857,199 filed on Jun. 4, 2019, and a co-pending application filed as PCT/US2019/039773 by Novobrantseva et al. (Verseau Therapeutics, Inc.) on Jun. 27, 2019 having the title "Compositions and Methods for Modulating Monocyte and Macrophage Inflammatory Phenotypes and Immunotherapy Uses Thereof" and published as PCT Publ. No. WO 2020/006385; the entire contents of each of said applications being incorporated herein in their entirety by this reference).

1. Modulatory and Treatment Methods

One aspect encompassed by the present invention relates to methods of modulating the amount (e.g., expression) and/or activity (e.g., modulating signaling, inhibiting binding to binding partners, etc.) of at least one biomarker (e.g., one or more targets listed in Table 1, the Examples, etc.) described herein, such as for therapeutic purposes. Such agents may be used to manipulate a particular subpopulation of myeloid cells, such as suppressive myeloid cells, monocytes, macrophages, and/or dendritic cells, and regulate their numbers and/or activities in a physiological condition, and uses thereof for treating macrophages associated diseases and other clinical conditions. For example, agents, including compositions and pharmaceutical formulations, encompassed by the present invention may modulate the amount and/or activity of biomarkers (e.g., at least one target listed in Table 1, the Examples, etc.) to thereby modulate the inflammatory phenotype of myeloid cells, such as suppressive myeloid cells, monocytes, macrophages, and/or dendritic cells, and further modulate immune responses. In some embodiments, cell activities (e.g., cytokine secretion, cell population ratios, etc.) are modulated rather than modulating immune responses per se. Methods for modulating monocyte and macrophage inflammatory phenotypes using the agents, compositions, and formulations disclosed herein, are provided. Accordingly, the agents, compositions, and methods may be used for modulating immune responses by modulating the amount and/or activity of biomarkers (e.g., at least one target listed in Table 1, the Examples, etc.) depletes or enriches for certain types of cells and/or to modulate the ratio of cell types. For example, certain targets listed in Table 1 are required for cell survival such that inhibiting the target leads to cell death. Such modulation may be useful for modulating immune responses because the ratio of cell types (e.g., pro-inflammatory versus anti-inflammatory cells) mediating immune responses is modulated. In some embodiments, the agents are used to treat cancer in a subject afflicted with a cancer.

The present disclosure demonstrates that the downregulation of the amount and/or activity of these genes in macrophages may re-polarize (e.g., change the phenotype of) the macrophages. In some embodiments, the phenotype of an M2 macrophage is changed to result in a macrophage with a Type 1 (M2-like) or M1 phenotype, or vice versa regarding M1 macrophages and Type 2 (M2-like) or M2 phenotypes. In some embodiments, agents encompassed by the present invention are used to modulate (e.g., inhibit) the trafficking, polarization, and/or activation of monocytes and macrophages with an M2 phenotype, or vice versa regarding Type 1 and M1 macrophages. The present invention further provides method for reducing populations of myeloid cells, such as suppressive myeloid cells, monocytes, macrophages, and/or dendritic cells, of interest, such as M1 macrophages, M2 macrophages (e.g., TAMs in a tumor), and the like.

In some embodiments, the present invention provides methods for changing the distribution of myeloid cells, such as suppressive myeloid cells, monocytes, macrophages, and/or dendritic cells, including subtypes thereof, such as protumoral macrophages and anti-tumoral macrophages. In one example, the present invention provides methods for driving macrophages towards a pro-inflammatory immune response from an anti-inflammatory immune response and vice versa. Cell types may be depleted and/or enriched by 5%, 10%, 15%, 20%, 25%, 30%, 35%, 40%, 45%, 50%, 55%, 60%, 65%, 70%, 75%, 80%, 85%, 90%, 95%, 99%, or more, or any range in between inclusive, such as 45-55%.

In some embodiments, the modulation occurs in cells, such as monocyte, macrophage, or other phagocyte, like a dendritic cell. In some embodiments, the cell is a macrophage subtype, such as a macrophage subtype described herein. For example, the macrophage may be a tissue resident macrophage (TAM) or a macrophage derived from a circulating monocyte in the bloodstream.

In some embodiments, modulating myeloid cell inflammatory phenotypes results in desired modulated immune responses, such as modulation of abnormal monocyte migration and proliferation, unregulated proliferation of tissue resident macrophages, unregulated pro-inflammatory macrophages, unregulated anti-inflammatory macrophages, unbalanced distribution of pro-inflammatory and anti-inflammatory macrophage subpopulations in a tissue, an abnormally adopted activation state of monocytes and macrophages in a disease condition, modulated cytotoxic T-cell activation and function, overcoming of resistance of cancer cells to therapy, and sensitivity of cancer cells to immunotherapy, such as immune checkpoint therapy. In some embodiments, such phenotypes are reversed.

Methods for treating and/or preventing a disease associated with monocytes and macrophages comprise contacting cells, either in vitro, ex vivo, or in vivo (e.g., administering to a subject), with agents and compositions encompassed by the present invention, wherein the agents and compositions manipulate the migration, recruitment, differentiation and polarization, activation, function, and/or survival of monocytes and macrophages. In some embodiments, modulating one or more biomarkers encompassed by the present invention is used to modulate (e.g., inhibit or deplete) the proliferation, recruitment, polarization, and/or activation of monocytes and macrophages in a tissue microenvironment, such as tumor tissue.

In one aspect encompassed by the present invention, methods for reducing anti-inflammatory activities of myeloid cells, such as suppressive myeloid cells, monocytes, macrophages, and/or dendritic cells, are provided.

In another aspect encompassed by the present invention, methods for increasing pro-inflammatory activities of myeloid cells, such as suppressive myeloid cells, monocytes, macrophages, and/or dendritic cells, are provided.

In another aspect encompassed by the present invention, methods for balancing pro-inflammatory monocytes and macrophages and anti-inflammatory monocytes and macrophages in a tissue are provided.

Modulatory methods encompassed by the present invention involve contacting a cell with one or more modulators of a biomarker encompassed by the present invention, including at least one biomarker (e.g., at least one target listed in Table 1) encompassed by the present invention, including at least one biomarker (e.g., at least one target listed in Table 1) and the Examples, or a fragment thereof or agent that modulates one or more of the activities of biomarker activity associated with the cell. An agent that modulates biomarker activity may be an agent as described herein, such as an antibody or antigen-binding fragment thereof. In addition, other agents may be used in combination with such antibodies or antigen-binding fragments thereof, as described above (e.g., a nucleic acid or a polypeptide, a naturally-occurring binding partner of the biomarker, a combination of antibodies against the biomarker and antibodies against other immune related targets, at least one biomarker (e.g., at least one target listed in Table 1) agonist or antagonist, a peptidomimetic of at least one biomarker (e.g., at least one target listed in Table 1) agonist or antagonist, at least one biomarker (e.g., at least one target listed in Table 1) peptidomimetic, other small molecule, or small RNA directed against or a mimic of at least one biomarker (e.g., at least one target listed in Table 1) nucleic acid gene expression product, and the like).

a. Subjects

The present invention provides methods of treating an individual afflicted with a condition or disorder that would benefit from up- or down-modulation of at least one biomarker (e.g., at least one target listed in Table 1) encompassed by the present invention and the Examples or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. Subjects in need of therapy may be treated according to methods described herein and additional methods, such as those also described herein, may be combined with such therapeutic methods, such as methods to diagnose, prognose, monitor, and the like (e.g., modulation of populations of myeloid cells, such as suppressive myeloid cells, monocytes, macrophages, and/or dendritic cells, confirmed to have expression of the biomarker of interest, and subjects comprising such myeloid cells, such as suppressive myeloid cells, monocytes, macrophages, and/or dendritic cells).

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In some embodiments, the subject is an animal. The animal may be of either sex and may be at any stage of development. In some embodiments, the animals is a vertebrate, such as a mammal. In some embodiments, the subject is a non-human mammal. In some embodiments, the subject is a domesticated animal, such as a dog, cat, cow, pig, horse, sheep, or goat. In some embodiments, the subject is a companion animal, such as a dog or cat. In some embodiments, the subject is a livestock animal, such as a cow, pig, horse, sheep, or goat. In some embodiments, the subject is a zoo animal. In some embodiments, the subject is a research animal, such as a rodent (e.g., mouse or rat), dog, pig, or non-human primate. In some embodiments, the animal is a genetically engineered animal. In some embodiments, the animal is a transgenic animal (e.g., transgenic mice and transgenic pigs). In some embodiments, the subject is a fish or reptile. In some embodiments, the subject is a human. In some embodiments, the subject is an animal model of cancer. For example, the animal model may be an orthotopic xenograft animal model of a human-derived cancer.

In some embodiments of the methods encompassed by the present invention, the subject has not undergone treatment, such as chemotherapy, radiation therapy, targeted therapy, and/or immunotherapies. In some embodiments, the subject has undergone treatment, such as chemotherapy, radiation therapy, targeted therapy, and/or immunotherapies.

In some embodiments, the subject has had surgery to remove cancerous or precancerous tissue. In some embodiments, the cancerous tissue has not been removed, e.g., the cancerous tissue may be located in an inoperable region of the body, such as in a tissue that is essential for life, or in a region where a surgical procedure would cause considerable risk of harm to the patient.

In some embodiments, the subject or cells thereof are resistant to a therapy of relevance, such as resistant to immune checkpoint inhibitor therapy. For example, modulating one or more biomarkers encompassed by the present invention may overcome resistance to immune checkpoint inhibitor therapy.

In some embodiments, the subjects are in need of modulation according to compositions and methods described herein, such as having been identified as having an unwanted absence, presence, or aberrante expression and/or activity of one or more biomarkers described herein.

In some embodiments, the subjects have a solid tumor that is infiltrated with macrophages that represent at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, or more, or any range in between, inclusive, such as at least about 5% to at least about 20%, of the mass, volume, and/or number of cells in the tumor or the tumor microenvironment. Such cells can be any described as being useful in other embodiments herein, such as Type 1 macrophages, M1 macrophages, TAMs, myeloid cells, such as suppressive myeloid cells, monocytes, macrophages, and/or dendritic cells, expressing CD11b or CD14 or both CD11 and CD14, and the like.

The methods encompassed by the present invention may be used to determine the responsiveness to cancer therapy (e.g., at least one modulator of biomarkers listed in Table 1) of many different cancers in subjects such as those described herein.

In addition, these modulatory agents may also be administered in combination therapy to further modulate a desired activity. For examples, agents and compositions that target to IL-4, IL-4Ra, IL-13, and CD40 may be used to modulate myeloid cell differentiation and/or polarization. Agents and compositions that target to CD11b, CSF-1R, CCL2, neuropilin-1 and ANG-2 may be used to modulate macrophage recruitment to a tissue. Agents and compositions that target to IL-6, IL-6R and TNF-α may be used to modulate macrophage function. Additional agents include, without limitations, chemotherapeutic agents, hormones, antiangiogens, radiolabelled, compounds, or with surgery, cryotherapy, and/or radiotherapy. The preceding treatment methods may be administered in conjunction with other forms of conventional therapy (e.g., standard-of-care treatments for cancer well-known to the skilled artisan), either consecutively with, pre- or post-conventional therapy. For example, these modulatory agents may be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular melanoma, being treated, the extent of the disease and other factors familiar to the physician of skill in the art and may be determined by the physician.

b. Cancer Therapies

In some embodiments, agents encompassed by the present invention are used to treat cancer. For example, the present invention provides methods for reducing pro-tumoral functions of myeloid cells, such as suppressive myeloid cells, monocytes, macrophages, and/or dendritic cells, (i.e., tumorigenicity) and/or increasing anti-tumoral functions of myeloid cells, such as suppressive myeloid cells, monocytes, macrophages, and/or dendritic cells. In some particular embodiments, the method encompassed by the present invention may reduce at least one of the pro-tumoral functions of macrophages including 1) recruitment and polarization of tumor associate macrophages (TAMs), 2) tumor angiogenesis, 3) tumor growth, 4) tumor cell differentiation, 5) tumor cell survival, 6) tumor invasion and metastasis, 7) immune inhibition, and 8) immunosuppressive tumor microenvironment.

Cancer therapy (e.g., at least one modulator of one or more targets listed in Table 1) or combinations of therapies (e.g., at least one modulator of one or more targets listed in Table 1, in combination with at least one immunotherapy) may be used to contact cancer cells and/or administered to a desired subject, such as a subject that is indicated as being a likely responder to cancer therapy (e.g., at least one modulator of one or more targets listed in Table 1). In another embodiment, such cancer therapy (e.g., at least one modulator of one or more targets listed in Table 1) may be avoided once a subject is indicated as not being a likely responder to the cancer therapy (e.g., at least one modulator of one or more targets listed in Table 1) and an alternative treatment regimen, such as targeted and/or untargeted cancer therapies may be administered. Combination therapies are also contemplated and may comprise, for example, one or more chemotherapeutic agents and radiation, one or more chemotherapeutic agents and immunotherapy, or one or more chemotherapeutic agents, radiation and chemotherapy, each combination of which may be with or without cancer therapy (e.g., at least one modulator of one or more targets listed in Table 1).

Representative exemplary agents useful for modulating biomarkers encompassed by the present invention (e.g., one or more targets listed in Table 1), are described above. As described further below, anti-cancer agents encompass biotherapeutic anti-cancer agents (e.g., interferons, cytokines (e.g., tumor necrosis factor, interferon α, interferon γ, etc.), vaccines, hematopoietic growth factors, monoclonal serotherapy, immunostimulants and/or immunodulatory agents (e.g., IL-1, 2, 4, 6, and/or 12), immune cell growth factors (e.g., GM-CSF), and antibodies (e.g., trastuzumab, T-DM1, bevacizumab, cetuximab, panitumumab, rituximab, tositumomab, and the like), as well as chemotherapeutic agents.

The term "targeted therapy" refers to administration of agents that selectively interact with a chosen biomolecule to thereby treat cancer. For example, targeted therapy regarding the inhibition of immune checkpoint inhibitor is useful in combination with the methods encompassed by the present invention.

The term "immunotherapy" or "immunotherapies" generally refers to any strategy for modulating an immune response in a beneficial manner and encompasses the treatment of a subject afflicted with, or at risk of contracting or suffering a recurrence of, a disease by a method comprising inducing, enhancing, suppressing or otherwise modifying an immune response, as well as any treatment that uses certain parts of a subject's immune system to fight diseases, such as cancer. The subject's own immune system is stimulated (or suppressed), with or without administration of one or more agent for that purpose. Immunotherapies that are designed to elicit or amplify an immune response are referred to as "activation immunotherapies." Immunotherapies that are designed to reduce or suppress an immune response are referred to as "suppression immunotherapies." In some embodiments, an immunotherapy is specific for cells of interest, such as cancer cells. In some embodiments, immunotherapy may be "untargeted," which refers to administration of agents that do not selectively interact with immune system cells, yet modulates immune system function. Representative examples of untargeted therapies include, without limitation, chemotherapy, gene therapy, and radiation therapy.

Some forms of immunotherapy are targeted therapies that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy may involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy may also focus on using the cytotoxic lymphocyte-recognized epitopes of cancer cell lines. Alternatively, antisense polynucleotides, ribozymes, RNA interference molecules, triple helix polynucleotides and the like, may be used to selectively modulate biomolecules that are linked to the initiation, progression, and/or pathology of a tumor or cancer. Similarly, immunotherapy may take the form of cell-based therapies. For example, adoptive cellular immunotherapy is a type of immunotherapy using immune cells, such as T cells, that have a natural or genetically engineered reactivity to a patient's cancer are generated and then transferred back into the cancer patient. The injection of a large number of activated tumor-specific T cells may induce complete and durable regression of cancers.

Immunotherapy may involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy may also focus on using the cytotoxic lymphocyte-recognized epitopes of cancer cell lines. Alternatively, antisense polynucleotides, ribozymes, RNA interference molecules, triple helix polynucleotides and the like, may be used to selectively modulate biomolecules that are linked to the initiation, progression, and/or pathology of a tumor or cancer.

In some embodiments, an immunotherapeutic agent is an agonist of an immune-stimulatory molecule; an antagonist of an immune-inhibitory molecule; an antagonist of a chemokine; an agonist of a cytokine that stimulates T cell activation; an agent that antagonizes or inhibits a cytokine that inhibits T cell activation; and/or an agent that binds to a membrane bound protein of the B7 family. In some embodiments, the immunotherapeutic agent is an antagonist of an immune-inhibitory molecule. In some embodiments, the immunotherapeutic agents may be agents for cytokines, chemokines and growth factors, for examples, neutralizing antibodies that neutralize the inhibitory effect of tumor associated cytokines, chemokines, growth factors and other soluble factors including IL-10, TGF-β and VEGF.

In some embodiments, immunotherapy comprises inhibitors of one or more immune checkpoints. The term "immune checkpoint" refers to a group of molecules on the cell surface of CD4+ and/or CD8+ T cells that fine-tune immune responses by modulating anti-cancer immune responses, such as down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD200R, CD160, gp49B, PIR-B, KRLG-1, MR family receptors, TIM-1, TIM-3, TIM-4, LAG-3 (CD223), IDO, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

Some immune checkpoints are "immune-inhibitory immune checkpoints" encompassing molecules (e.g., proteins) that inhibit, down-regulate, or suppress a function of the immune system (e.g., an immune response). For example, PD-L1 (programmed death-ligand 1), also known as CD274 or B7-H1, is a protein that transmits an inhibitory signal that reduces proliferation of T cells to suppress the immune system. CTLA-4 (cytotoxic T-lymphocyte-associated protein 4), also known as CD152, is a protein receptor on the surface of antigen-presenting cells that serves as an immune checkpoint ("off" switch) to downregulate immune responses. TIM-3 (T-cell immunoglobulin and mucin-domain containing-3), also known as HAVCR2, is a cell surface protein that serves as an immune checkpoint to regulate macrophage activation. VISTA (V-domain Ig suppressor of T cell activation) is a type I transmembrane protein that functions as an immune checkpoint to inhibit T cell effector function and maintain peripheral tolerance. LAG-3 (lymphocyte-activation gene 3) is an immune checkpoint receptor that negatively regulates proliferation, activation, and homeostasis of T cells. BTLA (B- and T-lymphocyte attenuator) is a protein that displays T cell inhibition via interactions with tumor necrosis family receptors (TNF-R). MR (killer-cell immunoglobulin-like receptor) is a family of proteins expressed on NK cells, and a minority of T cells, that suppress the cytotoxic activity of NK cells. In some embodiments, immunotherapeutic agents may be agents specific to immunosuppressive enzymes such as inhibitors that may block the activities of arginase (ARG) and indoleamine 2,3-dioxygenase (IDO), an immune checkpoint protein that suppresses T cells and NK cells, which change the catabolism of the amino acids arginine and tryptophan in the immunosuppressive tumor microenvironment. The inhibitors may include, but are not limited to, N-hydroxy-L-Arg (NOHA) targeting to ARG-expressing M2 macrophages, nitroaspirin or sildenafil (Viagra®), which blocks ARG and nitric oxide synthase (NOS) simultaneously; and IDO inhibitors, such as 1-methyl-tryptophan. The term further encompasses biologically active protein fragment, as well as nucleic acids encoding full-length immune checkpoint proteins and biologically active protein fragments thereof. In some embodiment, the term further encompasses any fragment according to homology descriptions provided herein.

By contrast, other immune checkpoints are "immune-stimulatory" encompassing molecules (e.g., proteins) that activate, stimulate, or promote a function of the immune system (e.g., an immune response). In some embodiments, the immune-stimulatory molecule is CD28, CD80 (B7.1), CD86 (B7.2), 4-1BB (CD137), 4-1BBL (CD137L), CD27, CD70, CD40, CD40L, CD122, CD226, CD30, CD30L, OX40, OX40L, HVEM, BTLA, GITR and its ligand GITRL, LIGHT, LTβR, LTαβ, ICOS (CD278), ICOSL (B7-H2), and NKG2D. CD40 (cluster of differentiation 40) is a costimulatory protein found on antigen presenting cells that is required for their activation. OX40, also known as tumor necrosis factor receptor superfamily member 4 (TNFRSF4) or CD134, is involved in maintenance of an immune response after activation by preventing T-cell death and subsequently increasing cytokine production. CD137 is a member of the tumor necrosis factor receptor (TNF-R) family that co-stimulates activated T cells to enhance proliferation and T cell survival. CD122 is a subunit of the interleukin-2 receptor (IL-2) protein, which promotes differentiation of immature T cells into regulatory, effector, or memory T cells. CD27 is a member of the tumor necrosis factor receptor superfamily and serves as a co-stimulatory immune checkpoint molecule. CD28 (cluster of differentiation 28) is a protein expressed on T cells that provides co-stimulatory signals required for T cell activation and survival. GITR (glucocorticoid-induced TNFR-related protein), also known as TNFRSF18 and AITR, is a protein that plays a key role in dominant immunological self-tolerance maintained by regulatory T cells. ICOS (inducible T-cell co-stimulator), also known as CD278, is a CD28-superfamily costimulatory molecule that is expressed on activated T cells and play a role in T cell signaling and immune responses.

Immune checkpoints and their sequences are well-known in the art and representative embodiments are described further below. Immune checkpoints generally relate to pairs of inhibitory receptors and the natural binding partners (e.g., ligands). For example, PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells. The term "PD-1 activity," includes the ability of a PD-1 polypeptide to modulate an inhibitory signal in an activated immune cell, e.g., by engaging a natural PD-1 ligand on an antigen presenting cell. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell inhibitory signals, and the ability to modulate the immune response. The term "PD-1 ligand" refers to binding partners of the PD-1 receptor and includes both PD-L1 (Freeman et al. (2000) *J. Exp. Med.* 192:1027-1034) and PD-L2 (Latchman et al. (2001) *Nat. Immunol.* 2:261). The term "PD-1 ligand activity" includes the ability of a PD-1 ligand polypeptide to bind its natural receptor(s) (e.g., PD-1 or B7-1), the ability to modulate immune cell inhibitory signals, and the ability to modulate the immune response.

As used herein, the term "immune checkpoint therapy" refers to the use of agents that inhibit immune-inhibitory immune checkpoints, such as inhibiting their nucleic acids and/or proteins. Inhibition of one or more such immune checkpoints may block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that may either bind and/or inactivate or inhibit immune checkpoint proteins, or fragments thereof; as well as RNA interference, antisense, nucleic acid aptamers, etc. that may downregulate the expression and/or activity of immune checkpoint nucleic acids, or fragments thereof. Exemplary agents for upregulating an immune response include antibodies against one or more immune checkpoint proteins that block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g., the extracellular portion of an immune checkpoint inhibition protein fused to the Fc portion of an antibody or immunoglobulin) that bind to its natural receptor (s); nucleic acid molecules that block immune checkpoint nucleic acid transcription or translation; and the like. Such agents may directly block the interaction between the one or more immune checkpoints and its natural receptor(s) (e.g., antibodies) to prevent inhibitory signaling and upregulate an immune response. Alternatively, agents may indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain may binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. Therapeutic agents used for blocking the PD-1 pathway include antagonistic antibodies and soluble PD-L1 ligands. The antagonist agents against PD-1 and PD-L1/2 inhibitory pathway may include, but are not limited to, antagonistic antibodies to PD-1 or PD-L1/2 (e.g., 17D8, 2D3, 4H1, 5C4 (also known as nivolumab or BMS-936558), 4A11, 7D3 and 5F4 disclosed in U.S. Pat. No. 8,008,449; AMP-224, pidilizumab (CT-011), pembrolizumab, and antibodies disclosed in U.S. Pat. Nos. 8,779,105; 8,552,154; 8,217,149; 8,168,757; 8,008,449; 7,488,802; 7,943,743; 7,635,757; and 6,808,710. Similarly, additional representative checkpoint inhibitors may be, but are not limited to, antibodies against inhibitory regulator CTLA-4 (anti-cytotoxic T-lymphocyte antigen 4 anti-cytotoxic T-lymphocyte antigen 4), such as ipilimumab, tremelimumab (fully humanized), anti-CD28 antibodies, anti-CTLA-4 adnectins, anti-CTLA-4 domain antibodies, single chain anti-CTLA-4 antibody fragments, heavy chain anti-CTLA-4 fragments, light chain anti-CTLA-4 fragments, and other antibodies, such as those disclosed in U.S. Pat. Nos. 8,748,815; 8,529,902; 8,318,916; 8,017,114; 7,744,875; 7,605,238; 7,465,446; 7,109,003; 7,132,281; 6,984,720; 6,682,736; 6,207,156; and 5,977,318, as well as EP Pat. No. 1212422, U.S. Pat Publ. Numbers 2002/0039581 and 2002/086014, and Hurwitz et al. (1998) *Proc. Natl. Acad. Sci. U.S.A.* 95:10067-10071.

The representative definitions of immune checkpoint activity, ligand, blockade, and the like exemplified for PD-1, PD-L1, PD-L2, and CTLA-4 apply generally to other immune checkpoints.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary agents include, but are not limited to, alkylating agents: nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Similarly, additional exemplary agents including platinum-containing compounds (e.g., cisplatin, carboplatin, oxaliplatin), vinca alkaloids (e.g., vincristine, vinblastine, vindesine, and vinorelbine), taxoids (e.g., paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), antimetabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, raltitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE®)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genentech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiment, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of beta-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard et. al. (2003) *Exp. Hematol.* 31:446-454); Herceg (2001) *Mut Res.* 477:97-110). Poly(ADP-ribose) polymerase 1 (PARP1) is a key molecule in the repair of DNA single-strand breaks (SSBs) (de Murcia J. et al. (1997) *Proc. Natl. Acad. Sci. U.S.A.* 94:7303-7307; Schreiber et al. (2006) *Nat. Rev. Mol. Cell Biol.* 7:517-528; Wang et al. (1997) *Genes Dev.* 11:2347-2358). Knockout of SSB repair by inhibition of PARP1 function induces DNA double-strand breaks (DSBs) that may trigger synthetic lethality in cancer cells with defective homology-directed DSB repair (Bryant et al. (2005) *Nature* 434:913-917; Farmer et al. (2005) *Nature* 434:917-921). The foregoing examples of chemotherapeutic agents are illustrative and are not intended to be limiting.

In another embodiment, radiation therapy is used. The radiation used in radiation therapy may be ionizing radiation. Radiation therapy may also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy may be administered as external beam radiation or teletherapy wherein the radiation is directed from a remote source. The radiation treatment may also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments may comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy may be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It may be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, may cause discomfort or even significant local pain in about half the patients treated. It may also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents may kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT may be directed through a fiber-optic (a very thin glass strand). The fiber-optic is placed close to the cancer to deliver the proper amount of light. The fiber-optic may be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and may include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also may be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser may remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser may penetrate deeper into tissue than light from the other types of lasers, and it may cause blood to clot quickly. It may be carried through optical fibers to less accessible parts of the body. This type of laser is sometimes used to treat throat cancers. Argon laser—This laser may pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light may be directed to parts of the body without making a large incision. More procedures may be done on an outpatient basis. Lasers may be used in two ways to treat cancer: by shrinking or destroying a tumor with heat, or by activating a chemical—known as a photosensitizing agent—that destroys cancer cells. In PDT, a photosensitizing agent is retained in cancer cells and may be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers may be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems may produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with cancer therapy (e.g., at least one modulator of biomarkers listed in Table 1) may vary according to the particular modulator of biomarkers listed in Table 1 or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods encompassed by the present invention is a factor in determining optimal treatment doses and schedules.

2. Screening Methods

Another aspect encompassed by the present invention encompasses screening assays.

In some embodiments, methods are provided for selecting agents (e.g., antibodies, fusion proteins, peptides, or small molecules) which modulate the amount and/or activity of one or more biomarkers encompassed by the present invention (e.g., one or more targets listed in Table 1) in myeloid cells, such as suppressive myeloid cells, monocytes, macrophages, and/or dendritic cells. In some embodiments, the selected agents also modulate immune responses mediated by such myeloid cells, such as suppressive myeloid cells, monocytes, macrophages, and/or dendritic cells (e.g., modulating CD8+ cytotoxic T cell killing; modulating sensitivity of cancer cells to immune checkpoint therapy; modulating resistance to anti-cancer therapies like immunecheckpoint therapy; modulating the modulating cancer therapy; modulating immune cell migration, recruitment, differentiation, and/or survival, such as of NK, neutrophil, and macrophage cells; and the like). Thus, any diagnostic, prognostic, or screening method described herein may use biomarkers described herein as readouts of a desired phenotype, such as modulated immune phenotype, as well as agents that modulate the amount and/or activity of one or more biomarkers described herein to confirm modulation of the one or more biomarkers and/or to confirm the effects of the agents on readouts of a desired phenotype, such as modulated immune responses, sensitivity to immune checkpoint blockade, and the like. Such methods may utilize screening assays, including cell-based and non-cell based assays.

For example, a method for screening for agents that sensitize cancer cells to cytotoxic T cell-mediated killing and/or immune checkpoint therapy comprising a) contacting cancer cells with cytotoxic T cells and/or immune checkpoint therapy in the presence of myeloid cells, such as suppressive myeloid cells, monocytes, macrophages, and/or dendritic cells, contacted with at least one agent that decreases the amount and/or activity of at least one target listed in Table; b) contacting cancer cells with cytotoxic T cells and/or immune checkpoint therapy in the presence of control myeloid cells, such as suppressive myeloid cells, monocytes, macrophages, and/or dendritic cells, that are not contacted with the at least one agent or agents; and c) identifying agents that sensitize cancer cells to cytotoxic T cell-mediated killing and/or immune checkpoint therapy by identifying agents that increase cytotoxic T cell-mediated killing and/or immune checkpoint therapy efficacy (such as cell killing) in a) compared to b), is provided.

In some embodiments, the assays are directed to identifying agents that inhibit immune cell proliferation and/or effector function, or to induce anergy, clonal deletion, and/or exhaustion by assaying the opposite modulation effect of the one or more biomarkers. The present invention further encompasses methods of inhibiting immune cell proliferation and/or effector function, or to induce anergy, clonal deletion, and/or exhaustion through such a modulation.

In another example, a method for screening for agents that sensitize cancer cells to cytotoxic T cell-mediated killing and/or immune checkpoint therapy comprising a) contacting cancer cells with cytotoxic T cells and/or immune checkpoint therapy in the presence of myeloid cells, such as suppressive myeloid cells, monocytes, macrophages, and/or dendritic cells, engineered to decrease the amount and/or activity of at least one target listed in Table 1; b) contacting cancer cells with cytotoxic T cells and/or immune checkpoint therapy in the presence of control myeloid cells, such as suppressive myeloid cells, monocytes, macrophages, and/or dendritic cells; and c) identifying agents that sensitize cancer cells to cytotoxic T cell-mediated killing and/or immune checkpoint therapy efficacy (such as cell killing) in a) compared to b), is provided.

Generally, the present invention encompasses assays for screening agents, such as test compounds, that bind to, or modulate the activity of, one or more biomarkers encompassed by the present invention (e.g., targets listed in Table 1, Examples, etc.). In one embodiment, a method for identifying an agent to modulate an immune response entails determining the ability of the agent to inhibit one or more targets listed in Table 1. Such agents include, without limitation, antibodies, proteins, fusion proteins, small molecules, and nucleic acids.

In some embodiments, a method for identifying an agent which enhances an immune response entails determining the ability of the candidate agent to modulate the one or more biomarkers and further modulate an immune response of interest, such as modulated inflammatory phenotype, cytotoxic T cell activation and/or activity, sensitivity of cancer cells to immune checkpoint therapy, and the like.

In some embodiments, an assay is a cell-free or cell-based assay, comprising contacting one or more biomarkers (e.g., one or more targets listed in Table 1), with a test agent, and determining the ability of the test agent to modulate (e.g., upregulate or downregulate) the amount and/or activity of the biomarker, such as by measuring direct or indirect parameters as described below.

In some embodiments, an assay is a cell-based assay, such as one comprising contacting (a) a cell of interest (e.g., myeloid cells, such as suppressive myeloid cells, monocytes, macrophages, and/or dendritic cells) with a test agent and determining the ability of the test agent to modulate (e.g. upregulate or downregulate) the amount and/or activity of the one or more biomarkers, such as binding between the one or more biomarkers and one or more natural binding partners. Determining the ability of the polypeptides to bind to, or interact with, each other may be accomplished, e.g., by measuring direct binding or by measuring a parameter of immune cell activation.

In another embodiment, an assay is a cell-based assay, comprising contacting a cancer cell with cytotoxic T cells, myeloid cells, and a test agent, and determining the ability of the test agent to modulate the amount and/or activity of at least one target listed in Table 1, and/or modulated immune responses, such as by measuring direct or indirect parameters as described below.

The methods described above and herein may also be adapted to test one or more agents that are already known to modulate the amount and/or activity of one or more biomarkers described herein to confirm modulation of the one or more biomarkers and/or to confirm the effects of the agents on readouts of a desired phenotype, such as modulated immune responses, sensitivity to immune checkpoint blockade, and the like.

In a direct binding assay, biomarker protein (or their respective target polypeptides or molecules) may be coupled with a radioisotope or enzymatic label such that binding may be determined by detecting the labeled protein or molecule in a complex. For example, the targets may be labeled with $^{125}I$, $^{35}S$, $^{14}C$, or $^{3}H$, either directly or indirectly, and the radioisotope detected by direct counting of radioemmission or by scintillation counting. Alternatively, the targets may be enzymatically labeled with, for example, horseradish peroxidase, alkaline phosphatase, or luciferase, and the enzymatic label detected by determination of conversion of an appropriate substrate to product. Determining the interaction between biomarker and substrate may also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target may be accomplished in any vessel suitable for containing the reactants. Non-limiting examples of such vessels include microtiter plates, test tubes, and micro-centrifuge tubes. Immobilized forms of the antibodies encompassed by the present invention may also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

For example, in a direct binding assay, the polypeptides may be coupled with a radioisotope or enzymatic label such that polypeptide interactions and/or activity, such as binding events, may be determined by detecting the labeled protein in a complex. For example, the polypeptides may be labeled with $^{125}I$, $^{35}S$, $^{14}C$, or $^{3}H$, either directly or indirectly, and the radioisotope detected by direct counting of radioemmission or by scintillation counting. Alternatively, the polypeptides may be enzymatically labeled with, for example, horseradish peroxidase, alkaline phosphatase, or luciferase, and the enzymatic label detected by determination of conversion of an appropriate substrate to product.

It is also within the scope of the present invention to determine the ability of an agent to modulate a parameter of interest without the labeling of any of the interactants. For example, a microphysiometer may be used to detect interaction between polypeptides without the labeling of polypeptides to be monitored (McConnell et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate may be used as an indicator of the interaction between compound and receptor.

In some embodiments, determining the ability of the blocking agents (e.g. antibodies, fusion proteins, peptides, or small molecules) to antagonize the interaction between a given set of polypeptides may be accomplished by determining the activity of one or more members of the set of polypeptides. For example, the activity of a protein and/or one or more natural binding partners may be determined by detecting induction of a cellular second messenger (e.g., intracellular signaling), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by the protein and/or the one or more natural binding partners. Determining the ability of the blocking agent to bind to or interact with said polypeptide may be accomplished, for example, by measuring the ability of a compound to modulate immune cell costimulation or inhibition in a proliferation assay, or by interfering with the ability of said polypeptide to bind to antibodies that recognize a portion thereof.

Agents that modulate biomarker amount and/or activity, such as interactions with one or more natural binding partners, may be identified by their ability to inhibit immune cell proliferation, and/or effector function, or to induce anergy, clonal deletion, and/or exhaustion when added to an in vitro assay. For example, cells may be cultured in the presence of an agent that stimulates signal transduction via an activating receptor. A number of recognized readouts of cell activation may be employed to measure, cell proliferation or effector function (e.g., antibody production, cytokine production, phagocytosis) in the presence of the activating agent. The ability of a test agent to block this activation may be readily determined by measuring the ability of the agent to effect a decrease in proliferation or effector function being measured, using techniques known in the art.

For example, agents encompassed by the present invention may be tested for the ability to inhibit or enhance costimulation in a T cell assay, as described in Freeman et al. (2000) *J. Exp. Med.* 192:1027 and Latchman et al. (2001) *Nat. Immunol.* 2:261. CD4+ T cells may be isolated from human PBMCs and stimulated with activating anti-CD3 antibody. Proliferation of T cells may be measured by $^{3}H$ thymidine incorporation. An assay may be performed with or without CD28 costimulation in the assay. Similar assays may be performed with Jurkat T cells and PHA-blasts from PBMCs.

Alternatively, agents encompassed by the present invention may be tested for the ability to modulate cellular production of cytokines which are produced by or whose production is enhanced or inhibited in immune cells in response to modulation of the one or more biomarkers. Indicative cytokines released by immune cells of interest may be identified by ELISA or by the ability of an antibody which blocks the cytokine to inhibit immune cell proliferation or proliferation of other cell types that is induced by the cytokine. For example, an IL-4 ELISA kit is available from Genzyme (Cambridge MA), as is an IL-7 blocking antibody. Blocking antibodies against IL-9 and IL-12 are available from Genetics Institute (Cambridge, MA). An in vitro immune cell costimulation assay may also be used in a method for identifying cytokines which may be modulated by modulation of the one or more biomarkers. For example, if a particular activity induced upon costimulation, e.g., immune cell proliferation, cannot be inhibited by addition of blocking antibodies to known cytokines, the activity may result from the action of an unknown cytokine. Following costimulation, this cytokine may be purified from the media by conventional methods and its activity measured by its ability to induce immune cell proliferation. To identify cytokines which may play a role the induction of tolerance, an in vitro T cell costimulation assay as described above may be used. In this case, T cells would be given the primary activation signal and contacted with a selected cytokine, but would not be given the costimulatory signal. After washing and resting the immune cells, the cells would be rechallenged with both a primary activation signal and a costimulatory signal. If the immune cells do not respond (e.g., proliferate or produce cytokines) they have become tolerized and the cytokine has not prevented the induction of tolerance. However, if the immune cells respond, induction of tolerance has been prevented by the cytokine. Those cytokines which are capable of preventing the induction of tolerance may be targeted for blockage in vivo in conjunction with reagents which block B lymphocyte antigens as a more efficient means to induce tolerance in transplant recipients or subjects with autoimmune diseases.

In some embodiments, an assay encompassed by the present invention is a cell-free assay for screening for agents that modulate the interaction between a biomarker and/or one or more natural binding partners, comprising contacting a polypeptide and one or more natural binding partners, or biologically active portion thereof, with a test agent and determining the ability of the test compound to modulate the interaction between the polypeptide and one or more natural binding partners, or biologically active portion thereof. Binding of the test compound may be determined either directly or indirectly as described above. In one embodiment, the assay includes contacting the polypeptide, or biologically active portion thereof, with its binding partner to form an assay mixture, contacting the assay mixture with a test compound, and determining the ability of the test compound to interact with the polypeptide in the assay mixture, wherein determining the ability of the test compound to interact with the polypeptide comprises determining the ability of the test compound to preferentially bind to the polypeptide or biologically active portion thereof, as compared to the binding partner.

In some embodiments, whether for cell-based or cell-free assays, a test agent may further be assayed to determine whether it affects binding and/or activity of the interaction between the polypeptide and the one or more natural binding partners, with other binding partners. Other useful binding analysis methods include the use of real-time Biomolecular Interaction Analysis (BIA) (Sjolander and Urbaniczky (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) may be used as an indication of real-time reactions between biological polypeptides. Polypeptides of interest may be immobilized on a BIAcore chip and multiple agents (blocking antibodies, fusion proteins, peptides, or small molecules) may be tested for binding to the polypeptide of interest. An example of using the BIA technology is described by Fitz et al. (1997) *Oncogene* 15:613.

The cell-free assays encompassed by the present invention are amenable to use of both soluble and/or membrane-bound forms of proteins. In the case of cell-free assays in which a membrane-bound form protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either polypeptides to facilitate separation of complexed from uncomplexed forms of one or both of the proteins, as well as to accommodate automation of the assay. Binding of a test compound to a polypeptide, may be accomplished in any vessel suitable for containing the reactants. Examples of such vessels include microtiter plates, test tubes, and microcentrifuge tubes. In one embodiment, a fusion protein may be provided which adds a domain that allows one or both of the proteins to be bound to a matrix. For example, glutathione-S-transferase-based polypeptide fusion proteins, or glutathione-S-transferase/target fusion proteins, may be adsorbed onto glutathione sepharose beads (Sigma Chemical, St. Louis, MO) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes may be dissociated from the matrix, and the level of polypeptide binding or activity determined using standard techniques.

In an alternative embodiment, determining the ability of the test compound to modulate the activity of a biomarker of interest (e.g., one or more targets listed in Table 1) may be accomplished as described above for cell-based assays, such as by determining the ability of the test compound to modulate the activity of a polypeptide that functions downstream of the polypeptide. For example, levels of second messengers may be determined, the activity of the interactor polypeptide on an appropriate target may be determined, or the binding of the interactor to an appropriate target may be determined as previously described.

The present invention further pertains to novel agents identified by the above-described screening assays. Accordingly, it is within the scope of the present invention to further use an agent identified as described herein in an appropriate animal model. For example, an agent identified as described herein may be used in an animal model to determine the efficacy, toxicity, or side effects of treatment with such an agent. Alternatively, an agent identified as described herein may be used in an animal model to 5 determine the mechanism of action of such an agent. Furthermore, the present invention pertains to uses of novel agents identified by the above-described screening assays for treatments as described herein.

3. Diagnostic Uses and Assays

The present invention provides, in part, methods, systems, and code for accurately classifying whether a biological sample is associated with an output of interest, such as expression of a biomarker of interest (e.g., a target listed in Table 1), myeloid cells, such as suppressive myeloid cells, monocytes, macrophages, and/or dendritic cells, that are able to have modulated phenotypes according to modulation of one or more biomarkers described herein, a cancer that is likely to respond to cancer therapy (e.g., at least one modulator of one or more targets listed in Table 1), and the like. In some embodiments, the present invention is useful for classifying a sample (e.g., from a subject) as associated with or at risk for responding to or not responding to cancer therapy (e.g., at least one modulator of biomarkers listed in Table 1) using a statistical algorithm and/or empirical data (e.g., the amount or activity of at least one target listed in Table 1). In some embodiments, the present invention encompasses methods of detecting the immune phenotype status of a myeloid cell (e.g., monocytes, macrophages, M1, Type 1, M2, Type 2, etc.) based on detecting the presence, absence, and/or modulated expression of a biomarker described herein, such as those listed in Table 1, the Examples, etc.

An exemplary method for detecting the amount or activity of a biomarker (e.g., one or more targets listed in Table 1), and thus useful for classifying whether a sample is likely or unlikely to respond to modulation of inflammatory phenotype, cancer therapy, and the like involves contacting a biological sample with an agent, such as a protein-binding agent like an antibody or antigen-binding fragment thereof, and/or a nucleic acid-binding agent like an oligonucleotide, capable of detecting the amount or activity of the biomarker in the biological sample. In some embodiments, the method further comprise obtaining a biological sample, such as from a test subject. In some embodiments, at least one agent is used, wherein two, three, four, five, six, seven, eight, nine, ten, or more such agents may be used in combination (e.g., in sandwich ELISAs) or in serial. In certain instances, the statistical algorithm is a single learning statistical classifier system. For example, a single learning statistical classifier system may be used to classify a sample as a based upon a prediction or probability value and the presence or level of the biomarker. The use of a single learning statistical classifier system typically classifies the sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method encompassed by the present invention further comprises sending the sample classification results to a clinician, e.g., an oncologist.

In some embodiments, the diagnosis of a subject is followed by administering to the individual a therapeutically effective amount of a defined treatment based upon the diagnosis.

In some embodiments, the methods further involve obtaining a control biological sample (e.g., biological sample from a subject who does not have a cancer or whose cancer is susceptible to cancer therapy, a biological sample from the subject during remission, or a biological sample from the subject during treatment for developing a cancer progressing despite cancer therapy.

4. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect encompassed by the present invention encompasses diagnostic assays for determining (e.g., detecting) the presence, absence, amount, and/or activity level of a biomarker described herein, such as those listed in Table 1, in the context of a biological sample (e.g., blood, serum, cells, or tissue) to thereby determine whether an individual afflicted with a cancer is likely to respond to cancer therapy (e.g., at least one modulator of biomarkers listed in Table 1), whether in an original or recurrent cancer. Such assays may be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method may use one or more (e.g., combinations) of biomarkers described herein, such as those listed in Table 1.

The diagnostic methods described herein may furthermore be utilized to identify subjects having or at risk of developing a disorder associated with expression or lack thereof of a biomarker of interest. As used herein, the term "aberrant" includes a upregulation or downregulation of a biomarker of interest which deviates from the normal levels. Aberrant expression or activity includes increased or decreased expression or activity, as well as expression or activity which does not follow the normal developmental pattern of expression or the subcellular pattern of expression. For example, aberrant levels is intended to include the cases in which a mutation in the biomarker gene or regulatory sequence, or amplification of the chromosomal gene, thereof causes upregulation or downregulation of the biomarker of interest. As used herein, the term "unwanted" includes an unwanted phenomenon involved in a biological response such as immune cell activation.

Many disorders associated with a biomarker of interest are known to the skilled artisan, as explained further herein and at least in the Examples.

The assays described herein, such as the preceding diagnostic assays or the following assays, may be utilized to identify a subject having or at risk of developing a disorder associated with a misregulation of a biomarker of interest. Thus, the present invention provides a method for identifying a disorder associated with aberrant or unwanted biomarker regulation in which a test sample is obtained from a subject and the biomarker is detected, wherein the presence of biomarker polypeptide is diagnostic for a subject having or at risk of developing the disorder associated with aberrant or unwanted biomarker expression and/or activity. As used herein, a "test sample" refers to a biological sample obtained from a subject of interest. For example, a test sample may be a biological fluid (e.g., cerebrospinal fluid or serum), cell sample, or tissue, such as a histopathological slide of the tumor microenvironment, peritumoral area, and/or intratumoral area.

Furthermore, the prognostic assays described herein may be used to determine whether a subject may be administered an agent (e.g., an antibody, an agonist, antagonist, peptidomimetic, polypeptide, peptide, nucleic acid, small molecule, or other drug candidate) to treat such a disorder associated with aberrant or unwanted biomarker expression and/or activity. For example, such methods may be used to determine whether a subject may be effectively treated with one or a combination of agents. Thus, the present invention provides methods for determining whether a subject may be effectively treated with one or more agents for treating a disorder associated with aberrant or unwanted biomarker expression and/or activity in which a test sample is obtained and the biomarker is detected (e.g., wherein the abundance of biomarker polypeptide is diagnostic for a subject that may be administered an antibody or antigen-binding fragment to treat the disorder).

The methods described herein may be performed, for example, by utilizing pre-packaged diagnostic kits comprising at least one antibody reagent described herein, which may be conveniently used, e.g., in clinical settings to diagnose patients exhibiting symptoms or family history of a disease or illness involving the biomarker of interest.

Furthermore, any cell type or tissue in which the biomarker of interest is expressed may be utilized in the prognostic assays described herein.

Another aspect of the present invention includes uses of the compositions and methods described herein for association and/or stratification analyses in which the biomarker of interest (e.g., biomarker alone, other stratification indicator of interest like CD11b+ status, CD14+ status, etc. alone, or in combinations thereof) in biological samples from individuals with a disorder associated with aberrant or unwanted biomarker expression and/or activity, are analyzed and the information is compared to that of controls (e.g., individuals who do not have the disorder; controls may be also referred to as "healthy" or "normal" individuals or at early timepoints in a given time lapse study) who are preferably of similar age and race. The appropriate selection of patients and controls is important to the success of association and/or stratification studies. Therefore, a pool of individuals with well-characterized phenotypes is extremely desirable. Criteria for disease diagnosis, disease predisposition screening, disease prognosis, determining drug responsiveness (pharmacogenomics), drug toxicity screening, etc. are described herein.

Different study designs may be used for genetic association and/or stratification studies (Modern Epidemiology, Lippincott Williams & Wilkins (1998), 609-622). Observational studies are most frequently carried out in which the response of the patients is not interfered with. The first type of observational study identifies a sample of persons in whom the suspected cause of the disease is present and another sample of persons in whom the suspected cause is absent, and then the frequency of development of disease in the two samples is compared. These sampled populations are called cohorts, and the study is a prospective study. The other type of observational study is case-control or a retrospective study. In typical case-control studies, samples are collected from individuals with the phenotype of interest (cases) such as certain manifestations of a disease, and from individuals without the phenotype (controls) in a population (target population) that conclusions are to be drawn from. Then the possible causes of the disease are investigated retrospectively. As the time and costs of collecting samples in case-control studies are considerably less than those for prospective studies, case-control studies are the more commonly used study design in genetic association studies, at least during the exploration and discovery stage.

After all relevant phenotypic and/or genotypic information has been obtained, statistical analyses are carried out to determine if there is any significant correlation between the presence of an allele or a genotype with the phenotypic characteristics of an individual. Preferably, data inspection and cleaning are first performed before carrying out statistical tests for genetic association. Epidemiological and clinical data of the samples may be summarized by descriptive statistics with tables and graphs well-known in the art. Data validation is preferably performed to check for data completion, inconsistent entries, and outliers. Chi-squared tests and t-tests (Wilcoxon rank-sum tests if distributions are not normal) may then be used to check for significant differences between cases and controls for discrete and continuous variables, respectively.

One possible decision in the performance of genetic association tests is the determination of the significance level at which significant association may be declared when the p-value of the tests reaches that level. In an exploratory analysis where positive hits will be followed up in subsequent confirmatory testing, an unadjusted p-value $<0.2$ (a significance level on the lenient side), for example, may be used for generating hypotheses for significant association of a level of a biomarker of interest with certain phenotypic characteristics of a disorder. It is preferred that a p-value $<0.05$ (a significance level traditionally used in the art) is achieved in order for the level to be considered to have an association with a disease. When hits are followed up in confirmatory analyses in more samples of the same source or in different samples from different sources, adjustment for multiple testing will be performed as to avoid excess number of hits while maintaining the experiment-wise error rates at 0.05. While there are different methods to adjust for multiple testing to control for different kinds of error rates, a commonly used but rather conservative method is Bonferroni correction to control the experiment-wise or family-wise error rate (Multiple comparisons and multiple tests, Westfall et al, SAS Institute (1999)). Permutation tests to control for the false discovery rates, FDR, may be more powerful (Benjamini and Hochberg, Journal of the Royal Statistical Society, Series B 57, 1289-1300, 1995, Resampling-based Multiple Testing, Westfall and Young, Wiley (1993)). Such methods to control for multiplicity would be preferred when the tests are dependent and controlling for false discovery rates is sufficient as opposed to controlling for the experiment-wise error rates.

Once individual risk factors, genetic or non-genetic, have been found for the predisposition to disease, a classification/prediction scheme may be set up to predict the category (for instance, disease or no-disease) that an individual will be in depending on his phenotype and/or genotype and other non-genetic risk factors. Logistic regression for discrete trait and linear regression for continuous trait are standard techniques for such tasks (Applied Regression Analysis, Draper and Smith, Wiley (1998)). Moreover, other techniques may also be used for setting up classification. Such techniques include, but are not limited to, MART, CART, neural network, and discriminant analyses that are suitable for use in comparing the performance of different methods (The Elements of Statistical Learning, Hastie, Tibshirani & Friedman, Springer (2002)).

Another aspect encompassed by the present invention encompasses monitoring the influence of agents (e.g., drugs, compounds, and small nucleic acid-based molecules) on the expression or activity of a target listed in Table 1 and/or inflammatory phenotypes of cells of interest. These and other agents are described in further detail in the following sections.

5. Monitoring of Effects During Clinical Trials

Monitoring the influence of agents (e.g., antibodies, compounds, drugs, small molecules, etc.) on a biomarker polypeptide of interest (e.g., the modulation of a monocyte and/or macrophage inflammatory phenotype) may be applied not only in basic drug screening, but also in clinical trials. For example, the effectiveness of an agent determined by a screening assay as described herein to modulate biomarker polypeptide levels or activity, may be monitored in clinical trials of subjects exhibiting modulated biomarker polypeptide levels or activity, such as using antibodies or fragments described herein. In such clinical trials, the expression or activity of a biomarker of interest and/or symptoms or markers of the disorder of interest, may be used as a "read out" or marker of the phenotype of a particular cell, tissue, or system.

In a preferred embodiment, the present invention provides a method for monitoring the effectiveness of treatment of a subject with an agent (e.g., antibodies, an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level and/or activity of biomarker polypeptide, in the preadministration sample; (iii) obtaining one or more post-administration samples from the subject; (iv) detecting the level and/or activity of the biomarker polypeptide in the post-administration samples; (v) comparing the biomarker polypeptide level and/or activity in the pre-administration sample with the biomarker polypeptide level and/or activity in the post administration sample or samples; and (vi) altering the administration of the agent to the subject accordingly. Biomarker polypeptide analysis, such as by immunohistochemistry (IHC), may also be used to select patients who will receive therapy, such as immunotherapy.

The skilled artisan will also appreciate that, in certain embodiments, the methods encompassed by the present invention implement a computer program and computer system. For example, a computer program may be used to perform the algorithms described herein. A computer system may also store and manipulate data generated by the methods encompassed by the present invention which comprises a plurality of biomarker signal changes/profiles which may be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part encompassed by the present invention. Numerous types of computer systems may be used to implement the analytic methods of this invention according to knowledge possessed by a skilled artisan in the bioinformatics and/or computer arts. Several software components may be loaded into memory during operation of such a computer system. The software components may comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods encompassed by the present invention may also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles may be accessed and used to perform comparisons of interest at a later point in time. For example, biomarker expression profiles of a sample derived from the non-cancerous tissue of a subject and/or profiles generated from population-based distributions of informative loci of interest in relevant populations of the same species may be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

Furthermore, the prognostic assays described herein may be used to determine whether a subject may be administered an agent (e.g., an agonist, antagonist, peptidomimetic, polypeptide, peptide, nucleic acid, small molecule, or other drug candidate) to treat a disease or disorder associated with the aberrant biomarker expression or activity.

6. Clinical Efficacy

Clinical efficacy may be measured by any method known in the art. For example, the response to a cancer therapy (e.g., at least one modulator of biomarkers listed in Table 1), relates to any response of the cancer, e.g., a tumor, to the therapy, preferably to a change in the number of cancer cells, tumor mass, and/or tumor volume, such as after initiation of neoadjuvant or adjuvant chemotherapy. Tumor response may be assessed in a neoadjuvant or adjuvant situation where the size of a tumor after systemic intervention may be compared to the initial size and dimensions as measured by CT, PET, mammogram, ultrasound or palpation and the cellularity of a tumor may be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol*. (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular modulator of biomarkers listed in Table 1 therapeutic regimen is at least 25%, 30%, 35%, 40%, 45%, 50%, 55%, 60%, 65%, 70%, 75%, 80%, 85%, or more.

Additional criteria for evaluating the response to cancer therapy (e.g., e.g., at least one modulator of biomarkers listed in Table 1) are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment may be expanded to include response to chemotherapy, probability of survival, probability of metastasis within a given time period, and probability of tumor recurrence.

For example, in order to determine appropriate threshold values, a particular modulator of one or more biomarkers (e.g., targets listed in Table 1) may be administered to a population of subjects and the outcome may be correlated to biomarker measurements that were determined prior to administration of any cancer therapy (e.g., e.g., at least one modulator of biomarkers listed in Table 1). The outcome measurement may be pathologic response to therapy given in the neoadjuvant setting. Alternatively, outcome measures, such as overall survival and disease-free survival may be monitored over a period of time for subjects following cancer therapy (e.g., at least one modulator of biomarkers listed in Table 1) for whom biomarker measurement values are known. In certain embodiments, the same doses of the agent modulating at least one biomarkers listed in Table 1 are administered to each subject. In related embodiments, the doses administered are standard doses known in the art for the agent modulating at least one biomarker encompassed by the present invention (e.g., one or more targets listed in Table 1). The period of time for which subjects are monitored may vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an cancer therapy (e.g., at least one modulator of biomarkers listed in Table 1) may be determined using methods such as those described in the Examples section.

7. Analyzing Biomarkers a. Sample Collection and Preparation

In some embodiments, biomarker amount and/or activity measurement(s) in a sample from a subject is compared to a pre-determined control (standard) sample. The sample from the subject is typically from a diseased tissue, such as cancer cells or tissues. The control sample may be from the same subject or from a different subject. The control sample is typically a normal, non-diseased sample. However, in some embodiments, such as for staging of disease or for evaluating the efficacy of treatment, the control sample may be from a diseased tissue. The control sample may be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment, evaluate a response to cancer therapy (e.g., at least one modulator of one or more biomarkers listed in Table 1), and/or evaluate a response to a combination cancer therapy (e.g., at least one modulator of one or more biomarkers listed in Table 1 in combination of at least one immunotherapy). A pre-determined biomarker amount and/or activity measurement(s) may be determined in populations of patients with or without cancer. The pre-determined biomarker amount and/or activity measurement(s) may be a single number, equally applicable to every patient, or the pre-determined biomarker amount and/or activity measurement(s) may vary according to specific subpopulations of patients. Age, weight, height, and other factors of a subject may affect the pre-determined biomarker amount and/or activity measurement(s) of the individual. Furthermore, the pre-determined biomarker amount and/or activity may be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis may be based on the ratio of pre-treatment biomarker measurement as compared to post-treatment biomarker measurement. Pre-treatment biomarker measurement may be made at any time prior to initiation of cancer therapy. Post-treatment biomarker measurement may be made at any time after initiation of cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of cancer therapy, and even longer toward indefinitely for continued monitoring. Treatment may comprise cancer therapy, such as a therapeutic regimen comprising one or more modulators of at least one target listed in Table 1, either alone or in combination with other cancer agents, such as immune checkpoint inhibitors.

The pre-determined biomarker amount and/or activity measurement(s) may be any suitable standard. For example, the pre-determined biomarker amount and/or activity measurement(s) may be obtained from the same or a different human for whom a patient selection is being assessed. In one embodiment, the pre-determined biomarker amount and/or activity measurement(s) may be obtained from a previous assessment of the same patient. In such a manner, the progress of the selection of the patient may be monitored over time. In addition, the control may be obtained from an assessment of another human or multiple humans, e.g., selected groups of humans, if the subject is a human. In such a manner, the extent of the selection of the human for whom selection is being assessed may be compared to suitable other humans, e.g., other humans who are in a similar situation to the human of interest, such as those suffering from similar or the same condition(s) and/or of the same ethnic group.

In some embodiments encompassed by the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cut-off values apply equally when the measurement is based on relative changes, such as based on the ratio of pre-treatment biomarker measurement as compared to post-treatment biomarker measurement.

Biological samples may be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit, and the like). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples may be collected from individuals repeatedly over a longitudinal period of time (e.g., once or more on the order of days, weeks, months, annually, biannually, etc.). Obtaining numerous samples from an individual over a period of time may be used to verify results from earlier detections and/or to identify an alteration in biological pattern as a result of, for example, disease progression, drug treatment, etc. For example, subject samples may be taken and monitored every month, every two months, or combinations of one, two, or three month intervals according to the present invention. In addition, the biomarker amount and/or activity measurements of the subject obtained over time may be conveniently compared with each other, as well as with those of normal controls during the monitoring period, thereby providing the subject's own values, as an internal, or personal, control for long-term monitoring.

Samples may contain live cells/tissue, fresh frozen cells, fresh tissue, biopsies, fixed cells/tissue, cells/tissue embedded in a medium, such as paraffin, histological slides, or any combination thereof.

Sample preparation and separation may involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation may also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample may be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermeable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which may be used to separate ionic molecules under the influence of an electric field. Electrophoresis may be conducted in a gel, capillary, or in a microchannel on a chip. Examples of gels used for electrophoresis include starch, acrylamide, polyethylene oxides, agarose, or combinations thereof. A gel may be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology may also be implemented on microfluidic chips. Depending on the types of capillary and buffers used, CE may be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography may be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

b. Analyzing Biomarker Polypeptides

The activity or level of a biomarker protein may be detected and/or quantified by detecting or quantifying the expressed polypeptide, such as by using antibodies, or antigen-binding fragments thereof, described herein. The polypeptide may be detected and quantified by any of a number of means well-known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to a modulator of T cell mediated cytotoxicity alone or in combination with an immunotherapy treatment. Any method known in the art for detecting polypeptides may be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Ten, eds., Appleton and Lange, Norwalk, Conn. pp 217-262, 1991). Preferred are binder-ligand immunoassay methods including reacting antibodies with an epitope or epitopes and competitively displacing a labeled polypeptide or derivative thereof.

In some embodiments, antibodies and antigen-binding fragments thereof described herein, may be used in any one of well-known immunoassay forms, including, without limitation, a radioimmunoassay, a Western blot assay, an immunofluorescence assay, an enzyme immunoassay, an immunoprecipitation assay, a chemiluminescence assay, an immunohistochemical assay, a dot blot assay, or a slot blot assay. General techniques to be used in performing the various immunoassays noted above and other variations of the techniques, such as in situ proximity ligation assay (PLA), fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA), ELISA, etc. alone or in combination or alternatively with NMR, MALDI-TOF, LC-MS/MS, are known to those of ordinary skill in the art.

Such reagents may also be used to monitor protein levels in a cell or tissue, e.g., white blood cells or lymphocytes, as part of a clinical testing procedure, e.g., in order to monitor an optimal dosage of an inhibitory agent. Detection may be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

For example, ELISA and RIA procedures may be conducted such that a desired biomarker protein standard is labeled (with a radioisotope such as $^{125}$I or $^{35}$S, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et al. (1979) *Proc. Nat. Acad. Sci. U.S.A.* 76:4350), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabeling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment may then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$ M, $10^{-7}$ M, $10^{-8}$ M, $10^{-9}$ M, $10^{-10}$ M, $10^{-11}$ M, or $10^{-12}$ M. The phrase "specifically binds" refers to binding of, for example, an antibody to an epitope or antigen or antigenic determinant in such a manner that binding may be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

In some embodiments, agents that specifically bind to a biomarker protein other than antibodies are used, such as peptides. Peptides that specifically bind to a biomarker protein may be identified by any means known in the art. For example, specific peptide binders of a biomarker protein may be screened for using peptide phage display libraries.

VII. Compositions, Including Formulations and Pharmaceutical Compositions

Compositions comprising agents encompassed by the present invention, such as antibodies, antigen-binding fragments thereof, cells, and the like, are contemplated without limitation. For example, agents may be used alone or in combination with other agents, such as nucleic acid-based compositions (e.g., messenger RNA (mRNA), cDNA, siRNA, antisense nucleic acids, oligonucleotides, ribozymes, DNAzymes, aptamers, nucleic acid decoys, nucleic acid chimeras, triple helical structures, etc.), protein-based compositions, cell-based compositions, as well as variants, modifications, and engineered versions thereof, are contemplated for use in the methods described herein as well as compositions per se. In some embodiments, siRNA molecules having a sense stranded nucleic acid sequence and an antisense strand nucleic acid sequence, each selected from sequences described herein, as well as sequence variant and/or chemically modified versions thereof, are encompassed by the present invention and are described in detail above. In some embodiments, cells modified as described herein, such as myeloid cells, such as suppressive myeloid cells, monocytes, macrophages, and/or dendritic cells, having a modulated inflammatory phenotype.

Such compositions may be comprised within pharmaceutical compositions and/or formulations. Such compositions may be prepared by any method known or hereafter developed in the art of pharmacology. In general, such preparatory methods include the step of bringing the agent, such as an active ingredient, into association with an excipient and/or one or more other accessory ingredients, and then, if necessary and/or desirable, dividing, shaping and/or packaging the product into a desired single- or multi-dose unit. As used herein, the term "active ingredient" refers to any chemical and biological substance that has a physiological effect in human or in animals, when exposed to it. In the context encompassed by the present invention, the active ingredient in the formulations may be any of the agents that modulate a biomarker encompassed by the present invention (e.g., at least one target listed in Table 1).

1. Composition Preparation

A composition in accordance with the invention may be prepared, packaged, and/or sold in bulk, as a single unit dose, and/or as a plurality of single unit doses. As used herein, a "unit dose" is discrete amount of the pharmaceutical composition comprising a pre-determined amount of the active ingredient. The amount of the active ingredient is generally equal to the dosage of the active ingredient which would be administered to a subject and/or a convenient fraction of such a dosage such as, for example, one-half or one-third of such a dosage.

The term "pharmaceutically acceptable" refers to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutical compositions encompassed by the present invention may be presented as anhydrous pharmaceutical formulations and dosage forms, liquid pharmaceutical formulations, solid pharmaceutical formulations, vaccines, and the like. Suitable liquid preparations may include, but are not limited to, isotonic aqueous solutions, suspensions, emulsions, or viscous compositions that are buffered to a selected pH.

As described in detail below, the agents and other compositions encompassed by the present invention may be specially formulated for administration in solid or liquid form, including those adapted for various routes of administration, such as (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound. Any appropriate form factor for an agent or composition described herein, such as, but not limited to, tablets, capsules, liquid syrups, soft gels, suppositories, and enemas, is contemplated.

Pharmaceutical compositions encompassed by the present invention may be presented as discrete dosage forms, such as capsules, sachets, or tablets, or liquids or aerosol sprays each containing a pre-determined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms may be prepared by any of the methods of pharmacy.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which may be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which may be used include polymeric substances and waxes. The active ingredient may also be in micro-encapsulated form, if appropriate, with one or more excipients.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions may also include adjuvants such as wetting agents, emulsifying and suspending agents, sweetening, flavoring, coloring, perfuming and preservative agents. Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to an agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Agent may be administered by aerosol. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which may result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of an agent to the body. Such dosage forms may be made by dissolving or dispersing the agent in the proper medium. Absorption enhancers may also be used to increase the flux of the peptidomimetic across the skin. The rate of such flux may be controlled by either providing a rate controlling membrane or dispersing the peptidomimetic in a polymer matrix or gel.

Ophthalmic formulations, eye ointments, powders, solutions and the like, are also contemplated as being within the scope of this invention.

In some embodiments, pharmaceutical compositions encompassed by the present invention are formulated in parenteral dosage forms. The parenteral formulations may be aqueous solutions containing carriers or excipients such as salts, carbohydrates and buffering agents (e.g., at a pH of from 3 to 9), or sterile non-aqueous solutions, or dried forms which may be used in conjunction with a suitable vehicle such as sterile, pyrogen-free water. For example, an aqueous solution of the therapeutic agents encompassed by the present invention comprises an isotonic saline, 5% glucose or other pharmaceutically acceptable liquid carriers such as liquid alcohols, glycols, esters, and amides, for example, as disclosed in U.S. Pat. No. 7,910,594. In another example, an aqueous solution of the therapeutic agents encompassed by the present invention comprises a phosphate buffered formulation (pH 7.4) for intravenous administration as disclosed in PCT Publ. No. WO 2011/014821. The parenteral dosage form may be in the form of a reconstitutable lyophilizate comprising the dose of the therapeutic agents encompassed by the present invention. Any prolonged release dosage forms known in the art may be utilized such as, for example, the biodegradable carbohydrate matrices described in U.S. Pat. Nos. 4,713,249; 5,266,333; and 5,417,982, or, alternatively, a slow pump (e.g., an osmotic pump) may be used. The preparation of parenteral formulations under sterile conditions, for example, by lyophilization under sterile conditions, may readily be accomplished using standard pharmaceutical techniques well-known to those skilled in the art. The solubility of a therapeutic agent encompassed by the present invention used in the preparation of a parenteral formulation may be increased by the use of appropriate formulation techniques, such as the incorporation of solubility-enhancing agents. Formulations for parenteral administration may comprise one or more agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release may be controlled. Examples of other biodegradable polymers include poly(orthoesters) and poly(anhydrides). Depot injectable formulations are also prepared by entrapping the drug in liposomes or microemulsions, which are compatible with body tissue.

When the agents encompassed by the present invention are administered as pharmaceuticals, to humans and animals, they may be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods encompassed by the present invention so as to obtain an amount of the active ingredient, which is effective to achieve the desired therapeutic response for a particular subject, composition, and mode of administration, without being toxic to the subject.

In some embodiments, pharmaceutical compositions encompassed by the present invention may be formulated for controlled release and/or targeted delivery. As used herein, "controlled release" refers to a pharmaceutical composition or compound release profile that conforms to a particular pattern of release to effect a therapeutic outcome. In one embodiment, the compositions encompassed by the present invention may be encapsulated into a delivery agent described herein and/or known in the art for controlled release and/or targeted delivery. As used herein, the term "encapsulate" means to enclose, surround or encase. As it relates to the formulation encompassed by the present invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of a therapeutic agent encompassed by the present invention may be enclosed, surrounded or encased within the particle. The term "partially encapsulation" means that less than 10, 10, 20, 30, 40 50 or less of the conjugate encompassed by the present invention may be enclosed, surrounded or encased within the particle. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound encompassed by the present invention are encapsulated in the formulation.

In some embodiments, such formulations may also be constructed or compositions altered such that they passively or actively are directed to different cell types in vivo, including but not limited to monocytes, macrophages, and other immune cells (e.g., dendritic cells, antigen presenting cells, T lymphocytes, B lymphocytes, and natural killer cells), cancer cells and the like. Formulations may also be selectively targeted through expression of different ligands on their surface as exemplified by, but not limited by, folate, transferrin, N-acetylgalactosamine (GalNAc), and antibody targeted approaches.

2. Additional Components

The pharmaceutical compositions encompassed by the present invention may be formulated using one or more excipients to: (1) increase stability; (2) permit the sustained or delayed release (e.g., from a depot formulation); (3) alter the biodistribution (e.g., target an agent to a specific tissue or cell type); (4) alter the release profile of the agent in vivo. Non-limiting examples of the excipients include any and all solvents, dispersion media, diluents, or other liquid vehicles, dispersion or suspension aids, surface active agents, isotonic agents, thickening or emulsifying agents, and preservatives. Excipients encompassed by the present invention may also include, without limitation, lipidoids, liposomes, lipid nanoparticles, polymers, lipoplexes, core-shell nanoparticles, peptides, proteins, hyaluronidase, nanoparticle mimics and combinations thereof.

The term "pharmaceutically acceptable carrier" or "pharmaceutically acceptable excipient" is intended to include any and all solvents, dispersion media, diluents or other liquid vehicles, dispersion or suspension agents, surface active agents, isotonic agents, thickening or emulsifying agents, disintegrating agents, preservatives, buffering agents, solid binders, lubricants, oils, coatings, antibacterial and antifungal agents, absorption delaying agents, and the like, as suited to the particular dosage form desired. Remington's The Science and Practice of Pharmacy, 21st Edition, A. R. Gennaro (Lippincott, Williams & Wilkins, Baltimore, M D, 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention. Supplementary active ingredients may also be incorporated into the described compositions.

In some embodiments, a pharmaceutically acceptable excipient is at least 95%, at least 96%, at least 97%, at least 98%, at least 99%, at least 99.5%, or at least 99.9% or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and VEEGUM® [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate [TWEEN® 20], polyoxyethylene sorbitan [TWEENn® 60], polyoxyethylene sorbitan monooleate [TWEEN® 80], sorbitan monopalmitate [SPAN® 40], sorbitan monostearate [SPAN® 60], sorbitan tristearate [SPAN® 65], glyceryl monooleate, sorbitan monooleate [SPAN® 80]), polyoxyethylene esters (e.g., polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g., CREMOPHOR®), polyoxyethylene ethers, (e.g., polyoxyethylene lauryl ether [BRIJ®30]), poly (vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC® F 68, POLOXAMER® 188, cetrimonium bromide, cetylpyridinium chloride, benzalkonium chloride, docusate sodium, etc. and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol,); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN® II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents may be present in the composition, according to the judgment of the formulator.

Pharmaceutical formulations may also comprise pharmaceutically acceptable salts. The term "pharmaceutically acceptable salt" refers to salts derived from a variety of organic and inorganic counter ions known in the art (see, e.g., Berge et al. (1977) *J. Pharm. Sci.* 66:1-19). These salts may be prepared in situ during the final isolation and purification of the agents, or by separately reacting a purified agent in its free base form with a suitable organic or inorganic acid, and isolating the salt thus formed. Pharmaceutically acceptable acid addition salts may be formed with inorganic acids and organic acids. Inorganic acids from which salts may be derived include, for example, hydrochloric acid, hydrobromic acid, sulfuric acid, nitric acid and phosphoric acid. Organic acids from which salts may be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts may be formed with inorganic and organic bases. Inorganic bases from which salts may be derived include, for example, sodium, potassium, lithium, ammonium, calcium, magnesium, iron, zinc, copper, manganese and aluminum. Organic bases from which salts may be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In some embodiments, agents encompassed by the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression. These salts may likewise be prepared in situ during the final isolation and purification of the agents, or by separately reacting the purified agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

The term "co-crystal" refers to a molecular complex derived from a number of co-crystal formers known in the art. Unlike a salt, a co-crystal typically does not involve hydrogen transfer between the co-crystal and the drug, and instead involves intermolecular interactions, such as hydrogen bonding, aromatic ring stacking, or dispersive forces, between the co-crystal former and the drug in the crystal structure.

Exemplary surfactants which may be used to form pharmaceutical compositions and dosage forms encompassed by the present invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed. Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof. Ionic surfactants may include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants may include, but are not limited to, fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

Solubilizers may be included in the present formulations to ensure good solubilization and/or dissolution of the agent (e.g., a chemical compound) encompassed by the present invention and to minimize precipitation of the drug modality encompassed by the present invention. This may be especially important for compositions for non-oral use, such as compositions for injection. A solubilizer may also be added to increase the solubility of the hydrophilic drug and/or other components, such as surfactants, or to maintain the composition as a stable or homogeneous solution or dispersion. Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ڗ-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, epsilon-caprolactone and isomers thereof, j-valerolactone and isomers thereof, û-butyrolactone and isomers thereof and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

Pharmaceutically acceptable additives may be included in a formulation as needed. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate may also be used. When the base is a salt, the cation may be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

IX. Administration and Dosing

Agents (e.g., compositions, formulations, cells, etc.) described herein may contact desired objects (e.g., cells, cell-free binding partners, and the like) and/or be administered to organisms using well-known methods in the art. For example, agents may be delivered into cells via chemical methods, such as cationic liposomes and polymers, or physical methods, such as gene gun, electroporation, particle bombardment, ultrasound utilization, and magnetofection.

Methods of administration to contact macrophages are well-known in the art, particularly because macrophages are generally present across tissue types (see Ries et al. (2014) *Cancer Cell* 25:846-859; Perry et al. (2018) *J. Exp. Med.* 215:877-893; Novobrantseva et al. (2012) *Mol. Ther. Nucl. Acids* 1:e4; Majmudar et al. (2013) *Circulation* 127:2038-2046; Leuschner et al. (2011) *Nat. Biotechnol.* 29:11) In addition, administration methods may be tailored to target macrophage populations of interest, such as by using local administration of agents to target spatially restricted populations of macrophages (e.g., intratumoral administration to target TAMs) (see Shirota et al. (2012) *J. Immunol.* 188:1592-1599; Wang et al. (October 2016) *Proc. Natl. Acad. Sci. U.S.A.* 113:11525-11530). Such differential administration methods may selectively target macrophage populations of interest while reducing or eliminating contact with other macrophage populations (e.g., intratumoral administration to target TAMs selectively from circulating macrophages).

Agents may also be administered in an effective amount by any route that results in therapeutically effective outcomes. The administration routes may include, but are not limited to, enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal.

Agents are typically formulated in dosage unit form for ease of administration and uniformity of dosage. It will be understood, however, that the total daily usage of the agents encompassed by the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific agent employed; the specific composition employed; the age, body weight, general health, sex and diet of the patient; the time of administration, route of administration, and rate of excretion of the specific agent employed; the duration of the treatment; drugs used in combination or coincidental with the specific compound employed; and like factors well-known in the medical arts.

In some embodiments, agents in accordance with the present invention may be administered at dosage levels sufficient to deliver from about 0.0001 mg/kg to about 1000 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, or from about 10 mg/kg to about 100 mg/kg, or from about 100 mg/kg to about 500 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks, or every two months. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used.

In some embodiments, an agent encompassed by the present invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody may include a single treatment or, preferably, may include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

As used herein, a "split dose" is the division of single unit dose or total daily dose into two or more doses, e.g., two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in 24 hour period. It may be administered as a single unit dose.

In some embodiments, the dosage forms may be liquid dosage forms. Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art including, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, compositions may be mixed with solubilizing agents such as CREMOPHOR®, alcohols, oils, modified oils, glycols, polysorbates, cyclodextrins, polymers, and/or combinations thereof.

In certain embodiments, the dosages forms may be injectable. Injectable preparations, for example, sterile injectable aqueous or oleaginous suspensions may be formulated according to the known art and may include suitable dispersing agents, wetting agents, and/or suspending agents. Sterile injectable preparations may be sterile injectable solutions, suspensions, and/or emulsions in nontoxic parenterally acceptable diluents and/or solvents, for example, a solution in 1,3-butanediol. Among the acceptable vehicles and solvents that may be employed include, but are not limited to, water, Ringer's solution, U.S.P., and isotonic sodium chloride solution. Sterile, fixed oils are conventionally employed as a solvent or suspending medium. For this purpose any bland fixed oil may be employed including synthetic mono- or diglycerides. Fatty acids, such as oleic acid, may be used in the preparation of injectables. Injectable formulations may be sterilized, for example, by filtration through a bacterial-retaining filter, and/or by incorporating sterilizing agents in the form of sterile solid compositions which may be dissolved or dispersed in sterile water or other sterile injectable medium prior to use.

In some embodiments, solid dosage forms of tablets, dragees, capsules, pills, and granules may be prepared with coatings and shells such as enteric coatings and other coatings well-known in the pharmaceutical formulating art. They may optionally comprise opacifying agents and may be of a composition that they release the active ingredient(s) only, or preferentially, in a certain part of the intestinal tract, optionally, in a delayed manner. Examples of embedding compositions which may be used include polymeric substances and waxes. Solid compositions of a similar type may be employed as fillers in soft and hard-filled gelatin capsules using such excipients as lactose or milk sugar as well as high molecular weight polyethylene glycols and the like.

Cells may be administered at $0.1\times10^6$, $0.2\times10^6$, $0.3\times10^6$, $0.4\times10^6$, $0.5\times10^6$, $0.6\times10^6$, $0.7\times10^6$, $0.8\times10^6$, $0.9\times10^6$, $1.0\times10^6$, $5.0\times10^6$, $1.0\times10^7$, $5.0\times10^7$, $1.0\times10^8$, $5.0\times10^8$, or more, or any range in between or any value in between, cells per kilogram of subject body weight. The number of cells transplanted may be adjusted based on the desired level of engraftment in a given amount of time. Generally, $1\times10^5$ to about $1\times10^9$ cells/kg of body weight, from about $1\times10^6$ to about $1\times10^8$ cells/kg of body weight, or about $1\times10^7$ cells/kg of body weight, or more cells, as necessary, may be transplanted. In some embodiment, transplantation of at least about $0.1\times10^6$, $0.5\times10^6$, $1.0\times10^6$, $2.0\times10^6$, $3.0\times10^6$, $4.0\times10^6$, or $5.0\times10^6$ total cells relative to an average size mouse is effective.

Cells may be administered in any suitable route as described herein, such as by infusion. Cells may also be administered before, concurrently with, or after, other anti-cancer agents.

Administration may be accomplished using methods generally known in the art. Agents, including cells, may be introduced to the desired site by direct injection, or by any other means used in the art including, but are not limited to, intravascular, intracerebral, parenteral, intraperitoneal, intravenous, epidural, intraspinal, intrasternal, intra-articular, intra-synovial, intrathecal, intra-arterial, intracardiac, or intramuscular administration. For example, subjects of interest may be engrafted with the transplanted cells by various routes. Such routes include, but are not limited to, intravenous administration, subcutaneous administration, administration to a specific tissue (e.g., focal transplantation), injection into the femur bone marrow cavity, injection into the spleen, administration under the renal capsule of fetal liver, and the like. In certain embodiment, the cancer vaccine encompassed by the present invention is injected to the subject intratumorally or subcutaneously. Cells may be administered in one infusion, or through successive infusions over a defined time period sufficient to generate a desired effect. Exemplary methods for transplantation, engraftment assessment, and marker phenotyping analysis of transplanted cells are well-known in the art (see, for example, Pearson et al. (2008) *Curr. Protoc. Immunol.* 81:15.21.1-15.21.21; Ito et al. (2002) *Blood* 100:3175-3182; Traggiai et al. (2004) *Science* 304:104-107; Ishikawa et al. *Blood* (2005) 106:1565-1573; Shultz et al. (2005) *J. Immunol.* 174:6477-6489; and Holyoake et al. (1999) *Exp. Hematol.* 27:1418-1427).

Two or more cell types may be combined and administered, such as cell-based therapy and adoptive cell transfer of stem cells, cancer vaccines and cell-based therapy, and the like. For example, adoptive cell-based immunotherapies may be combined with the cell-based therapies encompassed by the present invention. In some embodiments, the cell-based agents may be used alone or in combination with additional cell-based agents, such as immunotherapies like adoptive T cell therapy (ACT). For example, T cells genetically engineered to recognize CD19 used to treat follicular B cell lymphoma. Immune cells for ACT may be dendritic cells, T cells such as $CD^{8+}$ T cells and $CD^{4+}$ T cells, natural killer (NK) cells, NK T cells, cytotoxic T lymphocytes (CTLs), tumor infiltrating lymphocytes (TILs), lymphokine activated killer (LAK) cells, memory T cells, regulatory T cells (Tregs), helper T cells, cytokine-induced killer (CIK) cells, and any combination thereof. Well-known adoptive cell-based immunotherapeutic modalities, including, without limitation, irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies may be further modified to express one or more gene products to further modulate immune responses, such as expressing cytokines like GM-CSF, and/or to express tumor-associated antigen (TAA) antigens, such as Mage-1, gp-100, and the like. The ratio of an agent encompassed by the present invention, such as cancer cells, to another agent encompassed by the present invention or other composition may be 1:1 relative to each other (e.g., equal amounts of 2 agents, 3 agents, 4 agents, etc.), but may modulated in any amount desired (e.g., 1:1, 1.1:1, 1.2:1, 1.3:1, 1.4:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, or greater).

Engraftment of transplanted cells may be assessed by any of various methods, such as, but not limited to, tumor volume, cytokine levels, time of administration, flow cytometric analysis of cells of interest obtained from the subject at one or more time points following transplantation, and the like. For example, a time-based analysis of waiting 1, 2, 3, 4, 5, 6, 7, 8, 9, 10, 11, 12, 13, 14, 15, 16, 17, 18, 19, 20, 21, 22, 23, 24, 25, 26, 27, 28 days or may signal the time for tumor harvesting. Any such metrics are variables that may be adjusted according to well-known parameters in order to determine the effect of the variable on a response to anti-cancer immunotherapy. In addition, the transplanted cells may be co-transplanted with other agents, such as cytokines, extracellular matrices, cell culture supports, and the like.

X. Kits and Devices

The present invention also encompasses kits for detecting and/or modulating biomarkers described herein. A "kit" is any manufacture (e.g. a package or container) comprising at least one reagent, e.g. an antibody or antigen-binding fragment thereof, for specifically detecting and/or affecting the expression of a marker encompassed by the present invention. The kit may be promoted, distributed, or sold as a unit for performing the methods encompassed by the present invention. The kit may comprise one or more reagents necessary to detect, express, screen, and the like one or more agents useful in the methods encompassed by the present invention. For example, combinations of agents useful for detecting biomarkers encompassed by the present invention (e.g., targets listed in Table 1) may be provided in a kit to detect the biomarkers and modulation thereof, which is useful for identifying myeloid cell inflammatory phenotype, immune response, anti-cancer function, sensitivity to immune checkpoint therapy, and the like. Such combinations may include one or more agents to detect 1, 2, 3, 4, 5, 6, 7, 8, 9, 10, or more biomarkers inclusive, such as up to and including all of the biomarkers encompassed by the present invention.

In some embodiments, the kit may further comprise a reference standard, e.g., a nucleic acid encoding a protein that does not affect or regulate signaling pathways controlling cell growth, division, migration, survival or apoptosis. One skilled in the art may envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit may be included. A kit encompassed by the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

In still other embodiments, compositions encompassed by the present invention, such as antibodies and antigen-binding fragments thereof, may be associated with a component or device, such as for use in diagnostic applications. Non-limiting examples include antibodies immobilized on solid surfaces for use in these assays (e.g., linked and/or conjugated to a detectable label based on light or radiation emission as described above). In other embodiments, the antibodies are associated with a device or strip for detection of a biomarker of interest by use of an immunochromatographic or immunochemical assay, such as in a "sandwich"

or competitive assay, immunohistochemistry, immunofluorescence microscopy, and the like. Additional examples of such devices or strips are those designed for home testing or rapid point of care testing. Further examples include those that are designed for the simultaneous analysis of multiple analytes in a single sample. For example, an unlabeled antibody of the invention may be applied to "capture" biomarker polypeptides in a biological sample and the captured (or immobilized) biomarker polypeptides may be bound to a labeled form of an anti-biomarker antibody of the invention for detection. Other standard embodiments of immunoassays are well-known the skilled artisan, including assays based on, for example, immunodiffusion, immunoelectrophoresis, immunohistopathology, immunohistochemistry, and histopathology.

Other embodiments encompassed by the present invention are described in the following Examples. The present invention is further illustrated by the following examples which should not be construed as further limiting.

EXAMPLES

Figure 1B:

Example 1: VSIG4 is Expressed Dominantly on Suppressive Macrophage Subsets and not on Circulating Monocytes or T Cells VSIG4 is predominantly expressed on tumor-associated myeloid populations (TAMs; FIG. 1A) and, within those TAMs, VSIG4 has the highest density of expression on tumor-associated M2-like and M0-like suppressive populations (FIG. 1B) (see Zillionis et al. (2019) *Immunity* 50:1317-1334 providing single cell RNA sequencing data such as from seven non-small cell lung cancer patients). In order to characterize the expression of VSIG4 on populations of peripheral immune cells, live single cells obtained from PBMC populations were analyzed for VSIG4 protein expression at the cell surface using flow cytometry. For flow cytometry, cells were collected and resuspended in 50 ul FACS buffer (PBS with 2.5% FBS and 0.5% sodium azide) and blocked for 15 minutes with TruStain FcX™ (Biolegend Cat. No. 422302) on ice. Antibodies were diluted in FACS buffer according to the manufacturer's instructions and added to cells for 15 minutes on ice. Labeled cells were washed twice with FACS buffer and fixed with PBS plus 2% paraformaldehyde for flow cytometry analysis on an Attune™ flow cytometer (ThermoFisher). Data were analyzed via FlowJo software. Reagent antibodies used as controls and/or in flow cytometry are shown in Table 3 below.

TABLE 3

| Reagent/flow antibodies | | |
|---|---|---|
| Antigen | Clone | Source |
| CD163 | 215927 | RnD Systems |
| CD16 | 3a8 | BioLegend |
| CD206 | 15-2 | BioLegend |
| SIGLEC-9 | 191240 | RnD Systems |
| VSIG4 | Jav4 | eBioscience |
| CD45 | 2D1 | BioLegend |
| CD3 | OKT3 | BioLegend |
| CD4 | A161A1 | BioLegend |
| CD19 | HIB19 | BioLegend |
| CD11b | ICRF44 | BioLegend |
| CD8a | RPA-T8 | BioLegend |
| CD14 | M5E2 | BioLegend |
| CD56 | 5.1H11 | BioLegend |

TABLE 3-continued

| Reagent/flow antibodies | | |
|---|---|---|
| Antigen | Clone | Source |
| PD-1 | KEYTRUDA ® | Merck |
| VSIG4 | 14C05 (vH) | Described herein as a representive anti-VSIG4 antibody |
| VSIG4 | 14C05 (vL kappa) | Described herein as a representative anti-VSIG4 antibody |
| LILRB2 | 1E1 (heavy chain) | US Pat. Publ. 2018-0298096 (SEQ ID NO: 57) formatted with human IgG4 (S228P) heavy chain (see Table 6 below) |
| LILRB2 | 1E1 (light chain) | US Pat. Publ. 2018-0298096 (SEQ ID NO: 58) formatted with human Vlambda light chain (see Table 6 below) |

Figure 1C:
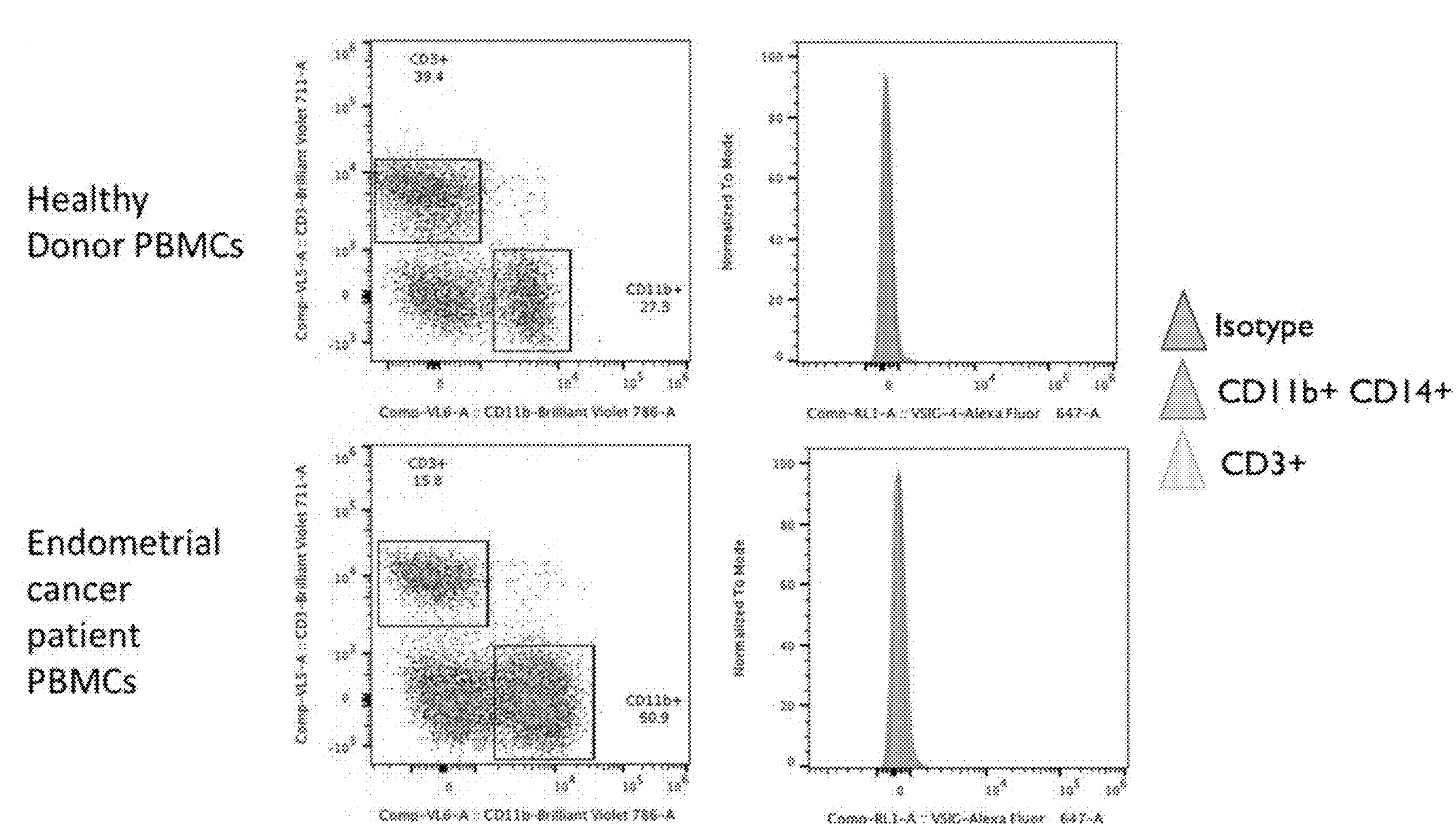

FIG. 1C shows that VSIG4 expression is absent on all peripheral immune cells of healthy donors. The presence of VSIG4 expression on the peripheral immune cells of cancer patients was analyzed. Just like the healthy donors, no VSIG4 expression was detected on the peripheral immune cells.

To better understand the expression patterns of VSIG4, in vitro derived macrophages were generated and analyzed for the surface expression of VSIG4. To generate macrophages in vitro, monocytes were isolated from fresh whole blood of healthy donors by Ficoll separation with RosetteSep™ Human Monocyte Enrichment Cocktail (Stemcell Technologies, Vancouver, Canada) according to manufacturer's instructions. Isolated monocytes were arrayed in 24-well plates overnight in Iscove's Modified Dulbecco's Medium (IMDM) containing 10% fetal bovine serum (FBS) and non-adherent cells were washed off after 24 hours. Monocytes were differentiated into macrophages by culturing for 6 days in IMDM 10% FBS plus 50 ng/ml human M-CSF for M2 macrophages, or 50 ng/ml GM-CSF (Biolegend, San Diego, CA) for M1 macrophages. siRNA lipid nanoparticles were formulated with a VSIG4-specific siRNA (sense: cguGAGAGAuAAGauuAcudTsdT (SEQ ID NO: 99); anti-sense: AGuAAUCUuAUCUCUcACGdTsdT (SEQ ID NO: 100)). siRNAs were synthesized by AXO Labs (Kulmbach, Germany). C12-200 lipid nanoparticles (LNPs) were formulated as described in Novobrantseva et al. (2012) *Mol. Ther. Nucl. Acids* 1:34. Briefly, an ethanolic phase containing the ionizable lipid C12-200 (described in Love et al. (2010) *Proc. Natl. Acad. Sci. U.S.A.* 107:1864-1869; AXO Labs, GmbH, Kulmbach, Germany), distearoyl-sn-glycero-3-phosphocholine (DSPC, Avanti Polar Lipids, Alabaster AL), cholesterol (MP Biomedicals, Santa Ana CA), and DMPE-PEG2000 (1,2-dimyristoyl-sn-glycero-3-phosphoethanolamine-N4methoxy(polyethylene glycol)-20001, Avanti) at a molar ratio of 50:10:38.5:1.5 were mixed together with an aqueous phase of siRNA in 10 mM citrate buffer via microfluidic mixing. The ethanol:aqueous volume ratio was 1:3, and the total lipid:siRNA weight ratio was approximately 9:1. The resulting LNPs were dialyzed against 1×PBS overnight.

Figure 2:
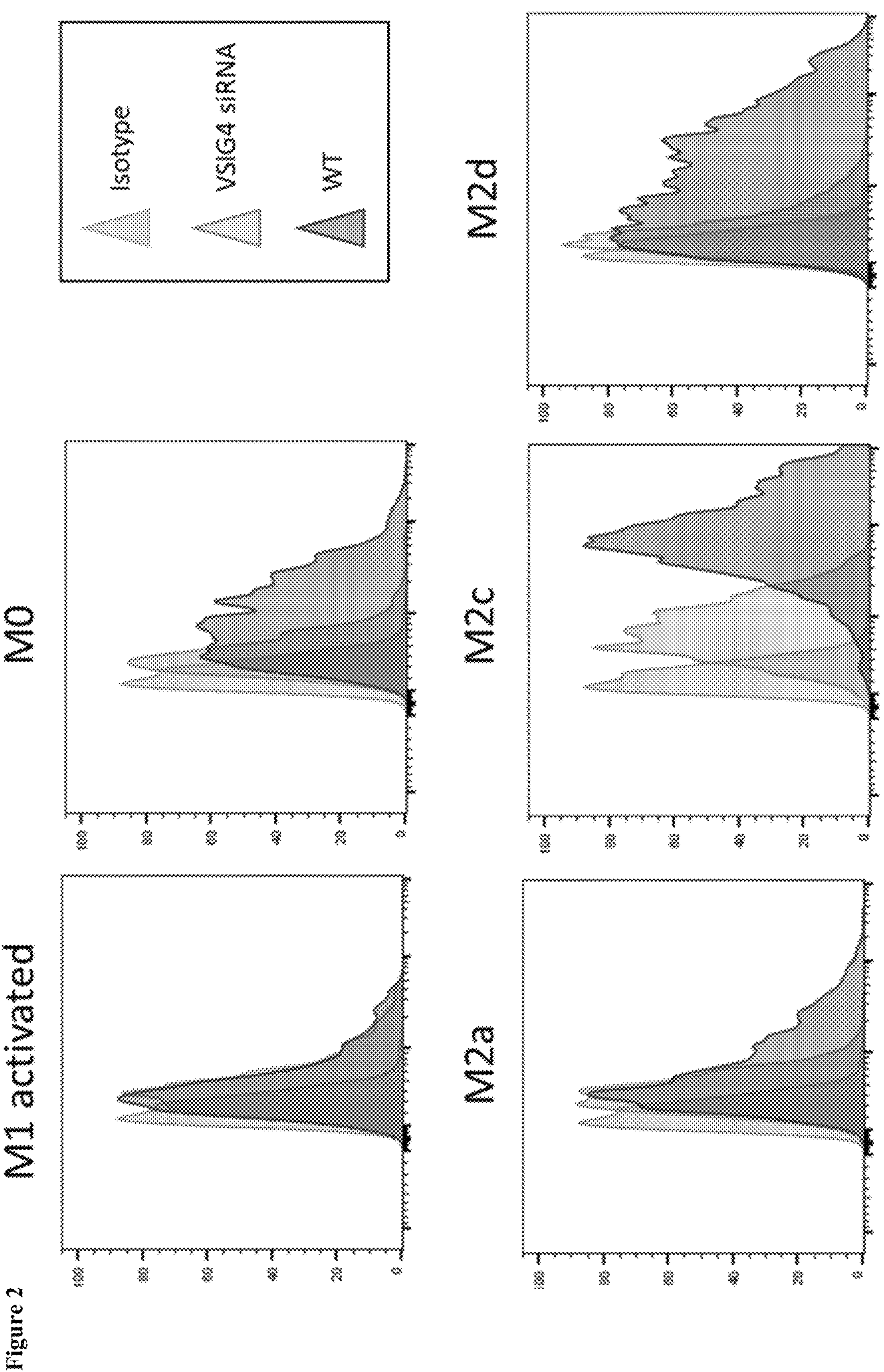
FIG. 2 further shows that VSIG4 expression is expressed on myeloid derived supp tumor-associated suppressive myeloid cell populations, myeloid derived suppressor cells including suppressive macrophage subsets.
Figure 3:
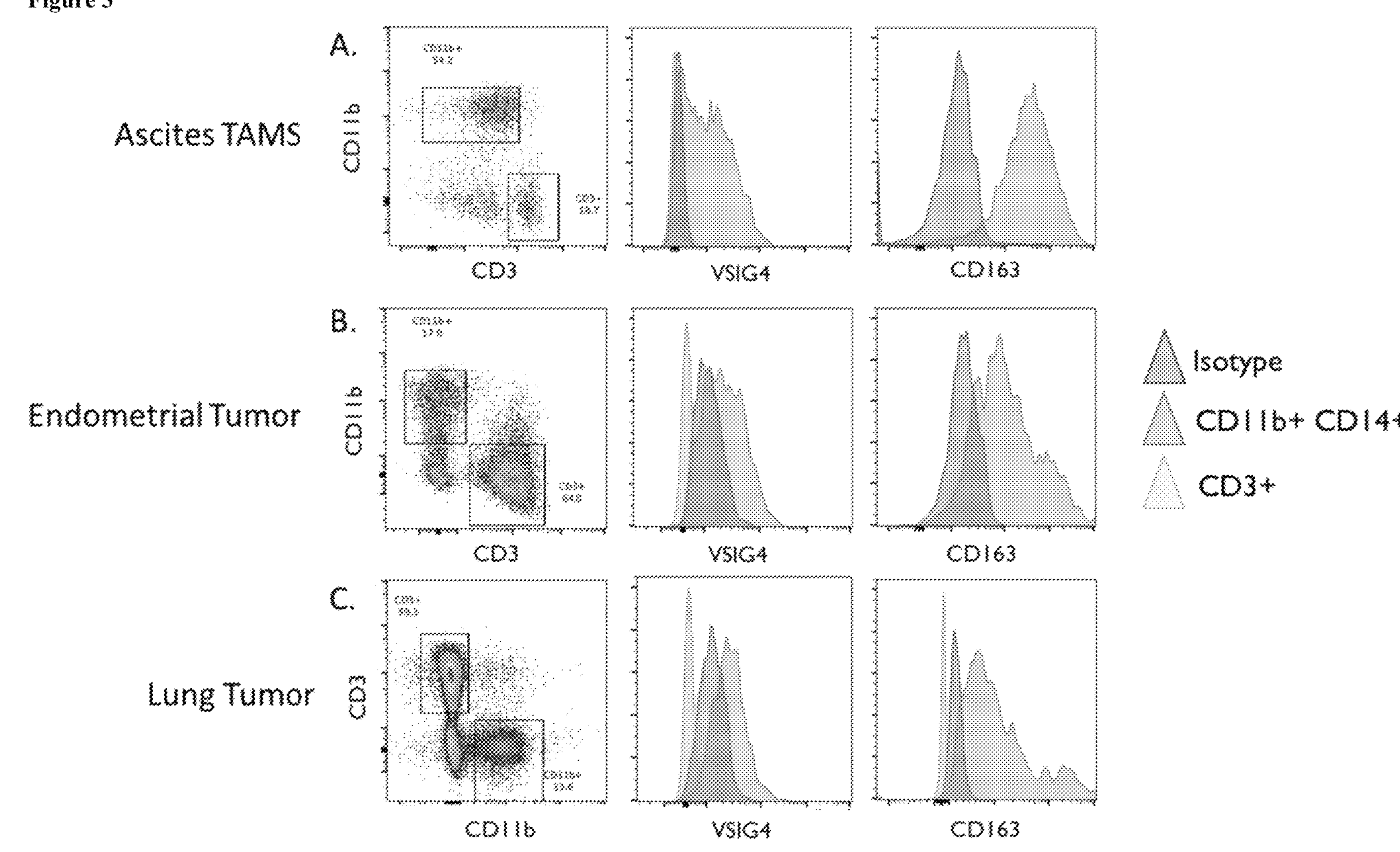
FIG. 3A-FIG. 3F show that TAMs (e.g., M2 TAMs expressing CD16 and CD163) that make up a large fraction of cells in ascites fluid samples obtained from gynecologic cancers (FIG. 3A), endometrial tumor (FIG. 3B), non-small cell lung cancer (NSCLC) tumor (FIG. 3C), kidney tumor (FIG. 3D), thyroid tumor (FIG. 3E), and breast tumor (FIG. 3F) also highly express VSIG4 protein on their cell surface.
Figure 3:
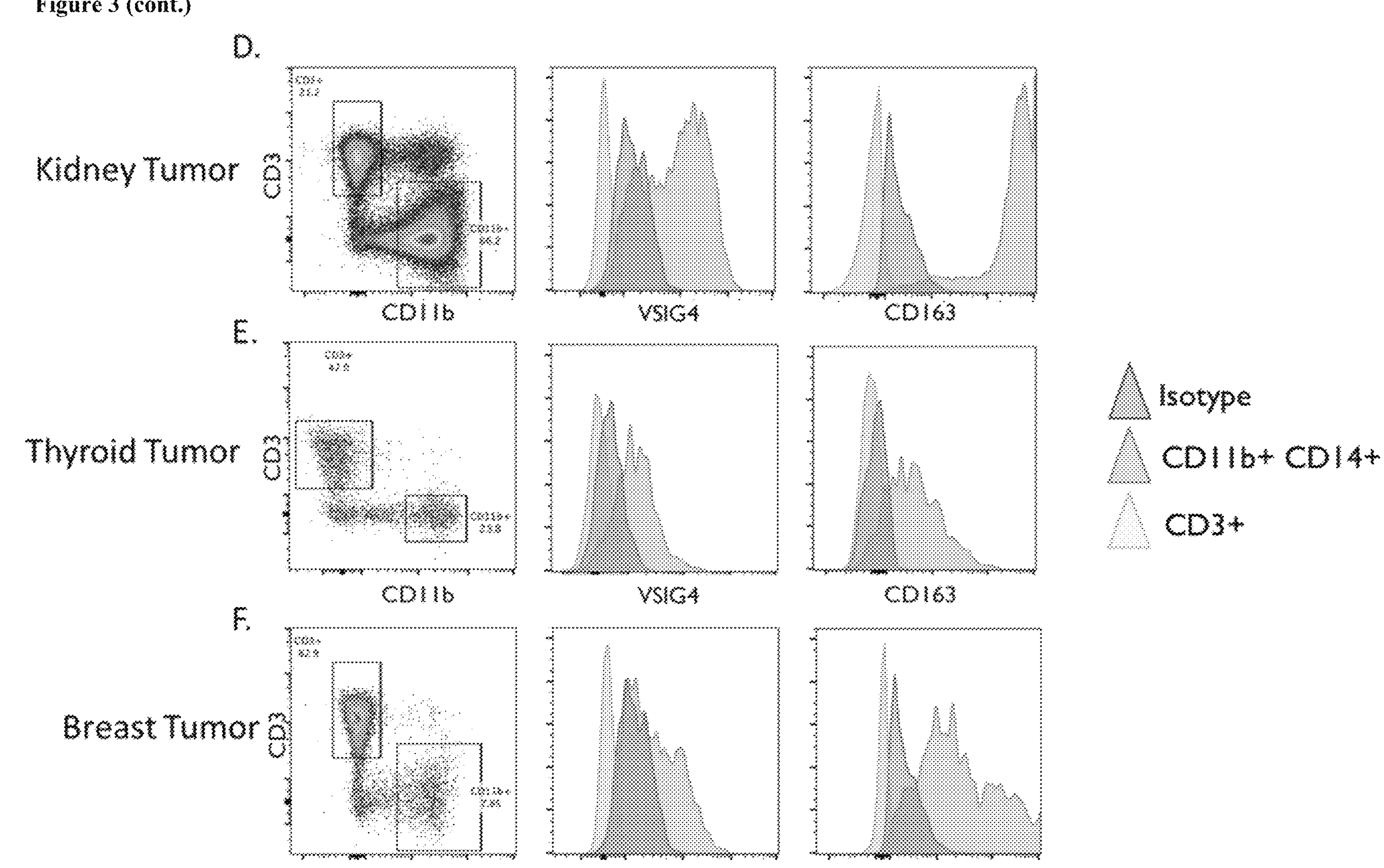

Formulated LNPs had median particle diameters of approximately 60-70 nm as measured by Nanoparticle Tracking Analysis (ZetaView, ParticleMetrix) and siRNA encapsulation efficiencies of approximately 80-90% as measured by a modified Quant-iT™ RiboGreen™ assay (Heyes et al. (2005) *J. Control. Rel.* 107:276-287). These siRNA LNPs were administered at a final concentration of 50 nM on day 1 and day 3. On day 6 of culture, M1 macrophages were activated with 10 ng/ml human interferon gamma and 100 ng/ml lipopolysaccharide (LPS) (Invivogen, San Diego, CA). M2 macrophages were left unpolarized for M0, polarized with 20 ng/ml human IL-4 (Biolegend, San Diego, CA) for M2a, polarized with 20 ng/ml human IL-10 (BioLegend, San Diego, CA) for M2c, or polarized with 20 ng/ml human IL-10 and 20 ng/ml TGF-beta (BioLegend, San Diego, CA) for M2d macrophages. Forty-eight hours later, macrophages were removed from plates by scraping and VSIG4 expression was assessed by flow cytometry. For flow cytometry, cells were collected and resuspended in 50 ul FACS buffer (PBS with 2.5% FBS and 0.5% sodium azide) and blocked for 15 minutes with TruStain FcX™ (Biolegend Cat. No. 422302) on ice. Antibodies were diluted in FACS buffer according to the manufacturer's instructions and added to cells for 15 minutes on ice. Labeled cells were washed twice with FACS buffer and fixed with PBS plus 2% paraformaldehyde for flow cytometry analysis on an Attune™ flow cytometer (ThermoFisher). Data were analyzed via FlowJo software. Reagent antibodies used as controls and/or in flow cytometry are shown in Table 3 below. FIG. 2 shows that VSIG4 expression is restricted to suppressive myeloid cells (e.g., macrophage subsets). In this figure, M1 macrophages represent pro-inflammatory macrophages that were differentiated in the presence of GM-CSF and polarized with IFNg and LPS. M0, and all M2 variants, represent suppressive macrophages that were differentiated in the presence of the suppressive cytokine MCSF and polarized with additional suppressive cytokines (e.g., IL-10) outlined above.

Beyond analyzing healthy PBMCs, it is important to determine the expression of VSIG4 at the site of disease. To this end, two patient-based cell sources were utilized; the ascites fluid from gynecologic tumors and tumor infiltrating immune cells from solid human tumors. Ascites fluid is drained from late stage cancer patients. Malignant ascites is a complication observed in terminal ovarian and sometimes other cancer. The excess accumulation of fluid in the peritoneal cavity arises from a combination of impaired fluid drainage and increased net filtration and can contain tumor cells, tumor associated leukocytes and has multiple cytokines and chemokines that are associated with the tumor-induced immunosuppression. (Penet et al. (2018) *Front. Oncol.* 8:595). Ascites is the closest one can get to the true unmanipulated tumor microenvironment. To perform analysis of tumors, each tumor was first prepared into a single cell suspension. The tumor was cut into small pieces of 2-4 $mm^3$. A Tumor Dissociation Kit enzyme mix (MACS Miltenyi Biotec) was prepared according to the manufacturer's protocol. Tumor pieces and dissociation enzymes were transferred into 5 ml Snaplock Microcentrifuge tubes and the tissue was minced using a pair of straight scissors. Tubes were placed in a 37° C. shaker at 200-250 rpm for 45 minutes to 1 hour. At the end of the incubation time, the digested tumor was filtered through 40 uM cell strainers into 50 mL Falcon™ conical centrifuge tubes. Each tube was filled with cold 2% to 5% FBS/PBS mix to stop the digestion. All of the remaining steps were performed on ice. In particular, each tube was centrifuged for 5 minutes at 300×g, the supernatant was discarded, and the cells were washed twice with cold 2% to 5% FBS/PBS mix. Following the last wash, the cells were resuspended in 1 to 5 ml of cold 2% to 5% FBS/PBS mix and a cell count was performed. Flow cytometry was performed as described above.

Tumor associated macrophages (TAMs) from both of these natural tumor or tumor-associated sources were found to express VSIG4. For example, FIG. 3A demonstrates that TAMs (e.g., M2 TAMs expressing CD16 and CD163) that make up a large fraction of cells in ascites fluid samples obtained from gynecologic cancers also highly express VSIG4 protein on their cell surface. Similarly, FIGS. 3B-F show that TAMs (e.g., CD11b+/CD14+ macrophages) obtained from an endometrial tumor, non-small cell lung tumor, kidney tumor, thyroid tumor, and a breast tumor that were dissociated into a single cell suspension and immune-phenotyped via flow cytometry. These tumors were all found to express VSIG4 protein on the surface of the tumor associated macrophages. By contrast, T cells and other immune cells were determined not to express VSIG4. Flow cytometry data from human tumors as well as in vitro differentiated macrophages highlights the restricted expression of this molecule to only suppressive types of macrophages. This also implies that any enhancement of T cell effector functions can be contributed by two non-mutually exclusive mechanisms: T cell activation by macrophages of the switched functionality, and/or by inhibiting the interaction of VSIG4 on macrophages with a yet unidentified inhibitory counter receptor on T cells.

Figure 4:
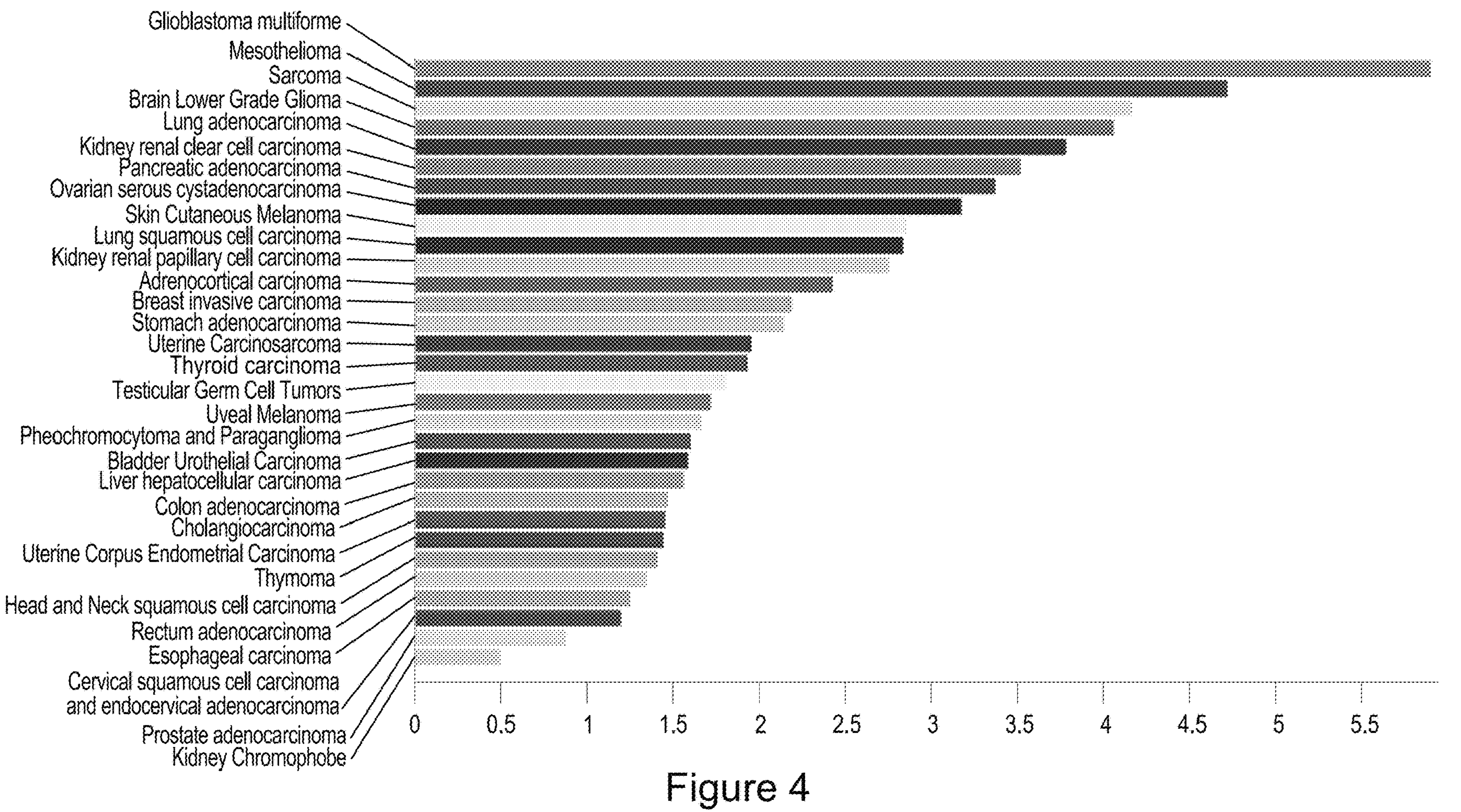
FIG. 4 shows a rank order distribution of macrophage-infiltrating tumors across cancer types of the large public dataset of human cancers (TCGA, The Cancer Genome Atlas, 2017 version, processed and distributed by OmicSoft/Qiagen) based upon their expression of VSIG4 with highest VSIG4 expression at the top.

FIG. 4 shows a rank order distribution of macrophage-infiltrating tumors across cancer types of the large public dataset of human cancers (TCGA, The Cancer Genome Atlas, 2017 version, processed and distributed by OmicSoft/Qiagen) based upon their expression of VSIG4 with highest VSIG4 expression at the top. Tumor infiltration is measured by the presence of a canonical myeloid marker CD11b above the cutoff. The cutoff is defined as a first quartile of the CD11b mRNA expression distribution across all primary tumors in the dataset. These VSIG4-positive macrophage-infiltrating tumors are believed to be particularly useful for modulation according to the compositions and methods described herein.

Example 2: Generation of Murine Fabs Against Human VSIG4

Murine anti-human VSIG4 antibodies were generated by phage display screening of mouse Fab libraries generated from spleen and lymph node RNA harvest from mice immunized with human VISG4 (phage libraries constructed by FairJourney Biologics, Porto, Portugal, and all phage selections and screening performed by FairJourney).

Sequences of peptides and polypeptides used in the antibody generation process are described in Table 4 below.

TABLE 4

Reagent polypeptides

| SEQ ID NO | Description | Sequence |
|---|---|---|
| SEQ ID NO: 19 | Human VSIG4-L-Fc | RPILEVPESVTGPWKGDVNLPCTYDPLQGYTQVLVKWLVQRGSDPVTIFLRDSSG DHIQQAKYQGRLHVSHKVPGDVSLQLSTLEMDDRSHYTCEVTWQTPDGNQVVRDK ITELRVQKLSVSKPTVTTGSGYGFTVPQGMRISLQCQARGSPPISYIWYKQQTNN QEPIKVATLSTLLFKPAVIADSGSYFCTAKGQVGSEQHSDIVKFVVKDSSKLLKT KTEAPTTMTYPLKATSTVKQSWDWTTDMDGYLGETSAGPGKSLPGSGGDKTHTCP |

TABLE 4-continued

Reagent polypeptides

| SEQ ID NO | Description | Sequence |
|---|---|---|
| | | PCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTIS KAKGOPREPQVYTLPPSREEMTKNQVSLTCLVKGFYPSDIAVEWESNGQPENNYK TTPPVLDSDGSFFLYSKLTVDKSRWQQGNVFSCSVMHEALHNHYTQKSLSLSPGK |
| SEQ ID NO: 20 | Human VSIG4-S-Fc | RPILEVPESVTGPWKGDVNLPCTYDPLQGYTQVLVKWLVQRGSDPVTIFLRDSSG DHIQQAKYQGRLHVSHKVPGDVSLQLSTLEMDDRSHYTCEVTWQTPDGNQVVRDK ITELRVQKHSSKLLKTKTEAPTTMTYPLKATSTVKQSWDWTTDMDGYLGETSAGP GKSLPGSGGDKTHTCPPCPAPELLGGPSVFLFPPKPKDTLMISRTPEVTCVVVDV SHEDPEVKFNWYVDGVEVHNAKTKPREEQYNSTYRVVSVLTVLHQDWLNGKEYKC KVSNKALPAPIEKTISKAKGQPREPQVYTLPPSREEMTKNQVSLTCLVKGFYPSD IAVEWESNGOPENNYKTTPPVLDSDGSFFLYSKLTVDKSRWQQGNVFSCSVMHEA LHNHYTQKSLSLSPGK |
| SEQ ID NO: 21 | Mouse VSIG4-Fc | HPTLKTPESVTGTWKGDVKIQCIYDPLRGYRQVLVKWLVRHGSDSVTIFLRDSTG DHIQQAKYRGRLKVSHKVPGDVSLQINTLQMDDRNHYTCEVTWQTPDGNQVIRDK IIELRVRKYNPPRINTEAPTTLHSSLEATTIMSSTSDLTTNGTGKLEETIAGSGR NLPGSGGDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEYKCKV SNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALH NHYTQKSLSLSPGK |
| SEQ ID NO: 22 | Human VSIG4-L-CHO | MGILLGLLLLGHLTVDTYGRPILEVPESVTGPWKGDVNLPCTYDPLQGYTQVLVK WLVQRGSDPVTIFLRDSSGDHIQQAKYQGRLHVSHKVPGDVSLQLSTLEMDDRSH YTCEVTWQTPDGNQVVRDKITELRVQKLSVSKPTVTTGSGYGFTVPQGMRISLQC QARGSPPISYIWYKQQTNNQEPIKVATLSTLLFKPAVIADSGSYFCTAKGQVGSE QHSDIVKFVVKDSSKLLKTKTEAPTTMTYPLKATSTVKQSWDWTTDMDGYLGETS AGPGKSLPVFAIILIISLCCMVVFTMAYIMLCRKTSQQEHVYEAARAHAREANDS GETMRVAIFASGCSSDEPTSQNLGNNYSDEPCIGQEYQIIAQINGNYARLLDTVP LDYEFLATEGKSVC |
| SEQ ID NO: 23 | Human VSIG4-S-CHO | MGILLGLLLLGHLTVDTYGRPILEVPESVTGPWKGDVNLPCTYDPLQGYTQVLVK WLVQRGSDPVTIFLRDSSGDHIQQAKYQGRLHVSHKVPGDVSLQLSTLEMDDRSH YTCEVTWQTPDGNQVVRDKITELRVQKHSSKLLKTKTEAPTTMTYPLKATSTVKQ SWDWTTDMDGYLGETSAGPGKSLPVFAIILIISLCCMVVFTMAYIMLCRKTSQQE HVYEAARAHAREANDSGETMRVAIFASGCSSDEPTSQNLGNNYSDEPCIGQEYQI IAQINGNYARLLDTVPLDYEFLATEGKSVC |
| SEQ ID NO: 24 | Mouse VSIG4-CHO | MEISSGLLFLGHLIVLTYGHPTLKTPESVTGTWKGDVKIQCIYDPLRGYRQVLVK WLVRHGSDSVTIFLRDSTGDHIQQAKYRGRLKVSHKVPGDVSLQINTLQMDDRNH YTCEVTWQTPDGNQVIRDKIIELRVRKYNPPRINTEAPTTLHSSLEATTIMSSTS DLTTNGTGKLEETIAGSGRNLPIFAIIFIISLCCIVAVTIPYILFRCRTFQQEYV YGVSRVFARKTSNSEETTRVTTIATDEPDSQALISDYSDDPCLSQEYQITIRSTM SIPAC |
| SEQ ID NO: 25 | Human VSIG4-L-His | RPILEVPESVTGPWKGDVNLPCTYDPLQGYTQVLVKWLVQRGSDPVTIFLRDSSG DHIQQAKYQGRLHVSHKVPGDVSLQLSTLEMDDRSHYTCEVTWQTPDGNQVVRDK ITELRVQKLSVSKPTVTTGSGYGFTVPQGMRISLQCQARGSPPISYIWYKQQTNN QEPIKVATLSTLLFKPAVIADSGSYFCTAKGQVGSEQHSDIVKFVVKDSSKLLKT KTEAPTTMTYPLKATSTVKQSWDWTTDMDGYLGETSAGPGKSLPGSGHHHHHHHH HH |
| SEQ ID NO: 26 | Cyno VSIG4-L-His | RPILEVPESITGPWKGDVNIPCTYGPLQGYTQVLVKWLVQRGSDPVTIFLRDSSG DHIQQAKYQGRLHVNQKVPGDVSLQLSTLEMDDQSHYTCEVTWQTPDGNQVVRDK ITELRVQKLSVSKPTVTTGSGYGFTVPQGMRISLQCQARGSPPISYIWYKEQTNN QEPIKVATLSTLLFKPAMVADSGSYFCAAKGRVGSEQRSDIVKFVVKDSSKLLKT KTEAPTTMRHPLKATSTVKQSWDWTTDVDGYLGATSAGPGKSLPGSGHHHHHHHH HH |
| SEQ ID NO: 27 | Human VSIG4-S-His | RPILEVPESVTGPWKGDVNLPCTYDPLQGYTQVLVKWLVQRGSDPVTIFLRDSSG DHIQQAKYQGRLHVSHKVPGDVSLQLSTLEMDDRSHYTCEVTWQTPDGNQVVRDK ITELRVQKHSSKLLKTKTEAPTTMTYPLKATSTVKQSWDWTTDMDGYLGETSAGP GKSLPGSGHHHHHHHHHH |
| SEQ ID NO: 28 | Mouse VSIG4-His | HPTLKTPESVTGTWKGDVKIQCIYDPLRGYRQVLVKWLVRHGSDSVTIFLRDSTG DHIQQAKYRGRLKVSHKVPGDVSLQINTLQMDDRNHYTCEVTWQTPDGNQVIRDK IIELRVRKYNPPRINTEAPTTLHSSLEATTIMSSTSDLTTNGTGKLEETIAGSGR NLPGSGHHHHHHHHHH |

Three BALB/c mice were immunized, intraperitoneally, with 50 μg of human long isoform VSIG4 (human VSIG4-L-His; SEQ ID NO: 25) protein in Freund's complete adjuvant followed by 25 μg of protein in Freund's incomplete adjuvant every two weeks for a total of four injections. On day 35 of the immunization schedule, mice were immunized, intravenously, with 25 μg of cynomolgus monkey VISG-4 (Cyno VISG4-L-His; SEQ ID NO: 26). An anti-histaminic drug was administrated to the mice one hour prior to this injection. Four days after the last immunization, animals were sacrificed and spleen and lymph nodes (inguinal and popliteal) were harvested for preparation of single cell suspensions for extraction of total RNA using the Direct-zol™ RNA MiniPrep kit (Zymo Research, Irvine, CA). The concentration of extracted RNA was determined by measuring the Absorbance 260 nm using an absorbance of 1.0 for a concentration of 40 μg/ml. Extracted RNA quality was assessed via RNA electrophoresis using Agilent 2100 Bioanalyzer equipment (Agilent, Santa Clara, CA). RNA was stored at −80° C.

Approximately 0.1 ml of blood was collected pre- and post-immunization to investigate the presence of antibodies against VSIG4. The immune response to human, long (human VSIG4-L-His; SEQ ID NO: 25) and short isoform (human VSIG4-S-His; SEQ ID NO: 27), and cynomolgus monkey long isoform (cyno VSIG4-L-His; SEQ ID NO: 26) VSIG4 proteins was assessed via ELISA. For this, MaxiSorp™ high protein-binding capacity 96-well microplates (Thermo Fisher Scientific, Waltham, MA) were coated with VSIG4 proteins at 2 μg/ml diluted in phosphate buffered saline buffer (PBS). Coated microplates were blocked with 4% dried skimmed milk in PBS. Three-fold serial dilutions of sera in assay buffer (1% dried skimmed milk in PBS), starting from 10% sera were prepared and 100 μl of diluted sera was added onto the coated wells and incubated for one hour at room temperature. Binding detection of total mouse IgG response to human full-length (human VSIG4-L-His; SEQ ID NO: 25) and cynomolgus monkey (Cyno VSIG4-L-His; SEQ ID NO: 26) VSIG4 proteins was measured using a donkey anti-mouse IgG, Horseradish Peroxidase (HRP)-conjugated detection antibody (Jackson Immuno Research, West Grove, PA). Optical density (OD) at 450 nm was determined using a standard absorbance microplate reader. Significant amounts of mouse anti-VSIG4 antibodies were shown to be present in the sera after the fifth immunization in comparison with the amounts of mouse anti-VSIG4 antibodies present in pre-immunized mouse sera.

Total RNA (45 μg) purified as described above was used as template for cDNA synthesis by RT-PCR using the SuperScript® III First Strand Synthesis System random priming (Invitrogen, Carlsbad, CA). The cDNA products were used directly for polymerase chain reaction (PCR) amplification of the variable domain of the heavy chain (CH), the first constant domain of IgG heavy chain and a portion of the hinge (CH1-Hinge), the variable domain (Vκ) and the constant domain (Cκ) of the antibody kappa light chain using the Expand™ High Fidelity System (Roche, Basel, Switzerland). The primers used in these PCR reactions were designed to anneal in the mouse hinge and in the 3' of CH or Cκ regions, as well as in the 5' region of the framework one region of all different mouse V genes. A secondary nested PCR was performed using the previous DNA amplification products as template and the same primers as used above tagged with the restriction sites needed for further cloning into a phagemid. Per mouse the genes codifying for the VH, CH1 and a small portion of hinge or the genes codifying for Vκ and Cκ were cloned separately into a phagemid and electroporated into electrocompetent *E. coli* TG1 cells leading to heavy chain and light chain sub-libraries respectively.

The complete Fab library was constructed by cloning the VHCH1-Hinge inserts obtained by endonuclease restriction digesting the heavy chain sub-library DNA into the phagemid vector containing the light chain sub-library and by electroporating electrocompetent *E. coli* TG1 cells. In total, three Fab display libraries, where the phage particles express the Fab fragments as a fusion protein with a C-terminal His6-c-myc tag and with the Gene-III protein, were generated with a library size above 1.0E+08. In total, three mouse Fab libraries were generated, corresponding to each mouse immunized.

Phage-expressing Fab fragments from the three mouse immune Fab libraries were produced according to standard protocols using VCSM13 helper phage and precipitated in PEG/NaCl. A total of three consecutive rounds of phage display selections were performed to enrich for human VSIG4- or human and cynomolgus monkey VSIG4-specific Fabs. A first round of phage display selections with biotinylated human VSIG4, long or short isoform, human Fc1 or His-tagged proteins (SEQ ID NOs: 19, 20, 25, and 28) at 100 nM captured in streptavidin magnetic beads was conducted. A second round followed using biotinylated human VSIG4, long or short isoform, and cynomolgus monkey VSIG4, human Fc1 or His tagged proteins (SEQ ID NOs: 19, 20, 25, and 28) at 20 nM or 2 nM captured in streptavidin magnetic beads. A final round using 4-5E+06 CHO-K1 cells expressing VSIG4 protein (Human VSIG4-L-CHO; SEQ ID NO: 22) was performed. All phage display selections were performed with total elution of the VSIG4 binding phage with trypsin according to standard phage display protocols.

Individual clones from the third round of cell phage display selections were picked randomly into 96-well master plates and screened as Fab periplasmic extracts (P.E.) for binding to human VSIG4 via a flow cytometry assay as a primary screen. Fab P.E. samples were produced by induction with isopropyl β-D-1-thiogalactopyranoside (IPTG) according to standard protocols. 150E+05 human VSIG4, long isoform or short isoform, CHO-K1 expressing cells (Human VSIG4-L-CHO; SEQ ID NO: 22, Human VSIG4-S-CHO; SEQ ID NO: 23) were incubated with 20 μl of Fab P.E, diluted 1:5 in assay buffer (0.5% of heat inactivated fetal bovine serum with 1:1000 ethylenediaminetetraacetic acid in PBS), for one hour. Binding detection was assessed using a mouse anti-c-myc antibody (Roche, Basel, Switzerland; clone 9E10; catalog #11667203001) followed by goat anti-mouse IgG antibody, APC conjugated (Biosciences, Franklin Lakes, New Jersey; Catalog #550826) and by acquisition of 10,000 cells per sample. Fluorescence was measured using the Attune™ NxT (Thermo Fisher Scientific, Waltham, MA).

As described above, five human VSIG4 isoforms have been described. Both major isoforms, isoform 3 (GenBank Ref. NP_001093901.1), the "short" form, and isoform 1 (GenBank Ref. NP_009199.1), the "long" form, contain an extracellular IgV-type domain. The long form also contains a membrane proximal IgC-type domain. Anti-VSIG4 antibody discovery was targeted at both the short and the long isoforms of the VSIG4 extracellular domain. The resulting anti-VSIG4 antibodies generally fell into three broad categories: i) human VSIG4-L-His and human VSIG4-S-His binding ii) human VSIG4-L-His and weakly human VSIG4-S-His binding and iii) human VSIG4-L-His only binding.

Numerous Fab clones that showed binding to human VSIG4 long or short isoform expressed on CHO-K1 cells were sequenced, and unique Fab sequences (V light gene and V heavy gene unique pairing) were selected for further characterization in secondary screening assays.

Cross-reactivity screening of the panel of mouse unique Fab clones that showed binding in primary screening assay to human VSIG4, long or short isoform, CHO-K1 expressing cells was performed (Human VSIG4-L-CHO SEQ ID NO: 22, Human VSIG4-S-CHO SEQ ID NO: 23). Cross-reactivity was assessed in human VSIG4, long and short isoform, cynomolgus monkey and mouse VSIG4 protein (SEQ ID NOs: 19, 20, 25, and 28) via ELISA.

For this, MaxiSorp™ high protein-binding capacity 96-well microplates were coated with human (long and short) and cynomolgus monkey VSIG4 proteins (SEQ ID NOs: 19, 20, and 26) at 1 μg/ml and mouse VSIG4 protein (SEQ ID NO: 28) at 2 μg/ml diluted in PBS. Coated microplates were blocked with dried skimmed milk at 4% in PBS. P.E. samples of the mouse unique Fab sequences were diluted 1:5 in assay buffer (1% dried skimmed milk in PBS), and 100 μl of diluted sample was added onto the coated wells and incubated for one hour at room temperature. Binding detection of the P.E. samples to the coated proteins was measured using a mouse anti-c-myc detection antibody (Roche, Basel, Switzerland; Clone 9E10; Catalog #11667203001) followed by donkey anti-mouse IgG HRP conjugated detection antibody (Jackson Immuno Research, West Grove, PA). Optical density (OD) at 450 nm was determined using a standard absorbance microplate reader.

Table 5 provides a summary of VSIG4 protein target binding characteristics for generated anti-VSIG4 Fab P.E. The anti-VSIG4 Fabs have a diversity of binding profiles and, by extension, epitopes. All Fabs bind the long form of the VSIG4 extracellular domain by ELISA and differ regarding the property of 1) ability to bind to the short form of the VSIG4 extracellular domain (ECD), 2) bind to cynomolgous monkey VSIG4 (cyno VSIG4-L), and 3) block the VISG4 ligands, C3b and/or iC3b. The Fab P.E. binding data demonstrate at least 5 binding profiles: 1) binds VSIG4-S, binds cyno VSIG4-L, blocks C3b, and blocks iC3b; 2) binds VSIG4-S, does not bind cyno VSIG4-L, blocks C3b, and does not block iC3b; 3) binds VSIG4-S, does not bind cyno VSIG4-L, does not block C3b, and does not block iC3b; 4) does not bind VSIG4-S, binds cyno VSIG4-L, blocks C3b, and blocks iC3b; and 5) does not bind VSIG4-S, does not bind cyno VSIG4-L, does not block C3b, and does not block iC3b.

Off-rate values of the mouse unique Fab clones were determined using surface plasmon resonance (SPR) in Biacore™ T200 equipment (GE Healthcare, Chicago, IL). Human VSIG4 long isoform protein (Human VSIG4-L-His; SEQ ID NO: 25) was immobilized on a CMS Series S Biacore™ chip. The immobilization was performed in accordance with a method provided by Biacore and by using the NHS/EDC kit (GE Healthcare, Chicago, IL). After activation of the chip, VSIG4 protein (Human VSIG4-L-His; SEQ ID NO: 25) was injected resulting in a surface density of approximately 1000 RU. Sixty μl of Fab P.E. samples, diluted 1:5 in HBS-EP+ assay buffer (0.1 M HEPES, 1.5 M NaCl, 0.03 M EDTA and 0.5% v/v Surfactant P20), were injected and passed through the flow cells at a flow rate of 30 μl/min. After binding of the samples to VSIG4 protein, the off-rate was monitored for a period of five minutes. The flow cell surface was regenerated by a double injection of 10 μl of 1 mM glycine at pH 1.5 in 1 M sodium chloride at 30 μl/min. Off-rate analysis was done using the BIAevaluation software (GE Healthcare, Chicago, IL) and using a 1:1 dissociation kinetic fit curve. As described above, results of biophysical characterization for representative anti-VSIG4 P.E.-derived Fabs are summarized in Table 5.

Blocking capability of the mouse unique Fab clones to C3b/iC3b ligands was tested in ligand blocking assay via ELISA. For this, MaxiSorp™ high protein-binding capacity 96-well microplates were coated with human VSIG4 long isoform protein (human VSIG4-L-Fc; SEQ ID NO: 19) at 1 and 0.25 μg/ml diluted in PBS for C3b and iC3b test, respectively. Coated microplates were blocked with casein (Sigma-Aldrich, St. Louis, MO) at 1% in PBS. P.E. samples of the mouse unique Fab sequences were diluted 1:5 in assay buffer (0.1% casein in PBS) and incubated with 0.5 μg/ml biotinylated C3b (EMD Millipore, Burlington, MA; Cat. 204860) or 0.15 μg/ml of biotinylated iC3b (EMD Millipore, Burlington, MA; Cat. 204863) ligands diluted in assay buffer. One hundred ill of the mixed sample was added onto the coated wells and incubated for one hour at room temperature. Binding detection of both biotinylated C3b and iC3b to the coated proteins was measured using streptavidin conjugated to HRP (BD Biosciences, San Jose, CA). OD at 450 nm was determined using a standard absorbance microplate reader. As described above, biophysical characterization of generated anti-VSIG4 P.E.-derived Fabs is summarized in Table 5.

Generally, Table 5 demonstrates that all VSIG4 Fabs bind to the long isoform of VSIG4. Some Fabs (e.g., 12A08, 12A12, 14C05, 14D12, 15C03, 16E03, and 16E10) also bind to the short isoform of VSIG4. Some Fabs (e.g., 12A08, 12A12, 13H11, 14C05, 14D12, and 16E10) also bind to cynomolgus VSIG4. Additionally, some Fabs (e.g., 12A08, 12A12, 14C05, and 14D12) block the binding interaction between VSIG4 and both of its ligands, C3b and iC3b; some Fabs (e.g., 13H11 and 15C03) only block the interaction between VSIG4 and C3b; and some Fabs (e.g., 15A06, 15C04, 16E03, and 16E10) don't block the interaction between VSIG4 and C3b or the interaction between VSIG4 and iC3b.

TABLE 5

Biophysical Characterization of Periplasmic Extract-derived Fabs

| Antibody | hVSIG4-L-Fc Off-Rate ($s^{-1}$) | ELISA (OD450 nM) hVSIG4-L (1:5) | hVSIG4-S (1:5) | cyVSIG4-L (1:5) | mVSIG4 (1:5) | Percent Blocking C3b | iC3b |
|---|---|---|---|---|---|---|---|
| 12A08 | 1.3E−02 | 4.45 | 4.09 | 4.27 | 0.057 | 57.6 | 53.4 |
| 12A12 | 3.8E−03 | 4.42 | 4.18 | 4.37 | 0.063 | 74.8 | 76.5 |
| 13H11 | 4.5E−02 | 4.33 | 0.06 | 4.34 | 0.057 | 46.9 | N.B.* |
| 14C05 | 3.7E−04 | 4.33 | 4.32 | 4.37 | 0.059 | 88.8 | 88.7 |
| 14D12 | 6.3E−03 | 4.32 | 4.18 | 4.32 | 0.054 | 70.3 | 56.0 |

TABLE 5-continued

Biophysical Characterization of Periplasmic Extract-derived Fabs

| Antibody | hVSIG4-L-Fc Off-Rate ($s^{-1}$) | ELISA (OD450 nM) hVSIG4-L (1:5) | hVSIG4-S (1:5) | cyVSIG4-L (1:5) | mVSIG4 (1:5) | Percent Blocking C3b | iC3b |
|---|---|---|---|---|---|---|---|
| 15A06 | 1.5E−03 | 4.42 | 0.06 | 0.05 | 0.054 | N.B. | 1.4 |
| 15C03 | 7.6E−03 | 4.20 | 4.05 | 0.05 | 0.065 | 42.7 | N.B. |
| 15C04 | 1.9E−03 | 4.21 | 0.06 | 0.05 | 0.054 | N.B. | N.B. |
| 16E03 | 1.3E−02 | 4.43 | 4.30 | 0.21 | 0.057 | N.B. | N.B. |
| 16E10 | 2.5E−02 | 1.86 | 1.32 | 1.88 | 0.058 | 7.1 | 7.6 |

*N.B.: no blocking

Selected antibodies were expressed as mouse/human chimeras with the mouse variable regions and human IgG4 backbone containing a S228P heavy chain mutation paired with a human kappa light chain. Variable heavy chain (HC) and light chain (LC) sequences were cloned into vectors containing the human IgG4 and human kappa antibody constant region sequences shown in Table 6.

TABLE 6

Antibody constant region sequences

| Region | Sequence |
|---|---|
| hIgG4 (S228P) | ASTKGPSVFPLAPCSRSTSESTAALGCLVKDYFPEPVTVSWNSGALTSGVHTFPAVLQS SGLYSLSSVVTVPSSSLGTKTYTCNVDHKPSNTKVDKRVESKYGPPCPPCPAPEFLGGP SVFLFPPKPKDTLMISRTPEVTCVVVDVSQEDPEVQFNWYVDGVEVHNAKTKPREEQFN STYRVVSVLTVLHQDWLNGKEYKCKVSNKGLPSSIEKTISKAKGQPREPQVYTLPPSQE EMTKNQVSLTCLVKGFYPSDIAVEWESNGQPENNYKTTPPVLDSDGSFFLYSRLTVDKS RWQEGNVFSCSVMHEALHNHYTQKSLSLSLGK (SEQ ID NO: 101) |
| hKappa LC | RTVAAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 102) |
| hLambda LC | GQPKAAPSVTLFPPSSEELQANKATLVCLISDFYPGAVTVAWKADSSPVKAGVETTTPS KQSNNKYAASSYLSLTPEQWKSHRSYSCQVTHEGSTVEKTVAPTECS (SEQ ID NO: 103) |

Protein expression and purification was performed by ATUM (Newark, CA), by transient transfection of heavy chain- and light chain-containing proprietary vectors into suspension-adapted HEK293 cells. Cell culture supernatant was purified by protein A affinity chromatography (MabSelect SuRe™ pcc, GE Life Sciences) according to the manufacturer's protocol. Eluted, neutralized proteins were buffer-exchanged into PBS, pH 7.4 (Corning) and filter-sterilized. Purified antibodies were quantified by OD280 using extinction coefficients calculated from the primary amino acid sequence. Purified antibodies were characterized by capillary gel electrophoresis (Perkin Elmer GXII) or SDS-PAGE (Bio-Rad Criterion™ Tris/Glycine/SDS, 4-20%) and HPLC-SEC. Endotoxin levels were also characterized (Charles River Endosafe™).

The binding characteristics of selected antibodies identified in the phage display selections and reformatted as mouse-human chimeric IgG4 antibodies was assessed by ELISA for their ability to bind plate-bound human VSIG4-L, human VSIG4-S, cynomolgus monkey VSIG4, and mouse VSIG4 (Table 7). Antibodies were also assessed by ELISA for specificity to human VSIG4 compared to related VSIG4 B7 family members, including human B7-H1, B7-H2, B7-H3, B7-H4, B7-DC, B7-1, and B7-2 (Table 8).

For this, MaxiSorp™ high protein-binding capacity 96-well microplates (Sigma Aldrich, St. Louis, MO) were coated with human (long and short isoforms), cynomolgus monkey and mouse VSIG4 proteins (SEQ ID NOs: 19, 20, 25, and 28) at 1 pg/ml diluted in PBS. Coated microplates were blocked with dried skimmed milk at 4% in PBS. Coated proteins were then incubated with each purified antibody at a concentration of 50 nM for 1 h to allow the binding to the proteins. Binding detection was measured using a goat anti-huIgG monoclonal detection antibody, HRP conjugated (Jackson Immune Research, West Gove, PA). As a control for specificity, an irrelevant antibody and protein were used. OD at 450 nm was determined using a standard absorbance microplate reader.

Table 7 shows the results of the assays and indicates which mAbs bind to human VSIG4-L, human VSIG4-S, cynomolgus monkey VSIG4, and mouse VSIG4.

Purified antibodies were tested for binding to wild type (WT) CHO-K1 cells and to human VSIG4 expressing CHO-K1 cells (Human VSIG4-L-CHO; SEQ ID NO: 22) for determination of EC50 values. Three-fold serial dilution of each antibody starting at 200 nM were prepared in in assay buffer (0.5% of heat inactivated Fetal bovine serum with 1:1000 Ethylenediaminetetraacetic acid in PBS). Diluted samples were incubated with 1.5E+05 WT or human VSIG4-L expressing CHO-K1 cells (Human VSIG4-L-CHO; SEQ ID NO: 22), for 1 hour to allow the binding. As a control for specificity, an irrelevant antibody was used. Binding detection was assessed using a goat anti-Human IgG (Fc specific), FITC conjugated polyclonal detection antibody (Sigma Aldrich, St. Louis, MO) and by acquisition of 10,000 cells per sample. Fluorescence was measured on an Attune™ NxT (Thermo Fisher Scientific, Waltham, MA). Fifty-six of the purified antibodies showed EC50 values below 10 nM on CHO-K1 expressing VSIG4-L protein (Table 7). No non-specific binding to WT cells was observed for any of the antibodies.

Generally, Table 7 demonstrates that representative VSIG4 mAbs have similar binding properties as VSIG4 Fabs as described in Table 5. Where there are differences in binding properties these likely reflect differences in avidity, where antibodies with relatively weaker binding affinity demonstrating increased and sufficient avidity in a bivalent IgG format versus a monovalent Fab format to bind a target, especially within an ELISA assay design that captures avid binding. In particular, all IgGs bind plate-coated cynomolgus VSIG4 by ELISA, however in a monovalent format when measured by ForteBio Octet® no binding is observed for 15A06, 15C03, and 16E03, and extremely weak binding (~180 nM) observed for 15C04. These data are consistent with the ELISAs using Fab P.E., which is also a monovalent assay format. Similarly, the ForteBio Octet® data with antibodies in the IgG format is consistent with the ELISA data using Fab P.E., suggesting that 15C04, which binds the plate-coated short isoform by ELISA binds weaker to this protein than other antibodies in the cohort tested. Increased percentage blocking was observed in the IgG format, which is useful in some settings. It is believed that the increased percentage blocking is likely the result of several factors, including increased avidity in the IgG format leading to a more stable blocking interaction, more controlled concentrations used in blocking assay with IgGs versus Fab P.E., and additional steric interaction effects of an IgG (~150 kDa) blocking a ligand versus a smaller Fab (~50 kDa).

TABLE 7

Biophysical characterization of anti-VSIG4 chimeric antibodies

| | ELISA (OD450 nM) | | | | Flow Cytometry (EC50) | Octet (KD) | | | Percent Blocking | |
|---|---|---|---|---|---|---|---|---|---|---|
| Antibody | hVSIG4-L | hVSIG4-S | cyVSIG4-L | mVSIG4 | hVSIG4-L (nM) | hVSIG4-L (M) | hVSIG4-S (M) | cyVSIG4-L (M) | C3b | iC3b |
| 12A08 | 4.44 | 3.37 | 4.43 | 0.056 | 6.8 | 2.06E−08 | 1.88E−08 | 1.57E−08 | 96 | 98 |
| 12A12 | 4.45 | 4.18 | 4.40 | 0.054 | 4.4 | 1.91E−08 | 1.58E−08 | 1.95E−08 | 96 | 98 |
| 13H11 | 4.27 | 0.44 | 4.37 | 0.048 | 1.2 | 5.06E−08 | No binding | 2.03E−08 | 75 | 78 |
| 14C05 | 4.51 | 4.36 | 4.52 | 0.055 | 4.4 | 3.46E−09 | 2.69E−09 | 3.00E−08 | 96 | N.D.** |
| 14D12 | 4.53 | 3.43 | 4.52 | 0.050 | 2.8 | 2.15E−08 | 2.87E−08 | 1.61E−08 | 97 | 98 |
| 15A06 | 4.38 | 0.24 | 4.35 | 0.067 | 2.4 | 2.85E−08 | No binding | No binding | N.B.* | N.B. |
| 15C03 | 4.40 | 3.64 | 4.50 | 0.057 | 2.3 | 3.21E−08 | 1.86E−08 | No binding | 90 | 90 |
| 15C04 | 4.43 | 3.28 | 4.53 | 0.052 | 8.9 | 2.54E−08 | No binding | 1.83E−07 | 93 | 94 |
| 16E03 | 4.50 | 4.13 | 4.36 | 0.054 | 1.0 | 4.93E−08 | 4.93E−08 | No binding | N.B. | N.B. |
| 16E10 | 4.44 | 2.04 | 4.50 | 0.048 | 1.0 | 6.85E−08 | 7.53E−08 | 3.76E−08 | 33 | 72 |

*N.B.: no blocking
**N.D.: no data

TABLE 8

VISG4 family member proteins

| Name | Vendor | Catalogue # |
|---|---|---|
| Recombinant Human B7-1/CD80 His-tag Protein, CF | R&D Systems | 9050-B1-100 |
| Recombinant Human B7-2/CD86 His Tag Protein, CF | R&D Systems | 9090-B2-100 |
| Recombinant Human PD-L1/B7-H1 His-tag Protein, CF | R&D Systems | 9049-B7-100 |
| Recombinant Human B7-H2 His-Tag Protein, CF | R&D Systems | 8206-B7-100 |
| Recombinant Human B7-H3 His-Tag Protein, CF | R&D Systems | 1949-B3-050/CF |
| Recombinant Human B7-H4 His-Tag Protein, CF | R&D Systems | 6576-B7-050 |
| Recombinant Human PD-L2/B7-DC His-tag Protein, CF | R&D Systems | 9075-PL-100 |

The binding affinity of chimeric antibodies was determined by biolayer interferometry (BLI), using a ForteBio Octet® Red384 system. All samples were prepared in black 96-well flat bottom plates (Greiner, Cat. #655209) diluted in kinetics buffer (lx DPBS (Gibco, Cat. #LS14190250) containing 0.1% bovine serum albumin, 0.05% sodium azide, and 0.02% Tween®20). Anti-VSIG4 antibodies (ligand) were diluted to a final concentration of 10 ug/mL and captured on anti-human IgG Fc capture (AHC) biosensors (ForteBio, Cat. #18-5060). Recombinant human VSIG4-L-His (human VSIG4-L-His; SEQ ID NO: 25), human VSIG4-S-His (VISG4-S-His; SEQ ID NO: 26), and cyno VSIG4-His (cyno VSIG4-L-His; SEQ ID NO: 26) were diluted to 100 nM. Biosensors were rehydrated prior to the assay in kinetics buffer for 10 minutes and then equilibrated in kinetics buffer for 60 seconds. Antibody was then immobilized for 300 seconds followed by a 120 second baseline wash in fresh kinetics buffer, 300 second analyte association, and 300 second dissociation in the same buffer wells as the baseline wash step. All assay steps occurred at 30° C. with an acquisition rate of 5.0 Hz Fitting was calculated using ForteBio Data Analysis HT software and results are shown in Table 7. Processing parameters included double reference subtraction, with human IgG4 used as an isotype control for reference sensor subtraction and immobilized ligand in kinetics buffer with no analyte used for reference sample subtraction. Y-axis data was aligned to the average baseline step for the last 5 seconds and all steps were inter-step corrected to the start of the dissociation step. High frequency noise was removed using Savitzky-Golay filtering and final fitting was a 1:1 global binding model to both association and dissociation. Representative affinities are shown in Table 7.

Epitopic diversity of functional antibodies was further assessed by antibody cross-blocking experiments, performed on a ForteBio Octet® Red384 system. All samples were prepared in black 384-well flat bottom plates from (Greiner, Cat. #781209) with a working volume of 120 uL and diluted in kinetics buffer (1×DPBS containing 0.1% bovine serum albumin, 0.05% sodium azide, and 0.02% Tween®20). Anti-VSIG4 antibodies and human VSIG4-L-Fc protein (Human VSIG4-L-Fc SEQ ID NOs: 19) were diluted in kinetics buffer to a final concentration of 10 ug/mL. Anti-human IgG Fc capture (AHC) biosensors (ForteBio, Cat. #18-5060) were rehydrated prior to the assay in kinetics buffer for 10 minutes then equilibrated in kinetics buffer for 60 seconds. Recombinant human VSIG4-L-Fc (Human VSIG4-L-Fc SEQ ID NOs: 19) was then immobilized for 120 seconds followed by a 30 second baseline wash in fresh kinetics buffer, 120 second Fc block (2001.1 g/mL), 30 second wash, 180 second association of a first antibody (antibody "a"), 30 second wash, and then 120 second association of a competitor antibody (antibody "b"). All assay steps occurred at 30° C. with an acquisition rate of 5.0 Hz.

Binning results were calculated using ForteBio Data Analysis HT software. Antibody "a" and antibody "b" steps were defined, and the maximum binding calculation was averaged at the last 10% of the step duration. Once the matrix was generated, the antibody "b" binding signal in the absence of any antibody "a" was used to normalize the maximum binding of the competitor antibodies. Hierarchical clustering was set with a similarity metric of Pearson and Lingang Criteria by Mean, and the normalized maximum binding nm shift is reported in Table 9 below. The varying levels of binding of antibody "b" (Columns) to VSIG4-L-Fc (Human VSIG4-L-Fc SEQ ID NOs: 19) in the presence of antibody "a" (Rows) demonstrates a variety of epitopes being covered by different antibodies.

Table 9 shows distinct patterns of antibody cross-blocking profiles. Overall, Table 9 demonstrates that the representative VSIG4 mAbs encompass 8 distinct epitope bins, such as an epitope bin comprising mAbs 14C05 and 14D12, an epitope comprising mAb 12A12, an epitope bin comprising mAb 16E10, an epitope bin comprising mAb 12A08, an epitope bin comprising mAb 16E03, an epitope bin comprising mAb 15C03, an epitope bin comprising mAb 13H11, and epitope bin comprising mAbs 15A06 and 15C04. Overlapping antibody cross-blocking profiles are consistent with the antibodies' ability to bind VSIG4-L and VSIG4-S isoforms. Clones 13H11, 15A06, and 15C04 all have weak to no binding to the VSIG4-S isoform, indicating weak to no binding to the IgV domain, and have slightly overlapping blocking profiles separate from the other antibodies. Clones 14C05, 14D12, 12A12, 16E10, 15C03, 12A08, and 16E03 all bind to both the VISG4-L and VSIG4-S isoforms, indicating binding to the IgV domain, and have overlapping antibody cross-blocking profiles that do not overlap with clones 13H11, 15A06, and 15C04. At a more granular level, within the IgV domain there are three clusters of antibody crossblocking profiles: i) 14C05 and 14D12, ii) 12A12, and iii) 16E10, 15C03, 12A08, and 16E03. Within the IgC2 domain there are two clusters of antibody crossblocking profiles: i) 13H11, and ii) 15A06 and 15C04.

TABLE 9

Representative epitope binning data

| mAb | 14C05 | 14D12 | 12A12 | 16E10 | 15C03 | 12A08 | 16E03 | 13H11 | 15A06 | 15C04 |
|---|---|---|---|---|---|---|---|---|---|---|
| 14C05 | 0.11 | 0.12 | 0.72 | 0.74 | 0.44 | 0.72 | 0.78 | 0.74 | 0.80 | 0.72 |
| 14D12 | 0.07 | 0.08 | 0.70 | 0.69 | 0.41 | 0.70 | 0.79 | 0.69 | 0.79 | 0.72 |
| 12A12 | 0.83 | 0.75 | 0.13 | 0.25 | 0.76 | 0.78 | 0.90 | 0.74 | 0.91 | 0.82 |
| 16E10 | 0.87 | 0.93 | 0.62 | 0.15 | 0.93 | 0.44 | 0.37 | 0.95 | 0.95 | 0.92 |
| 15C03 | 0.38 | 0.59 | 0.65 | 0.88 | 0.15 | 0.89 | 0.10 | 0.86 | 0.79 | 0.81 |
| 12A08 | 0.75 | 0.73 | 0.86 | 0.00 | 0.80 | 0.10 | 0.13 | 0.70 | 0.88 | 0.80 |
| 16E03 | 0.62 | 0.68 | 0.64 | 0.10 | 0.13 | 0.10 | 0.04 | 0.72 | 0.73 | 0.74 |
| 13H11 | 0.66 | 0.69 | 0.74 | 0.65 | 0.74 | 0.69 | 0.76 | 0.09 | 0.53 | 0.68 |
| 15A06 | 0.68 | 0.75 | 0.77 | 0.77 | 0.82 | 0.76 | 0.83 | 0.51 | 0.12 | 0.08 |
| 15C04 | 0.76 | 0.80 | 0.76 | 0.89 | 0.89 | 0.94 | 0.86 | 0.68 | 0.15 | 0.16 |

Example 3: Validation of Anti-VSIG4 Antibodies for Increasing Macrophage Inflammatory Phenotype Using Macrophage Assays Human macrophages exist in a differentiation spectrum from pro-inflammatory (M1-like, also referred to herein as Type 1) to pro-tumorigenic/anti-inflammatory (M2-like, also referred to herein as Type 2) (see, e.g., Biswas et al. (2010) *Nat. Immunol.* 11: 889-896; Mosser and Edwards (2008) *Nat. Rev. Immunol.* 8:958-969; Mantovani et al. (2009) *Hum. Immunol.* 70:325-330). Along this spectrum of functionality, macrophages alter their surface marker expression and morphology, in addition to altering multiple other characteristics. Understanding how these markers change with changing functionality in primary human macrophages is important for understanding what cells are present in a given immunological environment, such as within tumors (tumor-associated macrophages) and/or inflamed tissues, and for understanding how these macrophages affect the immune response within these tissues. Certain cell surface markers, including CD163, CD16, and CD206, traditionally have been used to classify macrophage subtypes.

In line with these differentiated states, macrophages are biologically optimized to either induce or suppress an immune response. Therefore, targeting VSIG4 on the surface of macrophages via an antibody will allow for the alteration of the initiation, suppression and/or perpetuation of immune responses.

For each monocyte/macrophage cell-based experiment described herein, primary human monocytes, macrophages, and/or PBMCs were used, as opposed to using cell lines, in order to recapitulate the biological properties mimicking in vivo existing cells in the closest possible way that any in vitro experimental system with isolated cell types allows. In particular, the system provides access to studying natural biological properties of primary cells and provides access to natural diversity arising from different donors having different genetic and environmental exposures. Therefore, it is important to consider natural genetic and immunological variability among the human population when interpreting the results of the assays.

The antibodies described in Example 2 have been utilized in functional assays. The effect of these antibodies on macrophage differentiation state was measured by readouts, including cytokine secretion and other functional characteristics, such as the ability to perpetuate a concerted immune response in complex multi-cellular assays.

Figure 5:
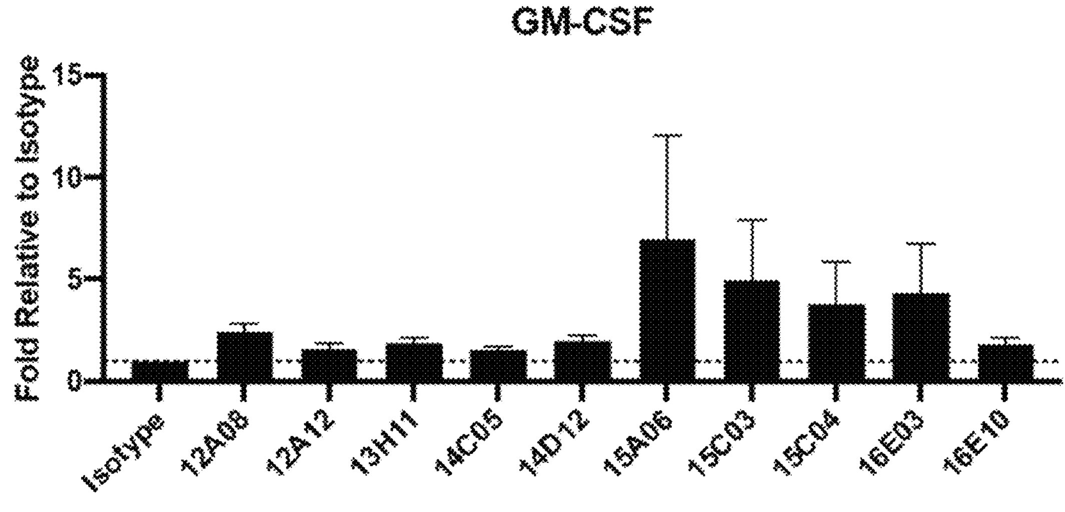
FIG. 5 shows the results of validating anti-VSIG4 antibodies in a macrophage functional assay. Anti-VSIG4 antibodies were demonstrated to modulate macrophage inflammatory phenotype in M2-skewing conditions after inhibition of VSIG4 in primary human macrophages, including an increase in M1 pro-inflammatory cytokines.
Figure 5:
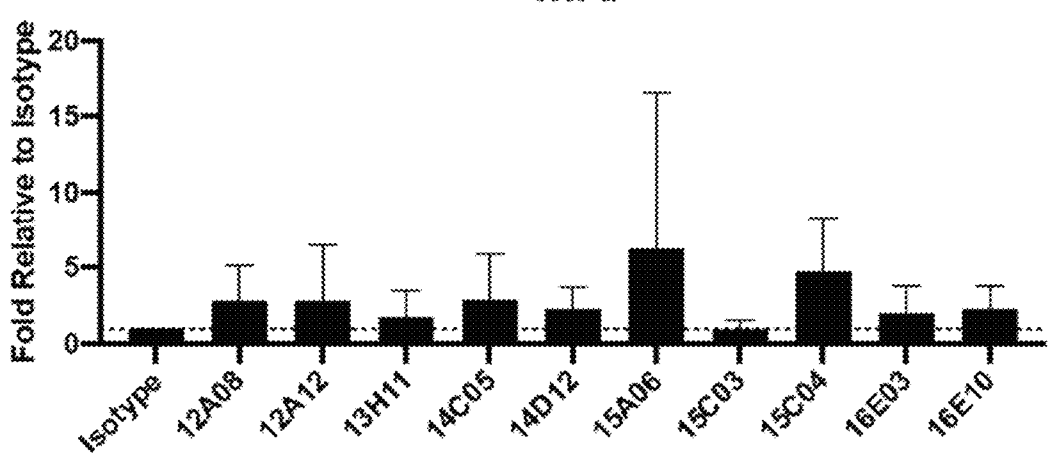

For example, FIG. 5 shows the results of the antibodies listed in Tables 2-5 that were utilized in a macrophage functional assay. Monocytes were differentiated in vitro to M2-like (Type 2) phenotypes (Ries et al. (2014) *Cancer Cell* 25:846-859; Vogel et al. (2014) *Immunobiol.* 219:695-703). In order to differentiate monocytes into M2 macrophages, monocytes were isolated from whole blood of healthy donors by Ficoll separation with RosetteSep™ Human Monocyte Enrichment Cocktail (Stemcell Technologies, Vancouver, Canada) according to the manufacturer's instructions. Isolated monocytes were arrayed in 24 or 96 well plates overnight in IMDM Media containing 10% fetal bovine serum and non-adherent cells were washed off after 24 hours. Monocytes were differentiated into macrophages by culturing for 6 days in IMDM 10% FBS plus 50 ng/ml human M-CSF for M2 macrophages. After 6 days, M2 macrophages were polarized with 20 ng/ml IL-10 and activated on day 7 with 100 ng/ml LPS.

Monoclonal antibodies listed in Table 2 were administered at a final concentration of 10 ug/ml on day 7 of culture prior to activation. On day eight, cell cytokines and chemokines were measured to assess ability the specific mAbs to alter the pro- or anti-inflammatory nature of the macrophages. Cytokines from supernatant were measured using the 25-Plex Human Cytokine Luminex panel, LHC0009M (Thermo Fisher, Waltham, MA) according to the manufacturer's protocol. Data are representative of at least 3-4 healthy donors.

Macrophages produce different cytokines and chemokines. For example, M1 macrophages produce more pro-inflammatory cytokines, including but not limited to, GM-CSF, IL-12, and TNF-alpha, whereas M2 macrophages produce more pro-tumorigenic and immunosuppressive cytokines, such as VEGF, IL-10, and TGFb. Throughout these assays the macrophages are strongly driven, via the presence of potent cytokines IL-10 and M-CSF, to an M2 phenotype. Multiple representative mAbs, such as 12A08, 12A12, 15A06, and 15C03 and others, were able to drive these M2 macrophages to a more M1-like state as exemplified by increased GM-CSF and TNFa. These figures further demonstrate the ability of anti-VSIG4 antibodies to alter the functional characteristics of M2 macrophages to a more M1-like state. Importantly, cells within these assays undergoing differentiation remain in the presence of potent skewing conditions through the entirety of the assay. Furthermore, the antibodies were only present in the cultures for 24 hours. This is more representative of a disease setting, such as a tumor, where it is known that the cells will already be differentiated to some extent along the M2 spectrum, as shown above. Even during this limited window, mAbs were able to dramatically effect polarization of M2 macrophages to a more M1-like state as demonstrated by the increase in pro-inflammatory cytokines. Even considering the challenging polarizing conditions of this assay, a mAb in this assay was considered functionally able to switch the M2-like macrophage to a M1-like macrophage if it was able to induce a 50% or greater change in one or more cytokines, including GM-CSF, IL-12, TNFa, IL-10, CXCL9, CCL-4, and IL-lb. As can be seen in FIG. 5, most of the mAbs effect not only a change in one of the cytokines or chemokines, but effect multiple changes. Furthermore, these figures demonstrate the ability of anti-VSIG4 antibodies to reverse the functional characteristics of M2 macrophages to make them more M1-like.

Example 4: Anti-VSIG4 Antibody-Mediated Macrophage Repolarization Leads to Increased Inflammation Using Complex Immune Cell Assays For macrophages to induce tumor immunogenicity or reverse the course of autoimmune and inflammatory disorders, they generally should able to induce or attenuate a concerted immune response. This would include having direct and downstream effects on both myeloid and lymphoid cells. Complex multi-cellular assays consisting of primary cells from both the lymphoid and myeloid lineage are needed to analyze such effects.

Given that VSIG4 is expressed only on suppressive myeloid cells, an experimental system was needed to interrogate the ability of VSIG4-mediated repolarization of myeloid cells to result in downstream T cell activation. In order to do so a macrophage SEB assay was utilized. This assay takes advantage of primary human cells, which are the most natural cells to study and have the best predictive power for in vivo disease, such as human disease. This assay naturally has high variability from donor to donor both in the amplitude of background activity and response.

For this assay, M2c macrophages were generated as described above. On day 7, anti-VSIG4 mAbs were added and macrophages were activated with LPS. On day 8, the SEB portion was begun. For the SEB assay, autologous T cells that had been previously isolated from the same blood of fresh donors by Ficoll® separation and frozen in 90% fetal bovine serum (FBS), 10% DMSO at −150° C. until day 8 of the assay. T cells were thawed into complete RPMI media containing 10% FBS, 50 nM 2-mercaptoethanol, non-essential amino acids, 1 mM sodium pyruvate, and 10 mM HEPES. Next, 5×10^4 T cells and mAbs were incubated at 37° C. for 30 minutes and Staphylococcal enterotoxin B (SEB) (EMD Millipore, Billerica, MA) was added at a final concentration of 0.1 μg/ml. After 4 days of activation, supernatant was collected and frozen at −20° C. Cytokine concentration was measured using multi-parameter ProcartaPlex™ Assay (ThermoFisher Scientific). Data are representative of at least 4-6 healthy donors.

Figure 6:
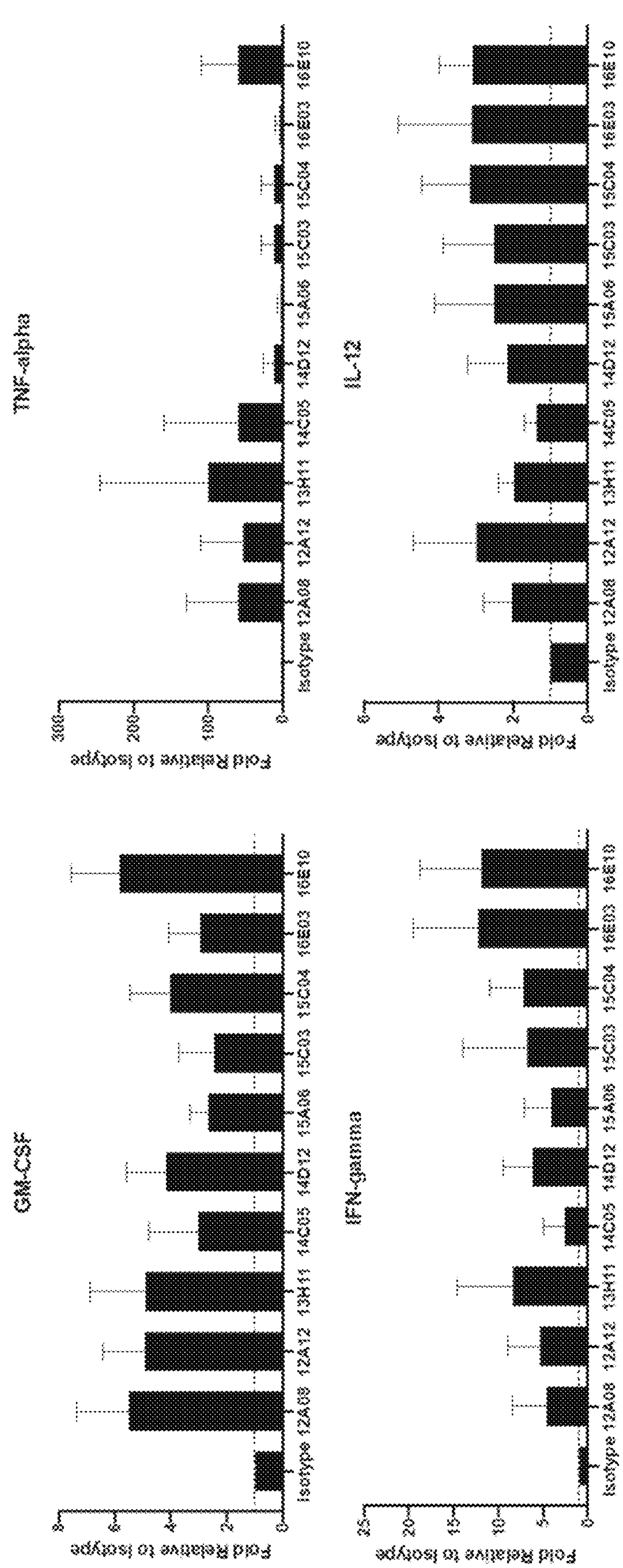
FIG. 6 shows the results of Staphylococcal enterotoxin B (SEB) assay experiments.

In this assay, specific antibodies to VSIG4 were demonstrated to be able to impact a concerted multi-cellular immune response. This concerted multi-cellular response included not only altering the function of myeloid cells as previously demonstrated but also the functional output of lymphoid cells, specifically T cells. In this assay, mAbs were considered functional if they were able to induce a 50% or greater change in one or more of the cytokines including GM-CSF, IL-12, TNFa, IL-10, CXCL9, CCL-4, IL-1b, and/or IFNg. FIG. 6 demonstrates secreted cytokine levels from the macrophage SEB assay. Treatment with mAbs led to changes in the production of myeloid-derived cytokines and chemokines (e.g., TNFa & IL-12) and T cell-derived cytokines (e.g., IFNγ). Importantly, the ability of these anti-VSIG4 mAbs were compared to Keytruda®, which is an approved therapy in immune oncology and a strong activator within the SEB arm of this assay. FIG. 6 demonstrates that anti-VSIG4 mAbs were able to equal or exceed the effects of the Keytruda®-treated samples.

As in the macrophage-only assay described in Example 3 above, the results clearly demonstrate that mAbs, such as 12A08, 12A12, 13H11, 16E10 and others, drive macrophages to a more pro-inflammatory M1-like state and this macrophage repolarization has a consistent effect in the activation of lymphoid immune cell types. As demonstrated above, expression of VSIG4 is restricted to the M2c macrophages in this assay so the increased IFNg production is not a direct result of the anti-VSIG4 mAbs binding to T cells or other lymphocytes. Rather this is believed to be induced by two non-mutually exclusive mechanisms, including 1) increased T cell activation via the newly repolarized cells and 2) inhibition of the interaction of VSIG4 on myeloid cells expressing VSIG4, such as macrophages, with a yet unidentified inhibitory counter receptor on T cells.

Example 5: Anti-VSIG4 Antibody-Mediated T Cell De-Repression

Figure 7:
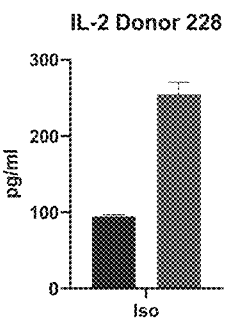
FIG. 7 shows the results of anti-VSIG4 antibody-mediated T cell de-repression.
Figure 7:
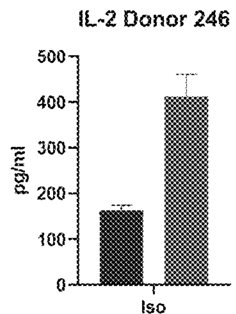
Figure 7:
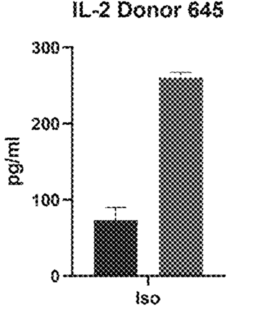
Figure 7:
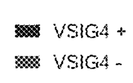

In Example 4 above two non-mutually exclusive mechanisms via which VSIG4 mAbs can lead to an indirect T cell activation were outlined. The second of these mechanisms was that an anti-VSIG4 mAb may block the interaction of VSIG4 on myeloid cells expressing VSIG4, such as macrophages, with a yet unidentified inhibitory counter receptor on T cells (Liao et al. (2014) *Laboratory Investigations* 94:706-715). FIG. 7 further supports this mechanism. Briefly, VSIG4+ HEK cells are able to suppress T cell activity. Specifically, HEK cells either stably expressing VSIG4 (VSIG+) or a parental non-VSIG4 expressing (VSIG4−) were plated at 5,000 cells per well. T cells were added at 50,000 cells per well. The T cells were activated with 1 ug/uL of plate-bound anti-CD3 and 0.05 ug/mL of soluble anti-CD28 in the presence of an isotype control antibody. The co-culture was allowed to incubate for 3 days and IL2 was subsequently measured via Luminex® analyses, as described above. In 3 different donors, the presence of VSIG4 on the HEK cells led to suppressed T cell activity (FIG. 7).

Example 6: Anti-VSIG4 Antibodies Lead to Increased Inflammation in Tumors

The above in vitro systems clearly show the ability of VSIG4 on macrophages to alter macrophage function, as well as function of complex multi-cellular systems that include T cells. Moreover, numerous representative anti-VSIG4 mAbs were validated to confirm in vitro VSIG4 target binding, macrophage polarization, functionality testing, and biophysical characterization. In order to further confirm the potency of such representative anti-VSIG4 antibodies, these data were further confirmed using patient tumor material in an ex vivo culture system. This type of system represents a close and generally accepted surrogate to a human in vivo study, therefore providing potent evidence of therapeutic benefit. Upon acquisition of fresh tumor tissue sample (less than 24 hrs after surgery), surrounding fat, fibrous, and necrotic areas were removed from the tumor sample as much as possible using scissors and scalpels. The tissue was embedded in the center of a tissue mold using 4% agarose. After solidifying, the agarose block was dislodged, and the mold was glued to a Leica VT1000 S microtome tissue holder and sectioned into 300 to 400 micron sections using the Leica VT1000 S microtome. Tissue slices were transferred to a cell culture insert and then into a well of a 6-well cell culture plate containing media (DMEM with L-Glutamine, 4.5 g/L glucose and sodium pyruvate (Fisher Scientific), Gibco™ GlutaMAX™ Supplement (Fisher Scientific), Gibco™ MEM Non-Essential Amino Acids Solution (Fisher Scientific), 2-mercaptoethanol (55 mM) (Fisher Scientific), heat inactivated from human male AB plasma (Sigma-Aldrich, Inc), bovine calf serum heat inactivated (BioFluid Technologies), 100× pen/strep, and human M-CSF (BioLegend)) and indicated antibodies. All antibodies were added at a concentration of 10 ug/mL. The slices were then incubated at 37° C. with 5% $CO_2$ for 1-5 days. At the end of the study, efficacy was evaluated by analyzing cytokine/chemokine amounts secreted into the culture supernatant measured using the Invitrogen™ Luminex™ Cytokine Human Magnetic 25-Plex Panel according to the manufacturer's instructions. If a tumor tissue sample was not appropriate to be sliced using a Leica VT1000 S microtome, it was cut using scalpels as thinly as possible and the slices were subsequently treated as described above. For all samples, a slice was taken prior to treatment and utilized for immunophenotyping. This slice was dissociated as described above and stained for flow cytometry analyses as described above.

Figure 8:
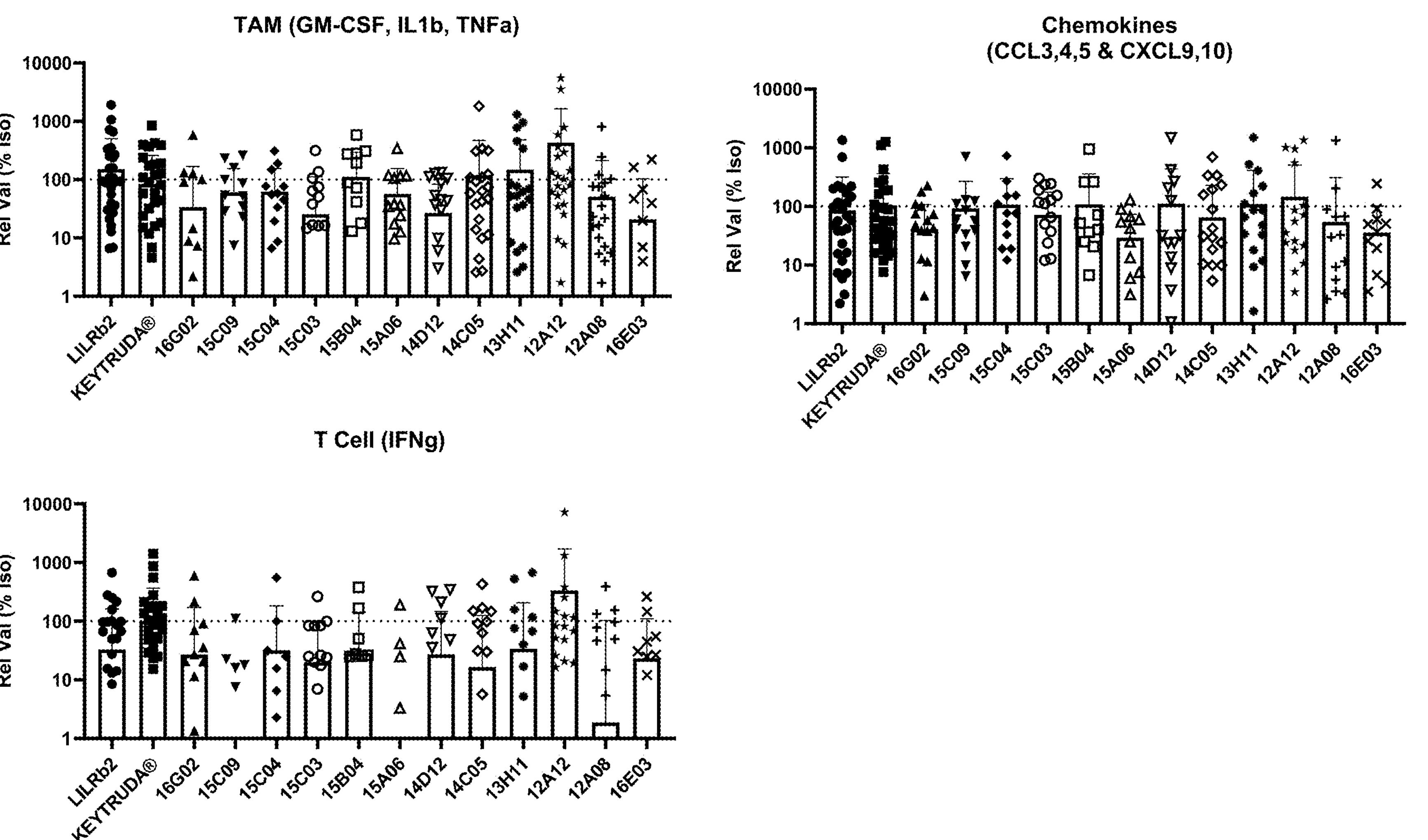
FIG. 8 shows the results of ex vivo tumor model experiments.

FIG. 8 demonstrates the function of selected antibodies across multiple tumor types and donors. In this figure, results from 34 primary human tumors across 9 tumor types (e.g., 2 breast tumor samples, 8 endometrial tumor samples, 1 glioblastoma tumor sample, 11 kidney tumor samples, 4 lung tumor samples, 1 momentum tumor sample, 3 ovarian tumor samples, 1 thyroid tumor sample, and 3 uterus tumor samples) treated with different sets of antibodies, are shown. Since the number of possible treatment arms is limited by the size of a tumor sample and the number of different test samples derived therefrom, the entire antibody panel was not tested entirely in the same individual tumors, although a large and representative number of tumors treated with antibodies were tested as summarized in Table 10 below.

TABLE 10

Summary of the tumor study composition summarizing different numbers of tumors and tumor types treated with a given antibody

| | Tumor Study Composition by Antibody | |
|---|---|---|
| Antibody Name | # of tumors | # of tumor types |
| Keytruda ® | 34 | 9 |
| 12A08 | 16 | 7 |
| 12A12 | 16 | 7 |
| 13H11 | 16 | 7 |
| 14C05 | 16 | 7 |
| 14D12 | 10 | 5 |
| 15C03 | 24 | 9 |
| 16G02 | 10 | 5 |

These ex vivo cultures maintain native tumor and tumor microenvironment (TME) conditions, including infiltration, ligands, tumor antigens, native suppressive and inflammatory stimuli, growth factors, natural mutational status, and the like. Therefore, ex vivo tumor cultures faithfully capture multiple aspects of actual tumors within patients. In particular, tumor architecture is preserved, tumor microenvironment is preserved, relationships between major immune components are preserved, and multiple aspects of clinical response to PD-1 inhibitors are captured. It is believed that anti-VSIG4 antibodies targeting macrophages and described herein have a pan-cancer profile. Indeed, the data shown in FIG. 8 are presented as the mean of the relative value (% of isotype control) across all individual tumors and tumor types treated with a particular mAb and have been broken down into three individual chemokine/cytokine groupings. These three groupings consist of myeloid-focused cytokines (such as TNFa, GM-CSF, and IL-1b), chemokines (such as CCL3, CCL4, CCL5, CXCL9, and CXCL10) and T cell activation (IFNg). These three groupings represent three important aspects of a macrophage-based anti-tumor immune response. First, the myeloid-focused cytokines indicate that the antibody has induced the repolarization of the macrophages resulting in pro-inflammatory cytokines being produced and starting the initiation of an immune response. Second, production of the key T cell cytokine, interferon gamma (IFNg), indicates that this repolarization of the TAMs and the initiation of the immune response translated to the T cells within the tumor microenvironment to create a more potent anti-tumor immune response. Third, the production of a broad panel of chemokines indicates that naïve immune cells will begin to be recruited to the tumor and lead to the perpetuation of an anti-tumor immune response.

In the ex vivo tumor model, a response of at least 30-50% upregulation of a single key cytokine (e.g., interferon gamma) is established in the field to be indicative of clinical responses (Jacquelot et al. (2017) *Nat. Commun.* 8:592; Jenkins et al. (2018) *Cancer Disc.* 8:196). In this system, average induction across multiple cytokines and chemokines is a high bar because it necessitates an effect in multiple aspects of an anti-tumor immune response. The data consistently demonstrate that, in agreement with in vitro data above, anti-VSIG4 mAbs increase myeloid- and T cell-derived cytokines. As noted above, a change of 30-50% of a single cytokine is indicative of a clinical response. Therefore a consistent upregulation of multiple cytokines and chemokines, in this same range, demonstrates an incredibly potent anti-VSIG4 mediated anti-tumor response. FIG. 8 demonstrates multiple antibodies that meet these criteria and also provides numerous representative mAbs, such as 15B04, 14C05, and 12A12, that lead to greater than 100% increase cytokines and chemokines.

One such cytokine was IFNg. As discussed above, VSIG4 is expressed on the suppressive myeloid cells (macrophages and DCs), but VSIG4-mediated repolarization of these suppressive myeloid cells can lead to increased activation of T cells. Additionally, VSIG4 has the capability of directly inhibiting T cells via the interaction with a yet unidentified receptor as described in Example 5 above. Both are useful functions of these anti-VSIG4 mAbs. To that end, IFNg production was measured and many mAbs were demonstrated to induce an increase level of IFNg by T cells. This effect can be compared directly to Keytruda®, which has a different mechanism of action that leads directly to greater IFNg production by T cells. The effect seen from multiple anti-VSIG4 mAbs is very similar to Keytruda® treatment.

Consistent changes were also demonstrated in the more myeloid-derived cytokines, such as TNFa, IL1b, and GM-CSF. Many anti-VSIG mAbs induced greater than 50% increase in these cytokines. This effect can be compared to an anti-LILRb2 mAb. LILRB2 is proposed to have a unique, but related mechanism, in myeloid cells (Chen et al. (2018) *J. Clin. Invest.* 128:5647-45662). Many anti-VSIG4 mAbs perform as well as or better than the anti-LILRB2 mAb.

As described above, anti-VSIG4 antibody-mediated responses to VSIG4 target inhibition were measured in part using a multi-plex system measuring a set of cytokines and chemokines in the culture media of each treatment arm well by the end of each experiment and effects can be represented by one or more of three interconnected but distinct mechanisms: macrophage inflammatory activation; chemokines that attract fresh immune cells into the tumor site and fuel the inflammatory reaction against the tumor; and T cell activation. In the data described below (e.g., FIGS. 9-14), averages for each individual antibody correspond to a representative number of individual tumors that this particular antibody was tested in, which is a subset of the total dataset, since not all antibodies were in all individual tumors due to physical tumor sample size limitations described above.

Figure 9:
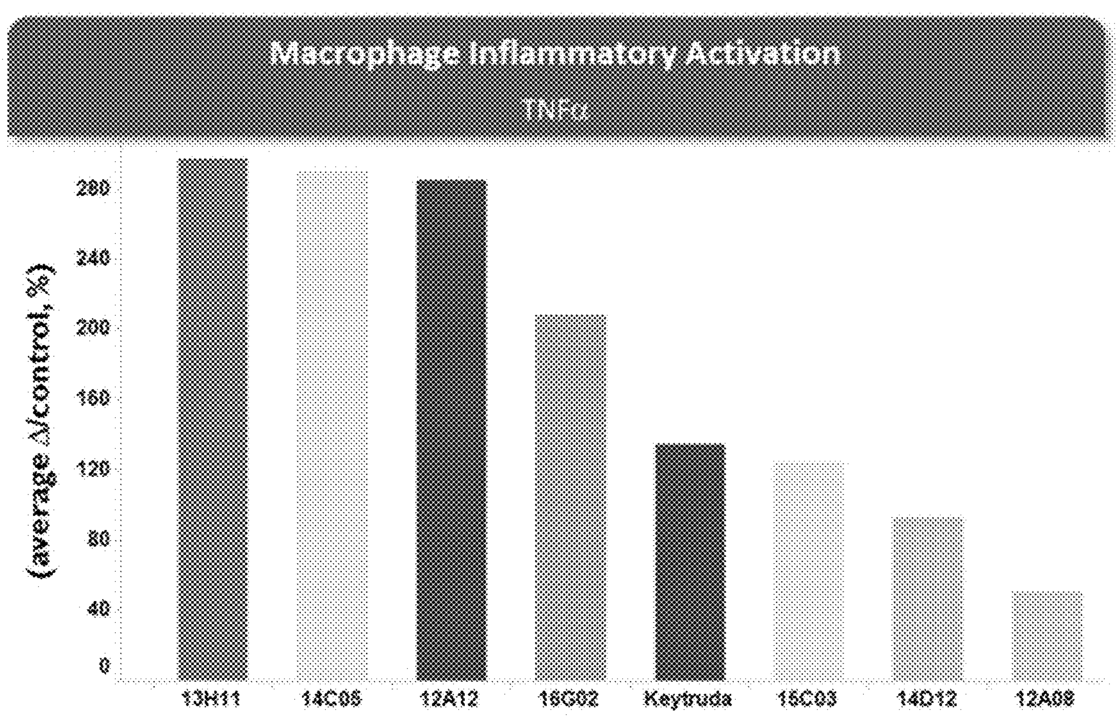
FIG. 9 shows the results of anti-VSIG4 antibodies on a macrophage inflammatory activation (e.g., increased secretion of TNFα and IL-1β) averaged across all tumors analyzed.
Figure 9:
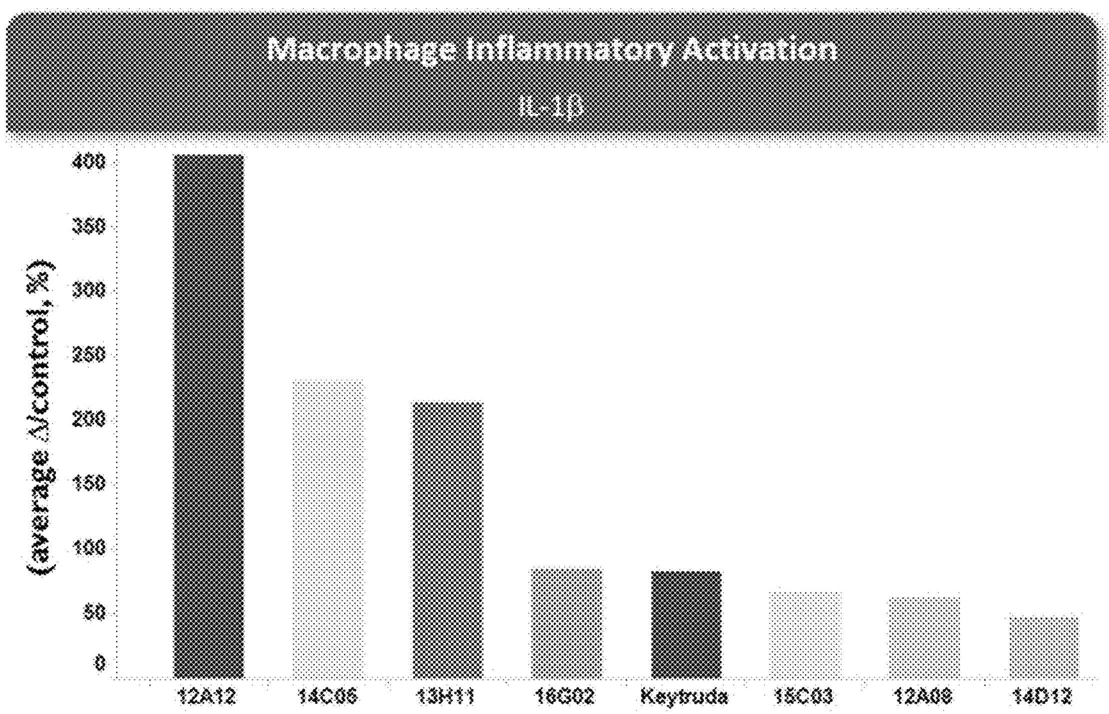

In a separate mode of showing aggregate data from that of FIG. 8, a macrophage inflammatory activation signature was further modeled by measuring two of the most well recognized inflammatory cytokines: TNFα and IL-1β. FIG. 9 shows how each anti-VSIG4 antibody induced secretion of these two cytokines on average across all tumors. As with similar figures described below, the Y-axis shows induced change over the isotype control arm as the percentage of the isotype control arm, representing a no-treatment background value for a given tumor. Also, the percentage change was then averaged across all tumors to show an overall effect across multiple tumors and tumor types.

A chemoattaction signature was also modeled by combining an effect across several chemokines that are observed to be endogenously expressed in "hot" T cell infiltrated tumors and considered in the art to be indicative of response to T cell checkpoint inhibitors: CCL3, CCL4, CCL5, CXCL9, and CXCL10 (Dangaj et al. (2019) *Cancer Cell* 885-900; House et al. (2020) *Transl. Cancer Mech. Ther.* 26:487-504; Lapteva et al. (2010) *Exp Opin Biol Ther.*

Figure 10:
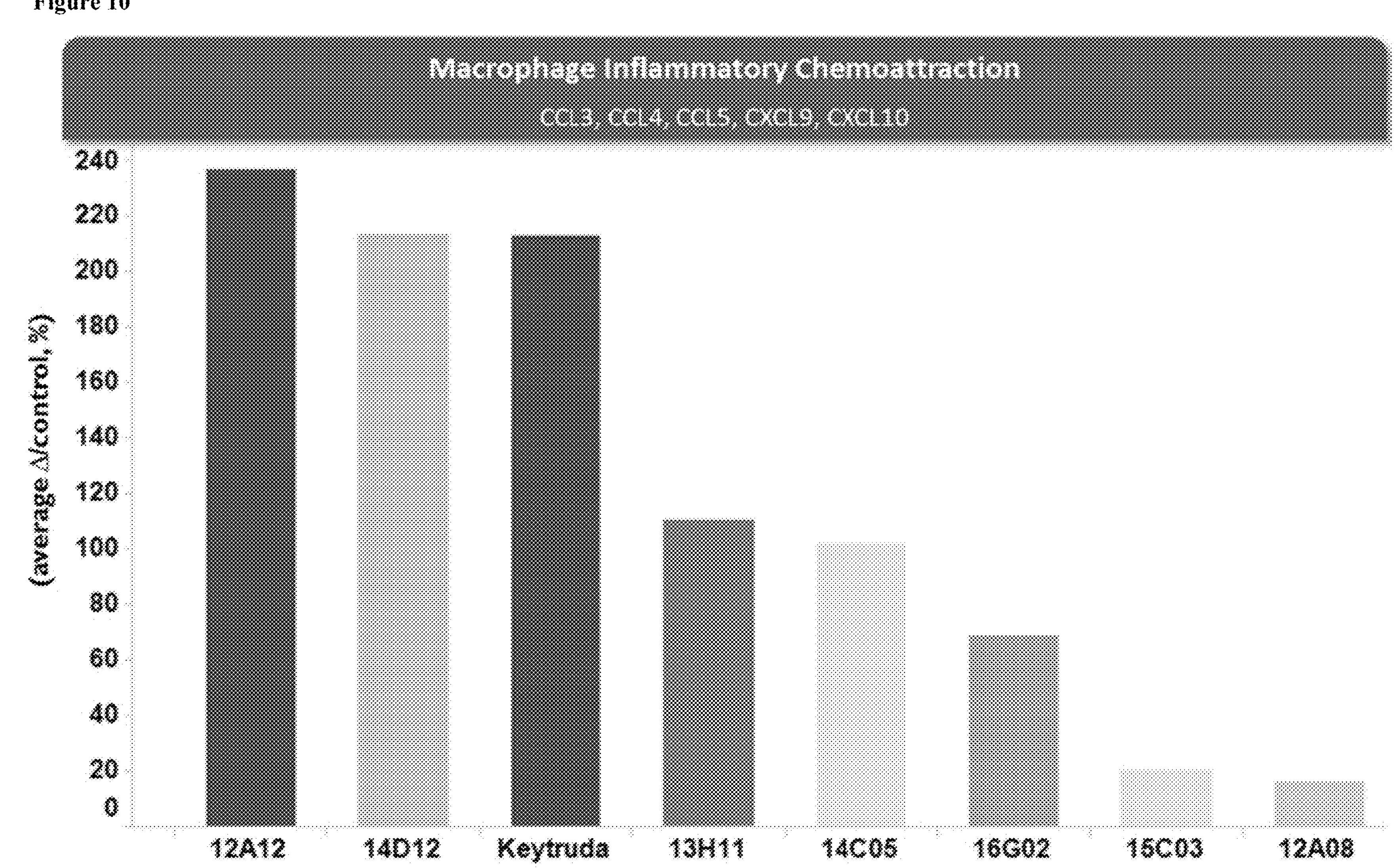
FIG. 10 shows the results of anti-VSIG4 antibodies on a chemokine signature (e.g., increased secretion of CCL3, CCL4, CCL5, CXCL9, and CXCL10) averaged across all tumors analyzed.

10:725-733). FIG. 10 shows how each anti-VSIG4 antibody induced secretion of the chemokines within a chemokine signature on average across all tumors.

Figure 11:
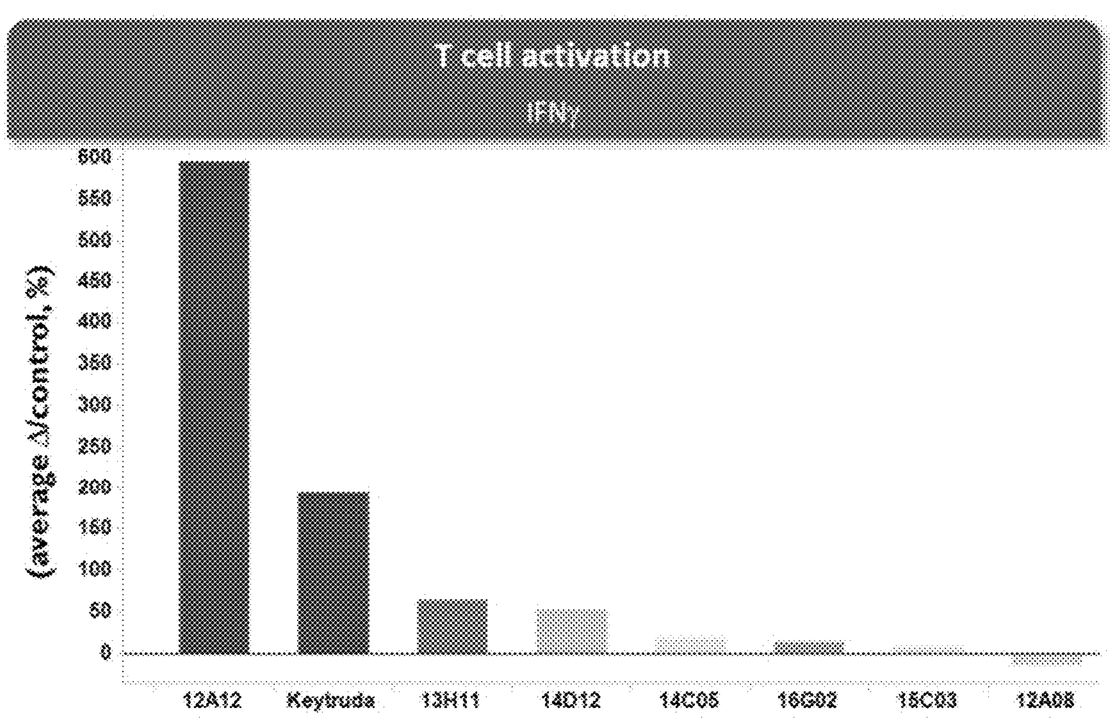
FIG. 11 shows the results of anti-VSIG4 antibodies on a T cell activation signature (e.g., increased secretion of IFNγ and IL-2) averaged across all tumors analyzed.
Figure 11:
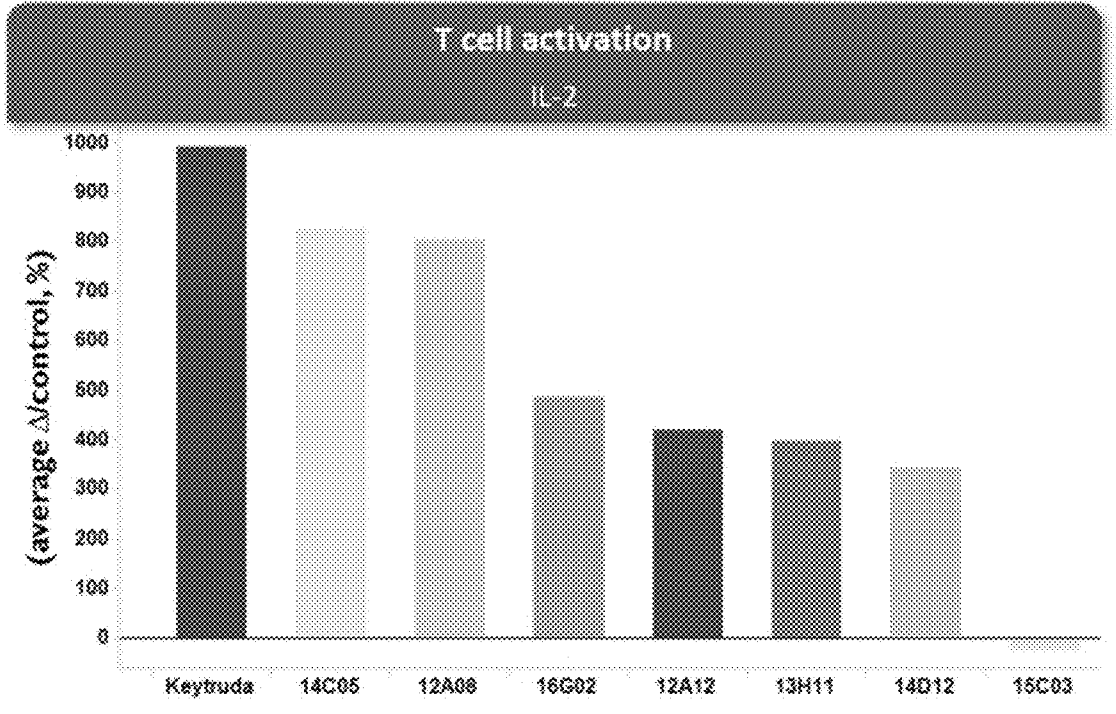

In addition, a T cell activation signature was modeled by measuring two of the most well-accepted T cell cytokines: IFNγ and IL-2. FIG. 11 shows how each anti-VSIG4 antibody induced secretion of these two cytokines on average across all tumors.

Figure 12:
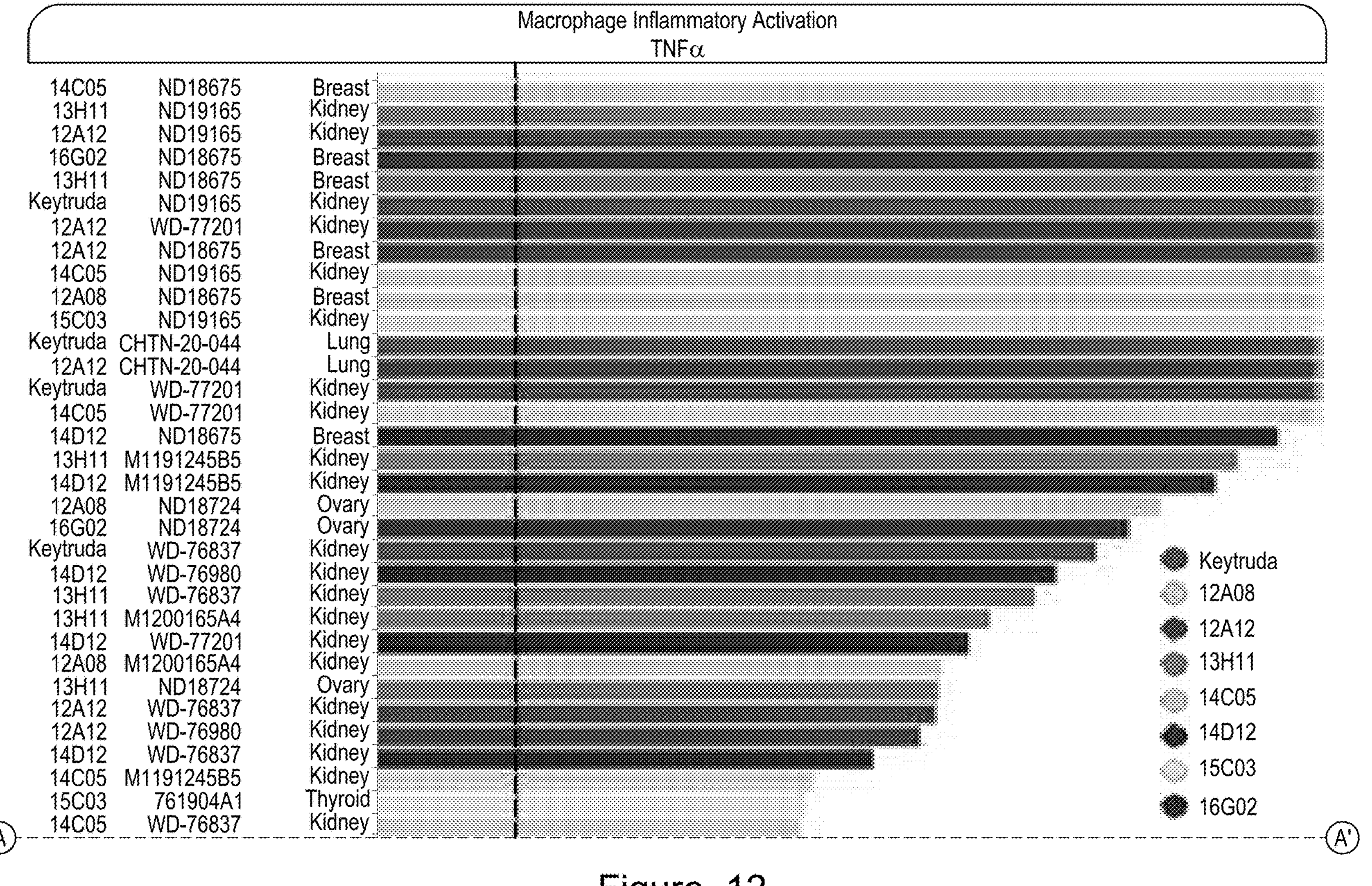
FIG. 12 shows the results of anti-VSIG4 antibodies on increasing secretion of TNFα and/or IL-1β in individual tumors.
Figure 12:
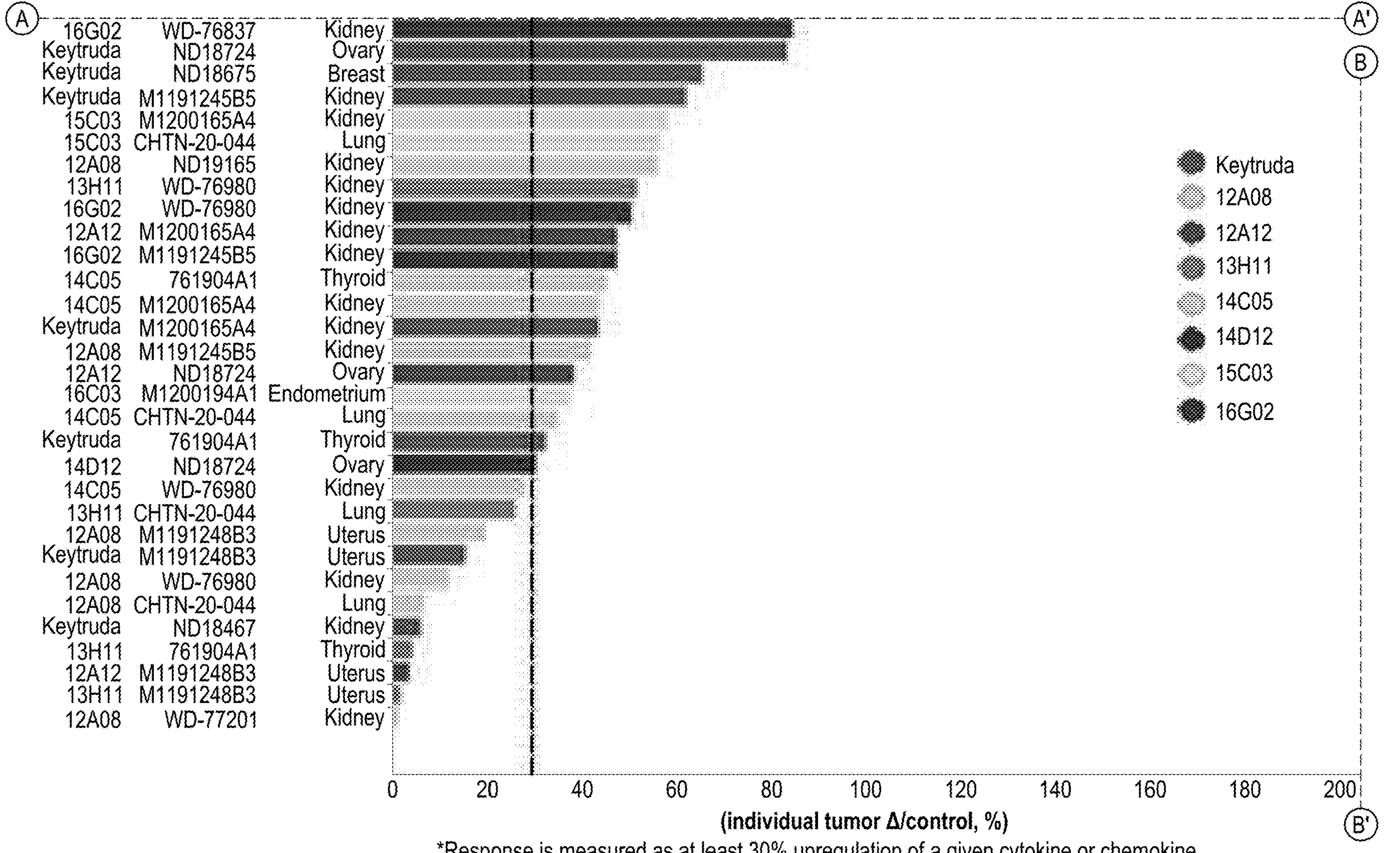
Figure 12:
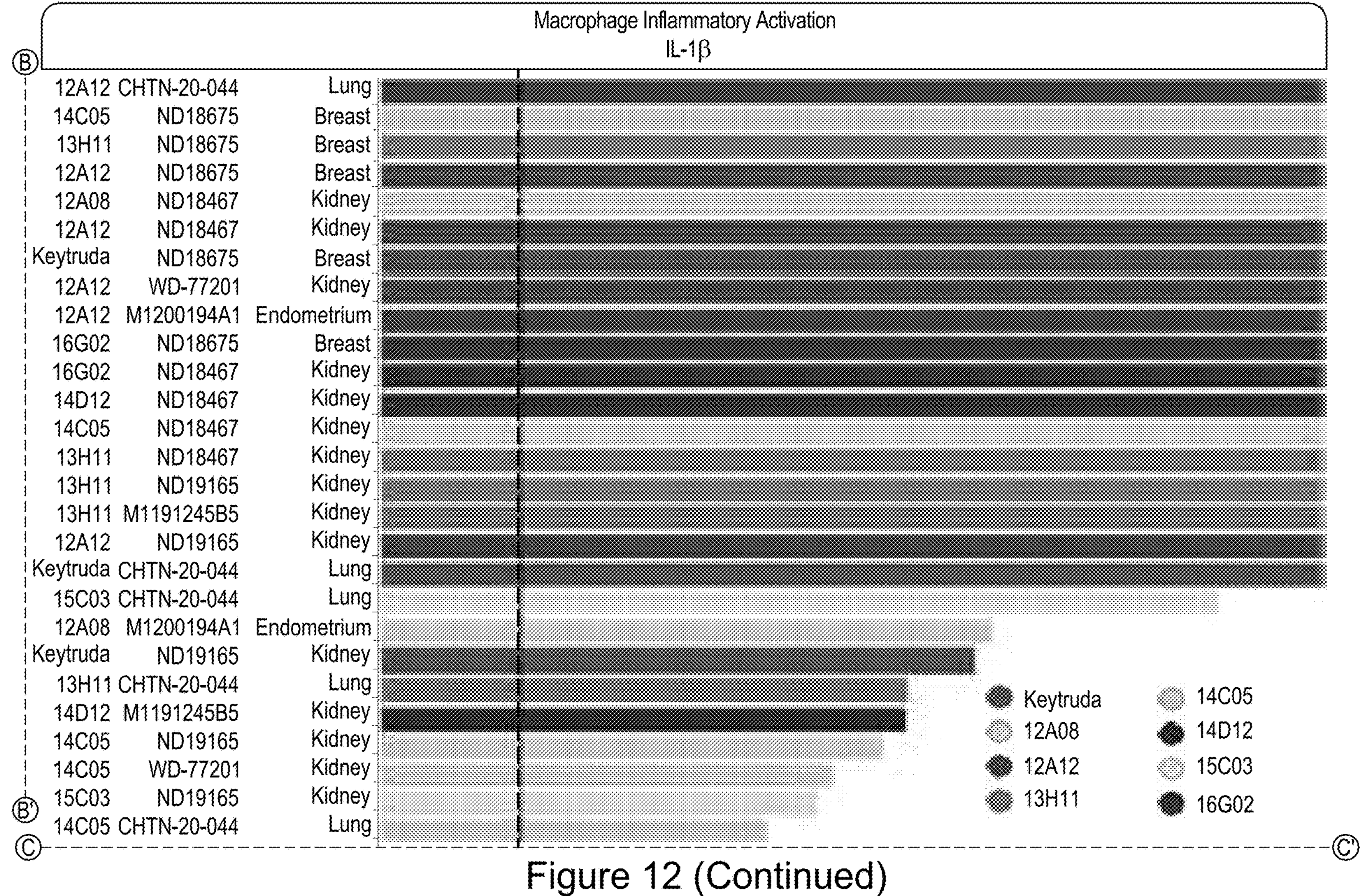
Figure 12:
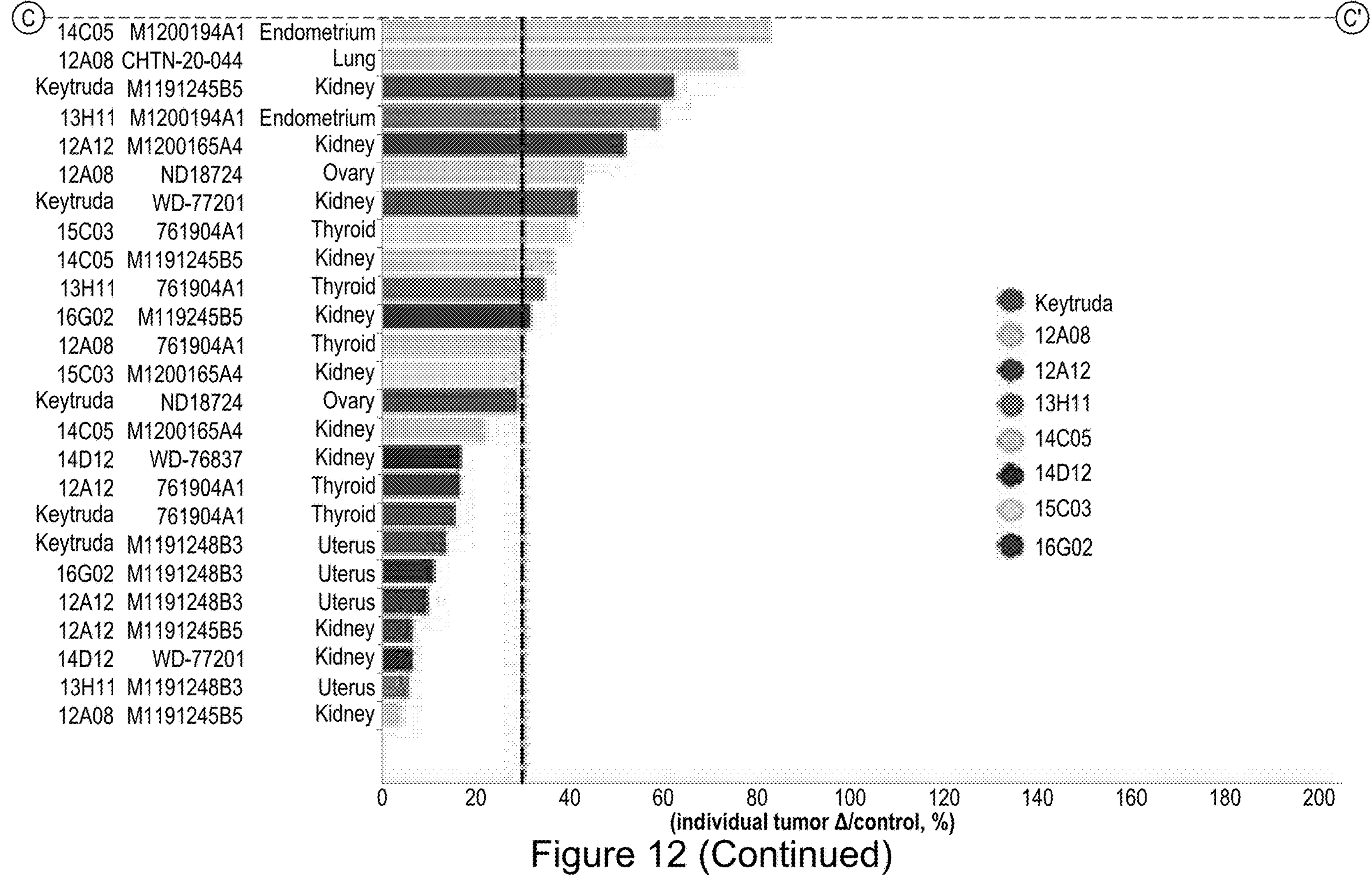
Figure 13:
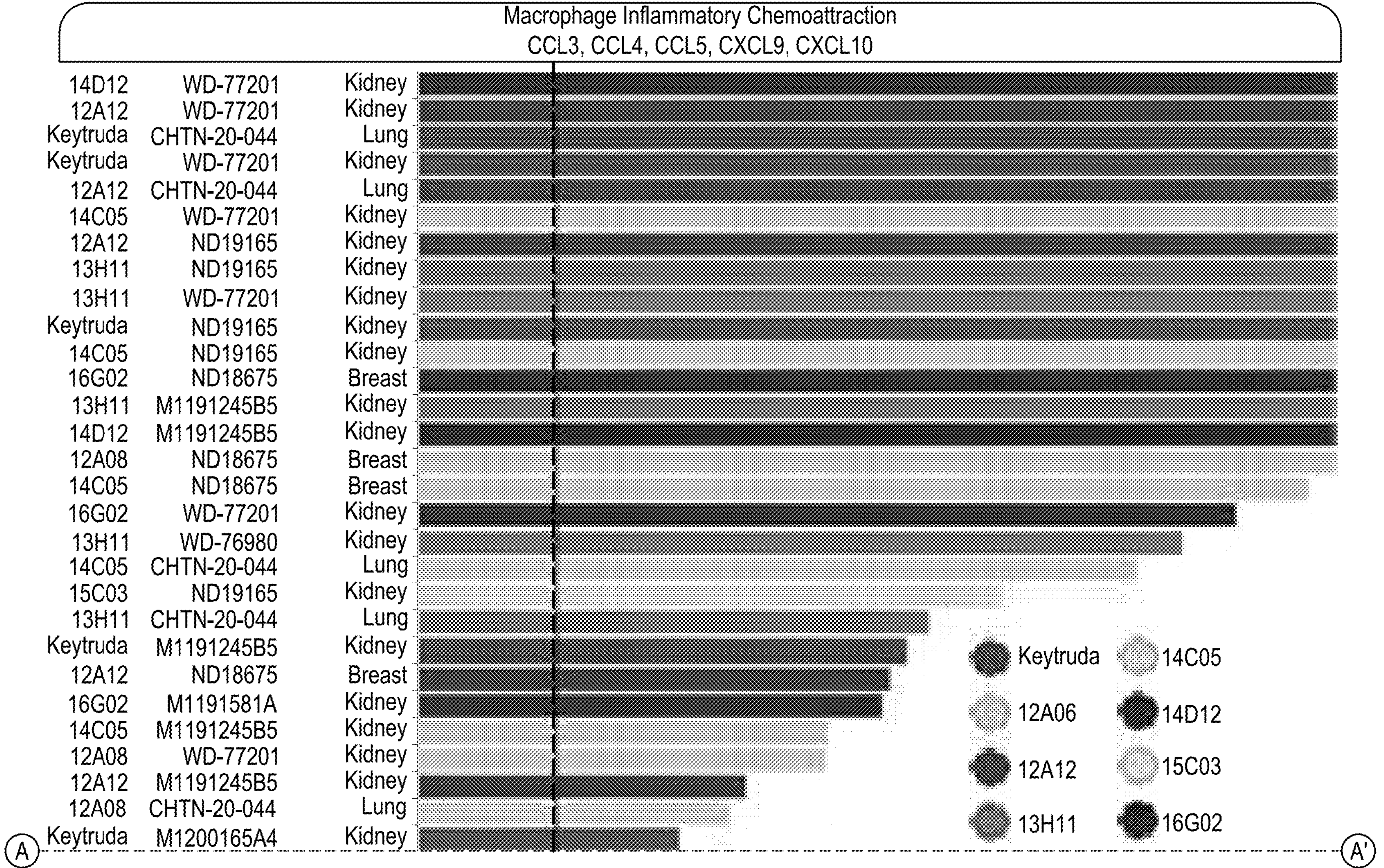
FIG. 13 shows the results of anti-VSIG4 antibodies on increasing secretion of CCL3, CCL4, CCL5, CXCL9, and/or CXCL10 in individual tumors.
Figure 13:
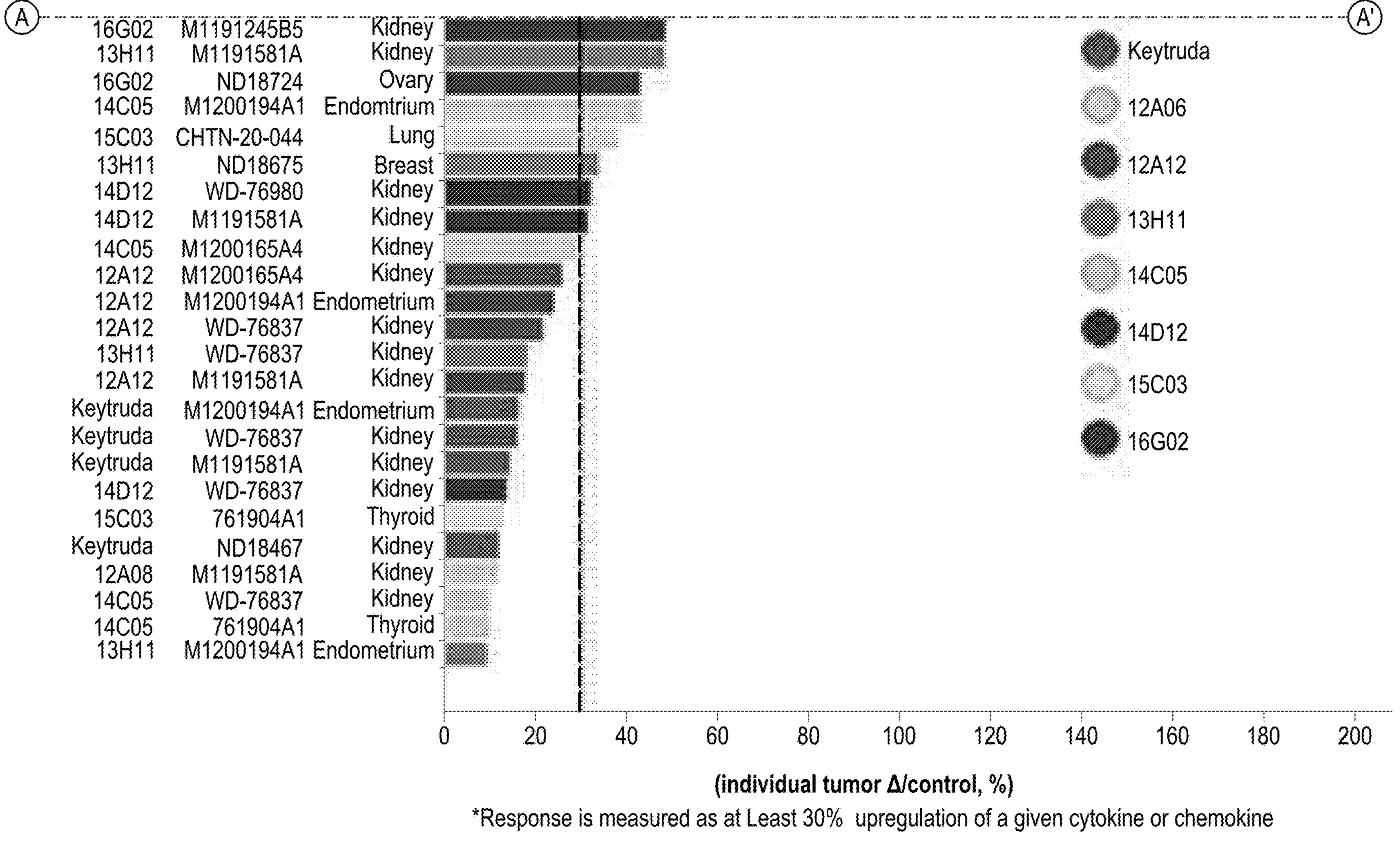
Figure 14:
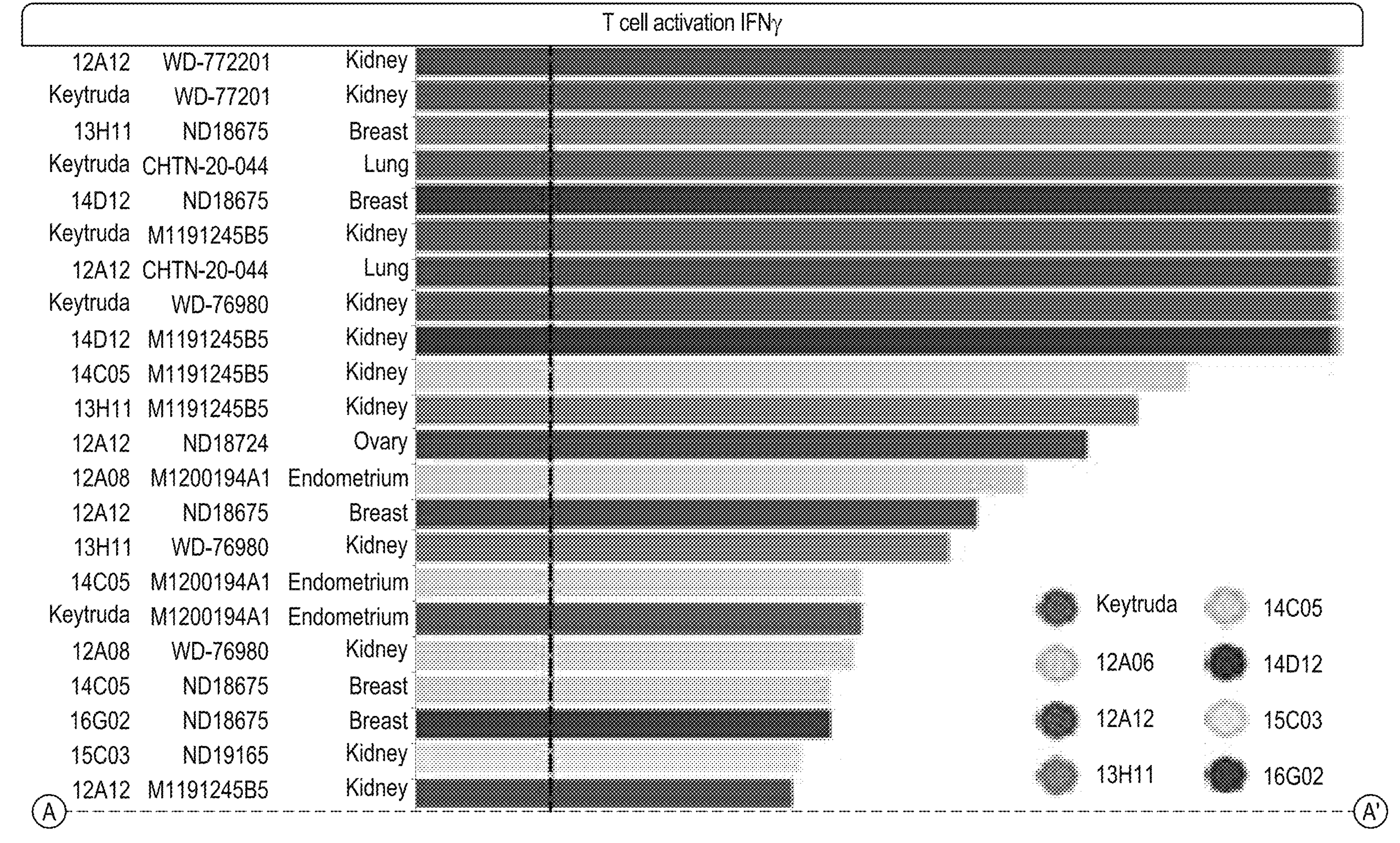
FIG. 14 shows the results of anti-VSIG4 antibodies on increasing secretion of IFNγ and/or IL-2 in individual tumors.
Figure 14:
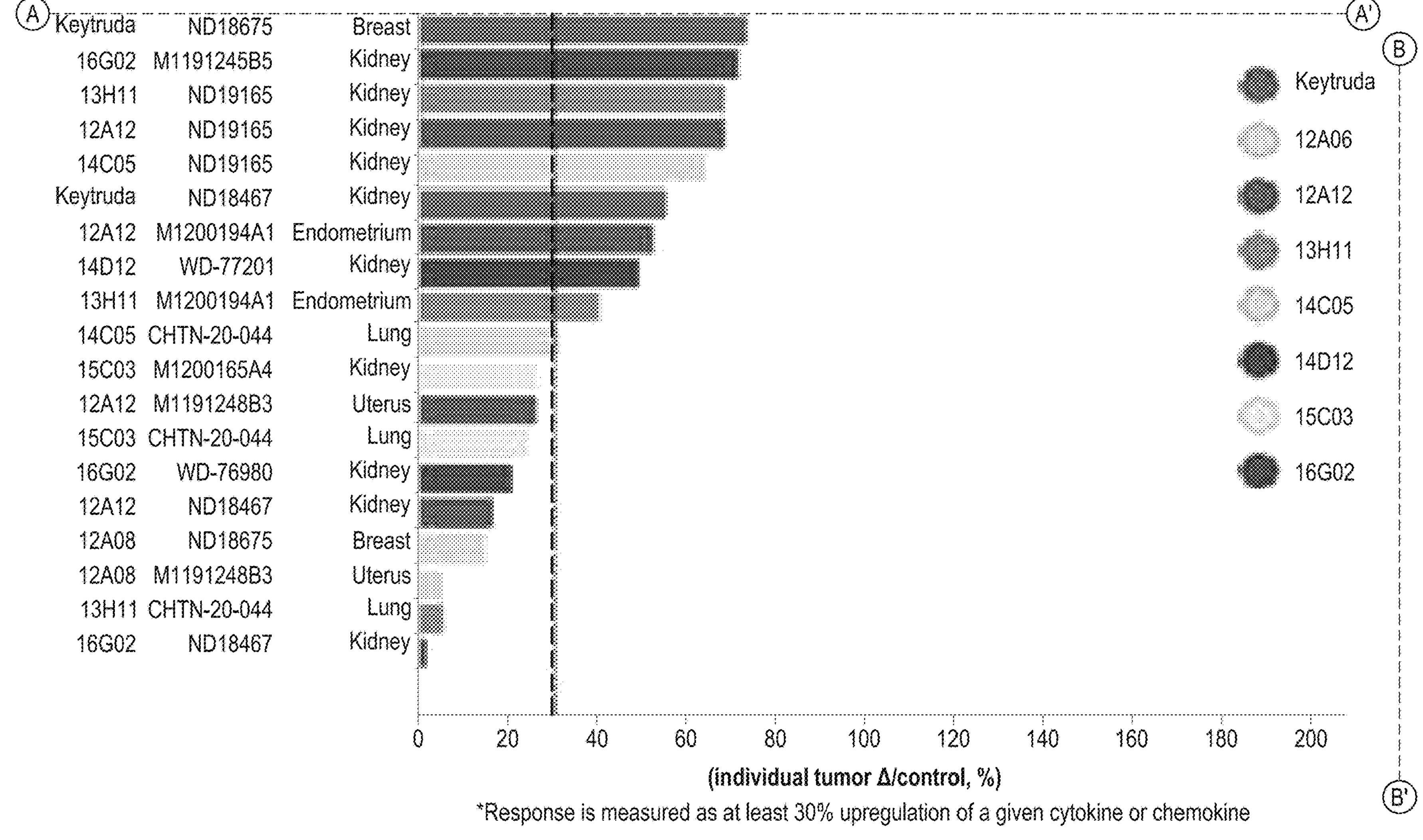
Figure 14:
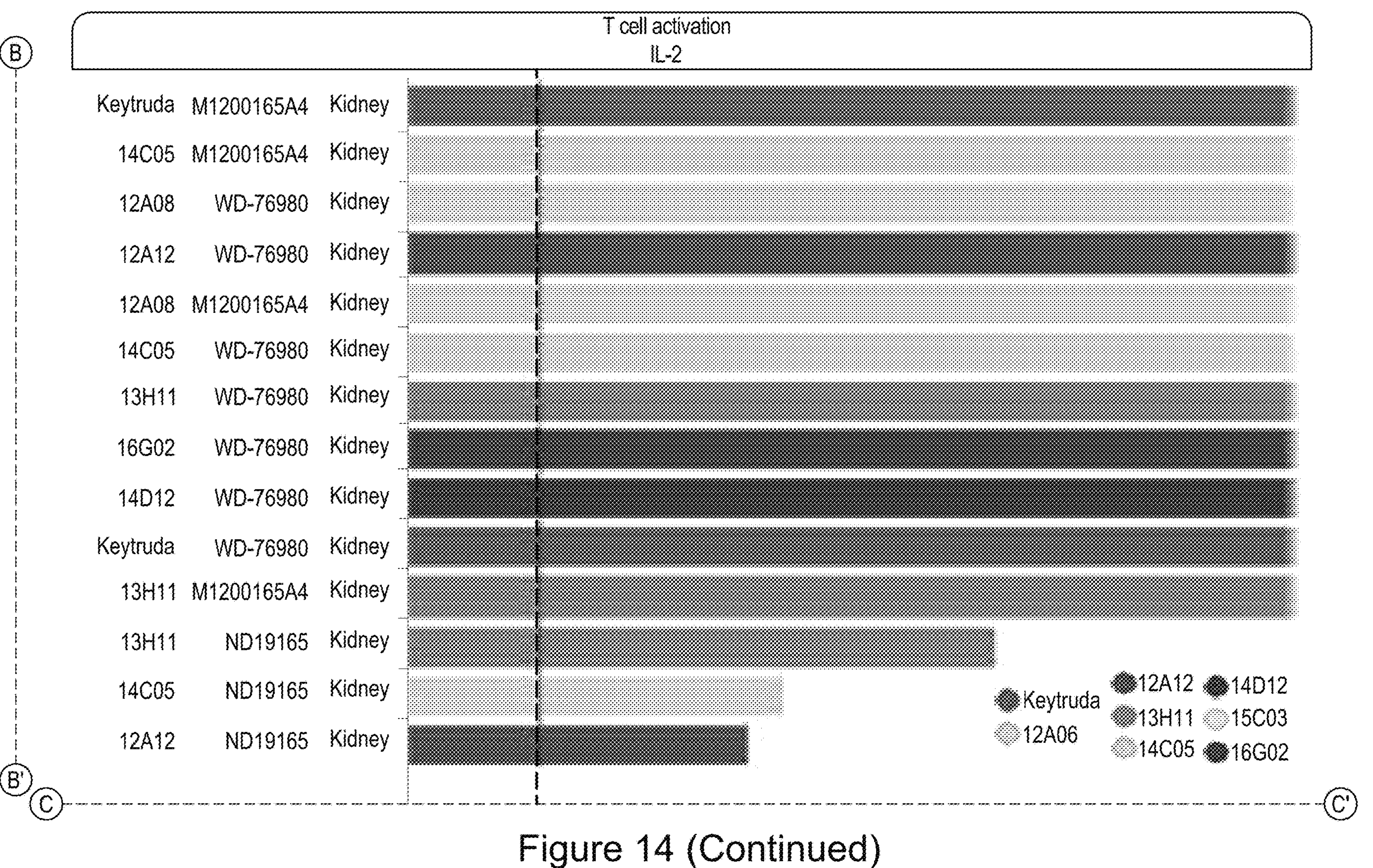
Figure 14:
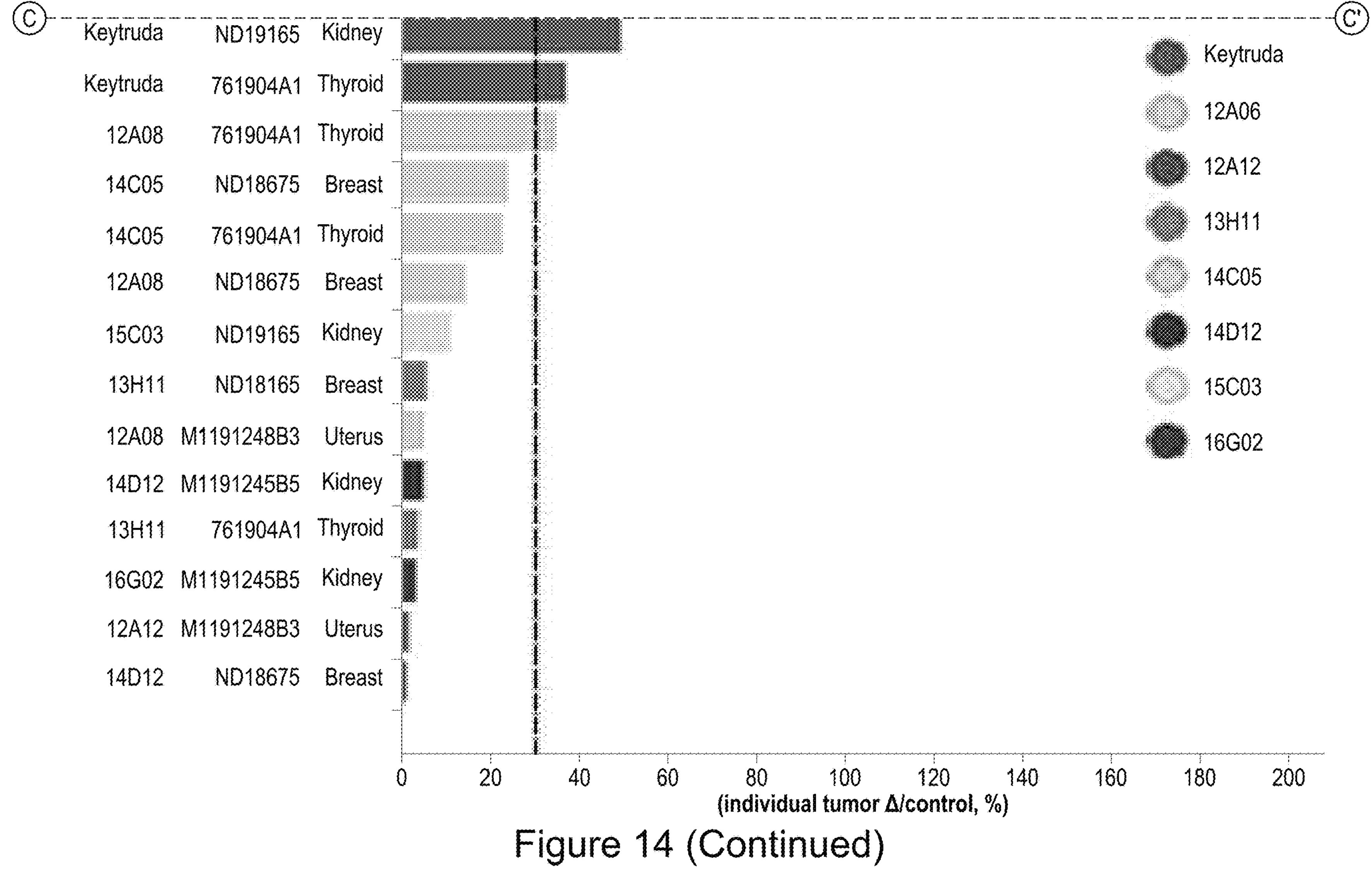

While averages are convenient for summarizing large quantities of data, FIGS. 12-14 show effects of particular representative anti-VSIG4 antibodies on individual tumors. In a given tumor, an effect of at least 30% induction is considered significant. These figures clearly demonstrate that a significant number of tumors representing multiple tumor types show significant responses to all representative anti-VSIG4 antibodies tested across all three mechanistic arms of response (e.g., macrophage inflammatory activation, chemoattraction, and T cell activation).

It is noted that none of the three measured mechanisms necessarily have a higher degree of physiological importance compared to each other, especially because different antibodies can induce different mechanisms with different kinetic dynamics leading to physiologically important results. It is well-known in the art that each mechanism feeds into the others over time to orchestrate a full immune reaction against a living tumor in a patient. Such effects would not necessarily be captured in the particular format of this assay where measurements are taken at a given time point. Nevertheless, the average and individual results provided clearly demonstrate strong confirmation of in vitro functional validation for a variety of representative anti-VSIG4 antibodies in clinically translatable primary tumors. For example, FIGS. 12-14 show that while 12A08 was relatively less potent on average in inducing chemoattraction, it was one of the strongest in inducing T cell activation by IL-2. By contrast, while 15C03 was relatively less potent on average in inducing T cell activation, it produced strong macrophage activation through secretion of TNFα. As described above, an observed effect in at least one of the three measured mechanisms in the primary tumor assay indicates a potent physiological response.

Table 11 provides a comprehensive summary of the data across all of the representative anti-VSIG4 antibodies tested based on the individualized results shown in FIGS. 12-14. Response in an individual tumor for a given mechanism is considered an induction above 30%. For example, assume that in a given tumor for a given cytokine, the isotype control arm gave a reading of "I" while an anti-VSIG4 antibody treatment arm gave a reading of "V". Then, the given VSIG4 treatment arm will be considered a responder if: $((V-I)/I)*100>=30$. Table 11 clearly shows that the efficacy of all of the anti-VSIG4 antibodies are generally comparable to Keytruda®, which is the current gold standard for immune-oncology in general and PD-1 inhibitors in particular. For macrophage inflammatory activation, all of the anti-VSIG4 antibodies demonstrated results that were as good as Keytruda® or better. Similarly, for the induction of the chemokine signature, nearly all anti-VSIG4 antibodies produced responses in the same or larger fraction of tumors than Keytruda® and anti-VSIG4 antibodies produced a broader response across different tumor types. T cell activation, which is directly induced by Keytruda® and only indirectly induced by anti-VSIG4 antibodies, producing a kinetic disadvantage for the latter in the confines of the assays, still demonstrated very strong performance of the anti-VSIG4 antibodies, with 12A12 being more potent than Keytruda® even in that mechanism.

TABLE 11

Summary of primary tumor results from representative anti-VSIG4 antibodies

| | Macrophage Activation Response (TNFalpha or IL-1beta) | | Macrophage Chemoattraction Response (Chemokine sig) | | T Cell Activation Response (IFNgamma or IL-2) | |
|---|---|---|---|---|---|---|
| Antibody Name | % tumors | % tumor types | % tumors | % tumor types | % tumors | % tumor types |
| Keytruda ® | 69 | 83 | 38 | 33 | 69 | 67 |
| 12A08 | 77 | 83 | 23 | 50 | 31 | 33 |
| 12A12 | 85 | 83 | 38 | 50 | 69 | 83 |
| 13H11 | 92 | 100 | 54 | 50 | 54 | 50 |
| 14C05 | 92 | 83 | 46 | 67 | 54 | 67 |
| 14D12 | 88 | 100 | 50 | 33 | 63 | 67 |
| 15C03 | 100 | 100 | 40 | 50 | 20 | 25 |
| 16G02 | 88 | 100 | 63 | 100 | 50 | 77 |

Accordingly, the results presented herein demonstrate that a set of representative anti-VSIG4 antibodies performs comparably to or better than Keytruda® in this assay. This conclusion is significant because the clinical utility of anti-VSIG4 antibodies rests not only in their overall strength of effect but also in the fact that the effects are different from Keytruda® and other checkpoint inhibitors (e.g., PD-1 pathway blockers like PD-1, PD-L1, and PD-L2). In fact, there are tumors and tumor types that produced no effect after Keytruda® and showed response to some of the anti-VSIG4 antibodies tested. These tumors and tumor types represent patient populations in the clinic that are not served well by the currently available treatments and need new mechanistic treatments.

Figure 15:
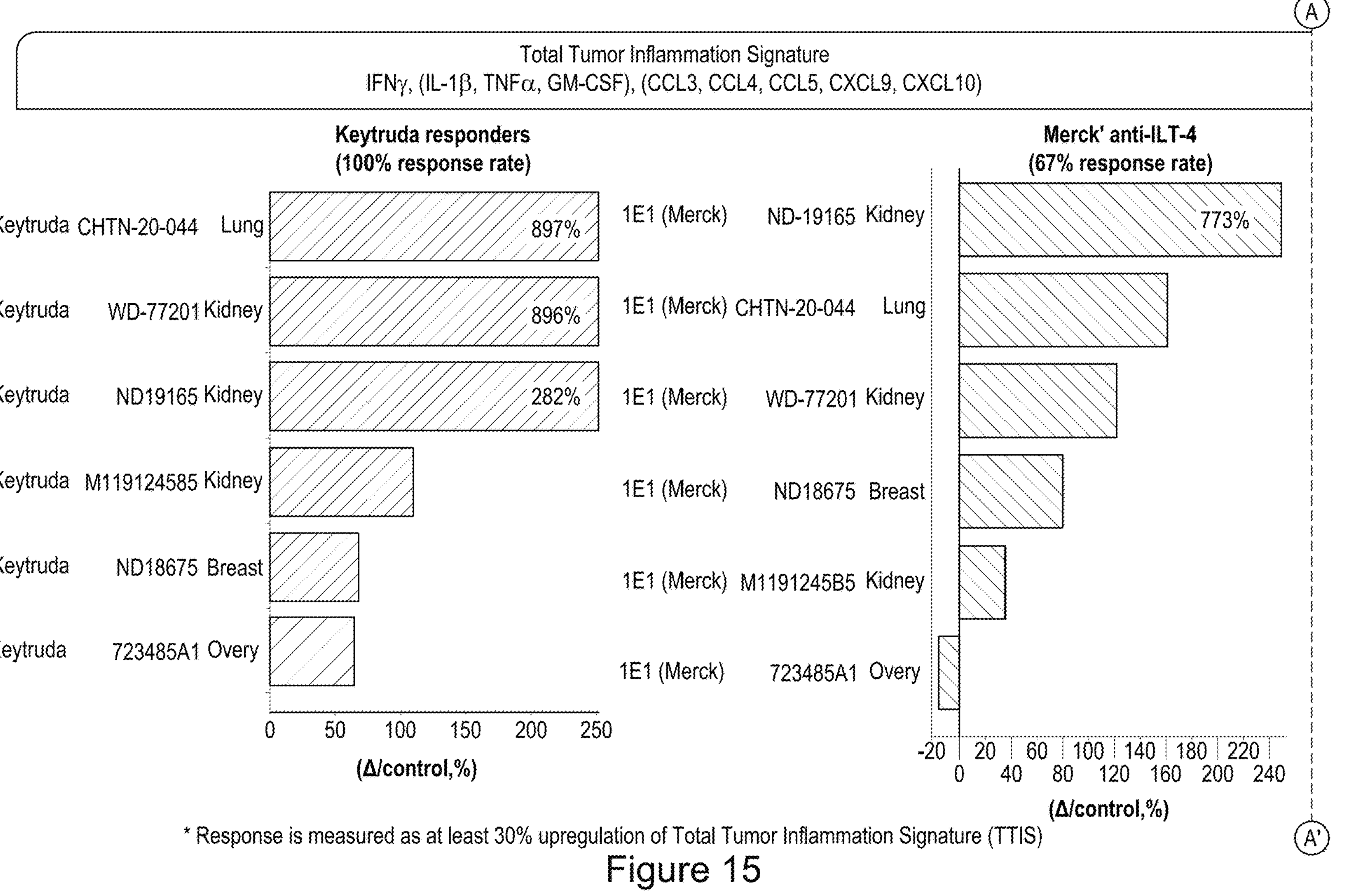
FIG. 15 shows tumor responses to a representative anti-VSIG4 antibody (12A12) in tumors that respond to Keytruda®.
Figure 15:
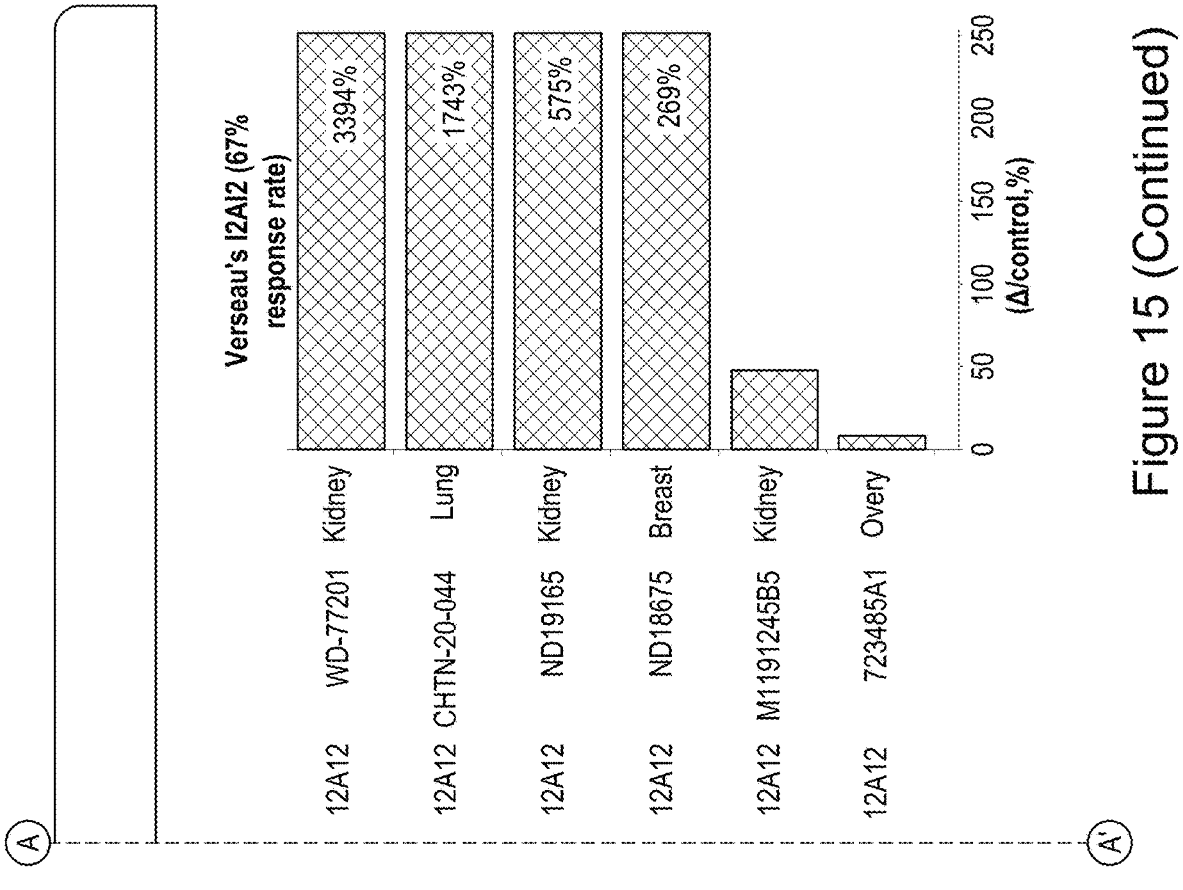
Figure 16:
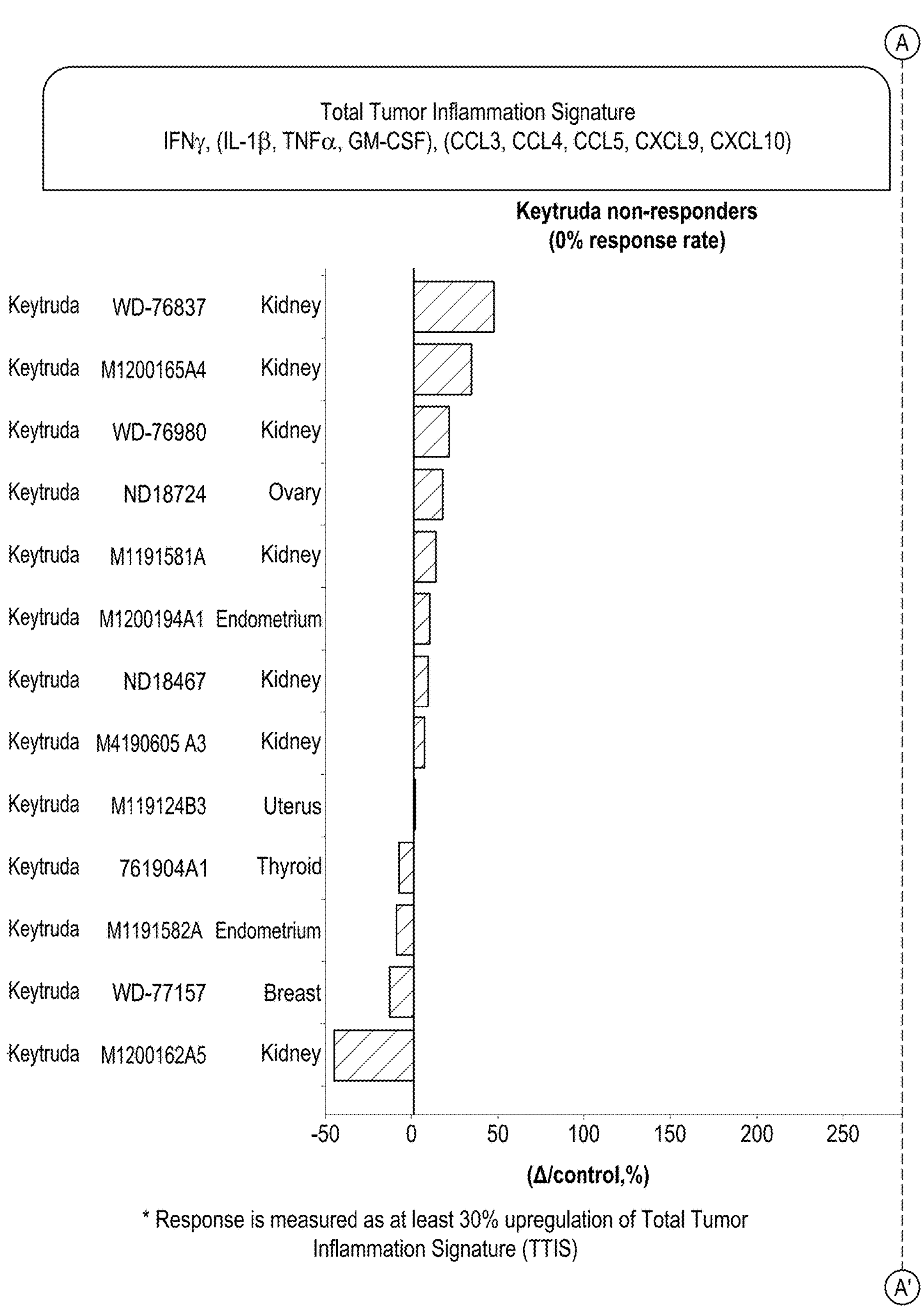
FIG. 16 shows tumor responses to a representative anti-VSIG4 antibody (12A12) in tumors that do not respond to Keytruda®.
Figure 16:
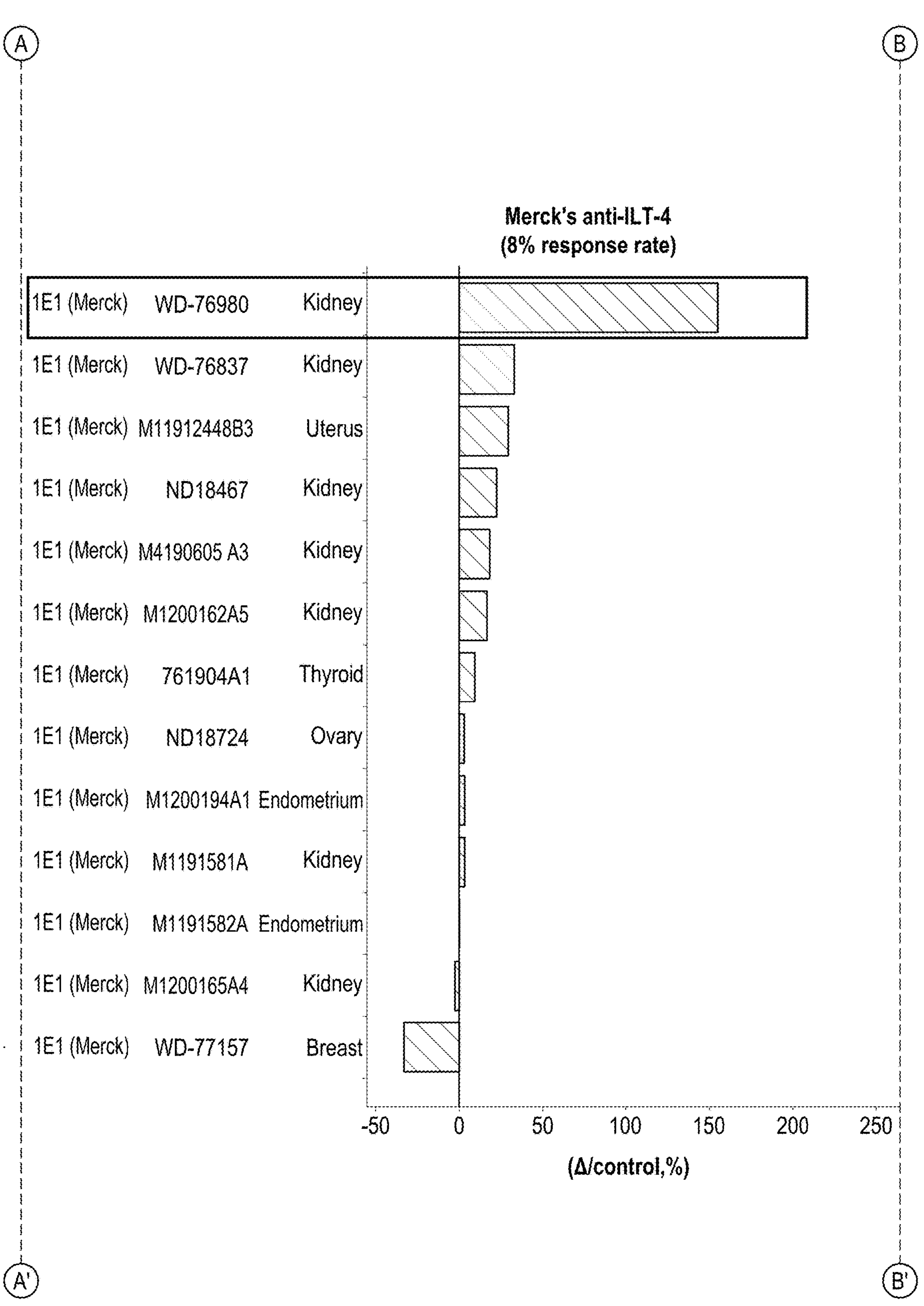
Figure 16:
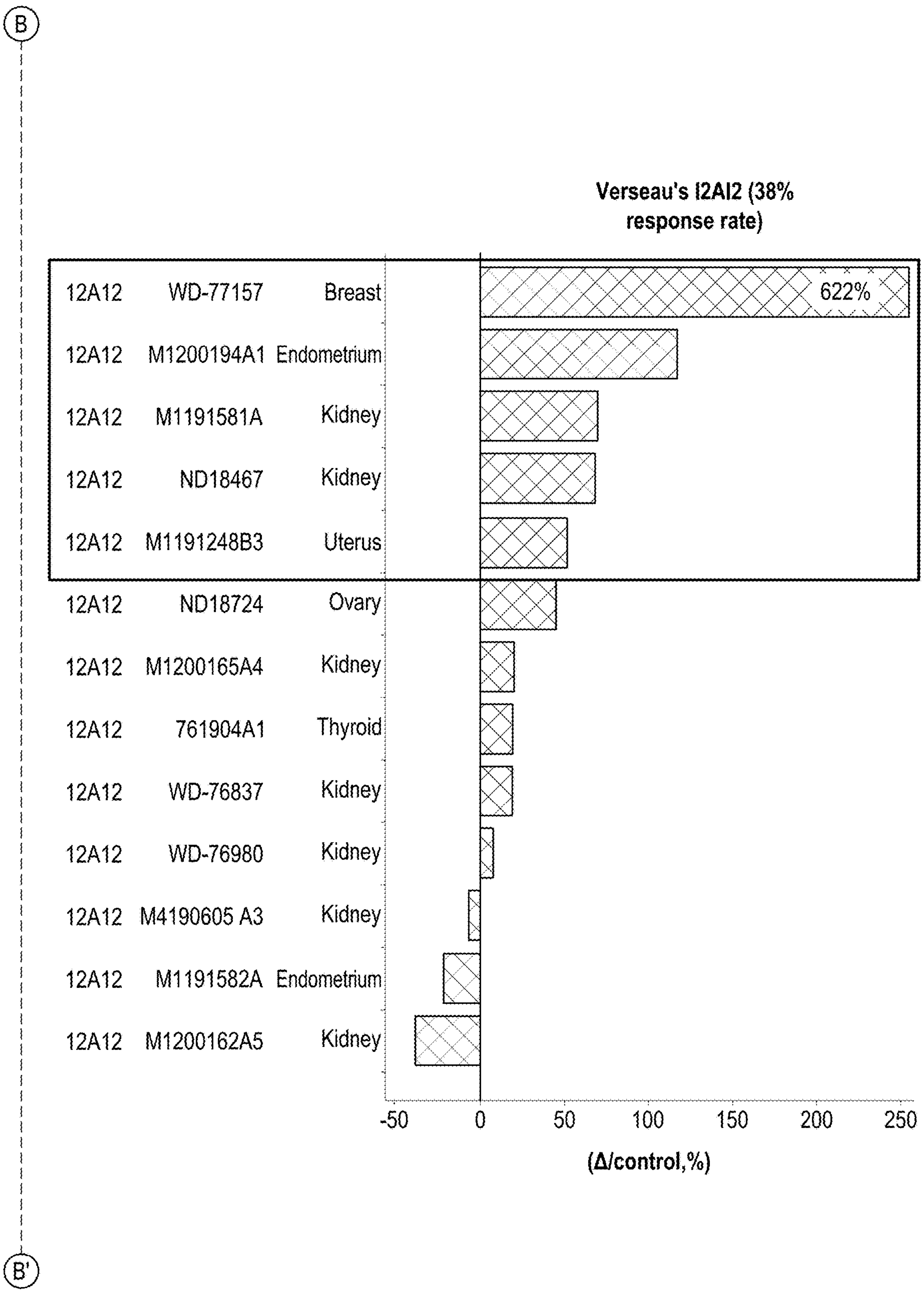

This is illustrated below using a representative example, anti-VSIG4 antibody 12A12. FIG. 15 shows that most Keytruda® responders also show response to anti-VSIG4 antibodies. For example, while several tumors (M1191245B5 kidney and 723485A1 ovary) have fallen below the response cut-off in the 12A12 treatment arm, response to Keytruda® in those tumors is only slightly above the cut-off. At the same time, the top three 12A12 responders are significantly stronger in an absolute sense compared to the top responders to Keytruda® (WD-77201 kidney, CHTN-20-044 lung, and ND19165 kidney): data analysis of Keytruda® non-responders demonstrates that a significant portion of those subjects responded to 12A12. While one ovarian (723485A1) and one breast (ND18675) tumor just made it slightly above the response cut-off for Keytruda®, the top four responders represent tumor types with known clinical activity (i.e., lung and kidney tumors). At the same time, FIG. 16 shows that 3 out of 5 anti-VSIG4 antibody 12A12 responders among the Keytruda® non-responder group showed significant response in tumor types that show no clinical activity to PD-1 inhibition (e.g., breast, endometrial, and uterus cancer). The above data indicate that VSIG4-targeting antibodies strengthen responses in indications where PD-1 inhibitors are known to work, and further open new patient population with a "cold" immunological profile, such that those that do not respond to PD-1 pathway blockers, for the next generation of immune-oncology agents. For example, "cold" tumors (e.g., having reduced or lack of tumor T cell infiltration and/or increased tumour myeloid cell infiltration; see Bonaventura et al. (2019) *Front. Immunol.* 10:168 for an example review) are well-known in the art not to respond to PD-1 pathway inhibitor therapy and includes, without limitation, ovarian, endometrial, uterine, colon, and other tumors where current PD-1 inhibitor therapies are not clinically approved. The above described data clearly indicate that anti-V SIG4antibodies, such as when used in monotherapy, will open up therapeutic treatment of tumors that are not responsive to immune checkpoint inhibitors, such as PD-1 pathway blockers.

These data demonstrate that anti-VSIG4 mAbs can repolarize suppressive myeloid cells. This repolarization leads to functional and phenotypic changes within the myeloid cell, which can, in turn, lead to greater activation of lymphoid cells, such as T cells.

Example 7: Generation of Representative Humanized Anti-VSIG4 Antibodies

Representative, non-limiting examples of humanized anti-VSIG4 antibodies were generated. For example, clones 12A08, 12A12, 13H11, 14C05, 14D12, 15A06, 15C03, 15C04, 16E03, and 16E10, which were derived from mouse immunizations, were humanized by CDR grafting of the murine CDRs into human germline VH and VL frameworks. Human VH and VL frameworks for each antibody were chosen based upon identity to the parent murine antibody, amongst a subset of human germline sequences that do not contain unwanted sequence liabilities, particularly N-linked glycosylation sites and free cysteines. Standard humanization was then performed by CDR grafting of the murine CDRs into the selected human framework, followed by back-mutation to murine framework amino acids predicted to be structurally important based upon in silico structural models of the murine Fv. In some cases, portions of the grafted murine CDRs were altered to be more similar to the human germline CDRs based upon prediction of CDR contribution to the antibody paratope.

Humanized antibodies were expressed in a human IgG4 backbone containing a S228P heavy chain mutation and each heavy chain was paired with a kappa light chain. Variable heavy chain (HC) and light chain (LC) sequences were cloned into vectors containing the antibody constant region sequences shown in Table 5. Protein expression and purification was performed by ATUM (Newark, CA), by transient transfection of heavy chain- and light chain-containing proprietary vectors into suspension-adapted HEK293 cells, as described above, and formulated in 20 mM histidine, 150 mM NaCl, pH 6.0, or PBS, pH 7.4.

The binding affinity of humanized antibodies and the parental chimeric antibodies was determined by biolayer interferometry (BLI), using a ForteBio Octet® Red384 system, as described above. Anti-VSIG4 antibodies (ligand) were diluted to a final concentration of 10 ug/mL in kinetics buffer and captured on anti-human IgG Fc capture (AHC) biosensors (ForteBio, Cat. #18-5060). Recombinant human VSIG4-L-His (human VSIG4-L-His SEQ ID NO: 25), human VSIG4-S-His (VISG4-S-His SEQ ID NO: 27), and cyno VSIG4-His (cyno VSIG4-L-His SEQ ID NO: 25) were diluted to 100 nM. Representative affinities of humanized antibodies are shown in Table 12. Data shown represent either the average of multiple experiments or single experiments, and affinities are shown as fold change relative to the parental chimeric murine antibody. Values less than or equal to 1.0 represent equivalent or higher affinity binding than the chimeric murine antibody.

Generally, the data shown in Table 12 demonstrate that the humanized VSIG4 antibodies maintain similar binding to both human and cynomolgus VSIG4 as the parental murine VSIG4 antibodies.

TABLE 12

Representative affinity of anti-VSIG4 chimeric antibodies.

| Antibody | Human VSIG4-L (relative to chimera) | Cyno VSIG4-L (relative to chimera) |
|---|---|---|
| 12A12 | 1.0 | 1.0 |
| h12A12.A | 0.7 | 1.0 |
| h12A12.B | 0.6 | 0.7 |
| h12A12.C | 0.5 | 0.5 |
| h12A12.D | 1.1 | 1.2 |
| h12A12.E | 0.6 | 0.6 |
| h12A12.F | 0.4 | 0.4 |
| h12A12.G | 0.7 | 1.1 |
| h12A12.H | 0.8 | 1.0 |
| 13H11 | 1.0 | 1.0 |
| h13H11.A | 2.6 | 1.0 |
| h13H11.B | 2.5 | 0.9 |
| h13H11.C | 1.2 | 3.7 |
| h13H11.D | 0.8 | 1.7 |
| h13H11.E | 1.4 | 1.1 |
| h13H11.F | 1.8 | 1.1 |

TABLE 12-continued

Representative affinity of anti-VSIG4 chimeric antibodies.

| Antibody | Human VSIG4-L (relative to chimera) | Cyno VSIG4-L (relative to chimera) |
|---|---|---|
| h13H11.G | 1.2 | 0.9 |
| h13H11.H | n.d. | 0.9 |
| 14C05 | 1.0 | 1.0 |
| h14C05.A | 0.8 | 0.7 |
| h14C05.B | 0.7 | 0.7 |
| h14C05.C | 0.6 | 0.6 |
| h14C05.D | 0.6 | 0.5 |
| h14C05.E | 0.5 | 0.3 |
| h14C05.F | 0.6 | 0.7 |
| h14C05.G | 0.8 | 0.7 |
| h14C05.H | 1.0 | 0.9 |
| 14D12 | 1.0 | 1.0 |
| h14D12.A | 1.1 | 1.2 |
| h14D12.B | 1.0 | 1.3 |
| h14D12.C | 1.4 | 1.5 |
| h14D12.D | 1.0 | 1.0 |
| h14D12.E | 0.9 | 0.9 |
| h14D12.F | 0.8 | 1.0 |
| h14D12.G | 1.0 | 1.1 |
| h14D12.H | 1.1 | 1.2 |
| 16E10 | 1.0 | 1.0 |
| h16E10.A | 1.0 | 1.4 |
| h16E10.B | 1.4 | 1.0 |
| h16E10.C | 1.7 | 1.1 |
| h16E10.D | 0.6 | 1.1 |
| h16E10.E | 0.8 | 1.3 |
| h16E10.F | 0.7 | 1.0 |
| h16E10.G | 0.9 | 0.4 |

All values expressed as affinity relative to the affinity of the parental chimeric antibody: $K_D$ humanized antibody (M)/$K_D$ chimeric antibody (M).
n.d. = not determined (poor fit)

Example 8: Anti-VSIG4 Antibody-Mediated T Cell De-Repression

Figure 27:
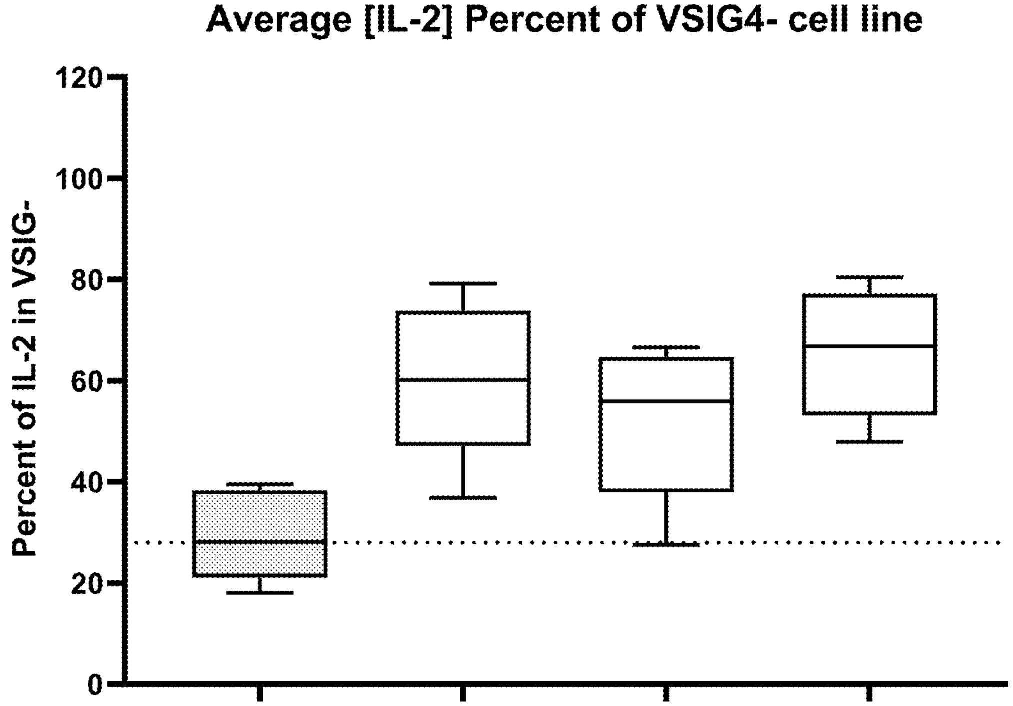
FIG. 27 shows functional data for representative anti-VSIG4 antibodies in reversing VSIG4-mediated suppression of IL-2 secretion from T cells.

In Example 5 above it was demonstrated that VSIG4+ HEK cells are able to suppress T cell activity, consistent with there existing an as yet unidentified inhibitory counter receptor on T cells (Liao et al. (2014) *Laboratory Investigations* 94:706-715). To determine if VSIG4-mediated repression of T cells could be reversed, representative anti-VSIG4 antibodies or human IgG4 isotype control antibody were incubated with HEK cells either stably expressing VSIG4 (VSIG+) or a parental non-VSIG4 expressing (VSIG4−) HEK cells in a 96-well plate. T cells were added at 50,000 cells per well and were activated with 1 ug/uL of plate-bound anti-CD3 and 0.05 ug/mL of soluble anti-CD28. The co-culture was allowed to incubate for 3 days and IL-2 was subsequently measured via Luminex® analyses, as described above. In 6 different donors, the presence of anti-VSIG4 antibodies reversed the VSIG4-mediated suppression of IL-2 secretion (FIG. 27).

Example 9: Generation of Additional Representative Anti-VSIG4 Antibodies

Additional representative, non-limiting examples of anti-VSIG4 antibodies were generated. Murine anti-human VSIG4 antibodies were generated by mouse immunizations followed by hybridoma generation. Three SJL mice were immunized with recombinant human VSIG4-L-Fc (SEQ ID NO: 19) by 28-day RIMMS protocol (immunizations and fusions performed at Green Mountain Antibodies; Burlington, VT), and anti-VSIG4 antibody titer determined by ELISA for binding to recombinant human VSIG4-L-His (SEQ ID NO: 25). Lymphocytes and splenocytes from the mouse with the highest serum titer were fused to generate hybridomas, and fused cells were plated into 96-well plates. In a primary screen, VSIG4-binding hybridomas were identified by ELISA for hybridoma supernatant binding to recombinant human VSIG4-L-His (SEQ ID NO: 25). VSIG4-binding hybridomas were expanded and hybridoma supernatant rescreened for binding to human VSIG4-L-His (SEQ ID NO: 25), human VSIG4-S-His (SEQ ID NO: 27), and cynomolgus monkey VSIG4-L-His (SEQ ID NO: 26) by ELISA. Hybridomas of interest were subcloned and confirmed for VSIG4 binding by ELISA, and antibodies were purified from supernatants from subcloned hybridomas by Protein G affinity chromatography. Eluted, neutralized proteins were buffer-exchanged into PBS, pH 7.4 and filter-sterilized, and quantified by OD280 for concentration. A subset of hybridomas were sequenced to determine their variable heavy (VH) and variable light (VL) domain sequences. Variable region sequences and CDRs for these antibodies are described in Table 2.

The binding affinity of murine hybridoma antibodies was determined by biolayer interferometry (BLI), using a ForteBio Octet® Red384 system. All samples were prepared in black 96-well flat bottom plates (Greiner, Cat. #655209) diluted in kinetics buffer (lx DPBS (Gibco, Cat. #LS14190250) containing 0.1% bovine serum albumin, 0.05% sodium azide, and 0.02% Tween®20). Anti-VSIG4 antibodies (ligand) were diluted to a final concentration of 10 ug/mL and captured on anti-murine IgG Fc capture (AMC) biosensors (ForteBio, Cat. #18-5089). Recombinant human VSIG4-L-His (human VSIG4-L-His; SEQ ID NO: 25), human VSIG4-S-His (VISG4-S-His; SEQ ID NO: 26), cyno VSIG4-His (cyno VSIG4-L-His; SEQ ID NO: 26), and murine VSIG4-His (mouse VSIG4-His; SEQ ID NO: 28) were diluted to 100 nM. Biosensors were rehydrated prior to the assay in kinetics buffer for 10 minutes and then equilibrated in kinetics buffer for 60 seconds. Antibody was then immobilized for 300 seconds followed by a 120 second baseline wash in fresh kinetics buffer, 300 second analyte association, and 300 second dissociation in the same buffer wells as the baseline wash step. All assay steps occurred at 30° C. with an acquisition rate of 5.0 Hz. Fitting was calculated using ForteBio Data Analysis software and representative affinities are shown in Table 13. Processing parameters included reference subtraction, with mouse IgG1 or mouse IgG2a used as an isotype control for reference sensor subtraction. Y-axis data was aligned to the average baseline step for the last 5 seconds and all steps were inter-step corrected to the start of the dissociation step. High frequency noise was removed using Savitzky-Golay filtering and final fitting was a 1:1 global binding model to both association and dissociation. Representative antibody affinities to human VSIG4-L-His ranged from 0.25 nM to 7 nM, and to human VSIG4-S-His from 0.5 nM to 20 nM. The antibodies bound the human and cynomolgus monkey forms of the VSIG4 extracellular domain with similar affinities.

TABLE 13

Biophysical characterization of murine anti-VSIG4 hybridoma antibodies

| Antibody | Affinity (KD) hVSIG4-L (M) | hVSIG4-S (M) | cyVSIG4-L (M) |
|---|---|---|---|
| 1C6.D6 | 1.03E−09 | 3.29E−09 | 1.13E−09 |
| 1H7.C7 | 6.83E−09 | 2.15E−08 | 6.45E−09 |
| 5D2.C8 | 4.75E−10 | 5.05E−10 | 4.35E−10 |

TABLE 13-continued

Biophysical characterization of murine anti-VSIG4 hybridoma antibodies

| Antibody | Affinity (KD) hVSIG4-L (M) | hVSIG4-S (M) | cyVSIG4-L (M) |
|---|---|---|---|
| 9A10.C4 | 9.65E−10 | 5.16E−09 | 1.23E−09 |
| 10E8.B6 | 2.13E−09 | 6.95E−09 | 1.56E−09 |
| 13E11.A4 | 1.76E−09 | 4.99E−09 | 1.40E−09 |
| 14F8.H6 | 1.72E−09 | 5.86E−09 | 2.02E−09 |
| 16F6.H6 | 4.72E−10 | 2.87E−09 | 8.02E−10 |

Example 10: Anti-VSIG4 Antibodies Cluster According to Cross-Blocking and Target Epitope Binding Criteria and Function to Modulate Macrophage Phenotypes and Immune Responses Experiments were performed to determine the ability of anti-VSIG4 antibodies to cross-block with each other and to further determine the target VSIG4 epitopes and binding residues recognized by each such antibody. The epitopic diversity of the murine hybridoma antibodies was assessed by antibody cross-blocking experiments against 12A12 and 14C05. Experiments were performed on a ForteBio Octet® Red384 system. All samples were prepared in black 96-well flat bottom plates (Greiner, Cat. #655209) with a working volume of 250 uL and diluted in kinetics buffer (1×DPBS containing 0.1% bovine serum albumin, 0.05% sodium azide, and 0.02% Tween®20). Anti-VSIG4 antibodies and human VSIG4-L-Fc protein (Human VSIG4-L-Fc SEQ ID NO: 19) were diluted in kinetics buffer to a final concentration of 15 ug/mL (100 nM) and 11 ug/mL (100 nM), respectively. Anti-human IgG Fc capture (AHC) biosensors (ForteBio, Cat. #18-5060) were rehydrated prior to the assay in kinetics buffer for 10 minutes then equilibrated in kinetics buffer for 60 seconds. Recombinant human VSIG4-L-Fc (Human VSIG4-L-Fc SEQ ID NOs: 19) was then immobilized for 120 seconds followed by a 30 second baseline wash in fresh kinetics buffer, 120 second Fc block (160 pg/mL), 30 second wash, 180 second association of a murine hybridoma antibody (antibody "a"), 30 second wash, and then 120 second association of a 12A12 or 14C05 (antibody "b"). All assay steps occurred at 30° C. with an acquisition rate of 5.0 Hz.

Binning results were calculated using ForteBio Data Analysis HT software. Antibody "a" and antibody "b" steps were defined, and the maximum binding calculation was averaged at the last 10% of the step duration. Once the matrix was generated, the antibody "b" binding signal in the absence of any antibody "a" was used to normalize the maximum binding of the competitor antibodies.

Table 14 shows the diminished binding of 12A12 and/or 14C05 (columns) to VSIG4-L-Fc (Human VSIG4-L-Fc SEQ ID NO: 19) in the presence of murine hybridoma antibody (rows), demonstrating that several hybridoma antibodies also share a similar binding epitope as 12A12. The antibodies comprise two classes of epitope profiles: i) antibodies that compete with 12A12 only (clones 106.D6 and 16F6.E1), and ii) antibodies that compete with both 12A12 and 14C05 (clones 1H7.C7, 5D2.C8, 9A10.C4, 10E8.B6, 13E11.A4, and 14F8.H6).

TABLE 14

Identification of murine hybridoma antibodies that share the 12A12 epitope

| mAb | 12A12 | 14C05 |
|---|---|---|
| isotype | 0.82 | 0.77 |
| 1C6.D6 | **0.12** | 0.69 |
| 1H7.C7 | **0.12** | **0.10** |
| 5D2.C8 | **0.26** | **0.21** |
| 9A10.C4 | **0.12** | **0.08** |
| 10E8.B6 | **0.28** | **0.23** |
| 13E11.A4 | **0.13** | **0.27** |
| 14F8.H6 | **0.11** | **0.06** |
| 16F6.E1 | **0.12** | 0.68 |

Data represent binding signal, in nm shift, of 12A12 and 14C05 to human VSIG4-Fc in the presence of hybridoma antibodies or isotype control.

Highlighted interactions represent antibody competition.

To confirm the sequence of the hybridoma antibodies, recombinantly produced chimeric murine/human IgG4 versions of the murine antibodies were generated and characterized. Antibodies were expressed as mouse/human chimeras with the mouse variable regions and human IgG4 backbone containing a S228P heavy chain mutation paired with a human kappa light chain. Variable heavy chain (HC) and light chain (LC) sequences were cloned into vectors containing the human IgG4 and human kappa antibody constant region sequences shown in Table 6. Protein expression and purification was performed by Sino Biological (Beijing, China), by transient transfection of heavy chain- and light chain-containing proprietary vectors into suspension-adapted HEK293 cells. Cell culture supernatant was purified by protein A affinity chromatography. Eluted, neutralized proteins were buffer-exchanged into PBS, pH 7.4 and filter-sterilized. Purified antibodies were quantified by OD280 using extinction coefficients calculated from the primary amino acid sequence. Purified antibodies were characterized by SDS-PAGE, HPLC-SEC, and endotoxin levels.

To confirm VSIG4 binding and epitope, chimeric antibodies were re-assayed for cross-blocking with 12A12 and 14C05 by ForteBio Octet. In addition to these antibodies, the anti-VSIG4 antibodies A1 and A2, described as inducing M2 to M1 macrophage repolarization (see, for example, U.S. Pat. Publ. 2020/0291126), were also assayed for cross-blocking with 12A12 and 14C05. The source and sequences for these antibodies are described in Table 15. Using similar conditions as described above, anti-human IgG Fc capture (AHC) biosensors (ForteBio, Cat. #18-5060) were rehydrated prior to the assay in kinetics buffer for 10 minutes then equilibrated in kinetics buffer for 60 seconds. Recombinant human VSIG4-L-Fc (Human VSIG4-L-Fc SEQ ID NOs: 19) was then immobilized for 120 seconds followed by a 30 second baseline wash in fresh kinetics buffer, 120 second Fc block (200 μg/mL), 30 second wash, 180 second association of a 12A12 or 14C05 (antibody "a"), 30 second wash, and then 120 second association of list antibodies (antibody "b"). All assay steps occurred at 30° C. with an acquisition rate of 5.0 Hz.

TABLE 15

| Sequences of A1, A2, and EU103.2 anti-VSIG4 antibodies All antibodies were expressed as human IgG4 (S228P) and human kappa antibody constant region sequences shown in Table 6. | | |
|---|---|---|
| Antibody | Sequence | Source |
| A1 VH | QVTLKESGPTLVKPTQTLTLTCTESGIS LTTSGMGVGWIRQPPGKALEWLADIFWD DNKYYNPSLKSRLTITKDTSKNQVVLTM INMDPVDTATYYCVRVYYKNDGYEDVWG KGTTVIVSS (SEQ ID NO: 104) | U.S. patent Publ. 2020/0291126 A1 SEQ ID NO: 6 |
| A1 VL | DIVITQSPLSLPVTLGQPASISCRASKS VTTSGYSFMHWYQQRPGQSPRLLIYLAS NLEPGVPDRESGSGSGTDETLKISRVEA EDVGVYYCQQSGELPYTFGQGTKLEIK (SEQ ID NO: 105) | U.S. patent Publ. 2020/0291126 A1 SEQ ID NO: 10 |
| A2 VH | QVTLKESGPTLVKPTQTLTLTCTESGIS LTTSGMGVGWIRQPPGKALEWLADIFWD DNKYYNPSLKSRLTITKDTSKNQVVLIM TNMDPVDTATYYCVRVYYKNDGYFDVWG KGTTVTVSS (SEQ ID NO: 104) | U.S. patent Publ. 2020/0291126 A1 SEQ ID NO: 6 |
| A2 VL | DIVLTQSPLSLPVILGQPASISCRASKS VTTSGYSEMHWYQQRPGQSPRLLIYLAS NLEPGVPDRFSGSGSGTDETLKIERVEA EDVGVYYCQQSGELPYTEGQGTKLEIK (SEQ ID NO: 106) | U.S. patent Publ. 2020/0291126 A1 SEQ ID NO: 12 |
| EU103.2 VH | QVQLQESGPGLVKPSQTLSLTCSFSGIS LTTSGMGVGWIRQPPGKGLEWLADIFWD DNKYYNPSLKSRVTISVDTSKNQFSLKL SSVTAADTAVYYCVRVYYKNDGYFDVWG QGTLVTVSS (SEQ ID NO: 107) | U.S. patent Publ. 2020/0291126 A1 SEQ ID NO: 2 |
| EU103.2 VL | EIVMTQSPATLSVSPGERATLSCRASKS VITSGYSEMHWYQQKPGQAPRILIYLAS NLEPGIPARESGSGSGTEFTLTISSLQS EDFAVYYCQHSRELPYTEGQGTKLEIK (SEQ ID NO: 108) | U.S. patent Publ. 2020/0291126 A1 SEQ ID NO: 4 |

Table 16 shows the binding of the assayed antibodies to VSIG4-L-Fc in the presence of 12A12 or 14C05. The antibody competition profile is similar to that of the fully murine hybridoma antibodies described in Table 14: 106.D6 and 16F6.E1 compete with 12A12 for binding to VSIG4, and 1H7.C7, 5D2.C8, 9A10.C4, 10E8.B6, 13E11.A4, and 14F8.H6 compete with both 12A12 and 14C05 for binding to VSIG4. The previously described anti-VSIG4 antibodies EU103.2, A1, and A2 do not compete with 12A12 or 14C05, indicating that these antibodies bind to a different epitope than 12A12 and 14C05.

TABLE 16

| Identification of murine hybridoma antibodies that share the 12A12 epitope | | |
|---|---|---|
| mAb | 12A12 | 14C05 |
| isotype | 0.00 | 0.00 |
| 1C6.D6 | **0.08** | 0.59 |
| 1H7.C7 | **0.08** | **0.13** |
| 5D2.C8 | **0.07** | **0.12** |
| 9A10.C4 | **0.10** | **0.14** |
| 10E8.B6 | **0.06** | **0.11** |
| 13E11.A4 | **0.07** | **0.24** |
| 14F8.H6 | **0.10** | **0.15** |
| 16F6.E1 | **0.09** | 0.56 |
| EU103.2 | 0.30 | 0.29 |

TABLE 16-continued

| Identification of murine hybridoma antibodies that share the 12A12 epitope | | |
|---|---|---|
| mAb | 12A12 | 14C05 |
| A1 | 0.57 | 0.55 |
| A2 | 0.60 | 0.57 |

Data represent binding signal, in nm shift, of chimeric antibodies or isotype control to human VSIG4-Fc in the presence of 12A12 and 14C05.
Highlighted interactions represent antibody competition.

Additional representative antibodies that share the 12A12 epitope were identified from the murine anti-human VSIG4 panel described in Example 2, under identical antibody competition experimental conditions as summarized in Table 9. Table 17 demonstrates that the antibody 16G02 also competes with 12A12.

TABLE 17

| Identification of mouse anti-human VSIG4 antibodies from phage display immune libraries that share the 12A12 epitope | | | |
|---|---|---|---|
| mAb | 14C05 | 12A12 | 16G02 |
| 14C05 | **0.11** | 0.72 | **0.11** |
| 12A12 | 0.83 | **0.13** | **0.10** |
| 16G02 | **0.16** | **0.16** | **0.11** |

Data represent binding signal, in nm shift, of chimeric antibodies human VSIG4-Fc in the presence of competitor antibody.
Highlighted interactions represent antibody competition.

To further refine the epitope of anti-VSIG4 antibodies, alanine scanning mutagenesis of VSIG4 was used to identify which amino acids within VSIG4 mediate antibody binding. This approach involved: i) identifying surface residues within VSIG4 that could be contacted by an antibody as candidates for alanine substitution, ii) producing recombinant VSIG4 alanine scan variants based upon the above designs, and iii) assaying anti-VSIG4 antibodies for binding to the collection of VSIG4 variants, to identify residues where antibody binding is sensitive to mutation to alanine.

Surface exposed residues within VSIG4 were identified using PyMOL software (Schrödinger, New York, NY). The PyMOL findSurfaceResidues script was run with a cutoff of 2 angstroms on the isoform 3 (short) VISG4 extracellular domain structure (PDB: 2icc), corresponding to the VSIG4 IgV domain. Residues highlighted as surface exposed were visually inspected to determine if they were amenable to alanine mutation. Additional residues in the IgC-type domain N-terminal were chosen by visual inspection of a homology model of the VSIG4 isoform 1 (long) form (homology model generated by Antibody Solutions (Santa Clara, CA)).

Alanine scan variants of the long form of the VSIG4 ECD were produced recombinantly as hFc1 fusion proteins (VSIG4(ECD)-hFc1) by Sino Biological (Beijing, China) in HEK293 cells and purified by Protein A affinity chromatography. The mature, wild-type VSIG4 ECD sequence and hFc1 tag sequence of the constructs are shown in Table 18. Variants are numbered according to their position in the mature VSIG4 ECD polypeptide sequence, excluding the signal sequence, for example where arginine is position 1 in the sequence (R1), proline is position 2 in the sequence (P2), isoleucine is position 3 in the sequence (13), and so forth. A list of all variants is shown in Table 18. Variants with a monomeric content below 70% measured by HPLC-SEC after single step purification were excluded from the analysis.

TABLE 19

VSIG4 ECD and hFc1 tag sequence used to epitope map anti-VSIG4 antibodies

| | Sequence |
|---|---|
| VSIG4 (ECD)-hFc1 | RPILEVPESVTGPWKGDVNLPCTYDPLQGYTQVLVKWLVQRGSDPVTIFLRDSSGD HIQQAKYQGRLHVSHKVPGDVSLQLSTLEMDDRSHYTCEVTWQTPDGNQVVRDKIT ELRVQKLSVSKPTVTTGSGYGFTVPQGMRISLQCQARGSPPISYIWYKQQTNNQEP IKVATLSTLLFKPAVIADSGSYFCTAKGQVGSEQHSDIVKFVVKDSSKLLKTKTEA PTTMTYPLKATSTVKQSWDWTTDMDGYLGETSAGPGKSLPGSGGDKTHTCPPCPAP ELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDS DGSFFLYSKLTVDKSRWQQGNVFSCSVMHEALHNHYTQKSLSLSPGK (SEQ ID NO: 19) |
| VSIG4 ECD | RPILEVPESVTGPWKGDVNLPCTYDPLQGYTQVLVKWLVQRGSDPVTIFLRDSSGD HIQQAKYQGRLHVSHKVPGDVSLQLSTLEMDDRSHYTCEVTWQTPDGNQVVRDKIT ELRVQKLSVSKPTVTTGSGYGFTVPQGMRISLQCQARGSPPISYIWYKQQTNNQEP IKVATLSTLLFKPAVIADSGSYFCTAKGQVGSEQHSDIVKFVVKDSSKLLKTKTEA PTTMTYPLKATSTVKQSWDWTTDMDGYLGETSAGPGKSLP (SEQ ID NO: 109) |
| Linker-hFc1 tag | GSGGDKTHTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCKVSNKAL PAPIEKTISKAKGQPREPQVYTLPPSREEMTKNQVSLTCLVKGFYPSDIAVEWESN GQPENNYKTTPPVLDSDGSFFLYSKLTVDKSRWQQGNVFSCSVMHEALHNHYTQKS LSLSPGK (SEQ ID NO: 110) |

TABLE 19

VSIG4 alanine variants used to epitope map anti-VSIG4 antibodies and % monomer after single step purification

| Alanine Variant | Protein Name | % Monomer |
|---|---|---|
| Wild Type | h-VSIG4-L-hFc1 | 93.4 |
| R1A | h-VSIG4-L-R1A-hFc1 | 96.1 |
| I3A | h-VSIG4-L-I3A-hFc1 | 93.1 |
| E5A | h-VSIG4-L-E5A-hFc1 | 73.4 |
| P7A | h-VSIG4-L-P7A-hFc1 | 93.2 |
| E8A | h-VSIG4-L-E8A-hFc1 | 94.0 |
| S9A | h-VSIG4-L-S9A-hFc1 | 98.0 |
| T11A | h-VSIG4-L-T11A-hFc1 | 87.7 |
| P13A | h-VSIG4-L-P13A-hFc1 | 91.6 |
| W14A | h-VSIG4-L-W14A-hFc1 | 64.6 |
| K15A | h-VSIG4-L-K15A-hFc1 | 90.0 |
| D17A | h-VSIG4-L-D17A-hFc1 | 89.6 |
| N19A | h-VSIG4-L-N19A-hFc1 | 92.7 |
| P21A | h-VSIG4-L-P21A-hFc1 | 85.9 |
| T23A | h-VSIG4-L-T23A-hFc1 | 77.2 |
| D25A | h-VSIG4-L-D25A-hFcl | 95.0 |
| P26A | h-VSIG4-L-P26A-hFc1 | 90.0 |
| L27A | h-VSIG4-L-L27A-hFc1 | 46.9 |
| Q28A | h-VSIG4-L-Q28A-hFc1 | 93.3 |
| G29A | h-VSIG4-L-G29A-hFc1 | 71.5 |
| Y30A | h-VSIG4-L-Y30A-hFc1 | 65.5 |
| T31A | h-VSIG4-L-T31A-hFc1 | 82.1 |
| Q32A | h-VSIG4-L-Q32A-hFc1 | 75.2 |
| L34A | h-VSIG4-L-L34A-hFc1 | 93.3 |
| K36A | h-VSIG4-L-K36A-hFc1 | 67.7 |
| Q40A | h-VSIG4-L-Q40A-hFc1 | 90.5 |
| R41A | h-VSIG4-L-R41A-hFc1 | 96.1 |
| G42A | h-VSIG4-L-G42A-hFc1 | 90.4 |
| S43A | h-VSIG4-L-S43A-hFc1 | 94.9 |
| D44A | h-VSIG4-L-D44A-hFc1 | 92.2 |
| P45A | h-VSIG4-L-P45A-hFc1 | 96.1 |
| V46A | h-VSIG4-L-V46A-hFc1 | 93.3 |
| L50A | h-VSIG4-L-L50A-hFc1 | 95.3 |
| D52A | h-VSIG4-L-D52A-hFc1 | 31.3 |
| S53A | h-VSIG4-L-S53A-hFc1 | 59.8 |
| S54A | h-VSIG4-L-S54A-hFc1 | 95.7 |
| G55A | h-VSIG4-L-G55A-hFc1 | 41.1 |
| D56A | h-VSIG4-L-D56A-hFc1 | 25.0 |
| Q59A | h-VSIG4-L-Q59A-hFc1 | 93.3 |
| A61G | h-VSIG4-L-A61G-hFc1 | 91.9 |
| K62A | h-VSIG4-L-K62A-hFc1 | 92.0 |
| Q64A | h-VSIG4-L-Q64A-hFc1 | 92.5 |
| G65A | h-VSIG4-L-G65A-hFc1 | 64.0 |
| H68A | h-VSIG4-L-H68A-hFc1 | 97.7 |
| H71A | h-VSIG4-L-H71A-hFc1 | 93.4 |
| K72A | h-VSIG4-L-K72A-hFc1 | 94.0 |
| V73A | h-VSIG4-L-V73A-hFc1 | 95.9 |
| P74A | h-VSIG4-L-P74A-hFc1 | 84.2 |
| D76A | h-VSIG4-L-D76A-hFc1 | 7.5 |
| Q80A | h-VSIG4-L-Q80A-hFc1 | 87.6 |
| T83A | h-VSIG4-L-T83A-hFc1 | 95.7 |
| E85A | h-VSIG4-L-E85A-hFc1 | 80.6 |
| M86A | h-VSIG4-L-M86A-hFc1 | 83.6 |
| D87A | h-VSIG4-L-D87A-hFc1 | 90.3 |
| R89A | h-VSIG4-L-R89A-hFc1 | 97.1 |
| H91A | h-VSIG4-L-H91A-hFc1 | 95.3 |
| E95A | h-VSIG4-L-E95A-hFc1 | 92.2 |
| Q99A | h-VSIG4-L-Q99A-hFc1 | 93.8 |
| P101A | h-VSIG4-L-P101A-hFc1 | 91.9 |
| D102A | h-VSIG4-L-D102A-hFc1 | 96.2 |
| G103A | h-VSIG4-L-G103A-hFc1 | 60.2 |
| N104A | h-VSIG4-L-N104A-hFc1 | 92.5 |
| Q105A | h-VSIG4-L-Q105A-hFc1 | 89.1 |
| V106A | h-VSIG4-L-V106A-hFc1 | 65.7 |
| V107A | h-VSIG4-L-V107A-hFc1 | 83.8 |
| R108A | h-VSIG4-L-R108A-hFc1 | 99.5 |
| D109A | h-VSIG4-L-D109A-hFc1 | 99.0 |
| K110A | h-VSIG4-L-K110A-hFc1 | 83.4 |
| I111A | h-VSIG4-L-I111A-hFc1 | 82.5 |
| R115A | h-VSIG4-L-R115A-hFc1 | 75.5 |
| V116A | h-VSIG4-L-V116A-hFc1 | 26.9 |
| Q117A | h-VSIG4-L-Q117A-hFc1 | 91.7 |
| K118A | h-VSIG4-L-K118A-hFc1 | 68.6 |
| L119A | h-VSIG4-L-L119A-hFc1 | 86.8 |
| S120A | h-VSIG4-L-S120A-hFc1 | 93.8 |
| V121A | h-VSIG4-L-V121A-hFc1 | 97.6 |
| S122A | h-VSIG4-L-S122A-hFc1 | 75.9 |
| K123A | h-VSIG4-L-K123A-hFc1 | 49.0 |
| P124A | h-VSIG4-L-P124A-hFc1 | 41.1 |
| T125A | h-VSIG4-L-T125A-hFc1 | 84.3 |
| R149A | h-VSIG4-L-R149A-hFc1 | 98.2 |
| G150A | h-VSIG4-L-G150A-hFc1 | 52.9 |
| S151A | h-VSIG4-L-S151A-hFc1 | 78.3 |
| P152A | h-VSIG4-L-P152A-hFc1 | 82.2 |
| P153A | h-VSIG4-L-P153A-hFc1 | 40.3 |
| I154A | h-VSIG4-L-I154A-hFc1 | 45.9 |
| S155A | h-VSIG4-L-S155A-hFc1 | 86.2 |
| K195A | h-VSIG4-L-K195A-hFc1 | 93.0 |
| G196A | h-VSIG4-L-G196A-hFc1 | 84.0 |
| Q197A | h-VSIG4-L-Q197A-hFc1 | 83.0 |
| V198A | h-VSIG4-L-V198A-hFc1 | 80.4 |
| G199A | h-VSIG4-L-G199A-hFc1 | 55.3 |
| S200A | h-VSIG4-L-S200A-hFc1 | 96.3 |
| E201A | h-VSIG4-L-E201A-hFc1 | 93.2 |

Representative antibodies were selected for epitope mapping. In order to capture the monovalent binding characteristics of antibody to VSIG4 ECD variant, Fab versions of the antibodies of interest were generated. Fabs were generated by either i) papain digest of human IgG1 and human IgG4 antibodies and purification of Fab fragments, or ii) recombinant expression and purification of Fab fragments. The following Fabs were generated by papain digest of human IgG1 antibodies: 12A08, 12A12, 13H11, 15C03, and 16E03. The following Fabs were generated by papain digest of human IgG4 antibodies: 1C6.D6b, 1H7.C7, 5D2.C8, 9A10.C4, 10E8.B6, 13E11.A4, 14F8.H6, 16F6.E1. Pierce Fab Preparation Kit (Thermo Fisher, Cat #44985) was used according to modified manufacturer's instructions. The antibody of interest (1 mg at 1.5-2 mg/mL) was buffer exchanged into the digestion buffer provided in the kit. The antibody was then added to a rehydrated immobilized papain resin and incubated with mixing at 37° C. for 4 hours (hIgG1) or 20 hours (hIgG4). The supernatant containing the digested antibody was collected from a spin column by centrifuging for 1 minute at 5,000 g. The resin was washed twice in half of the antibody volume and the two fractions were then combined and buffer exchanged into PBS using a Zeba Spin column (Thermo Fisher, Cat #89890). The Fab fragment was purified by incubating the digested antibody with MabSelect Protein A beads (Cytiva, Cat #17519902) for 1 hour at room temperature. The purified Fabs were collected in the supernatant fraction after centrifuging the beads for 5 minutes at 1,000 g, then analyzed by SDS-PAGE and HPLC size exclusion chromatography.

The following Fabs were prepared by transient expression in Expi293 cells and affinity purification: 14C05, 14D12, 15A06, 15C04, and 16E10. Variable heavy chain (HC) and light chain (LC) sequences of the above antibodies were cloned into vectors containing the human IgG1 CH1 and human kappa antibody constant region sequences shown in Table 20, to allow for Fab assembly via co-expression of the HC and LC vectors. Expi293 cells (Thermo Fisher Cat #A14635) were cultured and transfected in a culture volume of 50 mL according to the manufacturer instructions, using a 1:1 ratio of heavy and light chain DNA. Cell culture supernatants were harvested 5 days post transfection and Fabs were isolated by incubating the supernatant at 37° C. for 2 hours with 1 mL of CaptureSelect CH1 resin (Thermo Fisher Cat #194320010). The resin suspension was then transferred to a gravity flow column (Bio-Rad Cat #7321010), and after discarding the supernatant, the beads were washed with 5 column volumes of PBS. The Fabs were eluted in three fractions of 0.1 M glycine, pH 3.5, with 150 mM NaCl; there were 5 column volumes in each fraction. The final elution was in 5 column volumes of 0.1 M acetic acid. All fractions were immediately neutralized with 1 M Tris, buffer exchanged into PBS, and the concentration was measured by A280. Protein-containing fractions were combined and stored at −80° C.

TABLE 20

Antibody constant region sequences for Fab generation

| Region | Sequence |
|---|---|
| hCH1 | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKVEPKSC (SEQ ID NO: 111) |
| hKappa LC | RTVAAPSVFIFPPSDEQLKSGTASVVCLLNNFYPREAKVQWK VDNALQSGNSQESVTEQDSKDSTYSLSSTLTLSKADYEKHKV YACEVTHQGLSSPVTKSFNRGEC (SEQ ID NO: 102) |

The binding signal and kinetics of Fabs to VSIG4-Fc alanine scan variants was determined by biolayer interferometry (BLI), using a ForteBio Octet® Red384 system. All samples were prepared in black 96-well flat bottom plates (Greiner, Cat. #655209) diluted in kinetics buffer (1×DPBS (Gibco, Cat. #LS14190250) containing 0.1% bovine serum albumin, and 0.02% Tween®20). VSIG4-Fc variants (ligand) were diluted to a final concentration of 11 ug/mL (100 nM) and captured on anti-human IgG Fc capture (AHC) biosensors (ForteBio, Cat. #18-5060). VSIG4-L-binding Fab antibodies were diluted to 100 nM. Biosensors were rehydrated prior to the assay in kinetics buffer for 10 minutes and then equilibrated in kinetics buffer for 60 seconds. Antibody was then immobilized for 300 seconds followed by a 120 second baseline wash in fresh kinetics buffer, 300 second analyte association, and 300 second dissociation in the same buffer wells as the baseline wash step. All assay steps occurred at 30° C. with an acquisition rate of 5.0 Hz.

Fitting was calculated using ForteBio Data Analysis software. Processing parameters included reference subtraction, with human IgG4 used as an isotype control for reference sensor subtraction. Y-axis data was aligned to the average baseline step for the last 5 seconds and all steps were inter-step corrected to the start of the dissociation step. High frequency noise was removed using Savitzky-Golay filtering and final fitting was to either a 1:1 global binding model to both association and dissociation or a fit to the dissociation step only.

Figure 17:
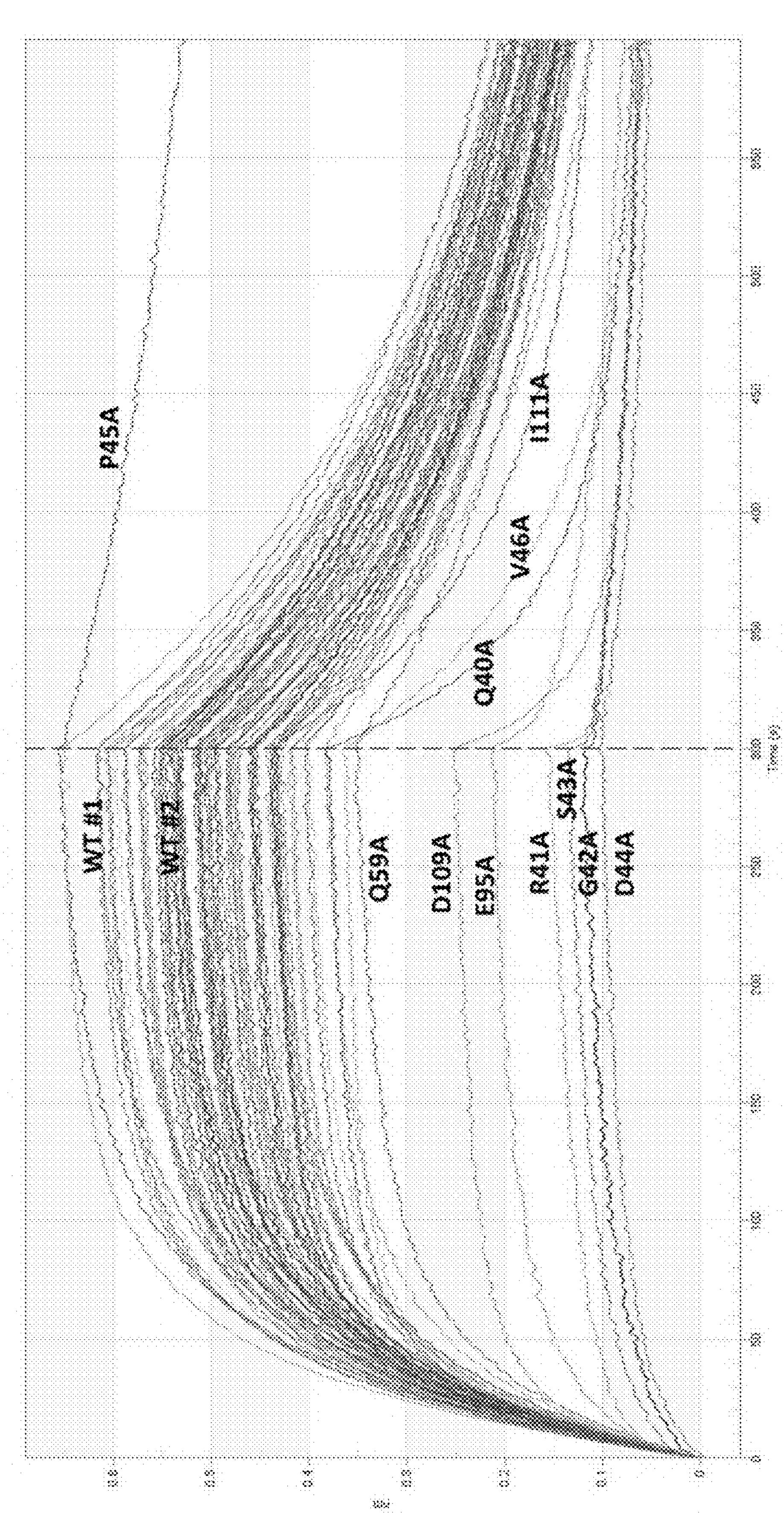
FIG. 17 shows binding curves for a representative anti-VSIG4 antibody to VSIG4 alanine scan variants.

FIG. 17 shows binding curves from a representative experiment. Visual inspection of the Octet sensograms shows that there are several VSIG4 residues where 12A12 Fab binding is sensitive to substitution and leads to a decreased binding signal and/or more rapid dissociation kinetics: D44A, G42A, S43A, R41A, E95A, D109A, Q40A, V46A, I111A, and Q59A. Interestingly, P45A leads to slower 12A12 dissociation, also suggesting that this position impacts 12A12 binding.

Figure 18:
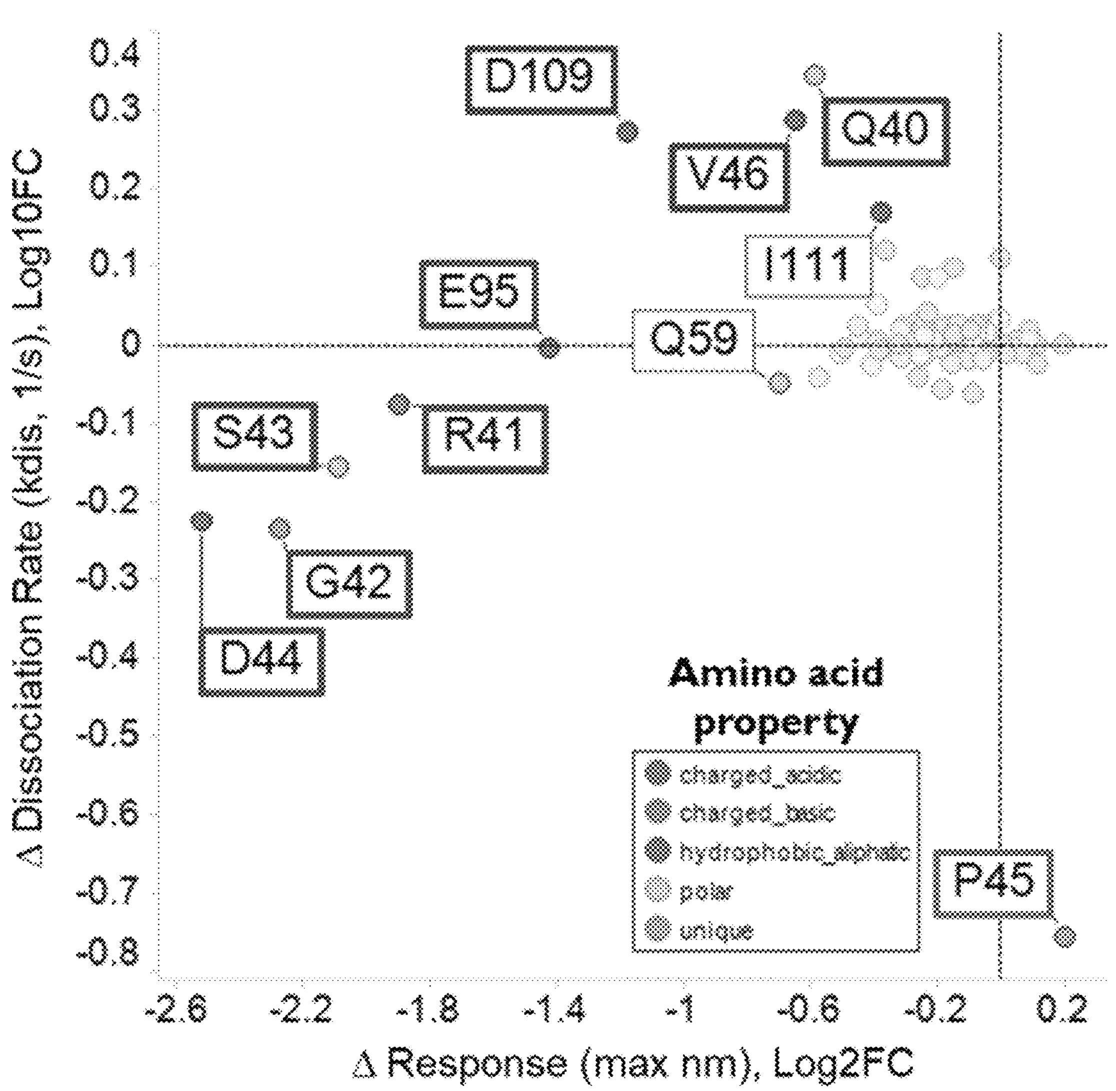
FIGS. 18-20 show binding data for representative anti-VSIG4 antibodies to VSIG4 alanine scan variants.
Figure 19:
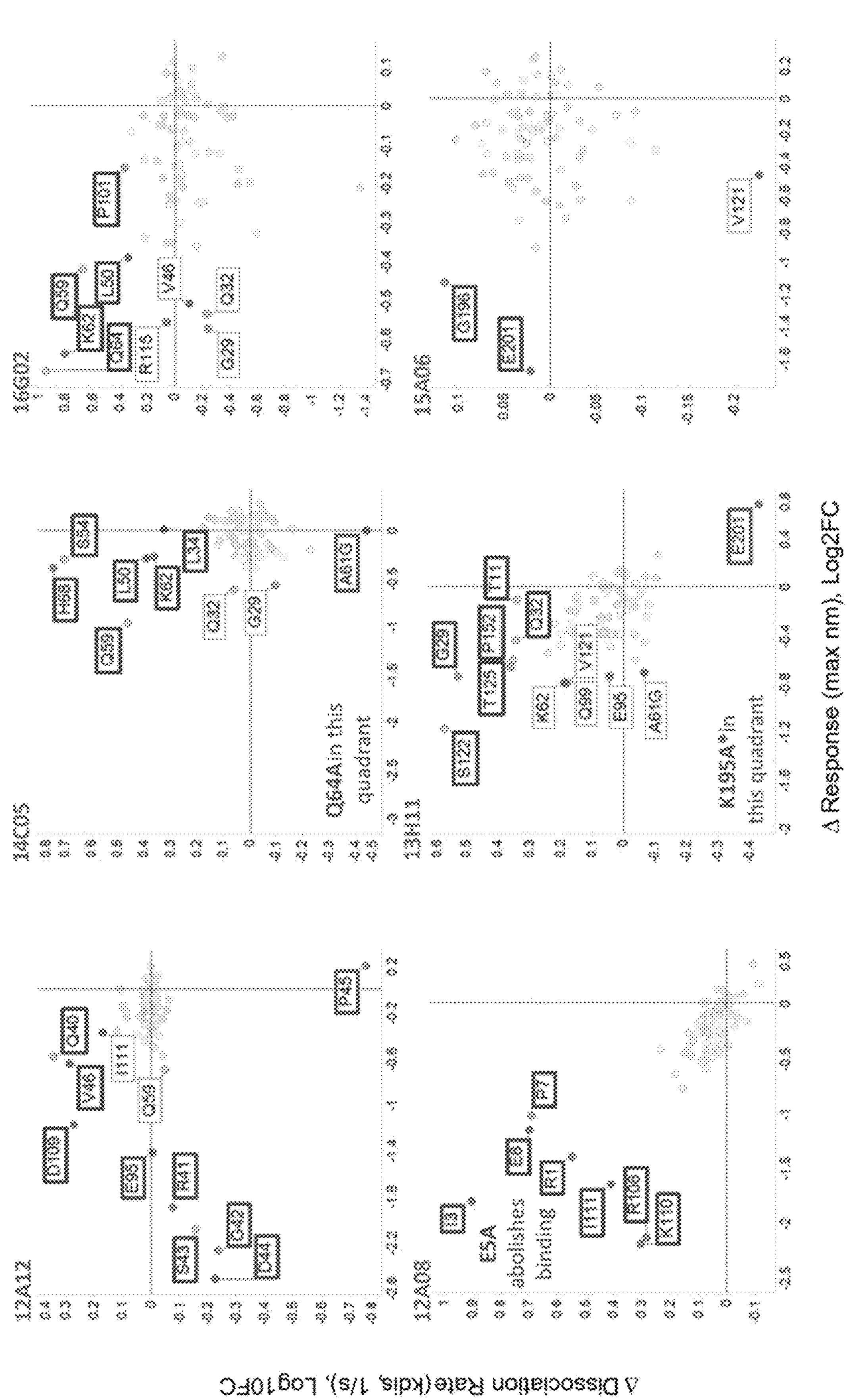
Figure 25:
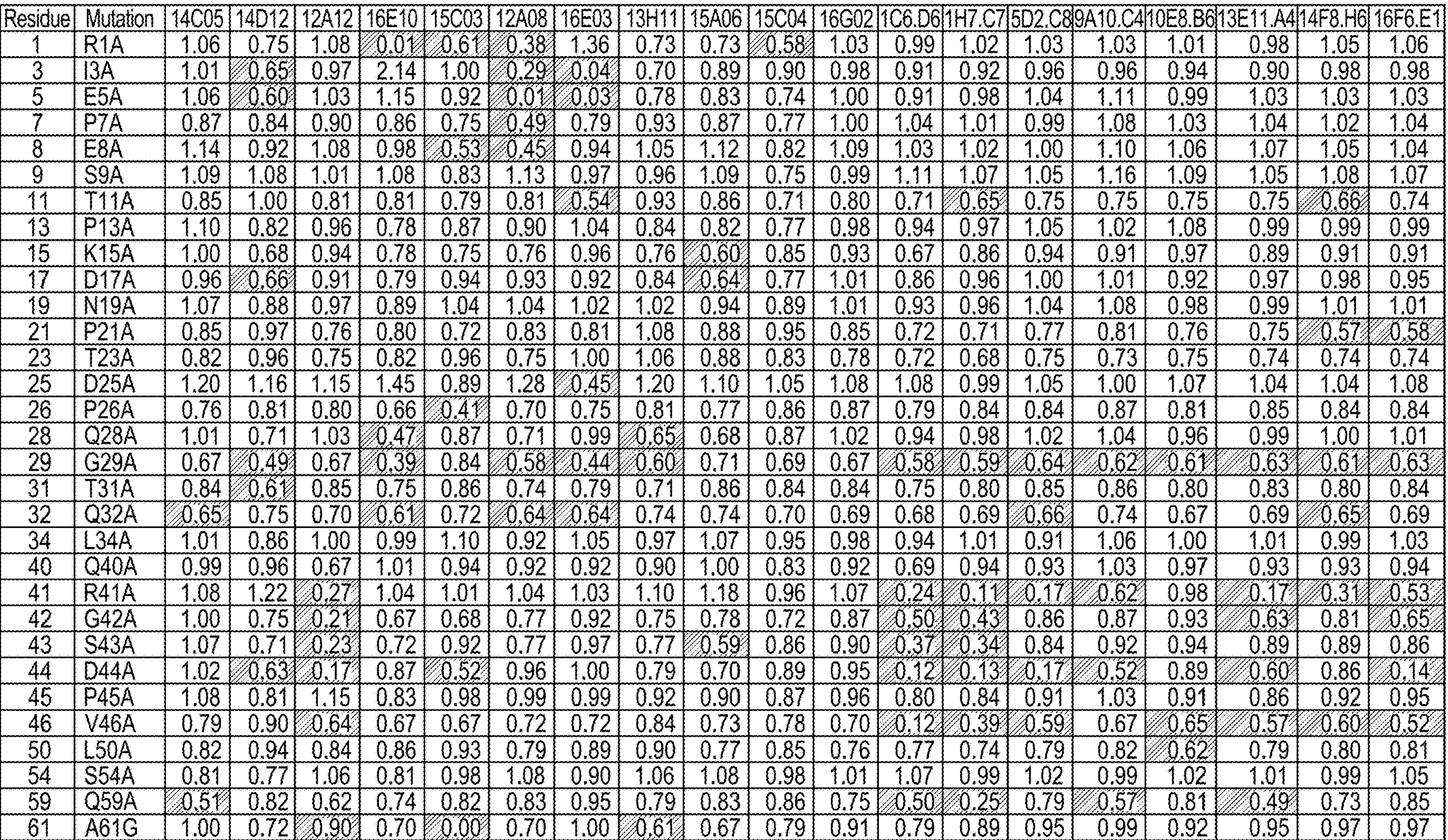
FIG. 25 provides a list of fold changes in binding signal (nm response) for representative anti-VSIG4 antibodies as compared to wild-type VSIG4.
Figure 25:
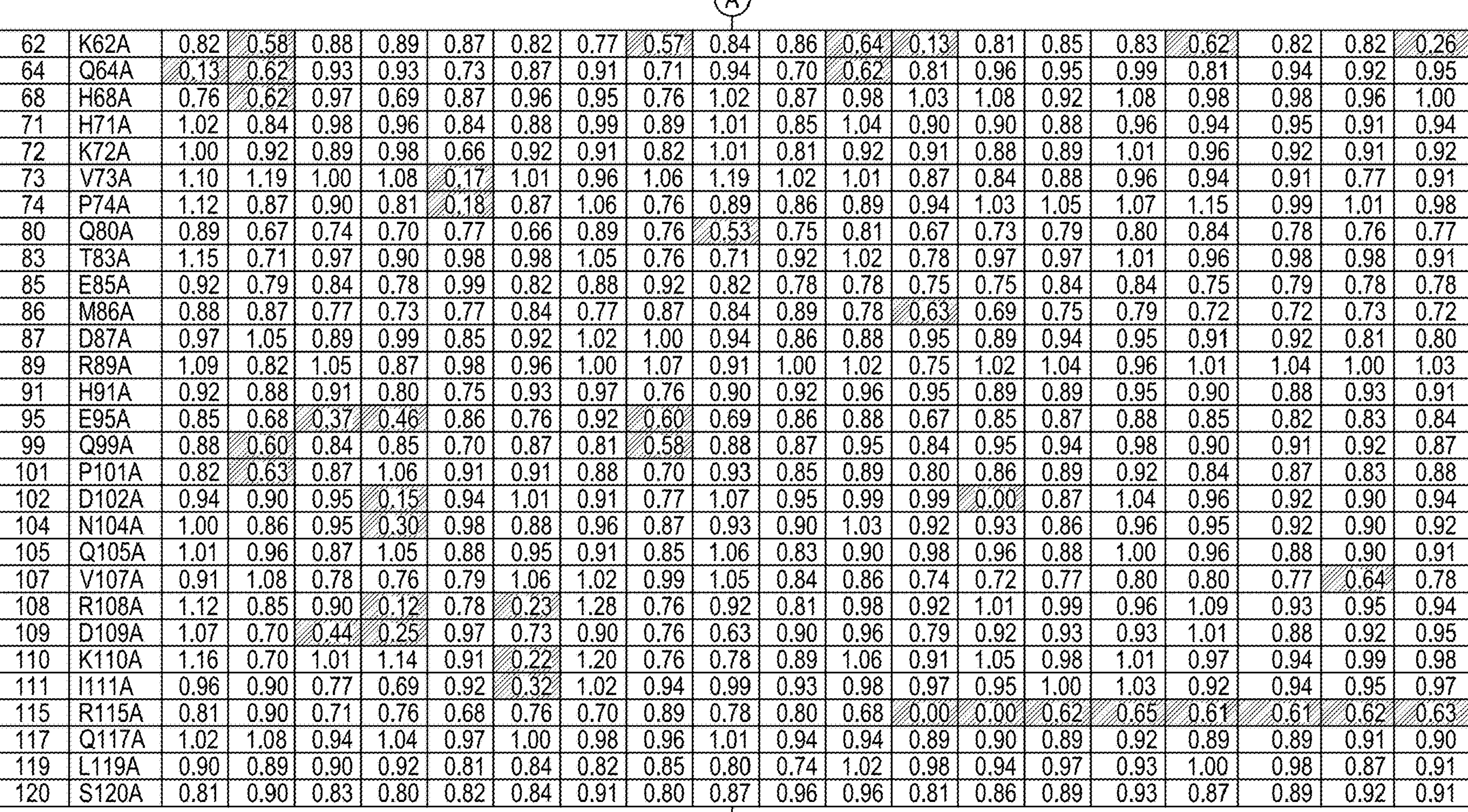
Figure 26:
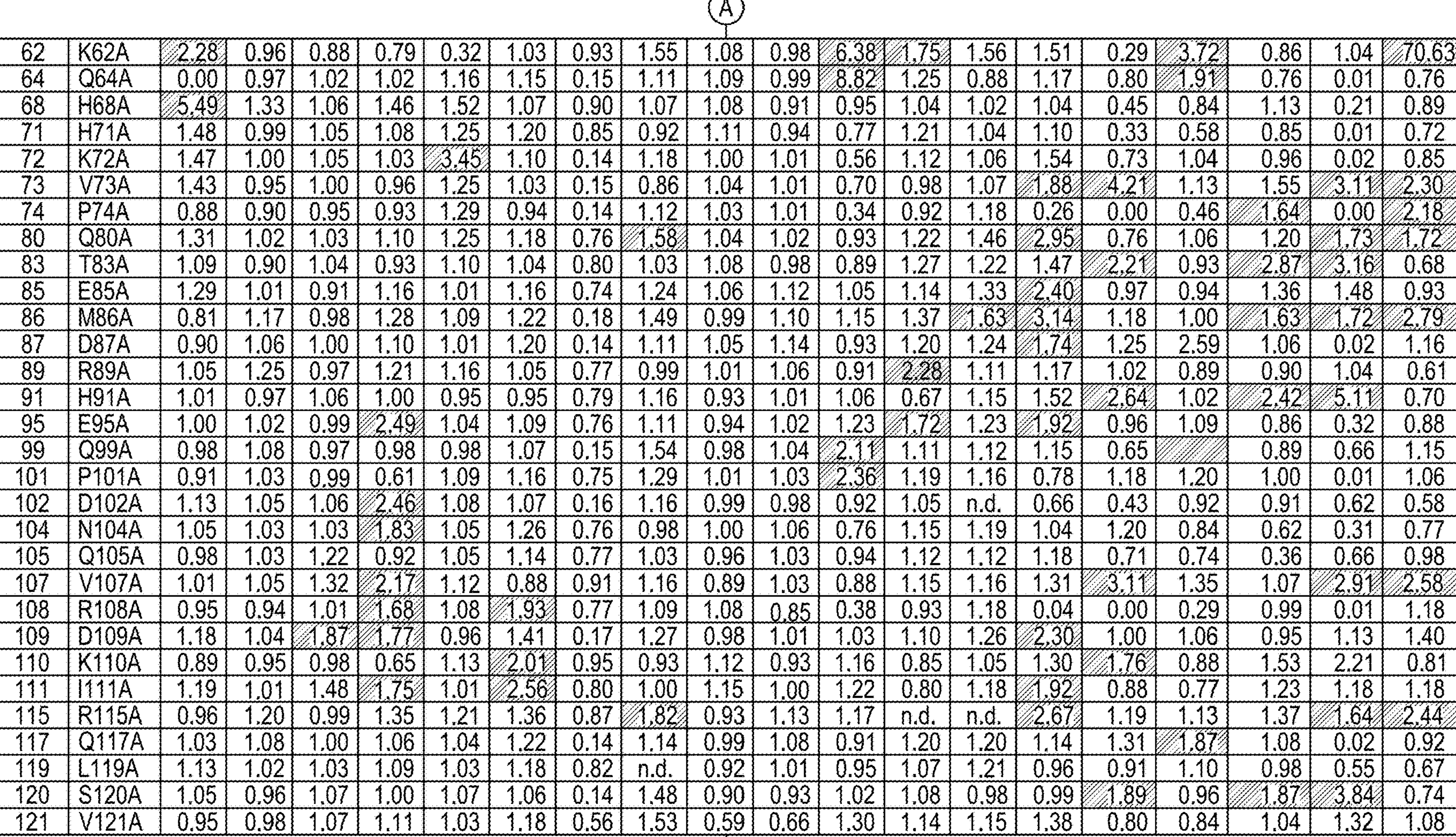
FIG. 26 provides a list of fold changes in dissociation rate for representative anti-VSIG4 antibodies as compared to wild-type VSIG4.

To more quantitatively identify VSIG4 residues where antibody binding is sensitive to substitution, data were further analyzed by calculating the fold change in binding signal compared to wild type VSIG4 and the fold change in dissociation kinetics compared to wild type VSIG4 for a given antibody binding to each alanine scan variant. FIG. 25 lists the fold change in binding signal (nm response) compared to wild-type VSIG4 for representative anti-VSIG4 antibodies. FIG. 26 lists the fold change in dissociation rate compared to wild-type VSIG4 for representative anti-VSIG4 antibodies. The change in binding signal versus the change in dissociation kinetics for antibody binding to each alanine-substituted VSIG4 residue was compared to classify the types of changes in antibody binding observed, as illustrated in FIG. 18 for 12A12 and FIGS. 19 and 20 for additional representative anti-VSIG4 antibodies. For binding signal (nm response) data, fold changes were log 2 transformed for visualization. A cutoff of log 2(fold change)<−0.6, corresponding to a 34% or greater reduction in response, was used to highlight important residues. For dissociation kinetics data, fold changes were log 10 transformed for visualization. A cutoff of log 10(fold change)>0.2, corresponding to 58% or greater increase in dissociation rate, was used to highlight important residues.

For 12A12, consistent with the data presented from visual inspection of the sensorgrams (FIG. 17), alanine substitution of D44, G42, S43, and R41 have the largest decreases in binding signal. Interestingly, these residues have only small changes in antibody dissociation rate, but this may be due to limits in fitting this value given the small binding signal. Alanine substitution of Q40, V46, and D109 have smaller but significant changes in antibody binding signal and the largest calculated changes in 12A12 binding kinetics.

Figure 21:
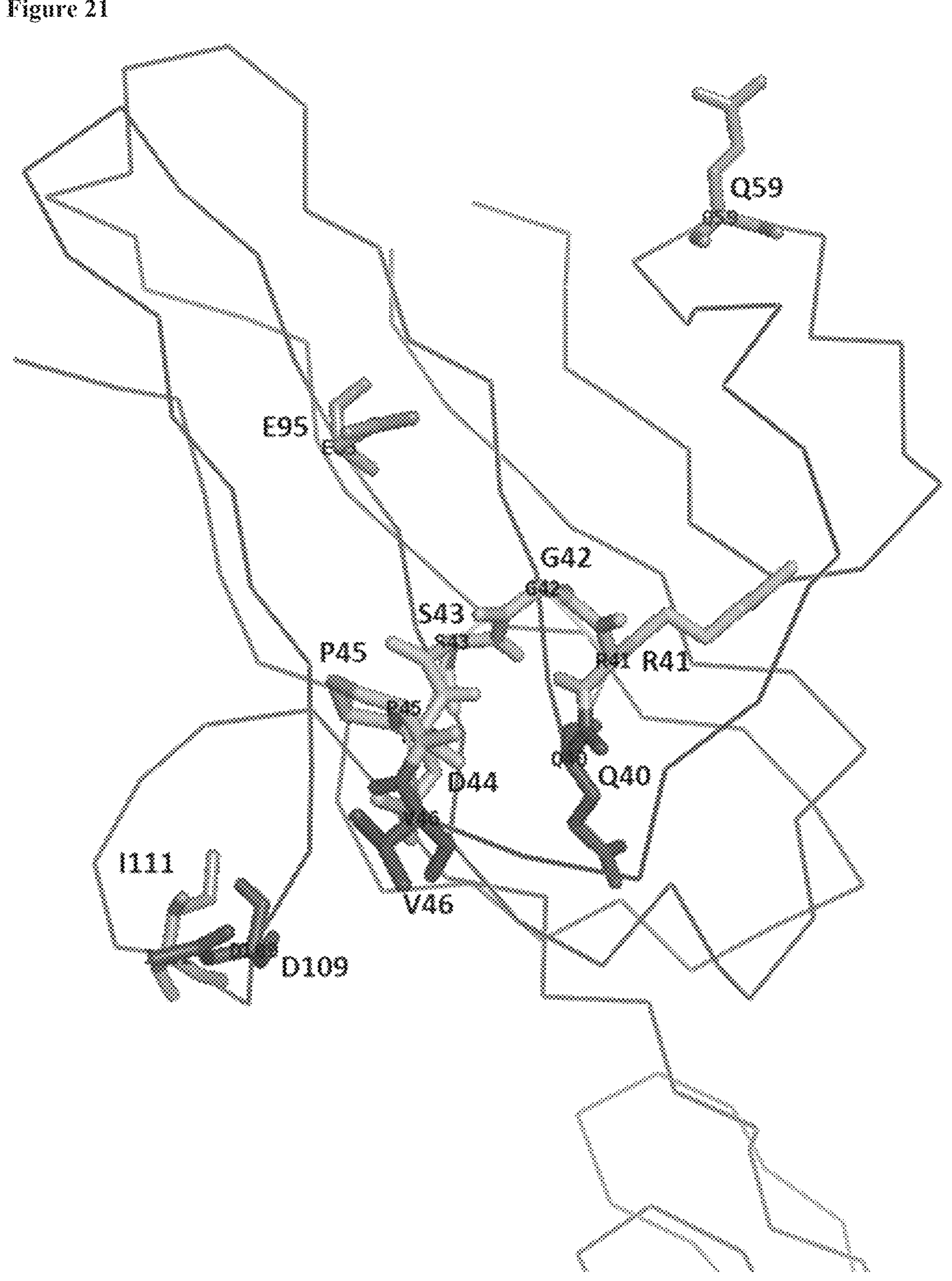
FIG. 21 shows the structure of human VSIG4 extracellular domain and residues making contact with an anti-VSIG4 antibody.

To visualize the residues important for 12A12 binding, the identified residues were mapped onto the structure of the human VSIG4 extracellular domain and annotated using PyMol software (FIG. 21). Shown is the human VSIG4 IgV domain as a ribbon structure, and residues identified as having an impact on 12A12 binding when substituted to alanine are shown as sticks and labeled. The continuous amino acids Q40, R41, G42, S43, D44A, P45, and V46 form a loop in the VSIG4 IgV domain, herein termed the "Q40-V46 loop". Interestingly, the discontinuous amino acids Q40, V46, and D109, which have the largest effect on 12A12 dissociation rate, are spatially close and could form a surface, herein termed the "Q40-V46-D109 surface," that comprises a conformational epitope. I111, E95, and Q59 also have effects upon 12A12 binding when substituted, and similar to the above residues these could be via direct contacts or by more subtle, conformational effects on 12A12 binding. The spatial proximity of D109 and I111 suggests that the loop bounded by V107-V116, herein termed the "V107-V116 loop," is also important for 12A12 binding.

Table 21 summarizes the VSIG4 residues identified as important for binding by alanine scanning mutagenesis for representative antibodies. The epitope mapping data are consistent with the epitope binning data (Table 9). For 12A12, several critical residues identified, such as the Q40-V46 loop, are not identified as being sensitive to antibody binding amongst the other antibodies described in Table 9, consistent with there no other antibody in Table 9 having strong cross-blocking of 12A12. Similarly, 15A06 and 15C04, which only compete with each other, share residues G196 and E201 in the IgC2 as critical for binding, consistent with 15A06 and 15C04 binding only to the long isoform of VSIG4 (Table 7). VSIG4 residues like G29, which appears across several of the antibodies described in Table 9 and consist of multiple epitope bins, likely have an effect on VSIG4 protein folding.

There are several common features of the nine additional antibodies that cross-block with 12A12 (16G02, 106.D6, 1H7.C7, 5D2.C8, 9A10.C4, 10E8.B6, 13E11.A4, 14F8.H6, and 16F6.E1). All antibodies are sensitive to substitution in the Q40-V46 loop. Several antibodies are sensitive to substitution at multiple residues within this loop, and at a more granular level all antibodies are sensitive to substitution at V46. Substitution at R41 and D44 have large effects on antibody binding for several antibodies. Most antibodies are also sensitive to substitution at R115 within the V107-V116 loop, as well as Q59. In some embodiments, anti-VSIG4 antibodies described herein bind to at least 1, 2, 3, 4, 5, 6, 7, 8, 9, 10, 11, 12, 13, 14, or more, or any range in between, inclusive, such as 1-10, VSIG4 residues, such as those listed in Table 21. In some embodiments, the binding to the at least one VSIG4 residue is within, or in addition to, a portion of VSIG4 described herein (e.g., the VSIG4 IgV domain, Q40-V46 loop, V107-V116 loop, Q40-V46-D109 surface, and the like).

TABLE 21

VSIG4 residues identified by alanine scanning mutagensis

| mAb | VSIG4 residues that impact antibody binding |
|---|---|
| 12A12 | **Q40,** R41, G42, S43, D44, **V46,** Q59, E95, **D109,** I111 |
| 14C05 | P7, **L34, L50, S54, Q59,** A61, **K62,** Q64, **H68** |
| 14D12 | **G29, S122, K195, Q197** |
| 12A08 | **R1, I3, E5, P7, E8, R108, K110, I111** |
| 15C03 | **R1, E5, P7, E8, P21,** T23, **D25, P26,** D44, K62, **H68, K72, V73, P74** |
| 16E03 | **I3,** T11, **D25,** G29, **Q32** |
| 16E10 | **Q28,** G29, **Q32, E95, D102, N104, V107, R108, D109, I111** |
| 13H11 | **T11, G29, Q32, S122, T125, P152,** K195 |
| 15C04 | **R1,** V121, **S122, P152,** K195, **G196, E201** |
| 15A06 | **G196, E201** |
| 16G02 | G29, Q32, **V46, L50, Q59, K62, Q64, P101, R115** |
| 1C6.D6 | **K15, Q40, R41, G42, S43, D44, V46, Q59, K62, R89** |
| 1H7.C7 | **R41, G42, S43, P45, V46, Q59** |
| 5D2.C8 | **R41, S43, P45, V46, Q59, R115** |
| 9A10.C4 | G29, **R41, D44, V46, Q59, R115** |
| 10E8.B6 | G29, Q32, V46, **L50, K62, R115** |
| 13E11.A4 | **R41, G42, D44, V46, Q59, T83, H91** |
| 14F8.H6 | G29, **T11, R41, V46, Q59, V107, R115, S155** |
| 16F6.E1 | **P21, R41, G42, V46, K62, R115** |

Residues highlighted in bold have significant changes in both antibody binding signal and dissociation kinetics when substituted with alanine.

The antibodies that share a similar epitope as 12A12, as determined by antibody cross-blocking competition experiments and epitope mapping by alanine scanning mutagenesis, have been utilized in functional assays to determine the effect of these antibodies on the macrophage differentiation state.

Figure 20:
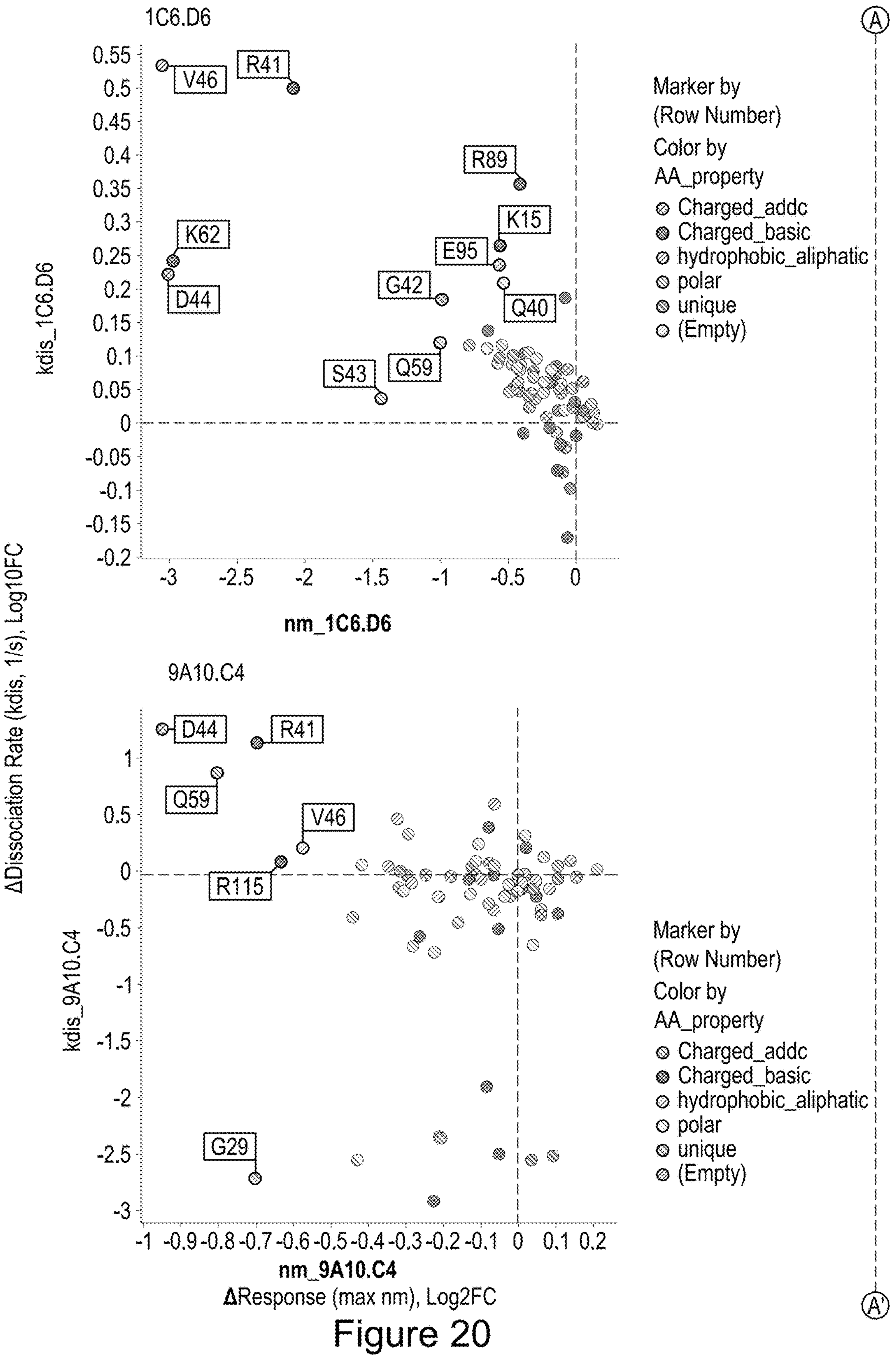
Figure 20:
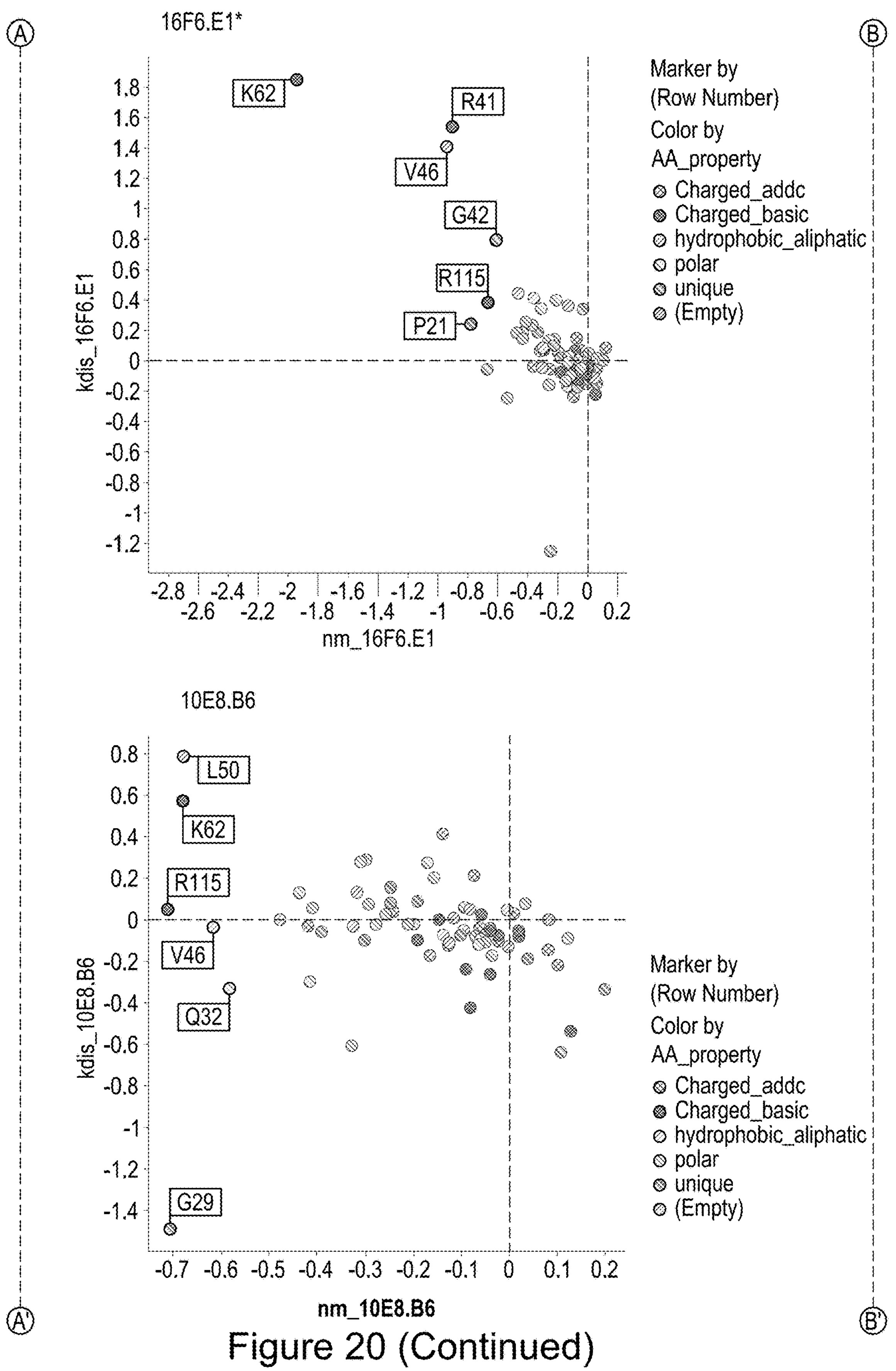
Figure 20:
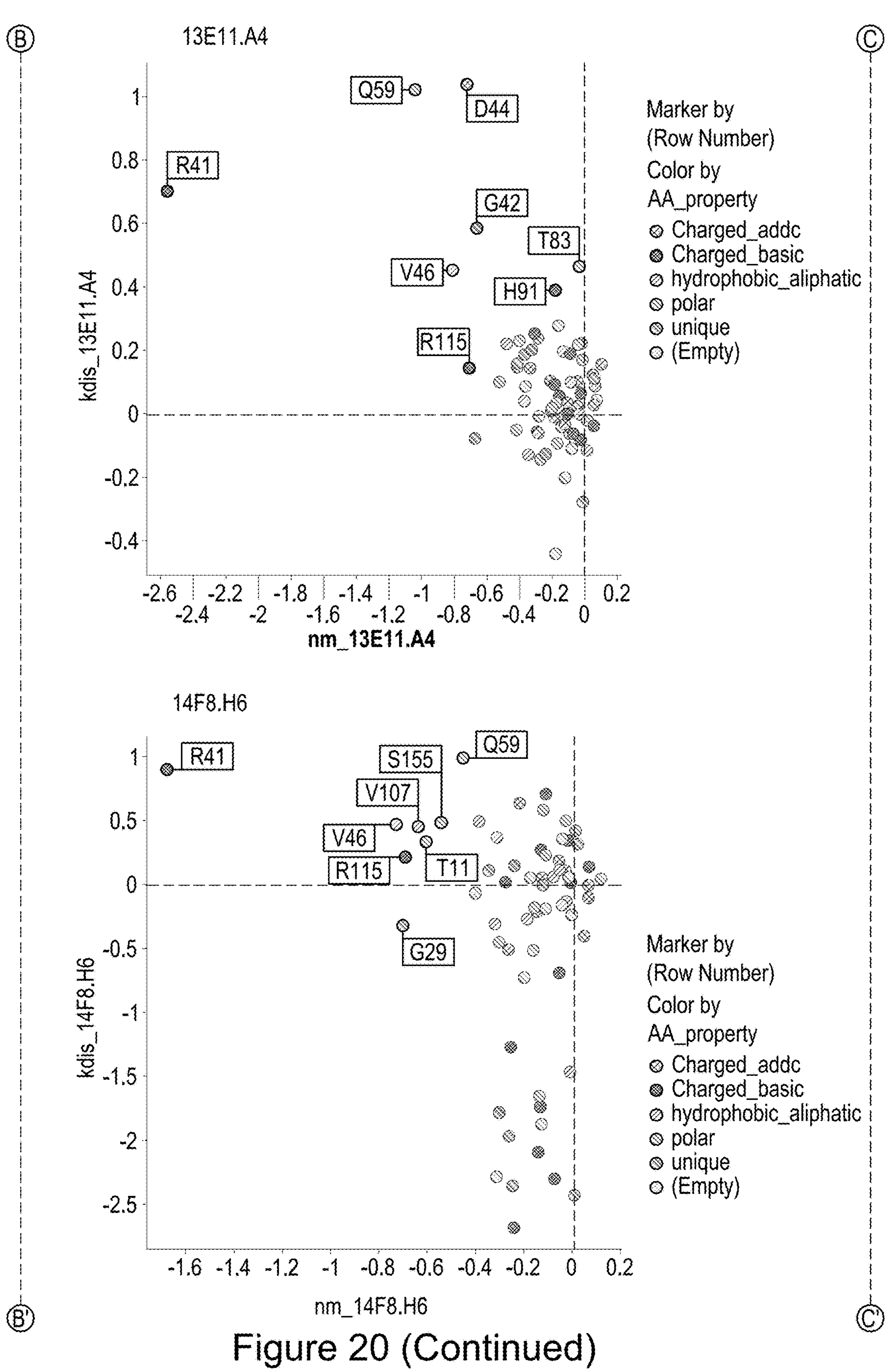
Figure 20:
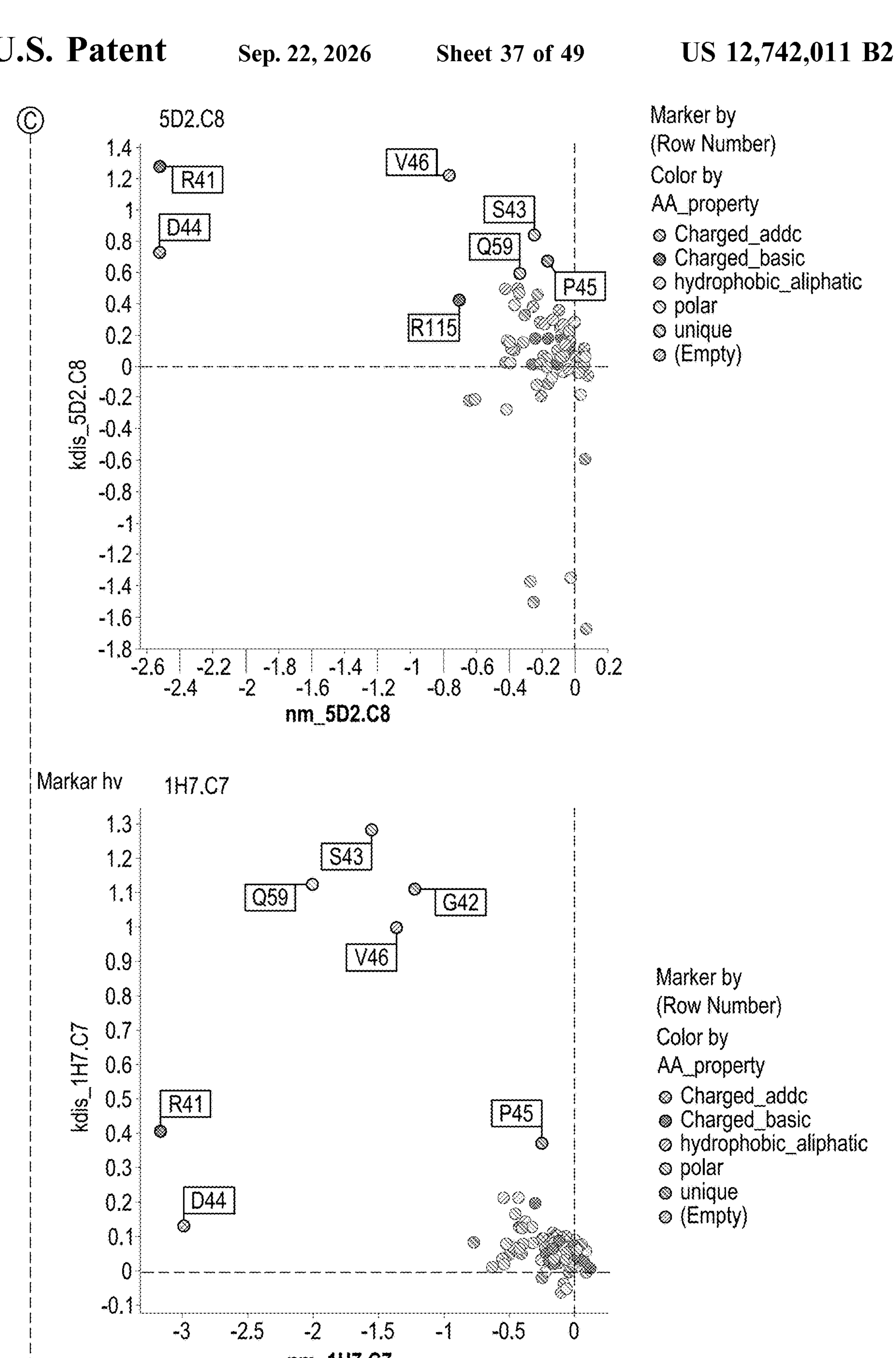
Figure 22:
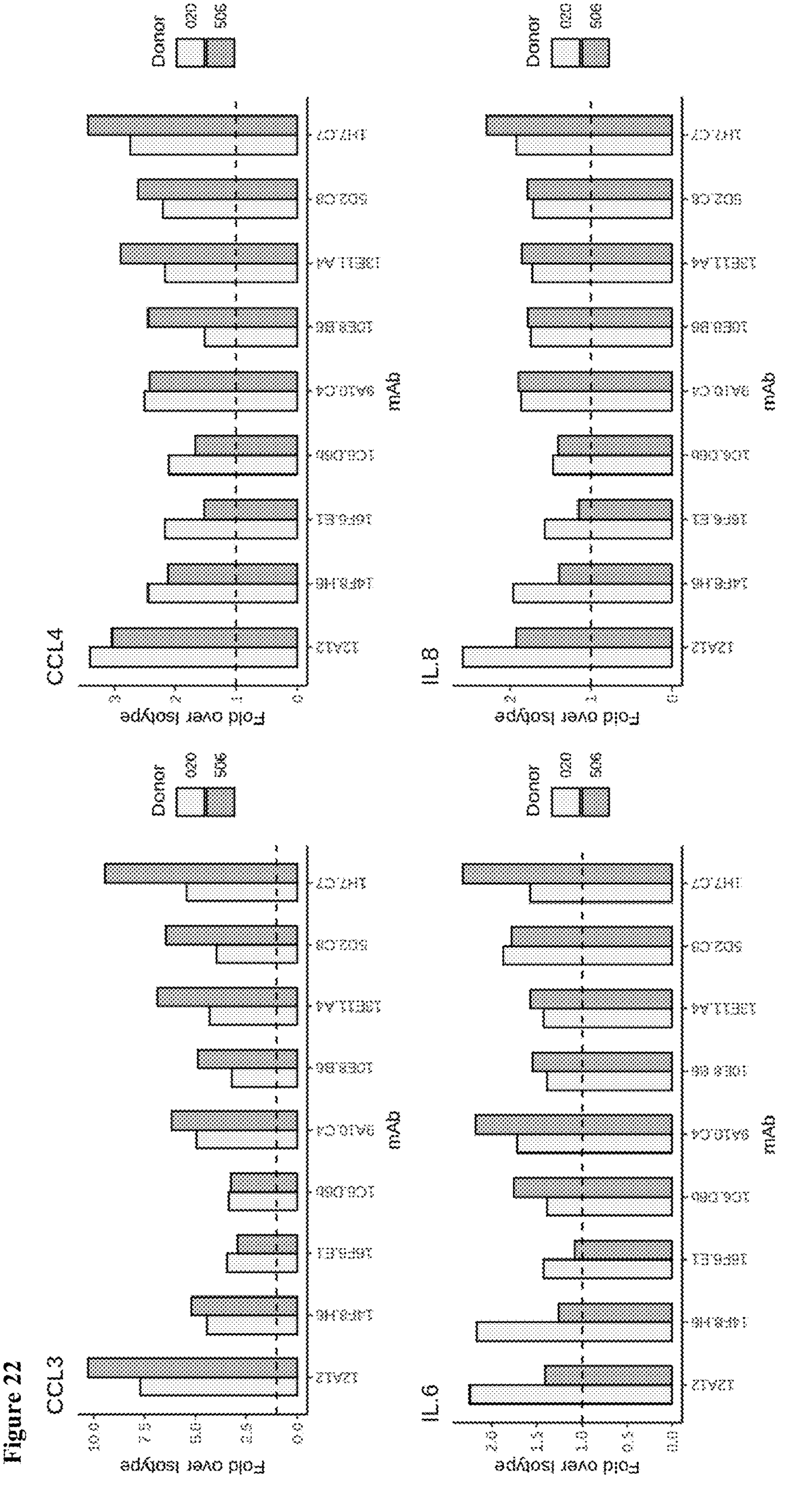
FIGS. 22-24 show functional data for representative anti-VSIG4 antibodies.

FIGS. 20, 21, and 22 show the results of the antibodies sharing a similar epitope as 12A12 that were utilized in macrophage functional assays. The effect of these antibodies on the macrophage differentiation state was measured by various readouts including cytokine secretion and surface marker expression. Similar to the assay described in Example 3, monocytes were differentiated in vitro to M2-like (Type 2) phenotypes. In order to differentiate monocytes into M2 macrophages, monocytes were isolated from PBMCs from healthy human donors by a standard Ficoll separation. Isolated monocytes were arrayed in 24 or 96 well plates overnight in IMDM Media containing 10% fetal bovine serum and non-adherent cells were washed off after 24 hours. Monocytes were differentiated into macrophages by culturing for 6 days in IMDM with 10% FBS plus 50 ng/ml human M-CSF for M2 macrophages. After 6 days, M2 macrophages were polarized with 20 ng/ml IL-10 with and without LPS stimulation. LPS stimulation is meant to increase soluble mediator secretion from M2 macrophages primed with M-CSF and differentiated/activated with IL-10. In some instances LPS stimulation was omitted to test how VSIG4 directed antibodies change the secretory capability of the M2 macrophages. The ability of VSIG4 antibodies to induce pro-inflammatory soluble mediator release without additional activation is an even stronger testament to the potency of these antibodies in inducing functional repolarization.

Monoclonal antibodies formatted as human IgG4 (S228P) chimeric antibodies were administered at several concentrations, including final concentrations of 10 ug/mL, 1 ug/mL, and 0.1 ug/mL, on day 7 of culture for a 24 hr incubation period. On day eight, secreted cytokines and chemokines were measured to assess ability the specific mAbs to alter the pro- or anti-inflammatory nature of the macrophages. Cytokines from supernatant were measured using the 25-Plex Human Cytokine Luminex panel, LHC0009M (Thermo Fisher, Waltham, MA) according to the manufacturer's protocol. Data are representative of at least 3 healthy donors.

Figure 23:
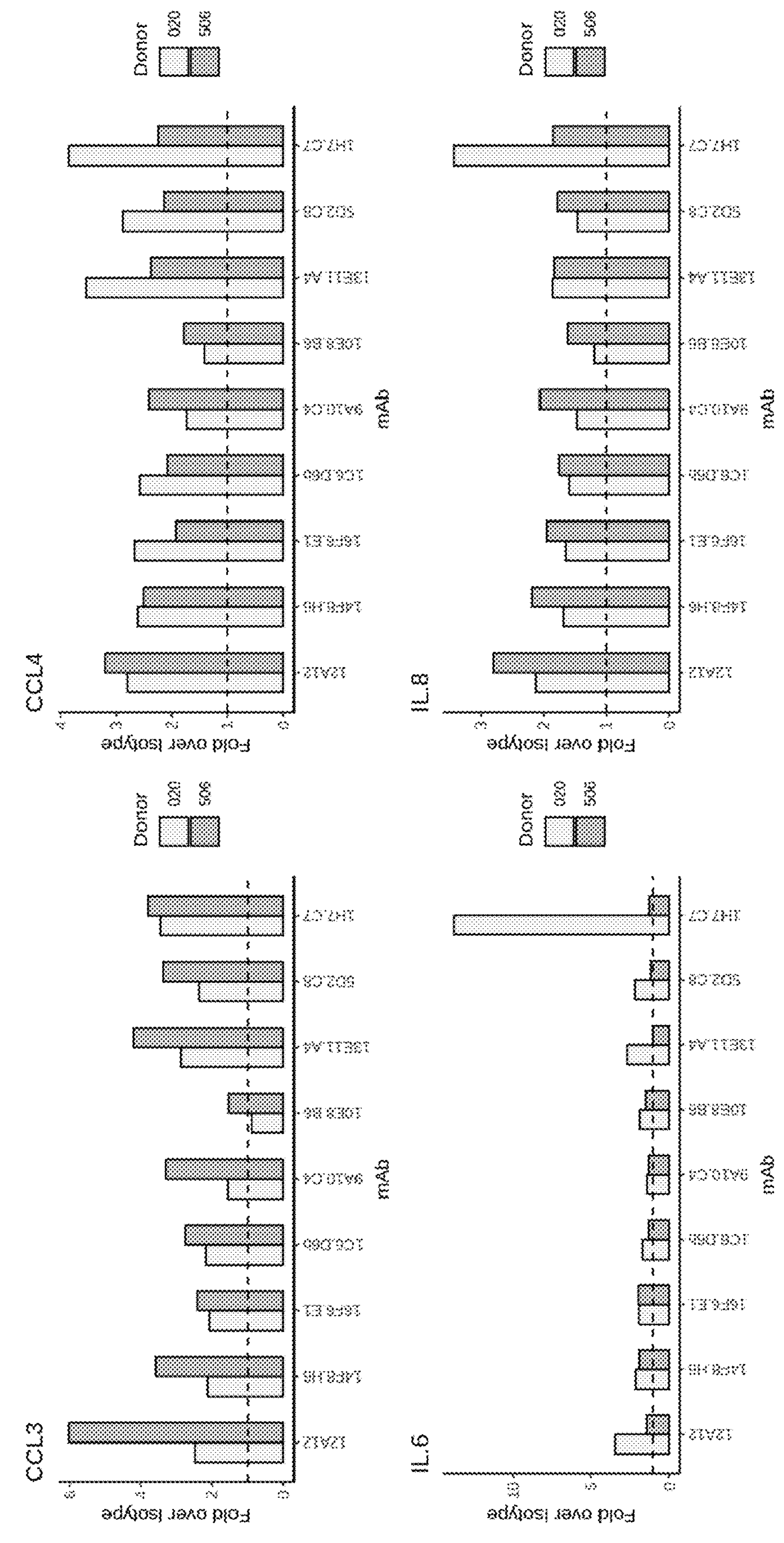
Figure 24:
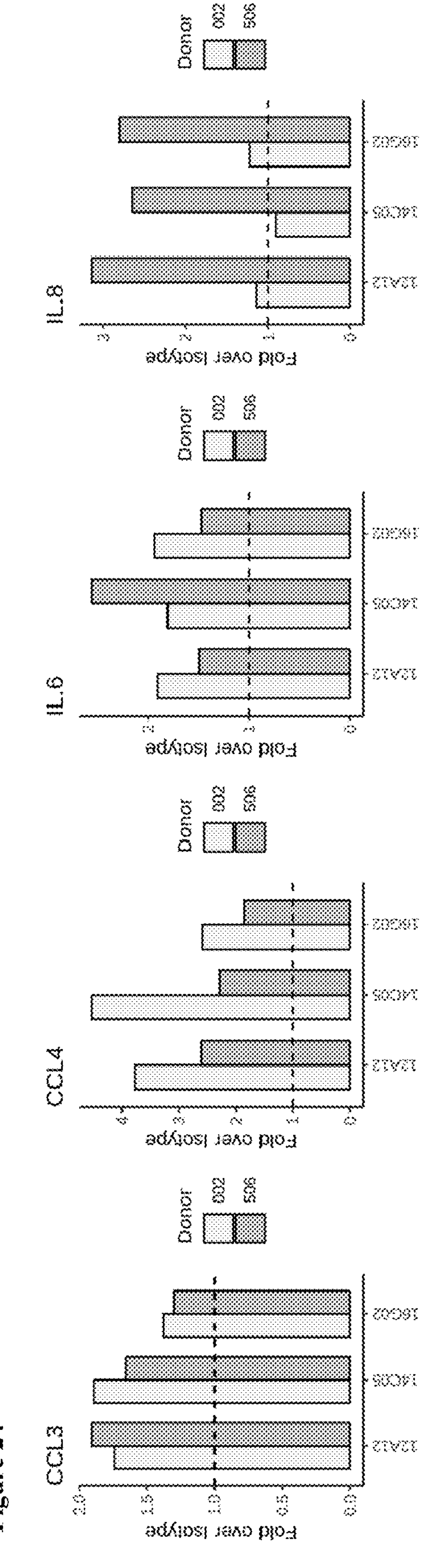

All representative antibodies that share the 12A12 epitope were demonstrated to repolarize M2 macrophages to a more M1-like state, as exemplified by the increased secretion of the M1-like mediators CCL3, CCL4, IL-6, and IL-8. For example, FIG. 22 provides representative data for anti-VSIG4 antibodies derived from murine hybridomas administered at a final concentration of 0.1 ug/mL. Similarly, FIG. 23 provides representative data for the same panel of anti-VSIG4 antibodies administered at a final concentration of 1 ug/mL, demonstrating a consistent pattern of repolarization towards M1-like mediators across antibody concentrations. FIG. 24 provides representative data for 16G02 administered at a final concentration of 10 ug/mL. These data demonstrate the ability of all representative anti-VSIG4 antibodies that share the 12A12 epitope to alter the functional characteristics of M2-like macrophages to a more M1-like state.

Example 11: Generated Anti-VSIG4 Antibodies have Both Common and Unique Biophysical and Functional Characteristics FIG. 28 summarizes the biophysical and functional properties of the generated anti-VSIG4 antibodies described herein.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web and/or the National Center for Biotechnology Information (NCBI) on the World Wide Web.

EQUIVALENTS AND SCOPE

The details of one or more embodiments encompassed by the present invention are set forth in the description above. Although the preferred materials and methods have been described above, any materials and methods similar or equivalent to those described herein may be used in the practice or testing of embodiments encompassed by the present invention. Other features, objects and advantages related to the present invention are apparent from the description. Unless defined otherwise, all technical and scientific terms used herein have the same meaning as commonly understood by one of ordinary skill in the art to which this invention belongs. In the case of conflict, the present description provided above will control.

Those skilled in the art will recognize or be able to ascertain using no more than routine experimentation, many equivalents to the specific embodiments encompassed by the present invention described herein. The scope encompassed by the present invention is not intended to be limited to the description provided herein and such equivalents are intended to be encompassed by the appended claims.

The articles "a" and "an" are used herein to refer to one or to more than one (i.e. to at least one) of the grammatical object of the article unless indicated to the contrary or otherwise evident from the context. By way of example, "an element" means one element or more than one element. Claims or descriptions that include "or" between one or more members of a group are considered satisfied if one, more than one, or all of the group members are present in, employed in, or otherwise relevant to a given product or process unless indicated to the contrary or otherwise evident from the context. The present invention includes embodiments in which exactly one member of the group is present in, employed in, or otherwise relevant to a given product or process. The present invention also includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges may assume any specific value or subrange within the stated ranges in different embodiments encompassed by the present invention, to the tenth of the unit of the lower limit of the range, unless the context clearly dictates otherwise.

In addition, it is to be understood that any particular embodiment encompassed by the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions encompassed by the present invention (e.g., any antibiotic, therapeutic or active ingredient; any method of production; any method of use; etc.) may be excluded from any one or more claims, for any reason, whether or not related to the existence of prior art.

It is to be understood that the words which have been used are words of description rather than limitation, and that changes may be made within the purview of the appended claims without departing from the true scope and spirit encompassed by the present invention in its broader aspects.

While the present invention has been described at some length and with some particularity with respect to several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope encompassed by the present invention.

What is claimed is:

1. A monoclonal antibody, or antigen-binding fragment thereof, that binds a V-Set and Immunoglobulin Domain Containing 4 (VSIG4) polypeptide, wherein the monoclonal antibody, or antigen-binding fragment thereof, comprises: a CDRH1 having residues 26-32 of SEQ ID NO: 64, CDRH2 having residues 52-57 of SEQ ID NO: 64, and CDRH3 having residues 99-107 of SEQ ID NO: 64; and a CDRL1 having residues 24-34 of SEQ ID NO: 67, CDRL2 having residues 50-56 of SEQ ID NO: 67, and CDRL3 having residues 89-97 of SEQ ID NO: 67.

2. The monoclonal antibody, or antigen-binding fragment thereof, of claim 1, wherein the monoclonal antibody, or antigen-binding fragment thereof, binds myeloid cells expressing the VSIG4 polypeptide and increases the inflammatory phenotype of the myeloid cells.

3. The monoclonal antibody, or antigen-binding fragment thereof, of claim 2, wherein the myeloid cells have one or more of the following properties after contact with the monoclonal antibody, or antigen-binding fragment thereof:

i) increased expression and/or secretion of cluster of differentiation 80 (CD80), CD86, MHCII, MHCI, interleukin 1-beta (IL-1B), IL-6, CCL3, CCL4, CXCL10, CXCL9, GM-CSF and/or tumor necrosis factor alpha (TNF-$\alpha$);

ii) decreased expression and/or secretion of CD206, CD163, CD16, CD53, VSIG4, TGFb and/or IL-10;

iii) increased secretion of at least one cytokine or chemokine selected from the group consisting of IL-12, IL-18, and IL-23;

iv) increased ratio of expression of IL-1$\beta$, IL-6, and/or TNF-$\alpha$ to expression of IL-10;

v) increased CD8+ cytotoxic T cell activation;

vi) increased recruitment of CD8+ cytotoxic T cell activation;

vii) increased CD4+ helper T cell activity;

viii) increased recruitment of CD4+ helper T cell activity;

ix) increased NK cell activity;

x) increased recruitment of NK cells;

xi) increased neutrophil activity;

xii) increased macrophage and/or dendritic cell activity; and/or xiii) increased spindle-shaped morphology, flatness of appearance, and/or number of dendrites, as assessed by microscopy.

4. The monoclonal antibody, or antigen-binding fragment thereof, of claim 1, wherein the monoclonal antibody, or antigen-binding fragment thereof, selectively binds a human VSIG4 polypeptide at least 1.1-fold greater than a polypeptide selected from the group consisting of C3b and iC3b, wherein the polypeptides are expressed on cells or in vitro.

5. The monoclonal antibody, or antigen-binding fragment thereof, of claim 1, wherein the monoclonal antibody, or antigen-binding fragment thereof, binds to a human VSIG4 polypeptide with a KD of between about 0.00001 nanomolar (nM) and 1000 nM.

6. The monoclonal antibody, or antigen-binding fragment thereof, of claim 1, wherein the monoclonal antibody, or antigen-binding fragment thereof, binds to a IgV domain of a human VSIG4 polypeptide and/or binds to a linear or conformational epitope of a human VSIG4 polypeptide.

7. The monoclonal antibody, or antigen-binding fragment thereof, of claim 6, wherein the human VSIG4 polypeptide has the amino acid sequence of SEQ ID NO: 19 or 20; and wherein the linear or conformational epitope comprises one or more residues selected from Q40, R41, G42, S43, D44, V46, Q59, E95, D109, and I111 either within or in addition to a portion of the human VSIG4 polypeptide selected from the group consisting of the IgV domain, a Q40-V46 loop, a V107-V116 loop, and a Q40-V46-D109 surface.

8. The monoclonal antibody, or antigen-binding fragment thereof, of claim 1, wherein the monoclonal antibody, or antigen-binding fragment thereof, binds one or more VSIG4 isoforms.

9. The monoclonal antibody, or antigen-binding fragment thereof, of claim 8, wherein the VSIG4 isoforms are VSIG4-L and/or VSIG4-S.

10. The monoclonal antibody, or antigen-binding fragment thereof, of claim 1, wherein the monoclonal antibody, or antigen-binding fragment thereof, cross-reacts with a cynomolgus VSIG4 polypeptide and/or murine VSIG4 polypeptide.

11. The monoclonal antibody, or antigen-binding fragment thereof, of claim 1, wherein the monoclonal antibody, or antigen-binding fragment thereof, competes with, inhibits, or blocks binding of the VSIG4 polypeptide with a VSIG4 ligand.

12. The monoclonal antibody, or antigen-binding fragment thereof, of claim 1, wherein the monoclonal antibody, or antigen-binding fragment thereof, i) does not activate unstimulated monocytes;

ii) does not have an ADCC activity against VSIG4-expressing cells;

iii) does not have a CDC activity against VSIG4-expressing cells;

iv) does not kill VSIG4-expressing cells upon binding the VSIG4-expressing cells and/or internalization by the VSIG4-expressing cells; and/or v) is not conjugated to another therapeutic moiety.

13. The monoclonal antibody, or antigen-binding fragment thereof, of claim 1, wherein the monoclonal antibody, or antigen-binding fragment thereof, i) competes with, inhibits, or blocks binding of the VSIG4 polypeptide with a T cell VSIG4 ligand;

ii) de-represses and/or activates T cells by inhibiting VSIG4-T cell interactions; and/or iii) indirectly de-represses and/or activates T cells by increasing the inflammatory phenotype of myeloid cells.

14. The monoclonal antibody, or antigen-binding fragment thereof, of claim 1, wherein the monoclonal antibody, or antigen-binding fragment thereof, has an antitumor activity in vivo.

15. The monoclonal antibody, or antigen-binding fragment thereof, of claim 1, wherein the monoclonal antibody, or antigen-binding fragment thereof, comprises:

i) a heavy chain variable domain sequence with at least 90% identity to SEQ ID NO: 64; and/or ii) a light chain variable domain sequence with at least 90% identity to SEQ ID NO: 67.

16. The monoclonal antibody, or antigen-binding fragment thereof, of claim 1, wherein the monoclonal antibody, or antigen-binding fragment thereof, comprises:

i) a heavy chain variable domain sequence of SEQ ID NO: 64; and/or ii) a light chain variable domain sequence of SEQ ID NO: 67.

17. The monoclonal antibody, or antigen-binding fragment thereof, of claim 1, wherein the monoclonal antibody, or antigen-binding fragment thereof, is chimeric, humanized, or murine.

18. The monoclonal antibody, or antigen-binding fragment thereof, of claim 1, wherein the monoclonal antibody, or antigen-binding fragment thereof, is detectably labeled, comprises an effector domain, and/or comprises an Fc domain.

19. The monoclonal antibody, or antigen-binding fragment thereof, of claim 1, wherein the monoclonal antibody, or antigen-binding fragment thereof, is selected from the group consisting of Fv, F(ab')2, Fab', dsFv, scFv, sc(Fv)2, and diabody fragments.

20. The monoclonal antibody, or antigen-binding fragment thereof, of claim 1, wherein the monoclonal antibody, or antigen-binding fragment thereof, comprises an immunoglobulin constant domain selected from the group consisting of IgG1, IgG2, IgG3, IgG4, IgA1, IgA2, IgD, IgE, and IgM.

21. The monoclonal antibody, or antigen-binding fragment thereof, of claim 1, wherein the monoclonal antibody, or antigen-binding fragment thereof, comprises a constant domain derived from a human immunoglobulin.

22. The monoclonal antibody, or antigen-binding fragment thereof, of claim 1, wherein the monoclonal antibody, or antigen-binding fragment thereof, is conjugated to an agent.

23. The monoclonal antibody, or antigen-binding fragment thereof, of claim 22, wherein the agent is selected from the group consisting of a binding protein, an enzyme, a drug, a chemotherapeutic agent, a biologic agent, a toxin, a radionuclide, an immunomodulatory agent, a detectable moiety, and a tag.

24. The monoclonal antibody, or antigen-binding fragment thereof, of claim 2, wherein the myeloid cells comprise suppressive myeloid cells, monocytes, macrophages, neutrophils, and/or dendritic cells.

25. The monoclonal antibody, or antigen-binding fragment thereof, of claim 2, wherein the myeloid cells comprise Type 1 macrophages, M1 macrophages, Type 2 macrophages, M2 macrophages, M2c macrophages, M2d macrophages, tumor-associated macrophages (TAM), CD11b+ cells, CD14+ cells, and/or CD11b+/CD14+ cells.

26. The monoclonal antibody, or antigen-binding fragment thereof, of claim 2, wherein the myeloid cells are primary myeloid cells.

27. The monoclonal antibody, or antigen-binding fragment thereof, of claim 2, wherein the myeloid cells are comprised within a tissue microenvironment.

28. The monoclonal antibody, or antigen-binding fragment thereof, of claim 2, wherein the myeloid cells are comprised within a human tumor model or an animal model of cancer.

29. A pharmaceutical composition comprising a therapeutically effective amount of at least one monoclonal antibody, or antigen-binding fragment thereof, of claim 1, and a pharmaceutically acceptable carrier or excipient.

30. A device or kit comprising at least one monoclonal antibody, or antigen-binding fragment thereof, of claim 1.

31. A method of producing at least one monoclonal antibody, or antigen-binding fragment thereof, of claim 1, which method comprises the steps of: (i) culturing a transformed host cell which has been transformed by a plasmid or vector comprising a sequence encoding the monoclonal antibody, or antigen-binding fragment thereof, according to claim 1 under conditions suitable to allow expression of said monoclonal antibody, or antigen-binding fragment thereof; and (ii) recovering the expressed monoclonal antibody, or antigen-binding fragment thereof.

* * * * *

SEQUENCE LISTING

```
<160> NUMBER OF SEQ ID NOS: 112

<210> SEQ ID NO 1
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Ile Leu Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys
            100                 105
```

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Asp Asp Phe
            20                  25                  30

Tyr Met Tyr Trp Val Arg Gln Thr Pro Glu Lys Arg Leu Glu Trp Val
        35                  40                  45

Ala Ser Ile Ser Asp Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Leu Ser Ser Leu Lys Ser Glu Asp Thr Ala Met Tyr Tyr Cys
                85                  90                  95

Ala Arg Gly Val Asp Lys Tyr Tyr Tyr Ala Met Asp Tyr Trp Gly Gln
            100                 105                 110

Gly Thr Ser Val Thr Val Ser Ser
        115                 120
```

<210> SEQ ID NO 3
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Leu Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Arg Gln Gly Asn Thr Leu Pro Trp
                85                  90                  95

Thr Phe Gly Gly Gly Thr Lys Leu Glu Ile Lys
            100                 105
```

<210> SEQ ID NO 4
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Gln Val Gln Met Lys Gln Ser Gly Ala Glu Leu Ala Lys Pro Gly Ala
```

```
1               5                   10                  15

Ser Val Lys Met Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Thr Asp Tyr Asn Gln Asn Phe
    50                  55                  60

Lys Asp Arg Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ile Arg Gly Ser Asp Tyr Tyr Gly Arg Asp Tyr Trp Gly Gln Gly Thr
            100                 105                 110

Thr Leu Thr Val Ser Ser
        115


<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Thr Thr Val Thr Gln Ser Pro Ala Ser Leu Ser Val Ala Thr Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ala Gly Thr Lys Leu Glu Leu Lys
            100                 105


<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Glu Asn Phe
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Ala Thr Tyr Ala Asp Asp Phe
    50                  55                  60

Lys Gly Arg Phe Ala Phe Ser Leu Glu Thr Ser Ala Ser Thr Ala Tyr
```

```
65                  70                  75                  80

Leu Gln Ile Asn Asn Leu Lys Asn Glu Asp Thr Ala Thr Tyr Phe Cys
                85                  90                  95

Ala Arg Asp Gly Gly Phe Arg His Phe Asp Val Trp Gly Ala Gly Thr
            100                 105                 110

Thr Val Thr Val Ser Ser
        115


<210> SEQ ID NO 7
<211> LENGTH: 1869
<212> TYPE: DNA
<213> ORGANISM: Homo sapiens

<400> SEQUENCE: 7

ggagtttgag tgagagatat agggaaggaa gggaagtaag cagtcacaga cgctggcggc      60

caccagaagt ttgagcctct ttggtagcag gaggctggaa gaaaggacag aagtagctct     120

ggctgtgatg gggatcttac tgggcctgct actcctgggg cacctaacag tggacactta     180

tggccgtccc atcctggaag tgccagagag tgtaacagga ccttggaaag ggggatgtgaa    240

tcttccctgc acctatgacc ccctgcaagg ctacacccaa gtcttggtga agtggctggt     300

acaacgtggc tcagaccctg tcaccatctt tctacgtgac tcttctggag accatatcca     360

gcaggcaaag taccagggcc gcctgcatgt gagccacaag gttccaggag atgtatccct     420

ccaattgagc accctggaga tggatgaccg gagccactac acgtgtgaag tcacctggca     480

gactcctgat ggcaaccaag tcgtgagaga taagattact gagctccgtg tccagaaact     540

ctctgtctcc aagcccacag tgacaactgg cagcggttat ggcttcacgg tgccccaggg     600

aatgaggatt agccttcaat gccaggctcg gggttctcct cccatcagtt atatttggta     660

taagcaacag actaataacc aggaacccat caaagtagca accctaagta ccttactctt     720

caagcctgcg gtgatagccg actcaggctc ctatttctgc actgccaagg gccaggttgg     780

ctctgagcag cacagcgaca ttgtgaagtt tgtggtcaaa gactcctcaa agctactcaa     840

gaccaagact gaggcaccta caaccatgac ataccccttg aaagcaacat ctacagtgaa     900

gcagtcctgg gactggacca ctgacatgga tggctacctt ggagagacca gtgctgggcc     960

aggaaagagc ctgcctgtct ttgccatcat cctcatcatc tccttgtgct gtatggtggt    1020

ttttaccatg gcctatatca tgctctgtcg gaagacatcc caacaagagc atgtctacga    1080

agcagccagg gcacatgcca gagaggccaa cgactctgga gaaaccatga gggtggccat    1140

cttcgcaagt ggctgctcca gtgatgagcc aacttcccag aatctgggca acaactactc    1200

tgatgagccc tgcataggac aggagtacca gatcatcgcc cagatcaatg gcaactacgc    1260

ccgcctgctg gacacagttc ctctggatta tgagtttctg gccactgagg gcaaaagtgt    1320

ctgttaaaaa tgccccatta ggccaggatc tgctgacata attgcctagt cagtccttgc    1380

cttctgcatg gccttcttcc ctgctacctc tcttcctgga tagcccaaag tgtccgccta    1440

ccaacactgg agccgctggg agtcactggc tttgccctgg aatttgccag atgcatctca    1500

agtaagccag ctgctggatt tggctctggg cccttctagt atctctgccg ggggcttctg    1560

gtactcctct ctaaatacca gagggaagat gcccatagca ctaggacttg gtcatcatgc    1620

ctacagacac tattcaactt tggcatcttg ccaccagaag acccgaggga ggctcagctc    1680

tgccagctca gaggaccagc tatatccagg atcatttctc tttcttcagg gccagacagc    1740

ttttaattga aattgttatt tcacaggcca gggttcagtt ctgctcctcc actataagtc    1800
```

```
taatgttctg actctctcct ggtgctcaat aaatatctaa tcataacagc aaaaaaaaaa   1860

aaaaaaaaa                                                           1869


<210> SEQ ID NO 8
<211> LENGTH: 399
<212> TYPE: PRT
<213> ORGANISM: Homo sapiens

<400> SEQUENCE: 8

Met Gly Ile Leu Leu Gly Leu Leu Leu Leu Gly His Leu Thr Val Asp
1               5                   10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45

Tyr Thr Gln Val Leu Val Lys Trp Leu Val Gln Arg Gly Ser Asp Pro
    50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys Leu Ser Val Ser Lys Pro Thr
    130                 135                 140

Val Thr Thr Gly Ser Gly Tyr Gly Phe Thr Val Pro Gln Gly Met Arg
145                 150                 155                 160

Ile Ser Leu Gln Cys Gln Ala Arg Gly Ser Pro Pro Ile Ser Tyr Ile
                165                 170                 175

Trp Tyr Lys Gln Gln Thr Asn Asn Gln Glu Pro Ile Lys Val Ala Thr
            180                 185                 190

Leu Ser Thr Leu Leu Phe Lys Pro Ala Val Ile Ala Asp Ser Gly Ser
        195                 200                 205

Tyr Phe Cys Thr Ala Lys Gly Gln Val Gly Ser Glu Gln His Ser Asp
    210                 215                 220

Ile Val Lys Phe Val Val Lys Asp Ser Ser Lys Leu Leu Lys Thr Lys
225                 230                 235                 240

Thr Glu Ala Pro Thr Thr Met Thr Tyr Pro Leu Lys Ala Thr Ser Thr
                245                 250                 255

Val Lys Gln Ser Trp Asp Trp Thr Thr Asp Met Asp Gly Tyr Leu Gly
            260                 265                 270

Glu Thr Ser Ala Gly Pro Gly Lys Ser Leu Pro Val Phe Ala Ile Ile
        275                 280                 285

Leu Ile Ile Ser Leu Cys Cys Met Val Val Phe Thr Met Ala Tyr Ile
    290                 295                 300

Met Leu Cys Arg Lys Thr Ser Gln Gln Glu His Val Tyr Glu Ala Ala
305                 310                 315                 320

Arg Ala His Ala Arg Glu Ala Asn Asp Ser Gly Glu Thr Met Arg Val
                325                 330                 335

Ala Ile Phe Ala Ser Gly Cys Ser Ser Asp Glu Pro Thr Ser Gln Asn
            340                 345                 350

Leu Gly Asn Asn Tyr Ser Asp Glu Pro Cys Ile Gly Gln Glu Tyr Gln
```

```
        355                 360                 365

Ile Ile Ala Gln Ile Asn Gly Asn Tyr Ala Arg Leu Leu Asp Thr Val
    370                 375                 380

Pro Leu Asp Tyr Glu Phe Leu Ala Thr Glu Gly Lys Ser Val Cys
385                 390                 395


<210> SEQ ID NO 9
<211> LENGTH: 1586
<212> TYPE: DNA
<213> ORGANISM: Homo sapiens

<400> SEQUENCE: 9

ggagtttgag tgagagatat agggaaggaa gggaagtaag cagtcacaga cgctggcggc      60

caccagaagt ttgagcctct ttggtagcag gaggctggaa gaaaggacag aagtagctct     120

ggctgtgatg ggatcttac tgggcctgct actcctgggg cacctaacag tggacactta      180

tggccgtccc atcctggaag tgccagagag tgtaacagga ccttggaaag gggatgtgaa     240

tcttccctgc acctatgacc ccctgcaagg ctacacccaa gtcttggtga agtggctggt     300

acaacgtggc tcagaccctg tcaccatctt tctacgtgac tcttctggag accatatcca     360

gcaggcaaag taccagggcc gcctgcatgt gagccacaag gttccaggag atgtatccct     420

ccaattgagc accctggaga tggatgaccg gagccactac acgtgtgaag tcacctggca     480

gactcctgat ggcaaccaag tcgtgagaga taagattact gagctccgtg tccagaaaca     540

ctcctcaaag ctactcaaga ccaagactga ggcacctaca accatgacat accccttgaa     600

agcaacatct acagtgaagc agtcctggga ctggaccact gacatggatg gctaccttgg     660

agagaccagt gctgggccag gaaagagcct gcctgtcttt gccatcatcc tcatcatctc     720

cttgtgctgt atggtggttt ttaccatggc ctatatcatg ctctgtcgga agacatccca     780

acaagagcat gtctacgaag cagccagggc acatgccaga gaggccaacg actctggaga     840

aaccatgagg gtggccatct tcgcaagtgg ctgctccagt gatgagccaa cttcccagaa     900

tctgggcaac aactactctg atgagccctg cataggacag gagtaccaga tcatcgccca     960

gatcaatggc aactacgccc gcctgctgga cacagttcct ctggattatg agtttctggc    1020

cactgagggc aaaagtgtct gttaaaaatg ccccattagg ccaggatctg ctgacataat    1080

tgcctagtca gtccttgcct tctgcatggc cttcttccct gctacctctc ttcctggata    1140

gcccaaagtg tccgcctacc aacactggag ccgctgggag tcactggctt tgccctggaa    1200

tttgccagat gcatctcaag taagccagct gctggatttg gctctgggcc cttctagtat    1260

ctctgccggg ggcttctggt actcctctct aaataccaga gggaagatgc ccatagcact    1320

aggacttggt catcatgcct acagacacta ttcaactttg gcatcttgcc accagaagac    1380

ccgagggagg ctcagctctg ccagctcaga ggaccagcta tatccaggat catttctctt    1440

tcttcagggc cagacagctt ttaattgaaa ttgttatttc acaggccagg gttcagttct    1500

gctcctccac tataagtcta atgttctgac tctctcctgg tgctcaataa atatctaatc    1560

ataacagcaa aaaaaaaaaa aaaaaa                                         1586


<210> SEQ ID NO 10
<211> LENGTH: 305
<212> TYPE: PRT
<213> ORGANISM: Homo sapiens

<400> SEQUENCE: 10

Met Gly Ile Leu Leu Gly Leu Leu Leu Leu Gly His Leu Thr Val Asp
```

```
1               5                   10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45

Tyr Thr Gln Val Leu Val Lys Trp Leu Val Gln Arg Gly Ser Asp Pro
    50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys His Ser Ser Lys Leu Leu Lys
    130                 135                 140

Thr Lys Thr Glu Ala Pro Thr Thr Met Thr Tyr Pro Leu Lys Ala Thr
145                 150                 155                 160

Ser Thr Val Lys Gln Ser Trp Asp Trp Thr Thr Asp Met Asp Gly Tyr
                165                 170                 175

Leu Gly Glu Thr Ser Ala Gly Pro Gly Lys Ser Leu Pro Val Phe Ala
            180                 185                 190

Ile Ile Leu Ile Ile Ser Leu Cys Cys Met Val Val Phe Thr Met Ala
        195                 200                 205

Tyr Ile Met Leu Cys Arg Lys Thr Ser Gln Gln Glu His Val Tyr Glu
    210                 215                 220

Ala Ala Arg Ala His Ala Arg Glu Ala Asn Asp Ser Gly Glu Thr Met
225                 230                 235                 240

Arg Val Ala Ile Phe Ala Ser Gly Cys Ser Ser Asp Glu Pro Thr Ser
                245                 250                 255

Gln Asn Leu Gly Asn Asn Tyr Ser Asp Glu Pro Cys Ile Gly Gln Glu
            260                 265                 270

Tyr Gln Ile Ile Ala Gln Ile Asn Gly Asn Tyr Ala Arg Leu Leu Asp
        275                 280                 285

Thr Val Pro Leu Asp Tyr Glu Phe Leu Ala Thr Glu Gly Lys Ser Val
    290                 295                 300

Cys
305
```

<210> SEQ ID NO 11
<211> LENGTH: 1927
<212> TYPE: DNA
<213> ORGANISM: Homo sapiens

<400> SEQUENCE: 11

```
ggagtttgag tgagagatat agggaaggaa gggaagtaag cagtcacaga cgctggcggc     60

caccagaagt ttgagcctct ttggtagcag gaggctggaa gaaaggacag aagtagctct    120

ggctgtgatg gggatcttac tgggcctgct actcctgggg cacctaacag tggacactta    180

tggccgtccc atcctggaag tgccagagag tgtaacagga ccttggaaag gggatgtgaa    240

tcttccctgc acctatgacc ccctgcaagg ctacacccaa gtcttggtga agtggctggt    300

acaacgtggc tcagaccctg tcaccatctt tctacgtgac tcttctggag accatatcca    360
```

-continued

```
gcaggcaaag taccagggcc gcctgcatgt gagccacaag gttccaggag atgtatccct    420

ccaattgagc accctggaga tggatgaccg gagccactac acgtgtgaag tcacctggca    480

gactcctgat ggcaaccaag tcgtgagaga taagattact gagctccgtg tccagaaaca    540

ctcctcaaag ctactcaaga ccaagactga ggcacctaca accatgacat accccttgaa    600

agcaacatct acagtgaagc agtcctggga ctggaccact gacatggatg gctaccttgg    660

agagaccagt gctgggccag gaaagagcct gcctgtcttt gccatcatcc tcatcatctc    720

cttgtgctgt atggtggttt ttaccatggc ctatatcatg ctctgtcgga agacatccca    780

acaagagcat gtctacgaag cagccaggta agaaagtctc tcctcttcca tttttgaccc    840

cgtccctgcc ctcaattttg attactggca ggaaatgtgg aggaaggggg gtgtggcaca    900

gacccaatcc taaggccgga ggccttcagg gtcaggacat agctgccttc cctctctcag    960

gcaccttctg aggttgtttt ggccctctga acacaaagga taatttagat ccatctgcct   1020

tctgcttcca gaatccctgg gtggtaggat cctgataatt aattggcaag aattgaggca   1080

gaagggtggg aaaccaggac cacagcccca agtcccttct tatgggtggt gggctcttgg   1140

gccatagggc acatgccaga gaggccaacg actctggaga aaccatgagg gtggccatct   1200

tcgcaagtgg ctgctccagt gatgagccaa cttcccagaa tctgggcaac aactactctg   1260

atgagccctg cataggacag gagtaccaga tcatcgccca gatcaatggc aactacgccc   1320

gcctgctgga cacagttcct ctggattatg agtttctggc cactgagggc aaaagtgtct   1380

gttaaaaatg ccccattagg ccaggatctg ctgacataat tgcctagtca gtccttgcct   1440

tctgcatggc cttcttccct gctacctctc ttcctggata gcccaaagtg tccgcctacc   1500

aacactggag ccgctgggag tcactggctt tgccctggaa tttgccagat gcatctcaag   1560

taagccagct gctggatttg gctctgggcc cttctagtat ctctgccggg ggcttctggt   1620

actcctctct aaataccaga gggaagatgc ccatagcact aggacttggt catcatgcct   1680

acagacacta ttcaactttg gcatcttgcc accagaagac ccgagggagg ctcagctctg   1740

ccagctcaga ggaccagcta tatccaggat catttctctt tcttcagggc cagacagctt   1800

ttaattgaaa ttgttatttc acaggccagg gttcagttct gctcctccac tataagtcta   1860

atgttctgac tctctcctgg tgctcaataa atatctaatc ataacagcaa aaaaaaaaaa   1920

aaaaaaa                                                             1927
```

```
<210> SEQ ID NO 12
<211> LENGTH: 227
<212> TYPE: PRT
<213> ORGANISM: Homo sapiens

<400> SEQUENCE: 12

Met Gly Ile Leu Leu Gly Leu Leu Leu Leu Gly His Leu Thr Val Asp
1               5                   10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45

Tyr Thr Gln Val Leu Val Lys Trp Leu Val Gln Arg Gly Ser Asp Pro
    50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95
```

```
Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys His Ser Ser Lys Leu Leu Lys
    130                 135                 140

Thr Lys Thr Glu Ala Pro Thr Thr Met Thr Tyr Pro Leu Lys Ala Thr
145                 150                 155                 160

Ser Thr Val Lys Gln Ser Trp Asp Trp Thr Thr Asp Met Asp Gly Tyr
                165                 170                 175

Leu Gly Glu Thr Ser Ala Gly Pro Gly Lys Ser Leu Pro Val Phe Ala
            180                 185                 190

Ile Ile Leu Ile Ile Ser Leu Cys Cys Met Val Val Phe Thr Met Ala
        195                 200                 205

Tyr Ile Met Leu Cys Arg Lys Thr Ser Gln Gln Glu His Val Tyr Glu
    210                 215                 220

Ala Ala Arg
225
```

<210> SEQ ID NO 13
<211> LENGTH: 2209
<212> TYPE: DNA
<213> ORGANISM: Homo sapiens

<400> SEQUENCE: 13

```
ggagtttgag tgagagatat agggaaggaa gggaagtaag cagtcacaga cgctggcggc      60

caccagaagt ttgagcctct ttggtagcag gaggctggaa gaaaggacag aagtagctct     120

ggctgtgatg gggatcttac tgggcctgct actcctgggg cacctaacag tggacactta     180

tggccgtccc atcctggaag tgccagagag tgtaacagga ccttggaaag gggatgtgaa     240

tcttccctgc acctatgacc ccctgcaagg ctacacccaa gtcttggtga agtggctggt     300

acaacgtggc tcagaccctg tcaccatctt tctacgtgac tcttctggag accatatcca     360

gcaggcaaag taccagggcc gcctgcatgt gagccacaag gttccaggag atgtatccct     420

ccaattgagc accctggaga tggatgaccg gagccactac acgtgtgaag tcacctggca     480

gactcctgat ggcaaccaag tcgtgagaga taagattact gagctccgtg tccagaaact     540

ctctgtctcc aagcccacag tgacaactgg cagcggttat ggcttcacgg tgccccaggg     600

aatgaggatt agccttcaat gccaggctcg gggttctcct cccatcagtt atatttggta     660

taagcaacag actaataacc aggaacccat caaagtagca accctaagta ccttactctt     720

caagcctgcg gtgatagccg actcaggctc ctatttctgc actgccaagg gccaggttgg     780

ctctgagcag cacagcgaca ttgtgaagtt tgtggtcaaa gactcctcaa agctactcaa     840

gaccaagact gaggcaccta caaccatgac ataccccttg aaagcaacat ctacagtgaa     900

gcagtcctgg gactggacca ctgacatgga tggctacctt ggagagacca gtgctgggcc     960

aggaaagagc ctgcctgtct ttgccatcat cctcatcatc tccttgtgct gtatggtggt    1020

tttaccatg gcctatatca tgctctgtcg gaagacatcc caacaagagc atgtctacga     1080

agcagccagg taagaaagtc tctcctcttc catttttgac cccgtccctg ccctcaattt    1140

tgattactgg caggaaatgt ggaggaaggg gggtgtggca cagacccaat cctaaggccg    1200

gaggccttca gggtcaggac atagctgcct tccctctctc aggcaccttc tgaggttgtt    1260

ttggccctct gaacacaaag gataatttag atccatctgc cttctgcttc cagaatccct    1320
```

```
gggtggtagg atcctgataa ttaattggca agaattgagg cagaagggtg ggaaaccagg   1380

accacagccc caagtccctt cttatgggtg gtgggctctt gggccatagg gcacatgcca   1440

gagaggccaa cgactctgga gaaaccatga gggtggccat cttcgcaagt ggctgctcca   1500

gtgatgagcc aacttcccag aatctgggca acaactactc tgatgagccc tgcataggac   1560

aggagtacca gatcatcgcc cagatcaatg gcaactacgc ccgcctgctg gacacagttc   1620

ctctggatta tgagtttctg gccactgagg gcaaaagtgt ctgttaaaaa tgccccatta   1680

ggccaggatc tgctgacata attgcctagt cagtccttgc cttctgcatg gccttcttcc   1740

ctgctacctc tcttcctgga tagcccaaag tgtccgccta ccaacactgg agccgctggg   1800

agtcactggc tttgccctgg aatttgccag atgcatctca agtaagccag ctgctggatt   1860

tggctctggg cccttctagt atctctgccg gggcttctg gtactcctct ctaaatacca    1920

gagggaagat gcccatagca ctaggacttg gtcatcatgc ctacagacac tattcaactt   1980

tggcatcttg ccaccagaag acccgaggga ggctcagctc tgccagctca gaggaccagc   2040

tatatccagg atcatttctc tttcttcagg gccagacagc ttttaattga aattgttatt   2100

tcacaggcca gggttcagtt ctgctcctcc actataagtc taatgttctg actctctcct   2160

ggtgctcaat aaatatctaa tcataacagc aaaaaaaaaa aaaaaaaaa              2209
```

<210> SEQ ID NO 14
<211> LENGTH: 321
<212> TYPE: PRT
<213> ORGANISM: Homo sapiens

<400> SEQUENCE: 14

```
Met Gly Ile Leu Leu Gly Leu Leu Leu Leu Gly His Leu Thr Val Asp
1               5                   10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45

Tyr Thr Gln Val Leu Val Lys Trp Leu Val Gln Arg Gly Ser Asp Pro
    50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys Leu Ser Val Ser Lys Pro Thr
    130                 135                 140

Val Thr Thr Gly Ser Gly Tyr Gly Phe Thr Val Pro Gln Gly Met Arg
145                 150                 155                 160

Ile Ser Leu Gln Cys Gln Ala Arg Gly Ser Pro Pro Ile Ser Tyr Ile
                165                 170                 175

Trp Tyr Lys Gln Gln Thr Asn Asn Gln Glu Pro Ile Lys Val Ala Thr
            180                 185                 190

Leu Ser Thr Leu Leu Phe Lys Pro Ala Val Ile Ala Asp Ser Gly Ser
        195                 200                 205

Tyr Phe Cys Thr Ala Lys Gly Gln Val Gly Ser Glu Gln His Ser Asp
```

```
    210                 215                 220

Ile Val Lys Phe Val Val Lys Asp Ser Ser Lys Leu Leu Lys Thr Lys
225                 230                 235                 240

Thr Glu Ala Pro Thr Thr Met Thr Tyr Pro Leu Lys Ala Thr Ser Thr
                245                 250                 255

Val Lys Gln Ser Trp Asp Trp Thr Thr Asp Met Asp Gly Tyr Leu Gly
            260                 265                 270

Glu Thr Ser Ala Gly Pro Gly Lys Ser Leu Pro Val Phe Ala Ile Ile
        275                 280                 285

Leu Ile Ile Ser Leu Cys Cys Met Val Val Phe Thr Met Ala Tyr Ile
    290                 295                 300

Met Leu Cys Arg Lys Thr Ser Gln Gln Glu His Val Tyr Glu Ala Ala
305                 310                 315                 320

Arg


<210> SEQ ID NO 15
<211> LENGTH: 1535
<212> TYPE: DNA
<213> ORGANISM: Homo sapiens

<400> SEQUENCE: 15

ggagtttgag tgagagatat agggaaggaa gggaagtaag cagtcacaga cgctggcggc     60

caccagaagt ttgagcctct ttggtagcag gaggctggaa gaaaggacag aagtagctct    120

ggctgtgatg gggatcttac tgggcctgct actcctgggg cacctaacag tggacactta    180

tggccgtccc atcctggaag tgccagagag tgtaacagga ccttggaaag gggatgtgaa    240

tcttccctgc acctatgacc ccctgcaagg ctacacccaa gtcttggtga agtggctggt    300

acaacgtggc tcagaccctg tcaccatctt tctacgtgac tcttctggag accatatcca    360

gcaggcaaag taccagggcc gcctgcatgt gagccacaag gttccaggag atgtatccct    420

ccaattgagc accctggaga tggatgaccg gagccactac acgtgtgaag tcacctggca    480

gactcctgat ggcaaccaag tcgtgagaga taagattact gagctccgtg tccagaaact    540

ctctgtctcc aagcccacag tgacaactgg cagcggttat ggcttcacgg tgccccaggg    600

aatgaggatt agccttcaat gccaggctcg gggttctcct cccatcagtt atatttggta    660

taagcaacag actaataacc aggaacccat caaagtagca accctaagta ccttactctt    720

caagcctgcg gtgatagccg actcaggctc ctatttctgc actgccaagg gccaggttgg    780

ctctgagcag cacagcgaca ttgtgaagtt tgtggtcaaa gactcctcaa agctactcaa    840

gaccaagact gaggcaccta caaccatgac ataccccttg aaagcaacat ctacagtgaa    900

gcagtcctgg gactggacca ctgacatgga tggctacctt ggagagacca gtgctgggcc    960

aggaaagagc ctgcctgtct ttgccatcat cctcatcatc tccttgtgct gtatggtggt   1020

tttaccatg gcctatatca tgctctgtcg gaagacatcc caacaagagc atgtctacga   1080

agcagccagc ccaaagtgtc cgcctaccaa cactggagcc gctgggagtc actggctttg   1140

ccctggaatt tgccagatgc atctcaagta agccagctgc tggatttggc tctgggccct   1200

tctagtatct ctgccggggg cttctggtac tcctctctaa ataccagagg gaagatgccc   1260

atagcactag gacttggtca tcatgcctac agacactatt caactttggc atcttgccac   1320

cagaagaccc gagggaggct cagctctgcc agctcagagg accagctata tccaggatca   1380

tttctctttc ttcagggcca gacagctttt aattgaaatt gttatttcac aggccagggt   1440

tcagttctgc tcctccacta taagtctaat gttctgactc tctcctggtg ctcaataaat   1500
```

atctaatcat aacagcaaaa aaaaaaaaaa aaaaa 1535

<210> SEQ ID NO 16
<211> LENGTH: 347
<212> TYPE: PRT
<213> ORGANISM: Homo sapiens

<400> SEQUENCE: 16

```
Met Gly Ile Leu Leu Gly Leu Leu Leu Leu Gly His Leu Thr Val Asp
1               5                   10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45

Tyr Thr Gln Val Leu Val Lys Trp Leu Val Gln Arg Gly Ser Asp Pro
    50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys Leu Ser Val Ser Lys Pro Thr
    130                 135                 140

Val Thr Thr Gly Ser Gly Tyr Gly Phe Thr Val Pro Gln Gly Met Arg
145                 150                 155                 160

Ile Ser Leu Gln Cys Gln Ala Arg Gly Ser Pro Pro Ile Ser Tyr Ile
                165                 170                 175

Trp Tyr Lys Gln Gln Thr Asn Asn Gln Glu Pro Ile Lys Val Ala Thr
            180                 185                 190

Leu Ser Thr Leu Leu Phe Lys Pro Ala Val Ile Ala Asp Ser Gly Ser
        195                 200                 205

Tyr Phe Cys Thr Ala Lys Gly Gln Val Gly Ser Glu Gln His Ser Asp
    210                 215                 220

Ile Val Lys Phe Val Val Lys Asp Ser Ser Lys Leu Leu Lys Thr Lys
225                 230                 235                 240

Thr Glu Ala Pro Thr Thr Met Thr Tyr Pro Leu Lys Ala Thr Ser Thr
                245                 250                 255

Val Lys Gln Ser Trp Asp Trp Thr Thr Asp Met Asp Gly Tyr Leu Gly
            260                 265                 270

Glu Thr Ser Ala Gly Pro Gly Lys Ser Leu Pro Val Phe Ala Ile Ile
        275                 280                 285

Leu Ile Ile Ser Leu Cys Cys Met Val Val Phe Thr Met Ala Tyr Ile
    290                 295                 300

Met Leu Cys Arg Lys Thr Ser Gln Gln Glu His Val Tyr Glu Ala Ala
305                 310                 315                 320

Ser Pro Lys Cys Pro Pro Thr Asn Thr Gly Ala Ala Gly Ser His Trp
                325                 330                 335

Leu Cys Pro Gly Ile Cys Gln Met His Leu Lys
            340                 345
```

<210> SEQ ID NO 17

<211> LENGTH: 1432
<212> TYPE: DNA
<213> ORGANISM: Mus musculus

<400> SEQUENCE: 17
agctaccagc acttccaggt tcttcagcag caagaggatg gaaggatgaa tagaagtagc 60
ttcaaatagg atggagatct catcaggctt gctgttcctg ggccacctaa tagtgctcac 120
ctatggccac cccaccctaa aaacacctga gagtgtgaca gggacctgga aaggagatgt 180
gaagattcag tgcatctatg atcccctgag aggctacagg caagttttgg tgaaatggct 240
ggtaagacac ggctctgact ccgtcaccat cttcctacgt gactccactg gagaccatat 300
ccagcaggca aagtacagag gccgcctgaa agtgagccac aaagttccag gagatgtgtc 360
cctccaaata aataccctgc agatggatga caggaatcac tatacatgtg aggtcacctg 420
gcagactcct gatggaaacc aagtaataag agataagatc attgagctcc gtgttcggaa 480
atataatcca cctagaatca atactgaagc acctacaacc ctgcactcct ctttggaagc 540
aacaactata atgagttcaa cctctgactt gaccactaat gggactggaa aacttgagga 600
gaccattgct ggttcaggga ggaacctgcc aatctttgcc ataatcttca tcatctccct 660
ttgctgcata gtagctgtca ccatacctta tatcttgttc cgctgcagga cattccaaca 720
agagtatgtc tatggagtga gcagggtgtt tgccaggaag acaagcaact ctgaagaaac 780
cacaagggtg actaccatcg caactgatga accagattcc caggctctga ttagtgacta 840
ctctgatgat ccttgcctca gccaggagta ccaaataacc atcagatcaa caatgtctat 900
tcctgcctgc tgaacacagt ttccagaaac taagaagttc ttgctactga agaaaataac 960
atctgctaaa atgcccctac taagtcaagg tctactggcg taattacctg ttacttattt 1020
actacttgcc ttcaacatag ctttctccct ggcttccttt cttcttagac aacctaaagt 1080
atctatctag tctgccaatt ctggggccat tgagaaatcc tgggtttggc taagaatata 1140
ctacatgcac ctcaagaaat ctagcttctg ggcttcaccc agaacaattt tcttcctagg 1200
gccttcacaa ctcttctcca aacagcagag aaattccata gcagtagagg ttctttatca 1260
tgcctccaga cagcgtgagt ctcagtccta caaactcaga caagcacatg ggtctaggat 1320
tactcctctt tctctagggc cagatgactt ttaattgata ttactattgc tacattatga 1380
atctaatgca catgtattct tttgttgtta ataaatgttt aatcatgaca tc 1432

<210> SEQ ID NO 18
<211> LENGTH: 280
<212> TYPE: PRT
<213> ORGANISM: Mus musculus

<400> SEQUENCE: 18

Met Glu Ile Ser Ser Gly Leu Leu Phe Leu Gly His Leu Ile Val Leu
1 5 10 15

Thr Tyr Gly His Pro Thr Leu Lys Thr Pro Glu Ser Val Thr Gly Thr
20 25 30

Trp Lys Gly Asp Val Lys Ile Gln Cys Ile Tyr Asp Pro Leu Arg Gly
35 40 45

Tyr Arg Gln Val Leu Val Lys Trp Leu Val Arg His Gly Ser Asp Ser
50 55 60

Val Thr Ile Phe Leu Arg Asp Ser Thr Gly Asp His Ile Gln Gln Ala
65 70 75 80

Lys Tyr Arg Gly Arg Leu Lys Val Ser His Lys Val Pro Gly Asp Val
85 90 95

```
Ser Leu Gln Ile Asn Thr Leu Gln Met Asp Asp Arg Asn His Tyr Thr
            100                 105                 110

Cys Glu Val Thr Trp Gln Thr Pro Asp Gly Asn Gln Val Ile Arg Asp
        115                 120                 125

Lys Ile Ile Glu Leu Arg Val Arg Lys Tyr Asn Pro Pro Arg Ile Asn
    130                 135                 140

Thr Glu Ala Pro Thr Thr Leu His Ser Ser Leu Glu Ala Thr Thr Ile
145                 150                 155                 160

Met Ser Ser Thr Ser Asp Leu Thr Thr Asn Gly Thr Gly Lys Leu Glu
                165                 170                 175

Glu Thr Ile Ala Gly Ser Gly Arg Asn Leu Pro Ile Phe Ala Ile Ile
            180                 185                 190

Phe Ile Ile Ser Leu Cys Cys Ile Val Ala Val Thr Ile Pro Tyr Ile
        195                 200                 205

Leu Phe Arg Cys Arg Thr Phe Gln Gln Glu Tyr Val Tyr Gly Val Ser
    210                 215                 220

Arg Val Phe Ala Arg Lys Thr Ser Asn Ser Glu Glu Thr Thr Arg Val
225                 230                 235                 240

Thr Thr Ile Ala Thr Asp Glu Pro Asp Ser Gln Ala Leu Ile Ser Asp
                245                 250                 255

Tyr Ser Asp Asp Pro Cys Leu Ser Gln Glu Tyr Gln Ile Thr Ile Arg
            260                 265                 270

Ser Thr Met Ser Ile Pro Ala Cys
        275                 280
```

<210> SEQ ID NO 19
<211> LENGTH: 495
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Arg Pro Ile Leu Glu Val Pro Glu Ser Val Thr Gly Pro Trp Lys Gly
1               5                   10                  15

Asp Val Asn Leu Pro Cys Thr Tyr Asp Pro Leu Gln Gly Tyr Thr Gln
            20                  25                  30

Val Leu Val Lys Trp Leu Val Gln Arg Gly Ser Asp Pro Val Thr Ile
        35                  40                  45

Phe Leu Arg Asp Ser Ser Gly Asp His Ile Gln Gln Ala Lys Tyr Gln
    50                  55                  60

Gly Arg Leu His Val Ser His Lys Val Pro Gly Asp Val Ser Leu Gln
65                  70                  75                  80

Leu Ser Thr Leu Glu Met Asp Asp Arg Ser His Tyr Thr Cys Glu Val
                85                  90                  95

Thr Trp Gln Thr Pro Asp Gly Asn Gln Val Val Arg Asp Lys Ile Thr
            100                 105                 110

Glu Leu Arg Val Gln Lys Leu Ser Val Ser Lys Pro Thr Val Thr Thr
        115                 120                 125

Gly Ser Gly Tyr Gly Phe Thr Val Pro Gln Gly Met Arg Ile Ser Leu
    130                 135                 140

Gln Cys Gln Ala Arg Gly Ser Pro Pro Ile Ser Tyr Ile Trp Tyr Lys
145                 150                 155                 160

Gln Gln Thr Asn Asn Gln Glu Pro Ile Lys Val Ala Thr Leu Ser Thr
```

```
                165                 170                 175

Leu Leu Phe Lys Pro Ala Val Ile Ala Asp Ser Gly Ser Tyr Phe Cys
            180                 185                 190

Thr Ala Lys Gly Gln Val Gly Ser Glu Gln His Ser Asp Ile Val Lys
        195                 200                 205

Phe Val Val Lys Asp Ser Ser Lys Leu Leu Lys Thr Lys Thr Glu Ala
    210                 215                 220

Pro Thr Thr Met Thr Tyr Pro Leu Lys Ala Thr Ser Thr Val Lys Gln
225                 230                 235                 240

Ser Trp Asp Trp Thr Thr Asp Met Asp Gly Tyr Leu Gly Glu Thr Ser
                245                 250                 255

Ala Gly Pro Gly Lys Ser Leu Pro Gly Ser Gly Gly Asp Lys Thr His
            260                 265                 270

Thr Cys Pro Pro Cys Pro Ala Pro Glu Leu Leu Gly Gly Pro Ser Val
        275                 280                 285

Phe Leu Phe Pro Pro Lys Pro Lys Asp Thr Leu Met Ile Ser Arg Thr
    290                 295                 300

Pro Glu Val Thr Cys Val Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Ala Leu Pro Ala Pro Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Arg Glu Glu Met Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Lys Leu Thr Val Asp Lys Ser Arg
    450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys
                485                 490                 495


<210> SEQ ID NO 20
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Arg Pro Ile Leu Glu Val Pro Glu Ser Val Thr Gly Pro Trp Lys Gly
1               5                   10                  15

Asp Val Asn Leu Pro Cys Thr Tyr Asp Pro Leu Gln Gly Tyr Thr Gln
            20                  25                  30
```

```
Val Leu Val Lys Trp Leu Val Gln Arg Gly Ser Asp Pro Val Thr Ile
        35                  40                  45

Phe Leu Arg Asp Ser Ser Gly Asp His Ile Gln Gln Ala Lys Tyr Gln
    50                  55                  60

Gly Arg Leu His Val Ser His Lys Val Pro Gly Asp Val Ser Leu Gln
65                  70                  75                  80

Leu Ser Thr Leu Glu Met Asp Asp Arg Ser His Tyr Thr Cys Glu Val
                85                  90                  95

Thr Trp Gln Thr Pro Asp Gly Asn Gln Val Val Arg Asp Lys Ile Thr
            100                 105                 110

Glu Leu Arg Val Gln Lys His Ser Ser Lys Leu Leu Lys Thr Lys Thr
        115                 120                 125

Glu Ala Pro Thr Thr Met Thr Tyr Pro Leu Lys Ala Thr Ser Thr Val
    130                 135                 140

Lys Gln Ser Trp Asp Trp Thr Thr Asp Met Asp Gly Tyr Leu Gly Glu
145                 150                 155                 160

Thr Ser Ala Gly Pro Gly Lys Ser Leu Pro Gly Ser Gly Gly Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
        275                 280                 285

Thr Ile Ser Lys Ala Lys Gly Gln Pro Arg Glu Pro Gln Val Tyr Thr
    290                 295                 300

Leu Pro Pro Ser Arg Glu Glu Met Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro Gly
385                 390                 395                 400

Lys


<210> SEQ ID NO 21
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 21

```
His Pro Thr Leu Lys Thr Pro Glu Ser Val Thr Gly Thr Trp Lys Gly
1               5                   10                  15

Asp Val Lys Ile Gln Cys Ile Tyr Asp Pro Leu Arg Gly Tyr Arg Gln
            20                  25                  30

Val Leu Val Lys Trp Leu Val Arg His Gly Ser Asp Ser Val Thr Ile
        35                  40                  45

Phe Leu Arg Asp Ser Thr Gly Asp His Ile Gln Gln Ala Lys Tyr Arg
    50                  55                  60

Gly Arg Leu Lys Val Ser His Lys Val Pro Gly Asp Val Ser Leu Gln
65                  70                  75                  80

Ile Asn Thr Leu Gln Met Asp Asp Arg Asn His Tyr Thr Cys Glu Val
                85                  90                  95

Thr Trp Gln Thr Pro Asp Gly Asn Gln Val Ile Arg Asp Lys Ile Ile
            100                 105                 110

Glu Leu Arg Val Arg Lys Tyr Asn Pro Pro Arg Ile Asn Thr Glu Ala
        115                 120                 125

Pro Thr Thr Leu His Ser Ser Leu Glu Ala Thr Thr Ile Met Ser Ser
    130                 135                 140

Thr Ser Asp Leu Thr Thr Asn Gly Thr Gly Lys Leu Glu Glu Thr Ile
145                 150                 155                 160

Ala Gly Ser Gly Arg Asn Leu Pro Gly Ser Gly Gly Asp Lys Thr His
                165                 170                 175

Thr Cys Pro Pro Cys Pro Ala Pro Glu Leu Leu Gly Gly Pro Ser Val
            180                 185                 190

Phe Leu Phe Pro Pro Lys Pro Lys Asp Thr Leu Met Ile Ser Arg Thr
        195                 200                 205

Pro Glu Val Thr Cys Val Val Val Asp Val Ser His Glu Asp Pro Glu
    210                 215                 220

Val Lys Phe Asn Trp Tyr Val Asp Gly Val Glu Val His Asn Ala Lys
225                 230                 235                 240

Thr Lys Pro Arg Glu Glu Gln Tyr Asn Ser Thr Tyr Arg Val Val Ser
                245                 250                 255

Val Leu Thr Val Leu His Gln Asp Trp Leu Asn Gly Lys Glu Tyr Lys
            260                 265                 270

Cys Lys Val Ser Asn Lys Ala Leu Pro Ala Pro Ile Glu Lys Thr Ile
        275                 280                 285

Ser Lys Ala Lys Gly Gln Pro Arg Glu Pro Gln Val Tyr Thr Leu Pro
    290                 295                 300

Pro Ser Arg Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Lys Leu Thr Val Asp Lys Ser Arg
        355                 360                 365

Trp Gln Gln Gly Asn Val Phe Ser Cys Ser Val Met His Glu Ala Leu
    370                 375                 380

His Asn His Tyr Thr Gln Lys Ser Leu Ser Leu Ser Pro Gly Lys
385                 390                 395
```

<210> SEQ ID NO 22
<211> LENGTH: 399
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Gly Ile Leu Leu Gly Leu Leu Leu Leu Gly His Leu Thr Val Asp
1               5                   10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45

Tyr Thr Gln Val Leu Val Lys Trp Leu Val Gln Arg Gly Ser Asp Pro
    50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys Leu Ser Val Ser Lys Pro Thr
    130                 135                 140

Val Thr Thr Gly Ser Gly Tyr Gly Phe Thr Val Pro Gln Gly Met Arg
145                 150                 155                 160

Ile Ser Leu Gln Cys Gln Ala Arg Gly Ser Pro Pro Ile Ser Tyr Ile
                165                 170                 175

Trp Tyr Lys Gln Gln Thr Asn Asn Gln Glu Pro Ile Lys Val Ala Thr
            180                 185                 190

Leu Ser Thr Leu Leu Phe Lys Pro Ala Val Ile Ala Asp Ser Gly Ser
        195                 200                 205

Tyr Phe Cys Thr Ala Lys Gly Gln Val Gly Ser Glu Gln His Ser Asp
    210                 215                 220

Ile Val Lys Phe Val Val Lys Asp Ser Ser Lys Leu Leu Lys Thr Lys
225                 230                 235                 240

Thr Glu Ala Pro Thr Thr Met Thr Tyr Pro Leu Lys Ala Thr Ser Thr
                245                 250                 255

Val Lys Gln Ser Trp Asp Trp Thr Thr Asp Met Asp Gly Tyr Leu Gly
            260                 265                 270

Glu Thr Ser Ala Gly Pro Gly Lys Ser Leu Pro Val Phe Ala Ile Ile
        275                 280                 285

Leu Ile Ile Ser Leu Cys Cys Met Val Val Phe Thr Met Ala Tyr Ile
    290                 295                 300

Met Leu Cys Arg Lys Thr Ser Gln Gln Glu His Val Tyr Glu Ala Ala
305                 310                 315                 320

Arg Ala His Ala Arg Glu Ala Asn Asp Ser Gly Glu Thr Met Arg Val
                325                 330                 335

Ala Ile Phe Ala Ser Gly Cys Ser Ser Asp Glu Pro Thr Ser Gln Asn
            340                 345                 350

Leu Gly Asn Asn Tyr Ser Asp Glu Pro Cys Ile Gly Gln Glu Tyr Gln
        355                 360                 365
```

```
Ile Ile Ala Gln Ile Asn Gly Asn Tyr Ala Arg Leu Leu Asp Thr Val
    370                 375                 380

Pro Leu Asp Tyr Glu Phe Leu Ala Thr Glu Gly Lys Ser Val Cys
385                 390                 395
```

<210> SEQ ID NO 23
<211> LENGTH: 305
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Gly Ile Leu Leu Gly Leu Leu Leu Leu Gly His Leu Thr Val Asp
1               5                   10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45

Tyr Thr Gln Val Leu Val Lys Trp Leu Val Gln Arg Gly Ser Asp Pro
    50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys His Ser Ser Lys Leu Leu Lys
    130                 135                 140

Thr Lys Thr Glu Ala Pro Thr Thr Met Thr Tyr Pro Leu Lys Ala Thr
145                 150                 155                 160

Ser Thr Val Lys Gln Ser Trp Asp Trp Thr Thr Asp Met Asp Gly Tyr
                165                 170                 175

Leu Gly Glu Thr Ser Ala Gly Pro Gly Lys Ser Leu Pro Val Phe Ala
            180                 185                 190

Ile Ile Leu Ile Ile Ser Leu Cys Cys Met Val Val Phe Thr Met Ala
        195                 200                 205

Tyr Ile Met Leu Cys Arg Lys Thr Ser Gln Gln Glu His Val Tyr Glu
    210                 215                 220

Ala Ala Arg Ala His Ala Arg Glu Ala Asn Asp Ser Gly Glu Thr Met
225                 230                 235                 240

Arg Val Ala Ile Phe Ala Ser Gly Cys Ser Ser Asp Glu Pro Thr Ser
                245                 250                 255

Gln Asn Leu Gly Asn Asn Tyr Ser Asp Glu Pro Cys Ile Gly Gln Glu
            260                 265                 270

Tyr Gln Ile Ile Ala Gln Ile Asn Gly Asn Tyr Ala Arg Leu Leu Asp
        275                 280                 285

Thr Val Pro Leu Asp Tyr Glu Phe Leu Ala Thr Glu Gly Lys Ser Val
    290                 295                 300

Cys
305
```

<210> SEQ ID NO 24

```
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Glu Ile Ser Ser Gly Leu Leu Phe Leu Gly His Leu Ile Val Leu
1               5                   10                  15

Thr Tyr Gly His Pro Thr Leu Lys Thr Pro Glu Ser Val Thr Gly Thr
            20                  25                  30

Trp Lys Gly Asp Val Lys Ile Gln Cys Ile Tyr Asp Pro Leu Arg Gly
        35                  40                  45

Tyr Arg Gln Val Leu Val Lys Trp Leu Val Arg His Gly Ser Asp Ser
    50                  55                  60

Val Thr Ile Phe Leu Arg Asp Ser Thr Gly Asp His Ile Gln Gln Ala
65                  70                  75                  80

Lys Tyr Arg Gly Arg Leu Lys Val Ser His Lys Val Pro Gly Asp Val
                85                  90                  95

Ser Leu Gln Ile Asn Thr Leu Gln Met Asp Asp Arg Asn His Tyr Thr
            100                 105                 110

Cys Glu Val Thr Trp Gln Thr Pro Asp Gly Asn Gln Val Ile Arg Asp
        115                 120                 125

Lys Ile Ile Glu Leu Arg Val Arg Lys Tyr Asn Pro Pro Arg Ile Asn
    130                 135                 140

Thr Glu Ala Pro Thr Thr Leu His Ser Ser Leu Glu Ala Thr Thr Ile
145                 150                 155                 160

Met Ser Ser Thr Ser Asp Leu Thr Thr Asn Gly Thr Gly Lys Leu Glu
                165                 170                 175

Glu Thr Ile Ala Gly Ser Gly Arg Asn Leu Pro Ile Phe Ala Ile Ile
            180                 185                 190

Phe Ile Ile Ser Leu Cys Cys Ile Val Ala Val Thr Ile Pro Tyr Ile
        195                 200                 205

Leu Phe Arg Cys Arg Thr Phe Gln Gln Glu Tyr Val Tyr Gly Val Ser
    210                 215                 220

Arg Val Phe Ala Arg Lys Thr Ser Asn Ser Glu Glu Thr Thr Arg Val
225                 230                 235                 240

Thr Thr Ile Ala Thr Asp Glu Pro Asp Ser Gln Ala Leu Ile Ser Asp
                245                 250                 255

Tyr Ser Asp Asp Pro Cys Leu Ser Gln Glu Tyr Gln Ile Thr Ile Arg
            260                 265                 270

Ser Thr Met Ser Ile Pro Ala Cys
        275                 280


<210> SEQ ID NO 25
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Arg Pro Ile Leu Glu Val Pro Glu Ser Val Thr Gly Pro Trp Lys Gly
1               5                   10                  15

Asp Val Asn Leu Pro Cys Thr Tyr Asp Pro Leu Gln Gly Tyr Thr Gln
            20                  25                  30
```

```
Val Leu Val Lys Trp Leu Val Gln Arg Gly Ser Asp Pro Val Thr Ile
        35                  40                  45

Phe Leu Arg Asp Ser Ser Gly Asp His Ile Gln Gln Ala Lys Tyr Gln
    50                  55                  60

Gly Arg Leu His Val Ser His Lys Val Pro Gly Asp Val Ser Leu Gln
65                  70                  75                  80

Leu Ser Thr Leu Glu Met Asp Asp Arg Ser His Tyr Thr Cys Glu Val
                85                  90                  95

Thr Trp Gln Thr Pro Asp Gly Asn Gln Val Val Arg Asp Lys Ile Thr
            100                 105                 110

Glu Leu Arg Val Gln Lys Leu Ser Val Ser Lys Pro Thr Val Thr Thr
        115                 120                 125

Gly Ser Gly Tyr Gly Phe Thr Val Pro Gln Gly Met Arg Ile Ser Leu
    130                 135                 140

Gln Cys Gln Ala Arg Gly Ser Pro Pro Ile Ser Tyr Ile Trp Tyr Lys
145                 150                 155                 160

Gln Gln Thr Asn Asn Gln Glu Pro Ile Lys Val Ala Thr Leu Ser Thr
                165                 170                 175

Leu Leu Phe Lys Pro Ala Val Ile Ala Asp Ser Gly Ser Tyr Phe Cys
            180                 185                 190

Thr Ala Lys Gly Gln Val Gly Ser Glu Gln His Ser Asp Ile Val Lys
        195                 200                 205

Phe Val Val Lys Asp Ser Ser Lys Leu Leu Lys Thr Lys Thr Glu Ala
    210                 215                 220

Pro Thr Thr Met Thr Tyr Pro Leu Lys Ala Thr Ser Thr Val Lys Gln
225                 230                 235                 240

Ser Trp Asp Trp Thr Thr Asp Met Asp Gly Tyr Leu Gly Glu Thr Ser
                245                 250                 255

Ala Gly Pro Gly Lys Ser Leu Pro Gly Ser Gly His His His His His
            260                 265                 270

His His His His His
        275


<210> SEQ ID NO 26
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Arg Pro Ile Leu Glu Val Pro Glu Ser Ile Thr Gly Pro Trp Lys Gly
1               5                   10                  15

Asp Val Asn Ile Pro Cys Thr Tyr Gly Pro Leu Gln Gly Tyr Thr Gln
            20                  25                  30

Val Leu Val Lys Trp Leu Val Gln Arg Gly Ser Asp Pro Val Thr Ile
        35                  40                  45

Phe Leu Arg Asp Ser Ser Gly Asp His Ile Gln Gln Ala Lys Tyr Gln
    50                  55                  60

Gly Arg Leu His Val Asn Gln Lys Val Pro Gly Asp Val Ser Leu Gln
65                  70                  75                  80

Leu Ser Thr Leu Glu Met Asp Asp Gln Ser His Tyr Thr Cys Glu Val
                85                  90                  95

Thr Trp Gln Thr Pro Asp Gly Asn Gln Val Val Arg Asp Lys Ile Thr
```

```
            100                 105                 110

Glu Leu Arg Val Gln Lys Leu Ser Val Ser Lys Pro Thr Val Thr Thr
        115                 120                 125

Gly Ser Gly Tyr Gly Phe Thr Val Pro Gln Gly Met Arg Ile Ser Leu
    130                 135                 140

Gln Cys Gln Ala Arg Gly Ser Pro Pro Ile Ser Tyr Ile Trp Tyr Lys
145                 150                 155                 160

Glu Gln Thr Asn Asn Gln Glu Pro Ile Lys Val Ala Thr Leu Ser Thr
                165                 170                 175

Leu Leu Phe Lys Pro Ala Met Val Ala Asp Ser Gly Ser Tyr Phe Cys
            180                 185                 190

Ala Ala Lys Gly Arg Val Gly Ser Glu Gln Arg Ser Asp Ile Val Lys
        195                 200                 205

Phe Val Val Lys Asp Ser Ser Lys Leu Leu Lys Thr Lys Thr Glu Ala
    210                 215                 220

Pro Thr Thr Met Arg His Pro Leu Lys Ala Thr Ser Thr Val Lys Gln
225                 230                 235                 240

Ser Trp Asp Trp Thr Thr Asp Val Asp Gly Tyr Leu Gly Ala Thr Ser
                245                 250                 255

Ala Gly Pro Gly Lys Ser Leu Pro Gly Ser Gly His His His His His
            260                 265                 270

His His His His His
        275


<210> SEQ ID NO 27
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Arg Pro Ile Leu Glu Val Pro Glu Ser Val Thr Gly Pro Trp Lys Gly
1               5                   10                  15

Asp Val Asn Leu Pro Cys Thr Tyr Asp Pro Leu Gln Gly Tyr Thr Gln
            20                  25                  30

Val Leu Val Lys Trp Leu Val Gln Arg Gly Ser Asp Pro Val Thr Ile
        35                  40                  45

Phe Leu Arg Asp Ser Ser Gly Asp His Ile Gln Gln Ala Lys Tyr Gln
    50                  55                  60

Gly Arg Leu His Val Ser His Lys Val Pro Gly Asp Val Ser Leu Gln
65                  70                  75                  80

Leu Ser Thr Leu Glu Met Asp Asp Arg Ser His Tyr Thr Cys Glu Val
                85                  90                  95

Thr Trp Gln Thr Pro Asp Gly Asn Gln Val Val Arg Asp Lys Ile Thr
            100                 105                 110

Glu Leu Arg Val Gln Lys His Ser Ser Lys Leu Leu Lys Thr Lys Thr
        115                 120                 125

Glu Ala Pro Thr Thr Met Thr Tyr Pro Leu Lys Ala Thr Ser Thr Val
    130                 135                 140

Lys Gln Ser Trp Asp Trp Thr Thr Asp Met Asp Gly Tyr Leu Gly Glu
145                 150                 155                 160

Thr Ser Ala Gly Pro Gly Lys Ser Leu Pro Gly Ser Gly His His His
                165                 170                 175
```

His His His His His His His
180

<210> SEQ ID NO 28
<211> LENGTH: 181
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

His Pro Thr Leu Lys Thr Pro Glu Ser Val Thr Gly Thr Trp Lys Gly
1 5 10 15

Asp Val Lys Ile Gln Cys Ile Tyr Asp Pro Leu Arg Gly Tyr Arg Gln
20 25 30

Val Leu Val Lys Trp Leu Val Arg His Gly Ser Asp Ser Val Thr Ile
35 40 45

Phe Leu Arg Asp Ser Thr Gly Asp His Ile Gln Gln Ala Lys Tyr Arg
50 55 60

Gly Arg Leu Lys Val Ser His Lys Val Pro Gly Asp Val Ser Leu Gln
65 70 75 80

Ile Asn Thr Leu Gln Met Asp Asp Arg Asn His Tyr Thr Cys Glu Val
85 90 95

Thr Trp Gln Thr Pro Asp Gly Asn Gln Val Ile Arg Asp Lys Ile Ile
100 105 110

Glu Leu Arg Val Arg Lys Tyr Asn Pro Pro Arg Ile Asn Thr Glu Ala
115 120 125

Pro Thr Thr Leu His Ser Ser Leu Glu Ala Thr Thr Ile Met Ser Ser
130 135 140

Thr Ser Asp Leu Thr Thr Asn Gly Thr Gly Lys Leu Glu Glu Thr Ile
145 150 155 160

Ala Gly Ser Gly Arg Asn Leu Pro Gly Ser Gly His His His His His
165 170 175

His His His His His
180

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Glu Thr Thr Val Thr Gln Ser His Lys Phe Met Ser Thr Ser Val Gly
1 5 10 15

Asp Arg Val Ser Ile Thr Cys Lys Ala Ser Gln Asp Val Ser Thr Ala
20 25 30

Val Ala Trp Tyr Gln Gln Lys Pro Gly Gln Ser Pro Lys Leu Leu Ile
35 40 45

Tyr Ser Ala Ser Tyr Arg Tyr Pro Gly Val Pro Asp Arg Phe Thr Gly
50 55 60

Ser Gly Ser Gly Thr Asp Phe Thr Phe Thr Ile Ser Ser Val Gln Ala
65 70 75 80

Glu Asp Leu Ala Val Tyr Tyr Cys Gln Gln Asp Tyr Ser Ser Pro Trp
85 90 95

```
Thr Phe Gly Gly Gly Thr Lys Leu Glu Ile Lys
            100                 105


<210> SEQ ID NO 30
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Met Leu Val Glu Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Ser Ile Asn Thr Tyr Thr Gly Glu Ala Thr Tyr Ala Asp Asp Phe
    50                  55                  60

Lys Gly Arg Phe Ala Phe Ser Leu Glu Thr Ser Ala Asn Thr Ala Tyr
65                  70                  75                  80

Leu Gln Ile Asp Asn Leu Lys Asn Glu Asp Thr Ala Thr Tyr Phe Cys
                85                  90                  95

Ala Arg Gly Asp Tyr Tyr Gly Arg Gly Thr Trp Phe Ala Tyr Trp Gly
            100                 105                 110

Gln Gly Thr Leu Val Thr Val Ser Ala
        115                 120


<210> SEQ ID NO 31
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Val Val Met Thr Gln Thr Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Arg Thr Phe Gly Gly Gly Thr Lys Leu Glu Ile Lys
            100                 105                 110


<210> SEQ ID NO 32
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 32

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Thr Pro Gly Lys Gly Leu Lys Trp Met
        35                  40                  45

Gly Leu Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Glu Arg Ile Tyr Gly Tyr Leu His Tyr Phe Asp Tyr Trp Gly
            100                 105                 110

Gln Gly Thr Thr Leu Thr Val Ser Ser
        115                 120

<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

<210> SEQ ID NO 34
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Met Lys Gln Ser Gly Pro Ser Leu Val Arg Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asp Lys Phe Glu Tyr Leu
        35                  40                  45

Gly Tyr Ile Ser Tyr Ser Gly Phe Thr Tyr Tyr Asn Pro Ser Leu Lys

```
    50                  55                  60

Ser Arg Val Ser Ile Thr Arg Asp Thr Ser Lys Asn Gln Tyr Tyr Leu
65                  70                  75                  80

Gln Leu His Ser Val Thr Thr Glu Asp Thr Ala Thr Tyr Tyr Cys Ala
                85                  90                  95

Ser Ser Lys Tyr Gly Ser Ser Leu Gly Phe Pro Tyr Trp Gly Gln Gly
            100                 105                 110

Thr Leu Val Thr Val Ser Ala
        115


<210> SEQ ID NO 35
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ser Gly Thr Lys Leu Glu Ile Lys
            100                 105


<210> SEQ ID NO 36
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Lys Leu Leu Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Thr Arg Tyr Asn Pro Ser Leu
    50                  55                  60

Lys Ser Arg Ile Ser Ile Thr Arg Asp Thr Ser Asn Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Gly Tyr Ala Ala Met Asp Tyr Trp Gly Gln Gly Thr Ser
            100                 105                 110

Val Thr Val Ser Ser
```

115

<210> SEQ ID NO 37
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 38
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Gln Ile Gln Leu Gln Glu Ser Gly Pro Ser Leu Val Arg Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asp Lys Leu Glu Tyr Leu
        35                  40                  45

Gly Tyr Ile Ser Tyr Ser Gly Phe Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Ser Ser Tyr Tyr Gly Ser Ser Leu Gly Phe Pro Tyr Trp Gly Gln Gly
            100                 105                 110

Thr Leu Val Thr Val Ser Ala
        115
```

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Glu Ile Gln Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105


<210> SEQ ID NO 40
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Ile Lys Gln Arg Pro Gly Gln Gly Leu Glu Trp Ile
        35                  40                  45

Gly Tyr Ile Asn Pro Ser Ser Gly His Thr Tyr Tyr Asn Gln Lys Phe
    50                  55                  60

Lys Asp Lys Ala Thr Leu Thr Pro Asp Lys Ser Ser Ser Thr Ala Tyr
65                  70                  75                  80

Met Gln Leu Thr Ser Leu Thr Ser Glu Asp Ser Ala Val Tyr Tyr Cys
                85                  90                  95

Ala Arg Arg Ile Pro Thr Ala Tyr Ala Met Asp Tyr Trp Gly Gln Gly
            100                 105                 110

Thr Ser Val Thr Val Ser Ser
        115


<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Val Leu Thr Gln Ser Pro Ser Ser Leu Ser Val Ser Ala Gly
1               5                   10                  15

Glu Lys Val Thr Leu Ser Cys Lys Ser Ser Gln Ser Leu Leu Asn Ser
            20                  25                  30

Gly Asn Gln Glu Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60
```

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asp His Ser Tyr Pro Leu Thr Phe Gly Ala Gly Thr Lys Leu Glu Leu
100 105 110

Lys

<210> SEQ ID NO 42
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Gln Val Gln Leu Gln Gln Ser Gly Ala Glu Leu Val Arg Pro Gly Thr
1 5 10 15

Ser Val Lys Ile Ser Cys Lys Ala Ser Gly Tyr Thr Phe Thr Asn Tyr
20 25 30

Trp Leu Gly Trp Val Lys Gln Arg Pro Gly His Gly Leu Glu Trp Ile
35 40 45

Gly Asp Ile Tyr Pro Gly Gly Gly Tyr Thr Asn Tyr Asn Glu Lys Phe
50 55 60

Lys Gly Lys Ala Thr Leu Thr Ala Asp Thr Ser Ser Ser Thr Ala Tyr
65 70 75 80

Met Gln Leu Ser Ser Leu Thr Ser Glu Asp Ser Ala Val Tyr Phe Cys
85 90 95

Ala Lys Phe Tyr Tyr Tyr Gly Ser Ser Tyr Tyr Phe Asp Ser Trp Gly
100 105 110

Gln Gly Thr Thr Leu Thr Val Ser Ser
115 120

<210> SEQ ID NO 43
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

Asn Ile Val Leu Thr Gln Ser Pro Pro Ser Leu Ala Val Ser Leu Gly
1 5 10 15

Gln Arg Ala Thr Ile Ser Cys Arg Ala Ser Glu Ser Val Asp Ser Tyr
20 25 30

Gly Asn Ser Phe Met His Trp Tyr Gln Gln Lys Pro Gly Gln Pro Pro
35 40 45

Lys Leu Leu Ile Tyr Leu Ala Ser Asn Leu Glu Ser Gly Val Pro Ala
50 55 60

Arg Phe Ser Gly Ser Gly Ser Arg Thr Asp Phe Thr Leu Thr Ile Asp
65 70 75 80

Pro Val Glu Ala Asp Asp Ala Ala Thr Tyr Phe Cys His Gln Asn Asn
85 90 95

Glu Asp Pro Trp Thr Phe Gly Gly Gly Thr Lys Leu Glu Ile Lys
100 105 110

<210> SEQ ID NO 44
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Gln Val Gln Leu Gln Gln Pro Gly Ala Glu Met Val Arg Pro Gly Ala
1               5                   10                  15

Ser Leu Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Lys Ile Asp Pro Ser Lys Asn Thr Thr His Tyr Asn Gln Asn Phe
    50                  55                  60

Arg Asp Lys Ala Thr Leu Thr Val Asp Arg Ser Ser Ser Thr Ala Tyr
65                  70                  75                  80

Met Gln Leu Asn Ser Leu Thr Ser Glu Asp Ser Ala Val Tyr Phe Cys
                85                  90                  95

Val Thr Trp Asp Gly Asp Phe Thr Tyr Trp Gly Gln Gly Thr Leu Val
            100                 105                 110

Thr Ile Ser Ala
        115
```

<210> SEQ ID NO 45
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Asn Ile Val Leu Thr Gln Ser Pro Ala Ser Leu Thr Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Ile Thr Ser Asn Leu Gln Ser Gly Val Pro Ala
    50                  55                  60

Arg Phe Ser Gly Gly Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Trp Thr Phe Gly Gly Gly Thr Lys Leu Glu Ile Lys
            100                 105                 110
```

<210> SEQ ID NO 46
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Gln Val Gln Leu Gln Gln Pro Gly Ala Glu Met Val Arg Pro Gly Thr
```

```
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Lys Ile Asp Pro Ser His Asn Lys Thr His Tyr Ile Gln Lys Phe
    50                  55                  60

Glu Asp Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Val Thr Trp Asp Gly Asp Phe Leu Tyr Trp Gly Gln Gly Thr Leu Val
            100                 105                 110

Thr Val Ser Ala
        115


<210> SEQ ID NO 47
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asp Leu Phe Thr Phe Gly Ser Gly Thr Lys Leu Glu Ile Lys
            100                 105                 110


<210> SEQ ID NO 48
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Gln Gln Ser Gly Pro Glu Leu Met Lys Pro Gly Asp
1               5                   10                  15

Ser Val Lys Met Ser Cys Lys Ala Ser Gly Tyr Thr Phe Thr Asp Tyr
            20                  25                  30

Tyr Met Asp Trp Val Lys Gln Ser His Gly Lys Ser Leu Glu Trp Ile
        35                  40                  45

Gly Tyr Ile Tyr Pro Asn Ile Asp Phe Thr Thr Tyr Asn Gln Lys Phe
    50                  55                  60

Lys Gly Lys Ala Thr Leu Thr Val Asp Lys Ser Ser Asn Thr Ala Tyr
```

```
65                  70                  75                  80

Met Glu Leu His Ser Leu Thr Ser Glu Asp Ser Ala Val Tyr Tyr Cys
                85                  90                  95

Thr Arg Arg Asp Leu Pro Leu His Gly Ser Ala Tyr Tyr Phe Asp Tyr
            100                 105                 110

Trp Gly Gln Gly Thr Thr Leu Thr Val Ser Ser
        115                 120


<210> SEQ ID NO 49
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Val Met Thr Gln Ser His Lys Phe Met Ser Thr Ser Val Gly
1               5                   10                  15

Asp Asn Val Ser Ile Thr Cys Lys Ala Ser Gln Tyr Val Ser Asn Thr
            20                  25                  30

Val Ala Trp Tyr Gln Gln Lys Pro Gly Gln Ser Pro Lys Leu Leu Ile
        35                  40                  45

Tyr Ser Ala Ser Tyr Arg Asn Thr Gly Val Pro Asp Arg Phe Thr Gly
    50                  55                  60

Ser Gly Ser Gly Thr Asn Phe Thr Phe Thr Ile Ser Asn Met Gln Ala
65                  70                  75                  80

Glu Asp Leu Ala Phe Tyr Tyr Cys Gln Gln His Tyr Thr Ser Pro Leu
                85                  90                  95

Thr Phe Gly Ala Gly Thr Lys Leu Glu Leu Lys
            100                 105


<210> SEQ ID NO 50
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Glu Ser Gly Gly Ala Leu Val Lys Pro Gly Gly
1               5                   10                  15

Ser Leu Lys Leu Ser Cys Val Ala Ser Arg Phe Asn Leu Asn Asn Cys
            20                  25                  30

Val Met Ser Trp Ile Arg Gln Thr Pro Glu Lys Arg Leu Glu Trp Val
        35                  40                  45

Ala Thr Ile Asp Ser Gly Ser Ile Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Val Tyr Tyr Cys
                85                  90                  95

Val Arg His Ile Tyr Gly Tyr Asp Val Val Asp Asn Trp Gly Gln Gly
            100                 105                 110

Thr Thr Leu Thr Val Ala Ser
        115
```

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Asp Ile Val Met Thr Gln Ser His Arg Phe Met Ser Thr Ser Val Gly
1               5                   10                  15

Asp Arg Val Ser Ile Thr Cys Lys Ala Ser His Asp Val Ser Asn Val
            20                  25                  30

Val Ala Trp Tyr Gln Gln Lys Pro Gly Gln Ser Pro Glu Leu Leu Ile
        35                  40                  45

Tyr Ser Ala Ser Tyr Arg Tyr Thr Gly Val Pro Ala Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Phe Cys Gln Gln His Phe Thr Thr Pro Leu
                85                  90                  95

Thr Phe Gly Ala Gly Thr Ser Leu Glu Val Arg
            100                 105
```

<210> SEQ ID NO 52
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Glu Val His Leu Val Glu Ser Gly Gly Ala Leu Val Lys Pro Gly Gly
1               5                   10                  15

Ser Leu Lys Leu Ser Cys Thr Ala Ser Gly Phe Thr Phe Ser Asn Ser
            20                  25                  30

Val Met Ser Trp Ile Arg Gln Thr Pro Glu Lys Arg Leu Glu Trp Val
        35                  40                  45

Ala Thr Ile Gly Ser Gly Gly Thr Tyr Ile Tyr Tyr Pro Asp Ser Val
    50                  55                  60

Lys Gly Arg Phe Thr Ile Ser Arg Asp Asn Ser Lys Asn Thr Leu Phe
65                  70                  75                  80

Leu Gln Met Thr Ser Leu Arg Ser Glu Asp Thr Ala Leu Tyr Tyr Cys
                85                  90                  95

Ala Arg His Ile Tyr Gly Tyr Asp Val Val Asp Tyr Trp Gly Gln Gly
            100                 105                 110

Thr Thr Leu Thr Val Ser Thr
        115
```

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Asp Ile Val Met Thr Gln Ser His Lys Phe Met Ser Thr Ser Val Gly
1               5                   10                  15
```

```
Asp Arg Val Thr Ile Thr Cys Lys Ala Ser Gln Asp Val Ser Asn Val
            20                  25                  30

Val Ala Trp Phe Gln Gln Lys Pro Gly Gln Ser Pro Lys Leu Leu Ile
        35                  40                  45

Tyr Ser Ala Ser Tyr Arg Phe Gly Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Asp Thr Pro Leu
                85                  90                  95

Thr Phe Gly Thr Gly Thr Thr Leu Glu Leu Lys
            100                 105


<210> SEQ ID NO 54
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Val Glu Ser Gly Gly Ala Leu Val Gln Pro Gly Gly
1               5                   10                  15

Ser Leu Lys Leu Ser Cys Val Ala Ser Gly Phe Ser Phe Ser Asn Cys
            20                  25                  30

Val Met Ser Trp Val Arg Gln Ser Pro Glu Lys Arg Leu Glu Trp Val
        35                  40                  45

Ala Thr Ile Gly Ser Asp Gly Ser Tyr Ser Tyr Tyr Gln Asp Asn Val
    50                  55                  60

Lys Gly Arg Phe Thr Val Ser Arg Asp Asn Ala Lys Asn Thr Leu Tyr
65                  70                  75                  80

Leu Gln Met Ser Ser Leu Gly Ser Glu Asp Thr Ala Leu Tyr Tyr Cys
                85                  90                  95

Gly Arg His Ile Tyr Gly Tyr Asp Val Val Asp Tyr Trp Gly Gln Gly
            100                 105                 110

Thr Ser Leu Thr Val Ser Ser
        115


<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Asn Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80
```

```
Glu Asp Ile Ala Asp Tyr Tyr Cys Gln Gln Ser Tyr Ser Trp Pro Leu
                85                  90                  95

Thr Phe Gly Thr Gly Thr Gln Leu Glu Leu Lys
            100                 105


<210> SEQ ID NO 56
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Lys Leu Val Glu Ser Gly Gly Gly Leu Val Lys Pro Gly Gly
1               5                   10                  15

Ser Leu Lys Leu Ser Cys Ala Val Ser Gly Phe Thr Phe Ser Asn Ser
            20                  25                  30

Ala Met Ser Trp Val Arg Gln Thr Pro Ala Lys Arg Leu Glu Trp Val
        35                  40                  45

Ala Tyr Ile Ser Ile Ser Gly Asp Asn Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Gly Tyr Asp Tyr Asp Gly Phe Thr His Trp Gly Gln Gly
            100                 105                 110

Thr Leu Val Thr Val Ser Ala
        115


<210> SEQ ID NO 57
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Asn Val
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Ala Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105


<210> SEQ ID NO 58
<211> LENGTH: 120
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 58

```
Glu Val Gln Leu Val Glu Ser Gly Gly Gly Leu Val Met Pro Gly Gly
1               5                   10                  15

Ser Arg Arg Leu Ser Cys Ala Ala Ser Gly Phe Thr Phe Ser Asp Ser
            20                  25                  30

Gly Met Tyr Trp Val Arg Gln Ala Pro Glu Lys Gly Leu Glu Trp Ile
        35                  40                  45

Ala Tyr Ile Ser Ser Gly Ser Asp Thr Leu Tyr Tyr Ala Ala Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Ile Tyr Tyr Cys
                85                  90                  95

Ala Lys Arg Asn Phe Tyr Gly Tyr Asp Val Met Asp Tyr Trp Gly Gln
            100                 105                 110

Gly Thr Ser Val Thr Val Ser Ser
        115                 120
```

<210> SEQ ID NO 59
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 59

```
Asp Ile Val Leu Thr Gln Ser Pro Ala Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Leu Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Asn Pro Leu Thr Phe Gly Ala Gly Thr Lys Leu Glu Leu
            100                 105                 110

Lys
```

<210> SEQ ID NO 60
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 60

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
```

```
            20                  25                  30

Trp Ile Glu Trp Val Lys Gln Arg Pro Gly His Gly Leu Glu Trp Ile
        35                  40                  45

Gly Glu Ile Leu Pro Gly Ser Ser Thr Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Asp His Phe Ile Thr Thr Ala Arg Tyr Ala Met Asp Tyr
            100                 105                 110

Trp Gly Gln Gly Thr Ser Val Thr Val Ser Ser
        115                 120


<210> SEQ ID NO 61
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Leu Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Phe Cys Arg Gln Gly Asn Thr Leu Pro Trp
                85                  90                  95

Thr Phe Gly Gly Gly Thr Lys Leu Glu Ile Lys
            100                 105


<210> SEQ ID NO 62
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Met Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Tyr Ile Asn Pro Ser Thr Gly Tyr Thr Asp Tyr Asn Gln Lys Phe
    50                  55                  60

Gln Gly Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
```

```
                85                  90                  95

Ile Arg Gly Ser Asp Tyr Tyr Gly Arg Asp Tyr Trp Gly Gln Gly Thr
            100                 105                 110

Thr Val Thr Val Ser Ser
        115


<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Leu Lys Leu Leu Ile
        35                  40                  45

Tyr Tyr Thr Ser Arg Leu His Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Arg Gln Gly Asn Thr Leu Pro Trp
                85                  90                  95

Thr Phe Gly Gly Gly Thr Lys Leu Glu Ile Lys
            100                 105


<210> SEQ ID NO 64
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Met Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Tyr Ile Asn Pro Ser Thr Gly Tyr Thr Asp Tyr Asn Gln Gly Phe
    50                  55                  60

Thr Gly Arg Phe Val Leu Ser Ala Asp Lys Ser Ser Ser Thr Ala Tyr
65                  70                  75                  80

Leu Gln Ile Ser Ser Leu Lys Ala Glu Asp Thr Ala Val Tyr Tyr Cys
                85                  90                  95

Ile Arg Gly Ser Asp Tyr Tyr Gly Arg Asp Tyr Trp Gly Gln Gly Thr
            100                 105                 110

Thr Val Thr Val Ser Ser
        115


<210> SEQ ID NO 65
<211> LENGTH: 107
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 65

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Leu Arg Leu Leu Ile
        35                  40                  45

Tyr Tyr Thr Ser Arg Arg His Thr Gly Ile Pro Ala Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Arg Gln Gly Asn Thr Leu Pro Trp
                85                  90                  95

Thr Phe Gly Gly Gly Thr Lys Leu Glu Ile Lys
            100                 105
```

<210> SEQ ID NO 66
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Gln Val Gln Met Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Tyr Ile Asn Pro Ser Thr Gly Tyr Thr Asp Tyr Asn Gln Gly Phe
    50                  55                  60

Thr Gly Arg Phe Val Phe Ser Ala Asp Lys Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ile Arg Gly Ser Asp Tyr Tyr Gly Arg Asp Tyr Trp Gly Gln Gly Thr
            100                 105                 110

Thr Val Thr Val Ser Ser
        115
```

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30
```

```
Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Arg Gln Gly Asn Thr Leu Pro Trp
                85                  90                  95

Thr Phe Gly Gly Gly Thr Lys Leu Glu Ile Lys
            100                 105


<210> SEQ ID NO 68
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Tyr Ile Asn Pro Ser Thr Gly Tyr Thr Asp Tyr Asn Gln Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ile Arg Gly Ser Asp Tyr Tyr Gly Arg Asp Tyr Trp Gly Gln Gly Thr
            100                 105                 110

Thr Val Thr Val Ser Ser
        115


<210> SEQ ID NO 69
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Tyr Ile Asn Pro Ser Thr Gly Tyr Thr Asp Tyr Asn Gln Gly Phe
    50                  55                  60

Thr Gly Arg Phe Val Phe Ser Ala Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95
```

```
Ile Arg Gly Ser Asp Tyr Tyr Gly Arg Asp Tyr Trp Gly Gln Gly Thr
            100                 105                 110

Thr Val Thr Val Ser Ser
        115


<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Thr Gln Val Thr Gln Ser Pro Ser Ser Leu Ser Ala Ser Val Gly
1               5                   10                  15

Asp Arg Val Thr Ile Thr Cys Gln Thr Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Thr Phe Thr Ile Ser Ser Leu Gln Pro
65                  70                  75                  80

Glu Asp Ile Ala Thr Tyr Tyr Cys Leu Gln Ser Asp Asn Leu Pro Leu
                85                  90                  95

Thr Phe Gly Gly Gly Thr Lys Leu Glu Ile Lys
            100                 105


<210> SEQ ID NO 71
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Glu Asn Phe
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Ala Thr Tyr Ala Asp Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Gly Gly Phe Arg His Phe Asp Val Trp Gly Gln Gly Thr
            100                 105                 110

Thr Val Thr Val Ser Ser
        115


<210> SEQ ID NO 72
<211> LENGTH: 118
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 72

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Asn Phe
            20                  25                  30

Gly Met Asn Trp Val Arg Gln Ala Pro Gly Gln Arg Leu Glu Trp Met
        35                  40                  45

Gly Trp Ile Asn Thr Tyr Thr Gly Glu Ala Thr Tyr Ala Asp Lys Phe
    50                  55                  60

Gln Gly Arg Val Thr Phe Thr Leu Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Gly Phe Arg His Phe Asp Val Trp Gly Gln Gly Thr
            100                 105                 110

Thr Val Thr Val Ser Ser
        115
```

<210> SEQ ID NO 73
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 73

```
Asp Thr Gln Val Thr Gln Ser Pro Ser Ser Leu Ser Ala Ser Val Gly
1               5                   10                  15

Asp Arg Val Thr Ile Thr Cys Gln Thr Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Glu Gly Asn Thr Leu Arg Thr Gly Val Pro Ser Arg Phe Ser Ser
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Ser Asp Asn Leu Pro Leu
                85                  90                  95

Thr Phe Gly Gly Gly Thr Lys Leu Glu Ile Lys
            100                 105
```

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 74

```
Asp Thr Gln Val Thr Gln Ser Pro Ser Ser Leu Ser Ala Ser Val Gly
1               5                   10                  15

Asp Arg Val Thr Ile Thr Cys Gln Thr Ser Thr Asp Ile Ser Asn Tyr
            20                  25                  30
```

```
Met Asn Trp Tyr Gln Gln Lys Pro Gly Lys Ala Pro Lys Leu Leu Ile
        35                  40                  45

Ser Glu Gly Asn Thr Leu Arg Pro Gly Val Pro Ser Arg Phe Ser Ser
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Ser Asp Asn Leu Pro Leu
                85                  90                  95

Thr Phe Gly Gly Gly Thr Lys Leu Glu Ile Lys
            100                 105


<210> SEQ ID NO 75
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Asn Phe
            20                  25                  30

Gly Met Asn Trp Val Arg Gln Ala Pro Gly Gln Arg Leu Glu Trp Met
        35                  40                  45

Gly Trp Ile Asn Thr Tyr Thr Gly Glu Ala Thr Tyr Ala Asp Lys Phe
    50                  55                  60

Gln Gly Arg Val Thr Ile Thr Leu Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Gly Phe Arg His Phe Asp Val Trp Gly Gln Gly Thr
            100                 105                 110

Thr Val Thr Val Ser Ser
        115


<210> SEQ ID NO 76
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Glu Asn Phe
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Ala Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95
```

```
Ala Arg Asp Gly Gly Phe Arg His Phe Asp Val Trp Gly Gln Gly Thr
            100                 105                 110

Thr Val Thr Val Ser Ser
        115


<210> SEQ ID NO 77
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Thr Gln Val Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gly Gly Thr Lys Leu Glu Ile Lys
            100                 105


<210> SEQ ID NO 78
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Met Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Ser Ile Asn Thr Tyr Thr Gly Glu Ala Thr Tyr Ala Asp Gly Phe
    50                  55                  60

Thr Gly Arg Phe Val Phe Ser Leu Asp Thr Ser Ala Asn Thr Ala Tyr
65                  70                  75                  80

Leu Gln Ile Ser Ser Leu Lys Ala Glu Asp Thr Ala Val Tyr Phe Cys
                85                  90                  95

Ala Arg Gly Asp Tyr Tyr Gly Arg Gly Thr Trp Phe Ala Tyr Trp Gly
            100                 105                 110

Gln Gly Thr Leu Val Thr Val Ser Ser
        115                 120


<210> SEQ ID NO 79
<211> LENGTH: 121
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 79

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Ser Ile Asn Thr Tyr Thr Gly Glu Ala Thr Tyr Ala Asp Gly Phe
    50                  55                  60

Thr Gly Arg Phe Val Phe Ser Leu Asp Thr Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asp Tyr Tyr Gly Arg Gly Thr Trp Phe Ala Tyr Trp Gly
            100                 105                 110

Gln Gly Thr Leu Val Thr Val Ser Ser
        115                 120
```

<210> SEQ ID NO 80
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Ser Ile Asn Thr Tyr Thr Gly Glu Ala Thr Tyr Ala Asp Lys Phe
    50                  55                  60

Gln Gly Arg Val Thr Met Thr Leu Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Tyr Gly Arg Gly Thr Trp Phe Ala Tyr Trp Gly
            100                 105                 110

Gln Gly Thr Leu Val Thr Val Ser Ser
        115                 120
```

<210> SEQ ID NO 81
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Glu Thr Val Val Thr Gln Ser Pro Ala Thr Leu Ser Leu Ser Pro Gly
1               5                   10                  15

Glu Arg Ala Thr Leu Ser Cys Arg Ala Ser Gln Asp Val Ser Thr Ala
```

```
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Pro Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asp Tyr Ser Ser Pro Trp
                85                  90                  95

Thr Phe Gly Gly Gly Thr Lys Leu Glu Ile Lys
            100                 105


<210> SEQ ID NO 82
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Ser Ile Asn Thr Tyr Thr Gly Glu Ala Thr Tyr Ala Asp Asp Phe
    50                  55                  60

Lys Gly Arg Phe Val Phe Ser Leu Asp Thr Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asp Tyr Tyr Gly Arg Gly Thr Trp Phe Ala Tyr Trp Gly
            100                 105                 110

Gln Gly Thr Leu Val Thr Val Ser Ser
        115                 120


<210> SEQ ID NO 83
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Ser Ile Asn Thr Tyr Thr Gly Glu Ala Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
```

```
                85                  90                  95

Ala Arg Gly Asp Tyr Tyr Gly Arg Gly Thr Trp Phe Ala Tyr Trp Gly
            100                 105                 110

Gln Gly Thr Leu Val Thr Val Ser Ser
        115                 120


<210> SEQ ID NO 84
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Ser Ile Asn Thr Tyr Thr Gly Glu Ala Thr Tyr Ala Gln Lys Phe
    50                  55                  60

Gln Gly Arg Val Thr Met Thr Leu Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Tyr Gly Arg Gly Thr Trp Phe Ala Tyr Trp Gly
            100                 105                 110

Gln Gly Thr Leu Val Thr Val Ser Ser
        115                 120


<210> SEQ ID NO 85
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Val Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Arg Thr Phe Gly Gly Gly Thr Lys Leu Glu Ile Lys
            100                 105                 110


<210> SEQ ID NO 86
<211> LENGTH: 121
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 86

```
Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Leu Ile Asn Thr Tyr Thr Gly Glu Pro Thr Tyr Ala Asp Gly Phe
    50                  55                  60

Thr Gly Arg Phe Val Phe Ser Leu Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Glu Arg Ile Tyr Gly Tyr Leu His Tyr Phe Asp Tyr Trp Gly
            100                 105                 110

Gln Gly Thr Thr Val Thr Val Ser Ser
        115                 120
```

<210> SEQ ID NO 87
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Leu Ile Asn Thr Tyr Thr Gly Glu Pro Thr Tyr Ala Asp Lys Phe
    50                  55                  60

Gln Gly Arg Val Thr Met Thr Leu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ile Tyr Gly Tyr Leu His Tyr Phe Asp Tyr Trp Gly
            100                 105                 110

Gln Gly Thr Thr Val Thr Val Ser Ser
        115                 120
```

<210> SEQ ID NO 88
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Asp Val Val Met Thr Gln Ser Pro Asp Ser Leu Ala Val Ser Leu Gly
1               5                   10                  15
```

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Arg Thr Phe Gly Gly Gly Thr Lys Leu Glu Ile Lys
            100                 105                 110

<210> SEQ ID NO 89
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Leu Ile Asn Thr Tyr Thr Gly Glu Pro Thr Tyr Ala Asp Lys Phe
    50                  55                  60

Gln Gly Arg Val Thr Phe Thr Leu Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Glu Arg Ile Tyr Gly Tyr Leu His Tyr Phe Asp Tyr Trp Gly
            100                 105                 110

Gln Gly Thr Thr Val Thr Val Ser Ser
        115                 120

<210> SEQ ID NO 90
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Val Gln Met Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

```
Ser Leu Gln Pro Glu Asp Phe Ala Thr Tyr Tyr Cys Gln Gln Ser Asn
                85                  90                  95

Glu Asp Pro Arg Thr Phe Gly Gly Gly Thr Lys Leu Glu Ile Lys
            100                 105                 110


<210> SEQ ID NO 91
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Leu Ile Asn Thr Tyr Thr Gly Glu Pro Thr Tyr Ala Asp Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Arg Ile Tyr Gly Tyr Leu His Tyr Phe Asp Tyr Trp Gly
            100                 105                 110

Gln Gly Thr Thr Val Thr Val Ser Ser
        115                 120


<210> SEQ ID NO 92
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Arg Thr Phe Gly Gly Gly Thr Lys Leu Glu Ile Lys
            100                 105                 110


<210> SEQ ID NO 93
<211> LENGTH: 113
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 93

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Glu Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Ser Tyr Pro Leu Thr Phe Gly Gly Gly Thr Lys Leu Glu Ile
            100                 105                 110

Lys


<210> SEQ ID NO 94
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Gln Gly Arg Val Thr Leu Thr Ala Asp Thr Ser Ser Ser Thr Ala Tyr
65                  70                  75                  80

Met Glu Leu Ser Ser Leu Arg Ser Glu Asp Thr Ala Val Tyr Phe Cys
                85                  90                  95

Ala Lys Phe Tyr Tyr Tyr Gly Ser Ser Tyr Tyr Phe Asp Ser Trp Gly
            100                 105                 110

Gln Gly Thr Thr Val Thr Val Ser Ser
        115                 120


<210> SEQ ID NO 95
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
```

```
            20                  25                  30

Gly Asn Gln Glu Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Ser Tyr Pro Leu Thr Phe Gly Gly Gly Thr Lys Leu Glu Ile
            100                 105                 110

Lys


<210> SEQ ID NO 96
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Gly Tyr Thr Asn Tyr Asn Glu Lys Phe
    50                  55                  60

Gln Gly Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Phe Tyr Tyr Tyr Gly Ser Ser Tyr Tyr Phe Asp Ser Trp Gly
            100                 105                 110

Gln Gly Thr Thr Val Thr Val Ser Ser
        115                 120


<210> SEQ ID NO 97
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asn Ser
            20                  25                  30

Gly Asn Gln Glu Asn Tyr Leu Ala Trp Tyr Leu Gln Lys Pro Gly Gln
        35                  40                  45

Ser Pro Gln Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80
```

```
Ile Ser Arg Val Glu Ala Glu Asp Val Gly Val Tyr Tyr Cys Gln Asn
                85                  90                  95

Asp His Ser Tyr Pro Leu Thr Phe Gly Gly Gly Thr Lys Leu Glu Ile
            100                 105                 110

Lys


<210> SEQ ID NO 98
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asn Ser
            20                  25                  30

Gly Asn Gln Glu Asn Tyr Leu Ala Trp Tyr Leu Gln Lys Pro Gly Gln
        35                  40                  45

Ser Pro Gln Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp His Ser Tyr Pro Leu Thr Phe Gly Gly Gly Thr Lys Leu Glu Ile
            100                 105                 110

Lys


<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99

cgugagagau aagauuacut t                                                21


<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100

aguaaucuua ucucucacgt t                                                21


<210> SEQ ID NO 101
<211> LENGTH: 327
<212> TYPE: PRT
```

<213> ORGANISM: Homo sapiens

<400> SEQUENCE: 101

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Pro Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 102
<211> LENGTH: 107
<212> TYPE: PRT
<213> ORGANISM: Homo sapiens

<400> SEQUENCE: 102

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe

```
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 103
<211> LENGTH: 106
<212> TYPE: PRT
<213> ORGANISM: Homo sapiens

<400> SEQUENCE: 103

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 104
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Val Thr Leu Lys Glu Ser Gly Pro Thr Leu Val Lys Pro Thr Gln
1               5                   10                  15

Thr Leu Thr Leu Thr Cys Thr Phe Ser Gly Ile Ser Leu Thr Thr Ser
            20                  25                  30

Gly Met Gly Val Gly Trp Ile Arg Gln Pro Pro Gly Lys Ala Leu Glu
        35                  40                  45

Trp Leu Ala Asp Ile Phe Trp Asp Asp Asn Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Arg Val Tyr Tyr Lys Asn Asp Gly Tyr Phe Asp Val Trp Gly
            100                 105                 110

Lys Gly Thr Thr Val Thr Val Ser Ser
```

115 120

<210> SEQ ID NO 105
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

Asp Ile Val Leu Thr Gln Ser Pro Leu Ser Leu Pro Val Thr Leu Gly
1 5 10 15

Gln Pro Ala Ser Ile Ser Cys Arg Ala Ser Lys Ser Val Thr Thr Ser
20 25 30

Gly Tyr Ser Phe Met His Trp Tyr Gln Gln Arg Pro Gly Gln Ser Pro
35 40 45

Arg Leu Leu Ile Tyr Leu Ala Ser Asn Leu Glu Pro Gly Val Pro Asp
50 55 60

Arg Phe Ser Gly Ser Gly Ser Gly Thr Asp Phe Thr Leu Lys Ile Ser
65 70 75 80

Arg Val Glu Ala Glu Asp Val Gly Val Tyr Tyr Cys Gln Gln Ser Gly
85 90 95

Glu Leu Pro Tyr Thr Phe Gly Gln Gly Thr Lys Leu Glu Ile Lys
100 105 110

<210> SEQ ID NO 106
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

Asp Ile Val Leu Thr Gln Ser Pro Leu Ser Leu Pro Val Thr Leu Gly
1 5 10 15

Gln Pro Ala Ser Ile Ser Cys Arg Ala Ser Lys Ser Val Thr Thr Ser
20 25 30

Gly Tyr Ser Phe Met His Trp Tyr Gln Gln Arg Pro Gly Gln Ser Pro
35 40 45

Arg Leu Leu Ile Tyr Leu Ala Ser Asn Leu Glu Pro Gly Val Pro Asp
50 55 60

Arg Phe Ser Gly Ser Gly Ser Gly Thr Asp Phe Thr Leu Lys Ile Phe
65 70 75 80

Arg Val Glu Ala Glu Asp Val Gly Val Tyr Tyr Cys Gln Gln Ser Gly
85 90 95

Glu Leu Pro Tyr Thr Phe Gly Gln Gly Thr Lys Leu Glu Ile Lys
100 105 110

<210> SEQ ID NO 107
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

Gln Val Gln Leu Gln Glu Ser Gly Pro Gly Leu Val Lys Pro Ser Gln
1 5 10 15

```
Thr Leu Ser Leu Thr Cys Ser Phe Ser Gly Ile Ser Leu Thr Thr Ser
            20                  25                  30

Gly Met Gly Val Gly Trp Ile Arg Gln Pro Pro Gly Lys Gly Leu Glu
        35                  40                  45

Trp Leu Ala Asp Ile Phe Trp Asp Asp Asn Lys Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Val Arg Val Tyr Tyr Lys Asn Asp Gly Tyr Phe Asp Val Trp Gly
            100                 105                 110

Gln Gly Thr Leu Val Thr Val Ser Ser
        115                 120


<210> SEQ ID NO 108
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Ile Val Met Thr Gln Ser Pro Ala Thr Leu Ser Val Ser Pro Gly
1               5                   10                  15

Glu Arg Ala Thr Leu Ser Cys Arg Ala Ser Lys Ser Val Thr Thr Ser
            20                  25                  30

Gly Tyr Ser Phe Met His Trp Tyr Gln Gln Lys Pro Gly Gln Ala Pro
        35                  40                  45

Arg Leu Leu Ile Tyr Leu Ala Ser Asn Leu Glu Pro Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln His Ser Arg
                85                  90                  95

Glu Leu Pro Tyr Thr Phe Gly Gln Gly Thr Lys Leu Glu Ile Lys
            100                 105                 110


<210> SEQ ID NO 109
<211> LENGTH: 264
<212> TYPE: PRT
<213> ORGANISM: Homo sapiens

<400> SEQUENCE: 109

Arg Pro Ile Leu Glu Val Pro Glu Ser Val Thr Gly Pro Trp Lys Gly
1               5                   10                  15

Asp Val Asn Leu Pro Cys Thr Tyr Asp Pro Leu Gln Gly Tyr Thr Gln
            20                  25                  30

Val Leu Val Lys Trp Leu Val Gln Arg Gly Ser Asp Pro Val Thr Ile
        35                  40                  45

Phe Leu Arg Asp Ser Ser Gly Asp His Ile Gln Gln Ala Lys Tyr Gln
    50                  55                  60

Gly Arg Leu His Val Ser His Lys Val Pro Gly Asp Val Ser Leu Gln
65                  70                  75                  80

Leu Ser Thr Leu Glu Met Asp Asp Arg Ser His Tyr Thr Cys Glu Val
                85                  90                  95
```

```
Thr Trp Gln Thr Pro Asp Gly Asn Gln Val Val Arg Asp Lys Ile Thr
            100                 105                 110

Glu Leu Arg Val Gln Lys Leu Ser Val Ser Lys Pro Thr Val Thr Thr
        115                 120                 125

Gly Ser Gly Tyr Gly Phe Thr Val Pro Gln Gly Met Arg Ile Ser Leu
    130                 135                 140

Gln Cys Gln Ala Arg Gly Ser Pro Pro Ile Ser Tyr Ile Trp Tyr Lys
145                 150                 155                 160

Gln Gln Thr Asn Asn Gln Glu Pro Ile Lys Val Ala Thr Leu Ser Thr
                165                 170                 175

Leu Leu Phe Lys Pro Ala Val Ile Ala Asp Ser Gly Ser Tyr Phe Cys
            180                 185                 190

Thr Ala Lys Gly Gln Val Gly Ser Glu Gln His Ser Asp Ile Val Lys
        195                 200                 205

Phe Val Val Lys Asp Ser Ser Lys Leu Leu Lys Thr Lys Thr Glu Ala
    210                 215                 220

Pro Thr Thr Met Thr Tyr Pro Leu Lys Ala Thr Ser Thr Val Lys Gln
225                 230                 235                 240

Ser Trp Asp Trp Thr Thr Asp Met Asp Gly Tyr Leu Gly Glu Thr Ser
                245                 250                 255

Ala Gly Pro Gly Lys Ser Leu Pro
            260


<210> SEQ ID NO 110
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gly Ser Gly Gly Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
```

-continued

```
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230


<210> SEQ ID NO 111
<211> LENGTH: 103
<212> TYPE: PRT
<213> ORGANISM: Homo sapiens

<400> SEQUENCE: 111

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100


<210> SEQ ID NO 112
<211> LENGTH: 7
<212> TYPE: PRT
<213> ORGANISM: Homo sapiens

<400> SEQUENCE: 112

Gln Arg Gly Ser Asp Pro Val
1               5
```